United States Patent
Duffey et al.

(10) Patent No.: US 9,695,154 B2
(45) Date of Patent: Jul. 4, 2017

(54) HETEROARYL INHIBITORS OF SUMO ACTIVATING ENZYME

(71) Applicant: MILLENNIUM PHARMACEUTICALS, INC., Cambridge, MA (US)

(72) Inventors: Matthew O. Duffey, Chicago, IL (US); Dylan B. England, Milford, MA (US); Zhigen Hu, Somerville, MA (US); Mitsuhiro Ito, Kanagawa (JP); Steven P. Langston, North Andover, MA (US); Charles McIntyre, Cambridge, MA (US); Hirotake Mizutani, Cambridge, MA (US); He Xu, Needham, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/901,809

(22) PCT Filed: Jul. 1, 2014

(86) PCT No.: PCT/US2014/045129
§ 371 (c)(1),
(2) Date: Dec. 29, 2015

(87) PCT Pub. No.: WO2015/002994
PCT Pub. Date: Jan. 8, 2015

(65) Prior Publication Data
US 2016/0355504 A1    Dec. 8, 2016

Related U.S. Application Data
(60) Provisional application No. 61/842,097, filed on Jul. 2, 2013.

(51) Int. Cl.
| | | |
|---|---|---|
| *C07D 239/28* | (2006.01) | |
| *C07D 401/14* | (2006.01) | |
| *A61K 31/505* | (2006.01) | |
| *C07D 403/06* | (2006.01) | |
| *A61K 31/506* | (2006.01) | |
| *C07D 401/06* | (2006.01) | |
| *C07D 403/14* | (2006.01) | |
| *C07D 405/14* | (2006.01) | |

(52) U.S. Cl.
CPC .......... *C07D 403/06* (2013.01); *A61K 31/505* (2013.01); *A61K 31/506* (2013.01); *C07D 239/28* (2013.01); *C07D 401/06* (2013.01); *C07D 401/14* (2013.01); *C07D 403/14* (2013.01); *C07D 405/14* (2013.01)

(58) Field of Classification Search
CPC .. C07D 239/28; C07D 401/14; A61K 31/505; A61K 31/506
USPC .................. 544/326, 327; 514/256
See application file for complete search history.

(56) References Cited

U.S. PATENT DOCUMENTS

| | | |
|---|---|---|
| 5,194,446 A | 3/1993 | Lo et al. |
| 7,078,525 B2 | 7/2006 | Guzi et al. |

(Continued)

FOREIGN PATENT DOCUMENTS

| | | |
|---|---|---|
| JP | 2005008581 A | 1/2005 |
| WO | WO 97/05132 A1 | 2/1997 |

(Continued)

OTHER PUBLICATIONS

Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1101 O, 1995.*

(Continued)

*Primary Examiner* — Deepak Rao
(74) *Attorney, Agent, or Firm* — Sterne, Kessler, Goldstein & Fox P.L.L.C.

(57) ABSTRACT

Disclosed are compounds of formula (I); or a pharmaceutically acceptable salt thereof; wherein Y, $R^a$, $R^{a'}$, $R^c$, $R^f$, $X_2$, $R^d$, $R^{d'}$, $R^e$, $R^{e'}$, m, and G have the values described herein and stereochemical configurations depicted at asterisked positions indicate absolute stereochemistry, useful as inhibitors of Sumo Activating Enzyme (SAE). Further provided are pharmaceutical compositions comprising a compound of the disclosure and methods of using the compositions in the treatment of proliferative, inflammatory, cardiovascular and neurodegenerative diseases or disorders.

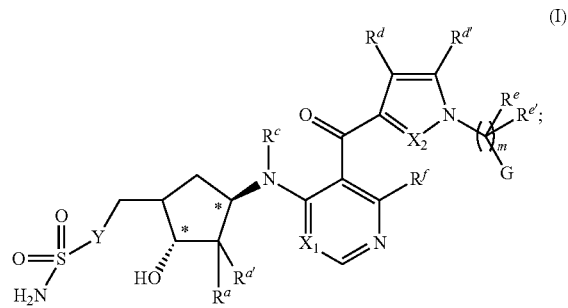

34 Claims, No Drawings

(56) References Cited

U.S. PATENT DOCUMENTS

| | | |
|---|---|---|
| 7,196,092 B2 | 3/2007 | Guzi et al. |
| 7,563,798 B2 | 7/2009 | Guzi et al. |
| 7,642,266 B2 | 1/2010 | Guzi et al. |
| 8,008,307 B2 | 8/2011 | Claiborne et al. |
| 8,207,177 B2 | 6/2012 | Langston et al. |
| 8,481,550 B2 | 7/2013 | Claiborne et al. |
| 8,809,356 B2 | 8/2014 | McCarron et al. |
| 8,901,136 B2 | 12/2014 | Critchley et al. |
| 9,150,525 B2 | 10/2015 | Claiborne et al. |
| 9,290,500 B2 | 3/2016 | Afroze et al. |
| 2004/0102451 A1 | 5/2004 | Guzi et al. |
| 2006/0166926 A1 | 7/2006 | Wilde et al. |
| 2007/0082901 A1 | 4/2007 | Guzi et al. |
| 2007/0191293 A1 | 8/2007 | Langston et al. |
| 2008/0051404 A1 | 2/2008 | Claiborne et al. |
| 2011/0021544 A1 | 1/2011 | Armitage et al. |
| 2012/0077814 A1 | 3/2012 | Wang et al. |
| 2012/0258927 A1 | 10/2012 | Langston et al. |
| 2013/0150388 A1 | 6/2013 | McCarron et al. |
| 2013/0217682 A1 | 8/2013 | Afroze et al. |
| 2015/0011572 A1 | 1/2015 | McCarron et al. |
| 2016/0039761 A1 | 2/2016 | Claiborne et al. |

FOREIGN PATENT DOCUMENTS

| | | |
|---|---|---|
| WO | WO 03/073989 A2 | 9/2003 |
| WO | WO 2004/009609 A2 | 1/2004 |
| WO | WO 2004/009610 A2 | 1/2004 |
| WO | WO 2004/022559 A1 | 3/2004 |
| WO | WO 2004/026229 A2 | 4/2004 |
| WO | WO 2004/043955 A1 | 5/2004 |
| WO | WO 2004/087707 A1 | 10/2004 |
| WO | WO 2005/037845 A1 | 4/2005 |
| WO | WO 2005/051949 A1 | 6/2005 |
| WO | WO 2006/002284 A1 | 1/2006 |
| WO | WO 2006/084281 A1 | 8/2006 |
| WO | WO 2007/044401 A2 | 4/2007 |
| WO | WO 2007/092213 A2 | 8/2007 |
| WO | WO 2008/154642 A2 | 12/2008 |
| WO | WO 2009/082691 A1 | 7/2009 |
| WO | WO 2010/022121 A1 | 2/2010 |
| WO | WO 2010/022125 A1 | 2/2010 |
| WO | WO 2010/022126 A1 | 2/2010 |
| WO | WO 2010/022128 A1 | 2/2010 |
| WO | WO 2010/039548 A2 | 4/2010 |
| WO | WO 2010/086040 A1 | 8/2010 |
| WO | WO 2010/088518 A2 | 8/2010 |
| WO | WO 2010/132110 A1 | 11/2010 |
| WO | WO 2011/022440 A2 | 2/2011 |
| WO | WO 2011/100131 A1 | 8/2011 |
| WO | WO 2011/103441 A1 | 8/2011 |
| WO | WO 2011/109059 A1 | 9/2011 |
| WO | WO 2012/016217 A1 | 2/2012 |
| WO | WO 2013/066729 A1 | 5/2013 |
| WO | WO 2013/151975 A1 | 10/2013 |
| WO | WO 2015/002994 A2 | 1/2015 |
| WO | WO 2015/048547 A2 | 4/2015 |
| WO | WO 2015/061247 A2 | 4/2015 |
| WO | WO 2015/110999 A1 | 7/2015 |

OTHER PUBLICATIONS

PCT International Search Report issued in International Application No. PCT/US2014/045129, dated Apr. 2, 2015, 4 pages.

Brownell et al., "Substrate-Assisted Inhibition of Ubiquitin-Like Protein-Activating Enzymes: The NEDD8 E1 Inhibitor MLN4924 Forms A NEDD8-AMP Mimetic In Situ," *Mol. Cell* 37:102-111, Elsevier, The Netherlands (2010).

Extended European Search Report for European patent Application No. 12825411.7 mailed Mar. 25, 2015, (5 pages).

International Search Report and Written Opinion PCT/US07/017463 dated Nov. 23, 2007 corresponding to U.S. Appl. No. 11/890,338.

International Search Report and Written Opinion for PCT/US15/38712 mailed Sep. 29, 2015.

PCT Notification of Transmittal of the International Search Report and the Written Opinion of the International Searching Authority, or the Declaration for International Application No. PCT/US2013/026113 mailed Apr. 11, 2013.

Supplementary European Search Report of European Application No. Ep 13 74 8707, Jun. 9, 2015.

Pearce et al., "Failure modes in anticancer drug discovery and development, Cancer Drug Design and Discovery," Edited by Stephen Neidle, Chapter 18, pp. 424-435, Elsevier, The Netherlands, (2008).

Gura, "Systems for identifying new drugs are often faulty," Cancer Models, *Science* 278(5340): 1041-1042, AAAS, The United States (Nov. 1997).

Johnson et al. "Relationships between drug activity in NCI preclinical in vitro and in vivo models and early clinical trials," British Journal of Cancer 84(10):1424-1431, Cancer Research Campaign, England (2001).

Simone, Oncology: Introduction, Cecil Textbook of Medicine, 20th Edition, vol. 1, pp. 1004-1010, W.B. Saunders Company, United states (1996).

Xu et al.. "The ubiquitin-activating enzyme E1 as a therapeutic target for the treatment of leukemia and multiple myeloma," *Blood* 115(11): 2251-2259, The American Society of Hematology, United States (Mar. 2010).

* cited by examiner

HETEROARYL INHIBITORS OF SUMO ACTIVATING ENZYME

PRIORITY CLAIM

This application claims priority to U.S. Provisional Application No. 61/842,097 filed on Jul. 2, 2013, the entire contents of which are incorporated herein by reference.

INTRODUCTION

Small ubiquitin-like modifier (SUMO) is a member of the ubiquitin-like protein (Ubl) family that is covalently conjugated to cellular proteins in a manner similar to Ub-conjugation (Kerscher, O., Felberbaum, R., and Hochstrasser, M. 2006. Modification of proteins by ubiquitin and ubiquitin-like proteins. *Annu Rev Cell Dev Biol.* 22:159-80). Mammalian cells express three major isoforms: SUMO1, SUMO2 and SUMO3. SUMO2 and SUMO3 share ~95% amino acid sequence homology but have ~45% sequence homology with SUMO1 (Kamitani, T., Kito, K., Nguyen, H. P., Fukuda-Kamitani, T., and Yeh, E. T. 1998. Characterization of a second member of the sentrin family of ubiquitin-like proteins. *J Biol Chem.* 273(18):11349-53). SUMO proteins can be conjugated to a single lysine residue of a protein (monosumoylation) or to a second SUMO protein that is already conjugated to a protein forming a SUMO chain (polysumoylation). Only SUMO2/3 can form such chains because they possess internal consensus SUMO modification sites (Tatham, M. H., Jaffray, E., Vaughan, O. A., Desterro, J. M., Botting, C. H., Naismith, J. H., Hay, R. T. 2001. Polymeric chains of SUMO-2 and SUMO-3 are conjugated to protein substrates by SAE1/SAE2 and Ubc9. *J Biol Chem.* 276(38):35368-74). SUMO4 is an isoform found in kidney, lymph node and spleen cells, but it is not known whether SUMO4 can be conjugated to cellular proteins.

All three SUMOs are activated in an ATP-dependent manner by the SUMO-activating enzyme (SAE). SAE is a heterodimer that consists of SAE1 (SUMO-activating enzyme subunit 1) and SAE2 (UBA2). SAE, like other E1 activating enzymes, uses ATP to adenylate the C-terminal glycine residue of SUMO. In a second step, a thioester intermediate is then formed between the C-terminal glycine of SUMO and a cysteine residue in SAE2. Next, SUMO is transferred from the E1 to the cysteine residue of the SUMO conjugating enzyme (E2), UBC9. Unlike the Ub pathway that contains many E2 enzymes, Ubc9 is the only known conjugating enzyme for SUMO and functions with all 3 SUMO proteins. SUMO proteins are then conjugated to the target protein, either directly or in conjunction with an E3 ligase, through isopeptide bond formation with the epsilon amino group of a lysine side chain on a target protein. Several SUMO E3 ligases, including PIAS (protein inhibitor of activated signal transducer and activator of transcription protein) proteins and Ran-binding protein 2 (RanBP2), and polycomb 2 (Pc2), have been identified (Johnson, E. S., and Gupta, A. A. 2001. An E3-like factor that promotes SUMO conjugation to the yeast septins. *Cell.* 106(6):735-44; Pichler, A., Gast, A., Seeler, J. S., Dejean, A.; Melchior, F. 2002. The nucleoporin RanBP2 has SUMO1 E3 ligase activity. *Cell.* 108(1):109-20; Kagey, M. H., Melhuish, T. A., and Wotton, D. 2003. The polycomb protein Pc2 is a SUMO E3. *Cell.* 113(1):127-37). Once attached to cellular targets, SUMO modulates the function, subcellular localization, complex formation and/or stability of substrate proteins (Müller, S., Hoege, C., Pyrowolakis, G., and Jentsch, S. 2001. SUMO, ubiquitin's mysterious cousin. *Nat Rev Mol Cell Biol.* 2(3):202-10). SUMO-conjugation is reversible through the action of de-sumoylating enzymes called SENPs (Hay, R. T. 2007. SUMO-specific proteases: a twist in the tail. *Trends Cell Biol.* 17(8):370-6) and the SUMO proteins can then participate in additional conjugation cycles.

SAE-initiated SUMO-conjugation plays a major role in regulating diverse cellular processes, including cell cycle regulation, transcriptional regulation, cellular protein targeting, maintenance of genome integrity, chromosome segregation, and protein stability (Hay, R. T. 2005. SUMO: a history of modification. *Mol Cell.* 18(1):1-12; Gill, G. 2004. SUMO and ubiquitin in the nucleus: different functions, similar mechanisms? *Genes Dev.* 18(17):2046-59). For example, SUMO-conjugation causes changes in the subcellular localization of RanGAP1 by targeting it to the nuclear pore complex (Mahajan, R., Delphin, C., Guan, T., Gerace, L., and Melchior, F. 1997. A small ubiquitin-related polypeptide involved in targeting RanGAP1 to nuclear pore complex protein RanBP2. *Cell.* 88(1):97-1070). Sumoylation counteracts ubiquitination and subsequently blocks the degradation of IκB, thereby negatively regulating NF-κB activation (Desterro, J. M., Rodriguez, M. S., Hay, R. T. 1998. SUMO-1 modification of IkappaBalpha inhibits NF-kappaB activation. *Mol Cell.* 2(2):233-9). Sumoylation has been reported to play an important role in transcription exhibiting both repressive and stimulatory effects. Many of the transcriptional nodes that are modulated play important roles in cancer. For example, sumoylation stimulates the transcriptional activities of transcription factors such as p53 and HSF2 (Rodriguez, M. S., Desterro, J. M., Lain, S., Midgley, C. A., Lane, D. P., and Hay, R. T. 1999. SUMO-1 modification activates the transcriptional response of p53. *EMBO J.* 18(22):6455-61; Goodson, M. L., Hong, Y., Rogers, R., Matunis, M. J., Park-Sarge, O. K., Sarge, K. D. 2001. Sumo-1 modification regulates the DNA binding activity of heat shock transcription factor 2, a promyelocytic leukemia nuclear body associated transcription factor. *J Biol Chem.* 276(21):18513-8). In contrast, SUMO-conjugation represses the transcriptional activities of transcription factors such as LEF (Sachdev, S., Bruhn, L., Sieber, H., Pichler, A., Melchior, F., Grosschedl, R. 2001. PIASy, a nuclear matrix-associated SUMO E3 ligase, represses LEF1 activity by sequestration into nuclear bodies. *Genes Dev.* 15(23): 3088-103) and c-Myb (Bies, J., Markus, J., and Wolff, L. 2002. Covalent attachment of the SUMO-1 protein to the negative regulatory domain of the c-Myb transcription factor modifies its stability and transactivation capacity. *J Biol Chem.* 277(11):8999-9009). Thus, SUMO-conjugation controls gene expression and growth control pathways that are important for cancer cell survival.

Altered expression of SAE pathway components have been noted in a variety of cancer types: (Moschos, S. J., Jukic, D. M., Athanassiou, C., Bhargava, R., Dacic, S., Wang, X., Kuan, S. F., Fayewicz, S. L., Galambos, C., Acquafondata, M., Dhir, R., and Becker, D. 2010. Expression analysis of Ubc9, the single small ubiquitin-like modifier (SUMO) E2 conjugating enzyme, in normal and malignant tissues. *Hum Pathol.* 41(9):1286-980); including multiple myeloma (Driscoll, J. J., Pelluru, D., Lefkimmiatis, K., Fulciniti, M., Prabhala, R. H., Greipp, P. R., Barlogie, B., Tai, Y. T., Anderson, K. C., Shaughnessy, J. D. Jr., Annunziata, C. M., and Munshi, N. C. 2010. The sumoylation pathway is dysregulated in multiple myeloma and is associated with adverse patient outcome. *Blood.* 115(14):2827-34); and breast cancer (Chen, S. F., Gong, C., Luo, M., Yao, H. R., Zeng, Y. J., and Su, F. X. 2011. Ubc9 expression predicts chemoresistance in breast cancer. *Chin J Cancer.* 30(9):638-44), In addition, preclinical studies indicate that Myc-driven cancers may be especially sensitive to SAE inhibition (Kessler, J. D., Kahle, K. T., Sun, T., Meerbrey, K. L., Schlabach, M. R., Schmitt, E. M., Skinner, S. O., Xu, Q., Li, M. Z., Hartman, Z. C., Rao, M., Yu, P., Dominguez-Vidana, R., Liang, A. C., Solimini, N. L., Bernardi, R. J., Yu, B., Hsu, T., Golding, I., Luo, J., Osborne, C. K., Creighton, C. J., Hilsenbeck, S. G., Schiff, R., Shaw, C. A., Elledge, S. J., and Westbrook, T. F. 2012. A SUMOylation-dependent transcriptional subprogram is required for Myc-driven tumorigenesis. *Science.* 335(6066):348-53). Since SUMO-conjugation regulates essential cellular functions that contribute to the growth and survival of tumor cells, targeting SAE could represent an approach to treat proliferative disorders such as cancer.

SAE inhibitors may also be applicable for the treatment of other diseases and conditions outside of oncology. For example, SUMO modifies proteins that play important roles in neurodegenerative diseases (Steffan, J. S., Agrawal, N., Pallos, J., Rockabrand, E., Trotman, L. C., Slepko, N., files, K., Lukacsovich, T., Zhu, Y. Z., Cattaneo, E., Pandolfi, P. P., Thompson, L. M., Marsh, J. L. 2004. SUMO modification of Huntington and Huntington's disease pathology. *Science.* 304(5667):100-4); Dorval, V., and Fraser, P. E. 2006. Small ubiquitin-like modifier (SUMO) modification of natively unfolded proteins tau and alpha-synuclein. *J Biol Chem.* 281(15):9919-24; Ballatore, C., Lee, V. M., and Trojanowski, J. Q. 2007. Tau-mediated neurodegeneration in Alzheimer's disease and related disorders. *Nat Rev Neurosci.* 8(9):663-72). Sumoylation also has been reported to play important role in pathogenic viral infection, inflammation and cardiac function (Lee, H. R., Kim, D. J., Lee, J. M., Choi, C. Y., Ahn, B. Y., Hayward, G. S., and Ahn, J. H. 2004. Ability of the human cytomegalovirus IE1 protein to modulate sumoylation of PML correlates with its functional activities in transcriptional regulation and infectivity in cultured fibroblast cells. *J Virol.* 78(12):6527-42; Liu, B., and Shuai, K. 2009. Summon SUMO to wrestle with inflammation. *Mol Cell.* 35(6):731-2; Wang, J., and Schwartz, R. J. 2010. Sumoylation and regulation of cardiac gene expression. *Circ Res.* 107(1):19-29).

It would be beneficial therefore to provide new SAE inhibitors that possess good therapeutic properties, especially for the treatment of proliferative, inflammatory, cardiovascular and neurodegenerative disorders.

This application provides compounds which are inhibitors of SAE and accordingly are useful for the treatment of proliferative, inflammatory, cardiovascular and neurodegenerative disorders. The compounds of the present disclosure are represented by Formula (I):

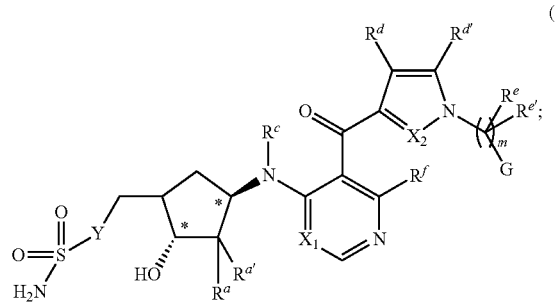

or a pharmaceutically acceptable salt thereof;

wherein:
stereochemical configurations depicted at asterisked positions indicate absolute stereochemistry;
Y is —O—, —CH$_2$—, —N(H)—;
R$^a$ is hydrogen, fluoro, —NH$_2$, or —OH;
R$^{a'}$ is hydrogen, or fluoro; provided that when R$^a$ is —NH$_2$ or —OH, R$^{a'}$ is hydrogen;
R$^c$ is hydrogen or C$_{1-4}$ alkyl;
X$_1$ is C(H), C(F) or N;
X$_2$ is C(R$^d$)— or N;
each occurrence of R$^d$ is independently hydrogen, halogen, cyano, C$_{1-4}$ aliphatic, or C$_{1-4}$ fluoroaliphatic;
R$^{d'}$ is hydrogen, halogen, cyano, C$_{1-4}$ aliphatic, C$_{1-4}$ fluoroaliphatic, or -T$_2$-R$^3$;
T$_2$ is a C$_1$-C$_2$ alkylene chain optionally substituted with 0-3 independent occurrences of R$^{3c}$;
R$^3$ is —CN, —NO$_2$, —N(R$^{3a}$)$_2$, —OR$^{3a}$, —C(O)R$^{3b}$, —C(O)OR$^{3a}$, —C(O)N(R$^{3a}$)$_2$, or —S(O)$_2$N(R$^{3a}$)$_2$;
each occurrence of R$^{3a}$ is independently hydrogen or C$_{1-4}$ alkyl;
R$^{3b}$ is C$_{1-4}$ alkyl;
each occurrence of R$^{3c}$ is independently C$_{1-4}$ alkyl;
R$^e$ is hydrogen or C$_{1-4}$ alkyl;
R$^{e'}$ is hydrogen or C$_{1-4}$ alkyl; or R$^e$ is taken together with R$^{e'}$ to form a 3-6 membered cycloaliphatic ring;
m is 0-2;
R$^f$ is hydrogen, chloro or C$_{1-4}$ alkyl;
G is R$^1$ or -L$_1$-R$^1$;
L$_1$ is

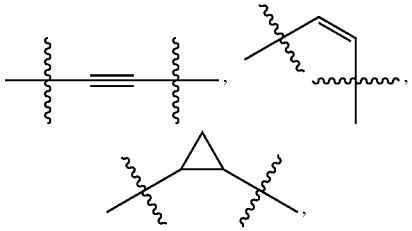

—C(O)—, or —SO$_2$—; provided that when L$_1$ is —SO$_2$—. m is zero;
R$^1$ is an optionally substituted group selected from C$_{1-6}$ aliphatic, 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur, wherein R$^1$ is optionally substituted with n occurrences of R$^2$; wherein each occurrence of R$^2$ is independently —R$^{2a}$, -T$_1$-R$^{2d}$, -T$_1$-R$^{2a}$, or —V$_1$-T$_1$-R$^{2d}$;
n is 1-5;
each occurrence of R$^{2a}$ is independently halogen, —CN, —NO$_2$, —R$^{2c}$, —N(R$^{2b}$)$_2$, —OR$^{2b}$, —SR$^{2c}$, —S(O)R$^{2c}$, —S(O)$_2$R$^{2c}$, —C(O)R$^{2b}$, —C(O)OR$^{2b}$, —C(O)N(R$^{2b}$)$_2$, —S(O)$_2$N(R$^{2b}$)$_2$, —OC(O)N(R$^{2b}$)$_2$, —N(R$^{2e}$)C(O)R$^{2b}$, —N(R$^{2e}$)SO$_2$R$^{2c}$, —N(R$^{2e}$)C(O)OR$^{2b}$, —N(R$^{2e}$)C(O)N(R$^{2b}$)$_2$, —N(R$^{2e}$)SO$_2$N(R$^{2b}$)$_2$, or Si(R$^{2c}$)$_3$, or an optionally substituted C$_1$-C$_6$ aliphatic or C$_1$-C$_6$ haloaliphatic;
each occurrence of R$^{2b}$ is independently hydrogen or an optionally substituted group selected from C$_1$-C$_6$ aliphatic, C$_1$-C$_6$ haloaliphatic, 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur, or two occurrences of $R^{2b}$, taken together with a nitrogen atom to which they are bound, form an optionally substituted 4- to -7-membered heterocyclyl ring having 0-1 additional heteroatoms selected from nitrogen, oxygen, and sulfur;

each occurrence of $R^{2c}$ is independently an optionally substituted group selected from $C_1$-$C_6$ aliphatic, $C_1$-$C_6$ haloaliphatic, 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur;

each occurrence of $R^{2d}$ is independently hydrogen or an optionally substituted group selected from 3- to 10-membered cycloaliphatic, 4- to 10-membered heterocyclyl having 1-5 heteroatoms independently selected from nitrogen, oxygen, and sulfur; 6- to 10-membered aryl, or 5- to 10-membered heteroaryl having 1-5 heteroatoms independently selected from nitrogen, oxygen, and sulfur;

each occurrence of $R^{2e}$ is independently hydrogen or an optionally substituted $C_{1-6}$ aliphatic group;

each occurrence of $V_1$ is independently —N($R^{2e}$)—, —O—, —S—, —S(O)—, —S(O)$_2$—, —C(O)—, —C(O)O—, —C(O)N($R^{2e}$)—, —S(O)$_2$N($R^{2e}$)—, —OC(O)N($R^{2e}$)—, —N($R^{2e}$)C(O)—, —N($R^{2e}$)SO$_2$—, —N($R^{2e}$)C(O)O—, —N($R^{2e}$)C(O)N($R^{2e}$)—, —N($R^{2e}$)SO$_2$N($R^{2e}$)—, —OC(O)—, or —C(O)N($R^{2e}$)—O—; and $T_1$ is an optionally substituted $C_1$-$C_6$ alkylene chain wherein the alkylene chain optionally is interrupted by —N($R^4$)—, —O—, —S—, —S(O)—, —S(O)$_2$—, —C(O)—, —C(O)O—, —C(O)N($R^4$)—, —S(O)$_2$N($R^4$)—, —OC(O)N($R^4$), —N($R^4$)C(O)—, —N($R^4$)SO$_2$—, —N($R^4$)C(O)O—, —N($R^4$)C(O)N($R^4$)—, —N($R^4$)S(O)$_2$N($R^4$)—, —OC(O)—, or —C(O)N($R^4$)—O— or wherein $T_1$ or a portion thereof optionally forms part of an optionally substituted 3- to -7 membered cycloaliphatic or heterocyclyl ring, wherein $R^4$ is hydrogen or an optionally substituted $C_{1-4}$ aliphatic group.

DETAILED DESCRIPTION

Compounds of the present disclosure include those described generally for formula (I), above, and are further illustrated by the classes, subclasses, and species disclosed herein. It will be appreciated that some subsets described for each variable herein can be used for any of the structural subsets as well. As used herein, the following definitions shall apply unless otherwise indicated.

As described herein, compounds of the present disclosure may be optionally substituted with one or more substituents, such as are disclosed generally above, or as exemplified by particular classes, subclasses, and species disclosed herein. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this disclosure are for instance, those that result in the formation of stable or chemically feasible compounds.

A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, "a 3-7-membered saturated, partially unsaturated, or aromatic monocyclic ring having 0-3 heteroatoms independently selected from nitrogen, oxygen, or sulfur, or an 8-10-membered partially unsaturated, or aromatic bicyclic ring system having 0-5 heteroatoms independently selected from nitrogen, oxygen, or sulfur" includes cycloaliphatic, heterocyclic, aryl and heteroaryl rings.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon, or a cyclic $C_{1-12}$ hydrocarbon which is completely saturated or which contains one or more units of unsaturation, but which is not aromatic (also referred to herein as "carbocycle", "cycloaliphatic", "cycloalkyl", or "cycloalkenyl"). For example, suitable aliphatic groups include optionally substituted linear, branched or cyclic alkyl, alkenyl, alkynyl groups and hybrids thereof, such as (cycloalkyl)alkyl, (cycloalkenyl)alkyl, or (cycloalkyl)alkenyl. Unless otherwise specified, in various embodiments, aliphatic groups have 1-12, 1-10, 1-8, 1-6, 1-5, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-5, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-5, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-5, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. In at least one embodiment, the aryl group is a $C_{6-10}$ aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. In at least one embodiment, the aralkyl group is $C_{6-10}$ aryl$C_{1-6}$alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, such as 5, 6, 9, or 10 ring atoms; having 6, 10, or 14π electrons shared in a cyclic array; and having, in addition to carbon atoms, from one to five heteroatoms. A heteroaryl group may be mono-, bi-, tri-, or polycyclic, for instance mono-, bi- or tricyclic, such as mono- or bicyclic. In the context of "heteroar" entities, the term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, for instance one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR$^+$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiamorpholinyl. A heterocyclyl group may be mono-, bi-, tri-, or polycyclic, for instance mono-, bi-, or tricyclic, such as mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., —(CH$_2$)$_n$—, wherein n is a positive integer, such as from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein, and include double and/or triple bonds between carbons in the alkylene chain.

For purposes of clarity, all bivalent groups described herein, including, e.g., the alkylene chain linkers described above, are intended to be read from left to right, with a corresponding left-to-right reading of the formula or structure in which the variable appears. Where a bivalent group, such as $X_1$ is part of an aromatic system such as an aryl or heteroaryl group, then aromaticity is maintained and the individual member of the bivalent group may be individually described as either $X_1$, —$X_1$— or =$X_1$—; for example when $X_1$ is N, this can be described as either N, —N— or =N—.

An aryl (including aralkyl, aralkoxy, aryloxyalkyl, and the like) or heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, —$NO_2$, —CN, —$R^+$, —C($R^+$)=C($R^+$)$_2$, —C≡C—$R^+$, —$OR^+$, —$SR^\circ$, —S(O)$R^\circ$, —$SO_2R^\circ$, —$SO_3R^+$, —$SO_2N(R^+)_2$, —N($R^+$)$_2$, —$NR^+C(O)R^+$, —$NR^+C(S)R^+$, —$NR^+C(O)N(R^+)_2$, —$NR^+C(S)N(R^+)_2$, —$N(R^+)C(=NR^+)$—$N(R^+)_2$, —$N(R^+)C(=NR^+)$—$R^\circ$, —$NR^+CO_2R^+$, —$NR^+SO_2R^\circ$, —$NR^+SO_2N(R^+)_2$, —O—C(O)$R^+$, —O—$CO_2R^+$, —OC(O)N($R^+$)$_2$, —C(O)$R^+$, —C(S)$R^\circ$, —$CO_2R^+$, —C(O)—C(O)$R^+$, —C(O)N($R^+$)$_2$, —C(S)N($R^+$)$_2$, —C(O)N($R^+$)—$OR^+$, —C(O)N($R^+$)C(=$NR^+$)—N($R^+$)$_2$, —N($R^+$)C(=$NR^+$)—N($R^+$)—C(O)$R^+$, —C(=$NR^+$)—N($R^+$)$_2$, —C(=$NR^+$)—$OR^+$, —N($R^+$)—N($R^+$)$_2$, —C(=$NR^+$)—N($R^+$)—$OR^+$, —C($R^\circ$)=N—$OR^+$, —P(O)($R^+$)$_2$, —P(O)($OR^+$)$_2$, —O—P(O)—$OR^+$, and —P(O)($NR^+$)—N($R^+$)$_2$, wherein $R^+$, independently, is hydrogen or an optionally substituted aliphatic, aryl, heteroaryl, cycloaliphatic, or heterocyclyl group, or two independent occurrences of $R^+$ are taken together with their intervening atom(s) to form an optionally substituted 5-7-membered aryl, heteroaryl, cycloaliphatic, or heterocyclyl ring. Each $R^\circ$ is an optionally substituted aliphatic, aryl, heteroaryl, cycloaliphatic, or heterocyclyl group.

An aliphatic or heteroaliphatic group, or a non-aromatic carbocyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C($R^*$)$_2$; =N—N($R^*$)$_2$, =N—$OR^*$, =N—NHC(O)$R^*$, =N—$NHCO_2R^\circ$=N—$NHSO_2R^\circ$ or =N—$R^*$ where $R^\circ$ is defined above, and each $R^*$ is independently selected from hydrogen or an optionally substituted $C_{1-6}$ aliphatic group.

In addition to the substituents defined above, and herein, optional substituents on the nitrogen of a non-aromatic heterocyclic ring also include and are generally selected from —$R^+$, —N($R^+$)$_2$, —C(O)$R^+$, —C(O)$OR^+$, —C(O)C(O)$R^+$, —C(O)$CH_2C$(O)$R^+$, —S(O)$_2R^+$, —S(O)$_2N(R^+)_2$, —C(S)N($R^+$)$_2$, —C(=NH)—N($R^+$)$_2$, or —N($R^+$)S(O)$_2R^+$; wherein each $R^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of $R^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of $R^+$ (or any other variable similarly defined in the specification and claims herein), are taken together with their intervening atom(s) include, but are not limited to the following: a) two independent occurrences of $R^+$ (or any other variable similarly defined in the specification or claims herein) that are bound to the same atom and are taken together with that atom to form a ring, for example, N($R^+$)$_2$, where both occurrences of $R^+$ are taken together with the nitrogen atom to form a piperidin-1-yl, piperazin-1-yl, or morpholin-4-yl group; and b) two independent occurrences of $R^+$ (or any other variable similarly defined in the specification or claims herein) that are bound to different atoms and are taken together with both of those atoms to form a ring, for example where a phenyl group is substituted with two occurrences of

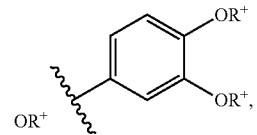

these two occurrences of $R^+$ are taken together with the oxygen atoms to which they are bound to form a fused 6-membered oxygen containing ring:

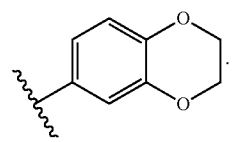 [SMILES: *c1ccc2c(c1)OCCO2]

It will be appreciated that a variety of other rings (e.g., spiro and bridged rings) can be formed when two independent occurrences of $R^+$ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the present disclosure. Unless otherwise stated, all tautomeric forms of the compounds disclosed herein are within the scope of the present disclosure. Additionally, unless otherwise stated, structures depicted herein are also meant to include compounds that differ only in the presence of one or more isotopically enriched atoms. For example, compounds having the present structures where there is a replacement of hydrogen by deuterium or tritium, or a replacement of a carbon by a $^{13}$C- or $^{14}$C-enriched carbon are within the scope of this disclosure. Such compounds are useful, as a nonlimiting example, as analytical tools or probes in biological assays.

It is to be understood that, when a disclosed compound has at least one chiral center, the present disclosure encompasses one enantiomer of inhibitor free from the corresponding optical isomer, racemic mixture of the inhibitor and mixtures enriched in one enantiomer relative to its corresponding optical isomer. When a mixture is enriched in one enantiomer relative to its optical isomers, the mixture contains, for example, an enantiomeric excess of at least 50%, 75%, 90%, 95% 99% or 99.5%.

The enantiomers of the present disclosure may be resolved by methods known to those skilled in the art; for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present disclosure encompasses a diastereomer free of other diastereomers, a pair of diastereomers free from other diastereomeric pairs, mixtures of diasteromers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s). When a mixture is enriched in one diastereomer or diastereomeric pair(s) relative to the other diastereomers or diastereomeric pair(s), the mixture is enriched with the depicted or referenced diastereomer or diasteromeric pair(s) relative to other diastereomers or diastereomeric pair(s) for the compound, for example, by a molar excess of at least 50%, 75%, 90%, 95%, 99% or 99.5%.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

For the avoidance of doubt, for compounds described herein, where the compound is a single diastereomer and the absolute configuration of the chiral centers is known the name of the compound reflects the assigned configuration at each stereochemical center; for example compound I-16: {(1R,2S,4R)-2-hydroxy-4-[(5-{[1-(2,3,6-trifluorobenzyl)-1H-pyrazol-3-yl]carbonyl}pyrimidin-4-yl)amino] cyclopentyl}methyl sulfamate. Where the compound is a single diastereomer and the absolute configuration is known at some of the chiral centers but is unknown at one chiral center, the name reflects the two possibilities separated by an "or"; for example compound I-10: [(1R,2S,4R)-4-{[5-({1-[(1R)-1-(3-ethynylphenyl)ethyl]-1H-pyrazol-3-yl}carbonyl)pyrimidin-4-yl]amino}-2-hydroxycyclopentyl] methyl sulfamate or [(1R,2S,4R)-4-{[5-({1-[(1S)-1-(3-ethynylphenyl)ethyl]-1H-pyrazol-3-yl}carbonyl)pyrimidin-4-yl]amino}-2-hydroxycyclopentyl]methyl sulfamate. Where the compound is a mixture of two or more diastereomers the name reflects the two or more possibilities by using "and" between the names of the individual diastereomers that make up the mixture; for example compound I-250: [(1R,2R,3R,4R)-4-({5-[(1-{[(2R)-5,5-dimethyltetrahydrofuran-2-yl]methyl}-1H-pyrrol-3-yl)carbonyl]pyrimidin-4-yl}amino)-3-fluoro-2-hydroxycyclopentyl]methyl sulfamate and [(1R,2R,3R,4R)-4-({5-[(1-{[(2S)-5,5-dimethyltetrahydrofuran-2-yl]methyl}-1H-pyrrol-3-yl)carbonyl]pyrimidin-4-yl}amino)-3-fluoro-2-hydroxycyclopentyl] methyl sulfamate.

In some embodiments, the compounds of formula (I) is represented by formula (II-a) or (II-b):

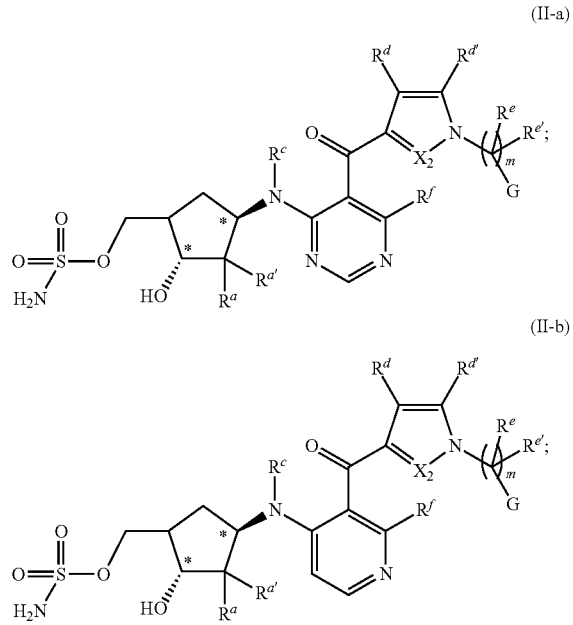

or a pharmaceutically acceptable salt thereof;
wherein $R^a$, $R^{a'}$, $R^c$, $R^f$, $X_2$, $R^d$, $R^{d'}$, $R^e$, $R^{e'}$, m, and G have the values described herein and stereochemical configurations depicted at asterisked positions indicate absolute stereochemistry. In some embodiments, the compound of formula (I) is represented by formula (II-a) wherein $R^a$, $R^{a'}$, $R^c$, $R^f$, $X_2$, $R^d$, $R^{d'}$, $R^e$, $R^{e'}$, m, and G have the values described herein and stereochemical configurations depicted at asterisked positions indicate absolute stereochemistry. In some embodiments, the compound of formula (I) is represented by formula (II-b) wherein $R^a$, $R^{a'}$, $R^c$, $R^f$, $X_2$, $R^d$, $R^{d'}$, $R^e$, $R^{e'}$, m, and G have the values described herein and stereochemical configurations depicted at asterisked positions indicate absolute stereochemistry.

In some embodiments, the compounds of formula (I) is represented by formula (III):

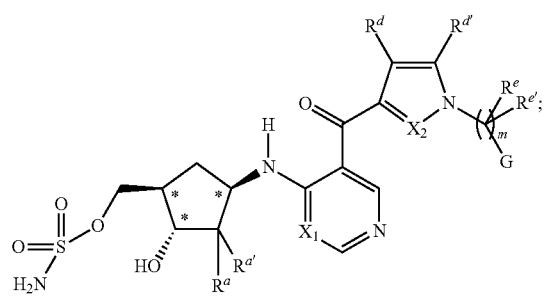

(III)

or a pharmaceutically acceptable salt thereof;

wherein $R^a$, $R^{a'}$, $X_1$, $X_2$, $R^d$, $R^{d'}$, $R^e$, $R^{e'}$, m, and G have the values described herein and stereochemical configurations depicted at asterisked positions indicate absolute stereochemistry.

In some embodiments, the compounds of formula (I) is represented by formula (III-a), (III-b), (III-c), or (III-d):

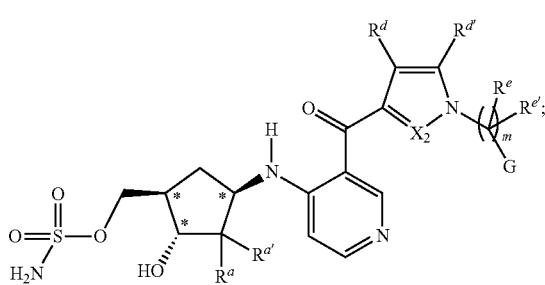

(III-a)

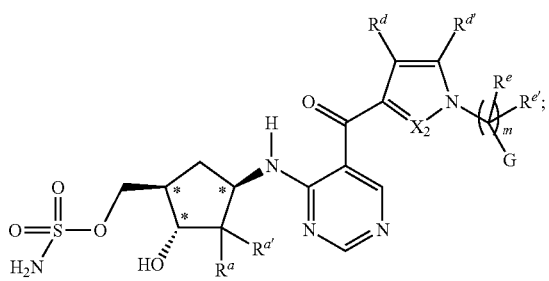

(III-b)

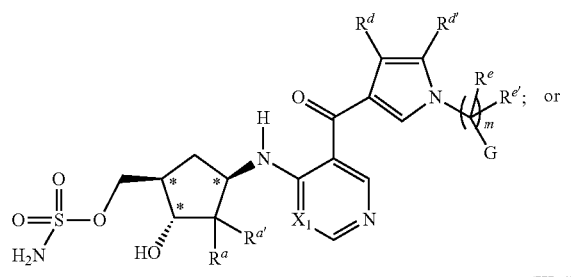

(III-c)

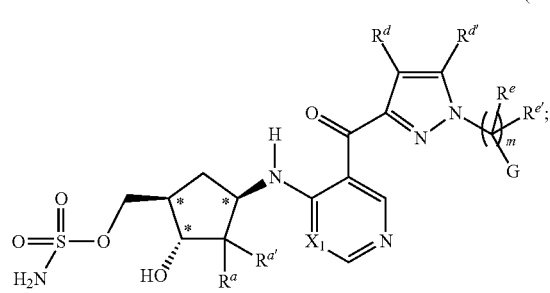

(III-d)

or a pharmaceutically acceptable salt thereof;

wherein $R^a$, $R^{a'}$, $X_1$, $X_2$, $R^d$, $R^{d'}$, $R^e$, $R^{e'}$, m, and G have the values described herein and stereochemical configurations depicted at asterisked positions indicate absolute stereochemistry. In some embodiments, the compound of formula (I) is represented by formula (III-a) wherein $R^a$, $R^{a'}$, $X_2$, $R^d$, $R^{d'}$, $R^e$, $R^{e'}$, m, and G have the values described herein and stereochemical configurations depicted at asterisked positions indicate absolute stereochemistry. In some embodiments, the compound of formula (I) is represented by formula (III-b) wherein $R^a$, $R^{a'}$, $X_2$, $R^d$, $R^{d'}$, $R^e$, $R^{e'}$, m, and G have the values described herein and stereochemical configurations depicted at asterisked positions indicate absolute stereochemistry. In some embodiments, the compound of formula (I) is represented by formula (III-c) wherein $R^a$, $R^{a'}$, $X_1$, $R^d$, $R^{d'}$, $R^e$, $R^{e'}$, m, and G have the values described herein and stereochemical configurations depicted at asterisked positions indicate absolute stereochemistry. In some embodiments, the compound of formula (I) is represented by formula (III-d) wherein $R^a$, $R^{a'}$, $X_1$, $R^d$, $R^{d'}$, $R^e$, $R^{e'}$, m, and G have the values described herein and stereochemical configurations depicted at asterisked positions indicate absolute stereochemistry.

In some embodiments, the compounds of formula (I) are represented by formula (IV-a), (IV-b), or (IV-c):

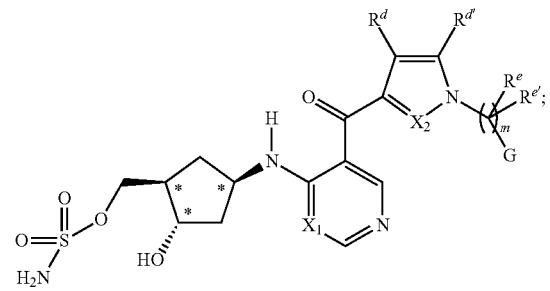

(IV-a)

-continued

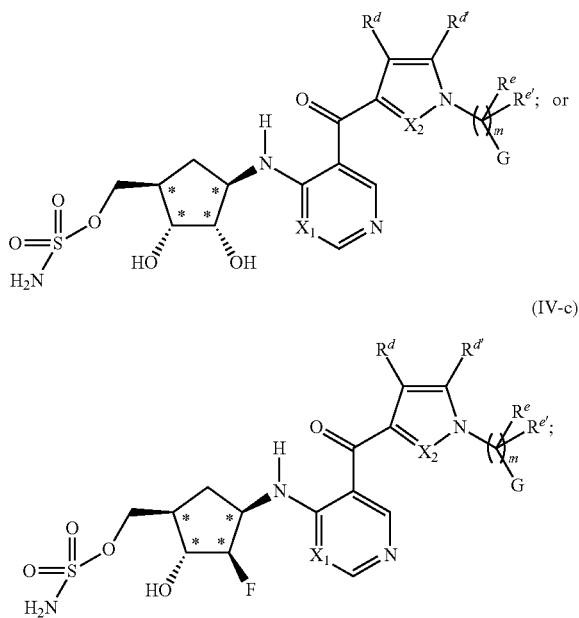

(IV-b)

(IV-c)

or a pharmaceutically acceptable salt thereof;
wherein $X_1$, $X_2$, $R^d$, $R^{d'}$, $R^e$, $R^{e'}$, m, and G have the values described herein and stereochemical configurations depicted at asterisked positions indicate absolute stereochemistry. In some embodiments, the compound of formula (I) is represented by formula (IV-a) wherein $X_1$, $X_2$, $R^d$, $R^{d'}$, $R^e$, $R^{e'}$, m, and G have the values described herein and stereochemical configurations depicted at asterisked positions indicate absolute stereochemistry. In some embodiments, the compound of formula (I) is represented by formula (IV-b) wherein X, $X_2$, $R^d$, $R^{d'}$, $R^e$, $R^{e'}$, m, and G have the values described herein and stereochemical configurations depicted at asterisked positions indicate absolute stereochemistry. In some embodiments, the compound of formula (I) is represented by formula (IV-c) wherein $X_1$, $X_2$, $R^d$, $R^{d'}$, $R^e$, $R^{e'}$, m, and G have the values described herein and stereochemical configurations depicted at asterisked positions indicate absolute stereochemistry.

The following values are described for any of formulas (I), (II), (II-a), (II-b), (III), (III-a), (III-b), (III-c), (III-d), (IV-a), (IV-b) or (IV-c).

In some embodiments, Y is —O—, —CH$_2$—, or —N(H)—. In some embodiments, Y is —O—. In some embodiments, Y is —CH$_2$—. In some embodiments, Y is —N(H)—.

In some embodiments, $R^a$ is hydrogen, fluoro, —NH$_2$, or —OH. In some embodiments, $R^a$ is hydrogen, fluoro or —OH. In some embodiments, $R^a$ is hydrogen or —OH. In some embodiments, $R^a$ is hydrogen. In some embodiments, $R^a$ is —OH.

In some embodiments, $R^{a'}$ is hydrogen or fluoro; provided that when $R^a$ is —NH$_2$ or —OH, $R^{a'}$ is hydrogen. In some embodiments, $R^{a'}$ is fluoro. In some embodiments, $R^{a'}$ is hydrogen.

In some embodiments, $R^a$ is hydrogen and $R^{a'}$ is hydrogen. In some embodiments, $R^a$ is fluoro and $R^{a'}$ is fluoro. In some embodiments, $R^a$ is —NH$_2$ and $R^{a'}$ is hydrogen. In some embodiments, $R^a$ is hydrogen and $R^{a'}$ is fluoro. In some embodiments, $R^a$ is —OH and $R^{a'}$ is hydrogen.

In some embodiments, $R^c$ is hydrogen or $C_{1-4}$ alkyl. In some embodiments, $R^c$ is hydrogen or methyl. In some embodiments, $R^c$ is hydrogen.

In some embodiments, $X_1$ is C(H), C(F) or N. In some embodiments, $X_1$ is C(H), or N, In some embodiments, $X_1$ is C(H). In some embodiments, $X_1$ is N.

In some embodiments, $X_2$ is C($R^d$) or N, wherein $R^d$ has the values described herein. In some embodiments, $X_2$ is N. In some embodiments, $X_2$ is C($R^d$), Wherein $R^d$ has the values described herein.

In some embodiments, each occurrence of $R^d$ is independently hydrogen, halogen, cyano, $C_{1-4}$ aliphatic, or $C_{1-4}$ fluoroaliphatic. In some embodiments, each occurrence of $R^d$ is independently hydrogen, chloro, bromo, fluoro, methyl, ethyl, or trifluoromethyl. In some embodiments, $R^d$ is hydrogen.

In some embodiments, $R^{d'}$ is hydrogen, halogen, cyano, $C_{1-4}$ aliphatic, $C_{1-4}$ fluoroaliphatic, or -T$_2$-R$^3$, wherein T$_2$ and R$^3$ have the values described herein. In some embodiments, $R^{d'}$ is hydrogen, chloro, bromo, fluoro, methyl, ethyl, trifluoromethyl, —CH$_2$—OR$^{3a}$, CH$_2$—N(H)R$^{3a}$, or —CH$_2$—C(O)—R$^{3b}$, wherein $R^{3a}$ and $R^{3b}$ have the values described herein. In some embodiments, $R^{d'}$ is hydrogen, chloro, bromo, fluoro, methyl, ethyl, trifluoromethyl, —CH$_2$—OH, —CH$_2$—OCH$_3$, —CH$_2$—N(H)CH$_3$, or —CH$_2$—C(O)—CH$_3$. In some embodiments, $R^{d'}$ is hydrogen, chloro, bromo, fluoro, methyl, ethyl, or trifluoromethyl. In some embodiments, $R^{d'}$ is hydrogen or methyl.

In some embodiments, T$_2$ is an optionally substituted $C_1$-$C_2$ alkylene chain. In some embodiments, T$_2$ is a $C_1$-$C_2$ alkylene chain optionally substituted with 0-3 independent occurrences of R$^{3c}$. In some embodiments, T$_2$ is —CH$_2$—CH$_2$—. In some embodiments, T$_2$ is —C(CH$_3$)$_2$—. In some embodiments, T$_2$ is —CH$_2$—.

In some embodiments, R$^3$ is —CN, —NO$_2$, —N(R$^{3a}$)$_2$, —OR$^{3a}$, —C(O)R$^{3b}$, —C(O)OR$^{3a}$, —C(O)N(R$^{3a}$)$_2$, or —S(O)$_2$N(R$^{3a}$)$_2$, wherein $R^{3a}$ and $R^{3b}$ have the values described herein. In some embodiments, R$^3$ is —N(R$^{3a}$)$_2$, —OR$^{3a}$, or —C(O)R$^{3b}$, wherein $R^{3a}$ and $R^{3b}$ have the values described herein. In some embodiments, R$^3$ is —N(R$^{3a}$)$_2$, wherein $R^{3a}$ has the values described herein. In some embodiments, R$^3$ is —OR$^{3a}$, wherein $R^{3a}$ has the values described herein. In some embodiments, R$^3$ is —C(O)R$^{3b}$, wherein $R^{3b}$ has the values described herein.

In some embodiments, each occurrence of $R^{3a}$ is independently hydrogen or $C_{1-4}$ alkyl. In some embodiments, each occurrence of $R^{3a}$ is independently hydrogen or methyl. In some embodiments, $R^{3a}$ is hydrogen. In some embodiments, $R^{3a}$ is methyl.

In some embodiments, $R^{3b}$ is $C_{1-4}$ alkyl. In some embodiments, $R^{3b}$ is methyl or ethyl. In some embodiments, $R^{3b}$ is methyl.

In some embodiments, each occurrence of $R^{3c}$ is independently $C_{1-4}$ alkyl. In some embodiments, each occurrence of $R^{3c}$ is independently methyl or ethyl. In some embodiments, $R^{3c}$ is methyl.

In some embodiments, $R^e$ is hydrogen or $C_{1-4}$ alkyl. In some embodiments, $R^e$ is hydrogen, methyl, or ethyl. In some embodiments, $R^e$ is hydrogen.

In some embodiments, $R^{e'}$ is hydrogen or $C_{1-4}$ alkyl. In some embodiments, $R^{e'}$ is hydrogen, methyl or ethyl. In some embodiments, $R^{e'}$ is hydrogen.

In some embodiments, $R^e$ is taken together with $R^{e'}$ to form a 3-6 membered cycloaliphatic ring. In some embodiments, $R^e$ is taken together with $R^{e'}$ to form a cyclopropyl, cyclobutyl, cyclopentyl, or cyclohexyl ring. In some embodiments, $R^e$ is taken together with $R^{e'}$ to form a cyclopropyl ring.

In some embodiments, m is 0-2. In some embodiments, m is 1-2. In some embodiments, m is 0. In some embodiments, m is 1. In some embodiments, m is 2.

In some embodiments, $R^f$ is hydrogen, chloro or $C_{1-4}$ alkyl. In some embodiments, $R^f$ is hydrogen, chloro, methyl, or ethyl. In some embodiments, $R^f$ is hydrogen.

In some embodiments, G is $R^1$ or $-L_1-R^1$. In some embodiments, G is $R^1$. In some embodiments, G is $-L_1-R^1$.

In some embodiments, $L_1$ is

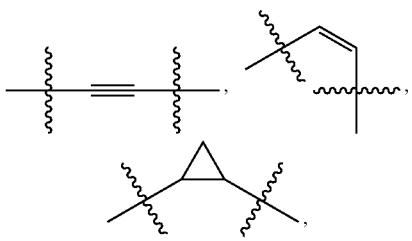

—C(O)—, or —SO$_2$—; provided that when $L_1$ is —SO$_2$—. m is zero. In some embodiments, $L_1$ is

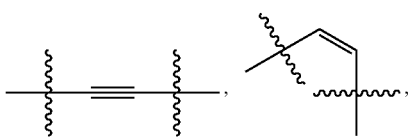

or —C(O)—. In some embodiments, $L_1$ is

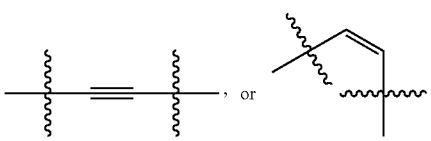

In some embodiments, $R^1$ is $C_{1-6}$ aliphatic, 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur, wherein $R^1$ is unsubstituted or substituted with n occurrences of $R^2$, wherein n and $R^2$ have the values described herein. In some embodiments, $R^1$ is 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur, wherein $R^1$ is optionally substituted with n occurrences of $R^2$, wherein n and $R^2$ have the values described herein.

In some embodiments, $R^1$ is furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, imidazopyridyl, indolyl, isoindolyl, indazolyl, benzimidazolyl, benzthiazolyl, benzothienyl, benzofuranyl, benzoxazolyl, benzodioxolyl, benzthiadiazolyl, 2,3-dihydrobenzofuranyl, 4H-furo[3,2-b]pyrrolyl, pyrazolopyrimidinyl, purinyl, quinolyl, isoquinolyl, tetrahydroquinolinyl, tetrahydronaphthyridinyl, tetrahydroisoquinolinyl, cinnolinyl, phthalazinyl, quinazolinyl, quinoxalinyl, naphthyridinyl, pteridinyl, tetrahydrofuranyl, tetrahydropyranyl, dihydropyranyl, tetrahydrothienyl, indanyl, tetrahydroindazolyl, pyrrolidinyl, pyrrolidonyl, piperidinyl, pyrrolinyl, decahydroquinolinyl, oxazolidinyl, piperazinyl, dioxanyl, diazepinyl, oxazepinyl, thiazepinyl, morpholinyl, thiomorpholinyl, quinuclidinyl, phenanthridinyl, tetrahydronaphthyl, oxodihydropyridyl, indolinyl, benzodioxanyl, chromanyl, oxetanyl, cyclopropyl, cyclobutyl, cyclopentyl, cyclohexyl, cycloheptyl, cyclooctyl, cyclopentenyl, cyclohexenyl, cycloheptenyl, cyclooctenyl, bicycloheptanyl, azabicyclooctanyl, oxabicyclooctanyl, bicyclononyl, bicyclooctanyl, or adamantyl, wherein $R^1$ is unsubstituted or substituted with n occurrences of $R^2$, wherein n and $R^2$ have the values described herein. In some embodiments, $R^1$ is furanyl, thienyl, phenyl, naphthyl, pyridyl, benzothienyl, benzofuranyl, cyclohexyl, or cyclohexenyl, wherein $R^1$ is unsubstituted or substituted with n occurrences of $R^2$, wherein n and $R^2$ have the values described herein.

In some embodiments, $R^1$ is:

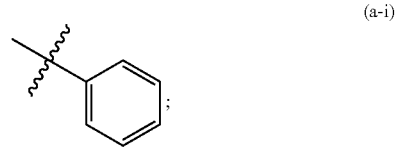
(a-i)

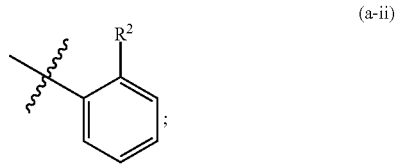
(a-ii)

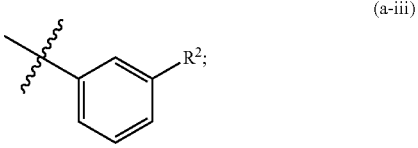
(a-iii)

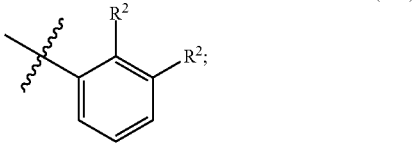
(a-iv)

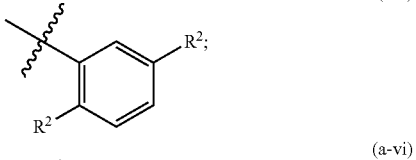
(a-v)

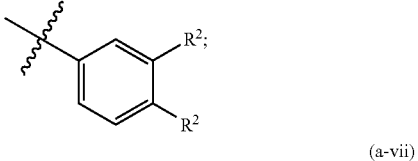
(a-vi)

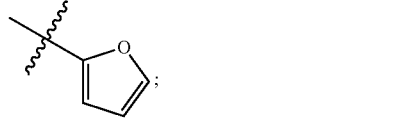
(a-vii)

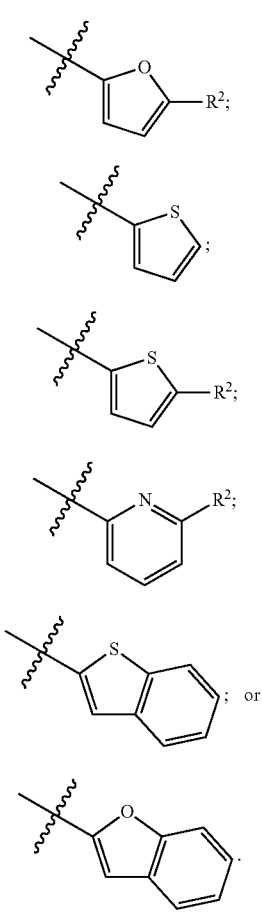

wherein R² has the values described herein.

In some embodiments, R¹ is (a-i), (a-iii), (a-iv), (a-v), (a-viii), or (a-xi), wherein R² has the values described herein.

In some embodiments, n is 1-5. In some embodiments, n is 1-4. In some embodiments, n is 1-3. In some embodiments, n is 1-2. In some embodiments, n is 1.

In some embodiments, each occurrence of R² is independently —R$^{2a}$, -T$_1$-R$^{2d}$, -T$_1$-R$^{2a}$, or —V$_1$-T$_1$-R$^{2d}$, wherein R$^{2a}$, T$_1$, R$^{2d}$, V$_1$ and T$_1$ have the values described herein. In some embodiments, each occurrence of R² is independently —R$^{2a}$ or -T$_1$-R$^{2a}$, wherein R$^{2a}$ and T$_1$ have the values described herein. In some embodiments, each occurrence of R² is independently —R$^{2a}$, wherein R$^{2a}$ has the values described herein. In some embodiments, each occurrence of R² is independently halogen, —R$^{2c}$, —N(R$^{2b}$)$_2$, —OR$^{2b}$, —SR$^{2c}$, C$_{1-6}$ aliphatic or C$_{1-6}$ fluoroaliphatic, wherein R$^{2b}$ and R$^{2c}$ have the values described herein.

In some embodiments, each occurrence of R² is independently chloro, bromo, fluoro, iodo, methyl, ethyl, propyl, tert-butyl, methoxy, ethoxy, isopropoxy, tert-butoxy, difluoromethyl, trifluoromethyl, difluoromethoxy, trifluoromethoxy, trifluoromethylthio, dimethylamino, diethylamino, ethyne, cyclopropyl, or phenyl. In some embodiments, each occurrence of R² is independently chloro, bromo, fluoro, iodo, methyl, ethyl, difluoromethoxy, trifluoromethoxy, ethyne, cyclopropyl, or phenyl. In some embodiments, each occurrence of R² is independently chloro, bromo, iodo, or methyl.

In some embodiments, each occurrence of R$^{2a}$ is independently halogen, —CN, —NO$_2$, —R$^{2c}$, —N(R$^{2b}$)$_2$, —OR$^{2b}$, —SR$^{2c}$, —S(O)R$^{2c}$, —S(O)$_2$R$^{2c}$, —C(O)R$^{2b}$, —C(O)OR$^{2b}$, —C(O)N(R$^{2b}$)$_2$, —S(O)$_2$N(R$^{2b}$)$_2$, —OC(O)N (R$^{2b}$)$_2$, —N(R$^{2e}$)C(O)R$^{2b}$, —N(R$^{2e}$)SO$_2$R$^{2c}$, —N(R$^{2e}$)C(O) OR$^{2b}$, —N(R$^{2e}$)C(O)N(R$^{2b}$), —N(R$^{2e}$)SO$_2$N(R$^{2b}$)$_2$, or Si(R$^{2c}$)$_3$, or an optionally substituted C$_1$-C$_6$ aliphatic or C$_1$-C$_6$ haloaliphatic, wherein R$^{2b}$, R$^{2c}$, and R$^{2e}$ have the values described herein. In some embodiments, each occurrence of R$^{2a}$ is independently halogen, —R$^{2c}$, —N(R$^{2b}$)$_2$, —N(R$^{2e}$)C(O)R$^{2b}$, —OR$^{2b}$, —SR$^{2c}$, —S(O)R$^{2c}$, —S(O)$_2$ R$^{2c}$, or an optionally substituted C$_{1-6}$ aliphatic, or C$_{1-6}$ fluoroaliphatic, wherein R$^{2b}$ and R$^{2c}$ have the values described herein. In some embodiments, each occurrence of R$^{2a}$ is independently halogen, —R$^{2e}$, —N(R$^{2b}$)$_2$, —OR$^{2b}$, —SR$^{2c}$, C$_{1-6}$ aliphatic, or C$_{1-6}$ fluoroaliphatic, wherein R$^{2b}$ and R$^{2c}$ have the values described herein. In some embodiments, each occurrence of R$^{2a}$ is independently chloro, bromo, fluoro, iodo, cyano, methyl, ethyl, propyl, isopropyl, tert-butyl, methoxy, ethoxy, isopropoxy, tert-butoxy, difluoromethyl, trifluoromethyl, difluoromethoxy, trifluoromethoxy, trifluoromethylthio, trimethylsilyl, dimethylamino, diethylamino, 2-methoxy 2-methylpropyl, 2-hydroxy 2-methyl propyl, or ethyne. In some embodiments, each occurrence of R$^{2a}$ is independently chloro, bromo, fluoro, iodo, methyl, ethyl, propyl, tert-butyl, methoxy, ethoxy, isopropoxy, tert-butoxy, difluoromethyl, trifluoromethyl, difluoromethoxy, trifluoromethoxy, trifluoromethylthio, dimethylamino, diethylamino, or ethyne. In some embodiments, each occurrence of R$^{2a}$ is independently chloro, bromo, fluoro, iodo, methyl, ethyl, difluoromethyl, trifluoromethyl, difluoromethoxy, trifluoromethoxy, or ethyne.

In some embodiments, each occurrence of R$^{2b}$ is independently hydrogen or an optionally substituted group selected from C$_1$-C$_6$ aliphatic, C$_1$-C$_6$ haloaliphatic, 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur, or two occurrences of R$^{2b}$, taken together with a nitrogen atom to which they are bound, form an optionally substituted 4- to -7-membered heterocyclyl ring having 0-1 additional heteroatoms selected from nitrogen, oxygen, and sulfur. In some embodiments, each occurrence of R$^{2b}$ is independently hydrogen, C$_{1-6}$ aliphatic or C$_{1-6}$ fluoroaliphatic. In some embodiments, each occurrence of R$^{2b}$ is independently C$_{1-6}$ aliphatic or C$_{1-6}$ fluoroaliphatic. In some embodiments, each occurrence of R$^{2b}$ is independently optionally substituted phenyl. In some embodiments, each occurrence of R$^{2b}$ is independently methyl, ethyl, vinyl, phenyl, 4-fluorophenyl, —CH$_2$Cl, difluoromethyl, or trifluoromethyl.

In some embodiments, each occurrence of R$^{2c}$ is independently an optionally substituted group selected from C$_1$-C$_6$ aliphatic, C$_1$-C$_6$ haloaliphatic, 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur. In some embodiments, each occurrence of R$^{2c}$ is independently methyl, ethyl, propyl, isopropyl, tert-butyl, vinyl, difluoromethyl, trifluoromethyl, cyclopropyl, cyclobutyl, cyclopentyl, cyclohexyl, phenyl, morpholinyl or piperazinyl. In some embodiments, each occurrence of R$^{2c}$ is independently cyclopropyl or phenyl.

In some embodiment, each occurrence of $R^{2d}$ is independently hydrogen or an optionally substituted group selected from 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur.

In some embodiments, each occurrence of $R^{2e}$ is independently hydrogen or an optionally substituted $C_{1-6}$ aliphatic group. In some embodiments, each occurrence of $R^{2e}$ is independently hydrogen or methyl.

In some embodiments, each occurrence of $V_1$ is independently —$N(R^{2e})$—, —O—, —S—, —S(O)—, —S(O)$_2$—, —C(O)—, —C(O)O—, —C(O)N($R^{2e}$)—, —S(O)$_2$N($R^{2e}$)—, —OC(O)N($R^{2e}$)—, —N($R^{2e}$)C(O)—, —N($R^{2e}$)SO$_2$—, —N($R^{2e}$)C(O)O—, —N($R^{2e}$)C(O)N($R^{2e}$)—, —N($R^{2e}$)SO$_2$N($R^{2e}$)—, —OC(O)—, or —C(O)N($R^{2e}$)—O—, wherein $R^{2e}$ has the values described herein.

In some embodiments, each occurrence of $T_1$ is an optionally substituted $C_1$-$C_6$ alkylene chain wherein the alkylene chain optionally is interrupted by —N($R^4$)—, —O—, —S—, —S(O)—, —S(O)$_2$—, —C(O)—, —C(O)O—, —C(O)N($R^4$)—, —S(O)$_2$N($R^4$)—, —OC(O)N($R^4$)—, —N($R^4$)C(O)—, —N($R^4$)SO$_2$—, —N($R^4$)C(O)O—, —N($R^4$)C(O)N($R^4$)—, —N($R^4$)S(O)$_2$N($R^4$)—, —OC(O)—, or —C(O)N($R^4$)—O— or wherein $T_1$ or a portion thereof optionally forms part of an optionally substituted 3- to -7 membered cycloaliphatic or heterocyclyl ring, wherein $R^4$ is hydrogen or an optionally substituted $C_{1-4}$ aliphatic group.

In some embodiments, the compounds of formula (I) are represented by formula (V):

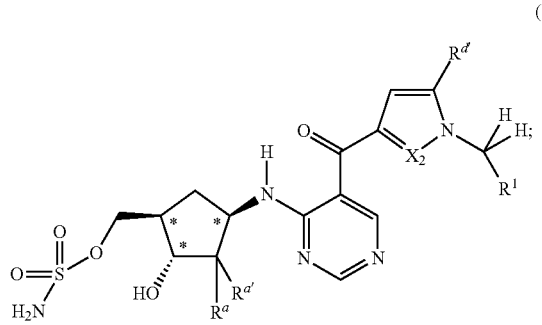

(V)

or a pharmaceutically acceptable salt thereof;
wherein:
stereochemical configurations depicted at asterisked positions indicate absolute stereochemistry;
$R^a$ is hydrogen and $R^{a'}$ is hydrogen; or $R^a$ is hydrogen and $R^{a'}$ is fluoro; or $R^a$ is OH and $R^{a'}$ is hydrogen;
$X_2$ is C($R^d$) or N;
$R^{d'}$ is hydrogen, chloro, bromo, fluoro, methyl, ethyl, or trifluoromethyl;
$R^1$ is furanyl, thienyl, phenyl, naphthyl, pyridyl, benzothienyl, benzofuranyl, cyclohexyl, or cyclohexenyl, wherein $R^1$ is unsubstituted or substituted with n occurrences of $R^2$;
n is 1-2; and
each occurrence of $R^2$ is independently halogen, —$R^{2c}$, —N($R^{2b}$)$_2$, —OR$^{2b}$, —SR$^{2c}$, $C_{1-6}$ aliphatic or $C_{1-6}$ fluoroaliphatic;
wherein $R^{2b}$ and $R^{2c}$ have the values described herein.

In some embodiments, the compounds of formula (I) are represented by formula (VI-a):

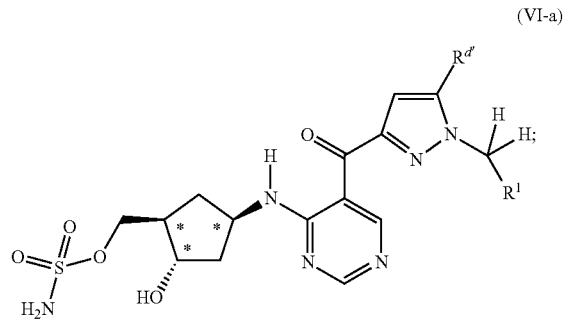

(VI-a)

or a pharmaceutically acceptable salt thereof;
wherein:
stereochemical configurations depicted at asterisked positions indicate absolute stereochemistry;
$R^{d'}$ is hydrogen, chloro, bromo, fluoro, methyl, ethyl, or trifluoromethyl;
$R^1$ is furanyl, thienyl, phenyl, naphthyl, pyridyl, benzothienyl, benzofuranyl, cyclohexyl, or cyclohexenyl, wherein $R^1$ is unsubstituted or substituted with n occurrences of $R^2$;
n is 1-2; and
each occurrence of $R^2$ is independently halogen, —$R^{2c}$, —N($R^{2b}$)$_2$, —OR$^{2b}$, —SR$^{2c}$, $C_{1-6}$ aliphatic or $C_{1-6}$ fluoroaliphatic;
wherein $R^{2b}$ and $R^{2c}$ have the values described herein.

In some such embodiments described directly above:
each occurrence of $R^2$ is independently chloro, bromo, fluoro, iodo, methyl, ethyl, difluoromethoxy, trifluoromethoxy, ethyne, cyclopropyl, or phenyl.

In some such embodiments described directly above:
$R^{d'}$ is hydrogen or methyl;
$R^1$ is (a-i), (a-iii), (a-iv), (a-v), (a-viii), or (a-xi); and
each occurrence of $R^2$ is independently chloro, bromo, iodo, or methyl.

In some embodiments, the compounds of formula (I) are represented by formula (VI-b):

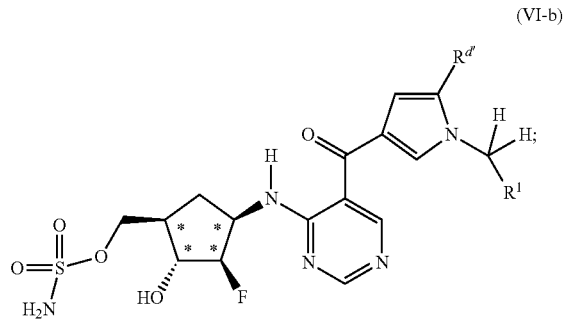

(VI-b)

or a pharmaceutically acceptable salt thereof;
wherein:
stereochemical configurations depicted at asterisked positions indicate absolute stereochemistry;
$R^{d'}$ is hydrogen, chloro, bromo, fluoro, methyl, ethyl, or trifluoromethyl;

R¹ is furanyl, thienyl, phenyl, naphthyl, pyridyl, benzothienyl, benzofuranyl, cyclohexyl, or cyclohexenyl, wherein R¹ is unsubstituted or substituted with n occurrences of R²;

n is 1-2; and each occurrence of R² is independently halogen, —R$^{2c}$, —N(R$^{2b}$)$_2$, —OR$^{2b}$, —SR$^{2c}$, C$_{1-6}$ aliphatic or C$_{1-6}$ fluoroaliphatic;

wherein R$^{2b}$ and R$^{2c}$ have the values described herein.

In some such embodiments described directly above:

each occurrence of R² is independently chloro, bromo, fluoro, iodo, methyl, ethyl, difluoromethoxy, trifluoromethoxy, ethyne, cyclopropyl, or phenyl.

In some such embodiments described directly above:

R$^{a'}$ is hydrogen or methyl;

R¹ is (a-i), (a-iii), (a-iv), (a-v), (a-viii), or (a-xi); and each occurrence of R² is independently chloro, bromo, iodo, or methyl.

wherein R$^{2b}$ and R$^{2c}$ have the values described herein.

Representative examples of the compounds of formula (I) are shown below in Table 1.

25
-continued
I-7
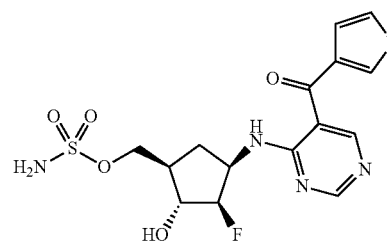
I-8
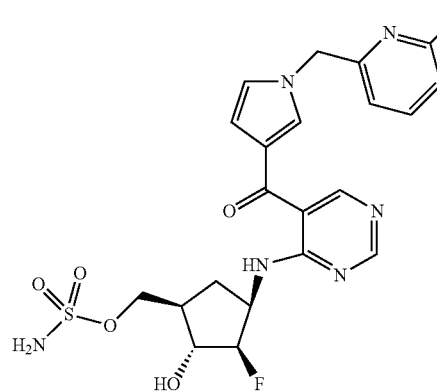
I-9
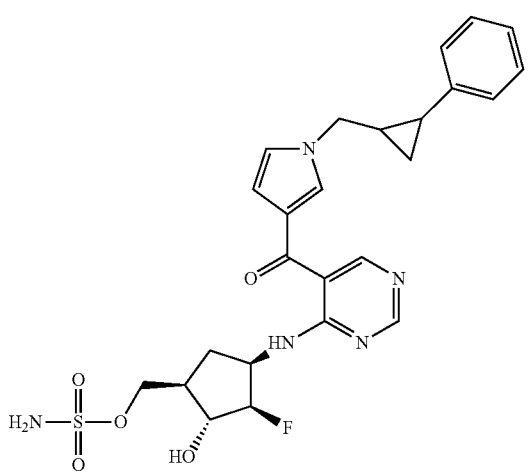
I-10
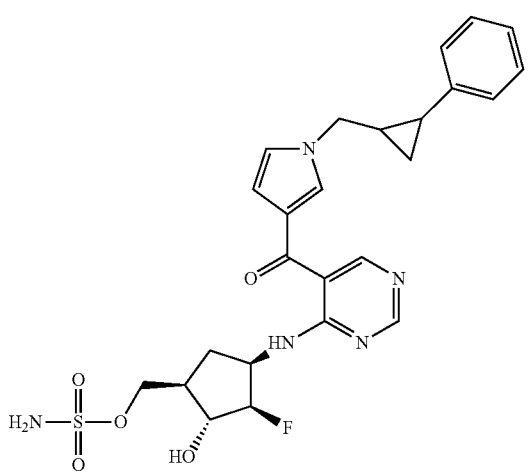
26
-continued
I-11
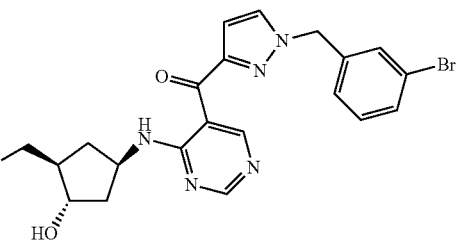
I-12
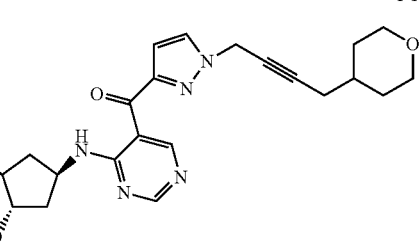
I-13
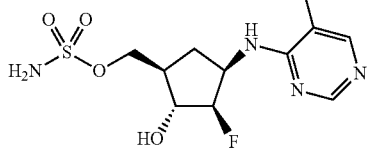
I-14
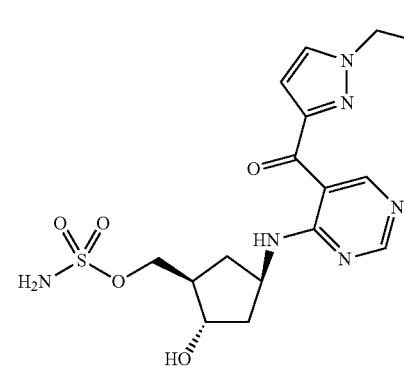
I-15
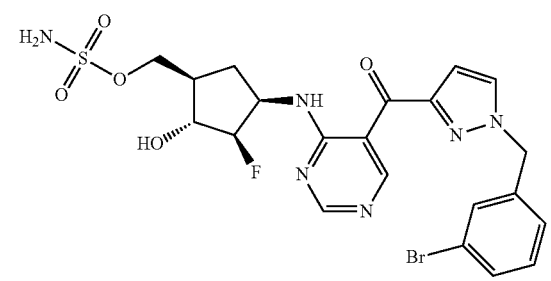

I-16
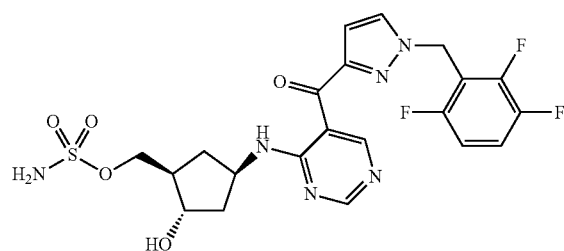
I-17
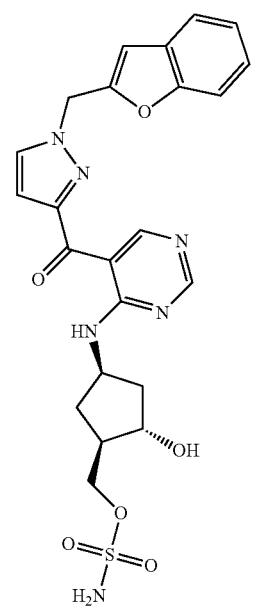
I-18
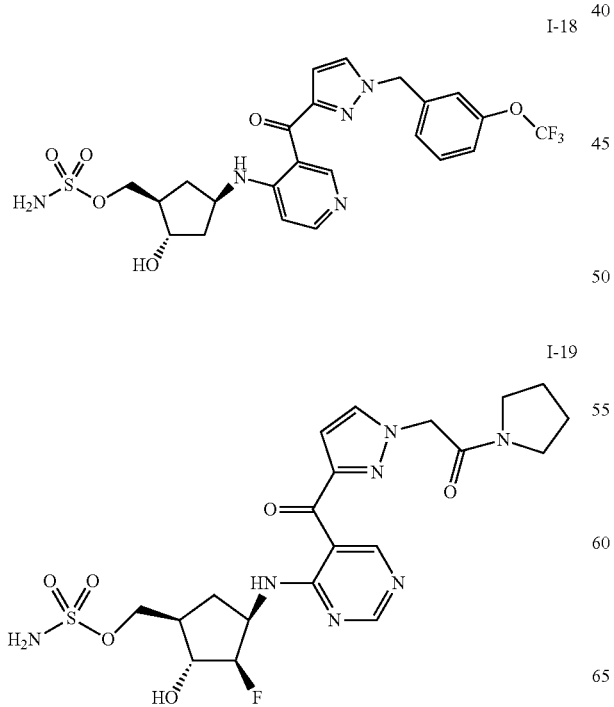
I-19
I-20
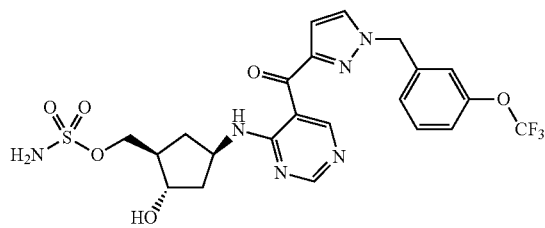
I-21
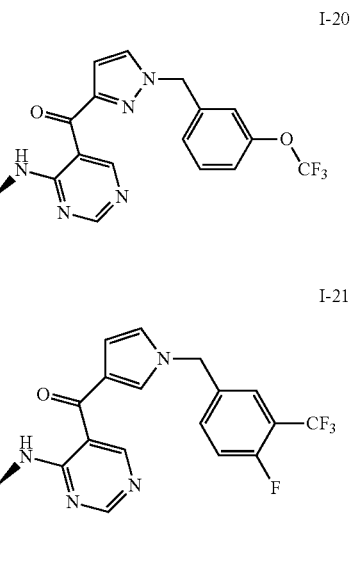
I-22
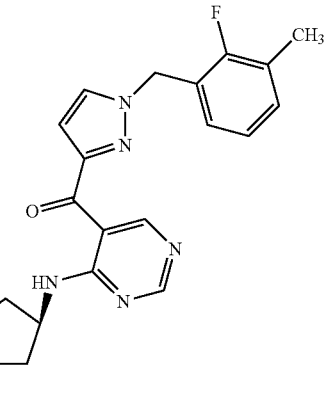
I-23
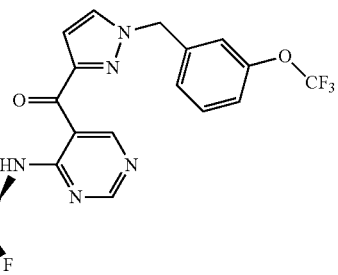
I-24
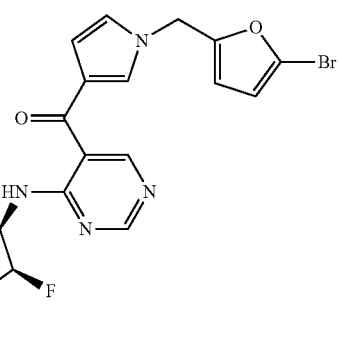

I-25
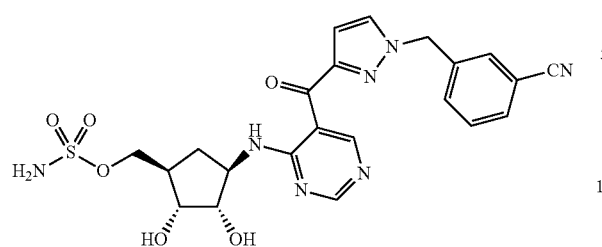
I-26
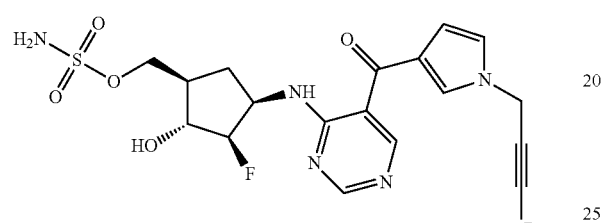
I-27
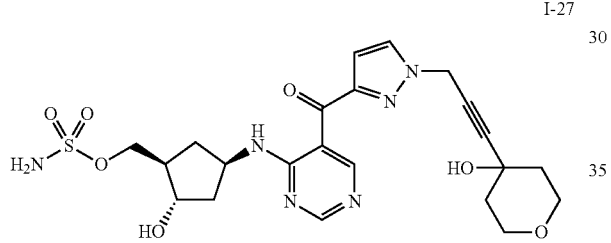
I-28
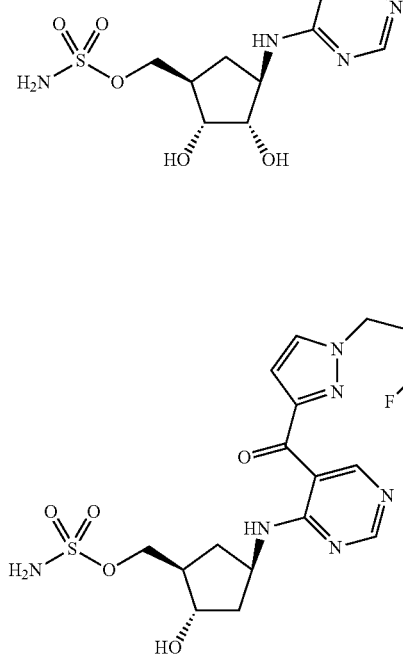
I-29
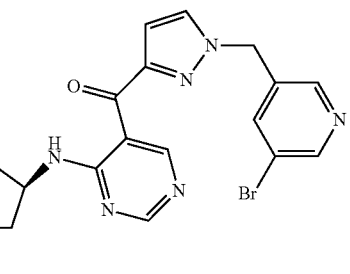
I-30
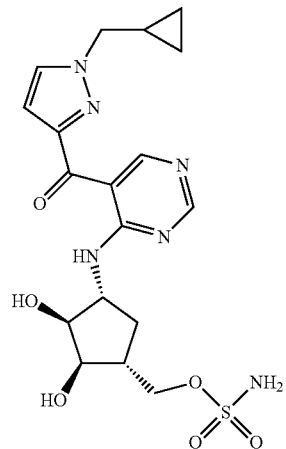
I-31
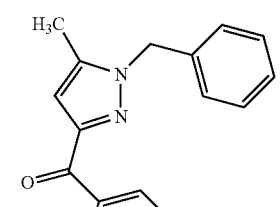
I-32

-continued
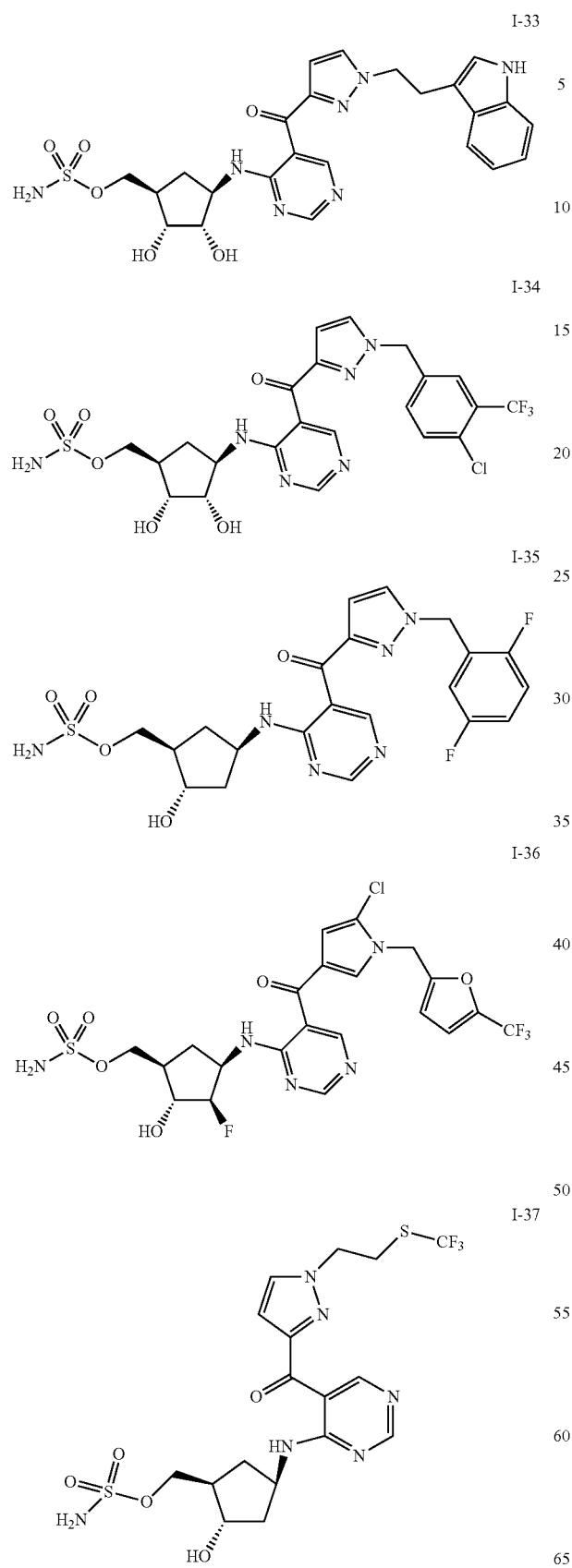
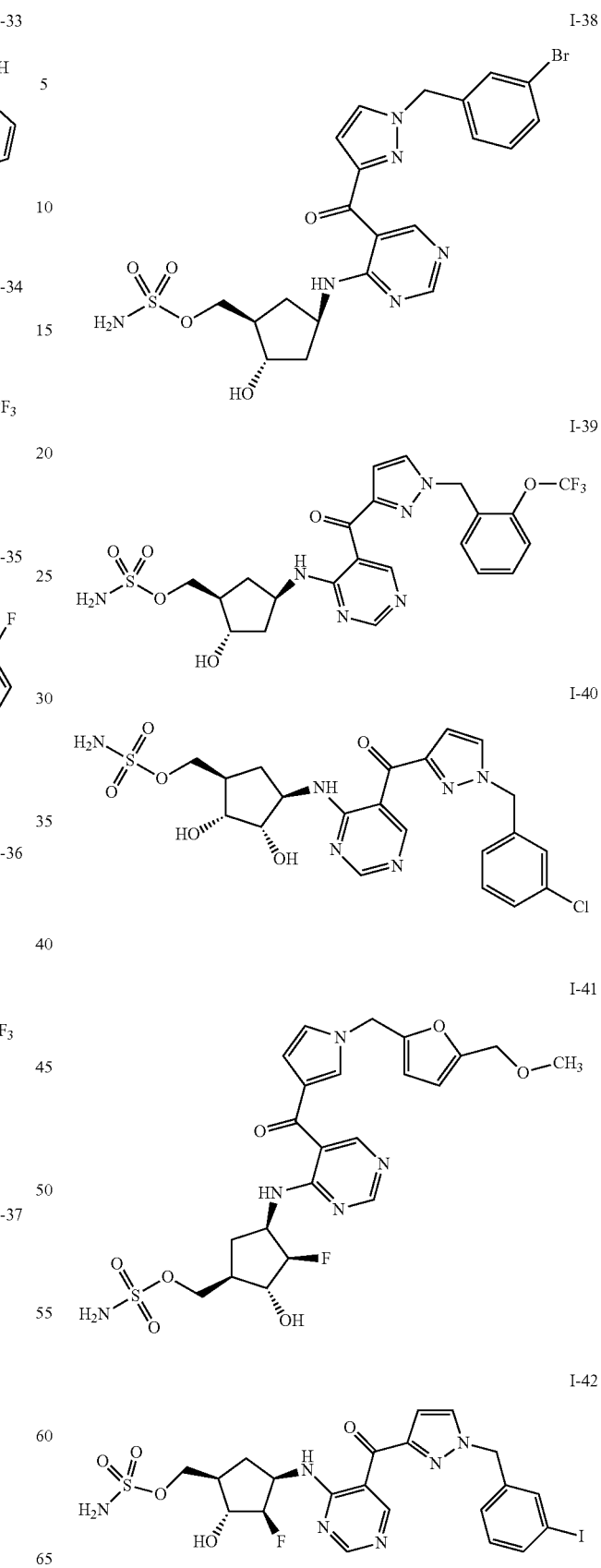

I-43
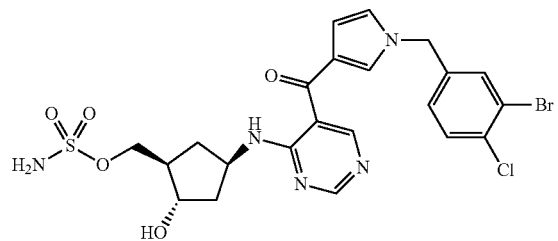
I-44
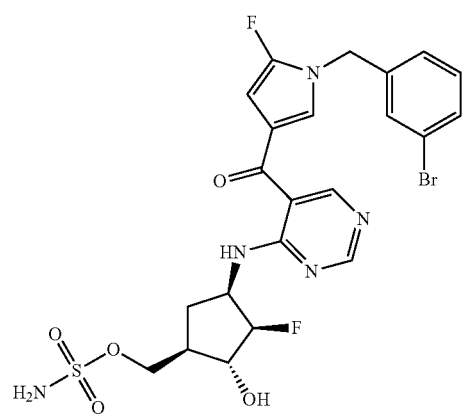
I-45
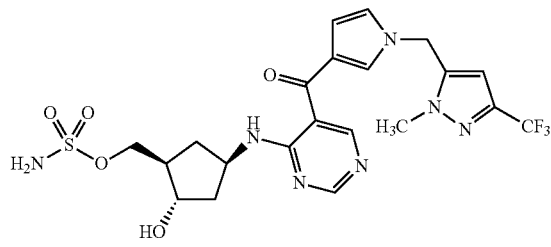
I-46
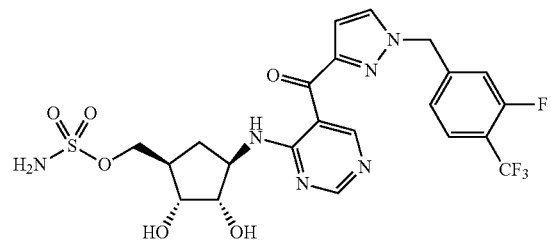
I-47
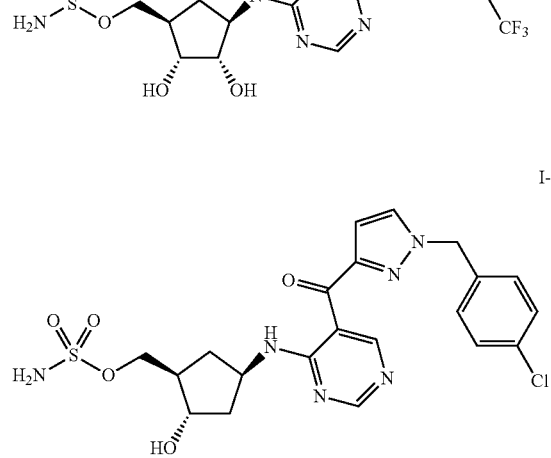
I-48
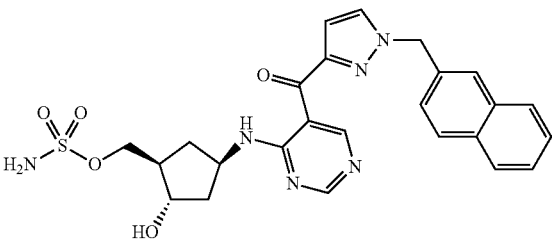
I-49
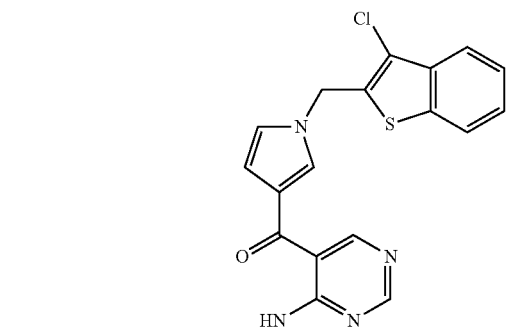
I-50
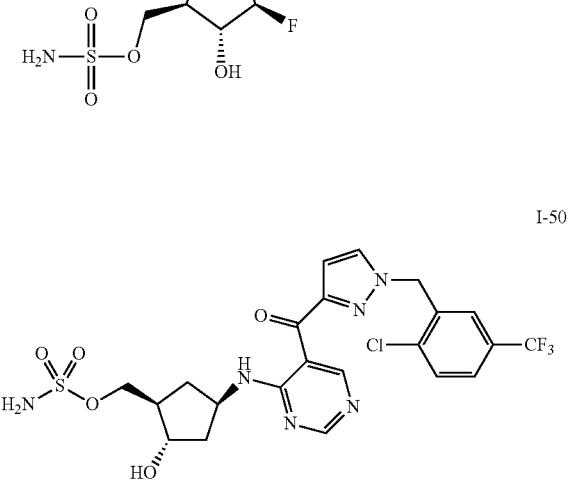
I-51
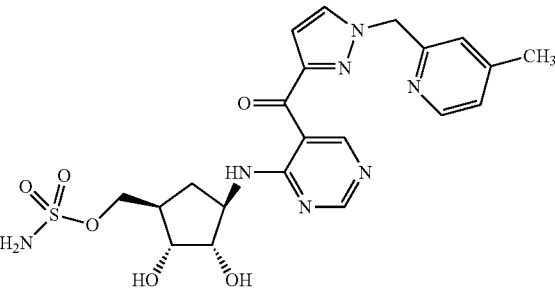

I-52
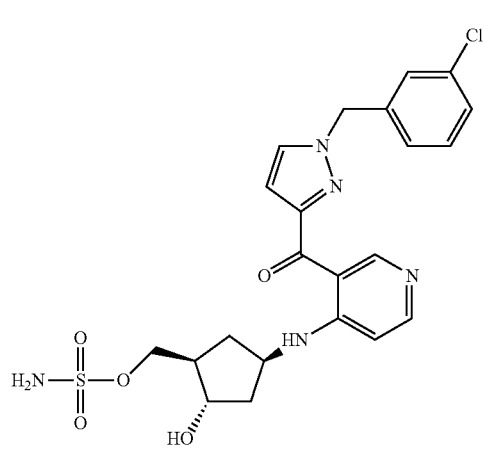
I-53
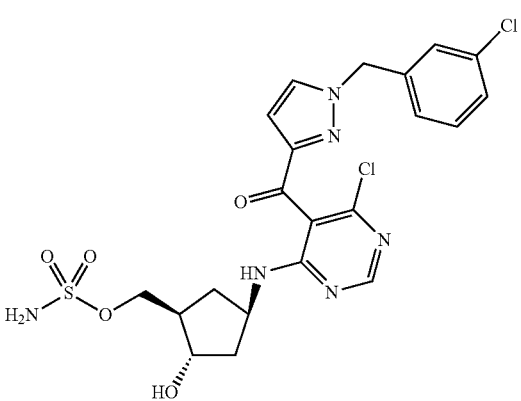
I-54
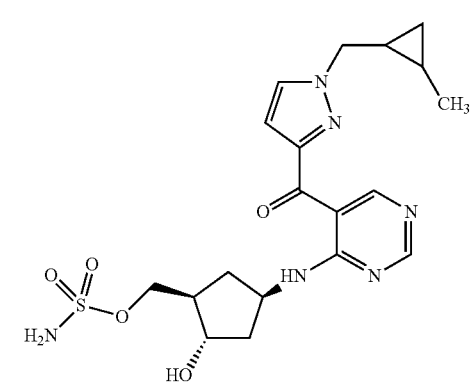
I-55
I-56
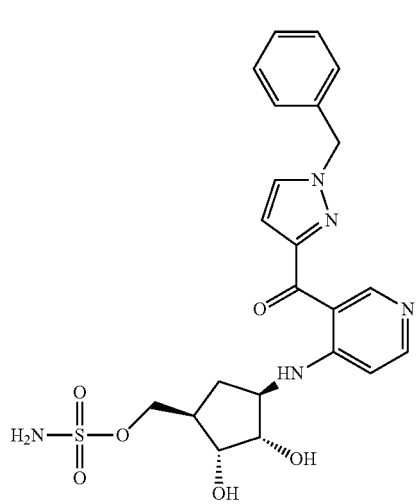
I-57
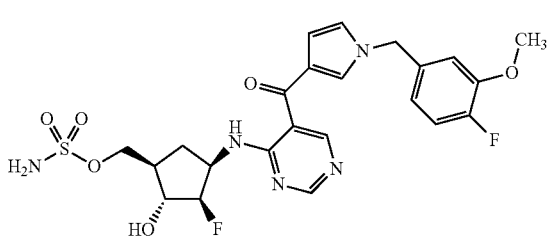
I-58
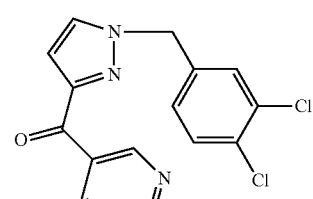
I-59
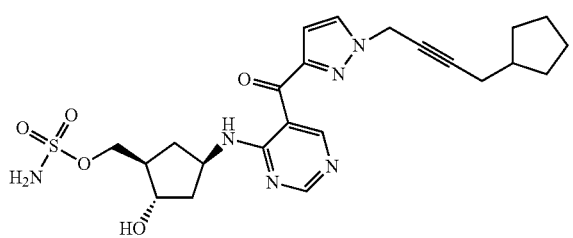

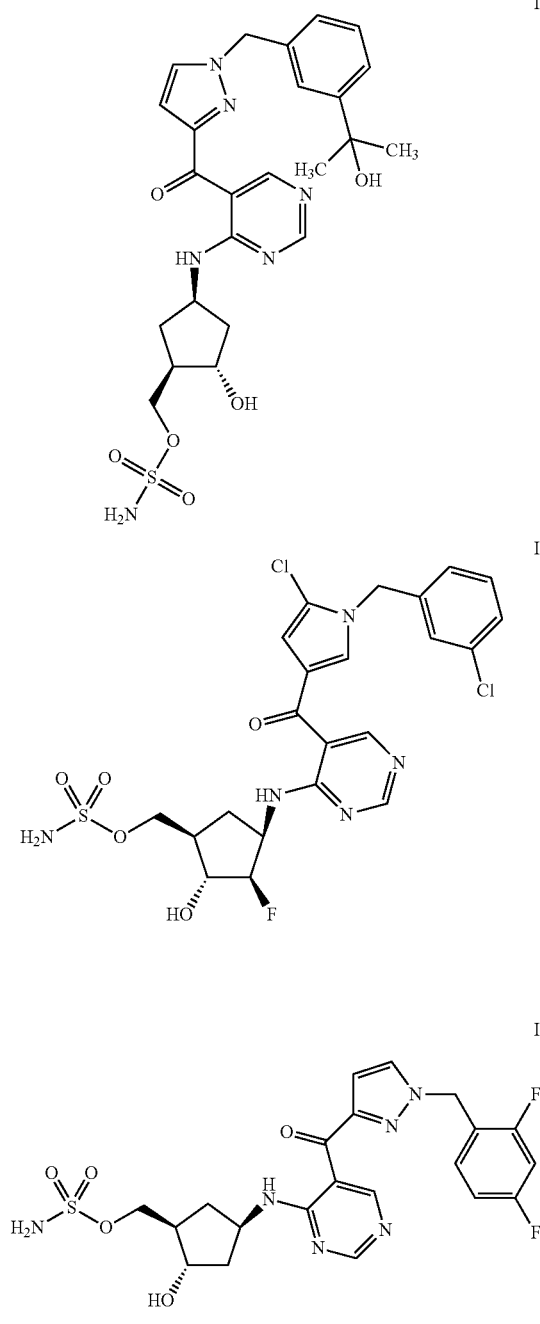
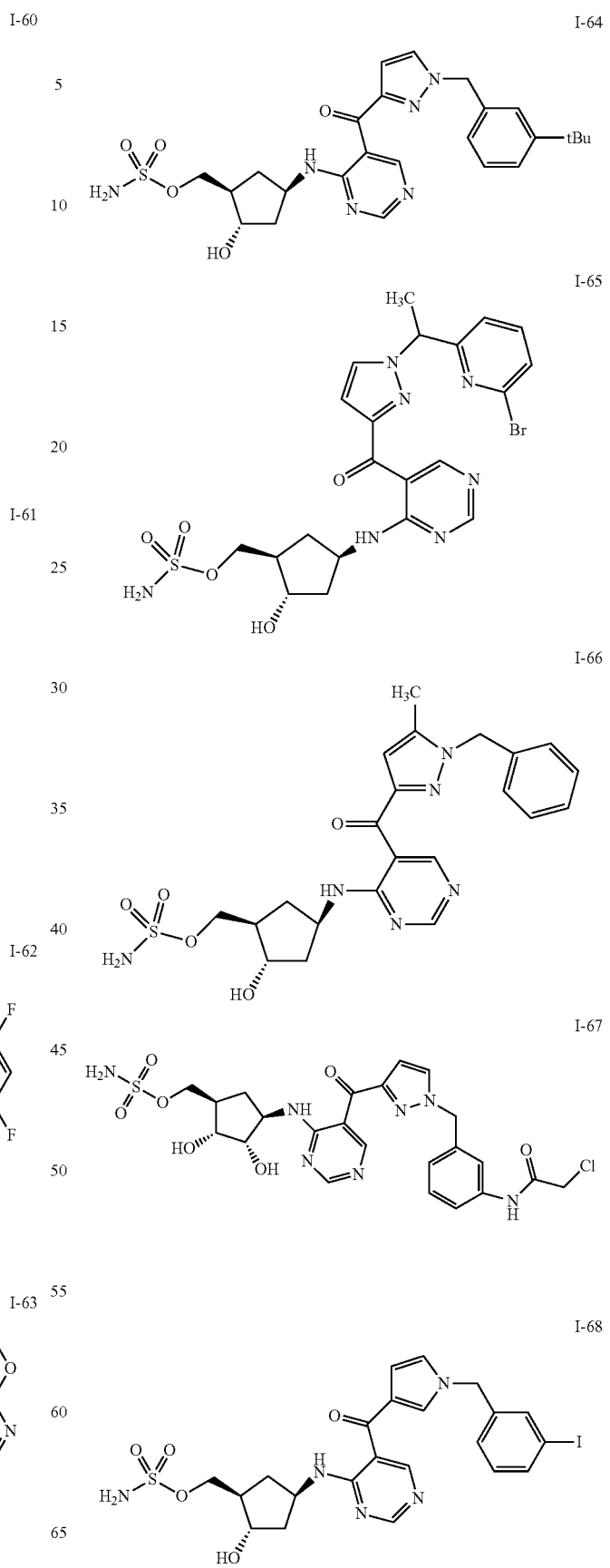

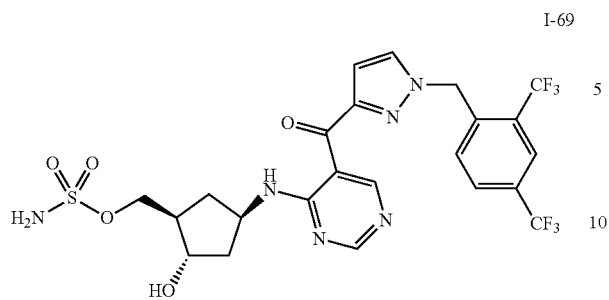
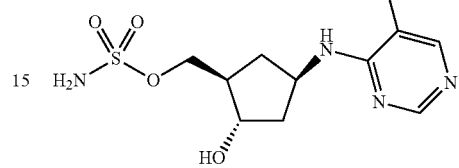
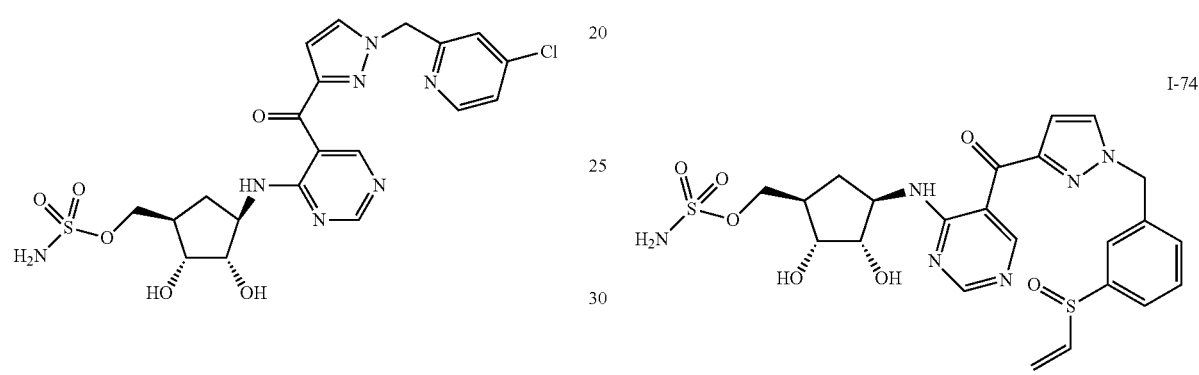
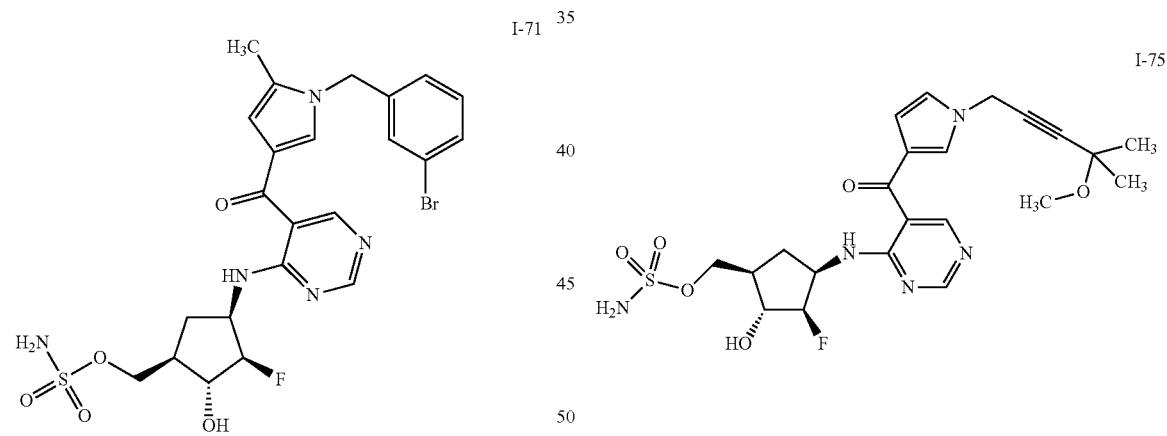
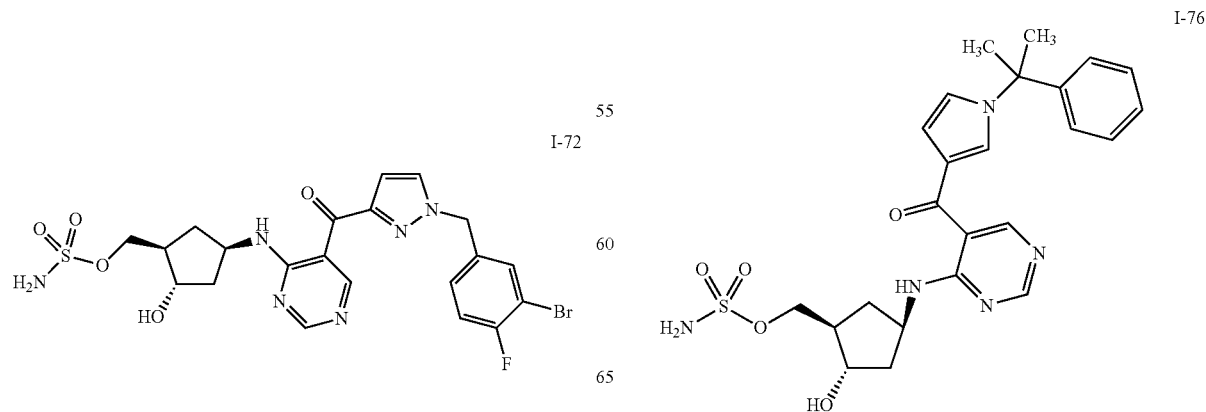

I-77
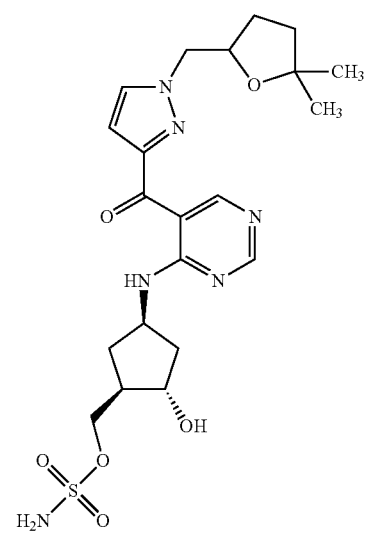
I-78
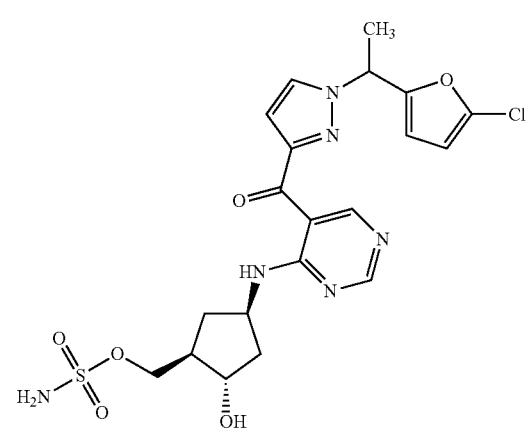
I-79
I-80
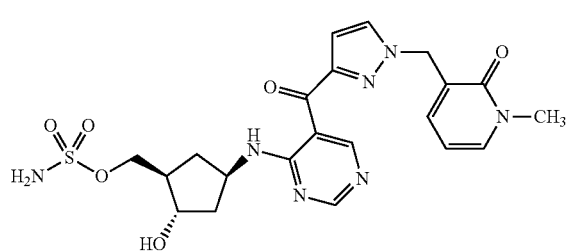
I-81
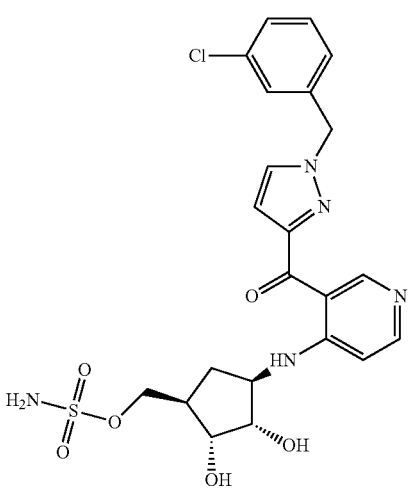
I-82
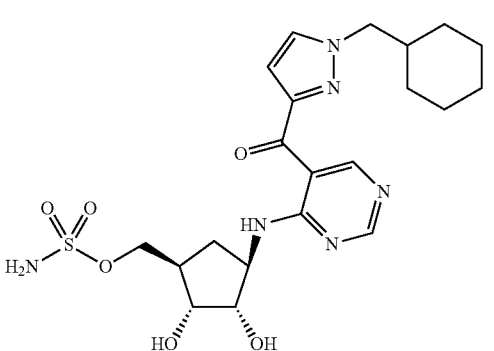
I-83
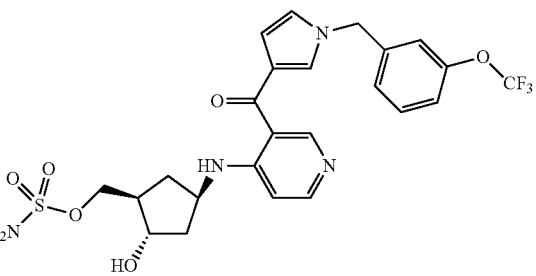
I-84

I-85
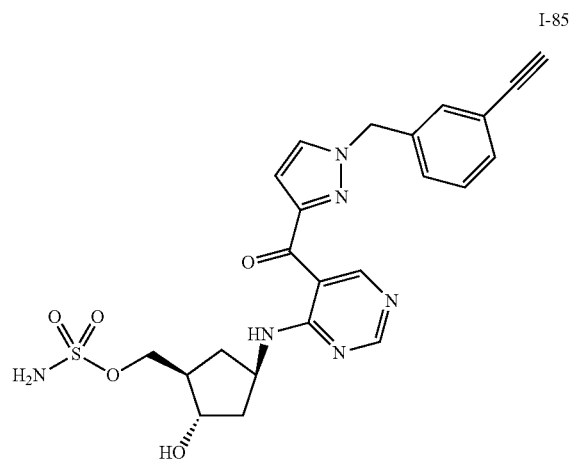
I-86
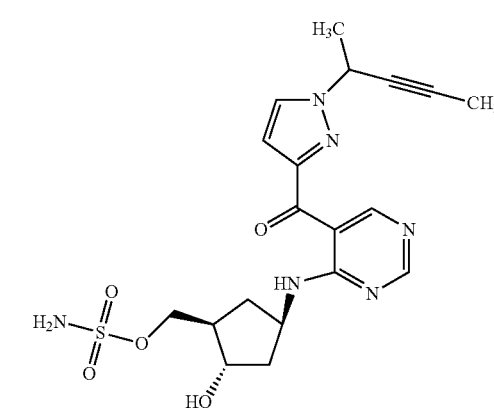
I-87
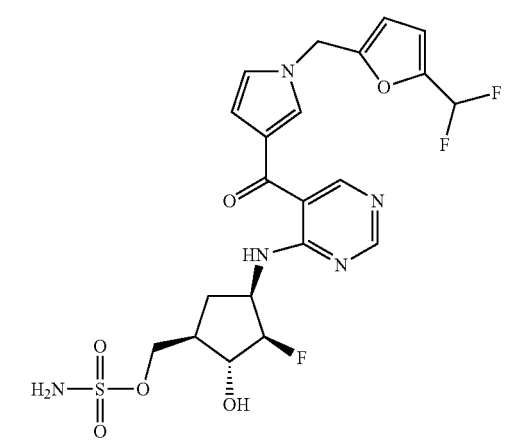
I-88
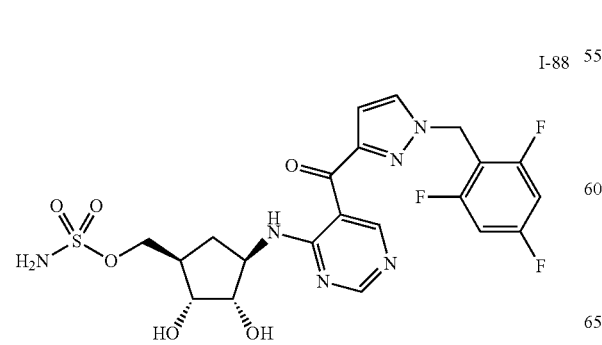
I-89
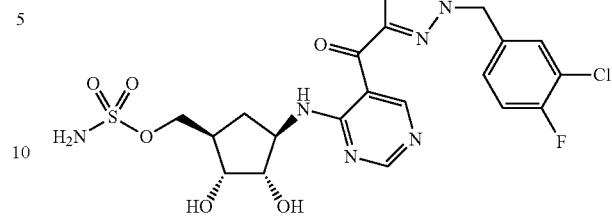
I-90
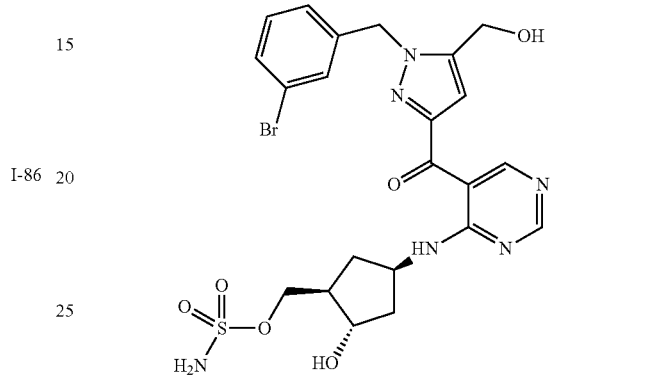
I-91
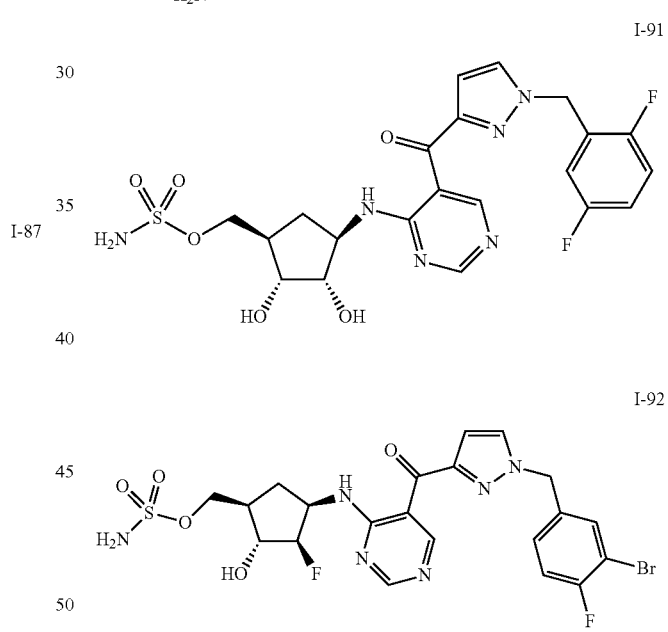
I-92
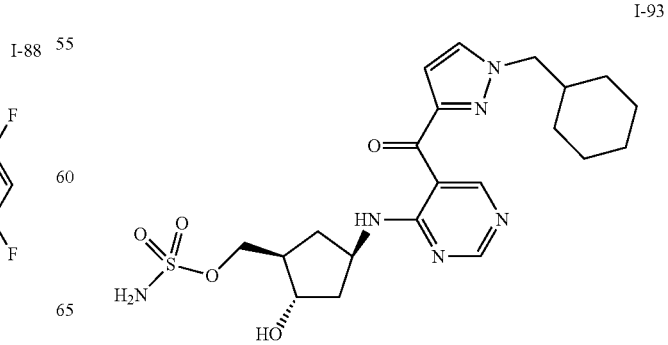
I-93

-continued
I-94
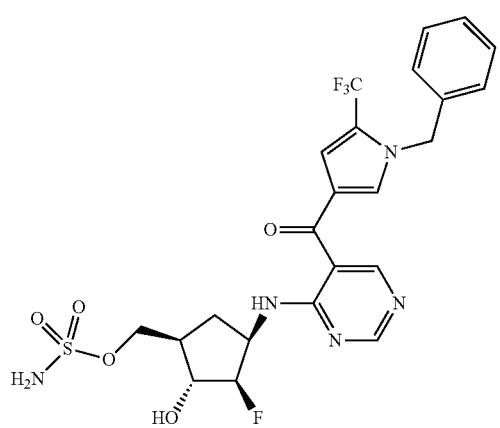
I-98
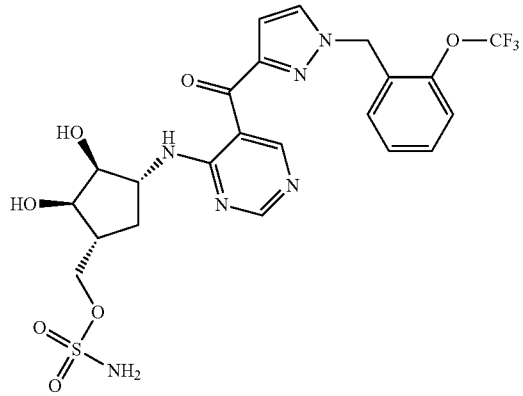
I-95
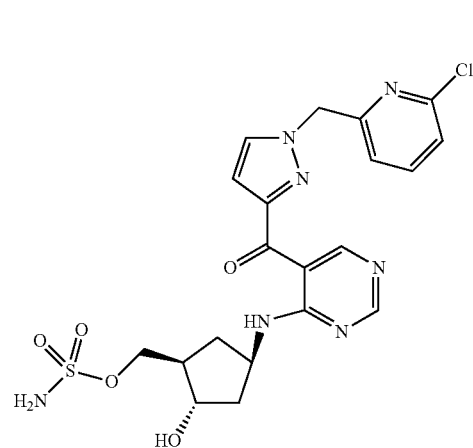
I-99
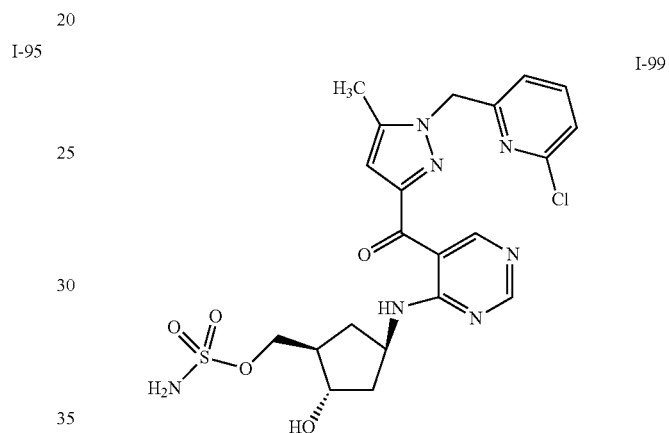
I-96
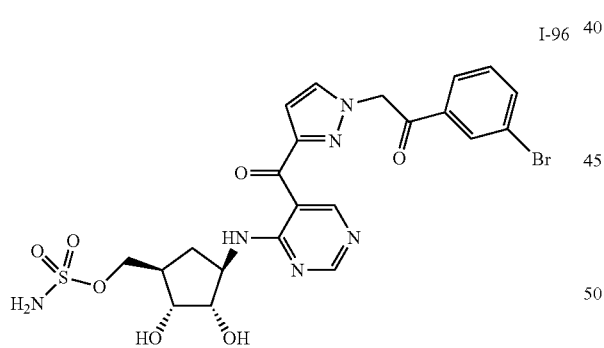
I-100
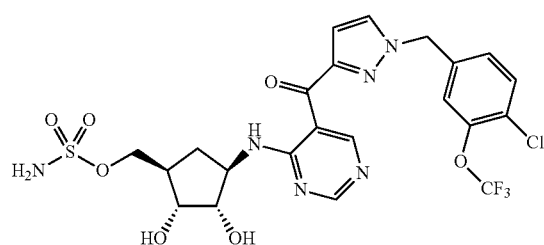
I-97
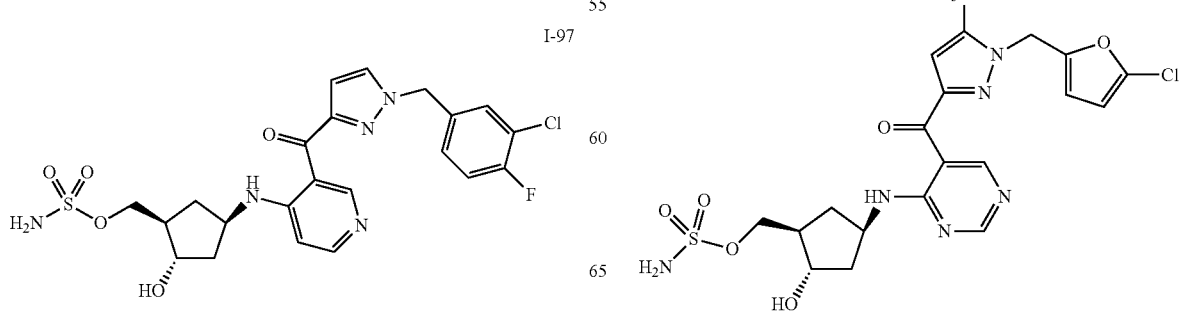
I-101
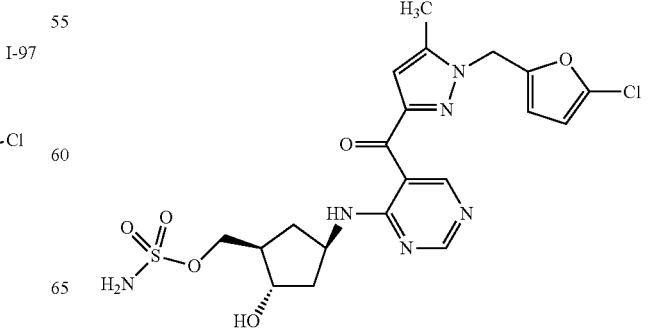

I-102 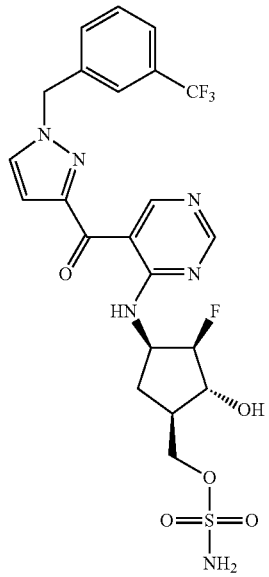
I-103 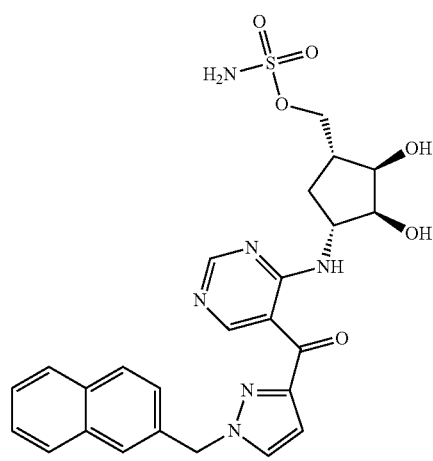
I-104 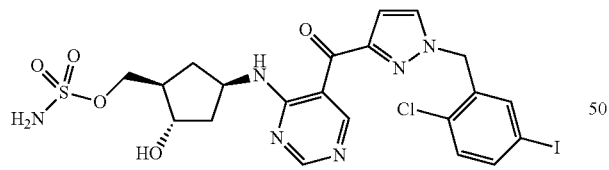
I-105 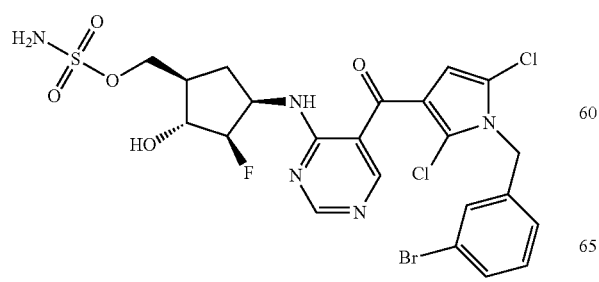
I-106 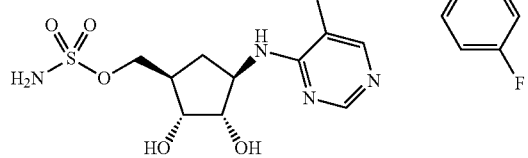
I-107 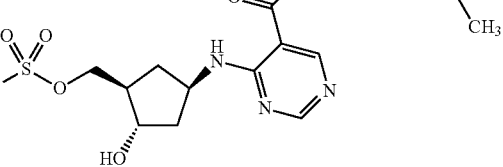
I-108 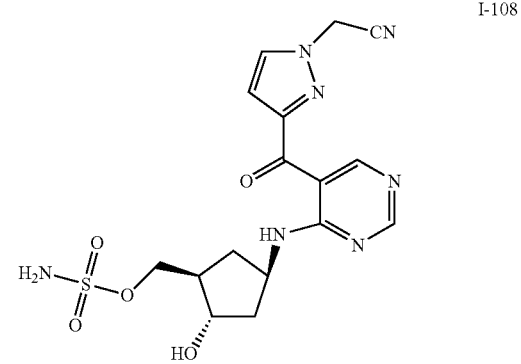
I-109 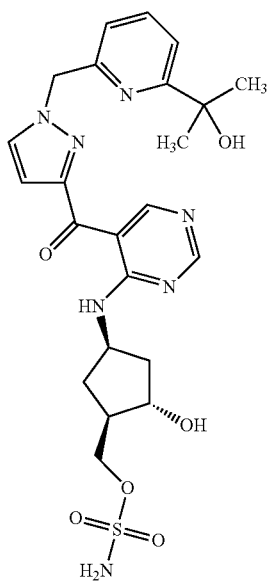

I-110
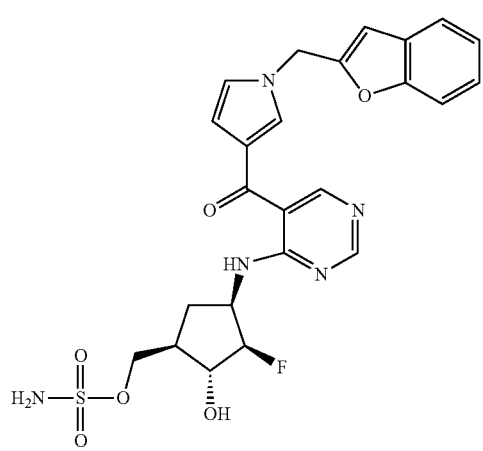
I-114
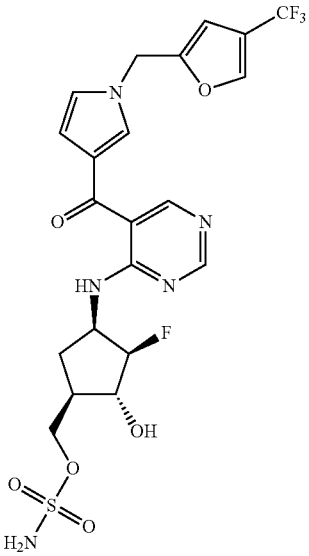
I-111
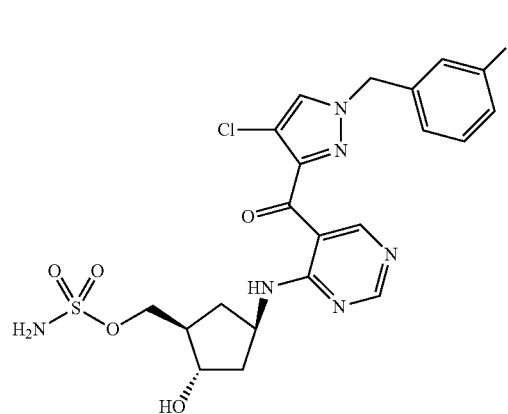
I-115
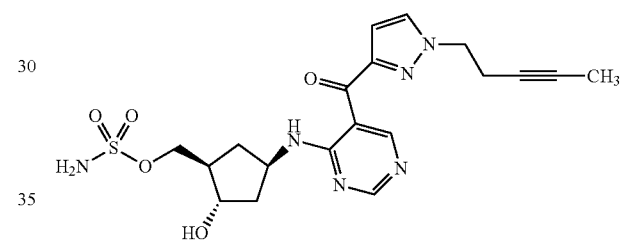
I-116
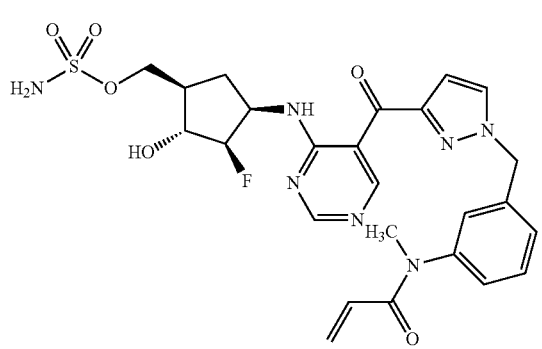
I-112
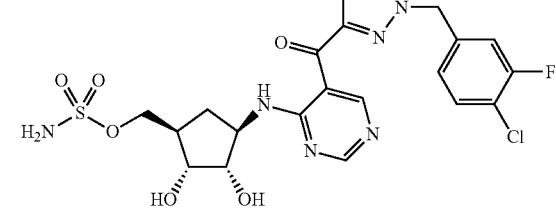
I-113
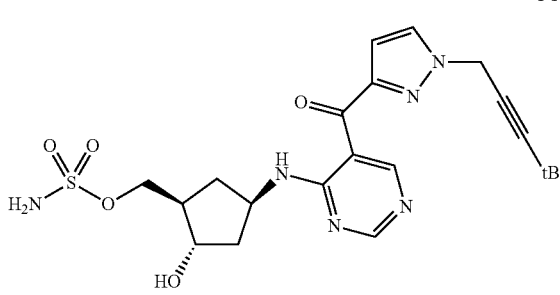
I-117
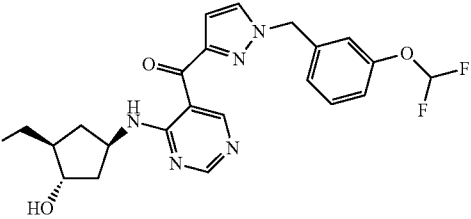

I-118
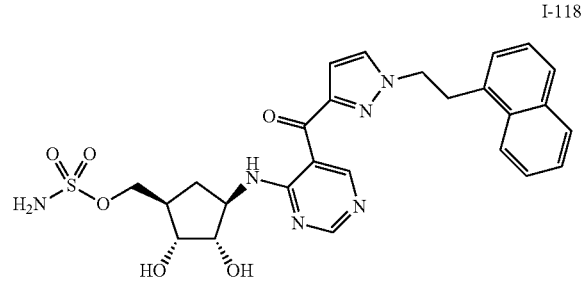
I-119
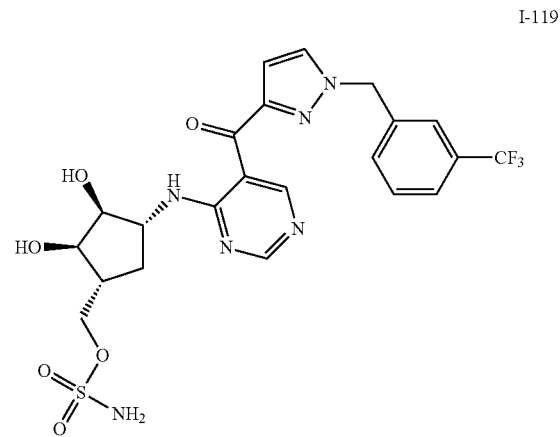
I-120
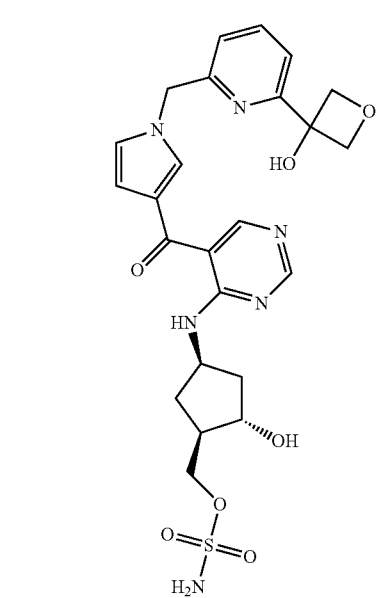
I-121
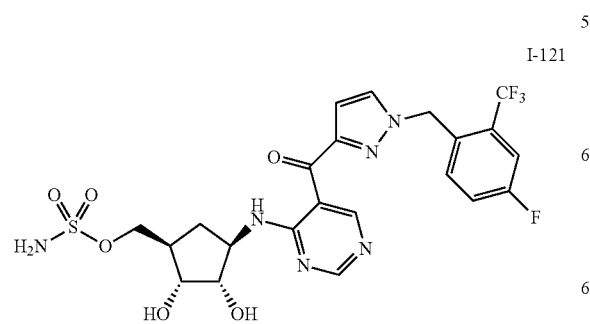
I-122
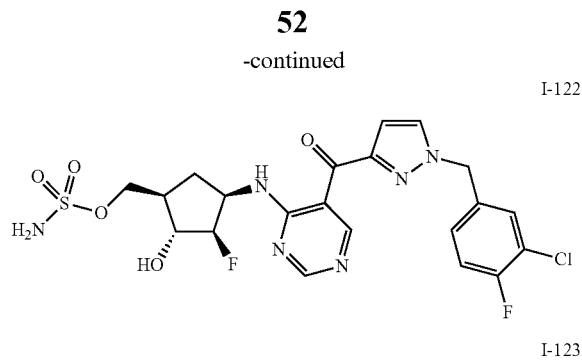
I-123
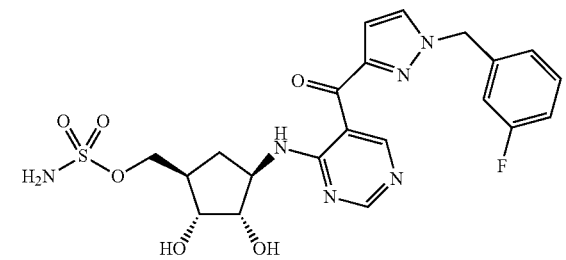
I-124
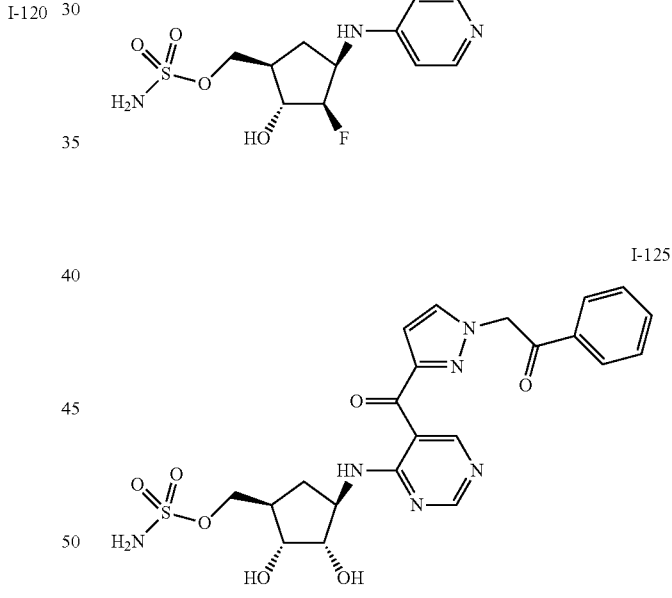
I-125
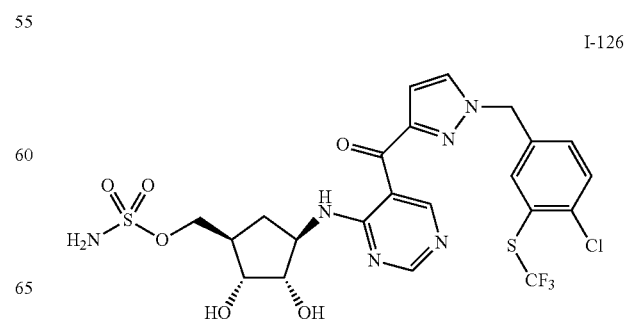
I-126

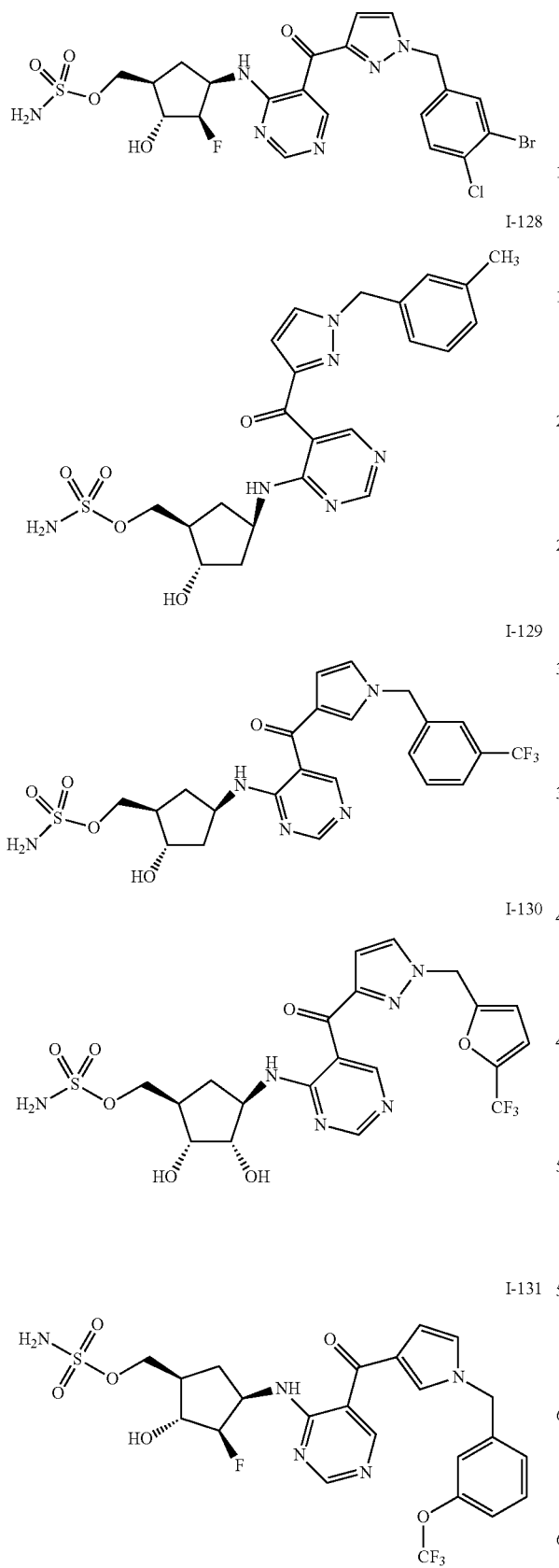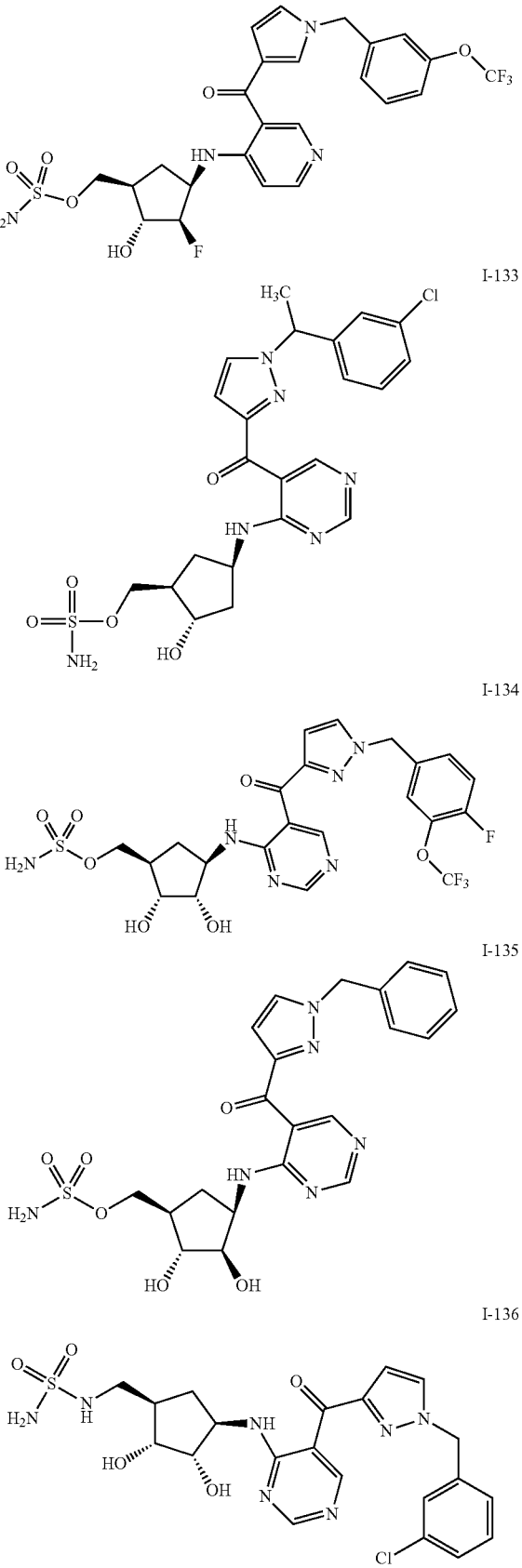

I-137
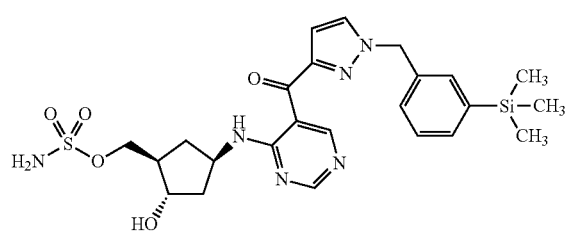
I-138
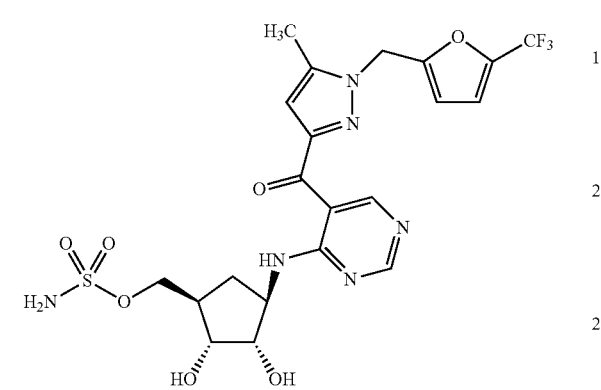
I-139
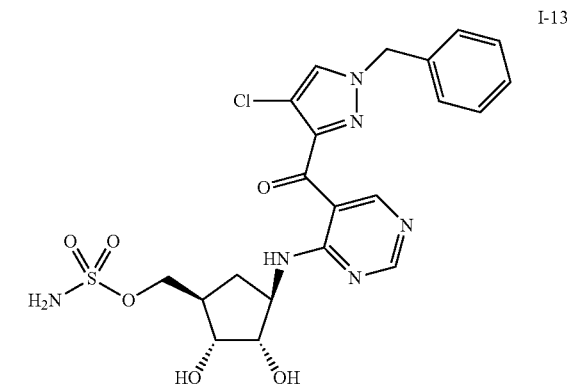
I-140
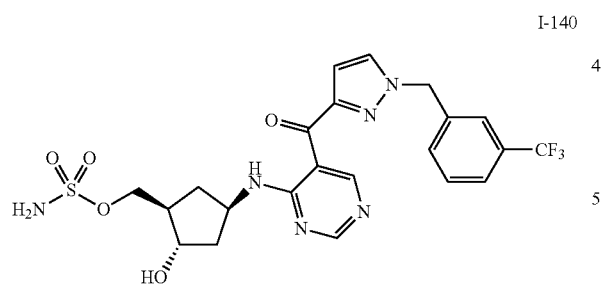
I-141
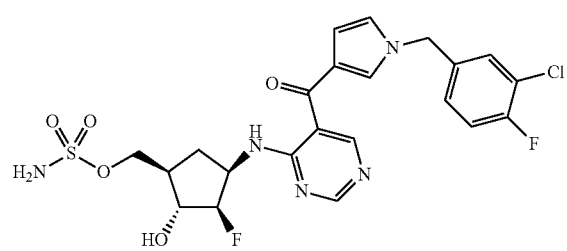
I-142
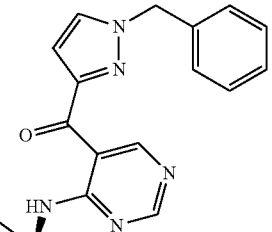
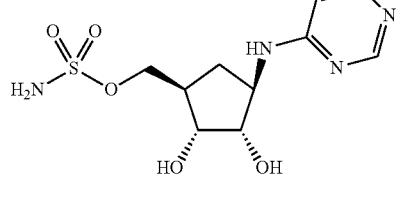
I-143
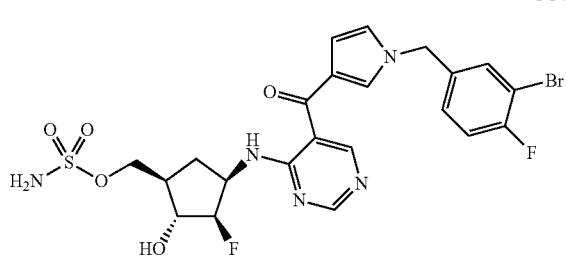
I-144
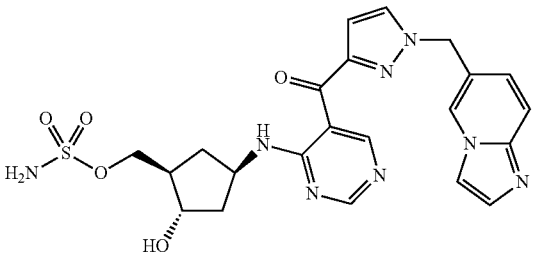
I-145
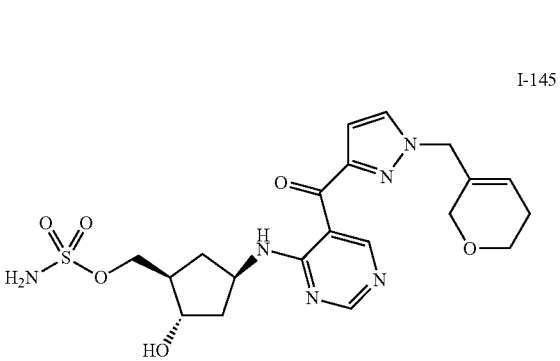
I-146
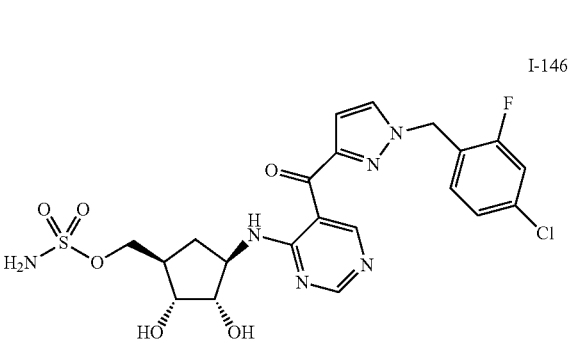

-continued
I-147
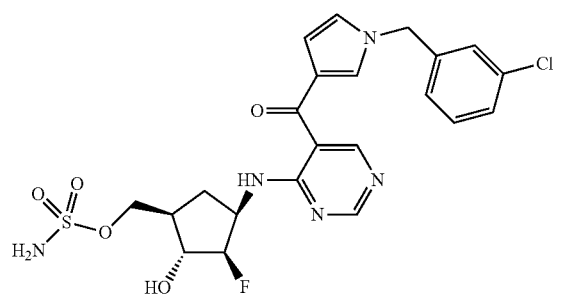
I-148
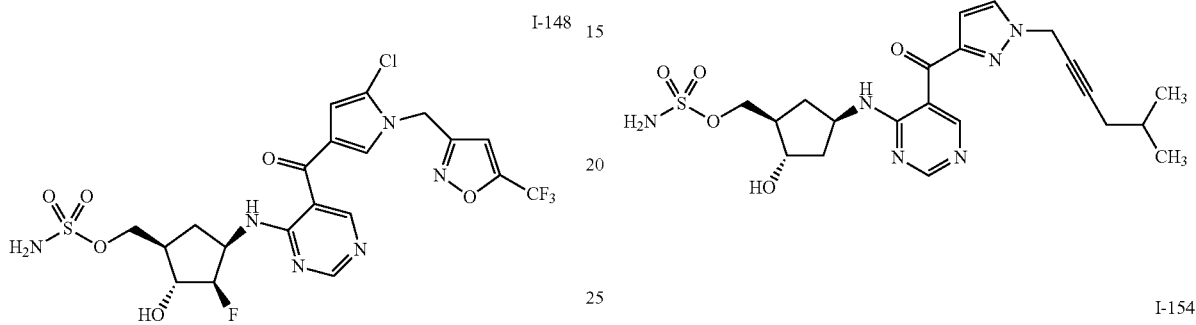
I-149
I-150
I-151
-continued
I-152
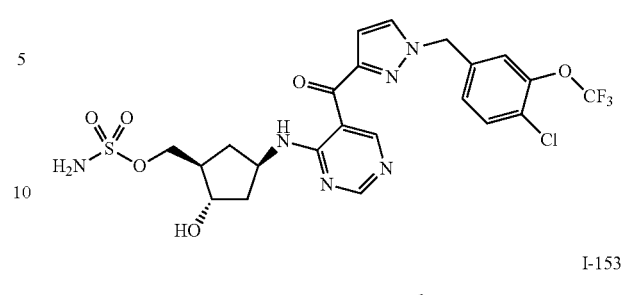
I-153
I-154
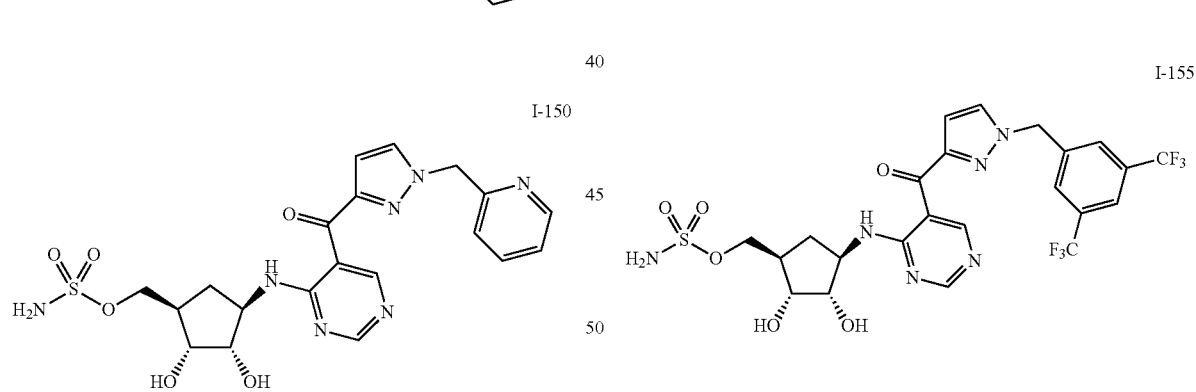
I-155
I-156
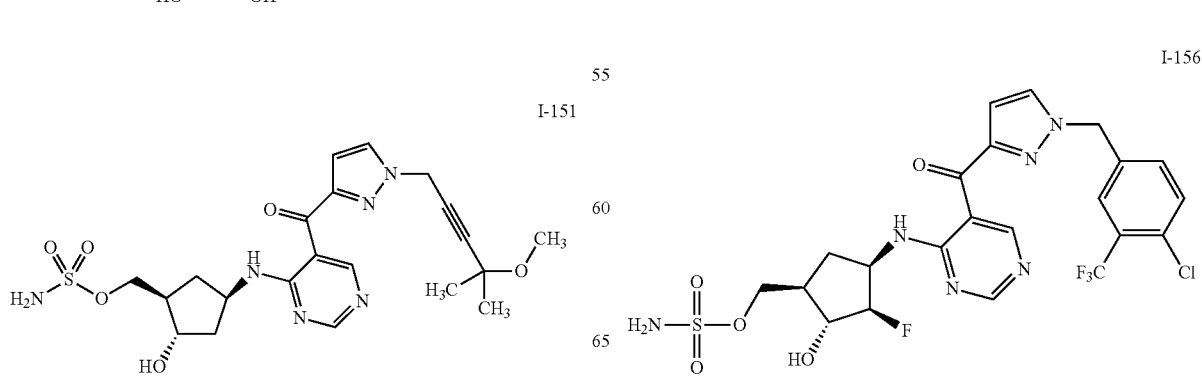

-continued
I-157
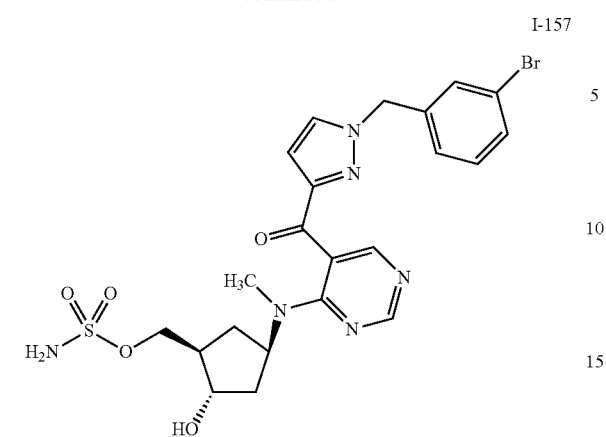
I-158
I-159
I-160
I-161
-continued
I-162
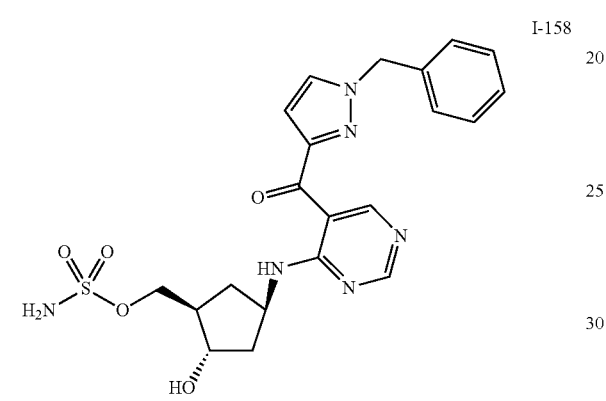
I-163
I-164
I-165

I-166
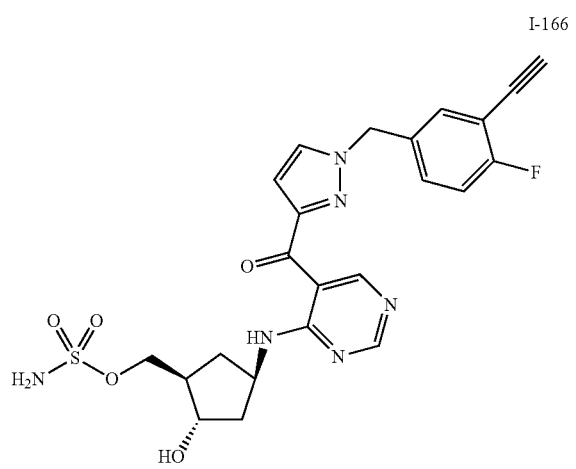
I-167
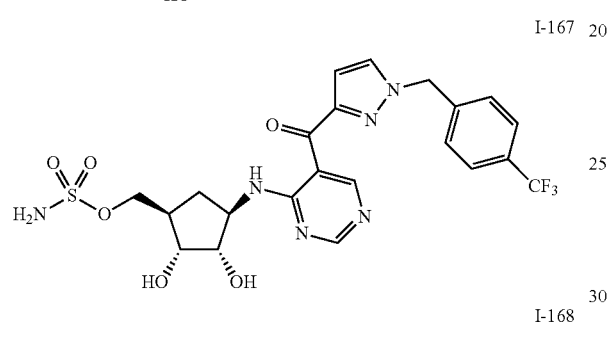
I-168
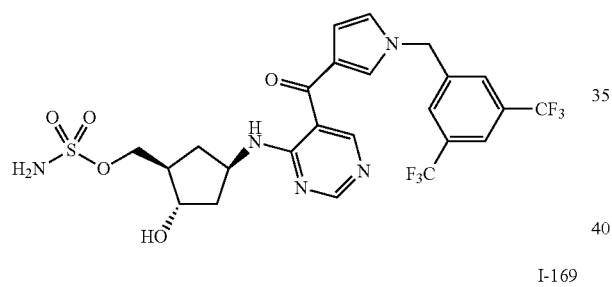
I-169
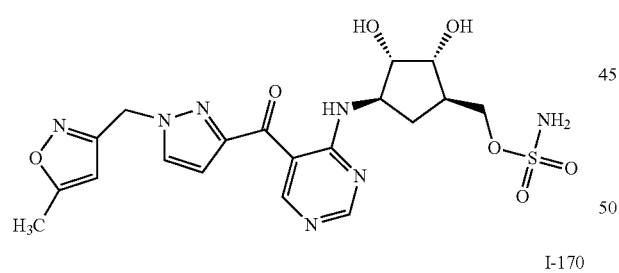
I-170
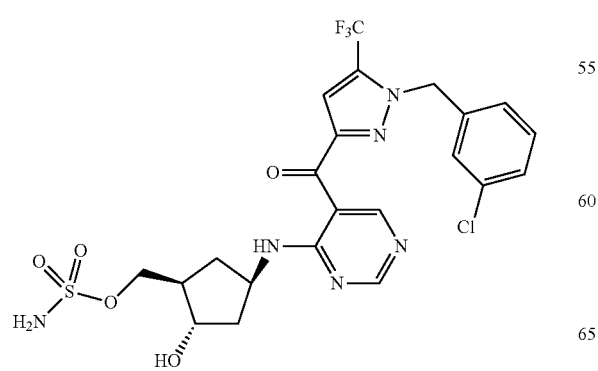
I-171
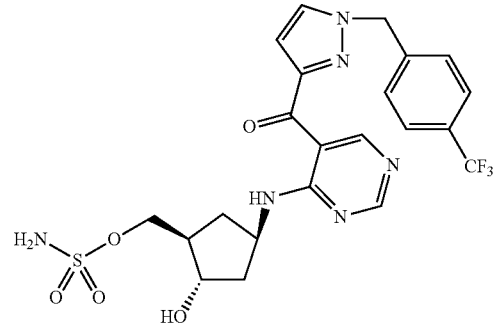
I-172
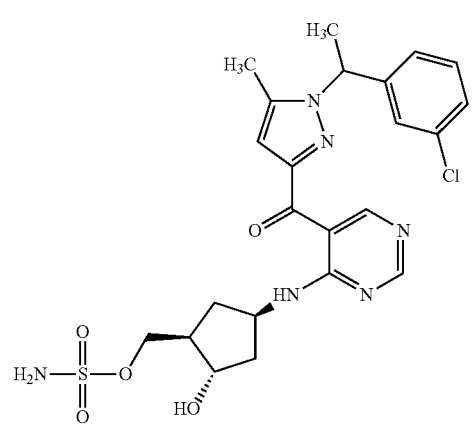
I-173
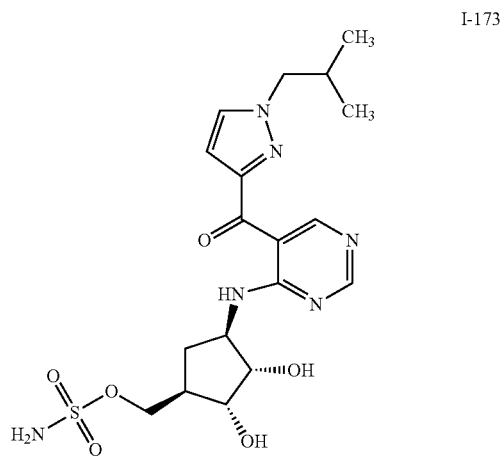
I-174
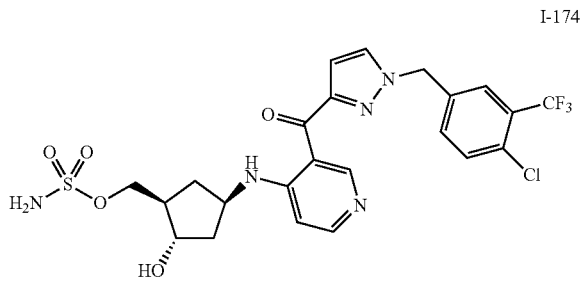

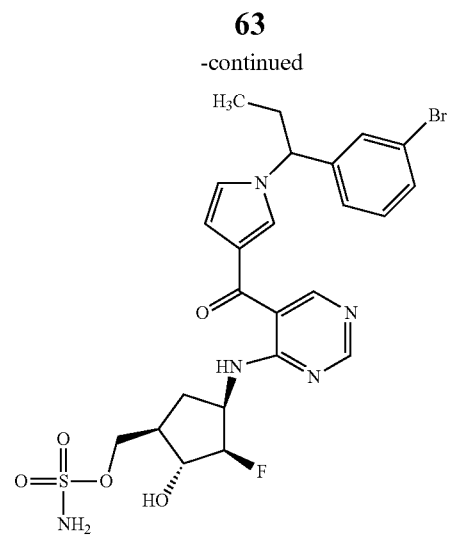
I-175
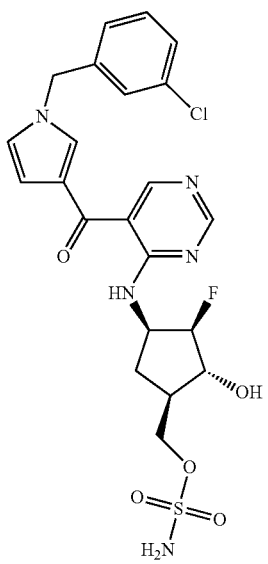
I-176
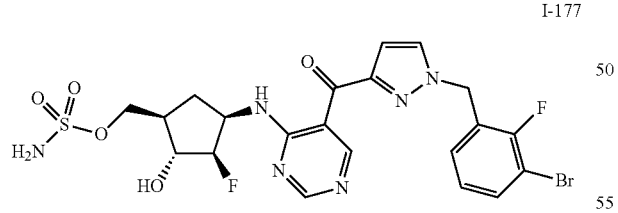
I-177
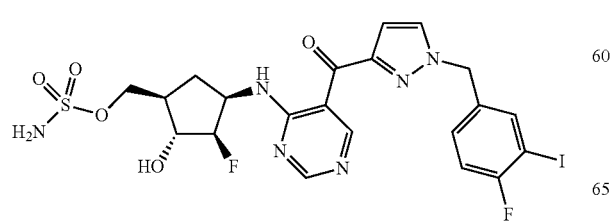
I-178
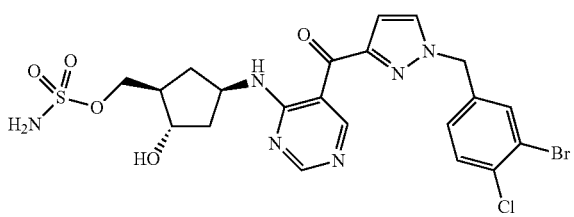
I-179
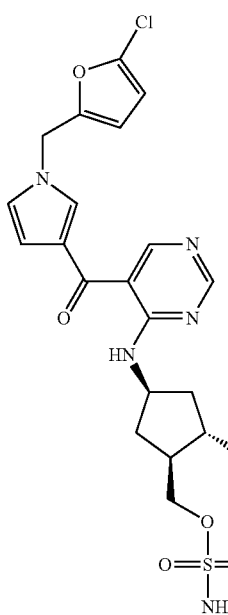
I-180
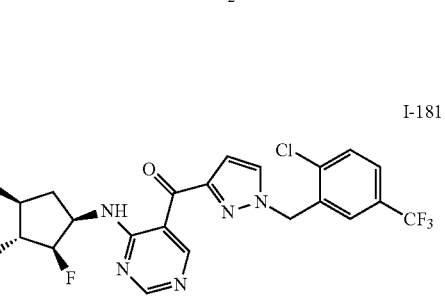
I-181
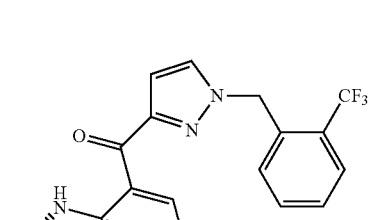
I-182

65
-continued
66
-continued
I-183
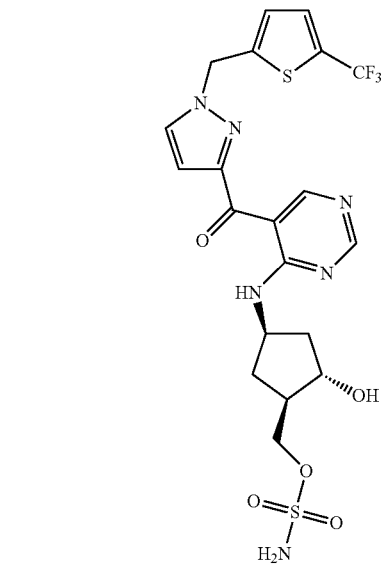
I-187
I-184
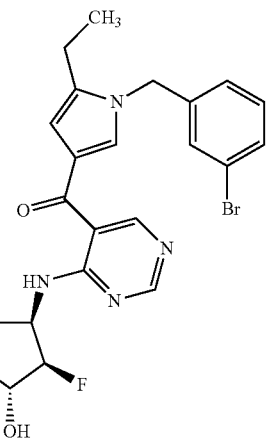
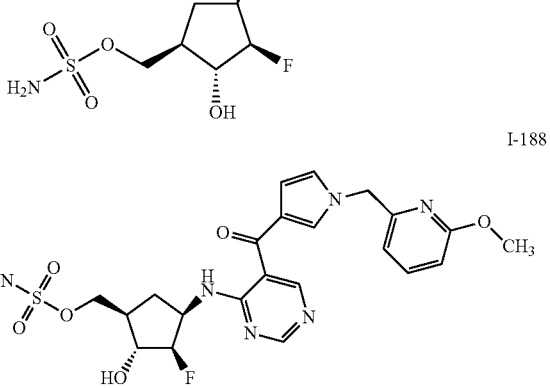
I-188
I-185
I-189
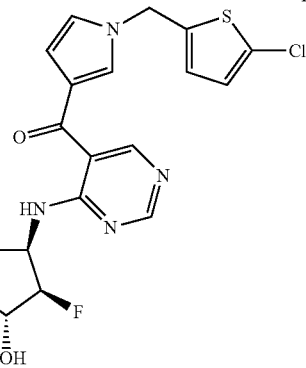
I-186
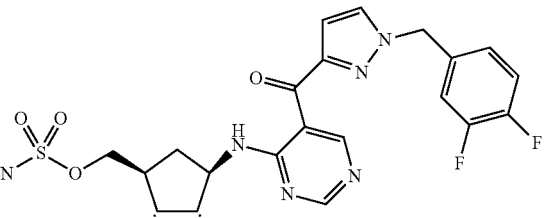
I-190
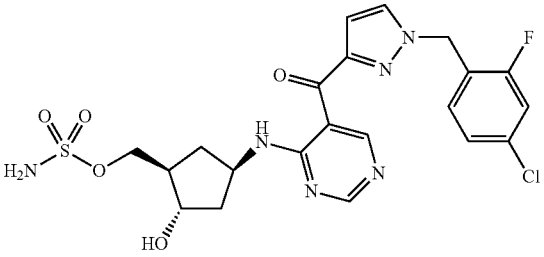
I-191

I-192 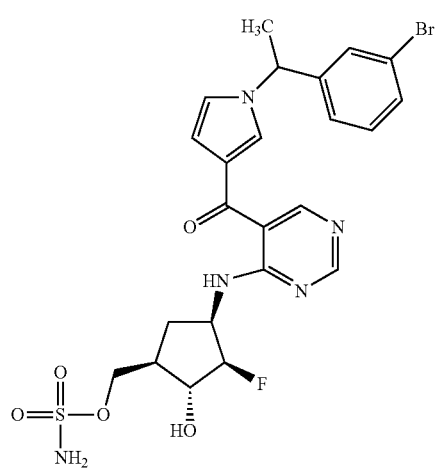
I-193 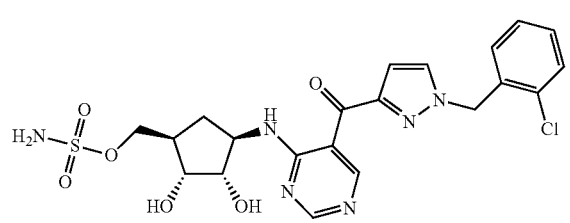
I-194 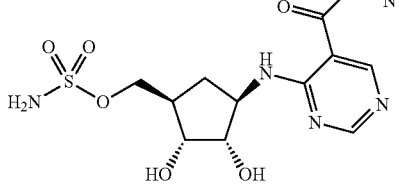
I-195 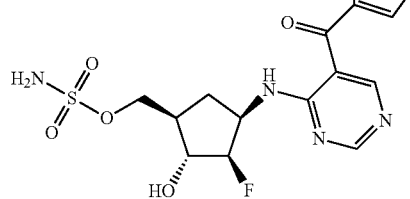
I-196 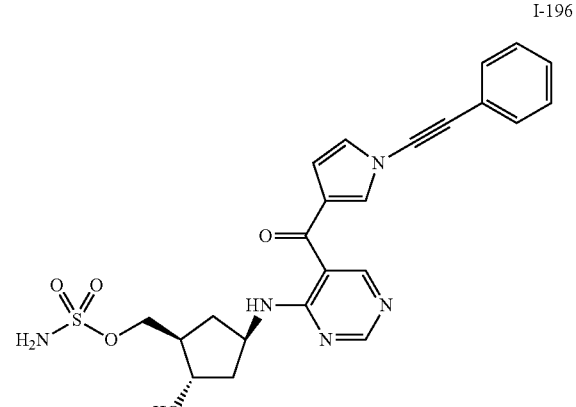
I-197 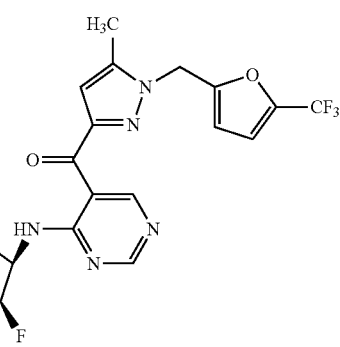
I-198 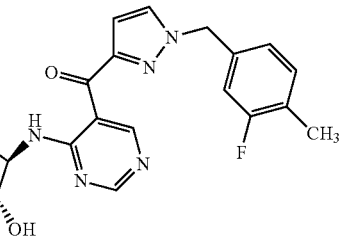
I-199 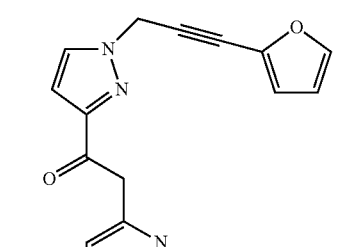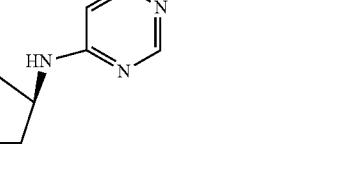

I-200
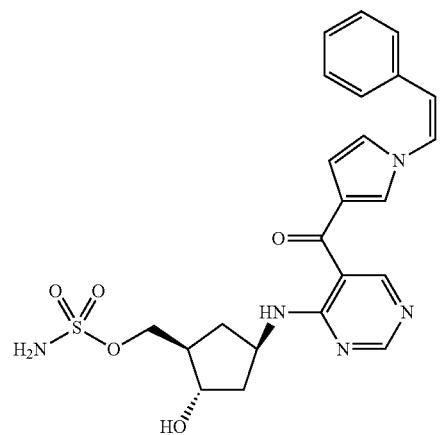
I-201
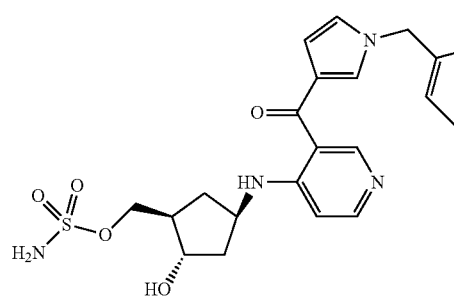
I-202
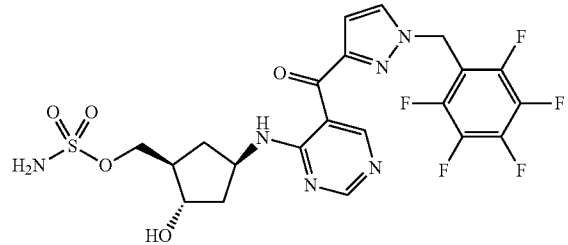
I-203
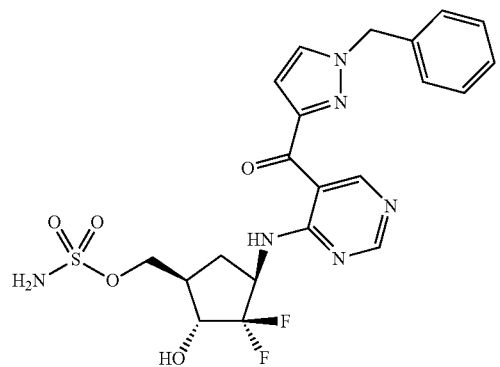
I-204
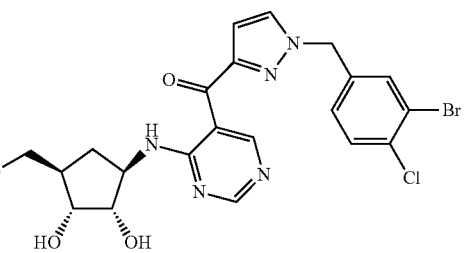
I-205
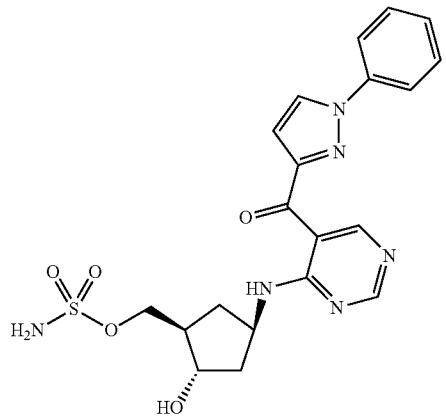
I-206
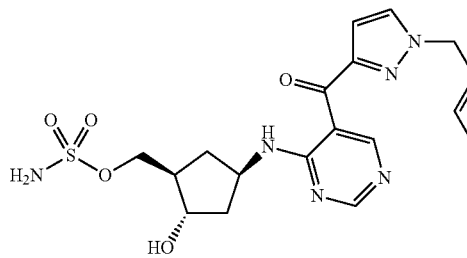
I-207
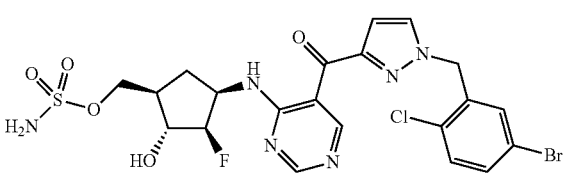
I-208
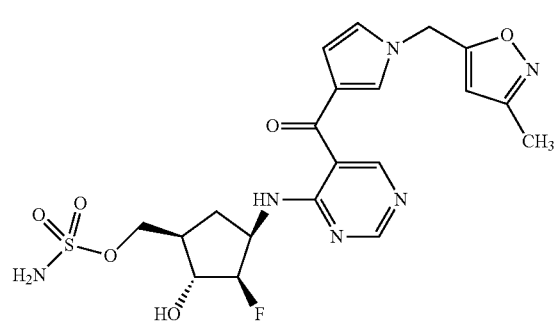

-continued
I-209
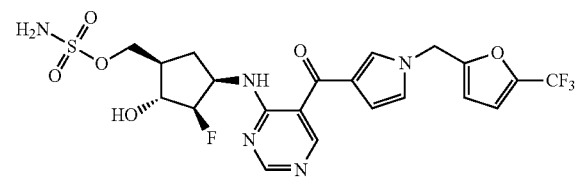
I-210
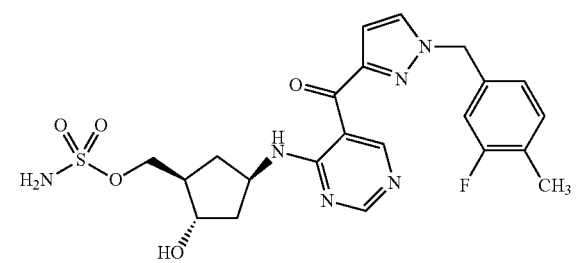
I-211
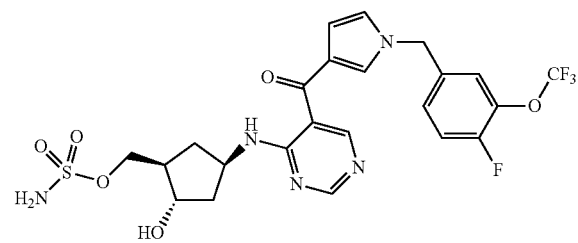
I-212
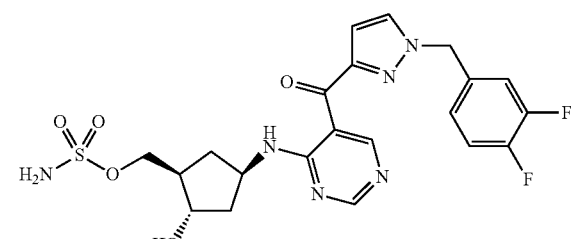
I-213
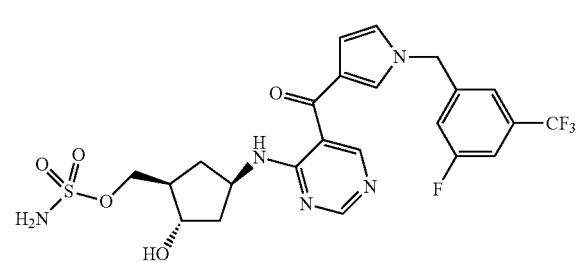
I-214
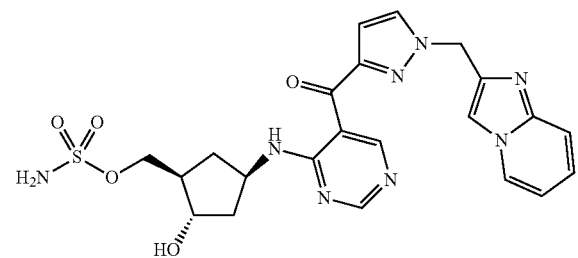
-continued
I-215
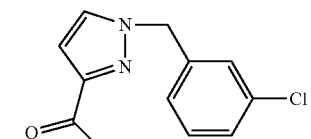
I-216
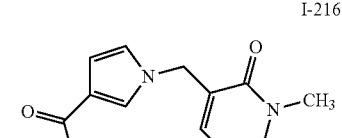
I-217
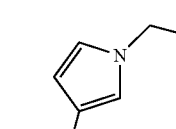
I-218
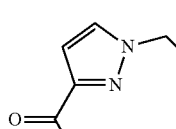
I-219
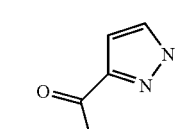

-continued
I-220
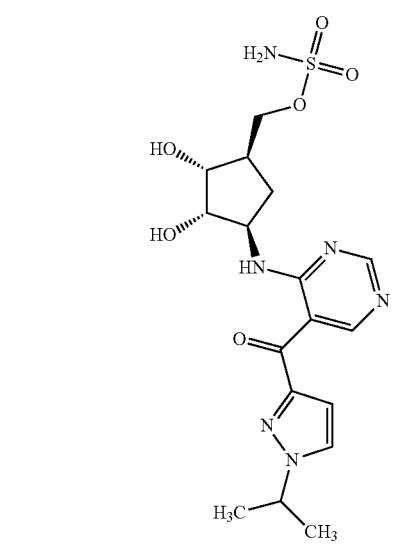
I-221
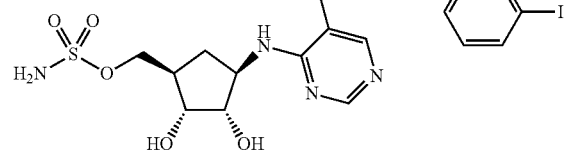
I-222
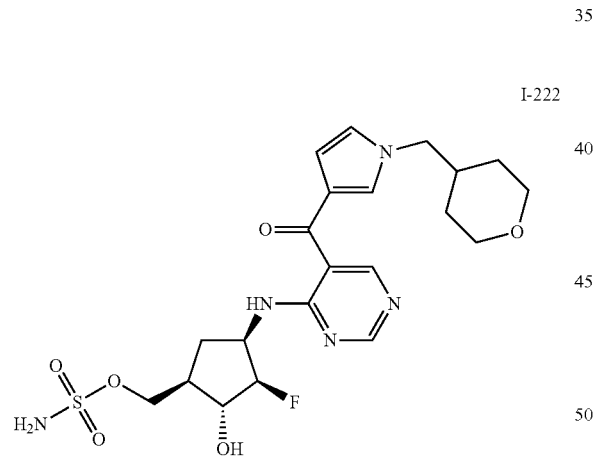
I-223
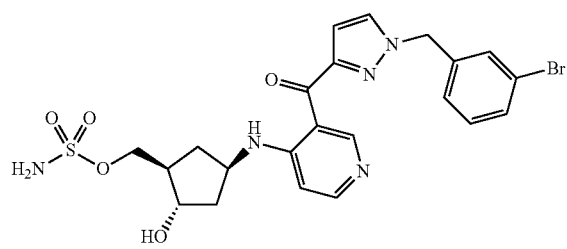
-continued
I-224
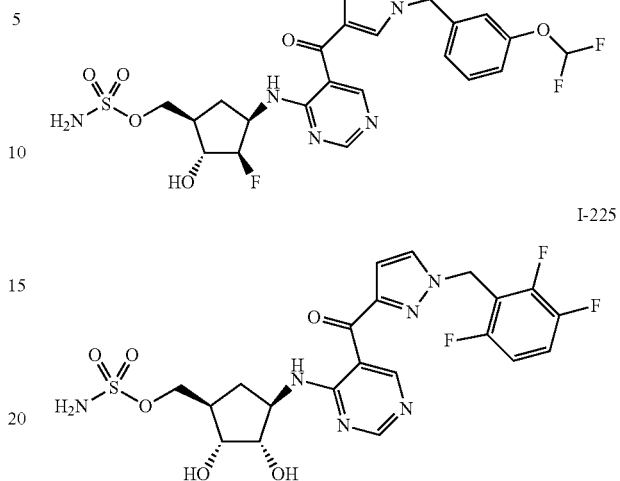
I-225
I-226
I-227
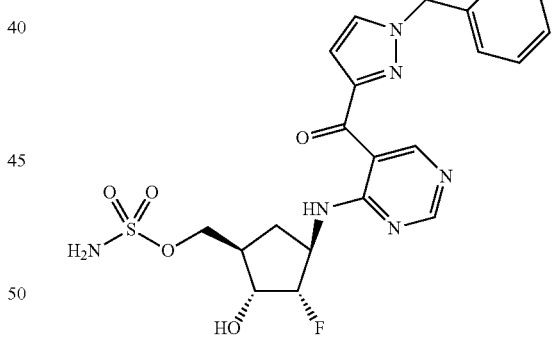
I-228
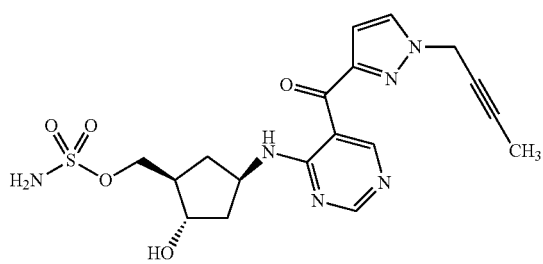

75
-continued
I-229
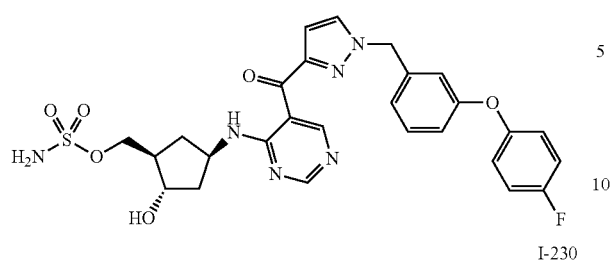
I-230
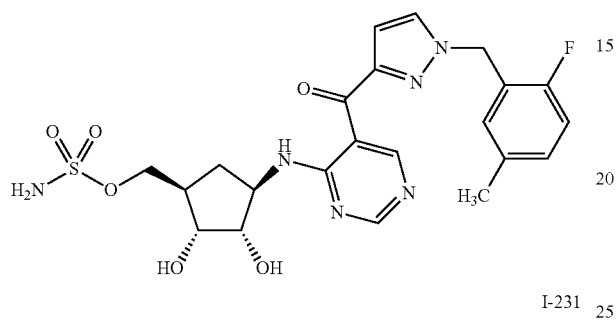
I-231
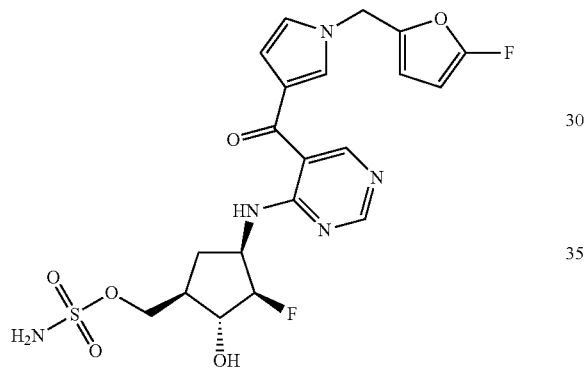
I-232
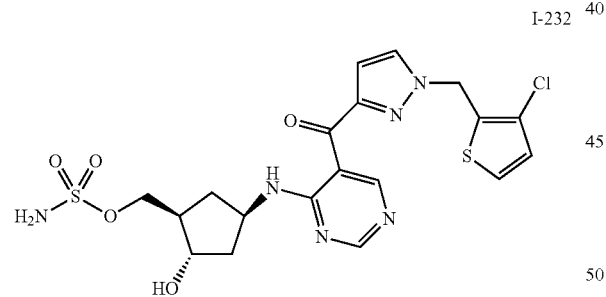
I-233
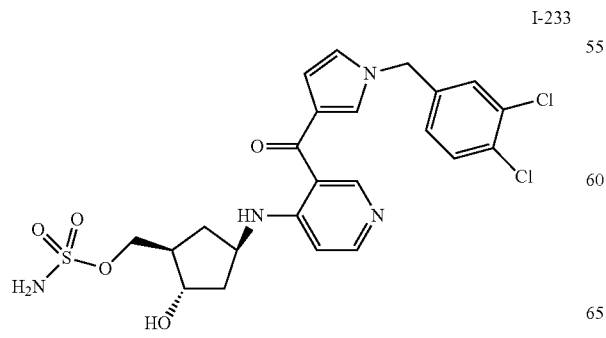
76
-continued
I-234
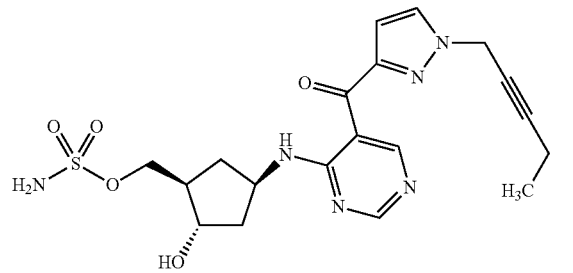
I-235
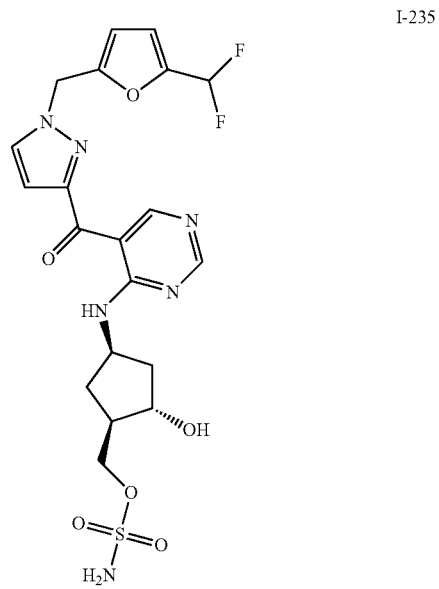
I-236
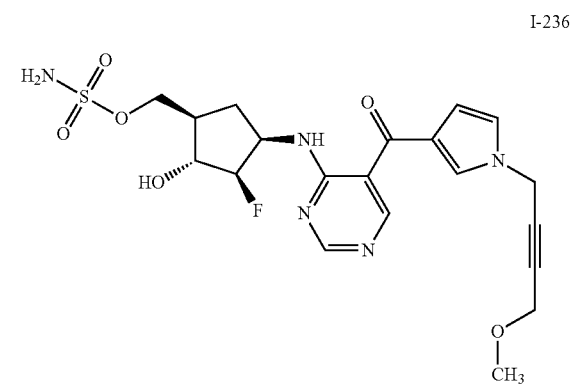
I-237
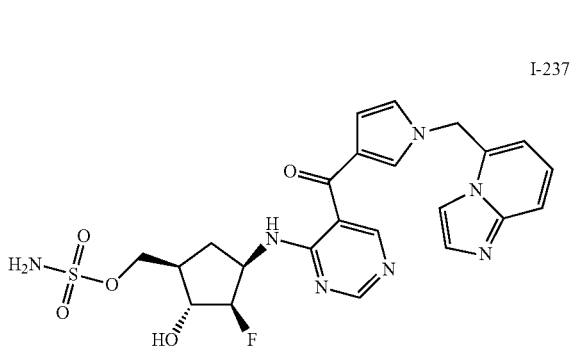

77
-continued
I-238
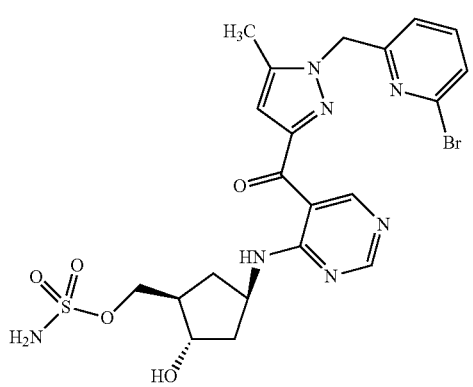
I-239
I-240
I-241
78
-continued
I-242
I-243
I-244
I-245
I-246

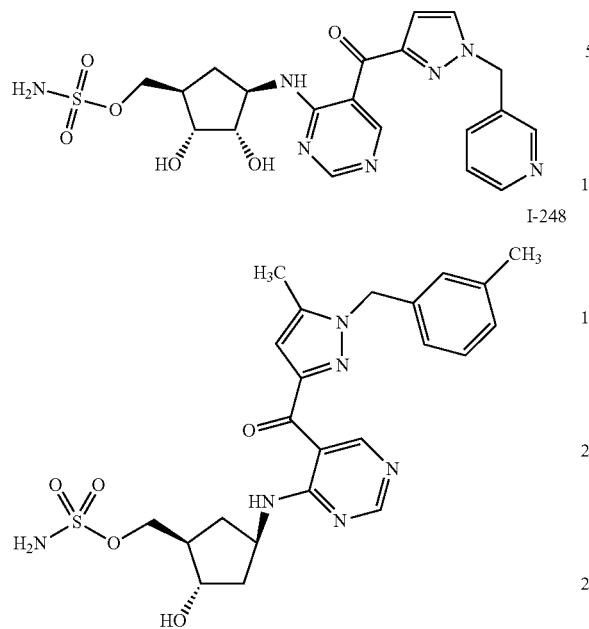
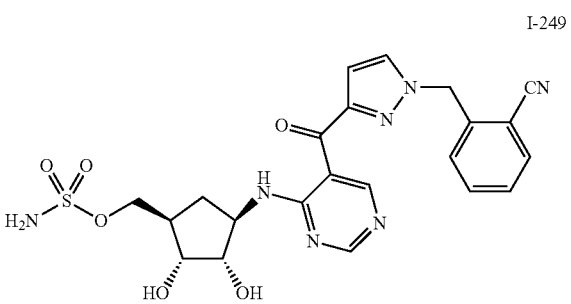
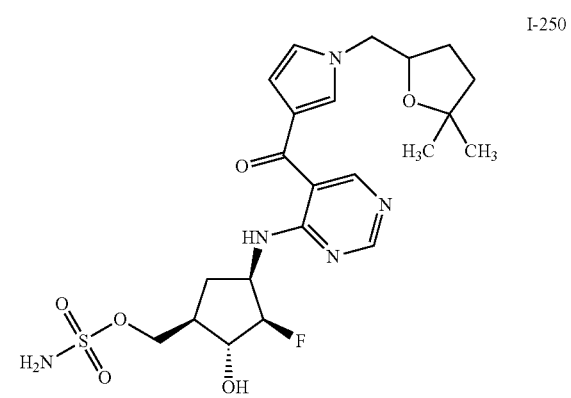
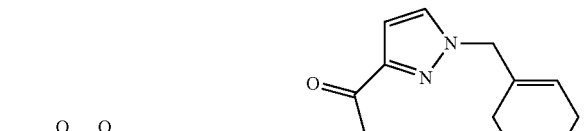

I-257
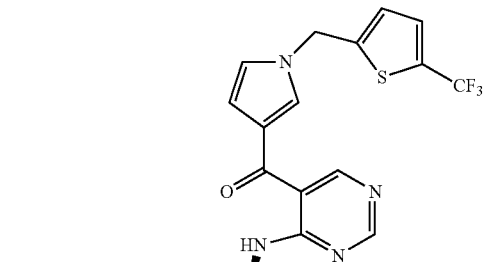
I-258
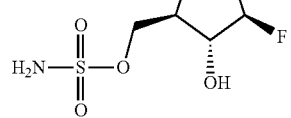
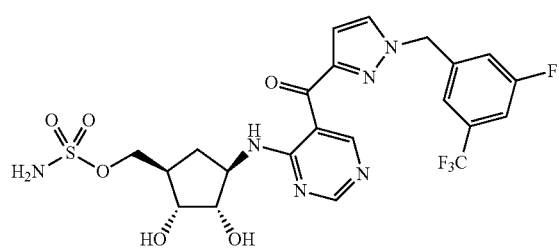
I-259
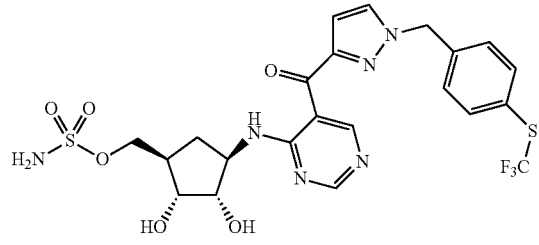
I-260
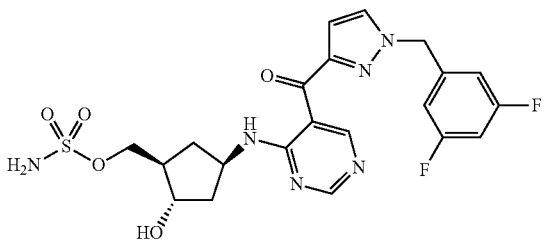
I-261
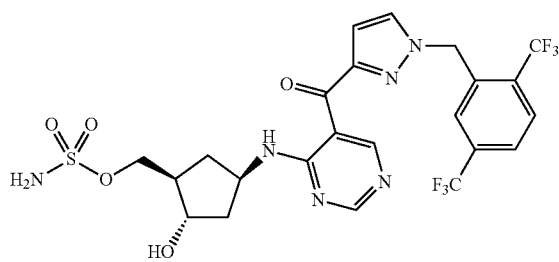
I-262
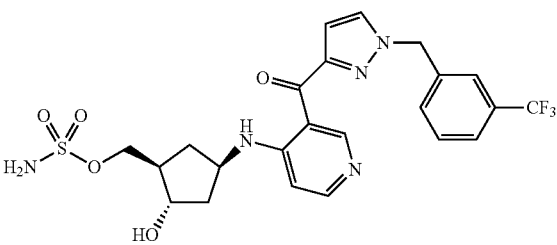
I-263
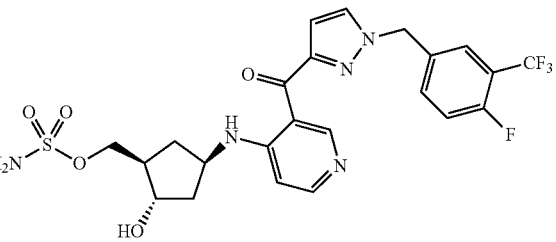
I-264
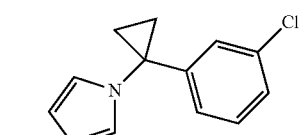
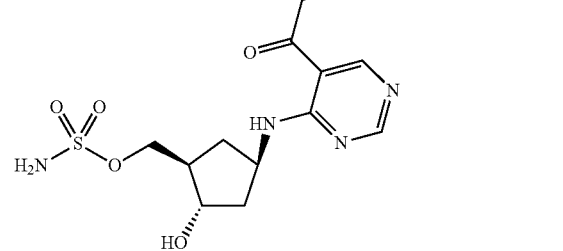
I-265
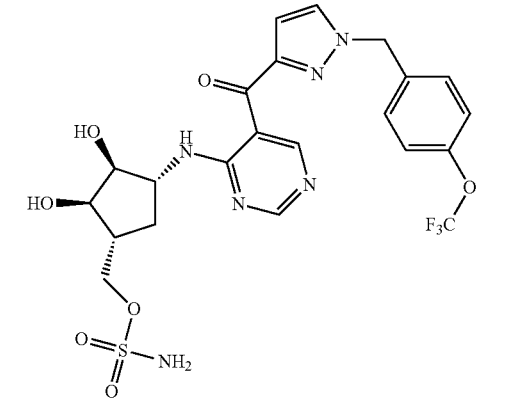
I-266

-continued
I-267

I-268
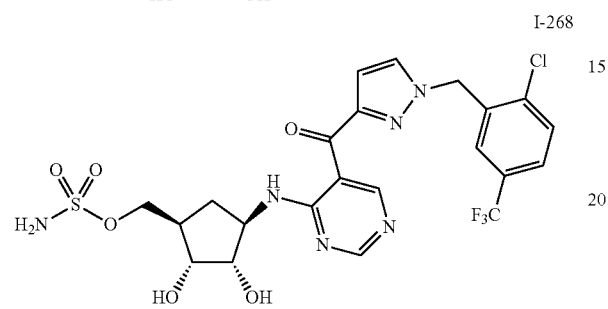
I-269
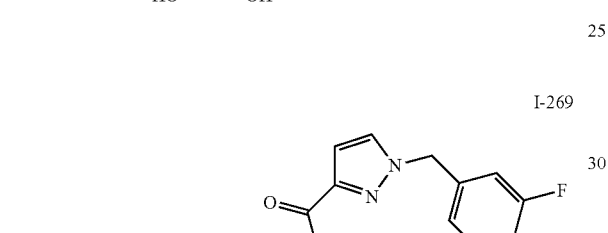
I-270
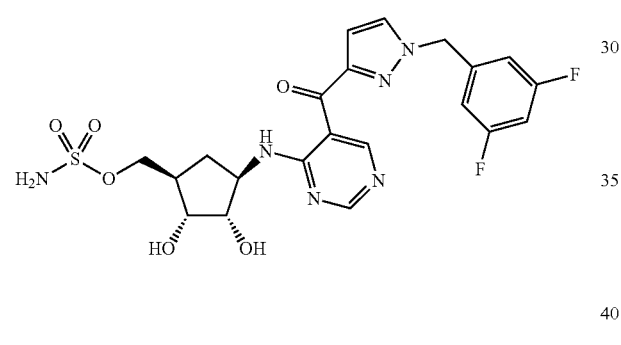
I-271
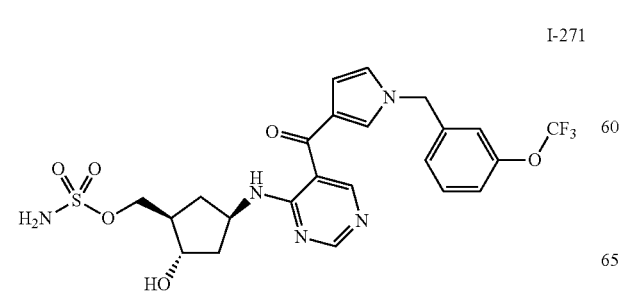
-continued
I-272
I-273
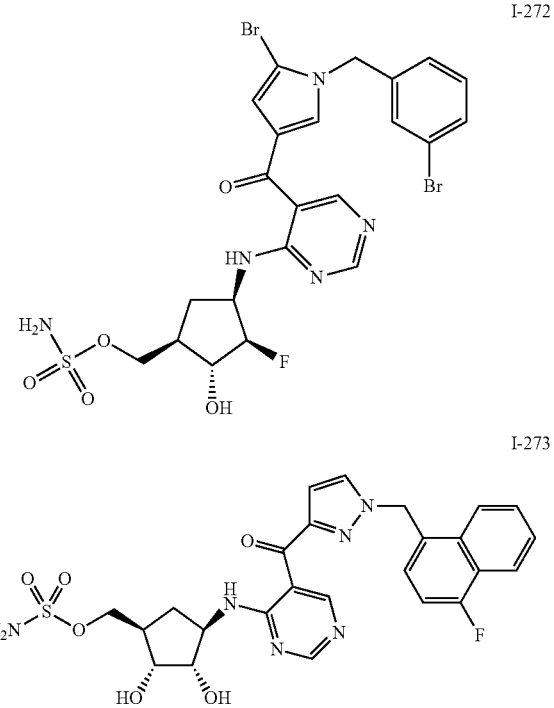
I-274
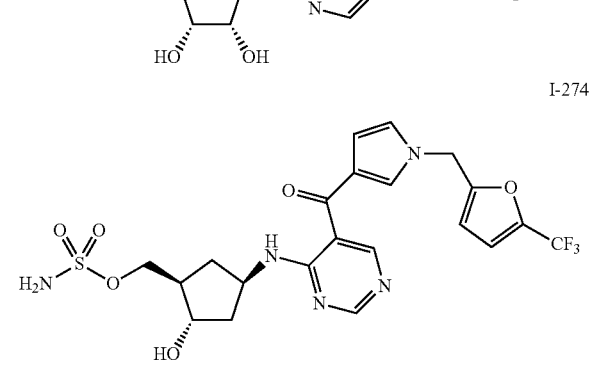
I-275
I-276
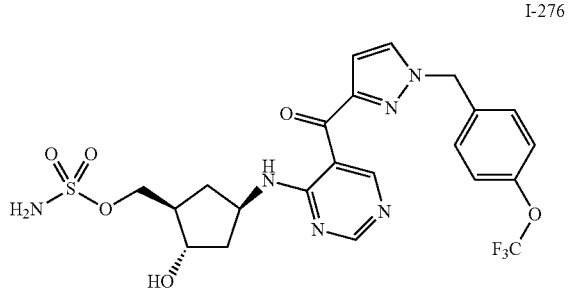

I-277
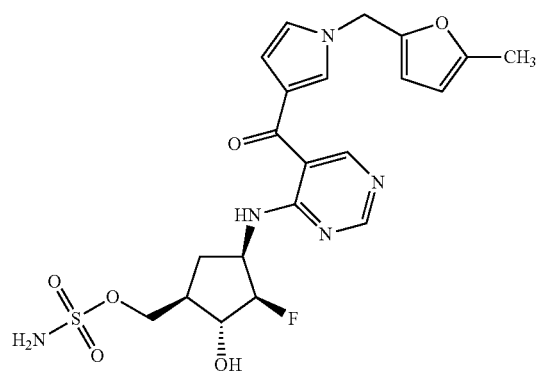
I-278
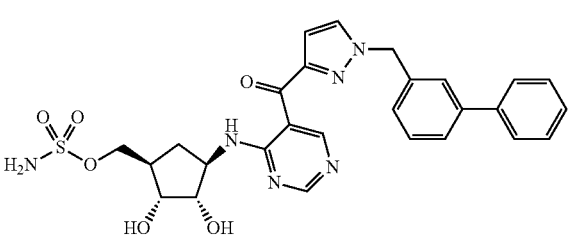
I-279
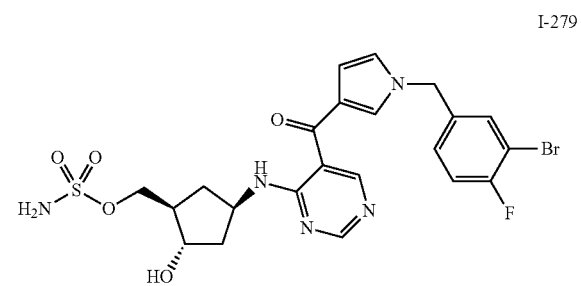
I-280
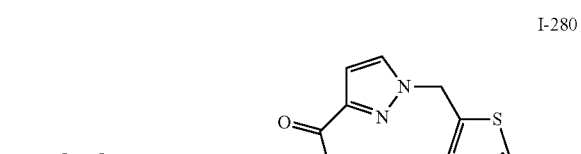
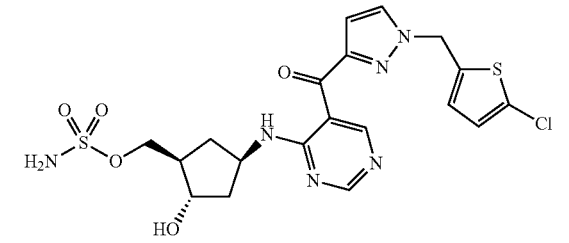
I-281
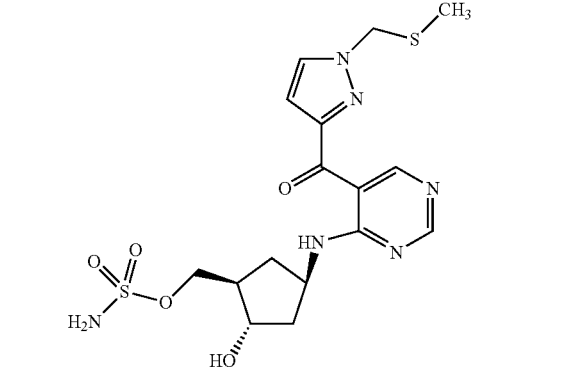
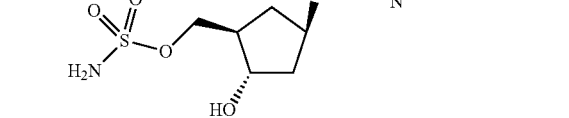
I-282
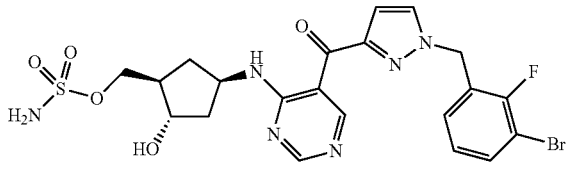
I-283
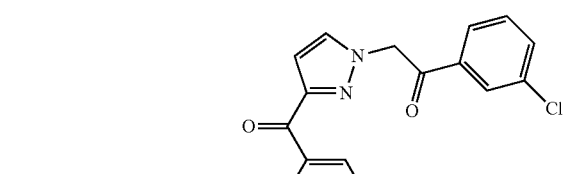
I-284
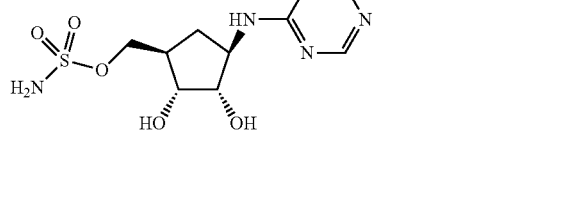
I-285
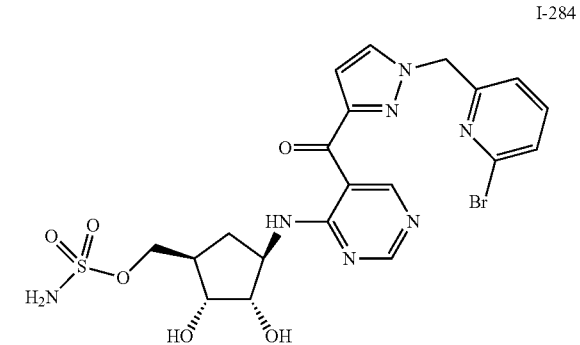
I-286
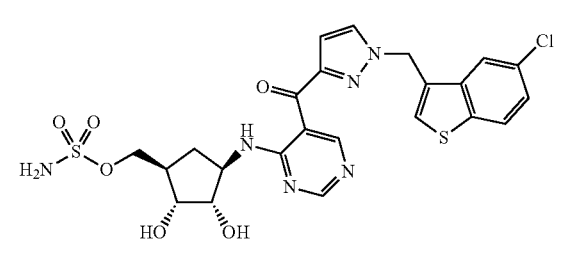

I-287
I-288
I-289
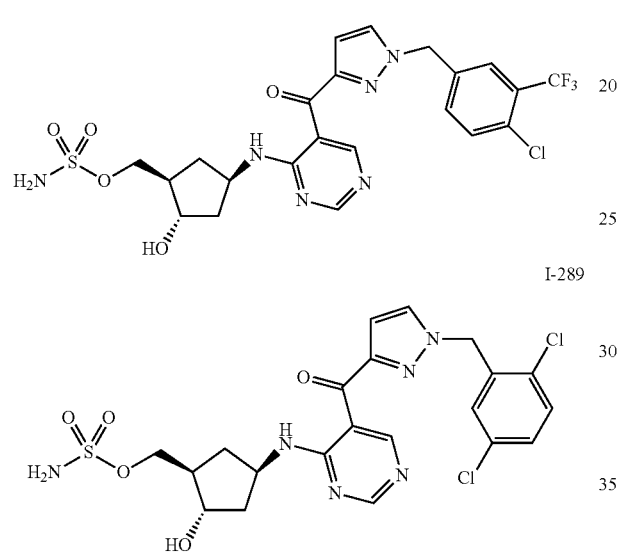
I-290
I-291
I-292
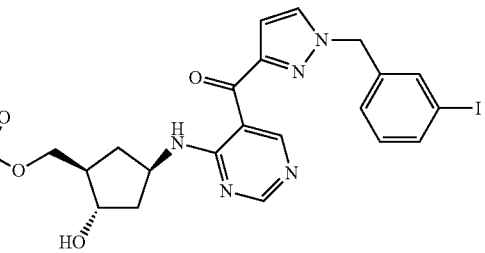
I-293
I-294
I-295

I-296
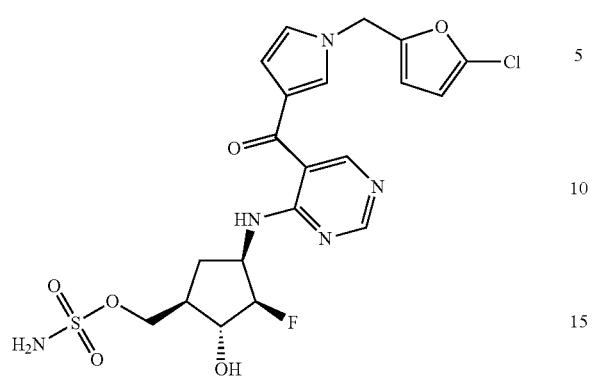
I-301
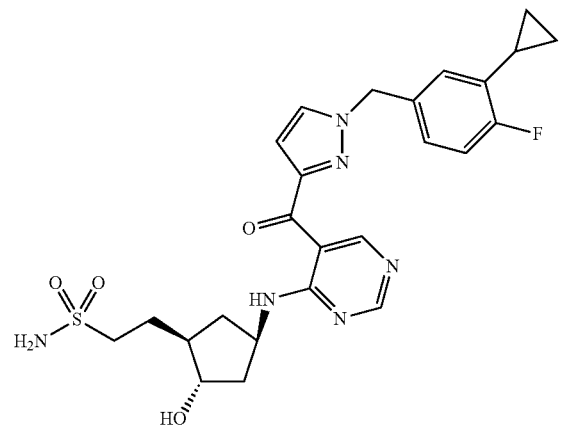
I-297
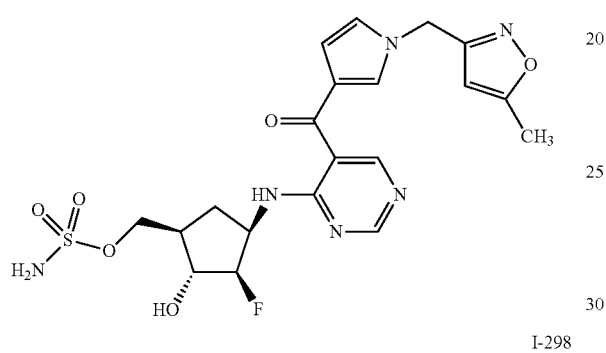
I-302
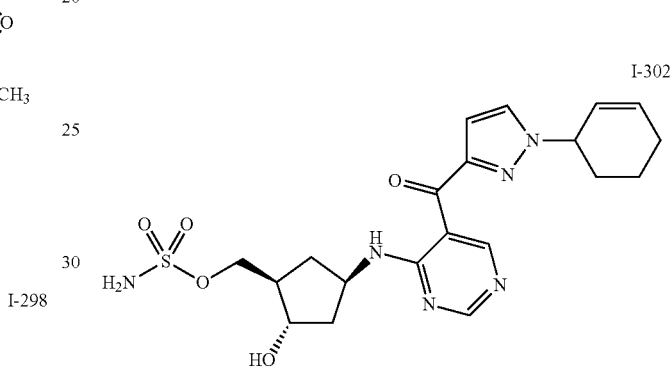
I-298
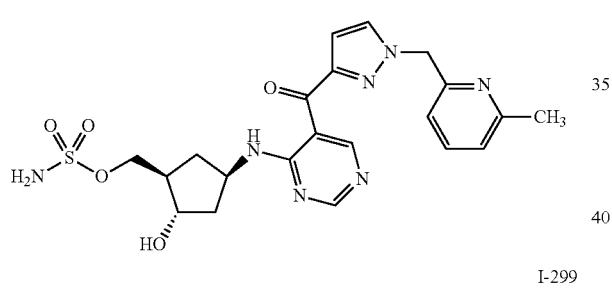
I-303
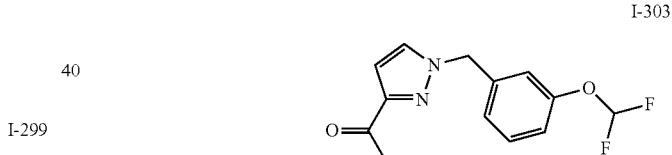
I-299
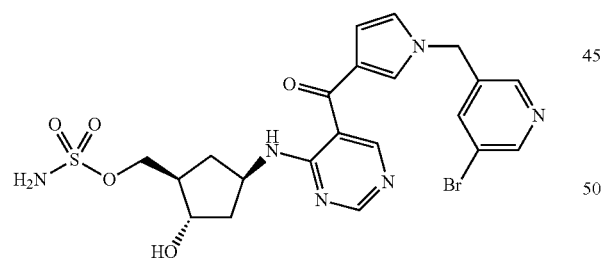
I-304
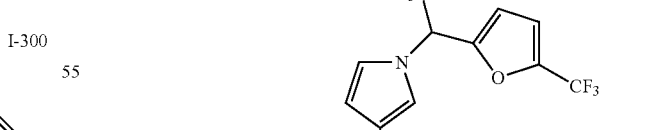
I-300
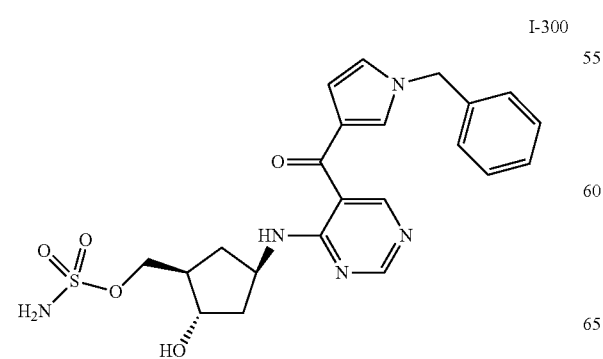

I-305
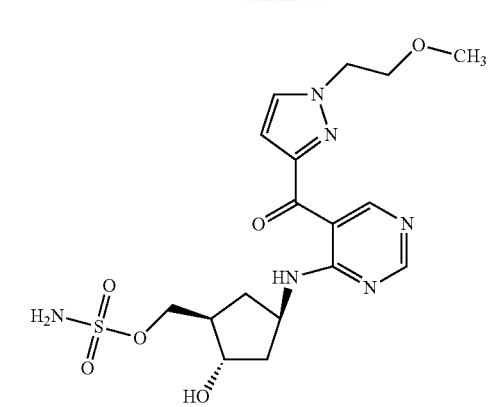
I-306
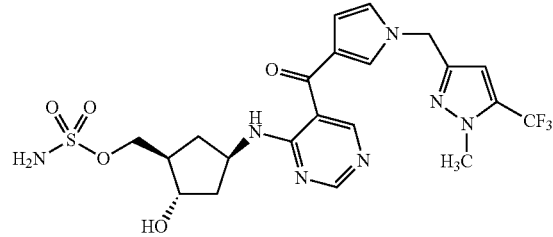
I-307
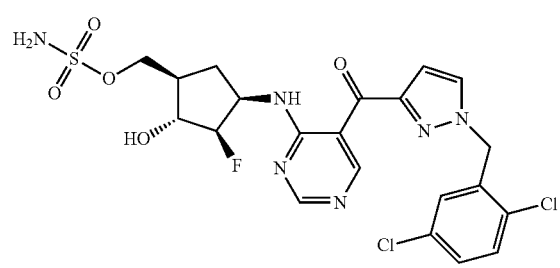
I-308
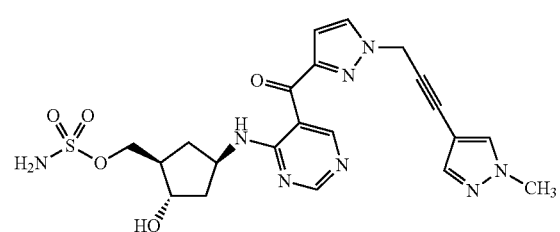
I-309
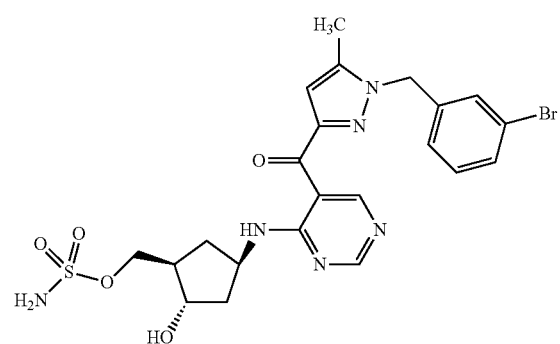
I-310
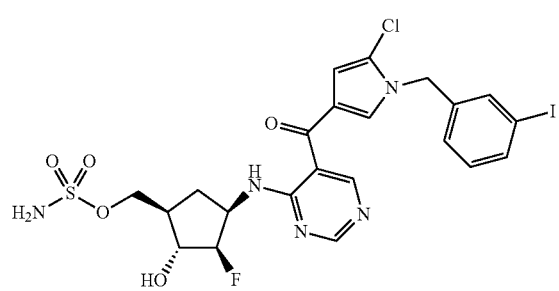
I-311
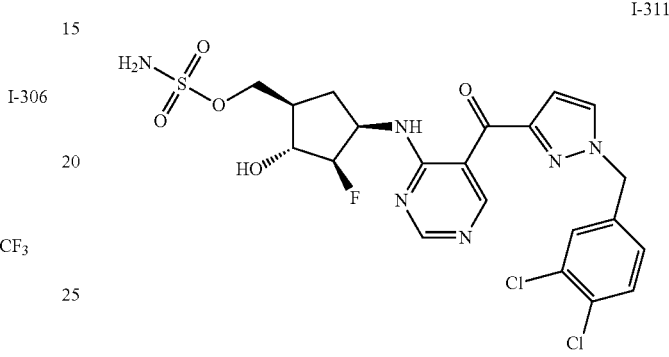
I-312
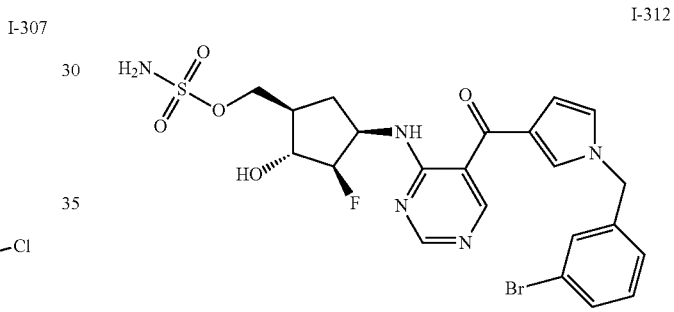
I-313
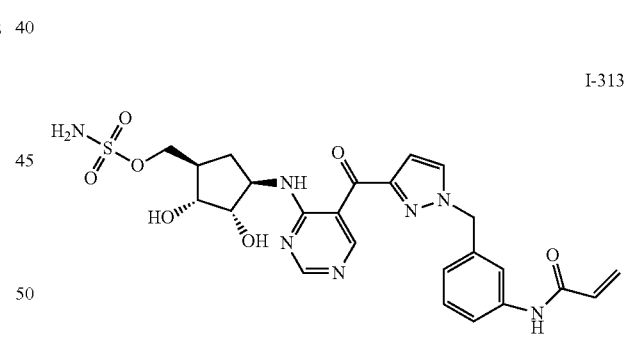
I-314
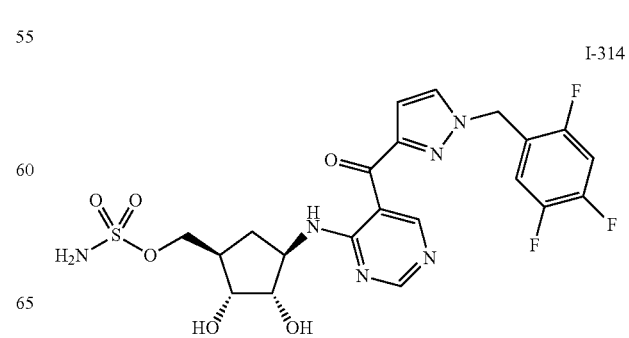

-continued
I-315
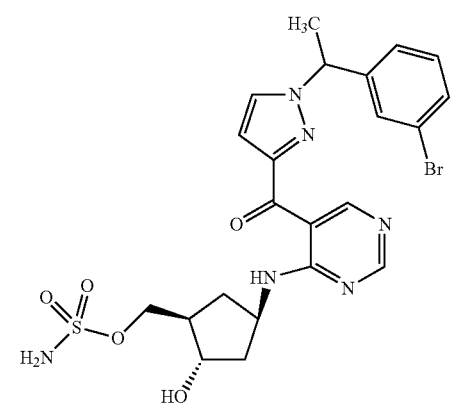
I-316
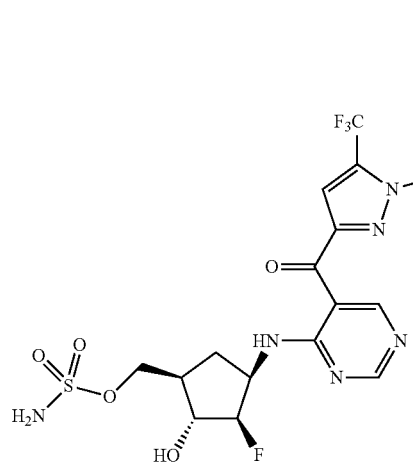
I-317
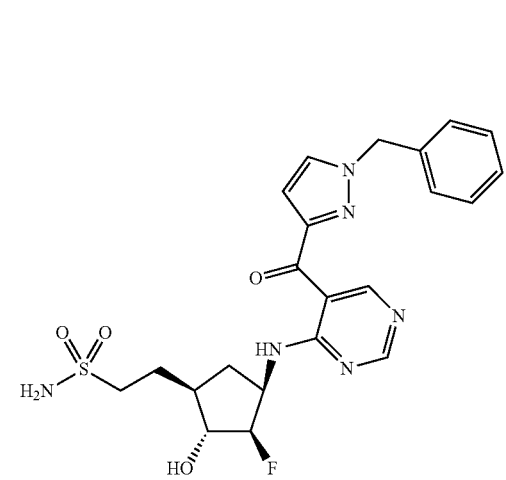
I-318
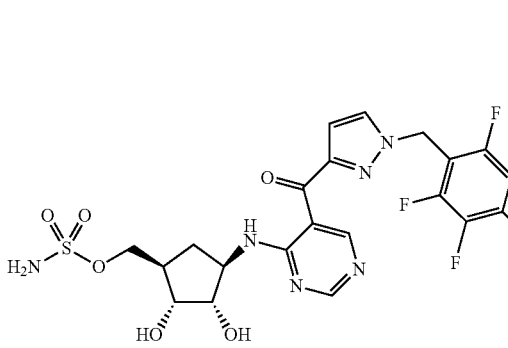
-continued
I-319
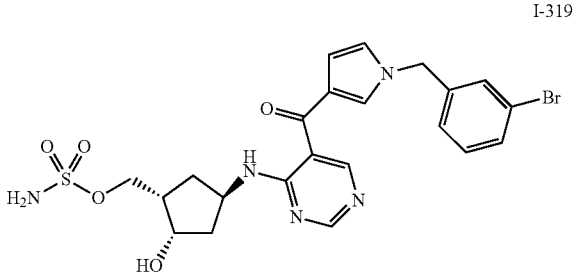
I-320
I-321
I-322
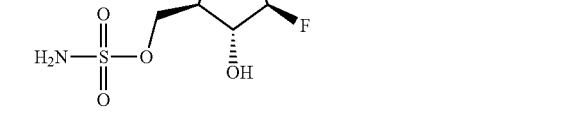

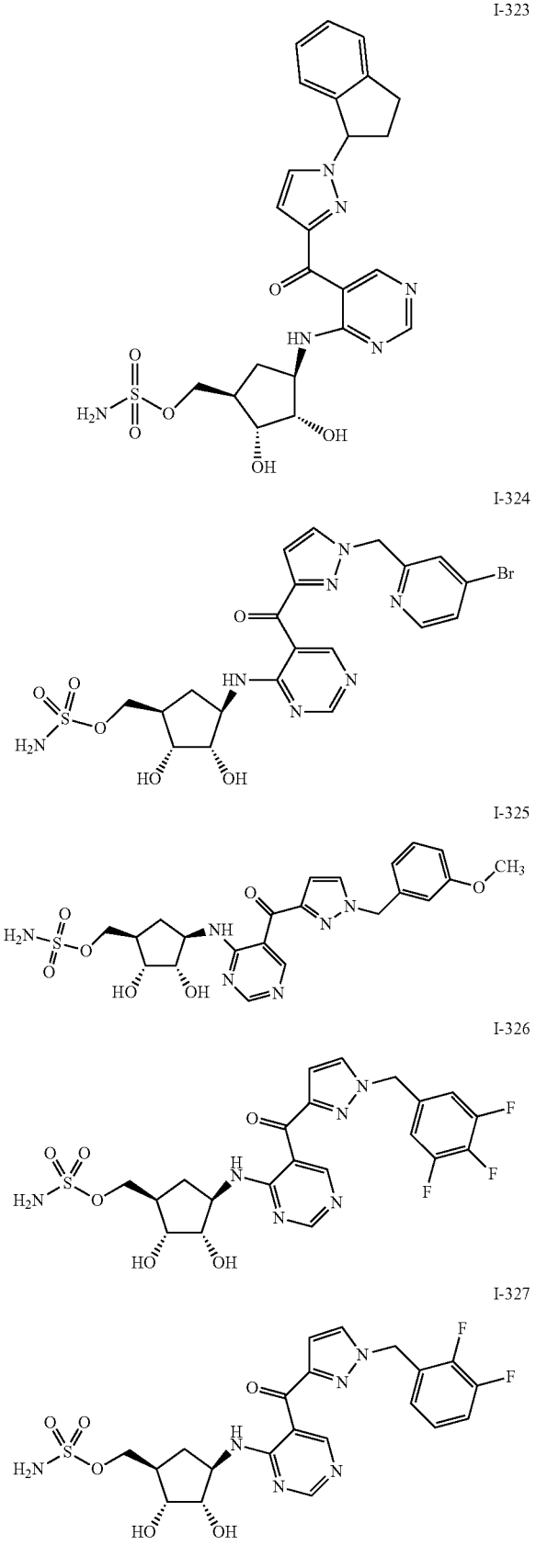
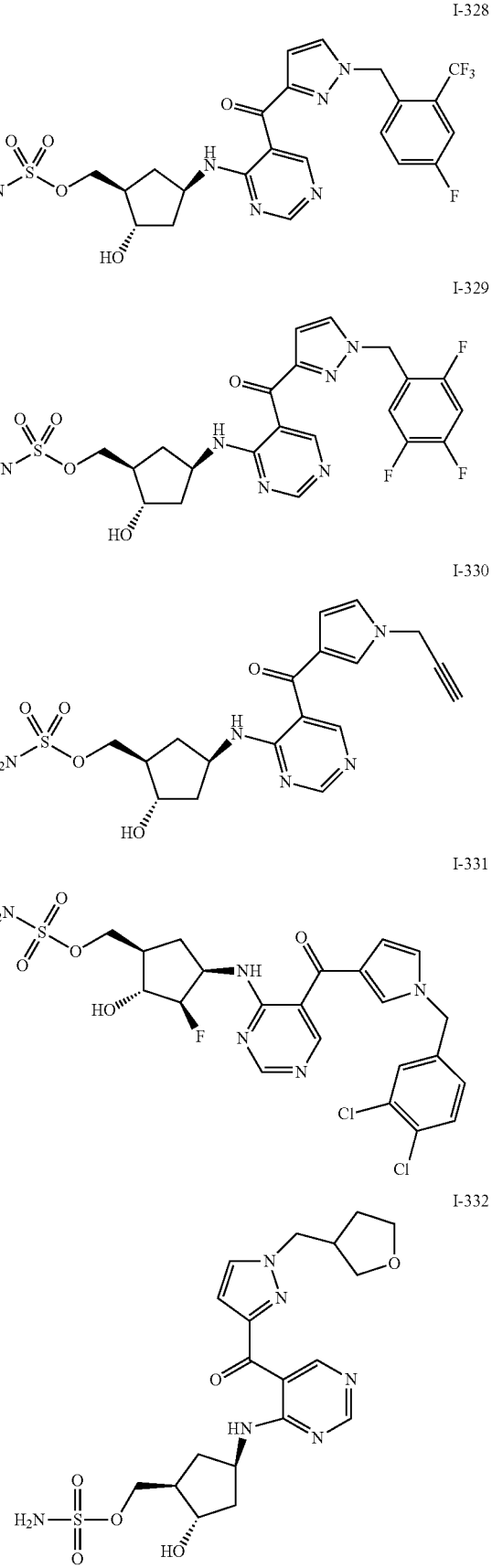

97
-continued
I-333
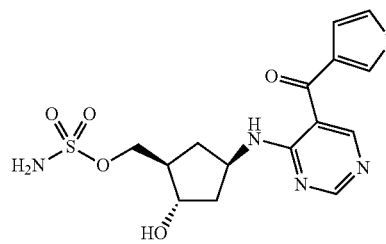
I-334
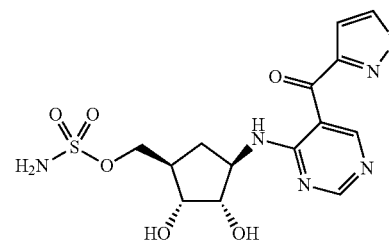
I-335
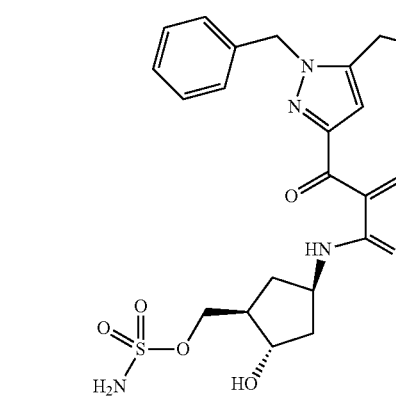
I-336
I-337
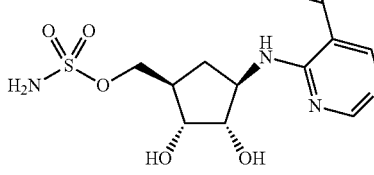
98
-continued
I-338
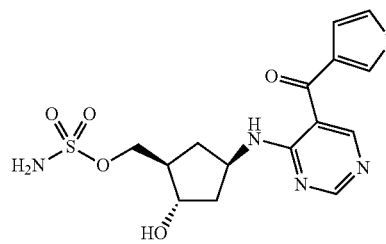
I-339
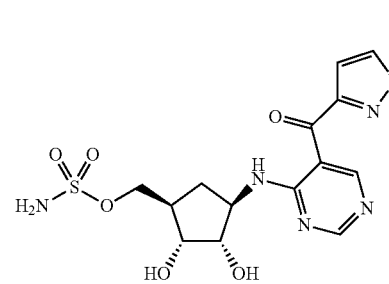
I-340
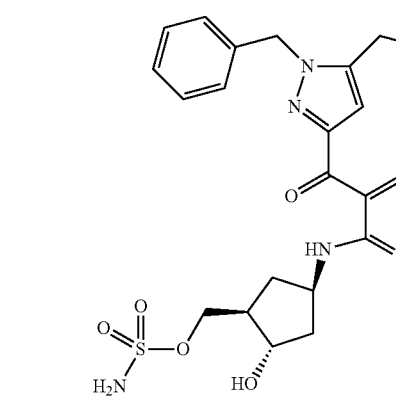
I-341
I-342
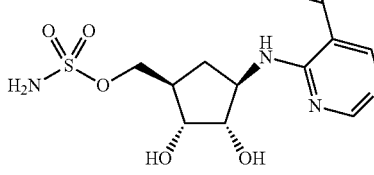
I-343
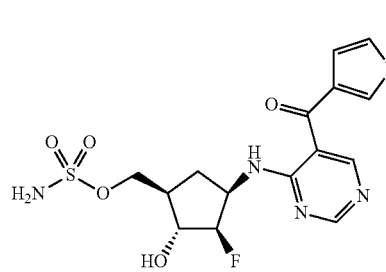

I-344
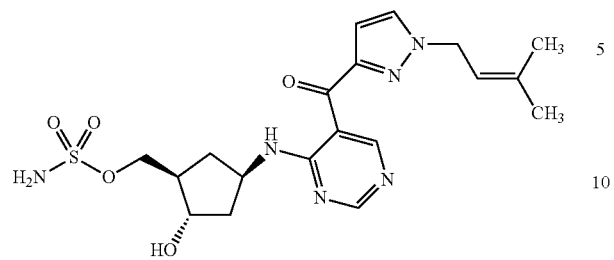
I-345
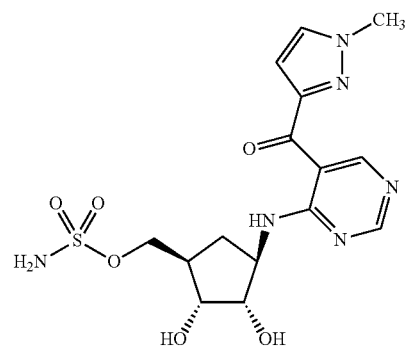
I-346
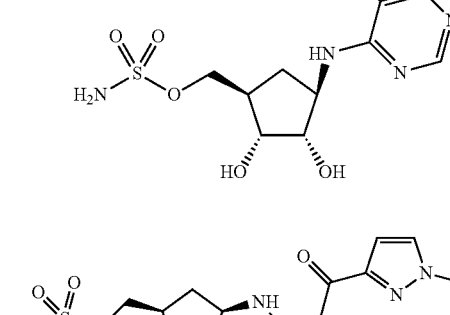
I-347
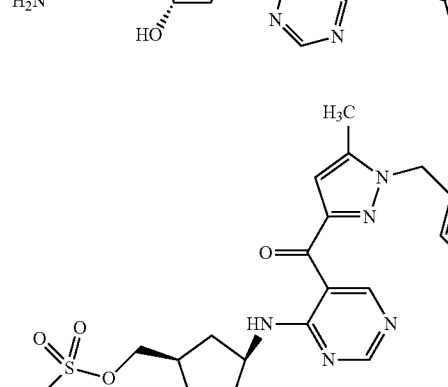
I-348
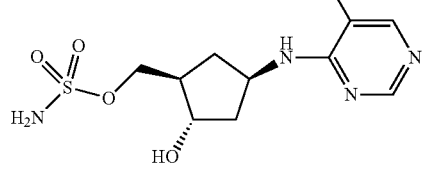
I-349
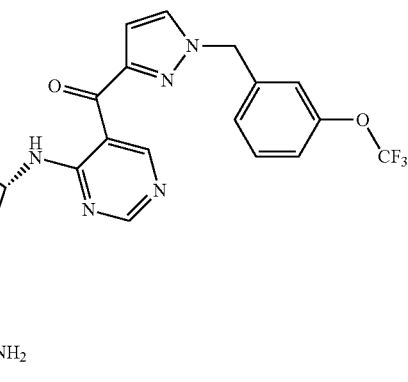
I-350
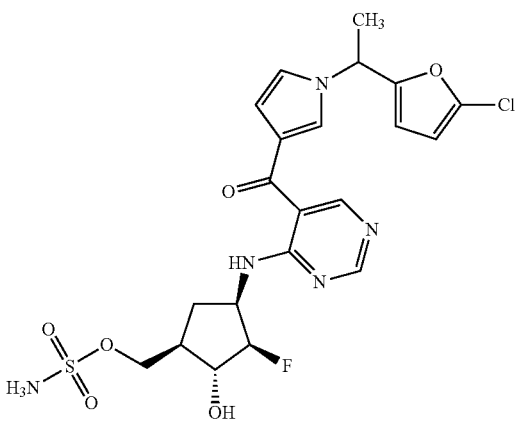
I-351
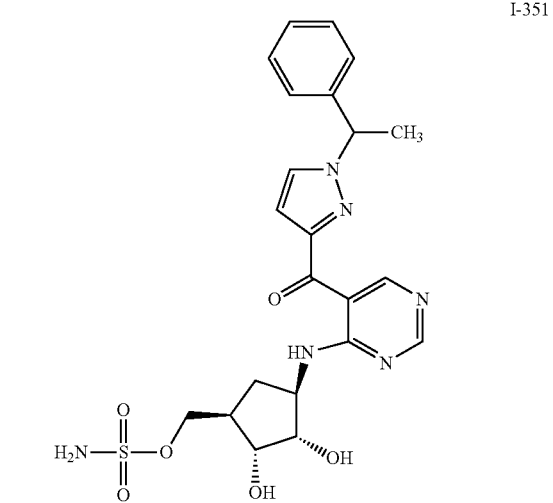

I-352
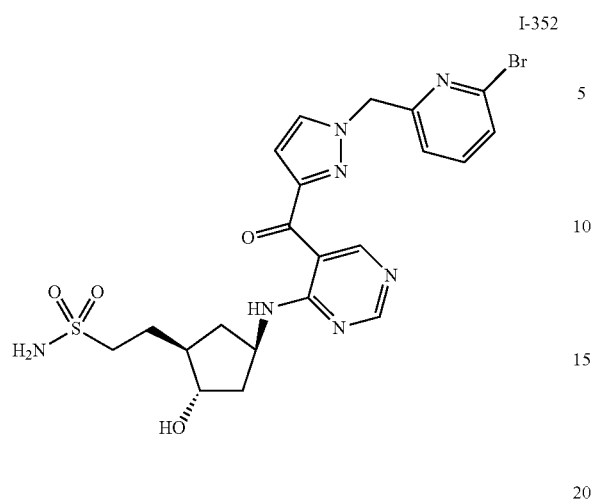
I-355
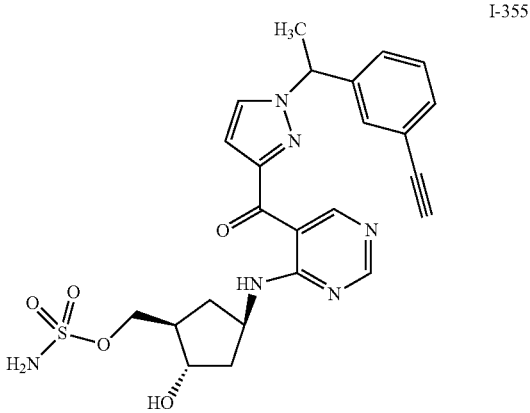
I-353
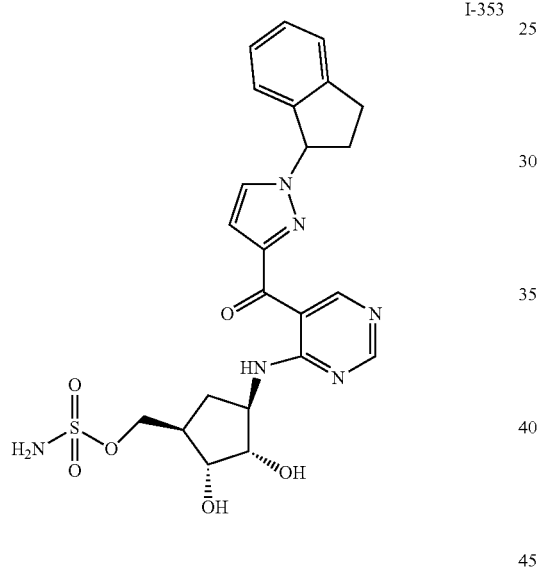
I-356
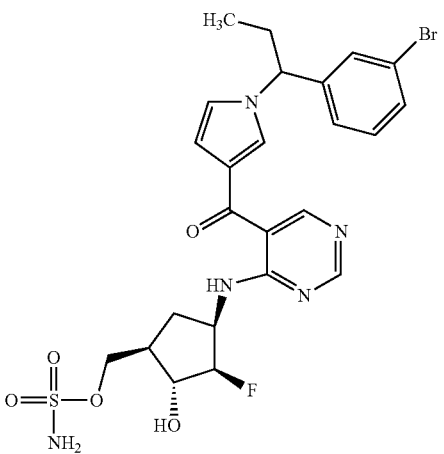
I-354
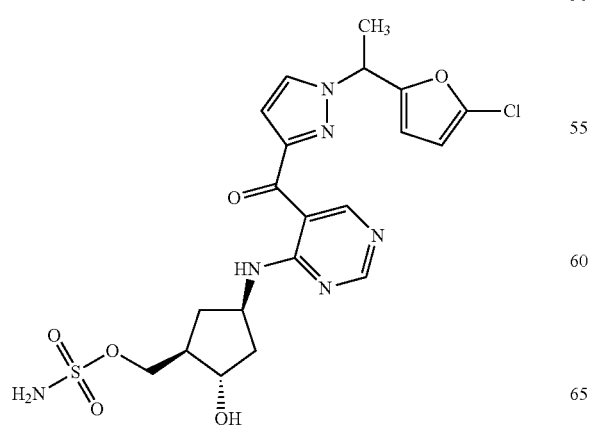
I-357
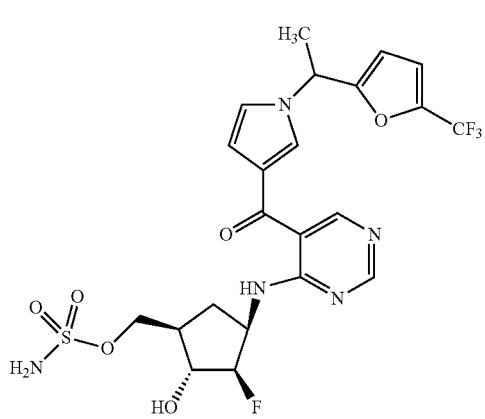

I-358
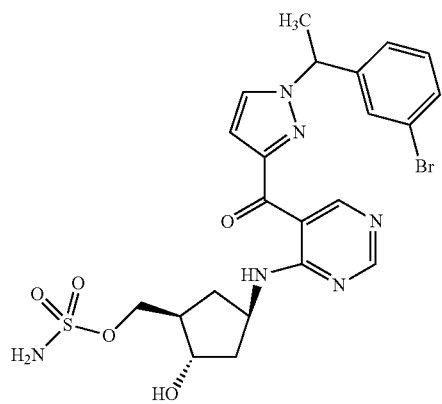
I-361
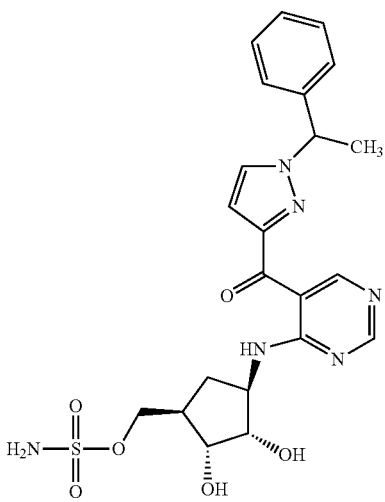
I-359
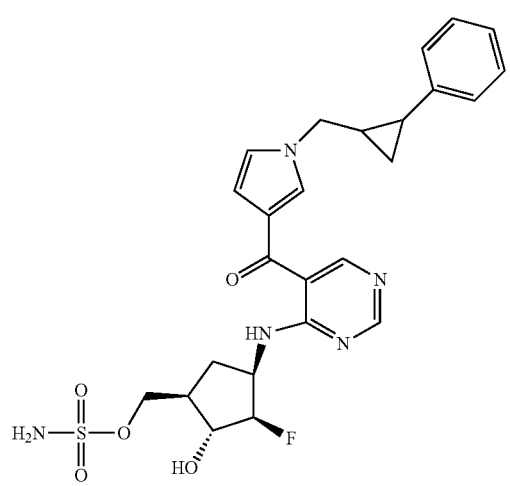
I-362
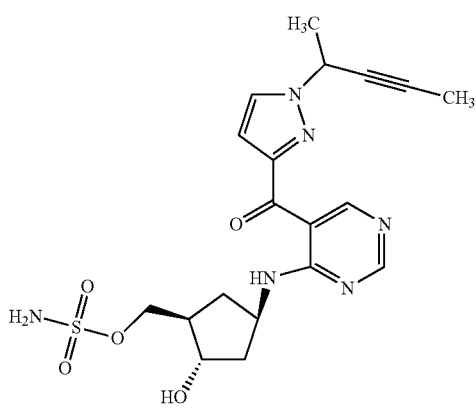
I-360
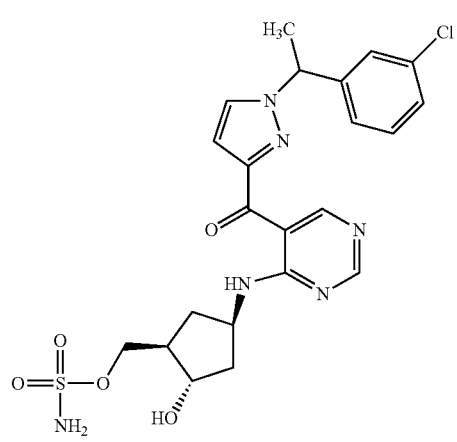
I-363

I-364
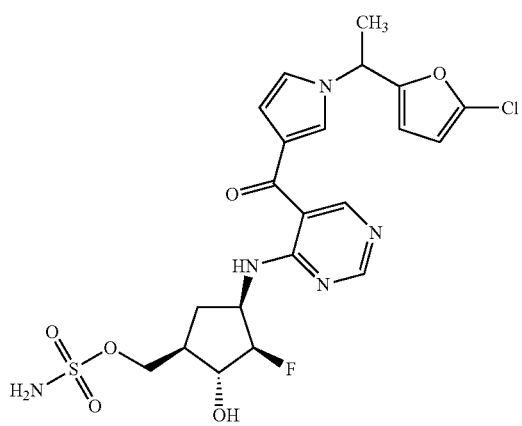
I-365
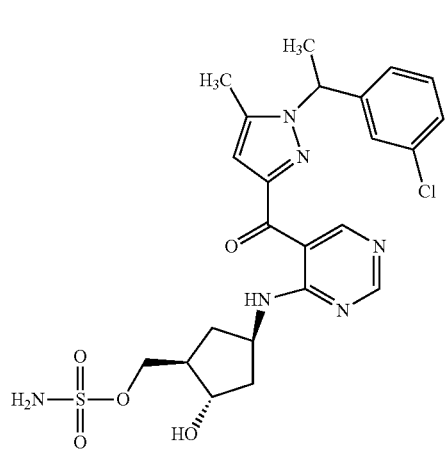
I-366
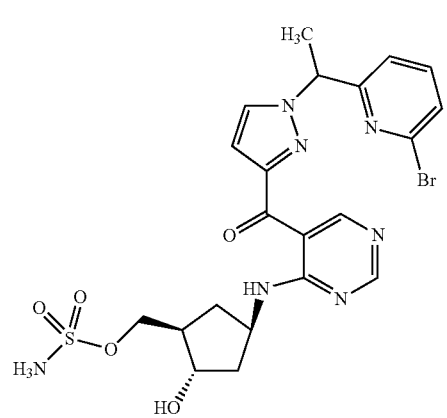
I-367
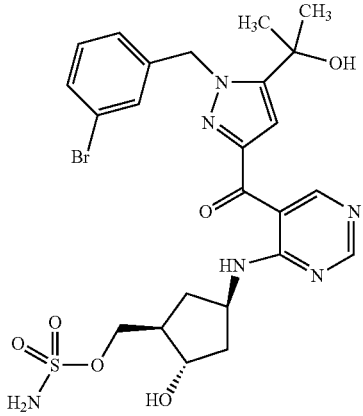
I-368
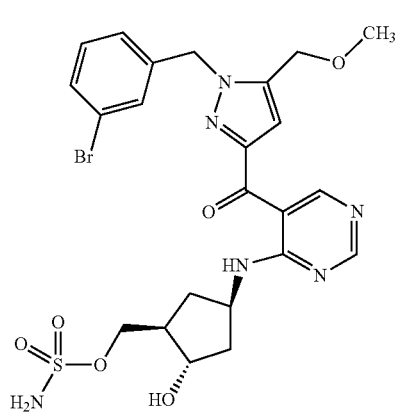
I-369
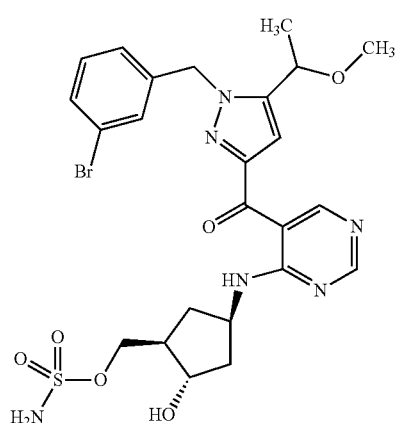
I-369a
I-369b -continued

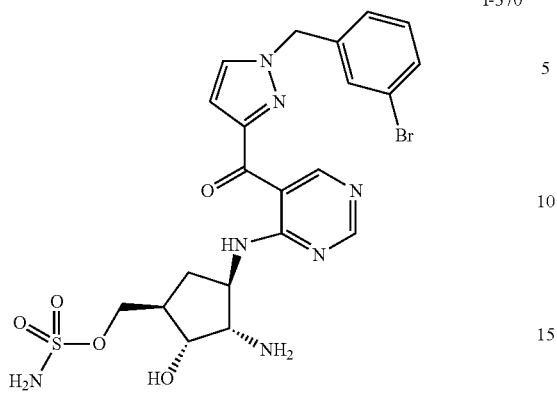

I-370

The compounds in Table 1 may also be identified by the following chemical names:

| Compound | Name |
| --- | --- |
| I-1 | [(1R,2R,3S,4R)-4-{[5-({1-[(3-bromophenyl)sulfonyl]-1H-pyrazol-3-yl}carbonyl)pyrimidin-4-yl]amino}-2,3-dihydroxycyclopentyl]methyl sulfamate |
| I-2 | {(1S,2S,4R)-4-[(5-{[1-(3-bromobenzyl)-1H-pyrazol-3-yl]carbonyl}pyrimidin-4-yl)amino]-2-hydroxycyclopentyl}methyl sulfamate |
| I-3 | [(1R,2S,4R)-2-hydroxy-4-({5-[(1-{[6-(trifluoromethyl)pyridin-2-yl]methyl}-1H-pyrazol-3-yl)carbonyl]pyrimidin-4-yl}amino)cyclopentyl]methyl sulfamate |
| I-4 | [(1R,2R,3S,4R)-2,3-dihydroxy-4-{[5-({1-[2-(3-methyl-1H-pyrazol-1-yl)ethyl]-1H-pyrazol-3-yl}carbonyl)pyrimidin-4-yl]amino}cyclopentyl]methyl sulfamate |
| I-5 | {(1R,2R,3R,4R)-4-[(5-{[1-(3,6-dihydro-2H-pyran-4-ylmethyl)-1H-pyrrol-3-yl]carbonyl}pyrimidin-4-yl)amino]-3-fluoro-2-hydroxycyclopentyl}methyl sulfamate |
| I-6 | {(1S,2S,4R)-4-[(5-{[1-(3-bromobenzyl)-5-methyl-1H-pyrazol-3-yl]carbonyl}pyrimidin-4-yl)amino]-2-hydroxycyclopentyl}methyl sulfamate |
| I-7 | [(1R,2R,3R,4R)-3-fluoro-2-hydroxy-4-{[5-({1-[3-(trifluoromethyl)benzyl]-1H-pyrrol-3-yl}carbonyl)pyrimidin-4-yl]amino}cyclopentyl]methyl sulfamate |
| I-8 | [(1R,2R,3R,4R)-4-{[5-({1-[(6-chloropyridin-2-yl)methyl]-1H-pyrrol-3-yl}carbonyl)pyrimidin-4-yl]amino}-3-fluoro-2-hydroxycyclopentyl]methyl sulfamate |
| I-9 | [(1R,2R,3R,4R)-3-fluoro-2-hydroxy-4-{[5-({1-[(1R,2R)-(2-phenylcyclopropyl)methyl]-1H-pyrrol-3-yl}carbonyl)pyrimidin-4-yl]amino}cyclopentyl]methyl sulfamate or [(1R,2R,3R,4R)-3-fluoro-2-hydroxy-4-{[5-({1-[(1S,2S)-(2-phenylcyclopropyl)methyl]-1H-pyrrol-3-yl}carbonyl)pyrimidin-4-yl]amino}cyclopentyl]methyl sulfamate |
| I-10 | [(1R,2S,4R)-4-{[5-({1-[(1R)-1-(3-ethynylphenyl)ethyl]-1H-pyrazol-3-yl}carbonyl)pyrimidin-4-yl]amino}-2-hydroxycyclopentyl]methyl sulfamate or [(1R,2S,4R)-4-{[5-({1-[(1S)-1-(3-ethynylphenyl)ethyl]-1H-pyrazol-3-yl}carbonyl)pyrimidin-4-yl]amino}-2-hydroxycyclopentyl]methyl sulfamate |
| I-11 | {(1R,2S,4R)-4-[(5-{[1-(3-bromobenzyl)-1H-pyrazol-3-yl]carbonyl}pyrimidin-4-yl)amino]-2-hydroxycyclopentyl}methyl sulfamate |
| I-12 | [(1R,2S,4R)-2-hydroxy-4-{[5-({1-[4-(tetrahydro-2H-pyran-4-yl)but-2-yn-1-yl]-1H-pyrazol-3-yl}carbonyl)pyrimidin-4-yl]amino}cyclopentyl]methyl sulfamate |
| I-13 | {(1R,2R,3R,4R)-3-fluoro-2-hydroxy-4-[(5-{[1-(3-iodobenzyl)-1H-pyrrol-3-yl]carbonyl}pyrimidin-4-yl)amino]cyclopentyl}methyl sulfamate |
| I-14 | {(1R,2S,4R)-4-[(5-{[1-(4-fluoro-3-methylbenzyl)-1H-pyrazol-3-yl]carbonyl}pyrimidin-4-yl)amino]-2-hydroxycyclopentyl}methyl sulfamate |
| I-15 | {(1R,2R,3R,4R)-4-[(5-{[1-(3-bromobenzyl)-1H-pyrazol-3-yl]carbonyl}pyrimidin-4-yl)amino]-3-fluoro-2-hydroxycyclopentyl}methyl sulfamate |
| I-16 | {(1R,2S,4R)-2-hydroxy-4-[(5-{[1-(2,3,6-trifluorobenzyl)-1H-pyrazol-3-yl]carbonyl}pyrimidin-4-yl)amino]cyclopentyl}methyl sulfamate |
| I-17 | {(1R,2S,4R)-4-[(5-{[1-(1-benzofuran-2-ylmethyl)-1H-pyrazol-3-yl]carbonyl}pyrimidin-4-yl)amino]-2-hydroxycyclopentyl}methyl sulfamate |
| I-18 | [(1R,2S,4R)-2-hydroxy-4-{[3-({1-[3-(trifluoromethoxy)benzyl]-1H-pyrazol-3-yl}carbonyl)pyridin-4-yl]amino}cyclopentyl]methyl sulfamate |
| I-19 | [(1R,2R,3R,4R)-3-fluoro-2-hydroxy-4-{[5-({1-[2-oxo-2-(pyrrolidin-1-yl)ethyl]-1H-pyrazol-3-yl}carbonyl)pyrimidin-4-yl]amino}cyclopentyl]methyl sulfamate |

-continued

| Compound | Name |
| --- | --- |
| I-20 | [(1R,2S,4R)-2-hydroxy-4-{[5-({1-[3-(trifluoromethoxy)benzyl]-1H-pyrazol-3-yl}carbonyl)pyrimidin-4-yl]amino}cyclopentyl]methyl sulfamate |
| I-21 | [(1R,2S,4R)-4-{[5-({1-[4-fluoro-3-(trifluoromethyl)benzyl]-1H-pyrrol-3-yl}carbonyl)pyrimidin-4-yl]amino}-2-hydroxycyclopentyl]methyl sulfamate |
| I-22 | {(1R,2S,4R)-4-[(5-{[1-(2-fluoro-3-methylbenzyl)-1H-pyrazol-3-yl]carbonyl}pyrimidin-4-yl)amino]-2-hydroxycyclopentyl}methyl sulfamate |
| I-23 | [(1R,2R,3R,4R)-3-fluoro-2-hydroxy-4-{[5-({1-[3-(trifluoromethoxy)benzyl]-1H-pyrazol-3-yl}carbonyl)pyrimidin-4-yl]amino}cyclopentyl]methyl sulfamate |
| I-24 | [(1R,2R,3R,4R)-4-{[5-({1-[(5-bromo-2-furyl)methyl]-1H-pyrrol-3-yl}carbonyl)pyrimidin-4-yl]amino}-3-fluoro-2-hydroxycyclopentyl]methyl sulfamate |
| I-25 | {(1R,2R,3S,4R)-4-[(5-{[1-(3-cyanobenzyl)-1H-pyrazol-3-yl]carbonyl}pyrimidin-4-yl)amino]-2,3-dihydroxycyclopentyl}methyl sulfamate |
| I-26 | {(1R,2R,3R,4R)-4-[(5-{[1-(4,4-dimethylpent-2-yn-1-yl)-1H-pyrrol-3-yl]carbonyl}pyrimidin-4-yl)amino]-3-fluoro-2-hydroxycyclopentyl}methyl sulfamate |
| I-27 | [(1R,2S,4R)-2-hydroxy-4-{[5-({1-[3-(4-hydroxytetrahydro-2H-pyran-4-yl)prop-2-yn-1-yl]-1H-pyrazol-3-yl}carbonyl)pyrimidin-4-yl]amino}cyclopentyl]methyl sulfamate |
| I-28 | {(1R,2R,3S,4R)-4-[(5-{[1-(2-ethoxyethyl)-1H-pyrazol-3-yl]carbonyl}pyrimidin-4-yl)amino]-2,3-dihydroxycyclopentyl}methyl sulfamate |
| I-29 | [(1R,2S,4R)-4-{[5-({1-[(5-bromopridin-3-yl)methyl]-1H-pyrazol-3-yl}carbonyl)pyrimidin-4-yl]amino}-2-hydroxycyclopentyl]methyl sulfamate |
| I-30 | {(1R,2R,3S,4R)-4-[(5-{[1-(cyclopropylmethyl)-1H-pyrazol-3-yl]carbonyl}pyrimidin-4-yl)amino]-2,3-dihydroxycyclopentyl}methyl sulfamate |
| I-31 | [(1R,2R,3S,4R)-4-({5-[(1-benzyl-5-methyl-1H-pyrazol-3-yl)carbonyl]pyrimidin-4-yl}amino)-2,3-dihydroxycyclopentyl]methyl sulfamate |
| I-32 | {(1R,2S,4R)-4-[(5-{[1-(2-fluoro-5-methylbenzyl)-1H-pyrazol-3-yl]carbonyl}pyrimidin-4-yl)amino]-2-hydroxycyclopentyl}methyl sulfamate |
| I-33 | [(1R,2R,3S,4R)-2,3-dihydroxy-4-{[5-({1-[2-(1H-indol-3-yl)ethyl]-1H-pyrazol-3-yl}carbonyl)pyrimidin-4-yl]amino}cyclopentyl]methyl sulfamate |
| I-34 | [(1R,2R,3S,4R)-4-{[5-({1-[4-chloro-3-(trifluoromethyl)benzyl]-1H-pyrazol-3-yl}carbonyl)pyrimidin-4-yl]amino}-2,3-dihydroxycyclopentyl] methyl sulfamate |
| I-35 | {(1R,2S,4R)-4-[(5-{[1-(2,5-difluorobenzyl)-1H-pyrazol-3-yl]carbonyl}pyrimidin-4-yl)amino]-2-hydroxycyclopentyl}methyl sulfamate |
| I-36 | [(1R,2R,3R,4R)-4-({5-[(5-chloro-1-{[5-(trifluoromethyl)-2-furyl]methyl}-1H-pyrrol-3-yl)carbonyl]pyrimidin-4-yl}amino)-3-fluoro-2-hydroxycyclopentyl]methyl sulfamate |
| I-37 | [(1R,2S,4R)-2-hydroxy-4-{[5-({1-[2-(methylsulfanyl)ethyl]-1H-pyrazol-3-yl}carbonyl)pyrimidin-4-yl]amino}cyclopentyl]methyl sulfamate |
| I-38 | 2-{(1R,2S,4R)-4-[(5-{[1-(3-bromobenzyl)-1H-pyrazol-3-yl]carbonyl}pyrimidin-4-yl)amino]-2-hydroxycyclopentyl}ethanesulfonamide |
| I-39 | [(1R,2S,4R)-2-hydroxy-4-{[5-({1-[2-(trifluoromethoxy)benzyl]-1H-pyrazol-3-yl}carbonyl)pyrimidin-4-yl]amino}cyclopentyl]methyl sulfamate |
| I-40 | {(1R,2R,3S,4R)-4-[(5-{[1-(3-chlorobenzyl)-1H-pyrazol-3-yl]carbonyl}pyrimidin-4-yl)amino]-2,3-dihydroxycyclopentyl}methyl sulfamate |
| I-41 | [(1R,2R,3R,4R)-3-fluoro-2-hydroxy-4-({5-[(1-{[5-(methoxymethyl)-2-furyl]methyl}-1H-pyrrol-3-yl)carbonyl]pyrimidin-4-yl}amino)cyclopentyl]methyl sulfamate |
| I-42 | {(1R,2R,3R,4R)-3-fluoro-2-hydroxy-4-[(5-{[1-(3-iodobenzyl)-1H-pyrazol-3-yl]carbonyl}pyrimidin-4-yl)amino]cyclopentyl}methyl sulfamate |
| I-43 | {(1R,2S,4R)-4-[(5-{[1-(3-bromo-4-chlorobenzyl)-1H-pyrrol-3-yl]carbonyl}pyrimidin-4-yl)amino]-2-hydroxycyclopentyl}methyl sulfamate |
| I-44 | {(1R,2R,3R,4R)-4-[(5-{[1-(3-bromobenzyl)-5-fluoro-1H-pyrrol-3-yl]carbonyl}pyrimidin-4-yl)amino]-3-fluoro-2-hydroxycyclopentyl}methyl sulfamate |
| I-45 | [(1R,2S,4R)-2-hydroxy-4-({5-[(1-{[1-methyl-3-(trifluoromethyl)-1H-pyrazol-5-yl]methyl}-1H-pyrrol-3-yl)carbonyl]pyrimidin-4-yl}amino)cyclopentyl]methyl sulfamate |
| I-46 | [(1R,2R,3S,4R)-4-{[5-({1-[3-fluoro-4-(trifluoromethyl)benzyl]-1H-pyrazol-3-yl}carbonyl)pyrimidin-4-yl]amino}-2,3-dihydroxycyclopentyl]methyl sulfamate |
| I-47 | {(1R,2S,4R)-4-[(5-{[1-(4-chlorobenzyl)-1H-pyrazol-3-yl]carbonyl}pyrimidin-4-yl)amino]-2-hydroxycyclopentyl}methyl sulfamate |
| I-48 | {(1R,2S,4R)-2-hydroxy-4-[(5-{[1-(2-naphthylmethyl)-1H-pyrazol-3-yl]carbonyl}pyrimidin-4-yl)amino]cyclopentyl}methyl sulfamate |
| I-49 | [(1R,2R,3R,4R)-4-{[5-({1-[(3-chloro-1-benzothiophen-2-yl)methyl]-1H-pyrrol-3-yl}carbonyl)pyrimidin-4-yl]amino}-3-fluoro-2-hydroxycyclopentyl]methyl sulfamate |

-continued

| Compound | Name |
|---|---|
| I-50 | [(1R,2S,4R)-4-{5 -({1-[2-chloro-5-(trifluoromethyl)benzyl]-1H-pyrazol-3-yl}carbonyl)pyrimidin-4-yl]amino}-2-hydroxycyclopentyl]methyl sulfamate |
| I-51 | [(1R,2R,3S,4R)-2,3-dihydroxy-4-{[5-({1-[(4-methylpyridin-2-yl)methyl]-1H-pyrazol-3-yl}carbonyl)pyrimidin-4-yl]amino}cyclopentyl]methyl sulfamate |
| I-52 | {(1R,2S,4R)-4-[(3-{[1-(3-chlorobenzyl)-1H-pyrazol-3-yl]carbonyl}pyridin-4-yl)amino]-2-hydroxycyclopentyl}methyl sulfamate |
| I-53 | [(1R,2S,4R)-2-hydroxy-4-({5-[(1-{[2-(trifluoromethyl)pyridin-4-yl]methyl}-1H-pyrazol-3-yl)carbonyl]pyrimidin-4-yl}amino)cyclopentyl]methyl sulfamate |
| I-54 | {(1R,2S,4R)-4-[(6-chloro-5-{[1-(3-chlorobenzyl)-1H-pyrazol-3-yl]carbonyl}pyrimidin-4-yl)amino]-2-hydroxycyclopentyl}methyl sulfamate |
| I-55 | [(1R,2S,4R)-hydroxy-4-{[5-({1-[((1S,2S)-2-methylcyclopropyl)methyl]-1H-pyrazol-3-yl}carbonyl)pyrimidin-4-yl]amino}cyclopentyl]methyl sulfamate and [(1R,2S,4R)-2-hydroxy-4-{[5-({1-[((1R,2R)-2-methylcyclopropyl)methyl]-1H-pyrazol-3-yl}carbonyl)pyrimidin-4-yl]amino}cyclopentyl]methyl sulfamate |
| I-56 | [(1R,2R,3S,4R)-4-({3-[(1-benzyl-1H-pyrazol-3-yl)carbonyl]pyridin-4-yl}amino)-2,3-dihydroxycyclopentyl]methyl sulfamate |
| I-57 | {(1R,2R,3R,4R)-3-fluoro-4-[(5-{[1-(4-fluoro-3-methoxybenzyl)-1H-pyrrol-3-yl]carbonyl}pyrimidin-4-yl)amino]-2-hydroxycyclopentyl}methyl sulfamate |
| I-58 | {(1R,2S,4R)-4-[(5-{[1-(3,4-dichlorobenzyl)-1H-pyrazol-3-yl]carbonyl}pyrimidin-4-yl)amino]-2-hydroxycyclopentyl}methyl sulfamate |
| I-59 | {(1R,2S,4R)-4-[(5-{[1-(4-cyclopentylbut-2-yn-1-yl)-1H-pyrazol-3-yl]carbonyl}pyrimidin-4-yl)amino]-2-hydroxycyclopentyl}methyl sulfamate |
| I-60 | [(1R,2S,4R)-2-hydroxy-4-{[5-({1-[3-(2-hydroxypropan-2-yl)benzyl]-1H-pyrazol-3-yl}carbonyl)pyrimidin-4-yl]amino}cyclopentyl]methyl sulfamate |
| I-61 | {(1R,2R,3R,4R)-4-[(5-{[5-chloro-1-(3-chlorobenzyl)-1H-pyrrol-3-yl]carbonyl}pyrimidin-4-yl)amino]-3-fluoro-2-hydroxycyclopentyl}methyl sulfamate |
| I-62 | {(1R,2S,4R)-4-[(5-{[1-(2,4-difluorobenzyl)-1H-pyrazol-3-yl]carbonyl}pyrimidin-4-yl)amino]-2-hydroxycyclopentyl}methyl sulfamate |
| I-63 | [(1R,2S,4R)-2-hydroxy-4-{[5-({1-[(2-methoxypyridin-3-yl)methyl]-1H-pyrazol-3-yl}carbonyl)pyrimidin-4-yl]amino}cyclopentyl]methyl sulfamate |
| I-64 | {(1R,2S,4R)-4-[(5-{[1-(3--tert-butylbenzyl)-1H-pyrazol-3-yl]carbonyl}pyrimidin-4-yl)amino]-2-hydroxycyclopentyl}methyl sulfamate |
| I-65 | [(1R,2S,4R)-4-{[5-({1-[(1S)-1-(6-bromopyridin-2-yl)ethyl]-1H-pyrazol-3-yl}carbonyl)pyrimidin-4-yl]amino}-2-hydroxycyclopentyl]methyl sulfamate or [(1R,2S,4R)-4-{[5-({1-[(1R)-1-(6-bromopyridin-2-yl)ethyl]-1H-pyrazol-3-yl}carbonyl)pyrimidin-4-yl]amino}-2-hydroxycyclopentyl]methyl sulfamate |
| I-66 | [(1R,2S,4R)-4-({5-[(1-benzyl-5-methyl-1H-pyrazol-3-yl)carbonyl]pyrimidin-4-yl}amino)-2-hydroxycyclopentyl]methyl sulfamate |
| I-67 | [(1R,2R,3S,4R)-4-({5-[(1-{3-[(chloroacetyl)amino]benzyl}-1H-pyrazol-3-yl)carbonyl]pyrimidin-4-yl}amino)-2,3-dihydroxycyclopentyl]methyl sulfamate |
| I-68 | {(1R,2S,4R)-2-hydroxy-4-[(5-{[1-(3-iodobenzyl)-1H-pyrrol-3-yl]carbonyl}pyrimidin-4-yl)amino]cyclopentyl}methyl sulfamate |
| I-69 | [(1R,2S,4R)-4-{[5-({1-[2,4-bis(trifluoromethyl)benzyl]-1H-pyrazol-3-yl}carbonyl)pyrimidin-4-yl]amino}-2-hydroxycyclopentyl]methyl sulfamate |
| I-70 | [(1R,2R,3S,4R)-4-{[5-({1-[(4-chloropyridin-2-yl)methyl]-1H-pyrazol-3-yl}carbonyl)pyrimidin-4-yI]amino}-2,3-dihydroxycyclopentyl]methyl sulfamate |
| I-71 | {(1R,2R,3R,4R)-4-[(5-{[1-(3-bromobenzyl)-5-methyl-1H-pyrrol-3-yl]carbonyl}pyrimidin-4-yl)amino]-3-fluoro-2-hydroxycyclopentyl}methyl sulfamate |
| I-72 | {(1R,2S,4R)-4-[(5-{[1-(3-bromo-4-fluorobenzyl)-1H-pyrazol-3-yl]carbonyl}pyrimidin-4-yl)amino]-2-hydroxycyclopentyl}methyl sulfamate |
| I-73 | [(1R,2S,4R)-2-hydroxy-4-({5-[(1-{[2-(trifluoromethyl)-1,3-thiazol-5-yl]methyl}-1H-pyrrol-3-yl)carbonyl]pyrimidin-4-yl}amino)cyclopentyl]methyl sulfamate |
| I-74 | [(1R,2R,3S,4R)-2,3-dihydroxy-4-{[5-({1-[3-((R)-vinylsulfinyl)benzyl]-1H-pyrazol-3-yl}carbonyl)pyrimidin-4-yl]amino}cyclopentyl]methyl sulfamate and [(1R,2R,3S,4R)-2,3-dihydroxy-4-{[5-({1-[3-((S)-vinylsulfinyl)benzyl]-1H-pyrazol-3-yl}carbonyl)pyrimidin-4-yl]amino}cyclopentyl]methyl sulfamate |
| I-75 | {(1R,2R,3R,4R)-3-fluoro-2-hydroxy-4-[(5-{[1-(4-methoxy-4-methylpent-2-yn-1-yl)-1H-pyrrol-3-yl]carbonyl}pyrimidin-4-yl)amino]cyclopentyl}methyl sulfamate |
| I-76 | {(1R,2S,4R)-2-hydroxy-4-[(5-{[1-(2-phenylpropan-2-yl)-1H-pyrrol-3-yl]carbonyl}pyrimidin-4-yl)amino]cyclopentyl}methyl sulfamate |
| I-77 | [(1R,2S,4R)-4-({5-[(1-{[(2R)-5,5-dimethyltetrahydrofuran-2-yl]methyl}-1H-pyrazol-3-yl)carbonyl]pyrimidin-4-yl}amino)-2-hydroxycyclopentyl]methyl sulfamate and [(1R,2S,4R)-4-({5-[(1-{[(2S)-5,5-dimethyltetrahydrofuran-2-yl]methyl}-1H-pyrazol-3-yl)carbonyl]pyrimidin-4-yl}amino)-2-hydroxycyclopentyl]methyl sulfamate |
| I-78 | {(1R,2S,4R)-4-[(3-{[1-(3,4-dichlorobenzyl)-1H-pyrazol-3-yl]carbonyl}pyridin-4-yl)amino]-2-hydroxycyclopentyl}methyl sulfamate |

-continued

| Compound | Name |
|---|---|
| I-79 | [(1R,2S,4R)-4-{[5-({1-[(1S)-1-(5-chloro-2-furyl)ethyl]-1H-pyrazol-3-yl}carbonyl)pyrimidin-4-yl]amino}-2-hydroxycyclopentyl]methyl sulfamate or [(1R,2S,4R)-4-{[5-({1-[(1R)-1-(5-chloro-2-furyl)ethyl]-1H-pyrazol-3-yl}carbonyl)pyrimidin-4-yl]amino}-2-hydroxycyclopentyl]methyl sulfamate |
| I-80 | [(1R,2S,4R)-2-hydroxy-4-{[5-({1-[(1-methyl-2-oxo-1,2-dihydropyridin-3-yl)methyl]-1H-pyrazol-3-yl}carbonyl)pyrimidin-4-yl]amino}cyclopentyl]methyl sulfamate |
| I-81 | {(1R,2R,3S,4R)-4-[(3-{[1-(3-chlorobenzyl)-1H-pyrazol-3-yl]carbonyl}pyridin-4-yl)amino]-2,3-dihydroxycyclopentyl}methyl sulfamate |
| I-82 | {(1R,2R,3S,4R)-4-[(5-{[1-(cyclohexylmethyl)-1H-pyrazol-3-yl]carbonyl}pyrimidin-4-yl)amino]-2,3-dihydroxycyclopentyl}methyl sulfamate |
| I-83 | [(1R,2S,4R)-2-hydroxy-4-{[3-({1-[3-(trifluoromethoxy)benzyl]-1H-pyrrol-3-yl}carbonyl)pyridin-4-yl]amino}cyclopentyl]methyl sulfamate |
| I-84 | [(1R,2S,4R)-2-hydroxy-4-{[5-({1-[3-(prop-1-yn-1-yl)benzyl]-1H-pyrazol-3-yl}carbonyl)pyrimidin-4-yl]amino}cyclopentyl]methyl sulfamate |
| I-85 | {(1R,2S,4R)-4-[(5-{[1-(3-ethynylbenzyl)-1H-pyrazol-3-yl]carbonyl}pyrimidin-4-yl)amino]-2-hydroxycyclopentyl}methyl sulfamate |
| I-86 | {(1R,2S,4R)-2-hydroxy-4-[(5-{[1-(2S)-(pent-3-yn-2-yl)-1H-pyrazol-3-yl]carbonyl}pyrimidin-4-yl)amino]cyclopentyl}methyl sulfamate or {(1R,2S,4R)-2-hydroxy-4-[(5-{[1-(2R)-(pent-3-yn-2-yl)-1H-pyrazol-3-yl]carbonyl}pyrimidin-4-yl)amino]cyclopentyl}methyl sulfamate |
| I-87 | [(1R,2R,3R,4R)-4-({5-[(1-{[5-(difluoromethyl)-2-furyl]methyl}-1H-pyrrol-3-yl)carbonyl]pyrimidin-4-yl}amino)-3-fluoro-2-hydroxycyclopentyl]methyl sulfamate |
| I-88 | {(1R,2R,3S,4R)-2,3-dihydroxy-4-[(5-{[1-(2,4,6-trifluorobenzyl)-1H-pyrazol-3-yl]carbonyl}pyrimidin-4-yl)amino]cyclopentyl}methyl sulfamate |
| I-89 | {(1R,2R,3S,4R)-4-[(5-{[1-(3-chloro-4-fluorobenzyl)-1H-pyrazol-3-yl]carbonyl}pyrimidin-4-yl)amino]-2,3-dihydroxycyclopentyl}methyl sulfamate |
| I-90 | {(1R,2S,4R)-4-[(5-{[1-(3-bromobenzyl)-5-(hydroxymethyl)-1H-pyrazol-3-yl]carbonyl}pyrimidin-4-yl)amino]-2-hydroxycyclopentyl}methyl sulfamate |
| I-91 | {(1R,2R,3S,4R)-4-[(5-{[1-(2,5-difluorobenzyl)-1H-pyrazol-3-yl]carbonyl}pyrimidin-4-yl)amino]-2,3-dihydroxycyclopentyl}methyl sulfamate |
| I-92 | {(1R,2R,3R,4R)-4-[(5-{[1-(3-bromo-4-fluorobenzyl)-1H-pyrazol-3-yl]carbonyl}pyrimidin-4-yl)amino]-3-fluoro-2-hydroxycyclopentyl}methyl sulfamate |
| I-93 | {(1R,2S,4R)-4-[(5-{[1-(cyclohexylmethyl)-1H-pyrazol-3-yl]carbonyl}pyrimidin-4-yl)amino]-2-hydroxycyclocarbonyl}methyl sulfamate |
| I-94 | {(1R,2R,3R,4R)-4-[(5-{[1-benzyl-5-(trifluoromethyl)-1H-pyrrol-3-yl]carbonyl}pyrimidin-4-yl)amino]-3-fluoro-2-hydroxycyclopentyl}methyl sulfamate |
| I-95 | [(1R,2S,4R)-4-{[5-({1-[(6-chloropyridin-2-yl)methyl]-1H-pyrazol-3-yl}carbonyl)pyrimidin-4-yl]amino}-2-hydroxycyclopentyl]methyl sulfamate |
| I-96 | [(1R,2R,3S,4R)-4-{[5-({1-[2-(3-bromophenyl)-2-oxoethyl]-1H-pyrazol-3-yl}carbonyl)pyrimidin-4-yl]amino}-2,3-dihydroxycyclopentyl]methyl sulfamate |
| I-97 | {(1R,2S,4R)-4-[(3-{[1-(3-chloro-4-fluorobenzyl)-1H-pyrazol-3-yl]carbonyl}pyridin-4-yl)amino]-2-hydroxycyclopentyl}methyl sulfamate |
| I-98 | [(1R,2R,3S,4R)-2,3-dihydroxy-4-{[5-({1-[2-(trifluoromethoxy)benzyl]-1H-pyrazol-3-yl}carbonyl)pyrimidin-4-yl]amino}cyclopentyl]methyl sulfamate |
| I-99 | [(1R,2S,4R)-4-{[5-({1-[(6-chloropyridin-2-yl)methyl]-5-methyl-1H-pyrazol-3-yl}carbonyl)pyrimidin-4-yl]amino}-2-hydroxycyclopentyl]methyl sulfamate |
| I-100 | [(1R,2R,3S,4R)-4-{[5-({1-[4-chloro-3-(trifluoromethoxy)benzyl]-1H-pyrazol-3-yl}carbonyl)pyrimidin-4-yl]amino}-2,3-dihydroxycyclopentyl]methyl sulfamate |
| I-101 | [(1R,2S,4R)-4-{[5-({1-[(5-chloro-2-furyl)methyl]-5-methyl-1H-pyrazol-3-yl}carbonyl)pyrimidin-4-yl]amino}-2-hydroxycyclopentyl]methyl sulfamate |
| I-102 | [(1R,2R,3R,4R)-3-fluoro-2-hydroxy-4-{[5-({1-[3-(trifluoromethyl)benzyl]-1H-pyrazol-3-yl}carbonyl)pyrimidin-4-yl]amino}cyclopentyl]methyl sulfamate |
| I-103 | {(1R,2R,3S,4R)-2,3-dihydroxy-4-[(5-{[1-(2-naphthylmethyl)-1H-pyrazol-3-yl]carbonyl}pyrimidin-4-yl)amino]cyclopentyl}methyl sulfamate |
| I-104 | {(1R,2S,4R)-4-[(5-{[1-(2-chloro-5-iodobenzyl)-1H-pyrazol-3-yl]carbonyl}pyrimidin-4-yl)amino]-2-hydroxycyclopentyl}methyl sulfamate |
| I-105 | {(1R,2R,3R,4R)-4-[(5-{[1-(3-bromobenzyl)-2,5-dichloro-1H-pyrrol-3-yl]carbonyl}pyrimidin-4-yl)amino]-3-fluoro-2-hydroxycyclopentyl}methyl sulfamate |
| I-106 | {(1R,2R,3S,4R)-4-[(5-{[1-(4-fluorobenzyl)-1H-pyrazol-3-yl]carbonyl}pyrimidin-4-yl)amino]-2,3-dihydroxycyclopentyl}methyl sulfamate |
| I-107 | [(1R,2S,4R)-4-{[5-({1-[(2E)-but-2-en-1-yl]-1H-pyrazol-3-yl}carbonyl)pyrimidin-4-yl]amino}-2-hydroxycyclopentyl]methyl sulfamate |
| I-108 | {(1R,2S,4R)-4-[(5-{[1-(cyanomethyl)-1H-pyrazol-3-yl]carbonyl}pyrimidin-4-yl)amino]-2-hydroxycyclopentyl}methyl sulfamate |

| Compound | Name |
| --- | --- |
| I-109 | [(1R,2S,4R)-2-hydroxy-4-({5-[(1-{[6-(2-hydroxypropan-2-yl)pyridin-2-yl]methyl}-1H-pyrazol-3-yl)carbonyl]pyrimidin-4-yl}amino)cyclopentyl]methyl sulfamate |
| I-110 | {(1R,2R,3R,4R)-4-[(5-{[1-(1-benzofuran-2-ylmethyl)-1H-pyrrol-3-yl]carbonyl}pyrimidin-4-yl)amino]-3-fluoro-2-hydroxycyclopentyl}methyl sulfamate |
| I-111 | {(1R,2S,4R)-4-[(5-{[1-(3-bromobenzyl)-4-chloro-1H-pyrazol-3-yl]carbonyl}pyrimidin-4-yl)amino]-2-hydroxycyclopentyl}methyl sulfamate |
| I-112 | {(1R,2R,3S,4R)-4-[(5-{[1-(4-chloro-3-fluorobenzyl)-1H-pyrazol-3-yl]carbonyl}pyrimidin-4-yl)amino]-2,3-dihydroxycyclopentyl}methyl sulfamate |
| I-113 | {(1R,2S,4R)-4-[(5-{[1-(4,4-dimethylpent-2-yn-1-yl)-1H-pyrazol-3-yl]carbonyl}pyrimidin-4-yl)amino]-2-hydroxycyclopentyl}methyl sulfamate |
| I-114 | [(1R,2R,3R,4R)-3-fluoro-2-hydroxy-4-({5-[(1-{[4-(trifluoromethyl)-2-furyl]methyl}-1H-pyrrol-3-yl)carbonyl]pyrimidin-4-yl}amino)cyclopentyl]methyl sulfamate |
| I-115 | {(1R,2S,4R)-2-hydroxy-4-[(5-{[1-(pent-3-yn-1-yl)-1H-pyrazol-3-yl]carbonyl}pyrimidin-4-yl)amino]cyclopentyl}methyl sulfamate |
| I-116 | [(1R,2R,3R,4R)-4-({5-[(1-{3-[acryloyl(methyl)amino]benzyl}-1H-pyrazol-3-yl)carbonyl]pyrimidin-4-yl}amino)-3-fluoro-2-hydroxycyclopentyl]methyl sulfamate |
| I-117 | [(1R,2S,4R)-4-{[5-({1-[3-(difluoromethoxy)benzyl]-1H-pyrazol-3-yl}carbonyl)pyrimidin-4-yl]amino}-2-hydroxycyclopentyl]methyl sulfamate |
| I-118 | [(1R,2R,3S,4R)-2,3-dihydroxy-4-{[5-({1-[2-(1-naphthyl)ethyl]-1H-pyrazol-3-yl}carbonyl)pyrimidin-4-yl]amino}cyclopentyl]methyl sulfamate |
| I-119 | [(1R,2R,3S,4R)-2,3-dihydroxy-4-{[5-({1-[3-(trifluoromethyl)benzyl]-1H-pyrazol-3-yl}carbonyl)pyrimidin-4-yl]amino}cyclopentyl]methyl sulfamate |
| I-120 | [(1R,2S,4R)-2-hydroxy-4-({5-[(1-{[6-(3-hydroxyoxetan-3-yl)pyridin-2-yl]methyl) 1H pyrazol-3-yl)carbonyl]pyrimidin-4-yl}amino)cyclopentyl]methyl sulfamate |
| I-121 | [(1R,2R,3S,4R)-4-{[5-({1-[4-fluoro-2-(trifluoromethyl)benzyl]-1H-pyrazol-3-yl}carbonyl)pyrimidin-4-yl]amino}-2,3-dihydroxycyclopentyl]methyl sulfamate |
| I-122 | {(1R,2R,3R,4R)-4-[(5-{[1-(3-chloro-4-fluorobenzyl)-1H-pyrazol-3-yl]carbonyl}pyrimidin-4-yl)amino]-3-fluoro-2-hydroxycyclopentyl}methyl sulfamate |
| I-123 | {(1R,2R,3S,4R)-4-[(5-{[1-(3-fluorobenzyl)-1H-pyrazol-3-yl]carbonyl}pyrimidin-4-yl)amino]-2,3-dihydroxycyclopentyl}methyl sulfamate |
| I-124 | {(1R,2R,3R,4R)-4-[(3-{[1-(3-chlorobenzyl)-1H-pyrrol-3-yl]carbonyl}pyridin-4-yl)amino]-3-fluoro-2-hydroxycyclopentyl}methyl sulfamate |
| I-125 | {(1R,2R,3S,4R)-2,3-dihydroxy-4-[(5-{[1-(2-oxo-2-phenylethyl)-1H-pyrazol-3-yl]carbonyl}pyrimidin-4-yl)amino]cyclopentyl}methyl sulfamate |
| I-126 | [(1R,2R,3S,4R)-4-({5-[(1-{4-chloro-3-[(trifluoromethyl)sulfanyl]benzyl}-1H-pyrazol-3-yl)carbonyl]pyrimidin-4-yl}amino)-2,3-dihydroxycyclopentyl]methyl sulfamate |
| I-127 | {(1R,2R,3R,4R)-4-[(5-{[1-(3-bromo-4-chlorobenzyl)-1H-pyrazol-3-yl]carbonyl}pyrimidin-4-yl)amino]-3-fluoro-2-hydroxycyclopentyl}methyl sulfamate |
| I-128 | {(1R,2S,4R)-2-hydroxy-4-[(5-{[1-(3-methylbenzyl)-1H-pyrazol-3-yl]carbonyl}pyrimidin-4-yl)amino]cyclopentyl}methyl sulfamate |
| I-129 | [(1R,2S,4R)-2-hydroxy-4-{[5-({1-[3-(trifluoromethyl)benzyl]-1H-pyrrol-3-yl}carbonyl)pyrimidin-4-yl]amino}cyclopentyl]methyl sulfamate |
| I-130 | [(1R,2R,3S,4R)-2,3-dihydroxy-4-({5-[(1-{[5-(trifluoromethyl)-2-furyl]methyl}-1H-pyrazol-3-yl)carbonyl]pyrimidin-4-yl}amino)cyclopentyl]methyl sulfamate |
| I-131 | [(1R,2R,3R,4R)-3-fluoro-2-hydroxy-4-{[5-({1-[3-(trifluoromethoxy)benzyl]-1H-pyrrol-3-yl}carbonyl)pyrimidin-4-yl]amino}cyclopentyl]methyl sulfamate |
| I-132 | [(1R,2R,3R,4R)-3-fluoro-2-hydroxy-4-{[3-({1-[3-(trifluoromethoxy)benzyl]-1H-pyrrol-3-yl}carbonyl)pyridin-4-yl]amino}cyclopentyl]methyl sulfamate |
| I-133 | [(1R,2S,4R)-4-{[5-({1-[(1S)-1-(3-chlorophenyl)ethyl]-1H-pyrazol-3-yl}carbonyl)pyrimidin-4-yl]amino}-2-hydroxycyclopentyl]methyl sulfamate or [(1R,2S,4R)-4-{[5-({1-[(1R)-1-(3-chlorophenyl)ethyl]-1H-pyrazol-3-yl}carbonyl)pyrimidin-4-yl]amino}-2-hydroxycyclopentyl]methyl sulfamate |
| I-134 | [(1R,2R,3S,4R)-4-{[5-({1-[4-fluoro-3-(trifluoromethoxy)benzyl]-1H-pyrazol-3-yl}carbonyl)pyrimidin-4-yl]amino}-2,3-dihydroxycyclopentyl]methyl sulfamate |
| I-135 | [(1R,2R,3R,4R)-4-({5-[(1-benzyl-1H-pyrazol-3-yl)carbonyl]pyrimidin-4-yl}amino)-2,3-dihydroxycyclopentyl]methyl sulfamate |
| I-136 | N-({(1R,2R,3S,4R)-4-[(5-{[1-(3-chlorobenzyl)-1H-pyrazol-3-yl]carbonyl}pyrimidin-4-yl)amino]-2,3-dihydroxycyclopentyl}methyl)sulfuric diamide |
| I-137 | [(1R,2S,4R)-2-hydroxy-4-{[5-({1-[3-(trimethylsilyl)benzyl]-1H-pyrazol-3-yl}carbonyl)pyrimidin-4-yl]amino}cyclopentyl]methyl sulfamate |

-continued

| Compound | Name |
|---|---|
| I-138 | [(1R,2R,3S,4R)-2,3-dihydroxy-4-({5-[(5-methyl-1-{[5-(trifluoromethyl)-2-furyl]methyl}-1H-pyrazol-3-yl)carbonyl]pyrimidin-4-yl}amino)cyclopentyl]methyl sulfamate |
| I-139 | [(1R,2R,3S,4R)-4-({5-[(1-benzyl-4-chloro-1H-pyrazol-3-yl]carbonyl]pyrimidin-4-yl}amino)-2,3-dihydroxycyclopentyl]methyl sulfamate |
| I-140 | [(1R,2S,4R)-2-hydroxy-4-{[5-({1-[3-(trifluoromethyl)benzyl]-1H-pyrazol-3-yl}carbonyl)pyrimidin-4-yl]amino}cyclopentyl]methyl sulfamate |
| I-141 | {(1R,2R,3R,4R)-4-[(5-{[1-(3-chloro-4-fluorobenzyl)-1H-pyrrol-3-yl]carbonyl}pyrimidin-4-yl)amino]-3-fluoro-2-hydroxycyclopentyl}methyl sulfamate |
| I-142 | [(1R,2R,3S,4R)-4-({5-[(1-benzyl-1H-pyrazol-3-yl)carbonyl]pyrimidin-4-yl}amino)-2,3-dihydroxycyclopentyl]methyl sulfamate |
| I-143 | {(1R,2R,3R,4R)-4-[(5-{[1-(3-bromo-4-fluorobenzyl)-1H-pyrrol-3-yl]carbonyl}pyrimidin-4-yl)amino]-3-fluoro-2-hydroxycyclopentyl}methyl sulfamate |
| I-144 | {(1R,2S,4R)-2-hydroxy-4-[(5-{[1-(imidazo[1,2-a]pyridin-6-ylmethyl)-1H-pyrazol-3-yl]carbonyl}pyrimidin-4-yl)amino]cyclopentyl}methyl sulfamate |
| I-145 | {(1R,2S,4R)-4-[(5-{[1-(5,6-dihydro-2H-pyran-3-ylmethyl)-1H-pyrazol-3-yl]carbonyl}pyrimidin-4-yl)amino]-2-hydroxycyclopentyl}methyl sulfamate |
| I-146 | {(1R,2R,3S,4R)-4-[(5-{[1-(4-chloro-2-fluorobenzyl)-1H-pyrazol-3-yl]carbonyl}pyrimidin-4-yl)amino]-2,3-dihydroxycyclopentyl}methyl sulfamate |
| I-147 | {(1R,2R,3R,4R)-4-[(5-{[1-(3-chlorobenzyl)-1H-pyrrol-3-yl]carbonyl}pyrimidin-4-yl)amino]-3-fluoro-2-hydroxycyclopentyl}methyl sulfamate |
| I-148 | [(1R,2R,3R,4R)-4-({5-[(5-chloro-1-{[5-(trifluoromethyl)isoxazol-3-yl]methyl}-1H-pyrrol-3-yl)carbonyl]pyrimidin-4-yl}amino)-3-fluoro-2-hydroxycyclopentyl]methyl sulfamate |
| I-149 | {(1R,2R,3R,4R)-4-[(5-{[1-(3-bromobenzyl)-4-methyl-1H-pyrrol-3-yl]carbonyl}pyrimidin-4-yl)amino]-3-fluoro-2-hydroxycyclopentyl}methyl sulfamate |
| I-150 | {(1R,2R,3S,4R)-2,3-dihydroxy-4-[(5-{[1-(pyridin-2-ylmethyl)-1H-pyrazol-3-yl]carbonyl}pyrimidin-4-yl)amino]cyclopentyl}methyl sulfamate |
| I-151 | {(1R,2S,4R)-2-hydroxy-4-[(5-{[1-(4-methoxy-4-methylpent-2-yn-1-yl)-1H-pyrazol-3-yl]carbonyl}pyrimidin-4-yl)amino]cyclopentyl}methyl sulfamate |
| I-152 | [(1R,2S,4R)-4-{[5-({1-[4-chloro-3-(trifluoromethoxy)benzyl]-1H-pyrazol-3-yl}carbonyl)pyrimidin-4-yl]amino}-2-hydroxycyclopentyl]methyl sulfamate |
| I-153 | {(1R,2S,4R)-2-hydroxy-4-[(5-{[1-(5-methylhex-2-yn-1-yl)-1H-pyrazol-3-yl]carbonyl}pyrimidin-4-yl)amino]cyclopentyl}methyl sulfamate |
| I-154 | {(1R,2S,4R)-2-hydroxy-4-[(5-{[1-(4-hydroxy-4-methylpent-2-yn-1-yl)-1H-pyrazol-3-yl]carbonyl}pyrimidin-4-yl)amino]cyclopentyl}methyl sulfamate |
| I-155 | [(1R,2R,3S,4R)-4-{[5-({1-[3,5-bis(trifluoromethyl)benzyl]-1H-pyrazol-3-yl}carbonyl)pyrimidin-4-yl]amino}-2,3-dihydroxycyclopentyl]methyl sulfamate |
| I-156 | [(1R,2R,3R,4R)-4-{[5-({1-[4-chloro-3-(trifluoromethyl)benzyl]-1H-pyrazol-3-yl}carbonyl)pyrimidin-4-yl]amino}-3-fluoro-2-hydroxycyclopentyl]methyl sulfamate |
| I-157 | {(1R,2S,4R)-4-[(5-{[1-(3-bromobenzyl)-1H-pyrazol-3-yl]carbonyl}pyrimidin-4-yl)(methyl)amino]-2-hydroxycyclopentyl}methyl sulfamate |
| I-158 | [(1R,2S,4R)-4-({5-[(1-benzyl-1H-pyrazol-3-yl)carbonyl]pyrimidin-4-yl}amino)-2-hydroxycyclopentyl]methyl sulfamate |
| I-159 | {(1R,2R,3S,4R)-4-[(5-{[1-(3,4-dichlorobenzyl)-1H-pyrazol-3-yl]carbonyl}pyrimidin-4-yl)amino]-2,3-dihydroxycyclopentyl}methyl sulfamate |
| I-160 | {(1R,2R,3S,4R)-2,3-dihydroxy-4-[(5-{[1-(pyridin-4-ylmethyl)-1H-pyrazol-3-yl]carbonyl}pyrimidin-4-yl)amino]cyclopentyl}methyl sulfamate |
| I-161 | {(1R,2S,4R)-4-[(5-{[1-(4-fluorobenzyl)-1H-pyrazol-3-yl]carbonyl}pyrimidin-4-yl)amino]-2-hydroxycyclopentyl}methyl sulfamate |
| I-162 | [(1R,2S,4R)-2-hydroxy-4-{[5-({1-[(4-methylpyridin-2-yl)methyl]-1H-pyrazol-3-yl}carbonyl)pyrimidin-4-yl]amino}cyclopentyl]methyl sulfamate |
| I-163 | [(1R,2S,4R)-2-hydroxy-4-({5-[(1-{[5-(trifluoromethyl)-2-furyl]methyl}-1H-pyrazol-3-yl)carbonyl]pyrimidin-4-yl}amino)cyclopentyl]methyl sulfamate |
| I-164 | {(1R,2S,4R)-4-[(5-{[1-(3-ethynylbenzyl)-5-methyl-1H-pyrazol-3-yl]carbonyl}pyrimidin-4-yl)amino]-2-hydroxycyclopentyl}methyl sulfamate |
| I-165 | {(1R,2S,4R)-4-[(5-{[1-(3-fluorobenzyl)-1H-pyrazol-3-yl]carbonyl}pyrimidin-4-yl)amino]-2-hydroxycyclopentyl}methyl sulfamate |
| I-166 | {(1R,2S,4R)-4-[(5-{[1-(3-ethynyl-4-fluorobenzyl)-1H-pyrazol-3-yl]carbonyl}pyrimidin-4-yl)amino]-2-hydroxycyclopentyl}methyl sulfamate |
| I-167 | [(1R,2R,3S,4R)-2,3-dihydroxy-4-{[5-({1-[4-(trifluoromethyl)benzyl]-1H-pyrazol-3-yl}carbonyl)pyrimidin-4-yl]amino}cyclopentyl]methyl sulfamate |
| I-168 | [(1R,2S,4R)-4-{[5-({1-[3,5-bis(trifluoromethyl)benzyl]-1H-pyrrol-3-yl}carbonyl)pyrimidin-4-yl]amino}-2-hydroxycyclopentyl]methyl sulfamate |
| I-169 | [(1R,2R,3S,4R)-2,3-dihydroxy-4-{[5-({1-[(5-methylisoxazol-3-yl)methyl]-1H-pyrazol-3-yl}carbonyl)pyrimidin-4-yl]amino}cyclopentyl]methyl sulfamate |

-continued

| Compound | Name |
| --- | --- |
| I-170 | {(1R,2S,4R)-4-[(5-{[1-(3-chlorobenzyl)-5-(trifluoromethyl)-1H-pyrazol-3-yl]carbonyl}pyrimidin-4-yl)amino]-2-hydroxycyclopentyl}methyl sulfamate |
| I-171 | [(1R,2S,4R)-2-hydroxy-4-{[5-({1-[4-(trifluoromethyl)benzyl]-1H-pyrazol-3-yl}carbonyl)pyrimidin-4-yl]amino}cyclopentyl]methyl sulfamate |
| I-172 | [(1R,2S,4R)-4-{[5-({1-[(1R)-1-(3-chlorophenyl)ethyl]-5-methyl-1H-pyrazol-3-yl}carbonyl)pyrimidin-4-yl]amino}-2-hydroxycyclopentyl]methyl sulfamate or [(1R,2S,4R)-4-{[5-({1-[(1S)-1-(3-chlorophenyl)ethyl]-5-methyl-1H-pyrazol-3-yl}carbonyl)pyrimidin-4-yl]amino}-2-hydroxycyclopentyl]methyl sulfamate |
| I-173 | [(1R,2R,3S,4R)-2,3-dihydroxy-4-({5-[(1-isobutyl-1H-pyrazol-3-yl)carbonyl]pyrimidin-4-yl}amino)cyclopentyl]methyl sulfamate |
| I-174 | [(1R,2S,4R)-4-{[3-({1-[4-chloro-3-(trifluoromethyl)benzyl]-1H-pyrazol-3-yl}carbonyl)pyridin-4-yl]amino}-2-hydroxycyclopentyl]methyl sulfamate |
| I-175 | [(1R,2R,3R,4R)-4-{[5-({1-[(1S)-1-(3-bromophenyl)propyl]-1H-pyrrol-3-yl}carbonyl)pyrimidin-4-yl]amino}-3-fluoro-2-hydroxycyclopentyl]methyl sulfamate or [(1R,2R,3R,4R)-4-{[5-({1-[(1R)-1-(3-bromophenyl)propyl]-1H-pyrrol-3-yl}carbonyl)pyrimidin-4-yl]amino}-3-fluoro-2-hydroxycyclopentyl]methyl sulfamate |
| I-176 | {(1R,2R,3R,4R)-4-[(5-{[1-(3-chlorobenzyl)-1H-pyrazol-3-yl]carbonyl}pyrimidin-4-yl)amino]-3-fluoro-2-hydroxycyclopentyl}methyl sulfamate |
| I-177 | {(1R,2R,3R,4R)-4-[(5-{[1-(3-bromo-2-fluorobenzyl)-1H-pyrazol-3-yl]carbonyl}pyrimidin-4-yl)amino]-3-fluoro-2-hydroxycyclopentyl}methyl sulfamate |
| I-178 | {(1R,2R,3R,4R)-3-fluoro-4-[(5-{[1-(4-fluoro-3-iodobenzyl)-1H-pyrazol-3-yl]carbonyl}pyrimidin-4-yl)amino]-2-hydroxycyclopentyl}methyl sulfamate |
| I-179 | {(1R,2S,4R)-4-[(5-{[1-(3-bromo-4-chlorobenzyl)-1H-pyrazol-3-yl]carbonyl}pyrimidin-4-yl)amino]-2-hydroxycyclopentyl}methyl sulfamate |
| I-180 | [(1R,2S,4R)-4-{[5-({1-[(5-chloro-2-furyl)methyl]-1H-pyrazol-3-yl}carbonyl)pyrimidin-4-yl]amino}-2-hydroxycyclopentyl]methyl sulfamate |
| I-181 | [(1R,2R,3R,4R)-4-{[5-({1-[2-chloro-5-(trifluoromethyl)benzyl]-1H-pyrazol-3-yl}carbonyl)pyrimidin-4-yl]amino}-3-fluoro-2-hydroxycyclopentyl]methyl sulfamate |
| I-182 | [(1R,2R,3S,4R)-2,3-dihydroxy-4-{[5-({1-[2-(trifluoromethyl)benzyl]-1H-pyrazol-3-yl}carbonyl)pyrimidin-4-yl]amino}cyclopentyl]methyl sulfamate |
| I-183 | [(1R,2S,4R)-2-hydroxy-4-({5-[(1-{[5-(trifluoromethyl)-2-thienyl]methyl}-1H-pyrazol-3-yl)carbonyl]pyrimidin-4-yl}amino)cyclopentyl]methyl sulfamate |
| I-184 | [(1R,2R,3R,4R)-4-{[5-({5-chloro-1-[3-(trifluoromethyl)benzyl]-1H-pyrrol-3-yl}carbonyl)pyrimidin-4-yl]amino}-3-fluoro-2-hydroxycyclopentyl]methyl sulfamate |
| I-185 | {(1R,2S,4R)-4-[(5-{[1-(2-chloro-4-fluorobenzyl)-1H-pyrazol-3-yl]carbonyl}pyrimidin-4-yl)amino]-2-hydroxycyclopentyl}methyl sulfamate |
| I-186 | {(1R,2R,3R,4R)-4-[(5-{[1-(3-bromobenzyl)-5-methyl-1H-pyrazol-3-yl]carbonyl}pyrimidin-4-yl)amino]-3-fluoro-2-hydroxycyclopentyl}methyl sulfamate |
| I-187 | {(1R,2R,3R,4R)-4-[(5-{[1-(3-bromobenzyl)-5-ethyl-1H-pyrrol-3-yl]carbonyl}pyrimidin-4-yl)amino]-3-fluoro-2-hydroxycyclopentyl}methyl sulfamate |
| I-188 | [(1R,2R,3R,4R)-3-fluoro-2-hydroxy-4-{[5-({1-[(6-methoxypyridin-2-yl)methyl]-1H-pyrrol-3-yl}carbonyl)pyrimidin-4-yl]amino}cyclopentyl]methyl sulfamate |
| I-189 | [(1R,2R,3R,4R)-4-{[5-({1-[(5-chloro-2-thienyl)methyl]-1H-pyrrol-3-yl}carbonyl)pyrimidin-4-yl]amino}-3-fluoro-2-hydroxycyclopentyl]methyl sulfamate |
| I-190 | {(1R,2R,3R,4R)-4-[(5-{[1-(3,4-difluorobenzyl)-1H-pyrazol-3-yl]carbonyl}pyrimidin-4-yl)amino]-2,3-dihydroxycyclopentyl}methyl sulfamate |
| I-191 | {(1R,2S,4R)-4-[(5-{[1-(4-chloro-2-fluorobenzyl)-1H-pyrazol-3-yl]carbonyl}pyrimidin-4-yl)amino]-2-hydroxycyclopentyl}methyl sulfamate |
| I-192 | [(1R,2R,3R,4R)-4-{[5-({1-[(1S)-1-(3-bromophenyl)ethyl]-1H-pyrrol-3-yl}carbonyl)pyrimidin-4-yl]amino}-3-fluoro-2-hydroxycyclopentyl]methyl sulfamate or [(1R,2R,3R,4R)-4-{[5-({1-[(1R)-1-(3-bromophenyl)ethyl]-1H-pyrrol-3-yl}carbonyl)pyrimidin-4-yl]amino}-3-fluoro-2-hydroxycyclopentyl]methyl sulfamate |
| I-193 | {(1R,2R,3S,4R)-4-[(5-{[1-(2-chlorobenzyl)-1H-pyrazol-3-yl]carbonyl}pyrimidin-4-yl)amino]-2,3-dihydroxycyclopentyl}methyl sulfamate |
| I-194 | {(1R,2R,3S,4R)-4-[(5-{[1-(2-chloro-4-fluorobenzyl)-1H-pyrazol-3-yl]carbonyl}pyrimidin-4-yl)amino]-2,3-dihydroxycyclopentyl}methyl sulfamate |
| I-195 | {(1R,2R,3R,4R)-4-[(5-{[1-(but-2-yn-1-yl)-1H-pyrrol-3-yl]carbonyl}pyrimidin-4-yl)amino]-3-fluoro-2-hydroxycyclopentyl}methyl sulfamate |
| I-196 | {(1R,2S,4R)-2-hydroxy-4-[(5-{[1-(phenylethynyl)-1H-pyrrol-3-yl]carbonyl}pyrimidin-4-yl)amino]cyclopentyl}methyl sulfamate |

| Compound | Name |
|---|---|
| I-197 | [(1R,2R,3R,4R)-3-fluoro-2-hydroxy-4-({5-[(5-methyl-1-{[5-(trifluoromethyl)-2-furyl]methyl}-1H-pyrazol-3-yl)carbonyl]pyrimidin-4-yl}amino)cyclopentyl]methyl sulfamate |
| I-198 | {(1R,2R,3S,4R)-4-[(5-{[1-(3-fluoro-4-methylbenzyl)-1H-pyrazol-3-yl]carbonyl}pyrimidin-4-yl)amino]-2,3-dihydroxycyclopentyl}methyl sulfamate |
| I-199 | [(1R,2S,4R)-4-{[5-({1-[3-(2-furyl)prop-2-yn-1-yl]-1H-pyrazol-3-yl}carbonyl)pyrimidin-4-yl]amino}-2-hydroxycyclopentyl]methyl sulfamate |
| I-200 | [(1R,2S,4R)-2-hydroxy-4-{[5-({1-[(Z)-2-penylvinyl]-1H-pyrrol-3-yl}carbonyl)pyrimidin-4-yl]amino}cyclopentyl]methyl sulfamate |
| I-201 | {(1R,2S,4R)-4-[(3-{[1-(3-chlorobenzyl)-1H-pyrrol-3-yl]carbonyl}pyridin-4-yl)amino]-2-hydroxycyclopentyl}methyl sulfamate |
| I-202 | {(1R,2S,4R)-2-hydroxy-4-[(5-{[1-(pentafluorobenzyl)-1H-pyrazol-3-yl]carbonyl}pyrimidin-4-yl)amino]cyclopentyl}methyl sulfamate |
| I-203 | [(1R,2R,4R)-4-({5-[(1-benzyl-1H-pyrazol-3-yl)carbonyl]pyrimidin-4-yl}amino)-3,3-difluoro-2-hydroxycyclopentyl]methyl sulfamate |
| I-204 | {(1R,2R,3S,4R)-4-[(5-{[1-(3-bromo-4-chlorobenzyl)-1H-pyrazol-3-yl]carbonyl}pyrimidin-4-yl)amino]-2,3-dihydroxycyclopentyl}methyl sulfamate |
| I-205 | [(1R,2S,4R)-2-hydroxy-4-({5-[(1-phenyl-1H-pyrazol-3-yl)carbonyl]pyrimidin-4-yl}amino)cyclopentyl]methyl sulfamate |
| I-206 | {(1R,2S,4R)-4-[(5-{[1-(2-chlorobenzyl)-1H-pyrazol-3-yl]carbonyl}pyrimidin-4-yl)amino]-2-hydroxycyclopentyl}methyl sulfamate |
| I-207 | {(1R,2R,3R,4R)-4-[(5-{[1-(5-bromo-2-chlorobenzyl)-1H-pyrazol-3-yl]carbonyl}pyrimidin-4-yl)amino]-3-fluoro-2-hydroxycyclopentyl}methyl sulfamate |
| I-208 | [(1R,2R,3R,4R)-3-fluoro-2-hydroxy-4-{[5-({1-[(3-methylisoxazol-5-yl)methyl]-1H-pyrrol-3-yl}carbonyl)pyrimidin-4-yl]amino)cyolopentyl]methyl sulfomate |
| I-209 | [(1R,2R,3R,4R)-3-fluoro-2-hydroxy-4-({5-[(1-{[5-(trifluoromethyl)-2-furyl]methyl}-1H-pyrrol-3-yl)carbonyl]pyrimidin-4-yl}amino)cyclopentyl]methyl sulfamate |
| I-210 | {(1R,2S,4R)-4-[(5-{[1-(3-fluoro-4-methylbenzyl)-1H-pyrazol-3-yl]carbonyl}pyrimidin-4-yl)amino]-2-hydroxycyclopentyl}methyl sulfamate |
| I-211 | [(1R,2S,4R)-4-{[5-({1-[4-fluoro-3-(trifluoromethoxy)benzyl]-1H-pyrrol-3-yl}carbonyl)pyrimidin-4-yl]amino}-2-hydroxycyclopentyl]methyl sulfamate |
| I-212 | {(1R,2S,4R)-4-[(5-{[1-(3,4-difluorobenzyl)-1H-pyrazol-3-yl]carbonyl}pyrimidin-4-yl)amino]-2-hydroxycyclopentyl}methyl sulfamate |
| I-213 | [(1R,2S,4R)-4-{[5-({1-[3-fluoro-5-(trifluoromethyl)benzyl]-1H-pyrrol-3-yl}carbonyl)pyrimidin-4-yl]amino}-2-hydroxycyclopentyl]methyl sulfamate |
| I-214 | {(1R,2S,4R)-2-hydroxy-4-[(5-{[1-(imidazo[1,2-a]pyridin-2-ylmethyl)-1H-pyrazol-3-yl]carbonyl}pyrimidin-4-yl)amino]cyclopentyl}methyl sulfamate |
| I-215 | {(1R,2S,4R)-4-[(5-{[1-(3-chlorobenzyl)-1H-pyrazol-3-yl]carbonyl}pyrimidin-4-yl)amino]-2-hydroxycyclopentyl}methyl sulfamate |
| I-216 | [(1R,2R,3R,4R)-3-fluoro-2-hydroxy-4-{[5-({1-[(1-methyl-2-oxo-1,2-dihydropyridin-3-yl)methyl]-1H-pyrrol-3-yl}carbonyl)pyrimidin-4-yl]amino}cyclopentyl]methyl sulfamate |
| I-217 | [(1R,2R,3S,4R)-4-({5-[(1-benzyl-1 H-pyrrol-3-yl)carbonyl]pyrimidin-4-yl}amino)-2,3-dihydroxycyclopentyl]methyl sulfamate |
| I-218 | [(1R,2R,3R,4R)-4-{[5-({1-[4-chloro-3-(trifluoromethoxy)benzyl]-1H-pyrazol-3-yl}carbonyl)pyrimidin-4-yl]amino}-3-fluoro-2-hydroxycyclopentyl]methyl sulfamate |
| I-219 | {(1R,2S,4R)-4-[(5-{[1-(2,3-difluorobenzyl)-1H-pyrazol-3-yl]carbonyl}pyrimidin-4-yl)amino]-2-hydroxycyclopentyl}methyl sulfamate |
| I-220 | [(1R,2R,3S,4R)-2,3-dihydroxy-4-({5-[(1-isopropyl-1H-pyrazol-3-yl)carbonyl]pyrimidin-4-yl}amino)cyclopentyl]methyl sulfamate |
| I-221 | {(1R,2R,3S,4R)-2,3-dihydroxy-4-[(5-{[1-(3-iodobenzyl)-1H-pyrazol-3-yl]carbonyl}pyrimidin-4-yl)amino]cyclopentyl}methyl sulfamate |
| I-222 | {(1R,2R,3R,4R)-3-fluoro-2-hydroxy-4-[(5-{[1-(tetrahydro-2H-pyran-4-ylmethyl)-1H-pyrrol-3-yl]carbonyl}pyrimidin-4-yl)amino]cyclopentyl}methyl sulfamate |
| I-223 | {(1R,2S,4R)-4-[(3-{[1-(3-bromobenzyl)-1H-pyrazol-3-yl]carbonyl}pyridin-4-yl)amino]-2-hydroxycyclopentyl}methyl sulfamate |
| I-224 | [(1R,2R,3R,4R)-4-{[5-({1-[3-(difluoromethoxy)benzyl]-1H-pyrrol-3-yl}carbonyl)pyrimidin-4-yl]amino}-3-fluoro-2-hydroxycyclopentyl]methyl sulfamate |
| I-225 | {(1R,2R,3S,4R)-2,3-dihydroxy-4-[(5-{[1-(2,3,6-trifluorobenzyl)-1H-pyrazol-3-yl]carbonyl}pyrimidin-4-yl)amino]cyclopentyl}methyl sulfamate |
| I-226 | [(1R,2S,4R)-2-hydroxy-4-{[5-({1-[2-(trifluoromethyl)benzyl]-1H-pyrazol-3-yl}carbonyl)pyrimidin-4-yl]amino}cyclopentyl]methyl sulfamate |
| I-227 | [(1R,2R,3S,4R)-4-({5-[(1-benzyl-1H-pyrazol-3-yl)carbonyl]pyrimidin-4-yl}amino)-3-fluoro-2-hydroxycyclopentyl]methyl sulfamate |
| I-228 | {(1R,2S,4R)-4-[(5-{[1-(but-2-yn-1-yl)-1H-pyrazol-3-yl]carbonyl}pyrimidin-4-yl)amino]-2-hydroxycyclopentyl}methyl sulfamate |
| I-229 | [(1R,2R,3S,4R)-4-{[5-({1-[3-(4-fluorophenoxy)benzyl]-1H-pyrazol-3-yl}carbonyl)pyrimidin-4-yl]amino}-2,3-dihydroxycyclopentyl]methyl sulfamate |

| Compound | Name |
| --- | --- |
| I-230 | [(1R,2R,3S,4R)-4-{[5-({1-[2-fluoro-5-(trifluoromethyl)benzyl]-1H-pyrazol-3-yl}carbonyl)pyrimidin-4-yl]amino}-2,3-dihydroxycyclopentyl]methyl sulfamate |
| I-231 | [(1R,2R,3R,4R)-3-fluoro-4-{[5-({1-[(5-fluoro-2-furyl)methyl]-1H-pyrrol-3-yl}carbonyl)pyrimidin-4-yl]amino}-2-hydroxycyclopentyl]methyl sulfamate |
| I-232 | [(1R,2S,4R)-4-{[5-({1-[(3-chloro-2-thienyl)methyl]-1H-pyrazol-3-yl}carbonyl)pyrimidin-4-yl]amino}-2-hydroxycyclopentyl]methyl sulfamate |
| I-233 | {(1R,2S,4R)-4-[(3-{[1-(3,4-dichlorobenzyl)-1H-pyrrol-3-yl]carbonyl}pyridin-4-yl)amino]-2-hydroxycyclopentyl}methyl sulfamate |
| I-234 | {(1R,2S,4R)-2-hydroxy-4-[(5-{[1-(pent-2-yn-1-yl)-1H-pyrazol-3-yl]carbonyl}pyrimidin-4-yl)amino]cyclopentyl}methyl sulfamate |
| I-235 | [(1R,2S,4R)-4-({5-[(1-{[5-(difluoromethyl)-2-furyl]methyl}-1H-pyrazol-3-yl)carbonyl]pyrimidin-4-yl}amino)-2-hydroxycyclopentyl]methyl sulfamate |
| I-236 | {(1R,2R,3R,4R)-3-fluoro-2-hydroxy-4-[(5-{[1-(4-methoxybut-2-yn-1-yl)-1H-pyrrol-3-yl]carbonyl}pyrimidin-4-yl)amino]cyclopentyl}methyl sulfamate |
| I-237 | {(1R,2R,3R,4R)-3-fluoro-2-hydroxy-4-[(5-{[1-(imidazo[1,2-a]pyridin-5-ylmethyl)-1H-pyrrol-3-yl]carbonyl}pyimidin-4-yl)amino]cyclopentyl}methyl sulfamate |
| I-238 | [(1R,2S,4R)-4-{[5-({1-[(6-bromopyridin-2-yl)methyl]-5-methyl-1H-pyrazol-3-yl}carbonyl)pyrimidin-4-yl]amino}-2-hydroxycyclopentyl]methyl sulfamate |
| I-239 | {(1R,2S,4R)-4-[(5-{[1-(5-bromo-2-chlorobenzyl)-1H-pyrazol-3-yl]carbonyl}pyrimidin-4-yl)amino]-2-hydroxycyclopentyl}methyl sulfamate |
| I-240 | {(1R,2R,3S,4R)-4-[(5-{[1-(3-bromobenzyl)-1H-pyrazol-3-yl]carbonyl}pyrimidin-4-yl)amino]-2,3-dihydroxycyclopentyl}methyl sulfamate |
| I-241 | {(1R,2S,4R)-4-[(5-{[1-(1-benzothiophen-2-ylmethyl)-1H-pyrazol-3-yl]carbonyl}pyrimidin-4-yl)amino]-2-hydroxycyclopentyl}methyl sulfamate |
| I-242 | {(1R,2R,3R,4R)-4-[(3-{[1-(3-chlorobenzyl)-1H-pyrazol-3-yl]carbonyl}pyridin-4-yl)amino]-3-fluoro-2-hydroxycyclopentyl}methyl sulfamate |
| I-243 | [(1R,2R,3R,4R)-4-{[5-({1-[2-(3-bromophenyl)ethyl]-1H-pyrrol-3-yl}carbonyl)pyrimidin-4-yl]amino}-3-fluoro-2-hydroxycyclopentyl]methyl sulfamate |
| I-244 | {(1R,2R,3R,4R)-4-[(5-{[1-(3-bromobenzyl)-5-chloro-1H-pyrrol-3-yl]carbonyl}pyrimidin-4-yl)amino]-3-fluoro-2-hydroxycyclopentyl}methyl sulfamate |
| I-245 | {(1R,2S,4R)-4-[(5-{[1-(4-fluoro-3-iodobenzyl)-1H-pyrazol-3-yl]carbonyl}pyrimidin-4-yl)amino]-2-hydroxycyclopentyl}methyl sulfamate |
| I-246 | [(1R,2S,4R)-4-{[3-({1-[3-(difluoromethoxy)benzyl]-1H-pyrazol-3-yl}carbonyl)pyridin-4-yl]amino}-2-hydroxycyclopentyl]methyl sulfamate |
| I-247 | {(1R,2R,3S,4R)-2,3-dihydroxy-4-[(5-{[1-(pyridin-3-ylmethyl)-1H-pyrazol-3-yl]carbonyl}pyrimidin-4-yl)amino]cyclopentyl}methyl sulfamate |
| I-248 | {(1R,2S,4R)-2-hydroxy-4-[(5-{[5-methyl-1-(3-methylbenzyl)-1H-pyrazol-3-yl]carbonyl}pyrimidin-4-yl)amino]cyclopentyl}methyl sulfamate |
| I-249 | {(1R,2R,3S,4R)-4-[(5-{[1-(2-cyanobenzyl)-1H-pyrazol-3-yl]carbonyl}pyrimidin-4-yl)amino]-2,3-dihydroxycyclopentyl}methyl sulfamate |
| I-250 | [(1R,2R,3R,4R)-4-({5-[(1-{[(2R)-5,5-dimethyltetrahydrofuran-2-yl]methyl}-1H-pyrrol-3-yl)carbonyl]pyrimidin-4-yl}amino)-3-fluoro-2-hydroxycyclopentyl]methyl sulfamate and [(1R,2R,3R,4R)-4-({5-[(1-{[(2S)-5,5-dimethyltetrahydrofuran-2-yl]methyl}-1H-pyrrol-3-yl)carbonyl]pyrimidin-4-yl}amino)-3-fluoro-2-hydroxycyclopentyl]methyl sulfamate |
| I-251 | [(1R,2S,4R)-2-hydroxy-4-{[5-({1-[3-(morpholin-4-yl)benzyl]-1H-pyrazol-3-yl}carbonyl)pyrimidin-4-yl]amino}cyclopentyl]methyl sulfamate |
| I-252 | {(1R,2S,4R)-4-[(5-{[1-(cyclohex-1-en-1-ylmethyl)-1H-pyrazol-3-yl]carbonyl}pyrimidin-4-yl)amino]-2-hydroxycyclopentyl}methyl sulfamate |
| I-253 | {(1R,2S,4R)-4-[(5-{[1-(2-cyanobenzyl)-1H-pyrazol-3-yl]carbonyl)pyrimidin-4-yl)amino]-2-hydroxycyclopentyl}methyl sulfamate |
| I-254 | [(1R,2R,3R,4R)-4-{[5-({5-chloro-1-[(5-chloro-2-furyl)methyl]-1H-pyrrol-3-yl}carbonyl)pyrimidin-4-yl]amino}-3-fluoro-2-hydroxycyclopentyl]methyl sulfamate |
| I-255 | [(1R,2S,4R)-4-{[5-({1-[(3-bromophenyl)sulfonyl]-1H-pyrrol-3-yl}carbonyl)pyrimidin-4-yl]amino}-2-hydroxycyclopentyl]methyl sulfamate |
| I-256 | [(1R,2R,3S,4R)-4-{[5-({1-[3-(difluoromethoxy)benzyl]-1H-pyrazol-3-yl}carbonyl)pyrimidin-4-yl]amino}-2,3-dihydroxycyclopentyl]methyl sulfamate |
| I-257 | [(1R,2R,3R,4R)-3-fluoro-2-hydroxy-4-({5-[(1-{[5-(trifluoromethyl)-2-thienyl]methyl}-1H-pyrrol-3-yl)carbonyl]pyrimidin-4-yl}amino)cyclopentyl]methyl sulfamate |
| I-258 | [(1R,2R,3S,4R)-4-{[5-({1-[3-fluoro-5-(trifluoromethyl)benzyl]-1H-pyrazol-3-yl}carbonyl)pyrimidin-4-yl]amino}-2,3-dihydroxycyclopentyl]methyl sulfamate |
| I-259 | [(1R,2R,3S,4R)-2,3-dihydroxy-4-({5-[(1-{4-[(trifluoromethyl)sulfanyl]benzyl}-1H-pyrazol-3-yl)carbonyl]pyrimidin-4-yl}amino)cyclopentyl]methyl sulfamate |

-continued

| Compound | Name |
|---|---|
| I-260 | {(1R,2S,4R)-4-[(5-{[1-(3,5-difluorobenzyl)-1H-pyrazol-3-yl]carbonyl}pyrimidin-4-yl)amino]-2-hydroxycyclopentyl}methyl sulfamate |
| I-261 | [(1R,2S,4R)-4-{(5-({1-[2,5-bis(trifluoromethyl)benzyl]-1H-pyrazol-3-yl}carbonyl)pyrimidin-4-yl]amino}-2-hydroxycyclopentyl]methyl sulfamate |
| I-262 | [(1R,2S,4R)-2-hydroxy-4-{[3-({1-[3-(trifluoromethyl)benzyl]-1H-pyrazol-3-yl}carbonyl)pyridin-4-yl]amino}cyclopentyl]methyl sulfamate |
| I-263 | [(1R,2S,4R)-4-{[3-({1-[4-fluoro-3-(trifluoromethyl)benzyl]-1H-pyrazol-3-yl}carbonyl)pyridin-4-yl]amino}-2-hydroxycyclopentyl]methyl sulfamate |
| I-264 | [(1R,2S,4R)-4-{[5-({1-[1-(3-chlorophenyl)cyclopropyl]1H-pyrrol-3-yl}carbonyl)pyrimidin-4-yl]amino}-2-hydroxycyclopentyl]methyl sulfamate |
| I-265 | [(1R,2R,3S,4R)-2,3-dihydroxy-4-{[5-({1-[4-(trifluoromethoxy)benzyl]-1H-pyrazol-3-yl}carbonyl)pyrimidin-4-yl]amino}cyclopentyl]methyl sulfamate |
| I-266 | [(1R,2R,3S,4R)-4-{[5-({1-[2,4-bis(trifluoromethyl)benzyl]-1H-pyrazol-3-yl}carbonyl)pyrimidin-4-yl]amino}-2,3-dihydroxycyclopentyl]methyl sulfamate |
| I-267 | [(1R,2R,3S,4R)-4-{[5-({1-[2,5-bis(trifluoromethyl)benzyl]-1H-pyrazol-3-yl}carbonyl)pyrimidin-4-yl]amino}-2,3-dihydroxycyclopentyl]methyl sulfamate |
| I-268 | [(1R,2R,3S,4R)-4-{[5-({1-[2-chloro-5-(trifluoromethyl)benzyl]-1H-pyrazol-3-yl}carbonyl)pyrimidin-4-yl]amino}-2,3-dihydroxycyclopentyl]methyl sulfamate |
| I-269 | {(1R,2R,3S,4R)-4-[(5-{[1-(3,5-difluorobenzyl)-1H-pyrazol-3-yl]carbonyl}pyrimidin-4-yl)amino]-2,3-dihydroxycyclopentyl}methyl sulfamate |
| I-270 | [(1R,2S,4R)-2-hydroxy-4-{[5-{{1-[3-(3-hydroxyoxetan-3-yl)benzyl]-1H-pyrazol-3-yl}carbonyl)pyrimidin-4-yl]amino}cyclopentyl]methyl sulfamate |
| I-271 | [(1R,2S,4R)-2-hydroxy-4-{[5-({1-[3-(trifluoromethoxy)benzyl]-1H-pyrrol-3-yl}carbonyl)pyrimidin-4-yl]amino}cyclopentyl]methyl sulfamate |
| I-272 | {(1R,2R,3R,4R)-4-[(5-{[5-bromo-1-(3-bromobenzyl)-1H-pyrrol-3-yl]carbonyl}pyrimidin-4-yl)amino]-3-fluoro-2-hydroxycyclopentyl}methyl sulfamate |
| I-273 | [(1R,2R,3S,4R)-4-{[5-({1-[(4-fluoro-1-naphthyl)methyl]-1H-pyrazol-3-yl}carbonyl)pyrimidin-4-yl]amino}-2,3-dihydroxycyclopentyl]methyl sulfamate |
| I-274 | [(1R,2S,4R)-2-hydroxy-4-({5-[(1-{[5-(trifluoromethyl)-2-furyl]methyl}-1H-pyrrol-3-yl)carbonyl]pyrimidin-4-yl}amino)cyclopentyl]methyl sulfamate |
| I-275 | [(1R,2S,4R)-2-hydroxy-4-{[5-({1-[3-(3-hydroxyoxetan-3-yl)prop-2-yn-1-yl]-1H-pyrazol-3-yl}carbonyl)pyrimidin-4-yl]amino}cyclopentyl]methyl sulfamate |
| I-276 | [(1R,2S,4R)-2-hydroxy-4-{[5-({1-[4-(trifluoromethoxy)benzyl]-1H-pyrazol-3-yl}carbonyl)pyrimidin-4-yl]amino}cyclopentyl]methyl sulfamate |
| I-277 | [(1R,2R,3R,4R)-3-fluoro-2-hydroxy-4-{[5-({1-[(5-methyl-2-furyl)methyl]-1H-pyrrol-3-yl}carbonyl)pyrimidin-4-yl]amino}cyclopentyl]methyl sulfamate |
| I-278 | {(1R,2R,3S,4R)-4-[(5-{[1-(biphenyl-3-ylmethyl)-1H-pyrazol-3-yl]carbonyl}pyrimidin-4-yl)amino]-2,3-dihydroxycyclopentyl}methyl sulfamate |
| I-279 | {(1R,2S,4R)-4-[(5-{[1-(3-bromo-4-fluorobenzyl)-1H-pyrrol-3-yl]carbonyl}pyrimidin-4-yl)amino]-2-hydroxycyclopentyl}methyl sulfamate |
| I-280 | [(1R,2S,4R)-4-{[5-({1-[(5-chloro-2-thienyl)methyl]-1H-pyrazol-3-yl}carbonyl)pyrimidin-4-yl]amino}-2-hydroxycyclopentyl]methyl sulfamate |
| I-281 | [(1R,2S,4R)-2-hydroxy-4-{[5-({1-[(methylsulfanyl)methyl]-1H-pyrazol-3-yl}carbonyl)pyrimidin-4-yl]amino}cyclopentyl]methyl sulfamate |
| I-282 | {(1R,2S,4R)-4-[(5-{[1-(3-bromo-2-fluorobenzyl)-1H-pyrazol-3-yl]carbonyl}pyrimidin-4-yl)amino]-2-hydroxycyclopentyl}methyl sulfamate |
| I-283 | [(1R,2R,3S,4R)-4-{[5-({1-[2-(3-chlorophenyl)-2-oxoethyl]-1H-pyrazol-3-yl}carbonyl)pyrimidin-4-yl]amino}-2,3-dihydroxyoyclopentyl]methyl sulfamate |
| I-284 | [(1R,2R,3S,4R)-4-{[5-({1-[(6-bromopyridin-2-yl)methyl]-1H-pyrazol-3-yl}carbonyl)pyrimidin-4-yl]amino}-2,3-dihydroxycyclopentyl]methyl sulfamate |
| I-285 | [(1R,2R,3S,4R)-4-{[5-({1-[(5-chloro-1-benzothiophen-3-yl)methyl]-1H-pyrazol-3-yl}carbonyl)pyrimidin-4-yl]amino}-2,3-dihydroxycyclopentyl]methyl sulfamate |
| I-286 | {(1R,2S,4R)-2-hydroxy-4-[(5-{[1-(2,4,6-trifluorobenzyl)-1H-pyrazol-3-yl]carbonyl}pyrimidin-4-yl)amino]cyclopentyl}methyl sulfamate |
| I-287 | {(1R,2S,4R)-4-[(5-{[1-(3-cyclopropylprop-2-yn-1-yl)-1H-pyrazol-3-yl]carbonyl}pyrimidin-4-yl)amino]-2-hydroxycyclopentyl}methyl sulfamate |
| I-288 | [(1R,2S,4R)-4-{[5-({1-[4-chloro-3-(trifluoromethyl)benzyl]-1H-pyrazol-3-yl}carbonyl)pyrimidin-4-yl]amino}-2-hydroxycyclopentyl]methyl sulfamate |
| I-289 | {(1R,2S,4R)-4-[(5-{[1-(2,5-dichlorobenzyl)-1H-pyrazol-3-yl]carbonyl}pyrimidin-4-yl)amino]-2-hydroxycyclopentyl}methyl sulfamate |
| I-290 | {(1R,2R,3S,4R)-4-[(5-{[1-(3-bromo-4-fluorobenzyl)-1H-pyrazol-3-yl]carbonyl}pyrimidin-4-yl)amino]-2,3-dihydroxycyclopentyl}methyl sulfamate |
| I-291 | [(1R,2S,4R)-4-({5-[(1-allyl-1H-pyrrol-3-yl)carbonyl]pyrimidin-4-yl}amino)-2-hydroxycyclopentyl]methyl sulfamate |

| Compound | Name |
|---|---|
| I-292 | {(1R,2S,4R)-2-hydroxy-4-[(5-{[1-(3-iodobenzyl)-1H-pyrazol-3-yl]carbonyl}pyrimidin-4-yl)amino]cyclopentyl}methyl sulfamate |
| I-293 | [(1R,2S,4R)-2-hydroxy-4-{[5-({1-[(2R)-tetrahydrofuran-2-ylmethyl]-1H-pyrazol-3-yl}carbonyl)pyrimidin-4-yl]amino}cyclopentyl]methyl sulfamate and [(1R,2S,4R)-2-hydroxy-4-{[5-({1-[(2S)-tetrahydrofuran-2-ylmethyl]-1H-pyrazol-3-yl}carbonyl)pyrimidin-4-yl]amino}cyclopentyl]methyl sulfamate |
| I-294 | {(1R,2R,3R,4R)-3-fluoro-2-hydroxy-4-[(5-{[1-(3-iodobenzyl)-5-methyl-1H-pyrazol-3-yl]carbonyl}pyrimidin-4-yl)amino]cyclopentyl}methyl sulfamate |
| I-295 | [(1R,2S,4R)-2-hydroxy-4-{[5-({1-[(6-methoxypyridin-2-yl)methyl]-1H-pyrazol-3-yl}carbonyl)pyrimidin-4-yl]amino}cyclopentyl]methyl sulfamate |
| I-296 | [(1R,2R,3R,4R)-4-{[5-({1-[(5-chloro-2-furyl)methyl]-1H-pyrrol-3-yl}carbonyl)pyrimidin-4-yl]amino}-3-fluoro-2-hydroxycyclopentyl]methyl sulfamate |
| I-297 | [(1R,2R,3R,4R)-3-fluoro-2-hydroxy-4-{[5-({1-[(5-methylisoxazol-3-yl)methyl]-1H-pyrrol-3-yl}carbonyl)pyrimidin-4-yl]amino}cyclopentyl]methyl sulfamate |
| I-298 | [(1R,2S,4R)-2-hydroxy-4-{[5-({1-[(6-methylpyridin-2-yl)methyl]-1H-pyrazol-3-yl}carbonyl)pyrimidin-4-yl]amino}cyclopentyl]methyl sulfamate |
| I-299 | [(1R,2S,4R)-4-{[5-({1-[(5-bromopyridin-3-yl)methyl]-1H-pyrrol-3-yl}carbonyl)pyrimidin-4-yl]amino}-2-hydroxycyclopentyl]methyl sulfamate |
| I-300 | [(1R,2S,4R)-4-({5-[(1-benzyl-1H-pyrrol-3-yl)carbonyl]pyrimidin-4-yl}amino)-2-hydroxycyclopentyl]methyl sulfamate |
| I-301 | {(1R,2S,4R)-4-[(5-{[1-(3-cyclopropyl-4-fluorobenzyl)-1H-pyrazol-3-yl]carbonyl}pyrimidin-4-yl)amino]-2-hydroxycyclopentyl}methyl sulfamate |
| I-302 | [(1R,2S,4R)-4-{[5-({1-[(1R)-cyclohex-2-en-1-yl]-1H-pyrazol-3-yl}carbonyl)pyrimidin-4-yl]amino}-2-hydroxycyclopentyl]methyl sulfamate and [(1R,2S,4R)-4-{[5-({1-[(1S)-cyclohex-2-en-1-yl]-1H-pyrazol-3-yl}carbonyl)pyrimidin-4-yl]amino}-2-hydroxycyclopentyl]methyl sulfamate |
| I-303 | [(1R,2R,3R,4R)-4-{[5-({1-[3-(difluoromethoxy)benzyl]-1H-pyrazol-3-yl}carbonyl)pyrimidin-4-yl]amino}-3-fluoro-2-hydroxycyclopentyl]methyl sulfamate |
| I-304 | [(1R,2R,3R,4R)-3-fluoro-2-hydroxy-4-({5-[(1-{(1S)-1-[5-(trifluoromethyl)-2-furyl]ethyl}-1H-pyrrol-3-yl)carbonyl]pyrimidin-4-yl}amino)cyclopentyl]methyl sulfamate or [(1R,2R,3R,4R)-3-fluoro-2-hydroxy-4-({5-[(1-{(1R)-1-[5-(trifluoromethyl)-2-furyl]ethyl}-1H-pyrrol-3-yl)carbonyl]pyrimidin-4-yl}amino)cyclopentyl]methyl sulfamate |
| I-305 | {(1R,2S,4R)-2-hydroxy-4-[(5-{[1-(2-methoxyethyl)-1H-pyrazol-3-yl]carbonyl}pyrimidin-4-yl)amino]cyclopentyl}methyl sulfamate |
| I-306 | [(1R,2S,4R)-2-hydroxy-4-({5-[(1-{[1-methyl-5-(trifluoromethyl)-1H-pyrazol-3-yl]methyl} 1H pyrrol-3-yl)carbonyl]pyrimidin-4-yl}amino)cyclopentyl]methyl sulfamate |
| I-307 | {(1R,2R,3R,4R)-4-[(5-{[1-(2,5-dichlorobenzyl)-1H-pyrazol-3-yl]carbonyl}pyrimidin-4-yl)amino]-3-fluoro-2-hydroxycyclopentyl}methyl sulfamate |
| I-308 | [(1R,2S,4R)-2-hydroxy-4-{[5-({1-[3-(1-methyl-1H-pyrazol-4-yl)prop-2-yn-1-yl]-1H-pyrazol-3-yl}carbonyl)pyrimidin-4-yl]amino}cyclopentyl]methyl sulfamate |
| I-309 | {(1R,2S,4R)-4-[(5-{[1-(3-bromobenzyl)-5-methyl-1H-pyrazol-3-yl]carbonyl}pyrimidin-4-yl)amino]-2-hydroxycyclopentyl}methyl sulfamate |
| I-310 | {(1R,2R,3R,4R)-4-[(5-{[5-chloro-1-(3-iodobenzyl)-1H-pyrrol-3-yl]carbonyl}pyrimidin-4-yl)amino]-3-fluoro-2-hydroxycyclopentyl}methyl sulfamate |
| I-311 | {(1R,2R,3R,4R)-4-[(5-{[1-(3,4-dichlorobenzyl)-1H-pyrazol-3-yl]carbonyl}pyrimidin-4-yl)amino]-3-fluoro-2-hydroxycyclopentyl}methyl sulfamate |
| I-312 | {(1R,2R,3R,4R)-4-[(5-{[1-(3-bromobenzyl)-1H-pyrrol-3-yl]carbonyl}pyrimidin-4-yl)amino]-3-fluoro-2-hydroxycyclopentyl}methyl sulfamate |
| I-313 | [(1R,2R,3S,4R)-4-{[5-({1-[3-(acryloylamino)benzyl]-1H-pyrazol-3-yl}carbonyl)pyrimidin-4-yl]amino}-2,3-dihydroxycyclopentyl]methyl sulfamate |
| I-314 | {(1R,2R,3S,4R)-2,3-dihydroxy-4-[(5-{[1-(2,4,5-trifluorobenzyl)-1H-pyrazol-3-yl]carbonyl}pyrimidin-4-yl)amino]cyclopentyl}methyl sulfamate |
| I-315 | [(1R,2S,4R)-4-{[5-({1-[(1S)-1-(3-bromophenyl)ethyl]-1H-pyrazol-3-yl}carbonyl)pyrimidin-4-yl]amino}-2-hydroxycyclopentyl]methyl sulfamate or [(1R,2S,4R)-4-{[5-({1-[(1R)-1-(3-bromophenyl)ethyl]-1H-pyrazol-3-yl}carbonyl)pyrimidin-4-yl]amino}-2-hydroxycyclopentyl]methyl sulfamate |
| I-316 | {(1R,2R,3R,4R)-4-[(5-{[1-(3-chlorobenzyl)-5-(trifluoromethyl)-1H-pyrazol-3-yl]carbonyl}pyrimidin-4-yl)amino]-3-fluoro-2-hydroxycyclopentyl}methyl sulfamate |
| I-317 | [(1R,2R,3R,4R)-4-({5-[(1-benzyl-1H-pyrazol-3-yl)carbonyl]pyrimidin-4-yl}amino)-3-fluoro-2-hydroxycyclopentyl]methyl sulfamate |
| I-318 | {(1R,2R,3S,4R)-2,3-dihydroxy-4-[(5-{[1-(pentafluorobenzyl)-1H-pyrazol-3-yl]carbonyl}pyrimidin-4-yl)amino]cyclopentyl}methyl sulfamate |
| I-319 | {(1S,2S,4R)-4-[(5-{[1-(3-bromobenzyl)-1H-pyrrol-3-yl]carbonyl}pyrimidin-4-yl)amino]-2-hydroxycyclopentyl}methyl sulfamate |

-continued

| Compound | Name |
|---|---|
| I-320 | {(1R,2R,3R,4R)-4-[(5-{[1-(3-bromo-4-fluorobenzyl)-5-chloro-1H-pyrrol-3-yl]carbonyl}pyrimidin-4-yl)amino]-3-fluoro-2-hydroxycyclopentyl}methyl sulfamate |
| I-321 | [(1R,2R,3S,4R)-2,3-dihydroxy-4-{[5-({1-[3-(vinylsulfonyl)benzyl]-1H-pyrazol-3-yl}carbonyl)pyrimidin-4-yl]amino}cyclopentyl]methyl sulfamate |
| I-322 | {(1R,2R,3R,4R)-4-[(5-{[1-(1-benzothiophen-2-ylmethyl)-1H-pyrrol-3-yl]carbonyl}pyrimidin-4-yl)amino]-3-fluoro-2-hydroxycyclopentyl}methyl sulfamate |
| I-323 | {(1R,2R,3S,4R)-4-[(5-{[1-((1R)-2,3-dihydro-1H-inden-1-yl)-1H-pyrazol-3-yl]carbonyl}pyrimidin-4-yl)amino]-2,3-dihydroxycyclopentyl}methyl sulfamate or {(1R,2R,3S,4R)-4-[(5-{[1-((1S)-2,3-dihydro-1H-inden-1-yl)-1H-pyrazol-3-yl]carbonyl}pyrimidin-4-yl)amino]-2,3-dihydroxycyclopentyl}methyl sulfamate |
| I-324 | [(1R,2R,3S,4R)-4-{[5-({1-[(4-bromopyridin-2-yl)methyl]-1H-pyrazol-3-yl}carbonyl)pyrimidin-4-yl]amino}-2,3-dihydroxycyclopentyl]methyl sulfamate |
| I-325 | {(1R,2R,3S,4R)-2,3-dihydroxy-4-[(5-{[1-(3-methoxybenzyl)-1H-pyrazol-3-yl]carbonyl}pyrimidin-4-yl)amino]cyclopentyl}methyl sulfamate |
| I-326 | {(1R,2R,3S,4R)-2,3-dihydroxy-4-[(5-{[1-(3,4,5-trifluorobenzyl)-1H-pyrazol-3-yl]carbonyl}pyrimidin-4-yl)amino]cyclopentyl}methyl sulfamate |
| I-327 | {(1R,2R,3S,4R)-4-[(5-{[1-(2,3-difluorobenzyl)-1H-pyrazol-3-yl]carbonyl}pyrimidin-4-yl)amino]-2,3-dihydroxycyclopentyl}methyl sulfamate |
| I-328 | [(1R,2S,4R)-4-{[5-({1-[4-fluoro-2-(trifluoromethyl)benzyl]-1H-pyrazol-3-yl}carbonyl)pyrimidin-4-yl]amino}-2-hydroxycyclopentyl]methyl sulfamate |
| I-329 | {(1R,2S,4R)-2-hydroxy-4-[(5-{[1-(2,4,5-trifluorobenzyl)-1H-pyrazol-3-yl]carbonyl}pyrimidin-4-yl)amino]cyclopentyl}methyl sulfamate |
| I-330 | {(1R,2S,4R)-2-hydroxy-4-[(5-{[1-{prop-2-yn-1-yl)-1H-pyrrol-3-yl]carbonyl}pyrimidin-4-yl)amino]cyclopentyl}methyl sulfamate |
| I-331 | {(1R,2R,3R,4R)-4-[(5-{[1-(3,4-dichlorobenzyl)-1H-pyrrol-3-yl]carbonyl}pyrimidin-4-yl)amino]-3-fluoro-2-hydroxycyclopentyl}methyl sulfamate |
| I-332 | [(1R,2S,4R)-2-hydroxy-4-{[5-({1-[(3R)-tetrahydrofuran-3-ylmethyl]-1H-pyrazol-3-yl}carbonyl)pyrimidin-4-yl]amino}cyclopentyl]methyl sulfamate and [(1R,2S,4R)-2-hydroxy-4-{[5-({1-[(3S)-tetrahydrofuran-3-ylmethyl]-1H-pyrazol-3-yl}carbonyl)pyrimidin-4-yl]amino}cyclopentyl]methyl sulfamate |
| I-333 | {(1R,2S,4R)-4-[(5-{[1-(3-bromobenzyl)-1H-pyrrol-3-yl]carbonyl}pyrimidin-4-yl)amino]-2-hydroxycyclopentyl}methyl sulfamate |
| I-334 | {(1R,2R,3S,4R)-4-[(5-{[1-(3-chloro-5-fluorobenzyl)-1H-pyrazol-3-yl]carbonyl}pyrimidin-4-yl)amino]-2,3-dihydroxycyclopentyl}methyl sulfamate |
| I-335 | {(1R,2S,4R)-4-[(5-{[1-benzyl-5-(hydroxymethyl)-1H-pyrazol-3-yl]carbonyl}pyrimidin-4-yl)amino]-2-hydroxycyclopentyl}methyl sulfamate |
| I-336 | {(1R,2R,3S,4R)-4-[(5-{[1-(2,4-difluorobenzyl)-1H-pyrazol-3-yl]carbonyl}pyrimidin-4-yl)amino]-2,3-dihydroxycyclopentyl}methyl sulfamate |
| I-337 | {(1R,2R,3R,4R)-4-[(5-{[1-(3-bromo-4-chlorobenzyl)-1H-pyrrol-3-yl]carbonyl}pyrimidin-4-yl)amino]-3-fluoro-2-hydroxycyclopentyl}methyl sulfamate |
| I-338 | {(1R,2R,3S,4R)-4-[(5-{[1-(2-fluorobenzyl)-1H-pyrazol-3-yl]carbonyl}pyrimidin-4-yl)amino]-2,3-dihydroxycyclopentyl}methyl sulfamate |
| I-339 | [(1R,2S,4R)-2-hydroxy-4-{[5-({1-[(1S,2S)-(2-phenylcyclopropyl)methyl]-1H-pyrrol-3-yl}carbonyl)pyrimidin-4-yl]amino}cyclopentyl]methyl sulfamate and [(1R,2S,4R)-2-hydroxy-4-{[5-({1-[(1R,2R)-(2-phenylcyclopropyl)methyl]-1H-pyrrol-3-yl}carbonyl)pyrimidin-4-yl]amino}cyclopentyl]methyl sulfamate |
| I-340 | {(1R,2S,4R)-4-[(5-{[1-(but-2-yn-1-yl)-1H-pyrrol-3-yl]carbonyl}pyrimidin-4-yl)amino]-2-hydroxycyclopentyl}methyl sulfamate |
| I-341 | [(1R,2S,4R)-4-{[5-({1-[(5-chloro-1-benzothiophen-3-yl)methyl]-1H-pyrrol-3-yl}carbonyl)pyrimidin-4-yl]amino}-2-hydroxycyclopentyl]methyl sulfamate |
| I-342 | [(1S,2S,4R)-4-({5-[(1-benzyl-1H-pyrazol-3-yl)carbonyl]pyrimidin-4-yl}amino)-2-hydroxycyclopentyl]methyl sulfamate |
| I-343 | [(1R,2R,3S,4R)-4-{[5-({1-[4-fluoro-3-(trifluoromethyl)benzyl]-1H-pyrazol-3-yl}carbonyl)pyrimidin-4-yl]amino}-2,3-dihydroxycyclopentyl]methyl sulfamate |
| I-344 | {(1R,2S,4R)-2-hydroxy-4-[(5-{[1-(3-methylbut-2-en-2-yl)-1H-pyrazol-3-yl]carbonyl}pyrimidin-4-yl)amino]cyclopentyl}methyl sulfamate |
| I-345 | [(1R,2R,3S,4R)-2,3-dihydroxy-4-({5-[(1-methyl-1H-pyrazol-3-yl)carbonyl]pyrimidin-4-yl}amino)cyclopentyl]methyl sulfamate |
| I-346 | {(1R,2S,4R)-4-[(5-{[1-(5-bromo-2-fluorobenzyl)-1H-pyrazol-3-yl]carbonyl}pyrimidin-4-yl)amino]-2-hydroxycyclopentyl}methyl sulfamate |
| I-347 | {(1R,2S,4R)-2-hydroxy-4-[(5-{[1-(3-iodobenzyl)-5-methyl-1H-pyrazol-3-yl]carbonyl}pyrimidin-4-yl)amino]cyclopentyl}methyl sulfamate |
| I-348 | [(1R,2S,4R)-2-hydroxy-4-{[5-({1-[(5-methylisoxazol-3-yl)methyl]-1H-pyrazol-3-yl}carbonyl)pyrimidin-4-yl]amino}cyclopentyl]methyl sulfamate |

| Compound | Name |
|---|---|
| I-349 | [(1R,2R,3S,4R)-2,3-dihydroxy-4-{[5-({1-[3-(trifluoromethoxy)benzyl]-1H-pyrazol-3-yl}carbonyl)pyrimidin-4-yl]amino}cyclopentyl]methyl sulfamate |
| I-350 | [(1R,2R,3R,4R)-4-{[5-({1-[(1S)-1-(5-chloro-2-furyl)ethyl]-1H-pyrrol-3-yl}carbonyl)pyrimidin-4-yl]amino}-3-fluoro-2-hydroxycyclopentyl]methyl sulfamate or [(1R,2R,3R,4R)-4-{[5-({1-[(1R)-1-(5-chloro-2-furyl)ethyl]-1H-pyrrol-3-yl}carbonyl)pyrimidin-4-yl]amino}-3-fluoro-2-hydroxycyclopentyl]methyl sulfamate |
| I-351 | {(1R,2R,3S,4R)-2,3-dihydroxy-4-[(5-{[1-((1S)-1-phenylethyl)-1H-pyrazol-3-yl]carbonyl}pyrimidin-4-yl)amino]cyclopentyl}methyl sulfamate or {(1R,2R,3S,4R)-2,3-dihydroxy-4-[(5-{[1-((1R)-1-phenylethyl)-1H-pyrazol-3-yl]carbonyl}pyrimidin-4-yl)amino]cyclopentyl}methyl sulfamate |
| I-352 | [(1R,2S,4R)-4-{[5-({1-[(6-bromopyridin-2-yl)methyl]-1H-pyrazol-3-yl}carbonyl)pyrimidin-4-yl]amino}-2-hydroxycyclopentyl]methyl sulfamate |
| I-353 | {(1R,2R,3S,4R)-4-[(5-{[1-((1R)-2,3-dihydro-1H-inden-1-yl)-1H-pyrazol-3-yl]carbonyl}pyrimidin-4-yl)amino]-2,3-dihydroxycyclopentyl}methyl sulfamate or {(1R,2R,3S,4R)-4-[(5-{[1-((1S)-2,3-dihydro-1H-inden-1-yl)-1H-pyrazol-3-yl]carbonyl}pyrimidin-4-yl)amino]-2,3-dihydroxycyclopentyl}methyl sulfamate |
| I-354 | [(1R,2S,4R)-4-{[5-({1-[(1 S)-1-(5-chloro-2-furyl)ethyl]-1H-pyrazol-3-yl}carbonyl)pyrimidin-4-yl]amino}-2-hydroxycyclopentyl]methyl sulfamate or [(1R,2S,4R)-4-{[5-({1-[(1R)-1-(5-chloro-2-furyl)ethyl]-1H-pyrazol-3-yl}carbonyl)pyrimidin-4-yl]amino}-2-hydroxycyclopentyl]methyl sulfamate |
| I-355 | [(1R,2S,4R)-4-{[5-({1-[(1S)-1-(3-ethynylphenyl)ethyl]-1H-pyrazol-3-yl}carbonyl)pyrimidin-4-yl]amino}-2-hydroxycyclopentyl]methyl sulfamate or [(1R,2S,4R)-4-{[5-({1-[(1R)-1-(3-ethynylphenyl)ethyl]-1H-pyrazol-3-yl}carbonyl)pyrimidin-4-yl]amino}-2-hydroxycyclopentyl]methyl sulfamate |
| I-356 | [(1R,2R,3R,4R)-4-{[5-({1-[(1S)-1-(3-bromophenyl)propyl]-1H-pyrrol-3-yl}carbonyl)pyrimidin-4-yl]amino}-3-fluoro-2-hydroxycyclopentyl]methyl sulfamate or [(1R,2R,3R,4R)-4-{[5-({1-[(1R)-1-(3-bromophenyl)propyl]-1H-pyrrol-3-yl}carbonyl)pyrimidin-4-yl]amino}-3-fluoro-2-hydroxycyclopentyl]methyl sulfamate |
| I-357 | [(1R,2R,3R,4R)-3-fluoro-2-hydroxy-4-({5-[(1-{(1S)-1-[5-(trifluoromethyl)-2-furyl]ethyl}-1H-pyrrol-3-yl)carbonyl]pyrimidin-4-yl}amino)cyclopentyl]methyl sulfamate or [(1R,2R,3R,4R)-3-fluoro-2-hydroxy-4-({5-[(1-{(1R)-1-[5-(trifluoromethyl)-2-furyl]ethyl}-1H-pyrrol-3-yl)carbonyl]pyrimidin-4-yl}amino)cyclopentyl]methyl sulfamate |
| I-358 | [(1R,2S,4R)-4-{[5-({1-[(1S)-1-(3-bromophenyl)ethyl]-1H-pyrazol-3-yl}carbonyl)pyrimidin-4-yl]amino}-2-hydroxycyclopentyl]methyl sulfamate or [(1R,2S,4R)-4-{[5-({1-[(1R)-1-(3-bromophenyl)ethyl]-1H-pyrazol-3-yl}carbonyl)pyrimidin-4-yl]amino}-2-hydroxycyclopentyl]methyl sulfamate |
| I-359 | [(1R,2R,3R,4R)-3-fluoro-2-hydroxy-4-{[5-({1-[(1R,2R)-(2-phenylcyclopropyl)methyl]-1H-pyrrol-3-yl}carbonyl)pyrimidin-4-yl]amino}cyclopentyl]methyl sulfamate or [(1R,2R,3R,4R)-3-fluoro-2-(hydroxy-4-{[5-({1-[(1S,2S)-(2-phenylcyclopropyl)methyl]-1H-pyrrol-3-yl}carbonyl)pyrimidin-4-yl]amino}cyclopentyl]methyl sulfamate |
| I-360 | [(1R,2S,4R)-4-{[5-({1-[(1S)-1-(3-chlorophenyl)ethyl]-1H-pyrazol-3-yl}carbonyl)pyrimidin-4-yl]amino}-2-hydroxycyclopentyl]methyl sulfamate or [(1R,2S,4R)-4-{[5-({1-[(1R)-1-(3-chlorophenyl)ethyl]-1H-pyrazol-3-yl}carbonyl)pyrimidin-4-yl]amino}-2-hydroxycyclopentyl]methyl sulfamate |
| I-361 | {(1R,2R,3S,4R)-2,3-dihydroxy-4-[(5-{[1-((1S)-1-phenylethyl)-1H-pyrazol-3-yl]carbonyl}pyrimidin-4-yl)amino]cyclopentyl}methyl sulfamate or {(1R,2R,3S,4R)-2,3-dihydroxy-4-[(5-{[1-((1R)-1-phenylethyl)-1H-pyrazol-3-yl]carbonyl}pyrimidin-4-yl)amino]cyclopentyl}methyl sulfamate |
| I-362 | {(1R,2S,4R)-2-hydroxy-4-[(5-{[(1S)-1-(pent-3-yn-2-yl)-1H-pyrazol-3-yl]carbonyl}pyrimidin-4-yl)amino]cyclopentyl}methyl sulfamate or {(1R,2S,4R)-2-hydroxy-4-[(5-{[(1R)-1-(pent-3-yn-2-yl)-1H-pyrazol-3-yl]carbonyl}pyrimidin-4-yl)amino]cyclopentyl}methyl sulfamate |
| I-363 | [(1R,2R,3R,4R)-4-{[5-({1-[(1S)-1-(3-bromophenyl)ethyl]-1H-pyrrol-3-yl}carbonyl)pyrimidin-4-yl]amino}-3-fluoro-2-hydroxycyolopentyl]methyl sulfamate or [(1R,2R,3R,4R)-4-{[5-({1-[(1R)-1-(3-bromophenyl)ethyl]-1H-pyrrol-3-yl}carbonyl)pyrimidin-4-yl]amino}-3-fluoro-2-hydroxycyclopentyl]methyl sulfamate |
| I-364 | [(1R,2R,3R,4R)-4-{[5-({1-[(1S)-1-(5-chloro-2-furyl)ethyl]-1H-pyrrol-3-yl}carbonyl)pyrimidin-4-yl]amino}-3-fluoro-2-hydroxycyclopentyl]methyl sulfamate or [(1R,2R,3R,4R)-4-{[5-({1-[(1R)-1-(5-chloro-2-furyl)ethyl]-1H-pyrrol-3-yl}carbonyl)pyrimidin-4-yl]amino}-3-fluoro-2-hydroxycyclopentyl]methyl sulfamate |
| I-365 | [(1R,2S,4R)-4-{[5-({1-[(1S)-1-(3-chlorophenyl)ethyl]-5-methyl-1H-pyrazol-3-yl}carbonyl)pyrimidin-4-yl]amino}-2-hydroxycyclopentyl]methyl sulfamate or [(1R,2S,4R)-4-{[5-({1-[(1R)-1-(3-chlorophenyl)ethyl]-5-methyl-1H-pyrazol-3-yl}carbonyl)pyrimidin-4-yl]amino}-2-hydroxycyclopentyl]methyl sulfamate |
| I-366 | [(1R,2S,4R)-4-{[5-({1-[(1S)-1-(6-bromopyridin-2-yl)ethyl]-1H-pyrazol-3-yl}carbonyl)pyrimidin-4-yl]amino}-2-hydroxycyclopentyl]methyl sulfamate or [(1R,2S,4R)-4-{[5-({1-[(1R)-1-(6-bromopyridin-2-yl)ethyl]-1H-pyrazol-3-yl}carbonyl)pyrimidin-4-yl]amino}-2-hydroxycyclopentyl]methyl sulfamate |

| Compound | Name |
|---|---|
| I-367 | {(1R,2S,4R)-4-[(5-{[1-(3-bromobenzyl)-5-(2-hydroxypropan-2-yl)-1H-pyrazol-3-yl]carbonyl}pyrimidin-4-yl)amino]-2-hydroxycyclopentyl}methyl sulfamate |
| I-368 | {(1R,2S,4R)-4-[(5-{[1-(3-bromobenzyl)-5-(methoxymethyl)-1H-pyrazol-3-yl]carbonyl}pyrimidin-4-yl)amino]-2-hydroxycyclopentyl}methyl sulfamate |
| I-369 | [(1R,2S,4R)-4-{[5-({1-(3-bromobenzyl)-5-[(1S)-1-methoxyethyl]-1H-pyrazol-3-yl}carbonyl)pyrimidin 4-yl]amino)-2-hydroxycyclopentyl]methyl sulfamate and [(1R,2S,4R)-4-{[5-({1-(3-bromobenzyl)-5-[(1R)-1-methoxyethyl]-1H-pyrazol-3-yl}carbonyl)pyrimidin-4-yl]amino}-2-hydroxycyclopentyl]methyl sulfamate |
| I-369a | [(1R,2S,4R)-4-{[5-({1-(3-bromobenzyl)-5-[(1S)-1-methoxyethyl]-1H-pyrazol-3-yl}carbonyl)pyrimidin-4-yl]amino}-2-hydroxycyclopentyl]methyl sulfamate or [(1R,2S,4R)-4-{[5-({1-(3-bromobenzyl)-5-[(1R)-1-methoxyethyl]-1H-pyrazol-3-yl}carbonyl)pyrimidin-4-yl]amino}-2-hydroxycyclopentyl]methyl sulfamate |
| I-369b | [(1R,2S,4R)-4-{[5-({1-(3-bromobenzyl)-5-[(1S)-1-methoxyethyl]-1H-pyrazol-3-yl}carbonyl)pyrimidin-4-yl]amino}-2-hydroxycyclopentyl]methyl sulfamate or [(1R,2S,4R)-4-{[5-({1-(3-bromobenzyl)-5-[(1R)-1-methoxyethyl]-1H-pyrazol-3-yl}carbonyl)pyrimidin-4-yl]amino}-2-hydroxycyclopentyl]methyl sulfamate |
| I-370 | {(1R,2R,3S,4R)-3-amino-4-[(5-{[1-(3-bromobenzyl)-1H-pyrazol-3-yl]carbonyl}pyrimidin-4-yl)amino]-2-hydroxycyclopentyl}methyl sulfamate |

As discussed above, the present disclosure provides compounds that are useful as inhibitors of SAE, and thus the present compounds can be useful for treating proliferative, inflammatory, cardiovascular and neurodegenerative disorders.

The compounds and pharmaceutical compositions of the present disclosure are can be useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors (hematologic malignancies). The term "cancer" encompasses diseases of skin, tissues, organs, bone, cartilage, blood, and vessels. The term "cancer" further encompasses primary and metastatic cancers.

In some embodiments, therefore, the present disclosure provides the compound of formula (I), or a pharmaceutically acceptable salt thereof, for use in treating cancer. In some embodiments, the present disclosure provides a pharmaceutical composition (as described herein) for the treatment of cancer comprising the compound of formula (I), or a pharmaceutically acceptable salt thereof. In some embodiments, the present disclosure provides the use of the compound of formula (I), or a pharmaceutically acceptable salt thereof, for the preparation of a pharmaceutical composition (as described herein) for the treatment of cancer. In some embodiments, the present disclosure provides the use of an effective amount of the compound of formula (I), or a pharmaceutically acceptable salt thereof, for the treatment of cancer. In some embodiments, the present disclosure provides the compound of formula (I), or a pharmaceutically acceptable salt thereof, for the preparation of a medicament for use in treating cancer.

Non-limiting examples of solid tumors that can be treated with the disclosed inhibitors include pancreatic cancer; bladder cancer including invasive bladder cancer; colorectal cancer; thyroid cancer, gastric cancer, breast cancer, including metastatic breast cancer; prostate cancer, including androgen-dependent and androgen-independent prostate cancer; renal cancer, including, e.g., metastatic renal cell carcinoma; liver cancer including e.g. hepatocellular cancer and intrahepatic bile duct; lung and bronchus cancer, including non-small cell lung cancer (NSCLC), squamous lung cancer, brochioloalveolar carcinoma (BAC), adenocarcinoma of the lung, and small cell lung cancer (SCLC); ovarian cancer, including, e.g., progressive epithelial or primary peritoneal cancer, cervical cancer; uterine cancer including e.g. uterine corpus and uterine cervix; endometrial cancer; gastric cancer; esophageal cancer; head and neck cancer, including, e.g., squamous cell carcinoma of the head and neck, nasopharyngeal cancer, oral cavity and pharynx; melanoma; neuroendocrine cancer, including metastatic neuroendocrine tumors; brain cancer, including, e.g., glioma/glioblastoma, anaplastic oligodendroglioma, adult glioblastoma multiforme, and adult anaplastic astrocytoma; neuroendocrine, including metastatic neuroendocrine tumors; bone cancer, and soft tissue sarcoma.

Non-limiting examples of hematologic malignancies that can be treated with the disclosed inhibitors include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma including diffuse large B-cell lymphoma (DLBCL); T-cell lymphoma; multiple myeloma (MM); amyloidosis; Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, compounds of the present disclosure are suitable for the treatment of breast cancer, lung cancer, ovarian cancer, multiple myeloma, acute myeloid leukemia or acute lymphoblastic leukemia.

In other embodiments, compounds of the present disclosure are suitable for the treatment of inflammatory, cardiovascular and neurodegenerative disorders including, but not limited to, allergies/anaphylaxis, acute and/or chronic inflammation, rheumatoid arthritis, autoimmunity disorders, thrombosis, hypertension, cardiac hypertrophy, heart failure, Huntington's disease and Alzheimers.

Accordingly, in another aspect of the present disclosure, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present disclosure can exist in free form for treatment, or where appropriate, as a pharmaceutically acceptable derivative thereof. According to the present disclosure, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower mammals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of SAE.

Pharmaceutically acceptable salts are well known in the art. For example, S. M. Berge et al., describe pharmaceutically acceptable salts in detail in *J. Pharmaceutical Sciences,* 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This present disclosure also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present disclosure additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the present disclosure, such as by producing any undesirable biological effect or otherwise interacting in a deleterious manner with any other component(s) of the pharmaceutically acceptable composition, its use is contemplated to be within the scope of the present disclosure. Some examples of materials which can serve as pharmaceutically acceptable carriers include, but are not limited to, ion exchangers; alumina; aluminum stearate; lecithin; serum proteins, such as human serum albumin; buffer substances such as phosphates (including but not limited to phosphate buffer solutions), glycine, sorbic acid, or potassium sorbate; partial glyceride mixtures of saturated vegetable fatty acids; water; salts or electrolytes, such as protamine sulfate, disodium hydrogen phosphate, potassium hydrogen phosphate, sodium chloride, and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, cardiovascular or neurodegenerative disorder is provided comprising administering an effective amount of a compound, or a pharmaceutical composition to a subject in need thereof. In certain embodiments of the present disclosure an "effective amount" of the compound or pharmaceutical composition is that amount effective for treating a proliferative, inflammatory, infectious, neurological or cardiovascular disorder, or is that amount effective for treating cancer. In other embodiments, an "effective amount" of a compound is an amount which inhibits binding of SAE.

The compounds and compositions, according to the method of the present disclosure, may be administered using any amount and any route of administration effective for treating the disease. The exact amount required will vary from subject to subject, depending on the species, age, and general condition of the subject, the severity of the infection, the particular agent, its mode of administration, and the like. The compounds of the present disclosure are frequently formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, for instance a mammal such as a human.

The pharmaceutically acceptable compositions of the present disclosure can be administered to humans and other animals orally, rectally, parenterally, intracisternally, intravaginally, intraperitoneally, topically (as by powders, ointments, lotions, or drops), bucally, as an oral or nasal spray, or the like, depending on the severity of the infection being treated. In certain embodiments, the compounds of the present disclosure may be administered orally or parenterally at dosage levels of about 0.01 mg/kg to about 50 mg/kg for instance from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (for instance, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present disclosure, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are for instance suppositories which can be prepared by mixing the compounds of the present disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or for instance in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or for instance in a certain part of the intestinal tract, optionally, in a delayed manner. Examples of embedding compositions that can be used include polymeric substances and waxes.

Dosage forms for topical or transdermal administration of a compound of the present disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of the present disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, the compounds of the present disclosure or a pharmaceutical composition thereof is administered in conjunction with an anticancer agent. As used herein, the term "anticancer agent" refers to any agent that is administered to a subject with cancer for purposes of treating the cancer. Combination therapy includes administration of the therapeutic agents concurrently or sequentially. Alternatively, the therapeutic agents can be combined into one composition which is administered to the patient.

In some embodiments, the compounds of the present disclosure are used in combination with other therapeutic agents. In some embodiments, a compound of the present disclosure is administered in conjunction with another therapeutic agent wherein the therapeutic agent is cytotoxic agents, radiotherapy or immunotherapy.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication. In certain embodiments, a compound of the present disclosure is administered in conjunction with a proteasome inhibitor.

Another aspect of the present disclosure relates to inhibiting SAE activity in a biological sample or a patient, which method comprises administering to the patient, or contacting said biological sample with a compound of formula (I), or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of the present disclosure is to provide a kit comprising separate containers in a single package, wherein a pharmaceutical compound or compositions and/or salts thereof disclosed herein is provided in combination with one or more pharmaceutically acceptable carriers for use in treating one or more disorders, symptoms and diseases where SAE plays a role.

General Synthetic Methods and Intermediates

The compounds of the present disclosure can be prepared by methods known to one of ordinary skill in the art and/or by reference to the schemes shown below and the synthetic examples. Exemplary synthetic routes are set forth in Schemes below and in the Examples.

Scheme 1: General method for the preparation of pyrazole and pyrrole aldehydes iii

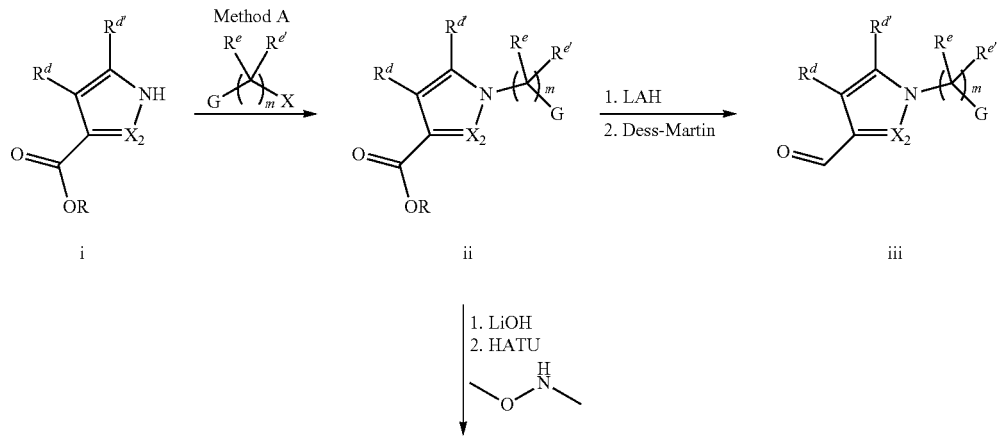

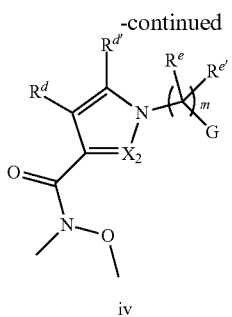

iv

Scheme 1 describes a general route to the substituted pyrazole and pyrrole aldehydes, iii, as well as Weinreb amide iv. Alkylation of i can provide compounds ii by treatment of the starting materials with a base such as DIEA, $Cs_2CO_3$, or $K_2CO_3$ in the presence of an appropriate electrophile in a solvent such as DMF or THF (Method A). In certain cases when m=0, a standard copper assisted cross-coupling reaction (CuI, $K_3PO_4$) will also achieve the desired transformation. Subsequent reduction of the ester and reoxidation to the aldehyde affords iii. Some substituted pyrroles can be converted to the corresponding Weinreb amide, iv, by conversion to the carboxylic acid using bases such as LiOH, KOH, or NaOH followed by amide formation.

Scheme 2: General method for the preparation of substituted pyrroles vi

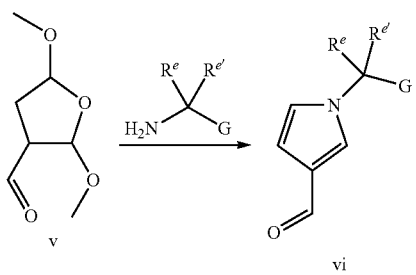

Scheme 2 demonstrates that N-substituted pyrroles, vi, can be generated by the reaction of 2,5-dimethoxy-3-tetrahydrofurancarboxaldehyde v with appropriately substituted tertiary amines in the presence of acetic acid as described by Yoshida, M. et al. (PCT Application Publication WO2009/148004).

Scheme 3: General method for the preparation of diaryl ketones ix

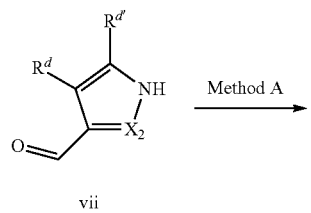

-continued
Method B

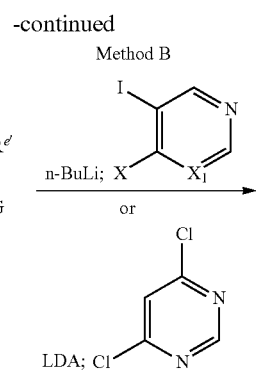

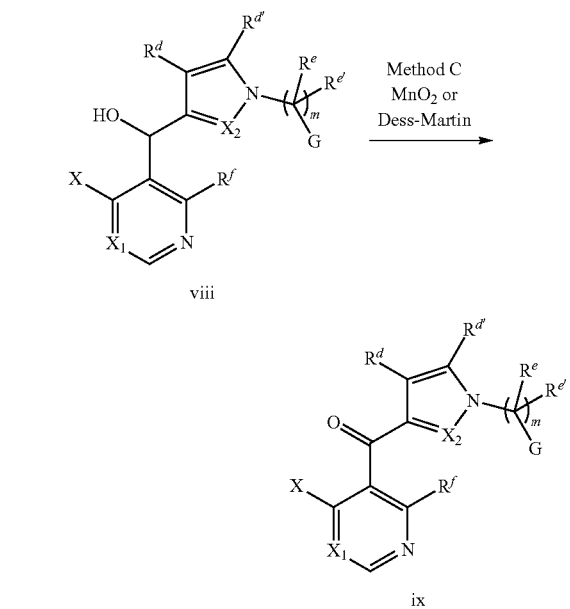

Scheme 3 depicts the synthesis of diaryl ketone intermediates ix. Pyrazole and pyrrole aldehydes vii can be N-alkylated with the desired electrophile via Method A. In this scheme Method A can also be an aryl coupling between vii and an aryl iodide to generate iii. Lithiation of a bis-halogenated pyrimidine or pyridine can be followed by addition of aldehydes iii to give secondary alcohols viii (Method B). The aldehydes iii generated in Scheme 1 could also be inserted into step 2 to give viii via Method B. Oxidation conditions (Method C: manganese(IV) oxide or Dess-Martin periodinane) can be utilized to complete diarylketones ix.

Scheme 4: General method for the preparation of diaryl ketones ix

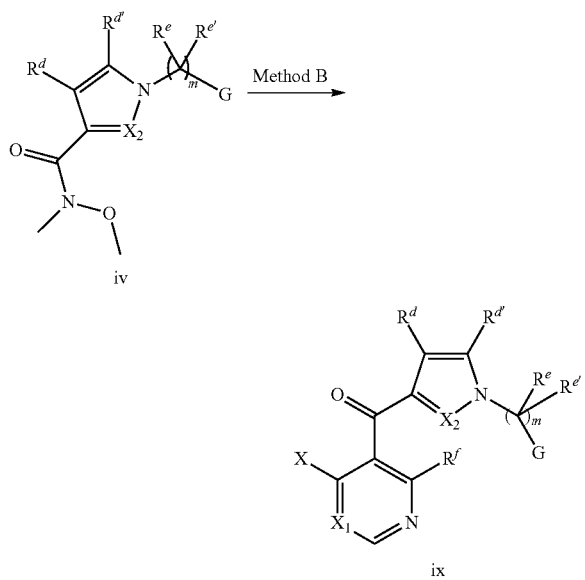

Scheme 4 demonstrates that in similar fashion Method B can also generate diaryl ketones ix from Weinreb amide iv by employment of Method B.

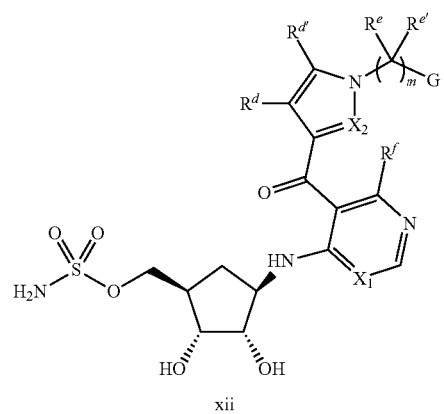

Scheme 5 shows a synthetic route for the preparation of compounds of formula xii. In Method D diaryl ketones ix can be treated with (1R,2S,3R,4R)-1-amino-2,3-(isopropylydenyl)dihydroxy-4-hydroxymethyl cyclopentane x (prepared according to Claiborne, C. F. et al; PCT Application Publication WO 2008/019124) in the presence of base ($K_2CO_3$, DIEA, TEA) in a polar solvent (iPrOH, PrOH, nBuOH, DMF). A two step sequence consisting of sulfamation and deprotection of the acetonide under acidic conditions (Method E) can complete the synthesis of ketopyrimidines xii.

Scheme 5: General method for the synthesis of keto arylamines xii

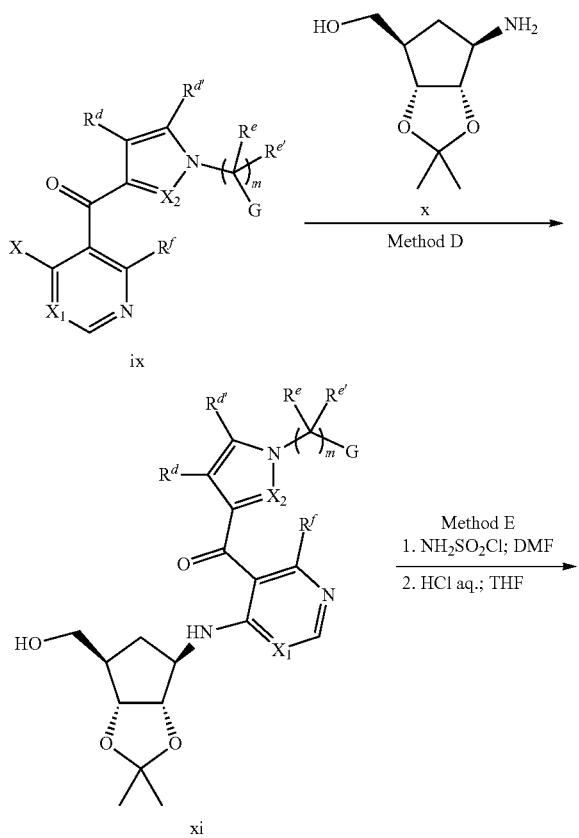

Scheme 6: General method for the preparation of keto arylamines xv

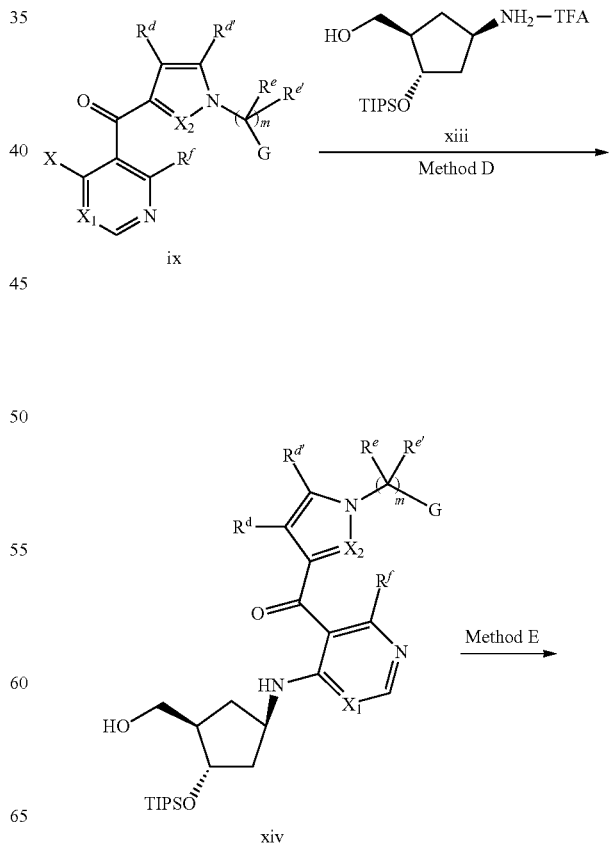

145
-continued

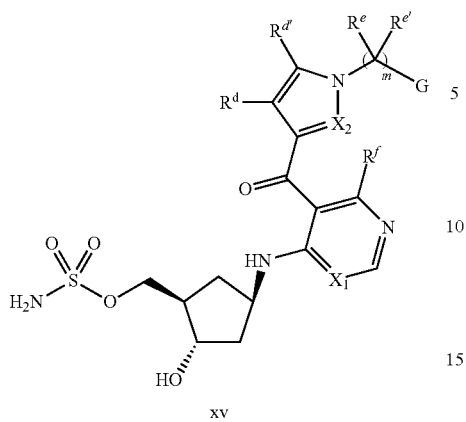

xv

Scheme 6 illustrates the syntheses of compounds with general structure xv. Diaryl ketones ix can be coupled with the TFA salt of cyclopentylamine xiii under conditions of Method D to provide compounds xiv. Employment of Method E (sulfamation followed by TIPS removal) can then lead to compounds xv.

146
-continued

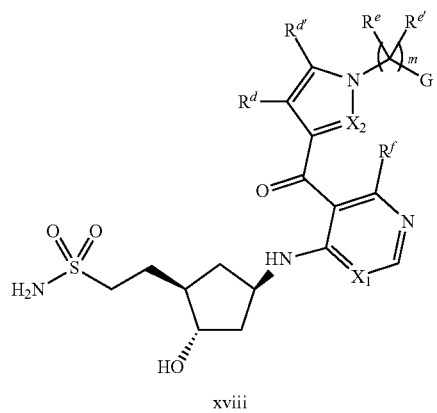

xviii

Scheme 7 illustrates that sulfonamides xviii can also be constructed by a similar route. Diaryl ketones ix can be coupled with cyclopentylamine xvi to give compounds of formula xvii (Method D). Removal of the TIPS protecting group on the secondary alcohol completes the synthesis of xviii.

Scheme 7: General method for the preparation of keto arylamines xviii

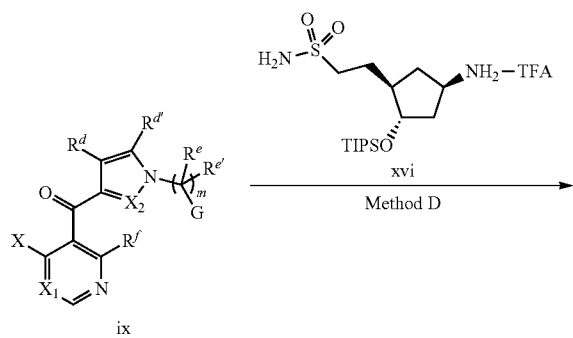

Scheme 8: General method for the preparation of keto arylamines xxii

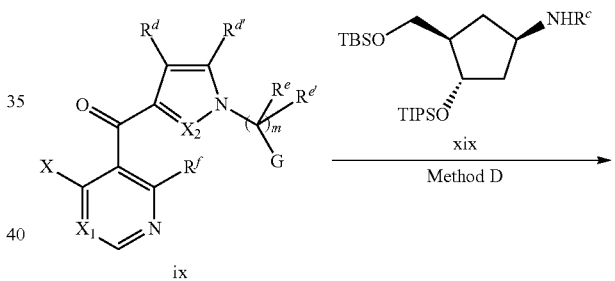

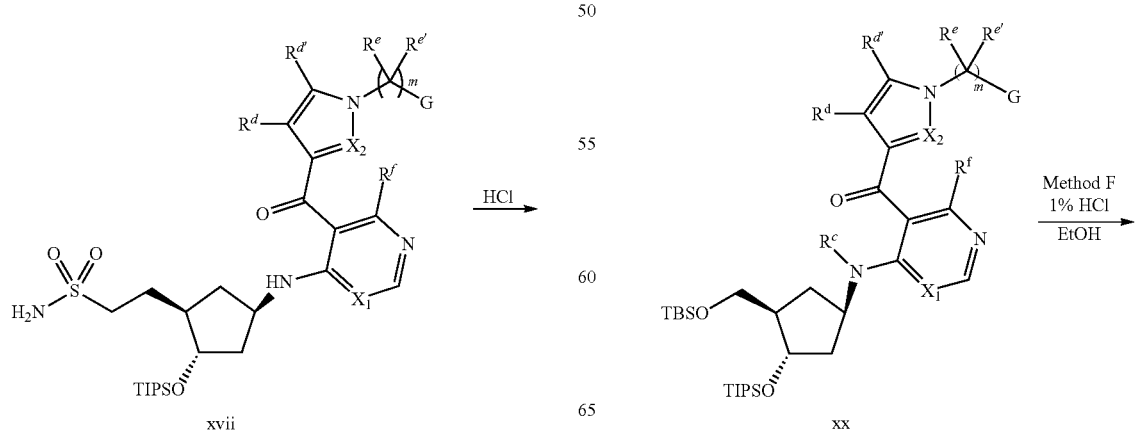

147
-continued

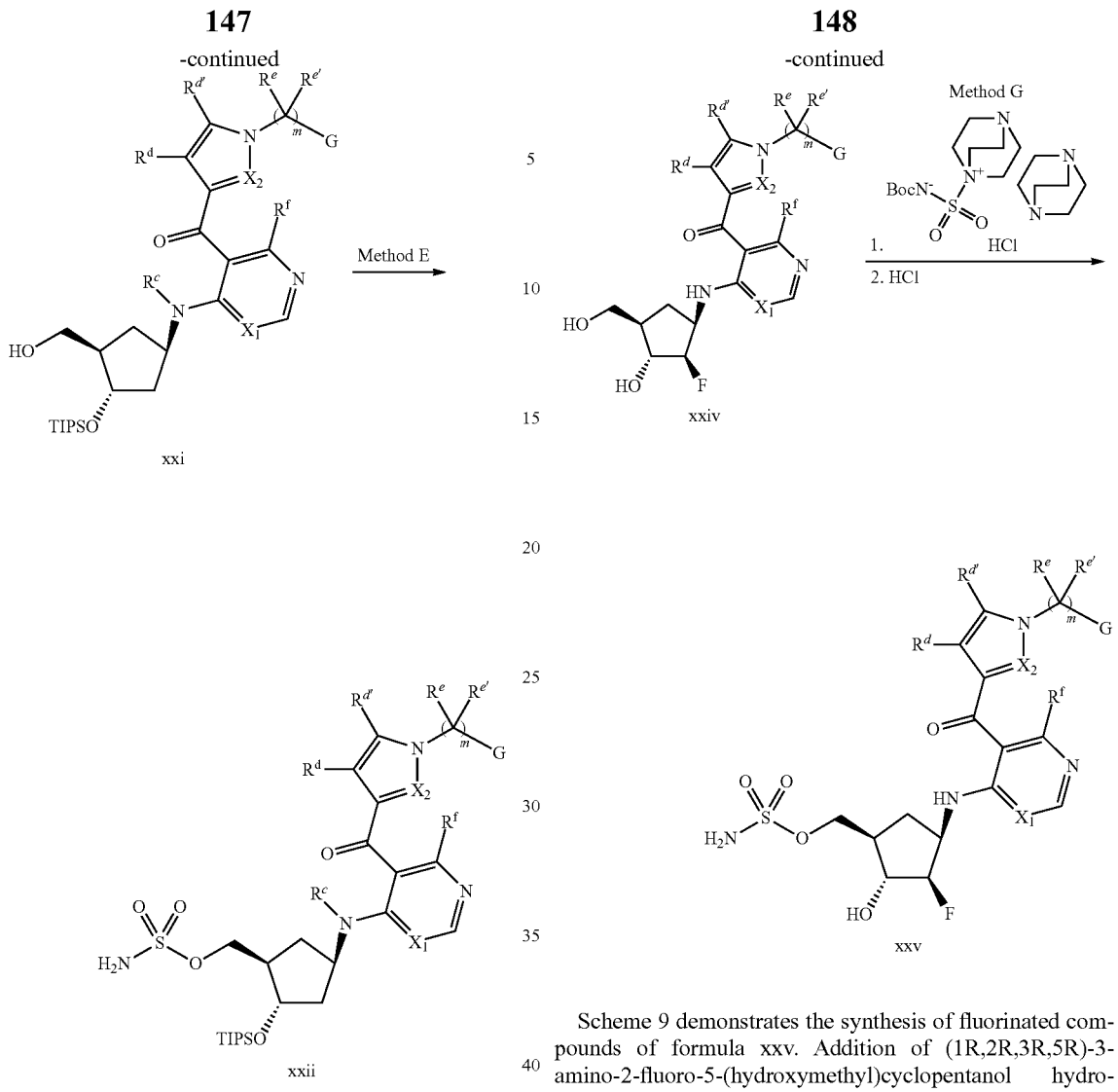

Scheme 8 describes a route for the preparation of compounds of formula xxii. By use of Method D diaryl ketones ix could be coupled to cyclopentylamine xix to give the corresponding aryl amines xx. In the second step these aryl amines can be subjected to a dilute acidic solution in ethanol to selectively remove the TBS protecting group in the presence of the TIPS protecting group (Method F). Sulfamation of the newly revealed primary alcohol followed by removal of the TIPS protecting group under acidic conditions (Method E) provides compounds of formula xxii.

Scheme 9 demonstrates the synthesis of fluorinated compounds of formula xxv. Addition of (1R,2R,3R,5R)-3-amino-2-fluoro-5-(hydroxymethyl)cyclopentanol hydrochloride xxiii (Biggadike, K. et al. *J. Chem. Soc. Perkin Trans.* 1988, 3, 549-554.; Borthwick, A. D. et al. *J. Med. Chem.* 1990, 33, 179-186.) to ix can lead to formation of aryl amines xxiv. A selective sulfamation of the primary alcohol by treatment with a modified Burgess reagent (Armitage, I. et al. *Org. Lett.* 2012, 14, 2626-2629.) can then be followed by treatment with acid to remove the Boc group on the sulfamate (Method G) and results in the synthesis of fluorinated compounds xxv.

Scheme 9: General method for the preparation of keto arylamines xxv

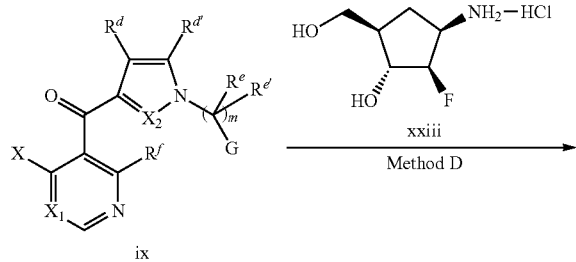

Scheme 10: General method for the preparation of keto arylamines xxx

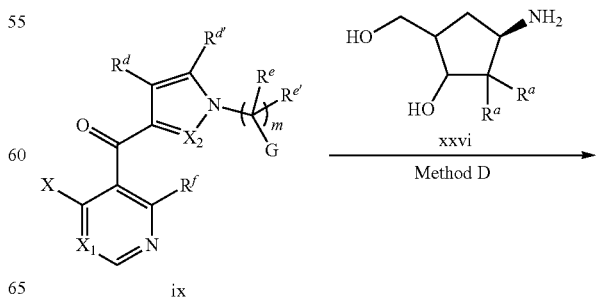

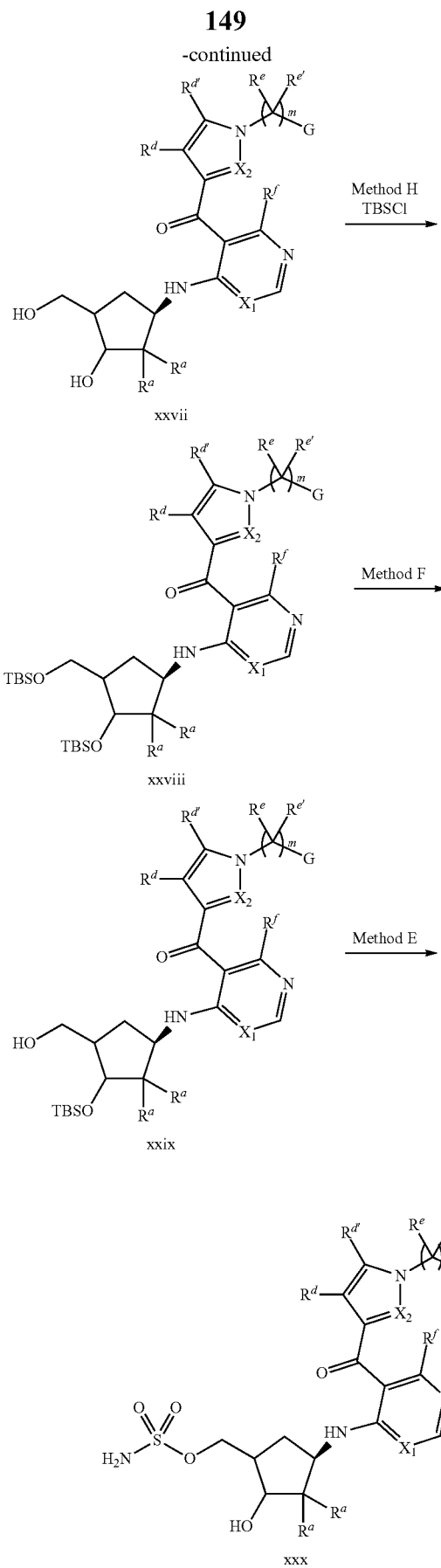

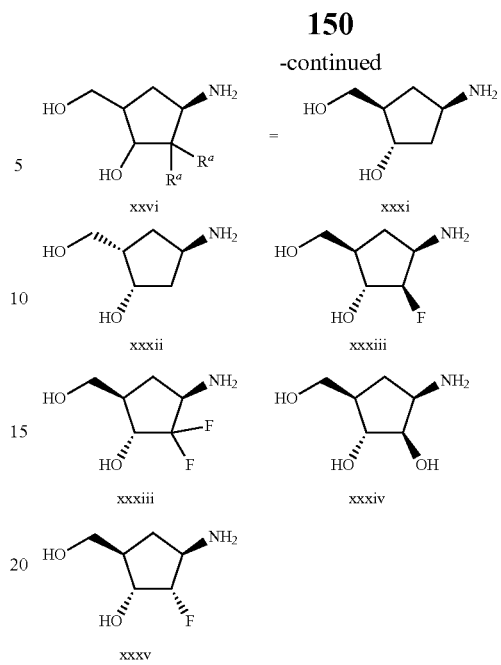

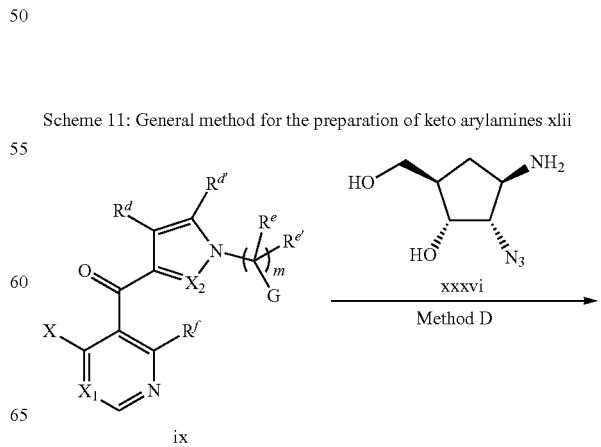

Scheme 10 illustrates the synthesis of compounds of general structure xxx. Method D can be exploited for the addition of cyclopentylamines of general structure xxvi to diaryl ketones ix. In this sequence xxvi can be any of the cyclopentylamines xxxi, xxxii, xxiii, xxxiii, xxxiv, and xxxv (for xxxi see: Ober, M. et al. *J. Am. Chem. Soc.* 2005, 127, 18143-18149.; for xxxii see: Armitage, I. et al. US Patent Application Publication 2009/0036678; for xxiii, xxxiii, xxxv see: Biggadike, K. at al. *J. Chem. Soc. Perkin Trans.* 1988, 3, 549-554.; Borthwick, A. D. et al. *J. Med. Chem.* 1990, 33, 179-186.). Protection of the free alcohols can be accomplished by prolonged treatment with TBSCl in DMF (Method H) to give compounds xxviii, which can then undergo selective deprotection of the primary silyl ether by use of Method F at reduced temperature (<4° C.). Subsequent sulfamation/acid deprotection (Method E) of the secondary silyl ether in compound xxix can provide analogues xxx.

Scheme 11: General method for the preparation of keto arylamines xlii

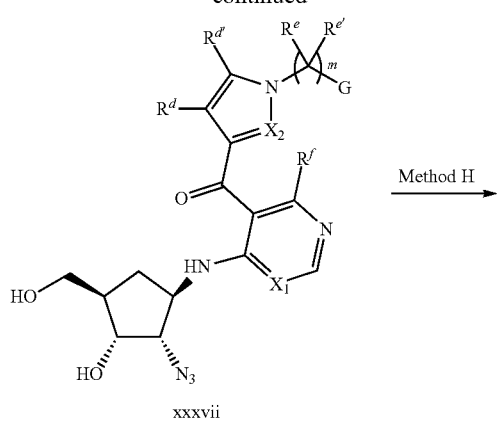

xxxvii

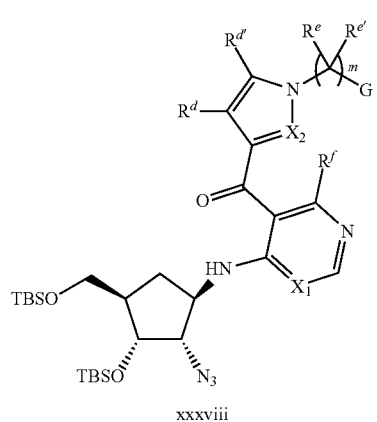

xxxviii

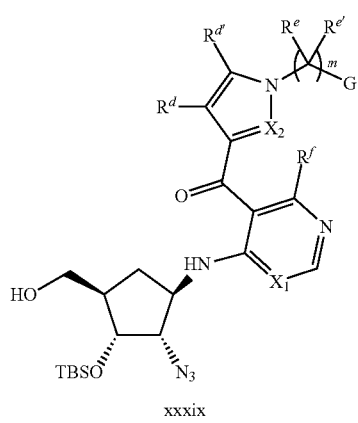

xxxix

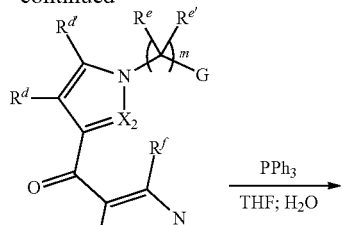

xl

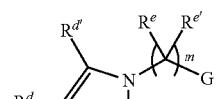

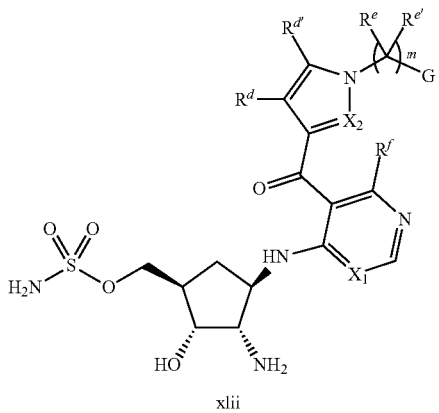

xli xlii

Scheme 11 depicts the synthesis of keto arylamines possessing an amino group at the 2' position of the cyclopentylamine. Similar to Scheme 10, the azide-containing cyclopentylamine xxxvi can be coupled with diaryl ketones ix to give xxxvii. (For the construction of xxxvi, an adapted synthesis of those reported in the following publications can be used. Biggadike, K. at al. *J. Chem. Soc. Perkin Trans.* 1988, 3, 549-554.; Borthwick, A. D. et al. *J. Med. Chem.* 1990, 33, 179-186.) Standard protecting group manipulations (Methods E, F) followed by sulfamation of xxxix can provide intermediates xl. The 2' azide can then be reduced to the corresponding amine via Staudinger reduction followed by removal of the remaining protecting groups under acidic conditions to generate compounds xlii.

Scheme 12: General method for the preparation of keto arylamines xlvi

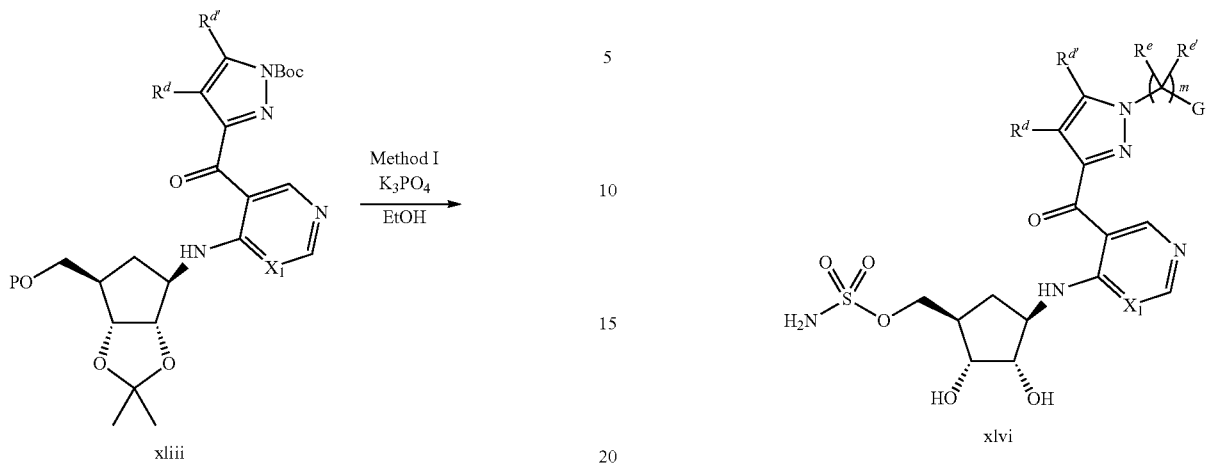

xliii

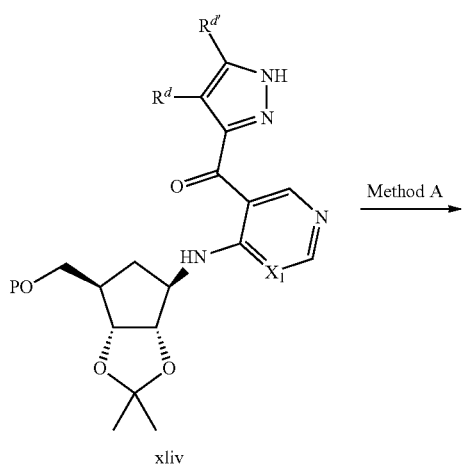

xliv

Scheme 12 shows the use of an advanced intermediate to make pyrazole analogues xlvi. Advanced intermediates xliii (P=H or TBS) can be generated by the routes outlined in Schemes 3 and 5 with the appropriate Boc-protected pyrazole intermediates. Removal of the Boc protecting group can be accomplished by treatment with $K_3PO_4$ in ethanol (Method I) to generate intermediates xliv. Intermediates xliv can then be alkylated by use of Method A. If P=TBS then treatment of xlv with an appropriate fluoride source (TASF, TBAF) can remove the TBS protecting group. The final steps in this sequence are Method E which can accomplish sulfamation and acetonide removal to produce compounds xlvi.

Scheme 13:
General method for an alternative synthesis of keto arylamines xlvi

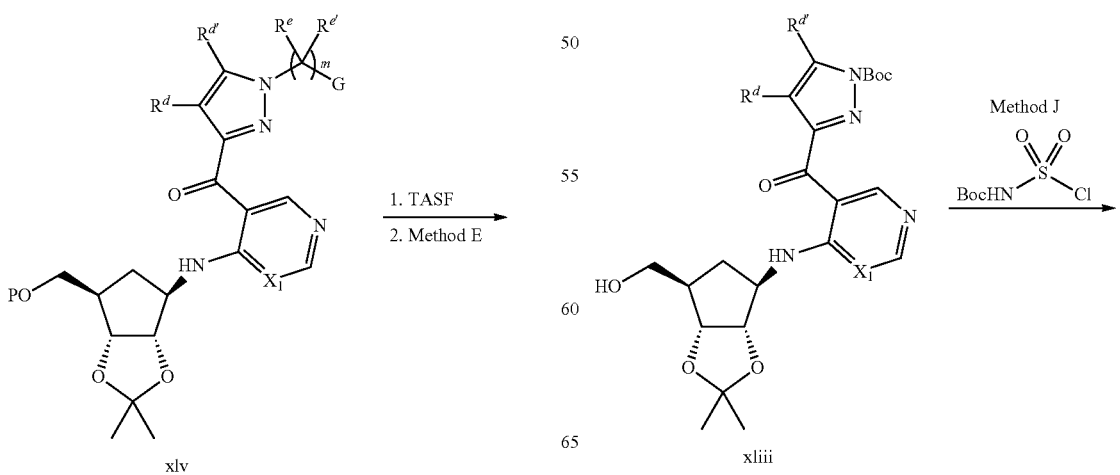

xlv    xliii

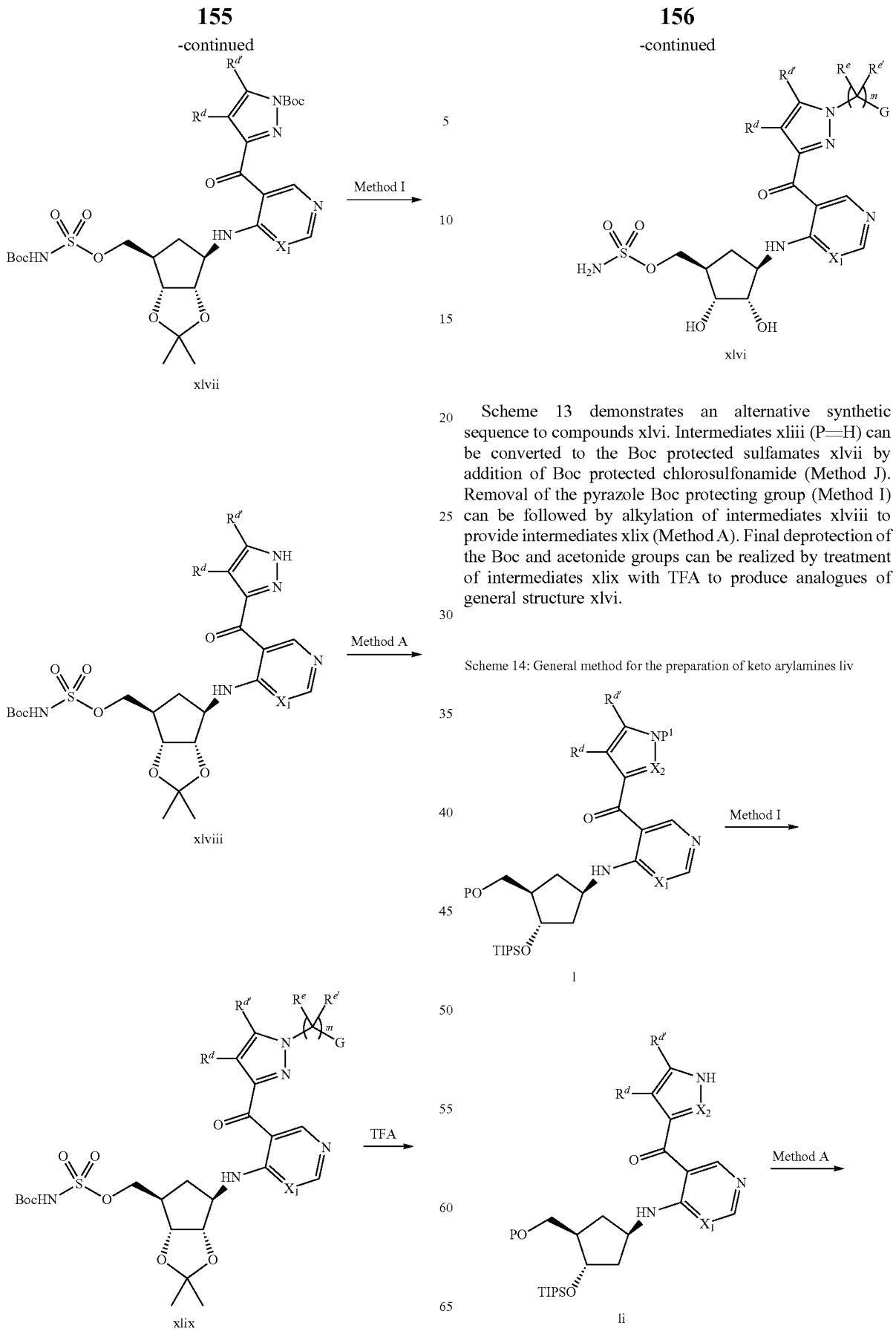

Scheme 13 demonstrates an alternative synthetic sequence to compounds xlvi. Intermediates xliii (P=H) can be converted to the Boc protected sulfamates xlvii by addition of Boc protected chlorosulfonamide (Method J). Removal of the pyrazole Boc protecting group (Method I) can be followed by alkylation of intermediates xlviii to provide intermediates xlix (Method A). Final deprotection of the Boc and acetonide groups can be realized by treatment of intermediates xlix with TFA to produce analogues of general structure xlvi.

Scheme 14: General method for the preparation of keto arylamines liv

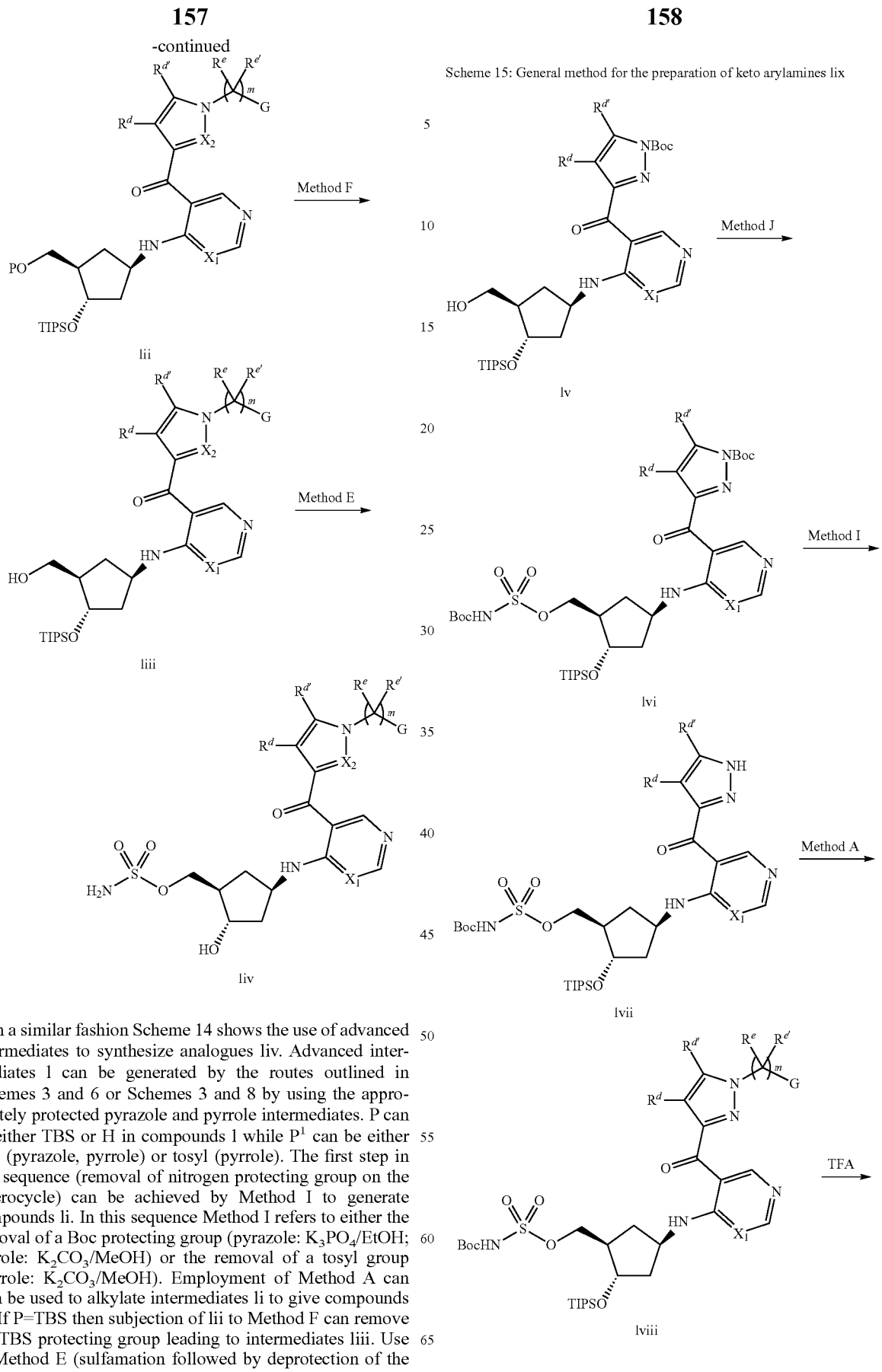

Scheme 15: General method for the preparation of keto arylamines lix

In a similar fashion Scheme 14 shows the use of advanced intermediates to synthesize analogues liv. Advanced intermediates 1 can be generated by the routes outlined in Schemes 3 and 6 or Schemes 3 and 8 by using the appropriately protected pyrazole and pyrrole intermediates. P can be either TBS or H in compounds 1 while $P^1$ can be either Boc (pyrazole, pyrrole) or tosyl (pyrrole). The first step in this sequence (removal of nitrogen protecting group on the heterocycle) can be achieved by Method I to generate compounds li. In this sequence Method I refers to either the removal of a Boc protecting group (pyrazole: $K_3PO_4$/EtOH; pyrrole: $K_2CO_3$/MeOH) or the removal of a tosyl group (pyrrole: $K_2CO_3$/MeOH). Employment of Method A can then be used to alkylate intermediates li to give compounds lii. If P=TBS then subjection of lii to Method F can remove the TBS protecting group leading to intermediates liii. Use of Method E (sulfamation followed by deprotection of the TIPS ether) can complete the synthesis of compounds liv.

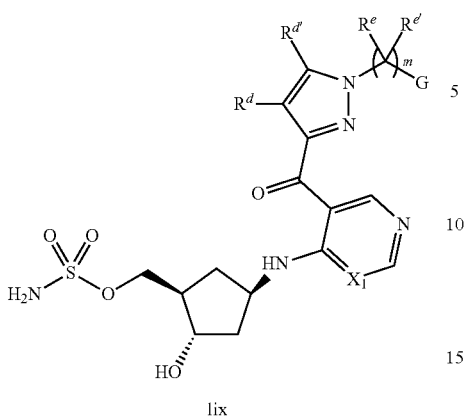

lix

Scheme 15 gives an alternative method for the synthesis of pyrazole analogues lix. Intermediates lv can be converted to the Boc protected sulfamates lvi via Method J. Method I can be utilized to remove the pyrazole Boc protecting group and subsequent alkylation of intermediates lvii by Method A can lead to formation of compounds lviii. Removal of the Boc and TIPS protecting groups by treatment with acid can finish construction of analogues of general structure lix.

Scheme 16: General method for the synthesis of keto arylamines lxv

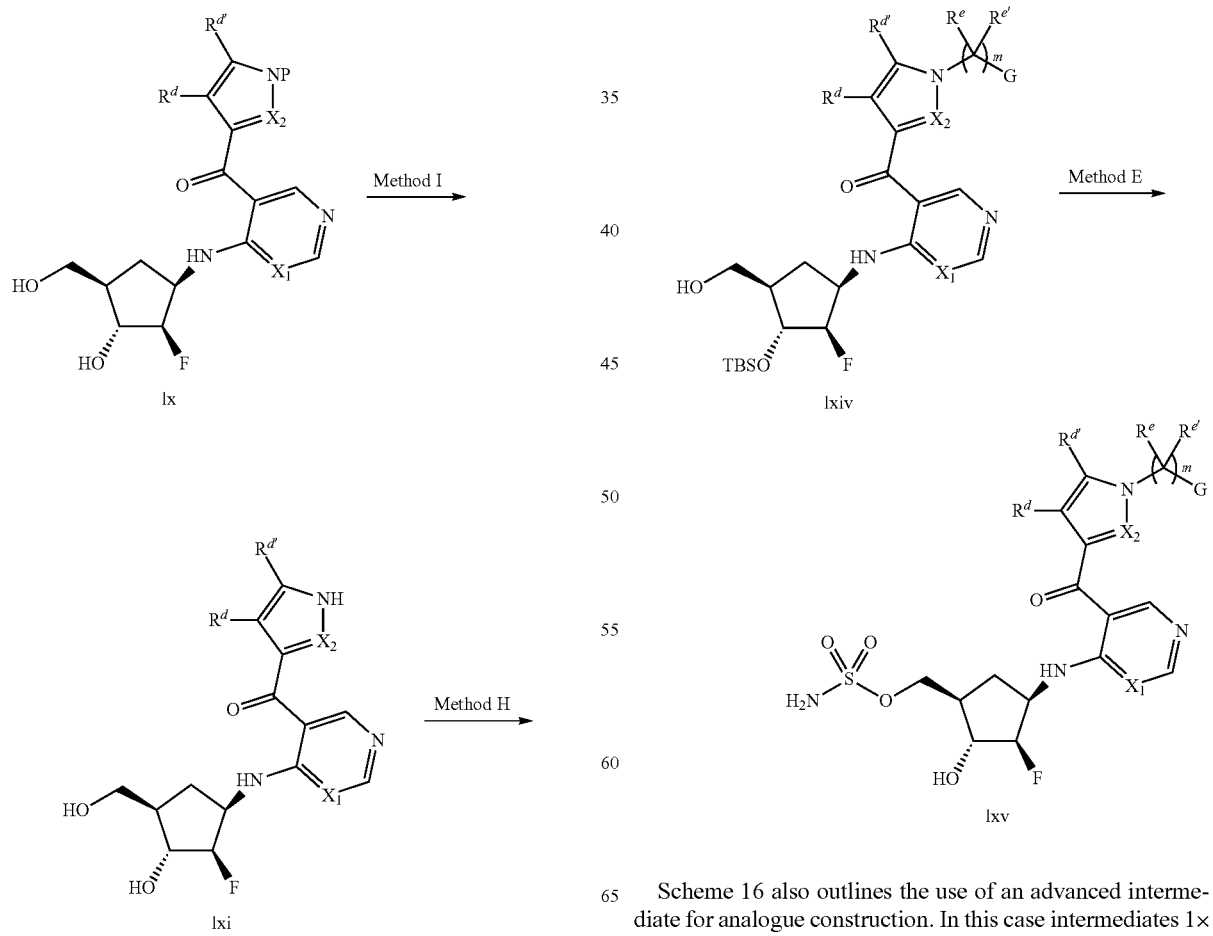

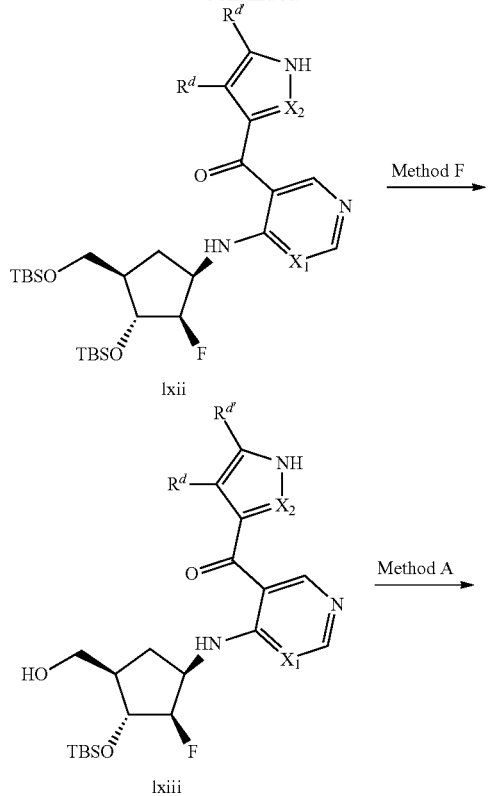

Scheme 16 also outlines the use of an advanced intermediate for analogue construction. In this case intermediates lx can be used to synthesize fluorinated analogues lxv.

Advanced intermediates 1x can be generated by use of the routes outlined in Schemes 3 and 9 implementing the appropriately protected pyrazole and pyrrole intermediates. Removal of the nitrogen protecting group on the heterocycle can be achieved by Method I to generate compounds lxi. Method I can refer to the removal of the Boc protecting group if the heterocycle is pyrazole (K₃PO₄/EtOH) or the removal of a tosyl group if the heterocycle is a pyrrole (K₂CO₃/MeOH). Use of Method H can promote protection of the alcohols as TBS ethers to produce intermediates lxii. Removal of the primary silyl protecting group (Method F) can be followed by alkylation of the nitrogen heterocycle (Method A) to achieve intermediates lxiv. These two steps can also be done in the reverse order (alkylation followed by deprotection). Again, the final steps in this sequence are employment of Method E (sulfamation, TBS removal) which can generate compounds lxv.

Scheme 17: General method for an alternative synthesis of keto arylamines lxv

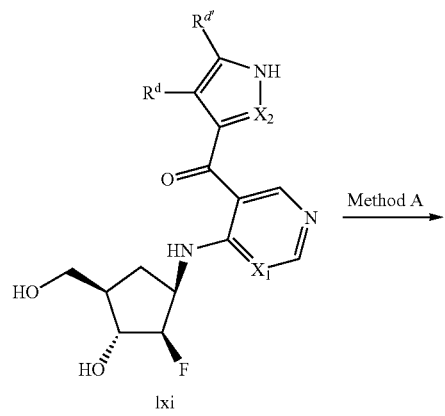

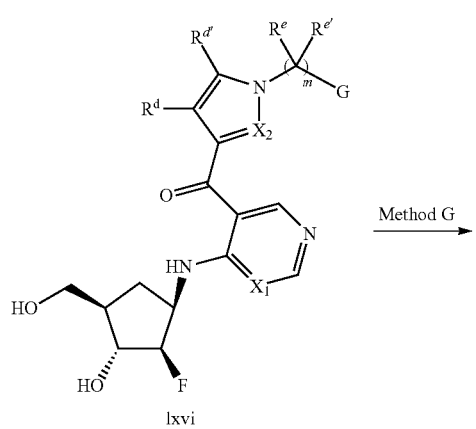

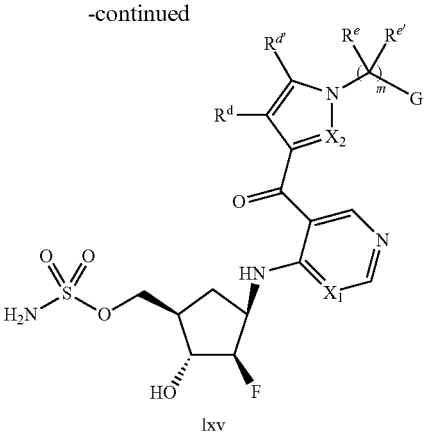

Alternatively, Scheme 17 illustrates that intermediates lxi can be alkylated (Method A) to give intermediates lxvi. The primary alcohol of lxvi may then be sulfamated in a selective manner by use of Method G and complete the construction of fluorinated analogues lxv.

Preparation of Exemplary Compounds

DEFINITIONS

AA LCMS method using ammonium acetate
aq. aqueous
Boc tert-butoxycarbonyl
C Celsius
DCM dichloromethane
DIBAl-H diisobutylaluminum hydride
DIEA diisopropylethylamine
DMA dimethyl acetamide
DMAP 4-dimethylaminopyridine
DMF dimethyl formamide
DMSO dimethyl sulfoxide
EtOAc ethyl acetate
EtOH ethanol
FA LCMS method using formic acid
h hour(s)
HATU (O-(7-azabenzotriazol-1-yl)-N,N,N',N'-tetramethyluronium hexafluorophosphate)
$IC_{50}$ inhibitory concentration 50%
LAH lithium aluminum hydride
LCMS liquid chromatography mass spectrometry
LDA lithium diisopropyl amide
m/z mass to charge
min minute(s)
NBS N-bromosuccinimide
NMP N-methylpyrrolidine
PPTS pyridinium para-toluenesulfonate
RBF round bottomed flask
rt room temperature
TBS tert-butyldimethylsilyl
TBAF tetra-n-butylammonium fluoride
TEA triethylamine
TFA trifluoroacetic acid
THF tetrahydrofuran
TIPS triisopropylsilyl
TLC thin layer chromatography
Tosyl p-toluenesulfonyl Analytical Methods NMR Conditions:

$^1$H NMR spectra are run on either a 300 MHz or 400 MHz Bruker instrument unless otherwise stated.

LCMS Conditions:

LCMS data are acquired on either an Agilent 1100 Series HPLC system or a Waters Acquity UPLC system, connected to a Waters ZQ Mass Spectrometer. Various gradients and run times are used in order to best characterize the compounds under reverse phase conditions using C18 columns. Mobile phase compositions are based on Water/MeCN mixtures containing one of two modifiers: 0.1% formic acid (methods indicated FA) or 10 mM ammonium acetate (methods indicated AA). An example of an HPLC FA gradient program that is applied is running from 100% A to 100% B at a flow rate of 1 mL/min over 16.5 min, Where A=99% Water+1% MeCN+0.1% Formic Acid and B=95% MeCN+5% Water+0.1% Formic Acid.

One of ordinary skill in the art will recognize that modifications of the gradient, column length, and flow rate are possible and that some conditions may be more suitable for compound characterization than others, depending on the chemical species being analyzed.

Starting materials described were either purchased commercially or prepared by the literature routes if a citation is shown.

Example 1: 1-(1-Bromoethyl)-3-chlorobenzene Int-1

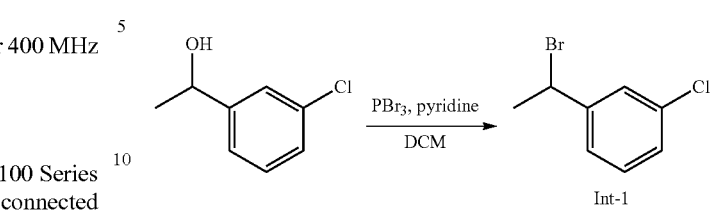

Step 1: 1-(1-Bromoethyl)-3-chlorobenzene Int-1

To a solution of m-chlorophenylmethylcarbinol (0.50 g, 3.2 mmol) and pyridine (0.052 mL, 0.64 mmol) in DCM (10 mL) at −75° C. was added phosphorus tribromide (0.30 mL, 3.2 mmol) dropwise. The mixture was stirred for 10 min and left to stand in a −25° C. freezer overnight. The mixture was then placed in an ice bath and 3 mL water was added slowly. The mixture was partitioned into DCM and water. The organic layer was washed successively with water, 1M NaHCO$_3$ and brine, dried over Na$_2$SO$_4$, filtered, and then concentrated to give 1-(1-bromoethyl)-3-chlorobenzene (700 mg, 100%). $^1$H NMR (CDCl$_3$) δ 7.43 (s, 1H), 7.33-7.29 (m, 1H), 7.28-7.24 (m, 2H), 5.13 (q, J=6.9 Hz, 1H), 2.03 (d, J=6.9 Hz, 3H).

The compounds listed in the table below were prepared in an analogous fashion to that described above starting from the listed starting materials. Standard bromination conditions employing NBS/PPh$_3$ in DCM or CBr$_4$/PPh$_3$ in DCM were used in some cases in lieu of the described reaction conditions in Example 1.

| Starting material | Compound Name/No. | Characterization Data |
|---|---|---|
| OH, isopropyl-alkyne structure | 2-Bromo-3-pentyne/Int-2 | $^1$H NMR (CDCl$_3$) δ 4.67-4.57 (m, 1H), 1.91-1.87 (m, 6H). |
| OH, 1-(3-bromophenyl)ethanol | 1-Bromo-3-(1-bromoethyl)benzene/Int-3 | $^1$H NMR (CDCl$_3$) δ 7.58 (s, 1H), 7.42 (d, J = 7.9 Hz, 1H), 7.36 (d, J = 7.8 Hz, 1H), 7.21 (t, J = 7.9 Hz, 1H), 5.12 (q, J = 6.9 Hz, 1H), 2.02 (d, J = 6.9 Hz, 3H). |
| HO-cyclopropyl-methyl (mixture of trans isomers) | (1R,2R)-1-(Bromomethyl)-2-methylcyclopropane and (1S,2S)-1-(Bromomethyl)-2-methylcyclopropane/Int-4 | $^1$H NMR (CDCl$_3$) δ 3.40-3.28 (m, 2H), 1.06 (d, J = 6.0 Hz, 3H), 1.04-0.96 (m, 1H), 0.81-0.70 (m, 1H), 0.55-0.47 (m, 2H). |
| HO-CH$_2$-tetrahydrofuran | 3-(Bromomethyl)tetrahydrofuran/Int-5 | $^1$H NMR (CDCl$_3$) δ 3.94-3.86 (m, 2H), 3.82-3.74 (m, 1H), 3.60 (dd, J = 9.0, 5.7 Hz, 1H), 3.45-3.35 (m, 2H), 2.76-2.63 (m, 1H), 2.13 (dtd, J = 13.0, 8.0, 5.4 Hz, 1H), 1.69 (dt, J = 13.0, 7.1 Hz, 1H). |
| HO-cyclopropyl-Ph (two trans enantiomers) | (1R,2R)-2-(Bromomethyl)cyclopropyl]benzene and (1S,2S)-2-(Bromomethyl)cyclopropyl]benzene/Int-6 | $^1$H NMR (CDCl$_3$) δ 6.99-7.51 (m, 5H), 3.55 (dd, J = 10.2, 7.4 Hz, 1H), 3.45 (dd, J = 10.2, 7.8 Hz, 1H), 1.90-2.04 (m, |

-continued

| Starting material | Compound Name/No. | Characterization Data |
|---|---|---|
| (mixture of trans isomers) | | 1H), 1.63 (m, 1H), 1.25 (m, 1H), 1.06 (dt, J = 9.0, 5.4 Hz, 1H). |
| HO-CH2-pyridine-4-Me | 2-(Bromomethyl)-4-methylpyridine/ Int-7 | $^1$H NMR (CDCl$_3$) δ 8.43 (d, J = 5.0 Hz, 1H), 7.26 (s, 1H), 7.03 (d, J = 4.6 Hz, 1H), 4.52 (s, 2H), 2.36 (s, 3H). |
| HO-CH2-pyridine-6-Cl | 2-(Bromomethyl)-6-chloropyridine/ Int-8 | $^1$H NMR (CDCl$_3$) δ 7.66 (t, J = 7.8 Hz, 1H), 7.38 (dd, J = 7.6, 0.7 Hz, 1H), 7.26 (d, J = 7.7 Hz, 1H), 4.49 (s, 2H). |
| 1-(3-bromophenyl)propan-1-ol | 1-Bromo-3-(1-bromopropyl)benzene/Int-9 | $^1$H NMR (CDCl$_3$) δ 7.54 (t, J = 1.8 Hz, 1H), 7.41 (ddd, J = 7.9, 1.9, 1.1 Hz, 1H), 7.34-7.29 (m, 1H), 7.21 (t, J = 7.8 Hz, 1H), 4.79 (dd, J = 7.9, 6.9 Hz, 1H), 2.33-2.20 (m, 1H), 2.13 (dp, J = 14.3, 7.2 Hz, 1H), 1.00 (t, J = 7.3 Hz, 3H). |
| 1-(6-bromopyridin-2-yl)ethan-1-ol | 2-Bromo-6-(1-bromoethyl)pyridine/ Int-109 | $^1$H NMR (CDCl$_3$) δ 7.64-7.53 (m, 1H), 7.47 (d, J = 7.3 Hz, 1H), 7.42 (d, J = 7.8 Hz, 1H), 5.19 (q, J = 6.9 Hz, 1H), 2.07 (d, J = 6.9 Hz, 3H). |
| HO-CH2-pyridine-4-Br | 4-Bromo-2-(bromomethyl)pyridine/ Int-110 | $^1$H NMR (CDCl$_3$) δ 8.42 (d, J = 5.3 Hz, 1H), 7.65 (d, J = 1.6 Hz, 1H), 7.42 (dd, J = 5.3, 1.8 Hz, 1H), 4.52 (s, 2H). |
| HO-CH2-pyridine-4-Cl | 2-(Bromomethyl)-4-chloropyridine/ Int-111 | $^1$H NMR (DMSO) δ 8.54 (d, J = 5.3 Hz, 1H), 7.73 (d, J = 1.6 Hz, 1H), 7.50 (dd, J = 5.4, 2.0 Hz, 1H), 4.69 (s, 2H). |

Example 2:
4-(Bromomethyl)-1-fluoro-2-iodobenzene Int-10

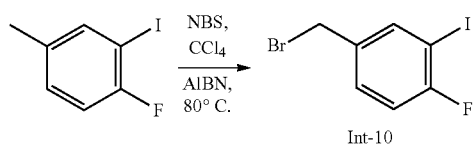

Step 1: 4-(Bromomethyl)-1-fluoro-2-iodobenzene Int-10

A mixture of 4-fluoro-3-iodotoluene (5 g, 21 mmol), NBS (3.77 g, 21 mmol) and azobisisobutyronitrile (35 mg, 0.21 mmol) in CCl$_4$ (30 mL) was heated to reflux for 4 h. The reaction was cooled to rt and concentrated. The residue was purified on silica gel to obtain 4-(bromomethyl)-1-fluoro-2-iodobenzene (1.7 g, 26%). $^1$H NMR (CDCl$_3$) δ 7.78-7.80 (m, 1H), 7.32-7.37 (m, 1H), 7.00-7.05 (m, 1H), 4.41 (s, 2H).

The compounds listed in the table below were prepared using similar methods to that described above starting from the listed starting materials:

| Starting material | Compound Name/ No. | Characterization Data |
|---|---|---|
| 3-tert-butyltoluene | 1-(Bromomethyl)-3-(tert-butyl)benzene/ Int-11 | $^1$H NMR (CDCl$_3$) δ 7.21-7.41 (m, 4H), 4.52 (s, 2H), 0.28 (s, 9H). |
| (3-methylphenyl)trimethylsilane | (3-(Bromomethyl) phenyl)trimethylsilane/ Int-12 | $^1$H NMR (CDCl$_3$) δ 7.30-7.53 (m, 4H), 4.52 (s, 2H), 1.33 (s, 9H). |

| Starting material | Compound Name/No. | Characterization Data |
|---|---|---|
| Ball, L.T. et al. Chem. Eur. J. 2012, 18, 2931-2937. | | |

Example 3: 2-[3-(Bromomethyl)phenyl]propan-2-ol Int-13

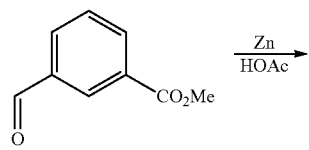

Step 1: 3-Hydroxymethyl-benzoic acid methyl ester

Methyl 3-formylbenzoate (1.64 g, 10.0 mmol) was dissolved in acetic acid (30 mL), and zinc (3.9 g, 60 mmol) was added to this solution at rt. It was then allowed to stir at rt for 2 h. The resulting solid was filtered and poured into 1N HCl (100 mL). The mixture was extracted with DCM (2×). The combined organic layers were then concentrated and the crude product was purified on silica gel to give 3-hydroxymethyl-benzoic acid methyl ester (0.94 g, 57%).

Step 2: 2-[3-(Hydroxymethyl)phenyl]propan-2-ol

3-Hydroxymethyl-benzoic acid methyl ester (0.94 g, 5.7 mmol) was dissolved in THF (70 mL) and the solution was cooled to 0° C. Methylmagnesium bromide (3.0 M solution in ether; 9.4 mL, 28 mmol) was added dropwise to this solution. The reaction was allowed to warm to rt and then stirred for 4 h. The reaction was then quenched with a saturated NH₄Cl solution (aq.) and the mixture extracted with DCM (3×). The combined organic layers were dried over MgSO₄, filtered, and concentrated. The residue was purified on silica gel to give 2-[3-(hydroxymethyl)phenyl]propan-2-ol (0.82 g, 87%).

Step 3: 2-[3-(Bromomethyl)phenyl]propan-2-ol Int-13

2-[3-(Hydroxymethyl)phenyl]propan-2-ol (0.82 g, 4.9 mmol) and carbon tetrabromide (0.49 g, 1.5 mmol) were dissolved in DCM (30 mL). Triphenylphosphine (0.39 g, 1.5 mmol) was added to this solution at rt and the reaction was allowed to stir for 16 h. The reaction mixture was then concentrated and the crude mixture purified on silica gel to provide 2-[3-(bromomethyl)phenyl]propan-2-ol (0.40 g, 36%). ¹H NMR (CDCl₃) δ 7.56 (s, 1H), 7.35 (m, 2H), 7.31 (dt, J=3.5, 1 Hz, 1H), 4.54 (s, 2H), 1.61 (s, 6H).

The compound listed in the table below were prepared in an analogous fashion to that described above starting from the listed starting materials in step 2:

| Starting Material | Compound Name/No. | Characterization Data |
|---|---|---|
| 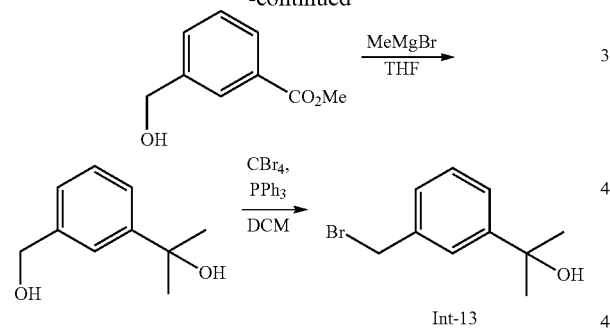 | 2-[6-(Bromomethyl)pyridin-2-yl]propan-2-ol/Int-14 | ¹H NMR (CDCl₃) δ 7.71 (dd, J = 9.5, 6.0 Hz, 1H), 7.31 (d, J = 10.9 Hz, 1H), 7.22 (d, J = 7.6, 1H), 4.77 (s, 2H), 1.56 (s, 6H). |

Example 4: 2-(Bromomethyl)-3-chlorobenzo[b]thiophene Int-15

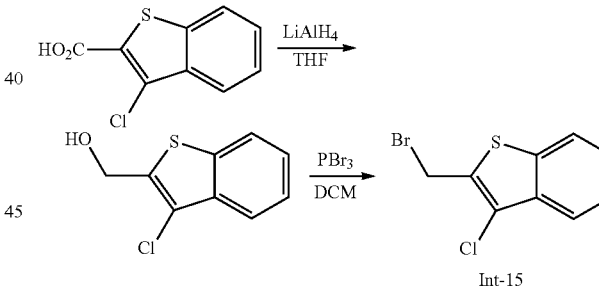

Step 1: (3-Chloro-1-benzothien-2-yl)methanol

To a RBF was added 3-chloro-1-benzothiophene-2-carboxylic acid (1.0 g, 4.7 mmol) in THF (15 mL) and cooled to 0° C. Lithium aluminium hydride (2.0 M solution in THF; 2.35 mL, 4.70 mmol) was then added slowly and the resulting mixture was stirred at 0° C. for 1 h. Additional lithium aluminium hydride (2.0 M solution in THF; 2.0 mL, 4.0 mmol) was then added and the reaction was stirred at rt for 2 h. The reaction was then quenched slowly with water and a saturated solution of Rochelle's salt was added and the mixture stirred for 30 min. The reaction was next extracted with EtOAc (3×). The combined organic layers were washed with water and brine, dried over Na₂SO₄, filtered and concentrated to give (3-chloro-1-benzothien-2-yl)methanol (0.53 g, 56%).

Step 2: 2-(Bromomethyl)-3-chlorobenzo[b]thiophene Int-15

To a solution of (3-chloro-1-benzothien-2-yl)methanol (0.25 g, 1.26 mmol) and pyridine (0.020 mL, 0.25 mmol) in DCM (5 mL) at −75° C. was added phosphorus tribromide (0.13 mL, 1.38 mmol) dropwise. The mixture was stirred at −75° C. for 1 h. The mixture was allowed to stand in a freezer (at −25° C.) for 2 h. The mixture was cooled to 0° C. and quenched slowly with water (3 ml). The mixture was then partitioned into DCM and water. The separated organic layer was washed successively with water, 1M NaHCO$_3$, and brine. The solution was then dried over Na$_2$SO$_4$, filtered and concentrated to provide 2-(bromomethyl)-3-chlorobenzo[b]thiophene (0.33 g, 100%). The crude product was used in the next step without purification (see Example 88).

The compounds listed in the table below were prepared using similar methods to that described above starting from the listed starting materials in the first step. Standard bromination conditions employing CBr$_4$/PPh$_3$ in DCM were used in some cases in lieu of the described reaction conditions for step 2.

Example 5: 2-Bromo-5-(bromomethyl)furan Int-21

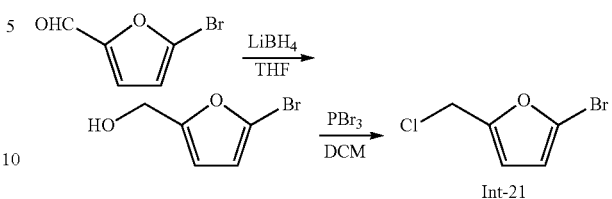

Step 1: 5-Bromo-furan-2-yl-methanol

To a RBF was added lithium borohydride (0.052 g, 2.4 mmol) and THF (18 mL). The resulting reaction mixture was stirred at 0° C. for 5 min then 5-bromo-2-furaldehyde (0.42 g, 2.4 mmol) was added and the mixture was allowed to warm to rt and stir for 16 h. 1 M HCl (aq.) was added carefully to quench the reaction. Solid NaCl was then added

| Starting material | Compound Name/No. | Characterization Data |
|---|---|---|
| HO$_2$C—thiophene—CF$_3$ | 2-(Bromomethyl)-5-(trifluoromethyl)thiophene/Int-16 | $^1$H NMR (CDCl$_3$) δ 7.30 (s, 1H), 7.10 (s, 1H), 4.70 (s, 2H). |
| HO$_2$C—pyridine—CF$_3$ | 4-(Bromomethyl)-2-(trifluoromethyl)pyridine/Int-17 | $^1$H NMR (CDCl$_3$) δ 8.72 (d, J = 5.0 Hz, 1H), 7.70 (s, 1H), 7.51 (dd, J = 5.0, 1.2 Hz, 1H), 4.45 (s, 2H). |
| methyl 3-morpholinobenzoate | 4-(3-(Bromomethyl)phenyl)morpholine/Int-18 | $^1$H NMR (CDCl$_3$) δ 7.22-7.27 (m, 1H), 6.83-6.93 (m, 3H), 4.46 (s, 2H), 3.85-3.88 (m, 4H), 3.16-3.19 (m, 4H). |
| methyl 5-chlorothiophene-2-carboxylate | 2-(Bromomethyl)-5-chlorothiophene/Int-19 | $^1$H NMR (CDCl$_3$) δ 6.88 (d, J = 4 Hz, 1H), 6.74 (d, J = 4 Hz, 1H), 4.62 (s, 2H), 3.85-3.88 (m, 4H), 3.16-3.19 (m, 4H). |
| methyl 3-chlorothiophene-2-carboxylate | 2-(Bromomethyl)-3-chlorothiophene/Int-20 | $^1$H NMR (CDCl$_3$) δ 7.31 (d, J = 5.4 Hz, 1H), 6.90 (d, J = 5.4 Hz, 1H), 4.68 (s, 2H). | until the solution was saturated and the mixture was extracted with EtOAc (2×). The combined organic extracts were washed with brine, dried over MgSO$_4$, and concentrated to give 5-bromo-furan-2-yl-methanol (0.38 g, 90%). $^1$H NMR (CDCl$_3$) δ 6.16 (s, 1H), 6.15 (s, 1H), 4.44 (s, 2H).

Step 2: 2-Bromo-5-(bromomethyl)furan Int-21

To a RBF was added 5-bromo-furan-2-yl-methanol (0.38 g, 2.1 mmol), ether (15 mL), and phosphorus tribromide (0.20 mL, 2.2 mmol). The resulting reaction mixture was stirred at rt for 18 h. Water was then added and the mixture was extracted with EtOAc (2×). The combined organic extracts were washed with brine, dried over MgSO$_4$, and concentrated to give 2-bromo-5-(bromomethyl)furan (0.45 g, 87%). $^1$H NMR (CDCl$_3$) δ 6.28 (d, J=3.3 Hz, 1H), 6.19 (d, J=3.3 Hz, 1H), 4.37 (s, 2H).

The compounds listed in the table below were prepared using similar methods to that described above starting from the listed starting materials.

| Starting material | Compound Name/No. | Characterization Data |
|---|---|---|
| 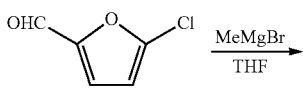 | 2-(Bromomethyl)-5-(methoxymethyl)furan/Int-22 | $^1$H NMR (CDCl$_3$) δ 6.37 (d, J = 3.3 Hz, 1H), 6.30 (d, J = 3.2 Hz, 1H), 4.51 (s, 2H), 4.41 (s, 2H), 3.44-3.37 (s, 3H). |
| 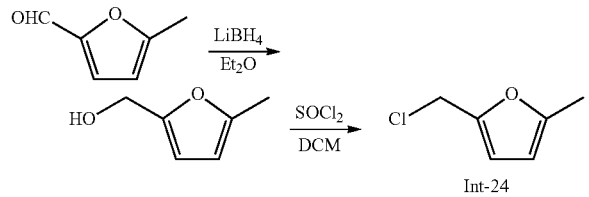 | 2-(Bromomethyl)-5-chlorofuran/Int-23 | $^1$H NMR (CDCl$_3$) δ 6.40 (d, J = 3.3 Hz, 1H), 6.15 (d, J = 3.3 Hz, 1H), 4.46 (s, 2H). |

Example 6: 2-(Chloromethyl)-5-methylfuran Int-24

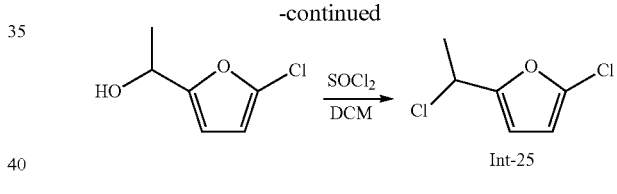

Int-24

Step 1: 5-Methyl-2-furanmethanol

To a RBF was added lithium borohydride (0.10 g, 4.5 mmol) and diethyl ether (10 mL). The resulting reaction mixture was stirred at 0° C. for 5 min then 5-methyl-2-furancarboxaldehyde (0.50 g, 4.5 mmol) was added and the mixture was allowed to warm to rt and stir for 16 h. 1 M HCl (aq.) was added carefully to quench the reaction. Solid NaCl was then added until the solution was saturated and the mixture was extracted with ether (2×). The combined organic extracts were washed with brine, dried over MgSO$_4$, and concentrated to give 5-methyl-2-furanmethanol (0.38 g, 90%). $^1$H NMR (CDCl$_3$) δ 6.18 (d, J=3.0 Hz, 1H), 5.93 (d, J=2.9 Hz, 1H), 4.56 (s, 2H), 2.30 (s, 3H).

Step 2: 2-(Chloromethyl)-5-methylfuran Int-24

To a RBF was added 5-methyl-2-furanmethanol (0.13 g, 1.1 mmol), DCM (15 mL), and TEA (0.16 mL, 1.1 mmol). The resulting reaction mixture was cooled in an ice bath and thionyl chloride (0.10 mL, 1.4 mmol) was added dropwise. The mixture was allowed to stir at 0° C. for 45 min whereupon water was added. The organic layer was separated, dried over MgSO$_4$, filtered and concentrated to give 2-(chloromethyl)-5-methylfuran (0.15 g, 100%). $^1$H NMR (CDCl$_3$) δ 6.31-6.25 (m, 1H), 5.95 (m, 1H), 4.59 (s, 2H), 2.33 (s, 3H).

Example 7: 2-Chloro-5-(1-chloroethyl)furan Int-25

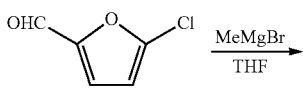

-continued

Int-25

Step 1: 1-(5-Chloro-2-furyl)ethanol

To a RBF was added 5-chloro-2-furaldehyde (0.74 g, 5.7 mmol) and THF (35 mL). The resulting reaction mixture was cooled to 0° C. and methylmagnesium bromide (3.0 M solution in ether; 3.5 mL, 10.50 mmol) was added dropwise. The mixture was then stirred at 0° C. for 25 min and the reaction was quenched by addition of a saturated solution of NH$_4$Cl. The mixture was extracted with EtOAc (2×). The combined organic extracts were washed with brine, dried over MgSO$_4$, and concentrated to give 1-(5-chloro-2-furyl)ethanol (0.82 g, 99%). $^1$H NMR (CDCl$_3$) δ 6.13 (dd, J=3.3, 0.7 Hz, 1H), 6.01 (d, J=3.3 Hz, 1H), 4.71 (q, J=6.4 Hz, 1H), 2.56 (s, 1H), 1.42 (d, J=6.6 Hz, 3H).

Step 2: 2-Chloro-5-(1-chloroethyl)furan Int-25

To a solution of 1-(5-chloro-2-furyl)ethanol (0.49 g, 3.3 mmol) in DCM (30 mL) at 0° C. was added thionyl chloride (0.49 mL, 6.7 mmol) dropwise. The mixture was stirred for 1 h at 0° C. then at rt overnight. Water (20 ml) and a saturated solution of NaHCO$_3$ (30 ml) were added. The organic layer was separated, dried over MgSO$_4$, filtered and concentrated to give 2-chloro-5-(1-chloroethyl)furan (0.55 g, 100%). ¹H NMR (CDCl₃) δ 6.33 (dd, J=3.3, 0.7 Hz, 1H), 6.14 (d, J=3.3 Hz, 1H), 5.14-5.05 (m, 1H), 1.87 (d, J=6.9 Hz, 3H).

Example 8: 2-(Bromomethyl)-5-(difluoromethyl)furan Int-26

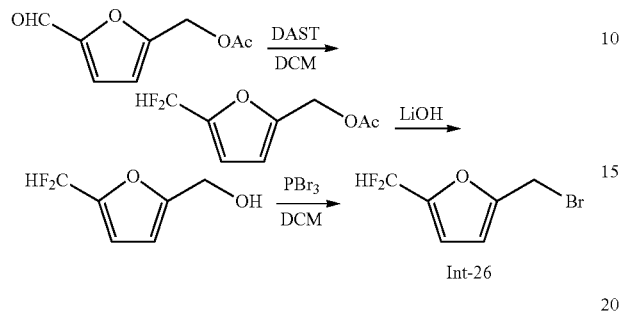

Step 1: [5-(Difluoromethyl)-2-furyl]methyl acetate

5-Acetoxymethyl-2-furaldehyde (3.0 g, 18 mmol) was dissolved in DCM (50 mL) and diethylaminosulfur trifluoride (DAST) (4.3 g, 27 mmol) was added to the solution at 0° C. The reaction mixture was then allowed to warm to rt and stir for 16 h. The mixture was then quenched with water and extracted with DCM (50 mL). The organic layer was concentrated and the resulting residue was purified on silica gel to give [5-(difluoromethyl)-2-furyl]methyl acetate (2.2 g, 66%).

Step 2: [5-(Difluoromethyl)-2-furyl]methanol

[5-(Difluoromethyl)-2-furyl]methyl acetate (2.2 g, 11.8 mmol) was dissolved in methanol (30 mL) and a solution of lithium hydroxide (0.85 g, 35 mmol) in water (10 mL) was added at rt. The resulting mixture was stirred at rt for 4 h. The mixture was concentrated to remove the methanol and the remaining aqueous mixture was neutralized by addition of 1N HCl (50 mL). The mixture was extracted with DCM (3×). The combined organic layers were dried over MgSO₄, filtered, and concentrated. The residue was purified on silica gel to give [5-(difluoromethyl)-2-furyl]methanol (1.1 g, 61%).

Step 3: 2-(Bromomethyl)-5-(difluoromethyl)furan Int-26

[5-(Difluoromethyl)-2-furyl]methanol (1.1 g, 7.2 mmol) and phosphorus tribromide (1.0 mL, 10.8 mmol) were dissolved in DCM (30 mL) and the reaction was allowed to stir for 16 h. The reaction mixture was then concentrated and the crude mixture purified on silica gel to yield 2-(bromomethyl)-5-(difluoromethyl)furan (0.98 g, 65%). ¹H NMR (CDCl₃) δ 6.65-6.62 (m, 1H), 6.45-6.50 (m, 2H), 4.50 (s, 2H).

Example 9: 3-[6-(Bromomethyl)pyridin-2-yl]oxetan-3-ol Int-27

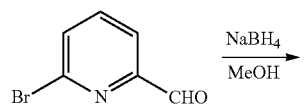

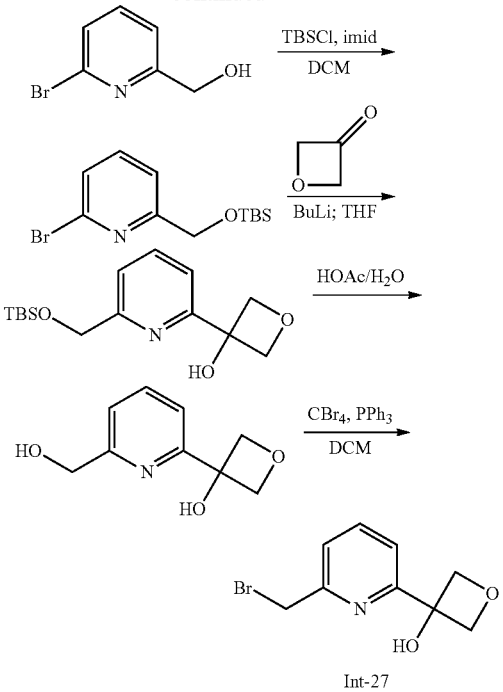

Step 1: 6-Bromo-2-(hydroxymethyl)pyridine

6-Bromo-2-pyridine carboxaldehyde (2.8 g, 15 mmol) was dissolved in methanol (30 mL) and cooled to 0° C. Sodium tetrahydroborate (0.87 g, 23 mmol) was added portionwise over a period of 5 min. It was allowed to stir at 0° C. for 1 h. The solution was then poured into water (80 mL), and the mixture was extracted with DCM (3×). The combined organic layers were washed with water and then concentrated to yield 6-bromo-2-(hydroxymethyl)pyridine (2.5 g, 88%).

Step 2: 2-Bromo-6-({[tert-butyl(dimethyl)silyl]oxy}methyl)pyridine

6-Bromo-2-(hydroxymethyl)pyridine (2.5 g, 13.2 mmol) and tert-butyldimethylsilyl chloride (2.4 g, 16 mmol) were dissolved in DCM (80 mL). 1H-Imidazole (1.2 g, 17 mmol) was then added to this solution at rt and it was allowed to stir for 4 h. The reaction was then washed with water and the organic layer was concentrated and purified on silica gel to afford 2-bromo-6-({[tert-butyl(dimethyl)silyl]oxy}methyl)pyridine (2.2 g, 55%) as a clear liquid.

Step 3: 3-[6-({[tert-Butyl(dimethyl)silyl]oxy}methyl)pyridin-2-yl]oxetan-3-ol

2-Bromo-6-({[tert-butyl(dimethyl)silyl]oxy}methyl)pyridine (2.2 g, 7.2 mmol) was dissolved in THF (50 mL) and then cooled to −78° C. n-Butyllithium (2.0 M solution in THF; 4.7 mL, 9.4 mmol) was then injected into the solution dropwise. The resulting deep brown solution was stirred at −78° C. for 30 min. A solution of 3-oxetanone (0.54 g, 7.6 mmol) in THF (5 mL) was next added to the reaction and the resulting light yellow solution was stirred at −78° C. for 2 h. The reaction was then quenched by addition of a saturated NH₄Cl solution (aq.), which was then extracted with EtOAc (2×). The combined organic layers were concentrated and purified on silica gel to provide 3-[6-({[tert-butyl(dimethyl) silyl]oxy}methyl)pyridin-2-yl]oxetan-3-ol (1.6 g, 75%).

Step 4:
3-[6-(Hydroxymethyl)pyridin-2-yl]oxetan-3-ol

3-[6-({[tert-Butyl(dimethyl)silyl]oxy}methyl)pyridin-2-yl]oxetan-3-ol (1.6 g, 5.4 mmol) was dissolved into a solution of acetic acid (30 mL) and water (10 mL). The reaction was then stirred at 35° C. for 16 h. The mixture was concentrated almost to dryness and then a saturated solution of NaHCO$_3$ was added to basify (pH>8). The mixture was extracted with EtOAc (5×). The combined organic layers were dried, filtered and concentrated. The crude product was purified on silica gel to give 3-[6-(hydroxymethyl)pyridin-2-yl]oxetan-3-ol (0.64 g, 65%).

Step 5: 3-[6-(Bromomethyl)pyridin-2-yl]oxetan-3-ol Int-27

3-[6-(Hydroxymethyl)pyridin-2-yl]oxetan-3-ol (0.64 g, 3.5 mmol) and carbon tetrabromide (1.4 g, 4.2 mmol) were dissolved in DCM (30 mL) at rt. Triphenylphosphine (1.1 g, 4.2 mmol) was added and the solution stirred for 16 h. The reaction mixture was concentrated and the residue purified on silica gel to yield 3-[6-(bromomethyl)pyridin-2-yl]oxetan-3-ol (0.68 g, 80%). $^1$H NMR (CDCl$_3$) δ 7.87-7.99 (m, 2H), 7.45-7.51 (m, 1H), 5.90 (s, 1H), 5.03-5.22 (d, 2H), 4.68-4.84 (d, 2H), 4.57 (s, 2H).

Example 10: 3-(3-Bromoprop-1-yn-1-yl)oxetan-3-ol Int-28

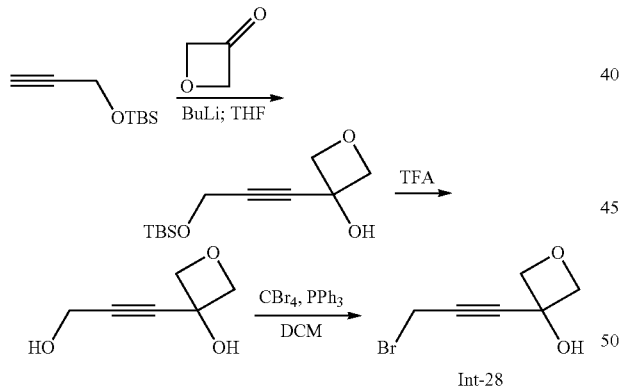

Step 1: 3-(3-{[tert-Butyl(dimethyl)silyl]oxy}prop-1-yn-1-yl)oxetan-3-ol tert-Butyldimethyl(2-propynyloxy)silane (2.0 g, 11.7 mmol) was dissolved in THF (40 mL) and cooled to −78° C. n-Butyllithium (2.5 M solution in hexanes; 5.15 mL, 12.9 mmol) was added dropwise and then the solution was warmed to −30° C. for 20 min. The reaction was cooled again to −78° C. and 3-oxetanone (0.84 g, 11.7 mmol) was added. After stirring at −78° C. for 30 min, it was allowed to warm to rt and stir for 30 min. The reaction mixture was poured into a saturated aqueous solution of NH$_4$Cl and then extracted with EtOAc (2×). The combined organic layers were concentrated and purified on silica gel to afford 3-(3-{[tert-butyl(dimethyl)silyl]oxy}prop-1-yn-1-yl)oxetan-3-ol (2.3 g, 81%).

Step 2: 3-(3-Hydroxyprop-1-yn-1-yl)oxetan-3-ol 3-(3-{[tert-butyl(dimethyl)silyl]oxy}prop-1-yn-1-yl)oxetan-3-ol (2.3 g, 9.5 mmol) was dissolved in DCM (50 mL) followed by addition of a solution of water (0.86 mL, 48 mmol) and TFA (5.4 g, 48 mmol). The mixture was stirred at rt for 4 h. The reaction mixture was concentrated and purified on silica gel to give 3-(3-hydroxyprop-1-yn-1-yl) oxetan-3-ol (0.98 g, 81%).

Step 3: 3-(3-Bromoprop-1-yn-1-yl)oxetan-3-ol Int-28

3-(3-Hydroxyprop-1-yn-1-yl)oxetan-3-ol (0.98 g, 7.7 mmol) and carbon tetrabromide (2.8 g, 8.4 mmol) were dissolved in DCM (30 mL) at rt. Triphenylphosphine (2.3 g, 8.8 mmol) was added and the solution stirred for 16 h. The reaction mixture was concentrated and the residue purified on silica gel to 3-(3-bromoprop-1-yn-1-yl)oxetan-3-ol (1.05 g, 72%). $^1$H NMR (CDCl$_3$) δ 4.85 (d, J=6.7, 0.9 Hz, 2H), 4.76-4.67 (d, 2H), 3.99 (s, 2H).

Example 11: 3-(4-Hydroxytetrahydro-2H-pyran-4-yl)prop-2-yn-1-yl methanesulfonate Int-29

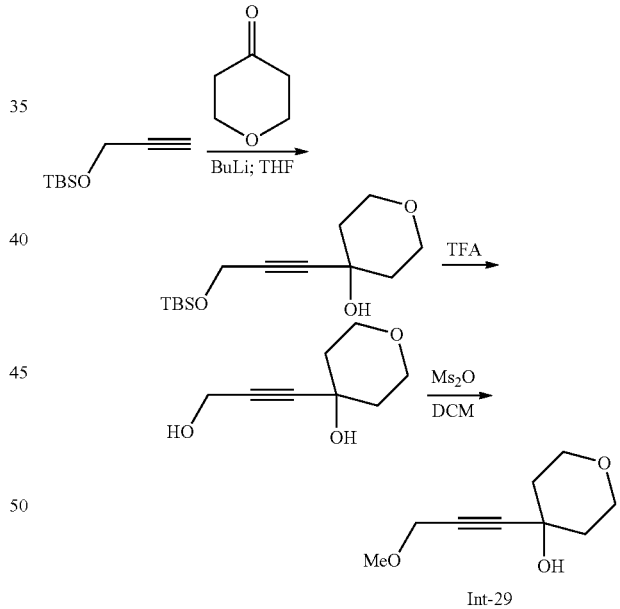

Step 1: 4-(3-{[tert-Butyl(dimethyl)silyl]oxy}prop-1-yn-1-yl)tetrahydro-2H-pyran-4-ol tert-Butyldimethyl(2-propynyloxy)silane (1.6 g, 9.3 mmol) was dissolved in THF (40 mL) and cooled to −78° C. n-Butyllithium (2.5 M solution in hexanes; 4.1 mL, 10.2 mmol) was added dropwise and then the solution was warmed to −30° C. for 20 min. The reaction was cooled again to −78° C. and tetrahydro-4H-pyran-4-one (0.93 g, 9.3 mmol) was added. After stirring at −78° C. for 30 min, it was allowed to warm to rt and stir for 30 min. The reaction mixture was poured into a saturated aqueous solution of NH₄Cl and then extracted with EtOAc (2×). The combined organic layers were concentrated and purified on silical gel to afford 4-(3-{[tert-butyl(dimethyl)silyl]oxy}prop-1-yn-1-yl)tetrahydro-2H-pyran-4-ol (1.9 g, 75%).

Step 2: 4-(3-Hydroxyprop-1-yn-1-yl)tetrahydro-2H-pyran-4-ol 4-(3-{[tert-butyl(dimethyl)silyl]oxy}prop-1-yn-1-yl)tetrahydro-2H-pyran-4-ol (1.9 g, 7.0 mmol) was dissolved in a solution of water (2 mL) and TFA (18 mL). The mixture was stirred at rt for 4 h then concentrated. The residue was dissolved in water (30 mL) and the mixture washed with DCM (2×). The aqueous layer was collected and concentrated to yield 4-(3-hydroxyprop-1-yn-1-yl)tetrahydro-2H-pyran-4-ol (0.56 g, 51%).

Step 3: 3-(4-Hydroxytetrahydro-2H-pyran-4-yl)prop-2-yn-1-yl methanesulfonate Int-29

4-(3-Hydroxyprop-1-yn-1-yl)tetrahydro-2H-pyran-4-ol (0.56 g, 3.6 mmol) was dissolved in THF (20 mL) and DIEA (1.4 g, 11 mmol) was added to this solution. The solution was cooled to 0° C. and methanesulfonic anhydride (0.81 g, 4.7 mmol) was added. It was then allowed to warm to rt and stir for 2 h. The solution was concentrated and the crude residue purified on silical gel to afford 3-(4-hydroxytetrahydro-2H-pyran-4-yl)prop-2-yn-1-yl methanesulfonate (0.52 g, 62%). ¹H NMR (CDCl₃) δ 4.85 (s, 2H), 3.84 (m, 2H), 3.58 (m, 2H), 3.05 (s, 3H), 1.92-1.82 (m, 2H), 1.76 (m, 2H).

Example 12: 3-(3-Hydroxyoxetan-3-yl)benzyl methanesulfonate Int-30

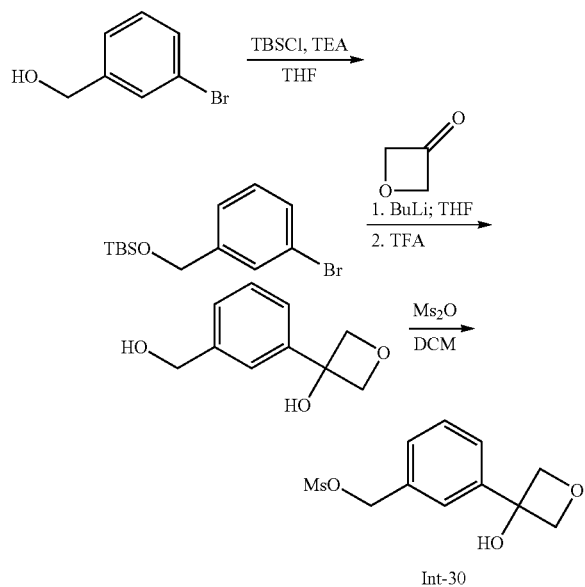

Int-30

Step 1: [(3-Bromobenzyl)oxy](tert-butyl)dimethylsilane

To a solution of 3-bromobenzyl alcohol (1.9 g, 10.0 mmol) in THF (30 mL) was added tert-butyldimethylsilyl chloride (1.96 g, 13.0 mmol) and TEA (2.0 g, 20.0 mmol). The solution was stirred for 16 h at rt. The reaction was then quenched by addition of water (5 mL). EtOAc (50 mL) was added and this solution was washed with water (3×10 mL). The organic layer was dried over MgSO₄, filtered, and concentrated to afford [(3-bromobenzyl)oxy](tert-butyl)dimethylsilane (3.5 g, 100%).

Step 2: 3-[3-(Hydroxymethyl)phenyl]oxetan-3-ol

[(3-Bromobenzyl)oxy](tert-butyl)dimethylsilane (3.5 g, 11.6 mmol) was dissolved in THF (60 mL) and cooled to −78° C. n-Butyllithium (2.5 M solution in hexanes; 7.6 mL, 15.1 mmol) was added dropwise and then the solution was warmed to −30° C. for 20 min. The reaction was cooled again to −78° C. and 3-oxetanone (0.84 g, 11.7 mmol) was added. After stirring at −78° C. for 30 min, it was allowed to warm to rt and stir for 30 min. The reaction mixture was poured into a saturated aqueous solution of NH₄Cl and then extracted with EtOAc (2×). The combined organic layers were concentrated and purified on silica gel to give the unprotected alcohol, which was then dissolved in a solution of water (4 mL) and TFA (16 mL). The mixture was stirred at 0° C. for 2 h. The reaction mixture was concentrated and purified on silica gel to give 3-[3-(hydroxymethyl)phenyl]oxetan-3-ol (0.53 g, 25%).

Step 3: 3-(3-Hydroxyoxetan-3-yl)benzyl methanesulfonate Int-30

3-[3-(Hydroxymethyl)phenyl]oxetan-3-ol (0.53 g, 2.9 mmol) was dissolved in THF (20 mL) and DIEA (1.4 g, 11 mmol) was added to this solution. The solution was cooled to 0° C. and methanesulfonic anhydride (0.67 g, 3.8 mmol) was added. It was then allowed to warm to rt and stir for 2 h. The solution was concentrated and the crude residue purified on silical gel to afford 3-(4-hydroxytetrahydro-2H-pyran-4-yl)prop-2-yn-1-yl methanesulfonate (0.33 g, 44%). ¹H NMR (CDCl₃) δ 7.70 (d, J=7.0 Hz, 2H), 7.49 (s, 1H), 7.36-7.47 (m, 1H), 5.29 (s, 2H), 4.92 (m, 4H), 2.98 (s, 3H).

Example 13: 2-(Bromomethyl)-4-(trifluoromethyl)furan Int-31

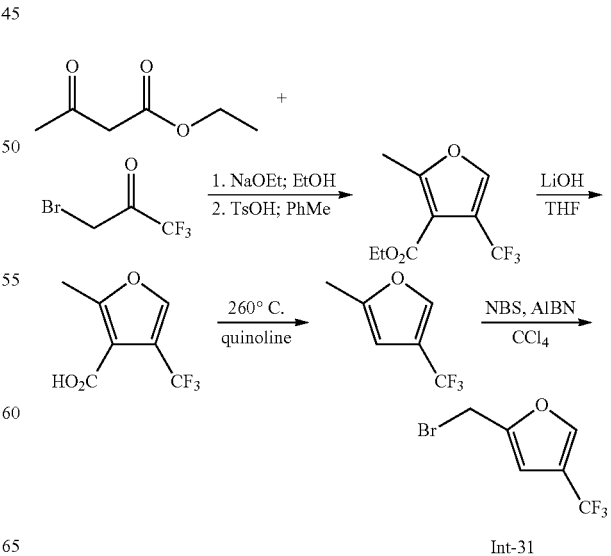

Int-31

Step 1: Ethyl 2-methyl-4-(trifluoromethyl)-3-furoate

3-Bromo-1,1,1-trifluoroacetone (8.7 g, 46 mmol) was dissolved into a solution of sodium ethoxide (6.2 g, 91 mmol) in EtOH (100 mL) and then cooled to 0° C. 3-Oxobutanoic acid ethyl ester (5.9 g, 46 mmol) was added to this solution while keeping the temperature under 10° C. The reaction was then allowed to warm to rt and stir for 16 h. The reaction mixture was quenched by addition of a saturated aqueous solution of $NH_4Cl$ (50 mL) and then extracted with DCM (3×). The combined organic layers were concentrated and the remaining residue dissolved in toluene (100 mL), followed by the addition of toluenesulfonic acid (1.6 g, 9.1 mmol). This mixture was heated to reflux for 4 h. The mixture was then allowed to cool to rt and washed with water (10 mL). The organic layer was concentrated and the crude product was purified on silica gel to give ethyl 2-methyl-4-(trifluoromethyl)-3-furoate (3.2 g, 31%).

Step 2: 2-Methyl-4-(trifluoromethyl)furan-3-carboxylic acid

Ethyl 2-methyl-4-(trifluoromethyl)-3-furoate (3.2 g, 14 mmol) was dissolved in THF (30 mL) then added to a solution of lithium hydroxide (1.0 g, 43 mmol) in water (20 mL). It was then stirred at rt for 16 h. 1N HCl (60 mL) was then added and it was extracted with EtOAc (3×). The combined organic layers were concentrated and purified on silica gel to yield 2-methyl-4-(trifluoromethyl)furan-3-carboxylic acid (1.0 g, 37%).

Step 3: 2-Methyl-4-(trifluoromethyl)furan

2-Methyl-4-(trifluoromethyl)furan-3-carboxylic acid (1.0 g, 5.2 mmol) was dissolved in quinoline (15 mL) and copper(II) sulfate (0.25 g, 1.5 mmol) was added. The reaction flask was fitted with a distillation apparatus and the reaction heated at 250° C. with stirring. 2-methyl-4-(trifluoromethyl)furan (0.34 g, 44%) was collected as a liquid (bp: 72-74° C.).

Step 4: 2-(Bromomethyl)-4-(trifluoromethyl)furan Int-31

2-Methyl-4-(trifluoromethyl)furan (0.34 g, 2.3 mmol) and 2,2'-azo-bis-isobutyronitrile (0.019 g, 0.11 mmol) were dissolved in carbon tetrachloride (20 mL). NBS (0.40 g, 2.3 mmol) was added and the solution was stirred at rt for 16 h. The reaction mixture was concentrated and the crude product was purified on silica gel to give 2-(bromomethyl)-4-(trifluoromethyl) (0.27 g, 52%). $^1$H NMR (CDCl$_3$) δ 7.71 (s, 1H), 6.50 (s, 1H), 4.35 (s, 2H).

Example 14: 5,6-Dihydro-2H-pyran-3-ylmethanol Int-32

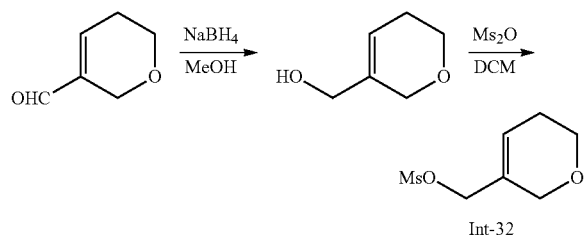

Step 1: 5,6-Dihydro-2H-pyran-3-ylmethanol 5,6-Dihydro-2H-pyran-3-carbaldehyde (0.49 g, 4.4 mmol) was dissolved in methanol (20 mL) and cooled to 0° C. Sodium tetrahydroborate (0.33 g, 8.7 mmol) was added portionwise over a period of 15 min. It was allowed to stir at 0° C. for 2 h. The solution was then poured into water (30 mL), and the mixture was extracted with DCM (3×). The combined organic layers were washed with water and then concentrated to yield 5,6-dihydro-2H-pyran-3-ylmethanol (0.27 g, 55%).

Step 2: 5,6-Dihydro-2H-pyran-3-ylmethyl methanesulfonate Int-32

5,6-Dihydro-2H-pyran-3-ylmethanol (0.27 g, 2.4 mmol) was dissolved in DCM (20 mL) and DIEA (0.9 g, 7.1 mmol) was added to this solution. The solution was cooled to 0° C. and methanesulfonic anhydride (0.62 g, 3.6 mmol) was added. It was then allowed to warm to rt and stir for 2 h. The reaction was diluted with DCM (100 mL) and washed with water (2×). The organic layer was dried over MgSO$_4$, filtered, and concentrated to afford 5,6-dihydro-2H-pyran-3-ylmethyl methanesulfonate (0.40 g, 89%). $^1$H NMR (CDCl$_3$) δ 6.10 (s, 1H), 4.65 (s, 2H), 4.20 (s, 2H), 3.75 (m, 2H), 3.0 (s, 3H), 2.25 (m, 2H).

Example 15: [1-Methyl-3-(trifluoromethyl)-1H-pyrazol-5-yl]methyl methanesulfonate Int-33

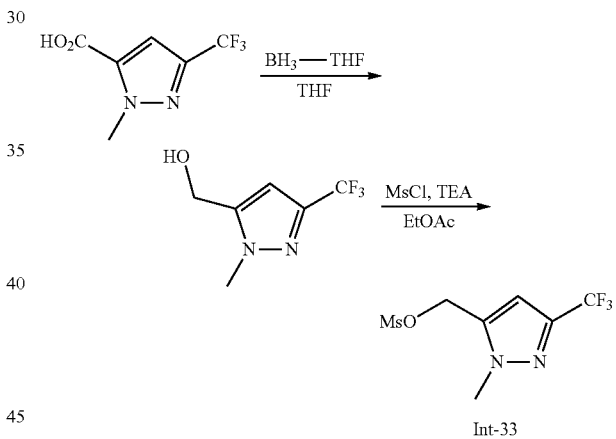

Step 1: 1-Methyl-3-(trifluoromethyl)-1H-pyrazol-5-yl]methanol

Borane (1M in THF; 9.0 mL, 9.0 mmol) was added to a solution of 1-methyl-5-(trifluoromethyl)pyrazole-3-carboxylic acid (350 mg, 1.8 mmol) in THF (10 mL) at rt. The mixture was stirred was stirred for 3 hours. It was then cooled to 0° C. and quenched with water. The mixture was extracted with EtOAc (3×) and the combined organic layers were washed with brine, dried over Na$_2$SO$_4$, filtered, and concentrated. The residue was purified on silica gel to afford [1-methyl-3-(trifluoromethyl)-1H-pyrazol-5-yl]methanol (188 mg; 58%) as a colorless oil. LCMS (FA): m/z=181 (M+H).

Step 2: [1-Methyl-3-(trifluoromethyl)-1H-pyrazol-5-yl]methyl methanesulfonate Int-33

To a solution of [1-methyl-3-(trifluoromethyl)-1H-pyrazol-5-yl]methanol (79 mg, 0.44 mmol) and methanesulfonyl chloride (0.037 mL, 0.47 mmol) in EtOAc (5 mL) was added TEA (0.091 mL, 0.65 mmol) and the mixture was stirred at RT for 3 h. The mixture was quenched with water and extracted with EtOAc (3×). The combined organic layers were washed with brine, dried over $Na_2SO_4$, filtered and concentrated to yield [1-methyl-3-(trifluoromethyl)-1H-pyrazol-5-yl]methyl methanesulfonate (112 mg, 100%). LCMS (FA): m/z=259.1 (M+H).

The compound listed in the table below was prepared in an analogous fashion to that described above starting from the listed starting material:

| Starting material | Compound Name/No. |
|---|---|
| 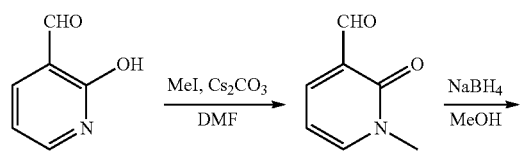 | [1-Methyl-5-(trifluoromethyl)-1H-pyrazol-3-yl]methyl methanesulfonate/Int-34 |

Example 16: 3-(Chloromethyl)-1-methylpyridin-2(1H)-one Int-35

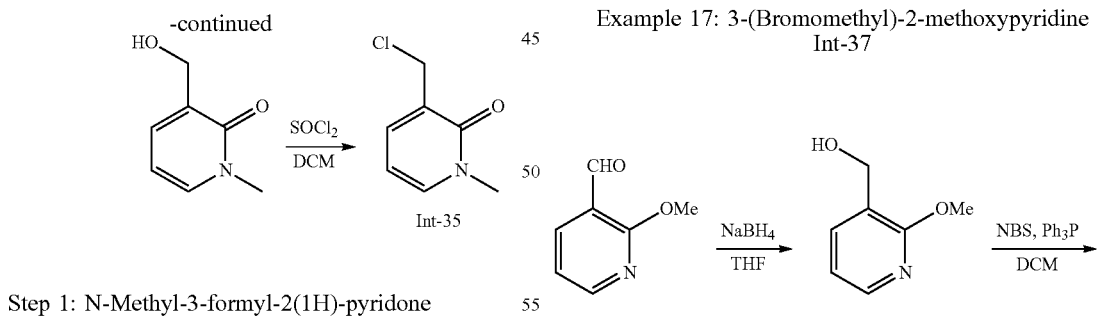

Step 1: N-Methyl-3-formyl-2(1H)-pyridone

To a solution of 2-oxo-1,2-dihydropyridine-3-carbaldehyde (1.0 g, 8.1 mmol) in DMF (20 mL) was added cesium carbonate (3.2 g, 9.8 mmol) at rt and the mixture was stirred for 15 minutes. Methyl iodide (0.61 mL, 9.8 mmol) was added to the mixture and it was stirred at rt for 3 hours. The mixture was quenched with aq. $NH_4Cl$ and extracted with EtOAc (3×). The organic layer was washed with brine, dried over $Na_2SO_4$ and concentrated. The crude product was purified on silica gel to afford methyl-3-formyl-2(1H)-pyridone as a yellow powder (0.57 g, 51%). LCMS (FA): m/z=138 (M+H).

Step 2: 3-(Hydroxymethyl)-1-methylpyridin-2(1H)-one

To a solution of N-methyl-3-formyl-2(1H)-pyridone (570 mg, 4.2 mmol) in methanol (10 mL) was added sodium tetrahydroborate (160 mg, 4.2 mmol) at rt and the mixture was stirred for 2 h. The mixture was quenched with water and extracted with EtOAc (3×). The organic layer was washed with brine, dried over $Na_2SO_4$ and concentrated. The crude product was purified on silica gel to give 3-(hydroxymethyl)-1-methylpyridin-2(1H)-one (613 mg, 100%).

Step 3: 3-(Chloromethyl)-1-methylpyridin-2(1H)-one Int-35

To a solution of 3-(hydroxymethyl)-1-methylpyridin-2(1H)-one (459 mg, 3.30 mmol) in DCM (10 mL) was added thionyl chloride (0.29 mL, 4.0 mmol) at rt and the mixture was stirred for 2 hours. The volatiles were removed under reduced pressure and the residue was quenched with aq. $NaHCO_3$ and extracted with EtOAc. The organic layer was washed with brine, dried over $Na_2SO_4$ and concentrated. The crude product was purified on silica gel to afford 3-(chloromethyl)-1-methylpyridin-2(1H)-one (370 mg, 71%). LCMS (FA): m/z=158 (M+H).

The compound listed in the table below was prepared in an analogous fashion to that described above starting from the listed starting material used in step 2:

| Starting material | Compound Name/No. | Characterization Data |
|---|---|---|
| ![CO2Me imidazo[1,2-a]pyridine] | 5-(Chloromethyl)imidazo[1,2-a]pyridine/Int-36 | LCMS (FA): m/z = 167 (M + H). |

Example 17: 3-(Bromomethyl)-2-methoxypyridine Int-37

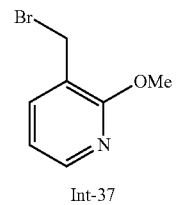

Int-37

Step 1: (2-Methoxypyridin-3-yl)methanol

To a solution of 2-methoxy-pyridine-3-carbaldehyde (2.03 g, 14.8 mmol) in THF (35 mL) was added sodium tetrahydroborate (617 mg, 16.3 mmol) at rt and the mixture was stirred for 1 h. The mixture was quenched with water and extracted with EtOAc. The organic layer was washed with brine, dried over $Na_2SO_4$ and concentrated. The crude product was purified on silica gel to give (2-methoxypyridin-3-yl)methanol (2.05 g, 99%) as a clear oil. LCMS (FA): m/z=140 (M+H).

Step 2: 3-(Bromomethyl)-2-methoxypyridine Int-37

To a solution of (2-methoxypyridin-3-yl)methanol (811 mg, 5.8 mmol) and N-bromosuccinimide (1.24 g, 7.0 mmol) in DCM (10 mL) was added triphenylphosphine (1.8 g, 7.0 mmol) at rt and the mixture was stirred for 2 h. The mixture was quenched with water and extracted with EtOAc. The organic layer was washed with brine, dried over $Na_2SO_4$ and concentrated. The crude product was purified on silica gel to give 3-(bromomethyl)-2-methoxypyridine (829 mg, 70%) as clear oil. $^1$H NMR (CDCl$_3$) 8.14 (dd, J=5.0, 1.9 Hz, 1H), 7.63 (dd, J=7.3, 1.9 Hz, 1H), 6.89 (dd, J=7.3, 5.0 Hz, 1H), 4.51 (s, 2H), 4.04 (s, 3H).

The compound listed in the table below was prepared in an analogous fashion to that described above starting from the listed starting material:

| Starting material | Compound Name/ No. | Characterization Data |
|---|---|---|
| 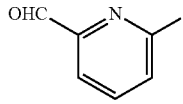 | 2-(bromomethyl)-6-methoxypyridine/ Int-38 | $^1$H NMR (CDCl$_3$) δ 7.56 (dd, J = 8.3, 7.2 Hz, 1H), 7.01 (dd, J = 7.2, 0.5 Hz, 1H), 6.68 (d, J = 8.3 Hz, 1H), 4.48 (s, 2H), 3.96 (s, 3H). |

Example 18: Imidazo[1,2-a]pyridin-6-ylmethyl methanesulfonate Int-39

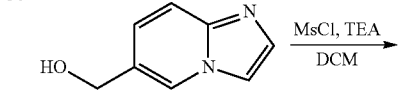

Int-39

Step 1: Imidazo[1,2-a]pyridin-6-ylmethyl methanesulfonate Int-39

To a solution of imidazo[1,2-a]pyridin-6-ylmethanol (54 mg, 0.37 mmol) and methanesulfonyl chloride (32 uL, 0.41 mmol) in DCM (3 mL) was added TEA (66 uL, 0.47 mmol) and the mixture was stirred at rt for 3 h. The mixture was filtered and the filtrate was concentrated to give imidazo[1, 2-a]pyridin-6-ylmethyl methanesulfonate (84 mg, 100%). LCMS (FA): m/z=227 (M+H).

Example 19: (3-Methylisoxazol-5-yl)methyl 4-methylbenzenesulfonate Int-40

Int-40

Step 1: 3-Methylisoxazol-5-yl)methyl 4-methylbenzesulfonate Int-40

TEA (1.2 mL, 8.8 mmol) was added to a solution of (3-methylisoxazol-5-yl)methanol (0.5 g, 4 mmol) and p-toluenesulfonyl chloride (1.3 g, 6.6 mmol) in THF (10 mL) at room temp under an atmosphere of argon. A catalytic amount of DMAP was added and the reaction stirred at rt. After 24 h the reaction was quenched by the addition of brine. The mixture was extracted with EtOAc (3×). The combined organic layers were dried over MgSO$_4$, filtered, and concentrated. The crude product was purified on silica gel to yield 3-methylisoxazol-5-yl)methyl 4-methylbenzenesulfonate (130 mg, 10%). LCMS (FA): m/z=268 (M+H).

The compounds listed in the table below were prepared in a similar fashion to that described above starting from the listed starting materials:

| Starting material | Compound Name/No. | Characterization Data |
|---|---|---|
| HO—CH$_2$—CH$_2$—C≡C—CH$_3$ | Pent-3-yn-1-yl 4-methylbenzenesulfonate/ Int-41 | LCMS (FA): m/z = 239.2 (M + H). |
| HO-CH$_2$-(3,6-dihydro-2H-pyran-4-yl) Hatano, M. et al. *J. Am. Chem. Soc.* 2003, 125, 4704-4705. | 3,6-Dihydro-2H-pyran-4-ylmethyl 4-methylbenzenesulfonate/ Int-42 | $^1$H NMR (CDCl$_3$) δ 7.76-7.89 (m, 2H), 7.37 (d, J = 8.0 Hz, 2H), 5.75-5.79 (m, 1H), 4.47 (s, 2H), 4.10 (m, 2H), 3.72 (t, J = 5.5 Hz, 2H), 2.48 (s, 3H), 2.06 (dd, J = 4.6, 2.6 Hz, 2H). |

Example 20: 3-Ethynyl-4-fluorobenzyl methanesulfonate Int-43

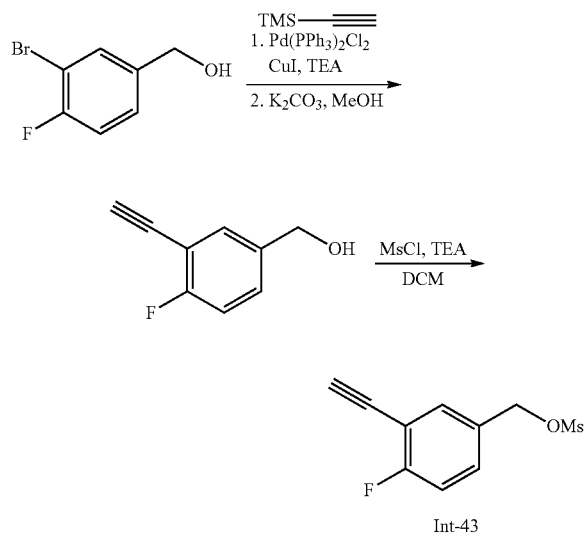

Step 1: {4-Fluoro-3-[(trimethylsilyl)ethynyl]phenyl}methanol

A reaction vial was charged with (3-bromo-4-fluorophenyl)methanol (1.0 g, 4.9 mmol), (PPh$_3$)$_2$PdCl$_2$ (68 mg, 0.10 mmol), CuI (37 mg, 0.20 mmol), and TEA (5.0 mL, 36 mmol). The vial was purged with argon and then sealed with a cap. After sonication, (trimethylsilyl)acetylene (1.0 mL, 7.3 mmol) was added to the mixture, and the resulting mixture was heated at 100° C. for 48 h. The reaction was diluted with EtOAc (100 mL) and the EtOAc layer was washed with 1 M HCl (60 mL×2), water (60 mL) and brine (60 mL). The organic layer was dried over Na$_2$SO$_4$, filtered, and concentrated in vacuo. The residue was purified on silica gel to give {4-fluoro-3-[(trimethylsilyl)ethynyl]phenyl}methanol (287 mg, 26%).

Step 2: (3-Ethynyl-4-fluorophenyl)methanol

To a solution of {4-fluoro-3-[(trimethylsilyl)ethynyl]phenyl}methanol (280 mg, 1.20 mmol) in MeOH (3 mL) was added K$_2$CO$_3$ (0.87 g, 6.30 mmol) at rt, and the mixture was stirred for 1 h. The reaction was concentrated in vacuo. To the residue was added water (50 mL) and extracted with Et$_2$O (50 mL×3). The combined organic layers were dried over Na$_2$SO$_4$, filtered, and concentrated in vacuo. The residue was purified by silica gel column chromatography to give (3-ethynyl-4-fluorophenyl)methanol (178 mg, 94%) as a light brown oil.

Step 3: 3-Ethynyl-4-fluorobenzyl methanesulfonate Int-43

To a solution of (3-ethynyl-4-fluorophenyl)methanol (180 mg, 1.2 mmol) in DCM (10 mL) was added TEA (0.24 mL, 1.8 mmol) followed by methanesulfonyl chloride (95 uL, 1.2 mmol) at 0° C. under an atmosphere of argon. The mixture was stirred for 4 h. The reaction was quenched by addition of water (50 mL) and DCM (50 mL). After separation, the DCM layer was washed with water (50 mL) followed by brine (50 mL) and then dried over Na$_2$SO$_4$. The mixture was filtered and concentrated in vacuo. The residue was purified on silica gel to give 3-ethynyl-4-fluorobenzyl methanesulfonate (145 mg, 55%) as a colorless solid. $^1$H NMR (CDCl$_3$) δ 7.55 (dd, J=6.5, 2.3 Hz, 1H), 7.43-7.37 (m, 1H), 7.13 (t, J=8.7 Hz, 1H), 5.18 (s, 2H), 3.34 (s, 1H), 2.98 (s, 3H)

The compound listed in the table below was prepared in an analogous fashion to that described above starting from the listed starting material:

| Starting material | Compound Name/No. | Characterization Data |
|---|---|---|
| HO-CH2-C6H4-I (3-iodo) | (3-Ethynylphenyl)methanol/ Int-44 | $^1$H NMR (CDCl$_3$) δ 7.50-7.60 (m, 2H), 7.35-7.45 (m, 2H), 5.23 (s, 2H), 3.15 (s, 1H), 2.95 (s, 3H). |

Example 21: 3-(Prop-1-yn-1-yl)benzyl methanesulfonate Int-45

Example 22: 3-Cyclopropyl-4-fluorobenzyl methanesulfonate Int-46

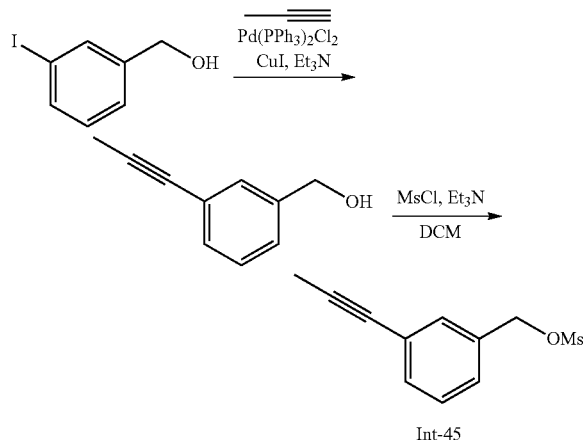

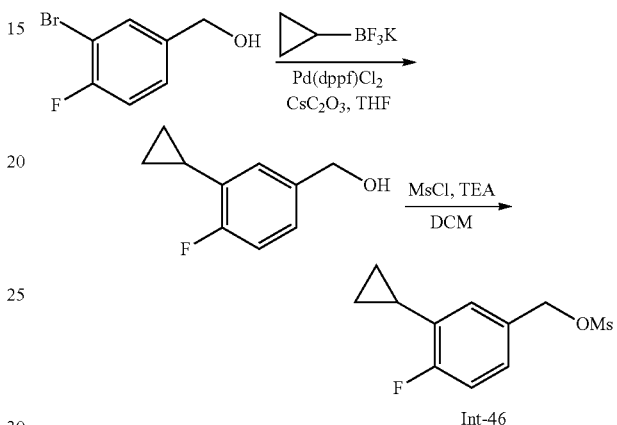

Step 1: [3-(Prop-1-yn-1-yl)phenyl]methanol

A 100 mL 2-necked RBF equipped with 3-way stopcock and septum was purged with argon and then the flask was cooled to −78° C. To the flask was attached a needle connected with a propyne gas cylinder. Liquid propyne (1.7 mL, 30 mmol) was condensed and collected in the flask. To the flask was added TEA (5.0 mL, 36 mmol) followed by bis(triphenylphosphine)palladium(II) chloride (30 mg, 0.04 mmol), CuI (16 mg, 0.08 mmol), and a solution of 3-iodobenzyl alcohol (700 mg, 3.0 mmol) in TEA (2.00 mL, 14.3 mmol) at −78° C., and the resulting mixture was heated at 50° C. for 2 h. The reaction was cooled to rt and diluted with EtOAc (70 mL). The mixture was filtered through a Celite pad and the residual solid was rinsed with EtOAc several times. The filtrate was washed with 1M HCl (×2), water, and brine. The organic layer was dried over Na$_2$SO$_4$, filtered, and concentrated in vacuo. The residue was purified on silica gel to give [3-(prop-1-yn-1-yl)phenyl]methanol (380 mg, 87%).

Step 2: 3-(Prop-1-yn-1-yl)benzyl methanesulfonate Int-45

To a solution of [3-(prop-1-yn-1-yl)phenyl]methanol (100 mg, 0.68 mmol) in DCM (5.0 mL) was added TEA (0.19 mL, 1.4 mmol) followed by methanesulfonyl chloride (0.06 mL, 0.72 mmol) at 0° C., and the mixture was stirred for 6 h at rt. The reaction was quenched by addition of water (50 mL) and extracted with EtOAc (50 mL×3). The combined organic layers were dried over Na$_2$SO$_4$, filtered, and concentrated in vacuo. The residue was purified on silica gel to give 3-(prop-1-yn-1-yl)benzyl methanesulfonate (61 mg, 40%) as a colorless oil. $^1$H NMR (CDCl$_3$) δ 7.44 (s, 1H), 7.43-7.37 (m, 1H), 7.36-7.29 (m, 2H), 5.20 (s, 2H), 2.93 (s, 3H), 2.05 (s, 3H).

Step 1: (3-Cyclopropyl-4-fluorophenyl)methanol

A microwave reaction vial was charged with (3-bromo-4-fluorophenyl)methanol (530 mg, 2.6 mmol), potassium cyclopropyltrifluoroborate (0.77 g, 5.2 mmol), Cs$_2$CO$_3$ (2.5 g, 7.8 mmol), 1,1′-bis(diphenylphosphino)ferrocenedichloropalladium(II) (95 mg, 0.13 mmol), THF (10.6 mL) and water (1.1 mL). After sealing with cap under an atmosphere of argon, the mixture was heated at 100° C. for 4 h. The reaction was diluted with EtOAc and the mixture was filtered through a celite pad. The residual solid was rinsed with EtOAc and water. The two layers were transferred into a separatory funnel and then separated. The water layer was extracted with EtOAc (×2). The combined organic layers were dried over Na$_2$SO$_4$, filtered, and concentrated. The residue was purified on silica gel to give (3-cyclopropyl-4-fluorophenyl)methanol (309 mg, 72%) as a light yellow oil.

Step 2: 3-Cyclopropyl-4-fluorobenzyl methanesulfonate Int-46

To a solution of (3-cyclopropyl-4-fluorophenyl)methanol (300 mg, 1.8 mmol) in DCM (10 mL) was added TEA (0.38 mL, 2.7 mmol) followed by methanesulfonyl chloride (0.15 mL, 1.9 mmol) at 0° C., and the mixture was stirred for 3 h at rt. The reaction was quenched by addition of water (50 mL) and extracted with DCM (50 mL×3). The combined organic layers were dried over Na$_2$SO$_4$, filtered, and concentrated. The residue was purified on silica gel to give 3-cyclopropyl-4-fluorobenzyl methanesulfonate (215 mg, 49%) as a colorless oil. $^1$H NMR (CDCl$_3$) δ 7.20-7.15 (m, 1H), 7.03 (dd, J=9.9, 8.4 Hz, 1H), 6.95 (dd, J=7.1, 2.3 Hz, 1H), 5.15 (s, 2H), 2.91 (s, 3H), 2.09 (tt, J=8.5, 5.2 Hz, 1H), 1.01 (ddd, J=8.5, 6.4, 4.6 Hz, 2H), 0.74 (dt, J=6.5, 4.7 Hz, 2H).

Example 23: 2-(3-Bromoprop-1-yn-1-yl)furan Int-47

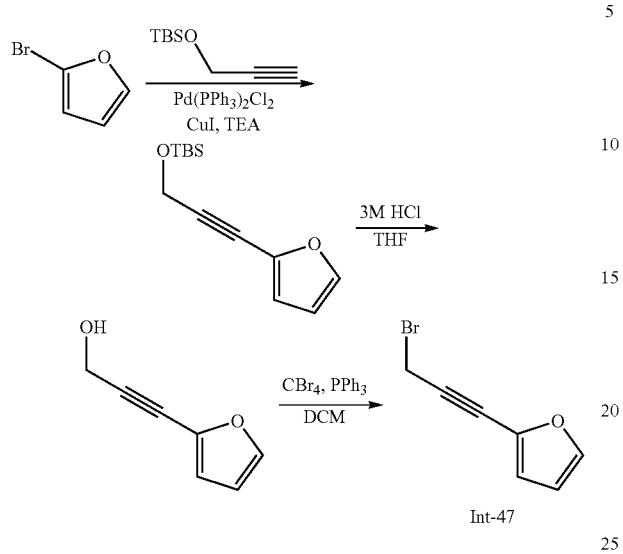

Int-47

Step 1: tert-Butyl {[3-(2-furyl)prop-2-yn-1-yl]oxy}dimethylsilane

Into a RBF was added 2-bromofuran (0.50 g, 3.4 mmol) dissolved in TEA (3.5 mL, 25 mmol). Copper(I) iodide (26 mg, 0.14 mmol) and bis(triphenylphosphine)palladium(II) chloride (48 mg, 0.07 mmol) were added next and the mixture was purged with argon. tert-Butyldimethyl(2-propynyloxy)silane (0.90 mL, 4.4 mmol) was then added and the mixture was heated at 70° C. overnight. The crude mixture was cooled to rt and extracted with EtOAc (3×). The combined organic layers were then washed with water and brine, dried over Na$_2$SO$_4$, filtered and concentrated. The crude product was purified on silica gel to give tert-butyl{[3-(2-furyl)prop-2-yn-1-yl]oxy}dimethylsilane (0.91 g, 100%).

Step 2: 3-(2-Furyl)prop-2-yn-1-ol

HCl (3 M solution in water; 0.13 mL, 0.38 mmol) was added to a solution of tert-butyl{[3-(2-furyl)prop-2-yn-1-yl]oxy}dimethylsilane (0.91 g, 3.8 mmol) in THF (20 mL) and the reaction was stirred overnight at rt. It was then quenched with a saturated solution of NaHCO$_3$ and extracted with EtOAc (3×). The combined organic layers were then washed with water and brine, dried over Na$_2$SO$_4$, filtered and concentrated. The crude product was purified on silica gel to give 3-(2-furyl)prop-2-yn-1-ol (0.48 g, 100%).

Step 3: 2-(3-Bromoprop-1-yn-1-yl)furan Int-47

To a mixture of 3-(2-furyl)prop-2-yn-1-ol (0.48 g, 3.9 mmol) in DCM (15 mL) cooled at 0° C. was added triphenylphosphine (1.2 g, 4.7 mmol) followed by carbon tetrabromide (1.96 g, 5.90 mmol). The reaction was then stirred at 0° C. for 15 min and then concentrated. The crude product was purified on silica gel to provide 2-(3-bromoprop-1-yn-1-yl)furan (0.57 g, 78%). $^1$H NMR (CDCl$_3$) δ 7.40 (dd, 0.1=1.8, 0.7 Hz, 1H), 6.64 (d, J=3.4 Hz, 1H), 6.40 (dd, J=3.4, 1.9 Hz, 1H), 4.17 (s, 2H).

Example 24: 4-(3-Bromoprop-1-yn-1-yl)-1-methyl-1H-pyrazole Int-48

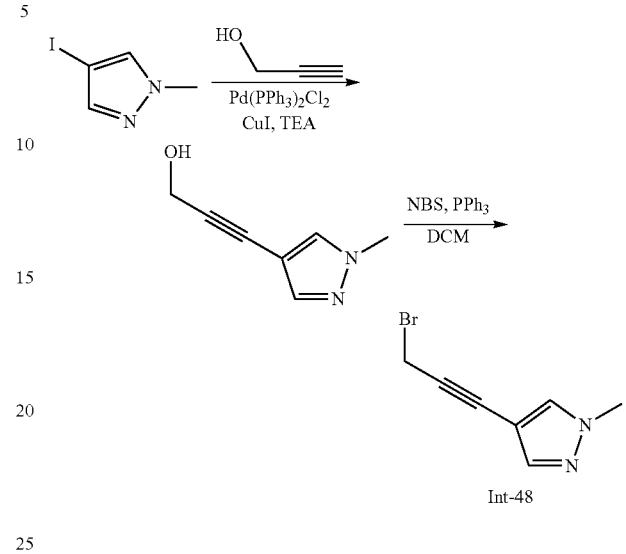

Int-48

Step 1: 3-(1-Methyl-1H-pyrazol-4-yl)prop-2-yn-1-ol

A mixture of 2-propyn-1-ol (0.25 mL, 4.2 mmol), 1-methyl-4-iodo-1H-pyrazole (0.80 g, 3.9 mmol), bis(triphenylphosphine)palladium(II) chloride (0.13 g, 0.19 mmol), copper(I) iodide (0.073 g, 0.38 mmol), and TEA (1.1 mL, 7.7 mmol) in DMF (5.0 mL) was stirred at rt for 4 h. The mixture was purified on silica gel (directly charged to column) to afford 3-(1-methyl-1H-pyrazol-4-yl)prop-2-yn-1-ol (403 mg; 77%). LCMS (FA): m/z=137 (M+H).

Step 2: 4-(3-Bromoprop-1-yn-1-yl)-1-methyl-1H-pyrazole Int-48

Triphenylphosphine (550 mg, 2.1 mmol) was added to a DCM (5 mL) solution of 3-(1-methyl-1H-pyrazol-4-yl)prop-2-yn-1-ol (258 mg, 1.9 mmol) and NBS (370 mg, 2.1 mmol) at rt and the mixture was stirred overnight. The mixture was purified on silica gel (directly charged to column) to afford 4-(3-bromoprop-1-yn-1-yl)-1-methyl-1H-pyrazole (297 mg; 79%) as a colorless oil. LCMS (FA): m/z=199 (M+H).

Example 25: 4-Methoxy-4-methylpent-2-yn-1-yl methanesulfonate Int-50

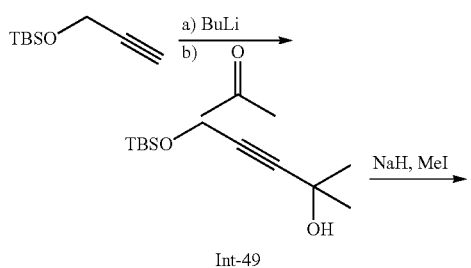

Int-49

-continued

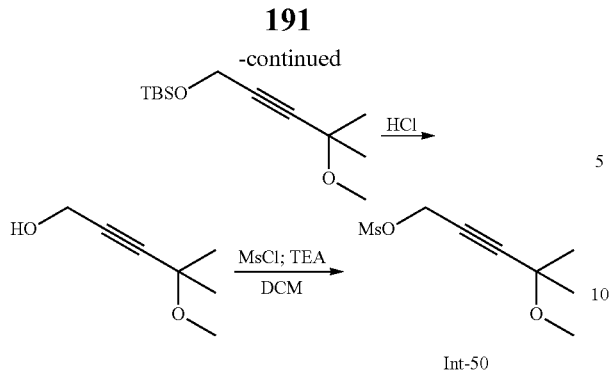

Int-50

Step 1: 5-{[tert-Butyl(dimethyl)silyl]oxy}-2-methyl-pent-3-yn-2-ol Int-49 tert-Butyldimethyl(2-propynyloxy)silane (2.4 mL, 12 mmol) was dissolved in THF (40 mL) then it was cooled to −78° C. n-Butyllithium (2.50 M in hexanes; 5.2 mL, 12.9 mmol) was added and the resulting solution allowed to stir for 30 min at −78° C. Acetone (1.0 mL, 14 mmol) was then added to the reaction, which was then allowed to stir at −78° C. for 30 min, followed by stirring at rt for 30 min. The reaction was then quenched by the addition of saturated aq solution of $NH_4Cl$. The mixture was extracted with ether (2×). The combined organic layers were dried over $MgSO_4$, filtered, and concentrated to provide 5-{[tert-butyl(dimethyl)silyl]oxy}-2-methylpent-3-yn-2-ol (2.7 g, 100%). $^1H$ NMR ($CDCl_3$) δ 4.25 (c, 7H), 3.60 (m, 1H), 1.30 (s, 6H), 0.80 (s, 9H), 0.0 (s, 6H).

Step 2: tert-Butyl[(4-methoxy-4-methylpent-2-yn-1-yl)oxy]dimethylsilane

5-{[tert-butyl(dimethyl)silyl]oxy}-2-methylpent-3-yn-2-ol (1.0 g, 4.4 mmol) was dissolved in THF (20 mL) under an atmosphere of argon and cooled to 0° C. in an ice bath. Sodium hydride (0.21 g, 5.2 mmol) was added and the resulting suspension was allowed to stir at 0° C. for 30 min. Methyl iodide (0.54 mL, 8.8 mmol) was then added and the reaction was allowed to slowly warm to rt. After stirring overnight at that temperature, TLC showed the reaction was complete. The reaction was quenched by addition of saturated $NH_4Cl$ solution (aq.) then extracted with EtOAc (2×). The combined organic layers were dried over $MgSO_4$, filtered, and concentrated to give tert-butyl[(4-methoxy-4-methylpent-2-yn-1-yl)oxy]dimethylsilane (0.95 g, 90%). $^1H$ NMR ($CDCl_3$) δ 4.25 (s, 2H), 3.23 (s, 3H), 1.30 (s, 6H), 0.80 (s, 9H), 0.0 (s, 6H).

Step 3: 4-Methoxy-4-methylpent-2-yn-1-ol

HCl (3.0 M solution in water; 0.13 mL, 0.39 mmol) was added to a solution of tert-butyl[(4-methoxy-4-methylpent-2-yn-1-yl)oxy]dimethylsilane (0.95 g, 3.9 mmol) in THF (20 mL) at rt. The solution was allowed to stir overnight. The reaction was concentrated then purified on silica gel to yield 4-methoxy-4-methylpent-2-yn-1-ol (0.33 g, 66%). $^1H$ NMR ($CDCl_3$) δ 4.30 (s, 2H), 3.30 (s, 3H), 1.45 (s, 6H).

Step 4: 4-Methoxy-4-methylpent-2-yn-1-yl methanesulfonate Int-50

Methanesulfonyl chloride (0.20 mL, 2.6 mmol) was added to a solution of 4-methoxy-4-methylpent-2-yn-1-ol (0.32 g, 2.5 mmol) and TEA (0.52 mL, 3.7 mmol) in DCM (9 mL) at 0° C. under an atmosphere of argon. The reaction was then allowed to stir at 0° C. for 1 h and the reaction was quenched by the addition of water. This mixture was extracted with DCM (3×). The combined organic layers were dried over $MgSO_4$, filtered, and concentrated. The crude product was purified on silica gel to give 4-methoxy-4-methylpent-2-yn-1-yl methanesulfonate (380 mg, 74%). $^1H$ NMR ($CDCl_3$) δ 4.90 (s, 2H), 3.30 (s, 3H), 3.15 (s, 3H), 1.50 (s, 6H).

Example 26: 4-Hydroxy-4-methylpent-2-yn-1-yl methanesulfonate Int-51

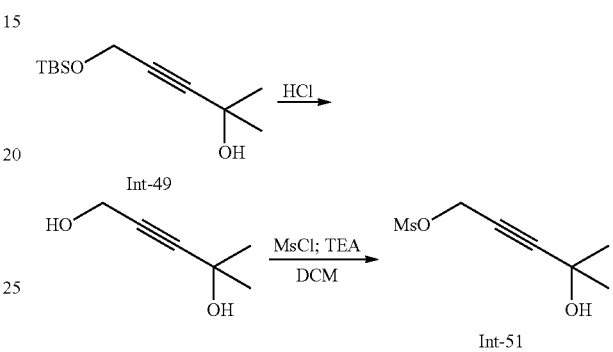

Int-51

Step 1: 4-Methylpent-2-yne-1,4-diol

HCl (3.0 M solution in water; 0.14 mL, 0.44 mmol) was added to a solution of 5-{[tert-butyl(dimethyl)silyl]oxy}-2-methylpent-3-yn-2-ol (1.0 g, 4.4 mmol) in THF (20 mL) at rt. After stirring overnight the reaction was concentrated and purified on silica gel to afford 4-methylpent-2-yne-1,4-diol (0.35 g, 70%). $^1H$ NMR ($CDCl_3$) δ 4.30 (s, 2H), 1.55 (s, 6H).

Step 2: 4-Hydroxy-4-methylpent-2-yn-1-yl methanesulfonate Int-51

Methanesulfonyl chloride (0.23 mL, 3.0 mmol) was added to a solution of 4-methylpent-2-yne-1,4-diol (0.33 g, 2.9 mmol) and TEA (0.60 mL, 4.3 mmol) in DCM (10 mL) at 0° C. under an atmosphere of argon. The reaction was allowed to stir at 0° C. for 1 h The reaction was then quenched by the addition of water and the resulting mixture was extracted with DCM (3×). The combined organic layers were dried over $MgSO_4$, filtered, and concentrated. The crude product was purified on silica gel to give 4-hydroxy-4-methylpent-2-yn-1-yl methanesulfonate (340 mg, 61%). $^1H$ NMR ($CDCl_3$) δ 4.90 (s, 2H), 3.15 (s, 3H), 1.60 (s, 6H).

Example 27: 4-(Tetrahydro-2H-pyran-4-yl)but-2-yn-1-yl 4-methylbenzenesulfonate Int-52

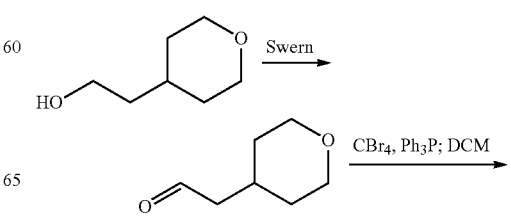

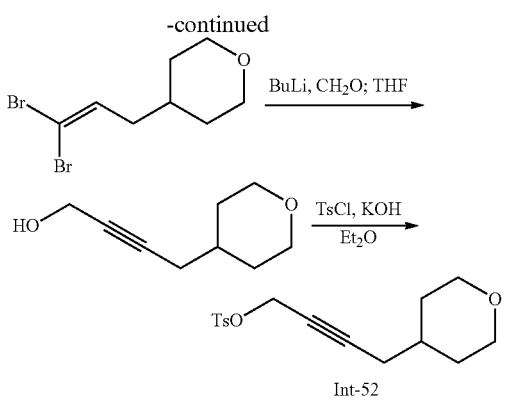

Step 1: (Tetrahydro-pyran-4-yl)-acetaldehyde

A 500 mL RBF under nitrogen charged with DCM (96 mL) and oxalyl chloride (3.6 mL, 42 mmol) was cooled to −60° C. Dimethyl sulfoxide (6.5 mL, 92 mmol) was added dropwise and the mixture stirred 10 min. A solution of 2-tetrahydropyran-4-ylethanol (5 g, 40 mmol) in DCM (40 mL) was added slowly and this mixture was stirred 15 minutes. TEA (30 mL, 200 mmol) was subsequently added slowly and the temperature allowed to rise to −30° C. The cooling bath was then removed and the reaction warmed to rt. The reaction was quenched with water and the aqueous layer was extracted with DCM (3×). The combined organic portions were washed with brine, dried over sodium sulfate, filtered, and concentrated. The crude oil was purified on silica gel to give (tetrahydro-pyran-4-yl)-acetaldehyde (3.7 g, 72%).

Step 2: 4-(3,3-Dibromoprop-2-en-1-yl)tetrahydro-2H-pyran

A RBF under nitrogen was charged with (tetrahydropyran-4-yl)-acetaldehyde (3.7 g, 29 mmol), DCM (10 mL), and triphenylphosphine (19 g, 71 mmol) and then cooled to 0° C. A solution of carbon tetrabromide (11.8 g, 36 mmol) in DCM was added dropwise keeping the internal temperature under 30° C. A precipitate formed. After stirring 30 min the solid was removed via filtration. The filtrate was concentrated and the resulting residue purified on silica gel to give 4-(3,3-dibromoprop-2-en-1-yl)tetrahydro-2H-pyran (6.04 g, 74%).

Step 3: 4-(Tetrahydro-2H-pyran-4-yl)but-2-yn-1-ol

A 500 mL oven-dried 2-neck RBF under nitrogen charged with 4-(3,3-dibromoprop-2-en-1-yl)tetrahydro-2H-pyran (3.0 g, 10.6 mmol) and THF (33 mL) was cooled to −10° C. n-Butyllithium (2.5 M solution in hexane; 8.4 mL, 21.0 mmol) was added slowly over 10 min keeping the internal temperature at 0° C. This mixture was kept at the same temperature and stirred 30 min. Paraformaldehyde (0.79 g, 26 mmol) was added in a single portion and the mixture allowed to warm slowly to rt and stir for 18 h. It was then cooled in an ice bath and quenched by slowly adding saturated ammonium chloride (10 mL). The organic solvents were removed in vacuo and water was added. The mixture was extracted with EtOAc (3×). The combined organic portions were washed with brine, dried over sodium sulfate, filtered, and concentrated. The crude product was purified on silica gel to give 4-(tetrahydro-2H-pyran-4-yl)but-2-yn-1-ol (593 mg, 36%).

Step 4: 4-(Tetrahydro-2H-pyran-4-yl)but-2-yn-1-yl 4-methylbenzenesulfonate Int-52

A 50 mL RBF under nitrogen charged with 4-(tetrahydro-2H-pyran-4-yl)but-2-yn-1-ol (0.59 g, 3.8 mmol), ether (10 mL) and p-toluenesulfonyl chloride (0.84 g, 4.4 mmol) was cooled to 0° C. in an ice bath. Potassium hydroxide (2.8 g, 50 mmol) was then added in small portions. The reaction mixture was kept at 0° C. and stirred for 1 h. The reaction was quenched with water and the aqueous layer was extracted with ether (3×). The combined organic portions were washed with brine, dried over magnesium sulfate, filtered, and concentrated. The crude product was purified on silica gel to give 4-(tetrahydro-2H-pyran-4-yl)but-2-yn-1-yl 4-methylbenzenesulfonate (520 mg, 44%). LCMS (FA): m/z=309 (M+H).

Example 28: (4-Bromobut-2-yn-1-yl)cyclopentane Int-53

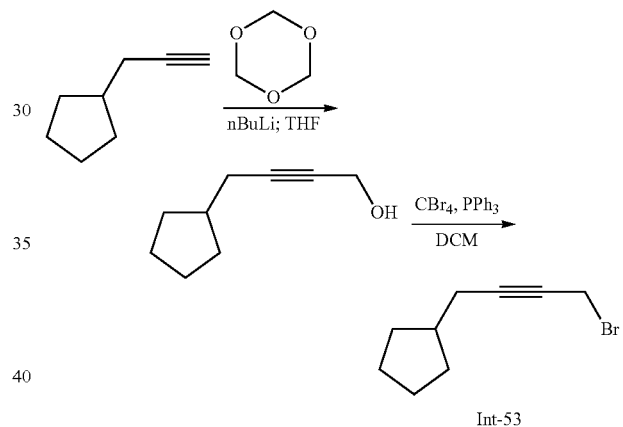

Step 1: 4-Cyclopentylbut-2-yn-1-ol

A 250 mL 2-necked round bottomed flask equipped with septum and 3-way stopcock was purged with argon. THF (12 mL) and 3-cyclopentyl-1-propyne (1 mL, 9 mmol) were added into the reaction vessel via syringe and the solution was cooled to −78° C. To the solution was added n-butyllithium (2.5 M solution in hexane; 3.5 mL, 8.8 mmol), and the mixture was stirred for 30 min at −78° C. To this mixture was added a suspension of 1,3,5-trioxane (0.83 g, 9.2 mmol) in THF (3.1 mL), and the resulting suspension was stirred for 30 min at −78° C. then warmed to rt gradually. The reaction was then quenched by addition of water (5 mL) and extracted with ether (8 mL). The ether layer was dried over $Na_2SO_4$, filtered, and concentrated in vacuo (at low temperature and low vacuum because of volatility of the product). The residue was purified on silica gel to provide 4-cyclopentylbut-2-yn-1-ol (785 mg, 63%).

Step 2: (4-Bromobut-2-yn-1-yl)cyclopentane Int-53

To a 50 mL RBF was added DCM (13 mL) followed by 4-cyclopentylbut-2-yn-1-ol (780 mg, 5.6 mmol) and carbon tetrabromide (2.8 g, 8.5 mmol). The reaction was cooled to 0° C. and triphenylphosphine (2.2 g, 8.5 mmol) was added. The reaction was kept at this temperature for 2 hours while stirring. The reaction was then quenched with a saturated NaHCO₃ solution followed by water, and the mixture was extracted with EtOAc (2×). The organic layers were combined and dried (MgSO₄), filtered, and concentrated. The residue was purified on silica gel to give (4-bromobut-2-yn-1-yl)cyclopentane (1.0 g, 89%). ¹H NMR (CDCl₃) δ 3.87 (s, 2H), 2.25-2.11 (m, 2H), 2.04-1.90 (m, 1H), 1.77-1.66 (m, 2H), 1.64-1.41 (m, 4H), 1.28-1.10 (m, 2H).

Example 29: 3-Cyclopropylprop-2-yn-1-yl methanesulfonate Int-54

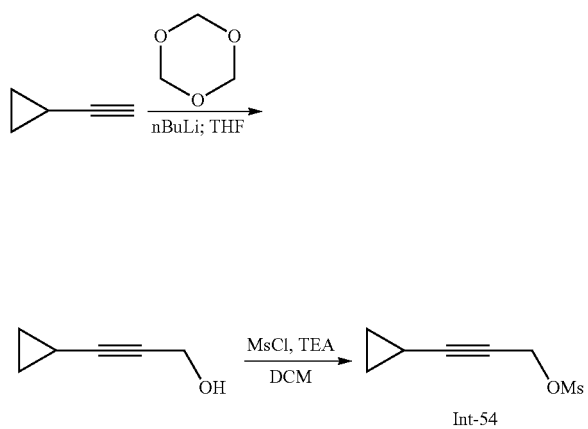

Step 1: 3-Cyclopropylprop-2-yn-1-ol

A 250 mL 2-necked round bottomed flask equipped with septum and 3-way stopcock was purged with argon. THF (40 mL) and cyclopropyl acetylene (2.5 mL, 30 mmol) were added into the reaction vessel and the solution was cooled to −78° C. To the solution was added n-butyllithium (2.50 M in hexane; 11.5 mL, 28.7 mmol), and the mixture was stirred for 30 min at −78° C. To the mixture was added a suspension of 1,3,5-trioxane (2.7 g, 30 mmol) in THF (10 mL), and the resulting suspension was stirred for 30 min at −78° C. then warmed up to rt gradually. The reaction was quenched by addition of water (50 mL) and extracted with Et₂O (80 mL). The organic layer was dried over Na₂SO₄, filtered, and concentrated. The residue was purified on silica gel to give 3-cyclopropylprop-2-yn-1-ol (2.61 g, 81%) as a colorless oil.

Step 2: 3-Cyclopropylprop-2-yn-1-yl methanesulfonate Int-54

To a solution of 3-cyclopropylprop-2-yn-1-ol (300 mg, 3.1 mmol) in DCM (15 mL) was added TEA (0.65 mL, 4.7 mmol) followed by methanesulfonyl chloride (0.25 mL, 3.3 mmol) at 0° C. under an atmosphere of argon. The mixture was stirred for 2 h and then quenched by the addition of water (80 mL) followed by extraction with DCM (100 mL). The DCM layer was washed with brine, dried over Na₂SO₄, filtered, and concentrated. The residue was purified on silica gel to afford 3-cyclopropylprop-2-yn-1-yl methanesulfonate (265 mg, 49%) as a colorless oil. ¹H NMR (CDCl₃) δ 4.82 (d, J=2.1 Hz, 2H), 3.10 (s, 3H), 1.34-1.24 (m, 1H), 0.87-0.81 (m, 2H), 0.76-0.70 (m, 2H).

Example 30: 4,4-Dimethylpent-2-yn-1-yl 4-methylbenzenesulfonate Int-55

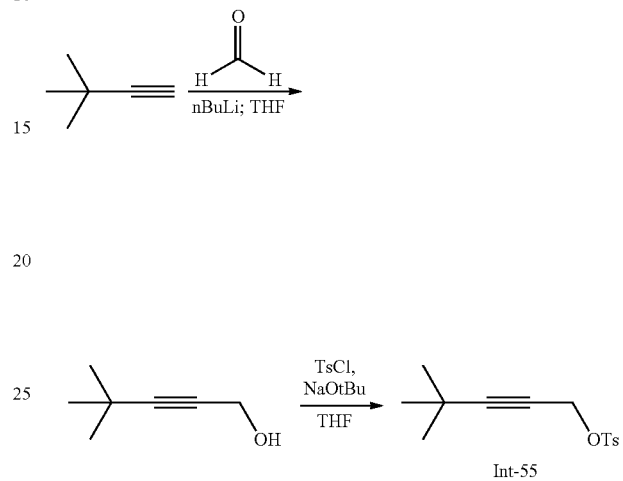

Step 1: 4,4-Dimethylpent-2-yn-1-ol 3,3-Dimethyl-1-butyne (3.0 mL, 25 mmol) was dissolved in THF (86 mL) and cooled to −78° C. n-Butyllithium (2.5 M solution in hexanes; 11.1 mL, 27.6 mmol) was added dropwise and then the solution was allowed to stir for 30 min. Formaldehyde (0.80 mL, 29 mmol) was then added and stirred at −78° C. for 30 min. It was then allowed to warm to rt and stir for 30 min. The reaction mixture was poured into a saturated aqueous solution of NH₄Cl and then extracted ether (2×). The combined organic layers were dried over MgSO₄, filtered, and concentrated to give 4,4-dimethylpent-2-yn-1-ol (2.8 g, 98%).

Step 2: 4,4-Dimethylpent-2-yn-1-yl 4-methylbenzenesulfonate Int-55

To a RBF was added 4,4-dimethylpent-2-yn-1-ol (0.28 g, 2.5 mmol), p-toluenesulfonyl chloride (0.57 g, 3.0 mmol), and THF (20 mL). The resulting reaction mixture was stirred at 0° C. and sodium tert-butoxide (0.72 g, 7.5 mmol) was added. The mixture was then stirred at 0° C. for 30 min followed by the addition of saturated NaHCO₃ (10 mL) and water (10 mL). The mixture was extracted with EtOAc (2×). The combined organic layers were dried over MgSO₄, filtered, and concentrated to give the crude product which was purified on silica gel to give 4,4-dimethylpent-2-yn-1-yl 4-methylbenzenesulfonate (0.37 g, 56%). ¹H NMR (CDCl₃) δ 7.79 (d, J=8.3 Hz, 2H), 7.32 (d, J=8.0 Hz, 2H), 4.70 (s, 2H), 2.45 (s, 3H), 1.20 (s, 9H).

The compound listed in the table below was prepared in an analogous fashion to that described above starting from the listed starting material:

| Starting material | Compound Name/No. | Characterization Data |
|---|---|---|
| ≡⟨ | 5-Methylhex-2-yn-1-yl 4-methylbenzenesulfonate/ Int-56 | $^1$H NMR (CDCl$_3$) δ 7.83 (d, J = 8.3 Hz, 2H), 7.36 (d, J = 8.0 Hz, 2H), 4.73 (s, 2H), 2.46 (s, 3H), 2.05-1.93 (m, 2H), 1.77-1.61 (m, 1H), 0.91 (d, J = 6.4 Hz, 6H). |

Example 31: 4-Methoxybut-2-yn-1-yl 4-methylbenzenesulfonate Int-57

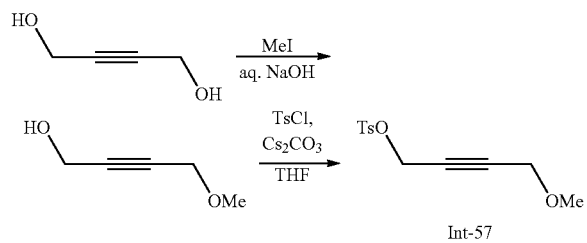

Step 1: 4-Methoxybut-2-yn-1-ol

To a RBF was added 2-butyne-1,4-diol (30 g, 350 mmol) and 50% aq NaOH (5.6 mL). The resulting reaction mixture was heated to 60° C. and methyl iodide (4.3 mL, 70 mmol) was added dropwise. After addition was complete, the mixture was stirred at 60° C. for 3 h. The mixture was then distilled to isolate 4-methoxybut-2-yn-1-ol (0.53 g, 8%). $^1$H NMR (CDCl$_3$) δ 4.38-4.31 (m, 2H), 4.16 (t, J=1.8 Hz, 2H), 3.41 (s, 3H), 1.88-1.79 (m, 1H).

Step 2: 4-Methoxybut-2-yn-1-yl 4-methylbenzenesulfonate Int-57

To a RBF were added 4-methoxybut-2-yn-1-ol (0.50 g, 5.0 mmol), p-toluenesulfonyl chloride (2.0 g, 11 mmol), THF (12 mL), and cesium carbonate (8.1 g, 25 mmol). The resulting reaction mixture was stirred at rt for 18 h. The mixture was then concentrated and water was added to the crude residue. The mixture was extracted with EtOAc (2×). The combined organic extracts were washed with brine, dried over MgSO$_4$, and concentrated. The crude product was purified on silica gel to give 4-methoxybut-2-yn-1-yl 4-methylbenzenesulfonate (0.11 g, 9%). $^1$H NMR (CDCl$_3$) δ 7.87-7.78 (m, 2H), 7.36 (dd, J=8.5, 0.6 Hz, 2H), 4.76 (t, J=1.8 Hz, 2H), 4.01 (t, J=1.8 Hz, 2H), 3.29 (s, 3H), 2.46 (s, 3H).

Example 32: 2-(Chloromethyl)-5-fluorofuran Int-58

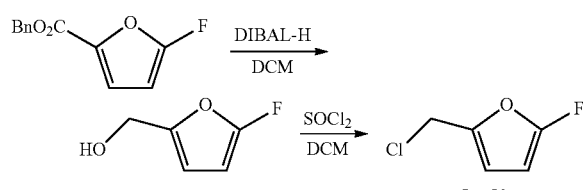

Step 1: (5-Fluoro-2-furyl)methanol

To a RBF was added benzyl 5-fluoro-2-furoate (0.40 g, 1.8 mmol; for prep see: Song, R.; Lin, W.; Jiang, Q. *Tetrahedron Lett.* 2011, 52, 4965-4966.) and DCM (20 mL). The resulting reaction mixture was stirred at 0° C. and DIBAl-H (1.0 M solution in DCM; 4.6 mL, 4.6 mmol) was added dropwise. The mixture was stirred at 0° C. for 10 min and then warmed to rt and stirred for 30 min. The mixture was subsequently cooled to 0° C. and 1M HCl was added to quench the reaction. The mixture was extracted with DCM (2×). The combined organic extracts were washed with brine, dried over MgSO$_4$, and concentrated. The crude product was purified on silica gel to afford (5-fluoro-2-furyl)methanol (0.24 g, 100%). $^1$H NMR (CDCl$_3$) δ 7.42 (s, 1H), 7.41 (d, J=1.4 Hz, 1H), 7.31 (s, 1H), 4.78-4.70 (s, 2H).

Step 2: 2-(Chloromethyl)-5-fluorofuran Int-58

To a solution of (5-fluoro-2-furyl)methanol (0.20 g, 1.7 mmol) and TEA (0.24 mL, 1.7 mmol) in DCM (23 mL) at 0° C. was added thionyl chloride (0.15 mL, 2.1 mmol) dropwise. The mixture was stirred for 1 h at 0° C. then at rt for 1 h. Water (20 ml) was added to quench and the organic layer was separated, dried over MgSO$_4$, filtered and concentrated to give 2-chloro-5-(1-chloroethyl)furan (0.55 g, 100%). The product was used crude in the next reaction without purification (see Example 92).

Example 33: 2-(1-Bromoethyl)-5-(trifluoromethyl)furan Int-59

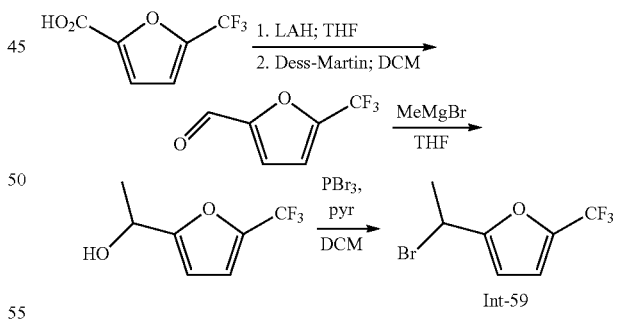

Step 1: 5-(Trifluoromethyl)-2-furaldehyde

To a round bottomed flask was added 5-(trifluoromethyl)-2-furoic acid (2.5 g, 14 mmol) and THF (50 mL). The solution was cooled to 0° C. A 2.0 M of lithium aluminium hydride in THF (9.0 mL, 18 mmol) was then added slowly and the resulting mixture was stirred at rt overnight. Water (1 mL) was added slowly to quench the reaction mixture. Na$_2$SO$_4$ solid was added and the mixture stirred at rt for 0.1 h. The mixture was filtered through a pad of celite and the filtrate concentrated. The alcohol intermediate was then dissolved in DCM (50 mL). Dess-Martin periodinane (7.1 g, 16.7 mmol) was added and the resulting reaction mixture was stirred at rt for 2 h. The reaction was then quenched by the addition of saturated $Na_2S_2O_3$, and extracted with DCM (3×). The combined organic layers were then washed with brine, dried over $Na_2SO_4$, filtered and concentrated. The crude product was purified on silica gel to provide 5-(trifluoromethyl)-2-furaldehyde (0.80 g, 38%).

Step 2: 1-[5-(Trifluoromethyl)-2-furyl]ethanol

Into a RBF was added 5-(trifluoromethyl)-2-furaldehyde (0.80 g, 4.9 mmol) dissolved in THF (12 mL). The solution was cooled to 0° C. and a 3.0 M solution of methylmagnesium bromide in ether (3.25 mL, 9.75 mmol) was added dropwise over 30 min. The resulting mixture was then stirred at 0° C. for 1 h. The reaction was quenched with a saturated solution of $NH_4Cl$ and extracted with EtOAc (3×). The combined organic layers were then washed with brine, dried over $Na_2SO_4$, filtered and concentrated to give 1-[5-(trifluoromethyl)-2-furyl]ethanol (0.92 g, 100%).

Step 3: 2-(1-Bromoethyl)-5-(trifluoromethyl)furan Int-59

To a solution of 1-[5-(trifluoromethyl)-2-furyl]ethanol (0.27 g, 1.5 mmol) and pyridine (0.024 mL, 0.30 mmol) in DCM (5 mL) at −75° C. was added phosphorus tribromide (0.14 mL, 1.5 mmol) dropwise. The mixture was stirred for 10 min and then allowed to stand in a freezer (−25° C.) overnight. The mixture was then cooled in an ice bath and water (3 mL) was added slowly. The mixture was then partitioned into DCM and water. The separated organic layer was washed successively with water, 1M $NaHCO_3$ and brine. It was then dried over $Na_2SO_4$, filtered, and concentrated to yield 2-(1-bromoethyl)-5-(trifluoromethyl)furan (0.36 g, 100%). $^1$H NMR ($CDCl_3$) δ 6.73 (dd, J=3.3, 1.0 Hz, 1H), 6.40 (d, J=3.4 Hz, 1H), 5.18 (q, J=7.0 Hz, 1H), 2.05 (d, J=7.0 Hz, 3H).

Example 34: 1-(Bromomethyl)cyclohexene Int-60

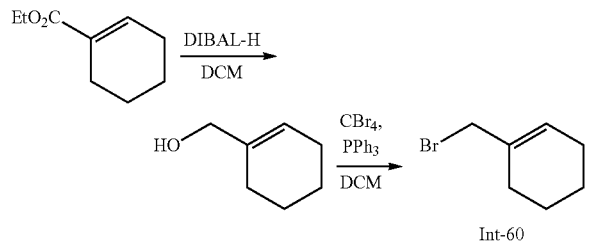

Step 1: Cyclohex-1-en-1-ylmethanol

To a solution of methyl 1-cyclohexene-1-carboxylate (1.50 mL, 11.0 mmol) in DCM (30 mL) was added diisobutylaluminum hydride (1M solution in toluene; 25 mL, 25 mmol) at −78° C. and the mixture was stirred for 1 h. TLC (3:1 hex:EtOAc) showed that the reaction was then complete. The mixture was quenched with methanol (10 mL) and 1N NaOH (10 mL) and then was allowed to stir at rt for 2.5 h. The mixture was extracted with DCM (3×). The combined organic layers were washed with brine, dried over $MgSO_4$, filtered and concentrated to give cyclohex-1-en-1-ylmethanol (1.3 g, 100%).

Step 2: 1-(Bromomethyl)cyclohexene Int-60

Triphenylphosphine (3.2 g, 12.3 mmol) was added to a solution of cyclohex-1-en-1-ylmethanol (1.25 g, 11.1 mmol) and carbon tetrabromide (4.4 g, 13.4 mmol) in DCM (25 mL) at 0° C. The mixture was then allowed to slowly warm to rt and stir overnight. After 16 h the mixture was concentrated and purified on silica gel. The product is very nonpolar and coelutes with carbon tribromide. Carbon tribromide was removed under reduced pressure to yield 1-(bromomethyl)cyclohexene (1.8 g, 92%). $^1$H NMR ($CDCl_3$) δ 5.90 (s, 1H), 3.97 (s, 2H), 2.18-2.11 (m, 2H), 2.10-2.02 (m, 2H), 1.75-1.65 (m, 2H), 1.65-1.52 (m, 2H).

Example 35: 1-[(2-Bromoethyl)sulfanyl]-3-(bromomethyl)benzene2-bromoethyl 3-(bromomethyl) phenyl sulfide Int-112

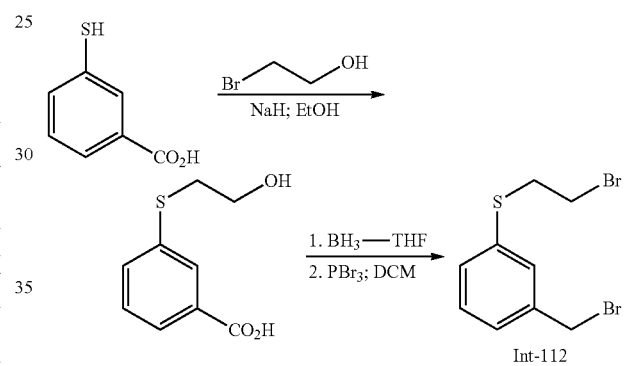

Step 1: 3-[(2-Hydroxyethyl)sulfanyl]benzoic acid

Sodium hydride (0.45 g, 19 mmol) was added slowly to a solution of m-mercaptobenzoic acid (0.97 g, 6.3 mmol) in ethanol (25.0 mL) a rt. Then, 2-bromoethanol (0.79 g, 6.3 mmol) was added to this solution at rt and the resulting mixture was allowed to stir for 2 h at rt. Acetic acid (5 mL) was added to the solution and the mixture was concentrated. Water (30 mL) was added to dissolve the crude residue and the mixture was extracted with DCM (2×). The combined organic layers were dried over $MgSO_4$, filtered and concentrated to provide 3-[(2-hydroxyethyl)sulfanyl]benzoic acid (1.2 g, 94%).

Step 2: 1-[(2-Bromoethyl)sulfanyl]-3-(bromomethyl)benzene2-bromoethyl 3-(bromomethyl)phenyl sulfide Int-112

Borane-THF complex (1.04 mL, 10.6 mmol) was added dropwise to a solution of 3-[(2-hydroxyethyl)sulfanyl]benzoic acid (1.05 g, 5.3 mmol) in THF (30 mL). The reaction was allowed to stir at rt for 6 h. The reaction was then diluted with ethyl acetate (80 mL) and the solution was washed with water (2×). The organic layer was dried over $MgSO_4$, filtered, and concentrated to give the crude alcohol intermediate. This intermediate was then stirred as a solution of 2-{[3-(hydroxymethyl)phenyl]sulfanyl}ethanol (0.60 g, 3.3 mmol) in DCM (20 mL) at rt. To this mixture was added phosphorus tribromide (1.8 g, 6.5 mmol) dropwise. The mixture was stirred for 1 hr at rt and then diluted with DCM (50 mL). The mixture was washed with water. The organic layer was then dried over $Na_2SO_4$, filtered, and concentrated. The crude product was purified on silica gel to yield 1-[(2-bromoethyl)sulfanyl]-3-(bromomethyl)benzene2-bromoethyl 3-(bromomethyl)phenyl sulfide (0.79 g, 78%). $^1$H NMR ($CDCl_3$) δ 7.40 (s, 1H), 7.23-7.31 (m, 3H), 4.45 (s, 2H), 3.40-3.50 (m, 2H), 3.25-3.35 (m, 2H).

Example 36: 1-Benzyl-1H-pyrazole-3-carbaldehyde Int-61

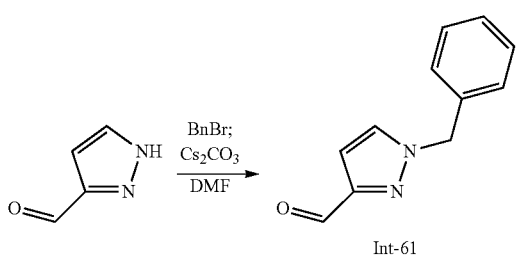

Int-61

Step 1: 1-Benzyl-1H-pyrazole-3-carbaldehyde Int-61

A 100 mL round bottomed flask was charged with pyrazol-3-carbaldehyde (250 mg, 2.60 mmol), $Cs_2CO_3$ (2.12 g, 6.50 mmol), and DMF (10 mL). To the suspension was added benzyl bromide (325 uL, 2.7 mmol), and the reaction was stirred for 1 h. The reaction mixture was poured into water (50 mL) and the mixture was extracted with EtOAc (50 mL×3). The combined organic layers were washed with brine, dried over $Na_2SO_4$, filtered, and concentrated in vacuo. The residue was purified on silica gel to provide 1-benzyl-1H-pyrazole-3-carbaldehyde (372 mg, 77%). $^1$H NMR ($CDCl_3$) δ 10.01-9.98 (m, 1H), 7.42 (d, J=2.3 Hz, 1H), 7.41-7.32 (m, 3H), 7.28-7.23 (m, 2H), 6.82 (d, J=2.4 Hz, 1H), 5.40 (s, 2H).

The compounds listed in the table below were prepared in a method similar to that described above starting from the listed starting materials:

| Starting material | Compound Name/No. | Characterization Data |
|---|---|---|
| Br─⟨CH(CH₃)⟩─Ph | 1-(1-Phenylethyl)-1H-pyrazole-3-carbaldehyde/Int-62 | LCMS (FA): m/z = 201 (M + H). |
| Br─CH(CH₃)₂ (isopropyl) | 1-isoPropyl-1H-pyrazole-3-carbaldehyde/Int-63 | $^1$H NMR ($CDCl_3$) δ 9.97 (s, 1H), 7.47 (d, J = 2.3 Hz, 1H), 6.80 (d, J = 2.3 Hz, 1H), 4.66-4.45 (m, 1H), 1.56 (d, J = 6.7 Hz, 6H). |
| Br─CH₂CH(CH₃)₂ (isobutyl) | 1-isoButyl-1H-pyrazole-3-carbaldehyde/Int-64 | $^1$H NMR ($CDCl_3$) δ 9.97 (s, 1H), 7.41 (d, J = 2.4 Hz, 1H), 6.80 (d, J = 2.4 Hz, 1H), 4.01 (d, J = 7.3 Hz, 2H), 2.34-2.16 (m, 1H), 0.94 (d, J = 6.7 Hz, 6H). |
| Br─indanyl<br>Arp, F. U. et al. *J. Am. Chem. Soc.* 2005, 127, 10482-10483. | 1-(2,3-Dihydro-1H-inden-1-yl)-1H-pyrazole-3-carbaldehyde/Int-65 | LCMS (FA): m/z = 213 (M + H). |
| Br─CH₂─cyclohexyl | 1-(Cyclohexylmethyl)-1H-pyrazole-3-carbaldehyde/Int-66 | LCMS (FA): m/z = 193 (M + H). |
| Br─CH(CH₃)─(3-Cl-C₆H₄)<br>Int-1 | 1-[1-(3-Chlorophenyl)ethyl]-1H-pyrazole-3-carbaldehyde/Int-67 | LCMS (FA): m/z = 235 (M + H). |

| Starting material | Compound Name/ No. | Characterization Data |
|---|---|---|
| 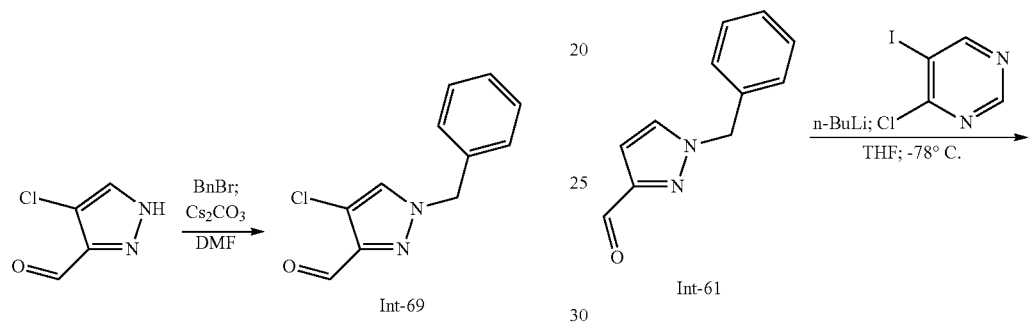 | 1-(3-Chlorobenzyl)-1H-pyrazole-3-carbaldehyde/Int-68 | LCMS (FA): m/z = 221 (M + H). |

Example 37:
1-Benzyl-4-chloro-1H-pyrazole-3-carbaldehyde
Int-69

Example 38: [(1R,2R,3S,4R)-4-({5-[(1-Benzyl-1H-pyrazol-3-yl)carbonyl]pyrimidin-4-yl}amino)-2,3-dihydroxycyclopentyl]methyl sulfamate I-142

Step 1: 1-Benzyl-4-chloro-1H-pyrazole-3-carbaldehyde Int-69

To a solution of 4-chloro-3-formylpyrazole (500 mg, 3.8 mmol) in DMF (20 mL) was added $Cs_2CO_3$ (3.1 g, 9.6 mmol) followed by benzyl bromide (0.50 mL, 4.2 mmol) at rt, and the mixture was stirred for 1 h. The reaction was quenched by addition of water (100 mL) and extracted with $Et_2O$ (100 mL×3). The combined organic layers were dried over $Na_2SO_4$, filtered, and concentrated. The residue was purified on silica gel to afford 1-benzyl-4-chloro-1H-pyrazole-3-carbaldehyde (570 mg, 67%). $^1$H NMR (DMSO) δ 9.87 (d, J=0.6 Hz, 1H), 8.35 (d, J=0.5 Hz, 1H), 7.41-7.30 (m, 5H), 5.44 (s, 2H).

The compound listed in the table below was prepared in an analogous fashion to that described above starting from the listed starting material:

| Starting material | Compound Name/No. | LCMS Data |
|---|---|---|
| 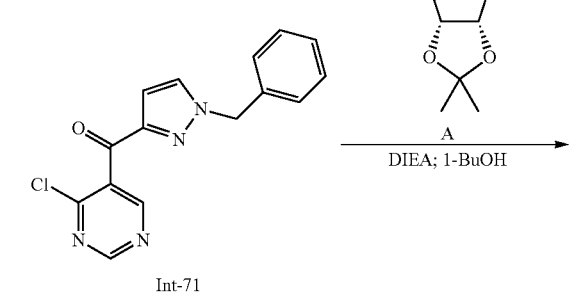 | 1-Benzyl-5-methyl-1H-pyrazole-3-carbaldehyde/Int-70 | LCMS (FA): m/z = 201.1 (M + H). |

Step 1: (1-Benzyl-1H-pyrazol-3-yl)(4-chloropyrimidin-5-yl)methanol

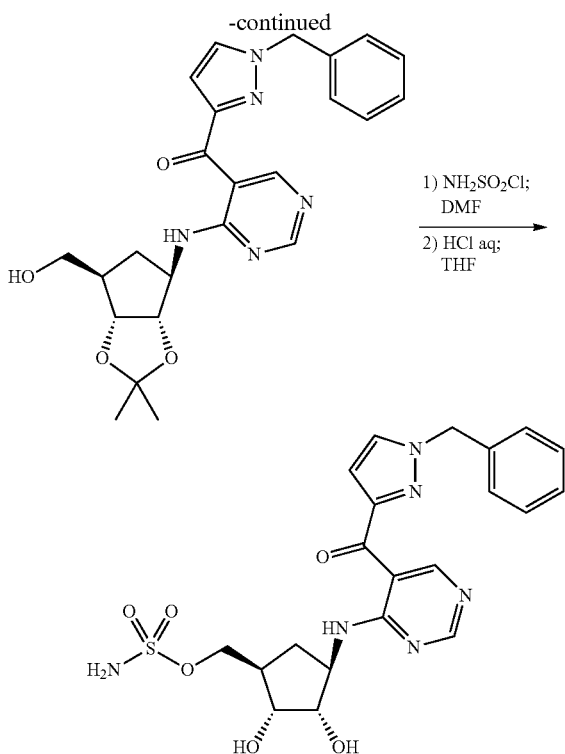

1) NH$_2$SO$_2$Cl; DMF
2) HCl aq; THF

4-Chloro-5-iodopyrimidine (300 mg, 1.25 mmol) was weighed into a 100 mL 2 necked RBF and the flask was purged with argon. This starting material was dissolved in THF (10 mL) and the solution was cooled to −78° C. To the solution was added n-Butyllithium (2.50 M in hexane; 1.0 mL, 2.5 mmol) at −78° C. and then the mixture was stirred for 30 min. To this mixture was added dropwise a solution of 1-benzyl-1H-pyrazole-3-carbaldehyde (211 mg, 1.1 mmol) in THF (4 mL), and the resulting mixture was stirred for 30 min. The reaction was quenched by addition of saturated NH$_4$Cl (50 mL) and extracted with EtOAc (50 mL×4). The combined organic layers were washed with brine, dried over Na$_2$SO$_4$, filtered, and concentrated in vacuo. The residue was purified on silica gel to provide (1-benzyl-1H-pyrazol-3-yl)(4-chloropyrimidin-5-yl)methanol (304 mg, 85%) as a light yellow oil. LCMS (FA): m/z=301.4 (M+H).

Step 2: (1-Benzyl-1H-pyrazol-3-yl)(4-chloropyrimidin-5-yl)methanone Int-71

To a solution of (1-benzyl-1H-pyrazol-3-yl)(4-chloropyrimidin-5-yl)methanol (285 mg, 0.95 mmol) in DCM (10 mL) was added manganese(IV) oxide (0.82 g, 9.5 mmol), and the mixture was stirred for 15 h at rt. The reaction was filtered through a celite pad and the residual solid was washed with DCM several times. The filtrate was concentrated in vacuo and the residue was purified on silica gel column to give (1-benzyl-1H-pyrazol-3-yl)(4-chloropyrimidin-5-yl)methanone (257 mg, 91%) as a colorless solid. LCMS (FA): m/z=299.4 (M+H).

Step 3: (1-Benzyl-1H-pyrazol-3-yl)(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)methanone (1-Benzyl-1H-pyrazol-3-yl)(4-chloropyrimidin-5-yl)methanone (120 mg, 0.40 mmol) and (1R,2S,3R,4R)-1-amino-2,3-(isoproplydenyl)dihydroxy-4-hydroxymethyl cyclopentane (A) (90 mg, 0.48 mmol) (for synthesis of this starting material see: Claiborne, C. F. et al. PCT Application Publication WO2008/019124) were weighed into a reaction vessel. To this mixture was added 1-BuOH (2.4 mL) and DIEA (0.14 mL, 0.80 mmol), and the tube was sealed under an atmosphere of argon. The resulting mixture was stirred for 2 h at 105° C. After cooling to rt, the reaction was concentrated in vacuo. To this residue was added water (30 mL) and the resulting mixture was extracted with EtOAc (50 mL×4). The combined organic layers were washed with brine, dried over Na$_2$SO$_4$, filtered, and concentrated in vacuo. The residue was purified on silica gel to make (1-benzyl-1H-pyrazol-3-yl)(4-{[(3aS,4R,6R,6aR)-6-(hydroxymethyl)-2,2-dimethyltetrahydro-3 aH-cyclopenta[d][1,3]dioxol-4-yl]amino}pyrimidin-5-yl)methanone (175 mg, 92%) as a colorless solid. LCMS (FA): m/z=450.5 (M+H).

Step 4: [(1R,2R,3S,4R)-4-({5-[(1-Benzyl-1H-pyrazol-3-yl)carbonyl]pyrimidin-4-yl}amino)-2,3-dihydroxycyclopentyl]methyl sulfamate I-142

To a solution of (1-benzyl-1H-pyrazol-3-yl)(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)methanone (162 mg, 0.36 mmol) in DMF (2.0 mL) was added chlorosulfonamide (83 mg, 0.72 mmol) at rt, and the mixture was stirred for 10 min. The reaction was quenched by addition of saturated NaHCO$_3$ (30 mL) and extracted with EtOAc (50 mL×3). The combined organic layers were dried over Na$_2$SO$_4$, filtered, and concentrated in vacuo. The residue was purified on silica gel to give the sulfamate intermediate [(162 mg, 81%); LCMS (FA): m/z=529.5 (M+H).] which was then dissolved in THF (2.0 mL). To this solution was added water (2 mL) and conc. HCl (0.35 mL, 4.2 mmol) at rt, and the mixture was stirred for 2 h. The reaction was quenched by addition of saturated NaHCO$_3$ (30 mL) and extracted with EtOAc (50 mL×4). The combined organic layers were dried over Na$_2$SO$_4$, filtered, and concentrated. The residue was purified on silica gel to give [(1R,2R,3S,4R)-4-({5-[(1-benzyl-1H-pyrazol-3-yl)carbonyl]pyrimidin-4-yl}amino)-2,3-dihydroxycyclopentyl]methyl sulfamate (128 mg, 89%). $^1$H NMR (DMSO) δ 9.47 (s, 1H), 9.07 (d, J=7.4 Hz, 1H), 8.61 (s, 1H), 8.07 (d, J=2.4 Hz, 1H), 7.45 (s, 2H), 7.41-7.26 (m, 5H), 6.92 (d, J=2.4 Hz, 1H), 5.51 (s, 2H), 4.92 (d, J=6.0 Hz, 1H), 4.74 (d, J=4.8 Hz, 1H), 4.50-4.41 (m, 1H), 4.07 (dd, J=9.7, 6.1 Hz, 1H), 3.98 (dd, J=9.7, 6.6 Hz, 1H), 3.79 (dd, J=13.0, 5.8 Hz, 1H), 3.71 (dd, J=9.5, 4.8 Hz, 1H), 2.38-2.28 (m, 1H), 2.25-2.15 (m, 1H), 1.15 (dt, J=12.9, 8.7 Hz, 1H); LCMS (FA): m/z=489.5 (M+H).

The compounds listed in the table below were prepared in an analogous fashion to that described above starting from the appropriate starting materials. The following alternative conditions could be employed in the described reaction steps. Step 2: Dess-Martin oxidation instead of manganese dioxide oxidation. Step 3: K$_2$CO$_3$/DMF; DIEA/1-propanol instead of DIEA/1-butanol. Step 5: aq. TFA and aq. H$_3$PO$_4$ instead of aq. HCl. I-351/I-361 and I-323/I-353 (benzylic centers) were made as diastereomeric mixtures and separated via HPLC (chiral column). Absolute configurations of the undefined stereocenters are unknown.

| Starting material | Compound No. | LCMS Data |
|---|---|---|
| 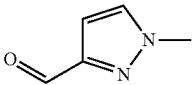 | I-345 | LCMS (FA): m/z = 413.5 (M + H). |
| 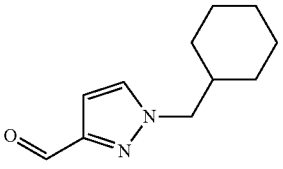
Int-66 | I-82 | LCMS (FA): m/z = 495.4 (M + H). |
| 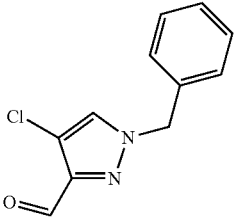
Int-69 | I-139 | LCMS (FA): m/z = 523.3 (M + H). |
| 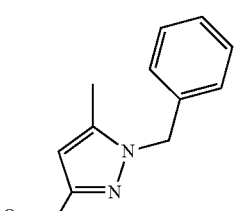
Int-70 | I-31 | LCMS (FA): m/z = 503.5 (M + H). |
| 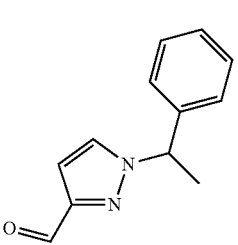
Int-62 | I-351 | LCMS (FA): m/z = 503.5 (M + H). |
| 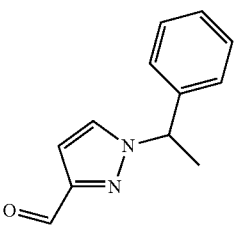
Int-62 | I-361 | LCMS (FA): m/z = 503.5 (M + H). |

-continued
| Starting material | Compound No. | LCMS Data |
|---|---|---|
| 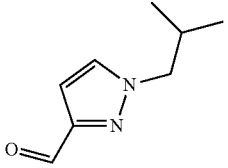<br>Int-64 | I-173 | LCMS (FA): m/z = 455.4 (M + H). |
| 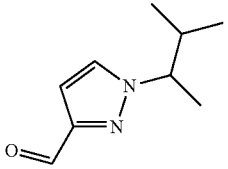<br>Int-63 | I-220 | LCMS (FA): m/z = 441.5 (M + H). |
| 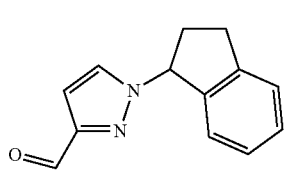<br>Int-65 | I-323 | LCMS (FA): m/z = 515.5 (M + H). |
| 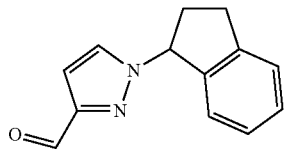<br>Int-65 | I-353 | LCMS (FA): m/z = 515.6 (M + H). |
Example 39: [(1R,2R,3S,4R)-4-({3-[(1-Benzyl-1H-pyrazol-3-yl)carbonyl]pyridin-4-yl}amino)-2,3-dihydroxycyclopentyl]methyl sulfamate I-56
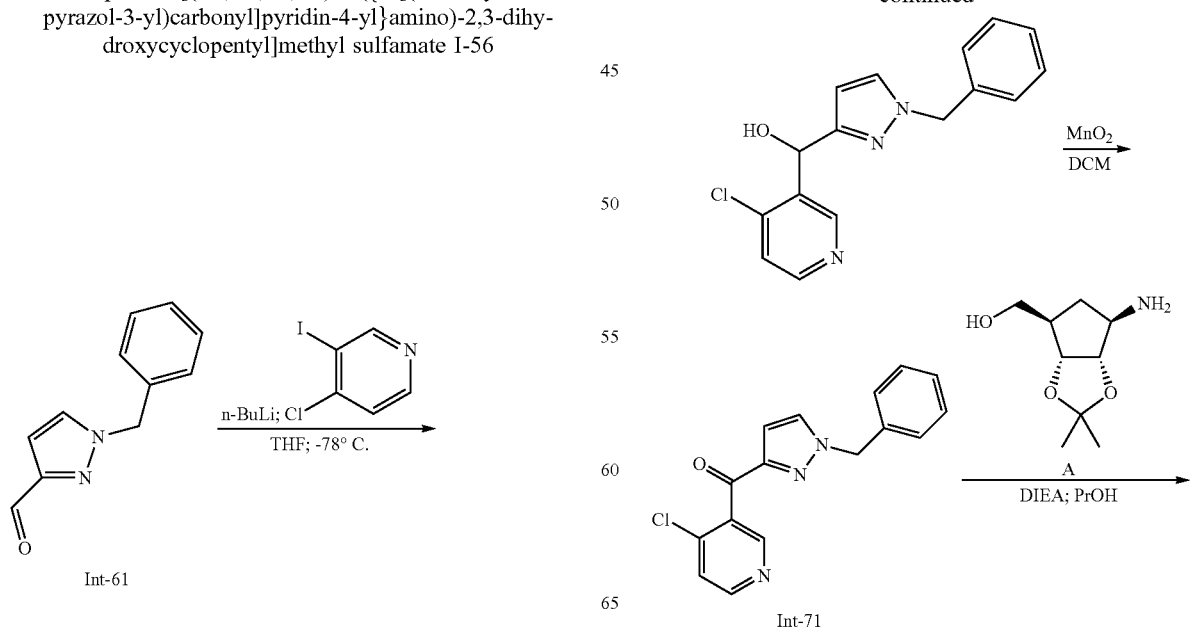

-continued

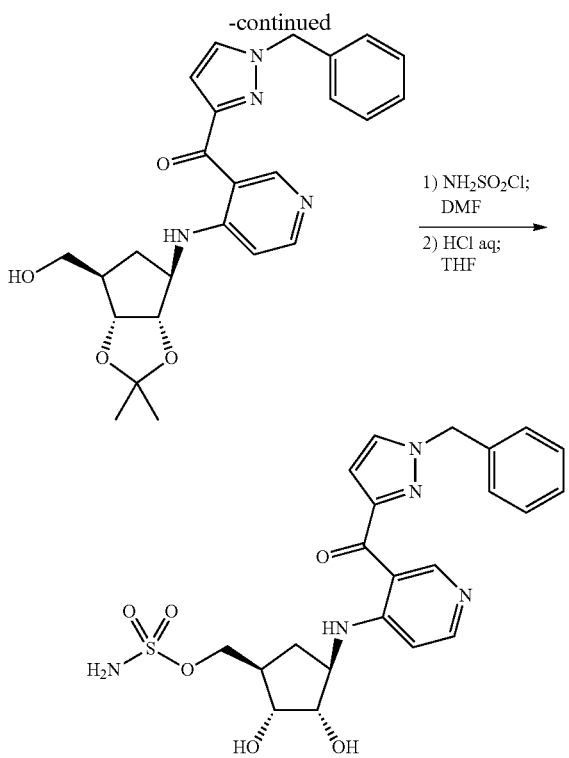

Step 1: (1-Benzyl-1H-pyrazol-3-yl)(4-chloropyridin-3-yl)methanol

Into a flame dried RBF with stirbar was added 4-chloro-5-iodopyrimidine (0.69 g, 2.9 mmol) dissolved in THF (15 mL). The flask was purged with argon and cooled to −78° C. To this solution was added dropwise n-butyllithium (2.5 M in hexane; 2.3 mL, 5.8 mmol) at −78° C. and the mixture was stirred for 30 min. To this mixture was added 1-benzyl-1H-pyrazole-3-carbaldehyde (0.49 g, 2.6 mmol) dissolved in THF (6 mL) dropwise. The reaction was stirred at −78° C. for 1 h. The reaction was quenched with a saturated solution of NH₄Cl and then extracted with EtOAc (3×). The combined organic layers were then washed with water and brine, dried over Na₂SO₄, filtered and concentrated. The crude product was purified on silica gel to give (1-benzyl-1H-pyrazol-3-yl)(4-chloropyridin-3-yl)methanol (0.57 g, 66%). LCMS (FA): m/z=300.4 (M+H).

Step 2: (1-Benzyl-1H-pyrazol-3-yl)(4-chloropyridin-3-yl)methanone

To a solution of (1-benzyl-1H-pyrazol-3-yl)(4-chloropyridin-3-yl)methanol (0.57 g, 1.9 mmol) in DCM (20 mL) was added manganese(IV) oxide (1.66 g, 19.1 mmol). The suspension was stirred for 19 h at rt. The reaction was then filtered through a celite pad and the residual solid was washed with DCM several times. The filtrate was then concentrated in vacuo and the residue was purified on silica gel to (1-benzyl-1H-pyrazol-3-yl)(4-chloropyridin-3-yl)methanone (0.53 g, 94%). LCMS (FA): m/z=298.3 (M+H).

Step 3: (1-Benzyl-1H-pyrazol-3-yl)(4-{[(3aS,4R,6R,6aR)-6-(hydroxymethyl)-2,2-dimethyltetrahydro-3aH-cyclopenta[d][1,3]dioxol-4-yl]amino}pyridin-3-yl)methanone (1-Benzyl-1H-pyrazol-3-yl)(4-chloropyridin-3-yl)methanone (0.26 g, 0.87 mmol) and A (0.18 g, 0.96 mmol) were weighed into a 20 mL reaction vessel. To this mixture was added 1-propanol (5 mL) and DIEA (0.30 mL, 1.7 mmol). The resulting mixture was sealed and stirred at 110° C. for 4 h. The reaction was then heated at 160° C. in a microwave reactor for 90 min. It was then cooled to rt and quenched with water. The reaction was then extracted with EtOAc (3×). The combined organic layers were washed with brine, dried over Na₂SO₄, filtered, and concentrated in vacuo. The crude product was purified on silica gel to afford (1-benzyl-1H-pyrazol-3-yl)(4-{[(3aS,4R,6R,6aR)-6-(hydroxymethyl)-2,2-dimethyltetrahydro-3aH-cyclopenta[d][1,3]dioxol-4-yl]amino}pyridin-3-yl)methanone (0.17 g, 43%); LCMS (FA): m/z=449.5 (M+H).

Step 4: [(1R,2R,3S,4R)-4-({3-[(1-Benzyl-1H-pyrazol-3-yl)carbonyl]pyridin-4-yl}amino)-2,3-dihydroxycyclopentyl]methyl sulfamate I-56

To a solution of (1-benzyl-1H-pyrazol-3-yl)(4-{[(3aS,4R,6R,6aR)-6-(hydroxymethyl)-2,2-dimethyltetrahydro-3aH-cyclopenta[d][1,3]dioxol-4-yl]amino}pyridin-3-yl)methanone (0.17 g, 0.37 mmol) in DMF (3 mL) was added chlorosulfonamide (86 mg, 0.74 mmol) at rt, and the mixture was stirred for 2 h. The reaction was quenched by addition of a saturated solution of NaHCO₃ and diluted with water. The mixture was extracted with EtOAc (3×). The combined organic layers were dried over MgSO₄, filtered, and concentrated. The crude sulfamate intermediate was dissolved in THF (3 mL) and water (3 mL). Concentrated HCl (0.47 mL, 5.6 mmol) was added to the solution. The reaction was stirred for 16 h at rt. The reaction was quenched by the addition of a saturated solution of NaHCO₃ and extracted with EtOAc (4×). The combined organic layers were dried over MgSO₄, filtered, and concentrated. The residue was purified by prep HPLC to afford [(1R,2R,3S,4R)-4-({3-[(1-Benzyl-1H-pyrazol-3-yl)carbonyl]pyridin-4-yl}amino)-2,3-dihydroxycyclopentyl]methyl sulfamate (0,075 g, 41%). ¹H NMR (DMSO) δ 9.34 (s, 1H), 8.91 (d, J=6.7 Hz, 1H), 8.20 (d, J=6.1 Hz, 1H), 8.04 (d, J=2.3 Hz, 1H), 7.41-7.25 (m, 5H), 6.91-6.84 (m, 2H), 5.49 (s, 2H), 4.12 (dd, J=9.7, 5.3 Hz, 1H), 4.00 (dd, J=9.7, 6.9 Hz, 1H), 3.85-3.75 (m, 1H), 3.72-3.66 (m, 2H), 2.45-2.36 (m, 1H), 2.29-2.19 (m, 1H), 1.21-1.10 (m, 1H); LCMS (FA): m/z=488.4 (M+H).

The compound listed in the table below was prepared in an analogous fashion to that described above starting from the listed starting material:

| Starting material | Compound No. | LCMS Data |
|---|---|---|
| Int-68 | I-81 | LCMS (FA): m/z = 522.5 (M + H). |

Example 40: (4-{[(3aS,4R,6R,6aR)-6-({[tert-Butyl (dimethyl)silyl]oxy}methyl)-2,2-dimethyltetrahydro-3aH-cyclopenta[d][1,3]dioxol-4-yl]amino}pyrimidin-5-yl)(1H-pyrazol-3-yl)methanone Int-75

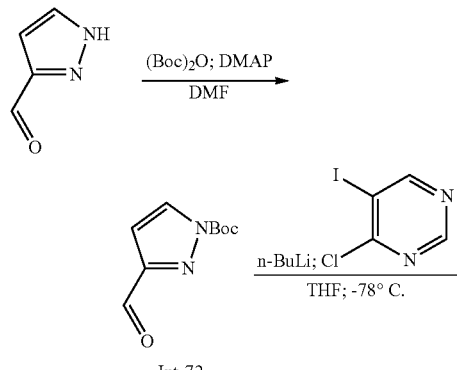

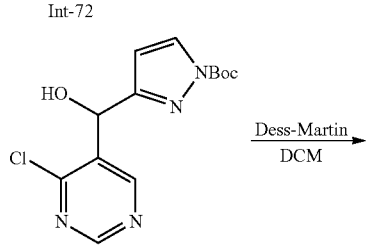

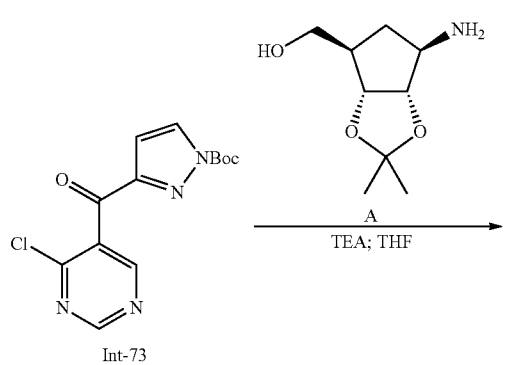

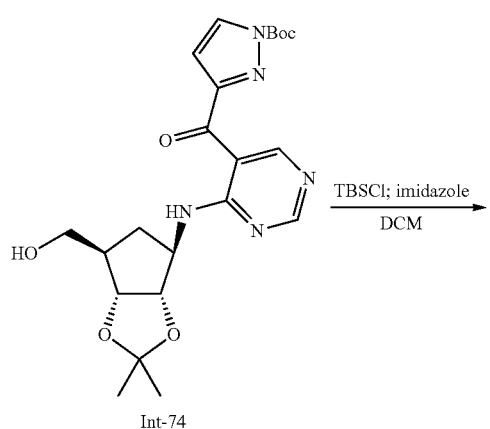

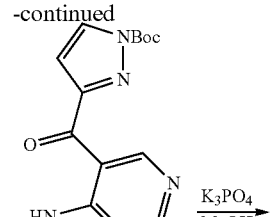

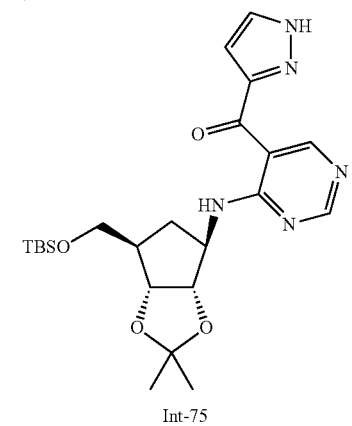 [SMILES: CC1(C)O[C@@H]2[C@@H](CO[Si](C)(C)C(C)(C)C)C[C@@H](Nc3ncncc3C(=O)c3cc[nH]n3)[C@@H]2O1]

Step 1: tert-Butyl 3-formyl-1H-pyrazole-1-carboxylate Int-72

Pyrazol-3-carbaldehyde (6.2 g, 65 mmol) and DMAP (0.79 g, 6.5 mmol) were dissolved in DMF (50.0 mL), di-tert-butyldicarbonate (21 g, 97 mmol) was added to this solution. It was cooled down to 0° C. and TEA (4.5 mL, 32 mmol) was added. It was allowed to stir for 1 h at 0° C. DCM (80 mL) was added to dilute the reaction, and it was washed with water (2×). The organic layer was concentrated and purified on silica gel to give tert-butyl 3-formyl-1H-pyrazole-1-carboxylate (9.1 g, 71%).

Step 2: tert-Butyl 3-[(4-chloropyrimidin-5-yl)(hydroxy)methyl]-1H-pyrazole-1-carboxylate Into a flame dried RBF with stirbar was added 4-chloro-5-iodopyrimidine (12.3 g, 51 mmol) dissolved in THF (200 mL). The flask was purged with argon and cooled to −95° C. To this solution was added dropwise n-butyllithium (2.5 M in hexane; 43 mL, 107 mmol) at −95° C. and the mixture was stirred for 10 min. To this mixture was added tert-butyl 3-formyl-1H-pyrazole-1-carboxylate (9.1 g, 46 mmol) dissolved in THF (30 mL) dropwise at −95° C. The reaction was stirred at −78° C. for 30 min. The reaction was quenched with a solution of acetic acid (7.9 mL) in THF (15 mL) and then allowed to warm to rt. Water (80 mL) was added and the mixture extracted with EtOAc (3×). The combined organic layers were then washed with water and brine, dried over $Na_2SO_4$, filtered and concentrated. The crude product was purified on silica gel to give tert-butyl 3-[(4-chloropyrimidin-5-yl)(hydroxy)methyl]-1H-pyrazole-1-carboxylate (10.2 g, 64%). LCMS (AA): m/z=311 (M+H).

Step 3: tert-Butyl 3-[(4-chloropyrimidin-5-yl)carbonyl]-1H-pyrazole-1-carboxylate Int-73 tert-Butyl 3-[(4-chloropyrimidin-5-yl)(hydroxy)methyl]-1H-pyrazole-1-carboxylate (1.0 g, 3.3 mmol) was dissolved in DCM (30 mL) and Dess-Martin periodinane (2.1 g, 4.9 mmol) was added to this solution. The mixture was then stirred at 40° C. for 2 h. TLC showed the reaction was done. The reaction was concentrated and purified on silica gel to provide tert-butyl 3-[(4-chloropyrimidin-5-yl)carbonyl]-1H-pyrazole-1-carboxylate (0.92, 90%). LCMS (AA): m/z=309 (M+H).

Step 4: tert-Butyl 3-[(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)carbonyl]-1H-pyrazole-1-carboxylate Int-74

A (1.9 g, 9.9 mmol) and [tert-butyl 3-[(4-chloropyrimidin-5-yl)carbonyl]-1H-pyrazole-1-carboxylate (2.8 g, 9.0 mmol) were weighed into a 50 mL RBF with stirbar. To this mixture was added 1-butanol (5 mL) followed by addition of DIEA (3.1 mL, 18 mmol) and the resulting mixture was stirred at rt for 16 h. Water (50 mL) was then added and the mixture was extracted with EtOAc (4×). The combined organic layers were washed with brine, dried over Na₂SO₄, filtered, and concentrated in vacuo. The crude product was purified on silica gel to afford [tert-butyl 3-[(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)carbonyl]-1H-pyrazole-1-carboxylate] (2.5 g, 61%). LCMS (AA): m/z=460 (M+H).

Step 5: tert-Butyl 3-[(4-{[(3aS,4R,6R,6aR)-6-({[tert-butyl(dimethyl)silyl]oxy}methyl)-2,2-dimethyltetrahydro-3aH-cyclopenta[d][1,3]dioxol-4-yl]amino}pyrimidin-5-yl)carbonyl]-1H-pyrazole-1-carboxylate tert-Butyl 3-[(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)carbonyl]-1H-pyrazole-1-carboxylate (0.3.1 g, 0.66 mmol) and 1H-imidazole (0.14 g, 2.0 mmol) were dissolved in DCM (15 mL). tert-Butyldimethylsilyl chloride (0.15 g, 1.0 mmol) was added to this solution and it was stirred at rt for 6 h. The reaction solution was concentrated and the residue was purified on silica gel to afford tert-butyl 3-[(4-{[(3aS,4R,6R,6aR)-6-({[tert-butyl(dimethyl)silyl]oxy}methyl)-2,2-dimethyltetrahydro-3aH-cyclopenta[d][1,3]dioxol-4-yl]amino}pyrimidin-5-yl)carbonyl]-1H-pyrazole-1-carboxylate (0.33 g, 86%). LCMS (AA): m/z=575 (M+H).

Step 6: (4-{[(3aS,4R,6R,6aR)-6-({[tert-Butyl(dimethyl)silyl]oxy}methyl)-2,2-dimethyltetrahydro-3aH-cyclopenta[d][1,3]dioxol-4-yl]amino}pyrimidin-5-yl)(1H-pyrazol-3-yl)methanone Int-75 tert-Butyl 3-[(4-{[(3aS,4R,6R,6aR)-6-({[tert-butyl(dimethyl)silyl]oxy}methyl)-2,2-dimethyltetrahydro-3aH-cyclopenta[d][1,3]dioxol-4-yl]amino}pyrimidin-5-yl)carbonyl]-1H-pyrazole-1-carboxylate (2.4 g, 4.1 mmol) was dissolved in methanol (25 mL) and a solution of potassium phosphate (0.44 g, 2.1 mmol) in water (3 mL) was added. It was allowed to stir at rt for 3 h. The reaction was concentrated and diluted with EtOAc (100 mL). This mixture was washed with water (2×). The organic layer was dried over MgSO₄, filtered, and concentrated to yield (4-{[(3aS,4R,6R,6aR)-6-({[tert-butyl(dimethyl)silyl]oxy}methyl)-2,2-dimethyltetrahydro-3aH-cyclopenta[d][1,3]dioxol-4-yl]amino}pyrimidin-5-yl)(1H-pyrazol-3-yl)methanone (1.8 g, 90%). LCMS (AA): m/z=475 (M+H).

Example 41: {(1R,2R,3S,4R)-4-[(5-{[1-(3-Chlorobenzyl)-1H-pyrazol-3-yl]carbonyl}pyrimidin-4-yl)amino]-2,3-dihydroxycyclopentyl}methyl sulfamate I-40

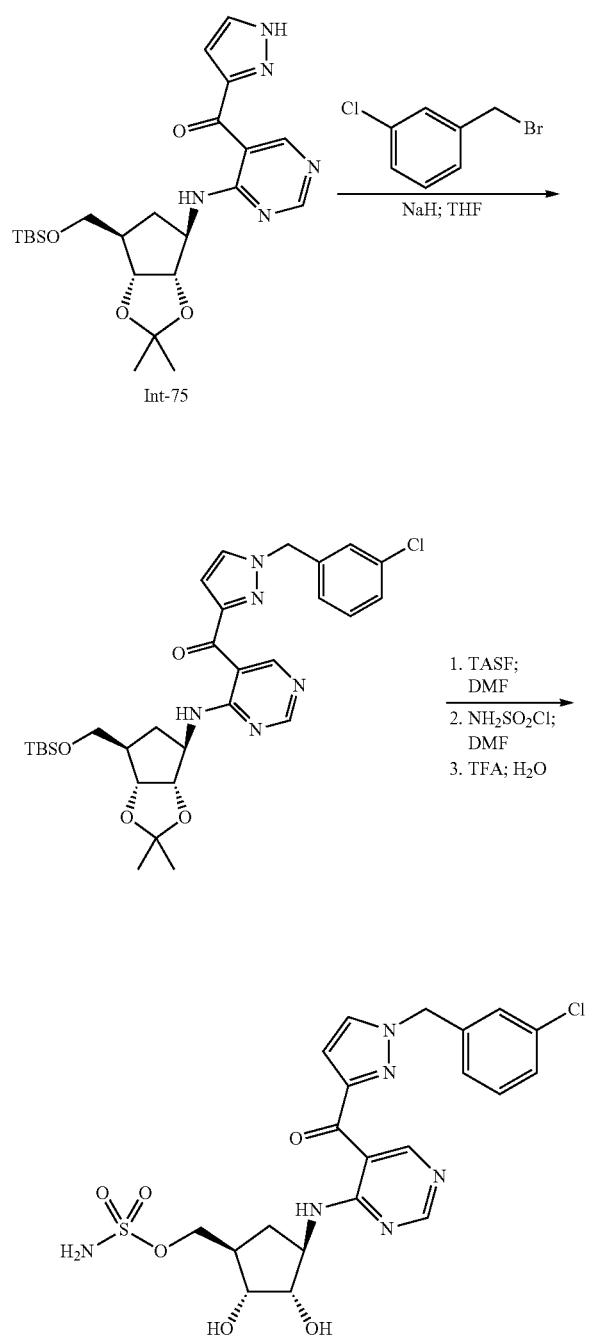

Step 1: (4-{[(3aS,4R,6R,6aR)-6-({[tert-Butyl(dimethyl)silyl]oxy}methyl)-2,2-dimethyltetrahydro-3aH-cyclopenta[d][1,3]dioxol-4-yl]amino}pyrimidin-5-yl)[1-(3-chlorobenzyl)-1H-pyrazol-3-yl]methanone (4-{[(3aS,4R,6R,6aR)-6-({[tert-Butyl(dimethyl)silyl]oxy}methyl)-2,2-dimethyltetrahydro-3aH-cyclopenta[d][1,3]dioxol-4-yl]amino}pyrimidin-5-yl)(1H-pyrazol-3-yl)methanone (0.13 g, 0.26 mmol) was dissolved in THF (15 mL). Sodium hydride (0.025 g, 1.0 mmol) was added to this solution at rt and it was stirred at rt for 1 h. 1-(Bromomethyl)-3-chloro-benzene (0.11 g, 0.52 mmol) was added to this solution and it was stirred at it for 6 h. A solution of acetic acid (1 mL) and methanol (2 mL) was next added to quench the reaction. The mixture was concentrated and the crude product was purified on silica gel to yield (4-{[(3aS,4R,6R,6aR)-6-({[tert-butyl(dimethyl)silyl]oxy}methyl)-2,2-dimethyltetrahydro-3aH-cyclopenta[d][1,3]dioxol-4-yl]amino}pyrimidin-5-yl)[1-(3-chlorobenzyl)-1H-pyrazol-3-yl]methanone (0.053 g, 34%). LCMS (AA): m/z=598 (M+H).

Step 2: {(1R,2R,3S,4R)-4-[(5-{[1-(3-Chlorobenzyl)-1H-pyrazol-3-yl]carbonyl}pyrimidin-4-yl)amino]-2,3-dihydroxycyclopentyl}methyl sulfamate I-40

(4-{[(3aS,4R,6R,6aR)-6-({[tert-butyl(dimethyl)silyl]oxy}methyl)-2,2-dimethyltetrahydro-3aH-cyclopenta[d][1,3]dioxol-4-yl]amino}pyrimidin-5-yl)[1-(3-chlorobenzyl)-1H-pyrazol-3-yl]methanone (0.053 g, 0.09 mmol) was dissolved in DMF (1 mL). Tris(dimethylamino)sulfonium trimethylsilyldifluoride (TASF) in DMF (0.25 M solution in DMF; 1.8 mL, 0.44 mmol) was added to this solution at rt and it was allowed to stir for 20 min. Chlorosulfonamide (0.051 g, 0.44 mmol) was next added to this solution and it was stirred for 20 min. Water was then added to the reaction mixture and it was extracted with EtOAc (2x). The combined organic layers were concentrated and dissolved in a solution of TFA (5.0 mL) and water (0.50 mL). The solution was allowed to stir at rt for 30 min then concentrated and the crude residue purified by prep HPLC to give {(1R,2R,3S,4R)-4-[(5-{[1-(3-chlorobenzyl)-1H-pyrazol-3-yl]carbonyl}pyrimidin-4-yl)amino]-2,3-dihydroxycyclopentyl}methyl sulfamate (25 mg, 50%). $^1$H NMR (MeOD) δ 9.62 (s, 1H), 8.56 (s, 1H), 7.84 (d, J=2.4 Hz, 1H), 7.38-7.29 (m, 3H), 7.23 (dd, J=6.4, 2.1 Hz, 1H), 6.96 (d, J=2.4 Hz, 1H), 5.46 (s, 2H), 4.64-4.51 (m, 1H), 4.18 (dd, J=8.3, 7.2 Hz, 2H), 3.94 (dd, 2H), 2.59-2.45 (m, 1H), 2.45-2.27 (m, 1H), 1.44-1.30 (m, 1H). LCMS (AA): m/z=523.1 (M+H).

The compounds listed in the table below were prepared using similar methods to that described above starting from the listed starting materials. The following alternative conditions could be employed in the described reaction steps. Step 1: Cs$_2$CO$_3$ instead of NaH. Step 2: HF/pyridine instead of TASF; aq. HCl is an acceptable replacement for aq. TFA.

| Starting material | Compound No. | LCMS Data |
|---|---|---|
| ![Br-CH2-C6H3(Cl)2] | I-159 | LCMS (FA): m/z = 557.1 (M + H). |
| ![Br-CH2-pyridin-4-yl] | I-160 | LCMS (FA): m/z = 490.1 (M + H). |
| ![Br-CH2-pyridin-3-yl] | I-247 | LCMS (FA): m/z = 490.1 (M + H). |
| ![Cl-SO2-C6H4-Br] | I-1 | LCMS (FA): m/z = 616.9 (M + H). |

Example 42: [(1R,2R,3S,4R)-4-{[5-({1-[3-(Acryloylamino)benzyl]-1H-pyrazol-3-yl}carbonyl)pyrimidin-4-yl]amino}-2,3-dihydroxycyclopentyl]methyl sulfamate I-313

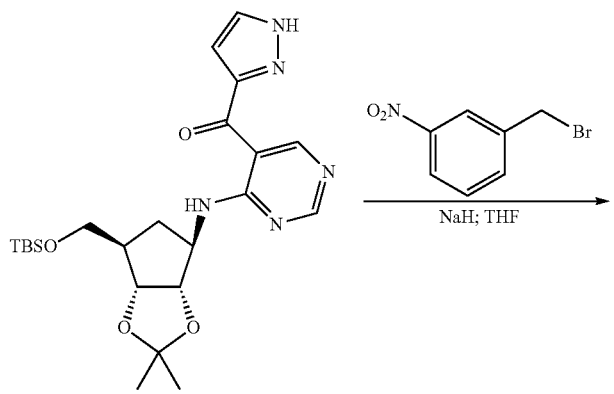

Int-76

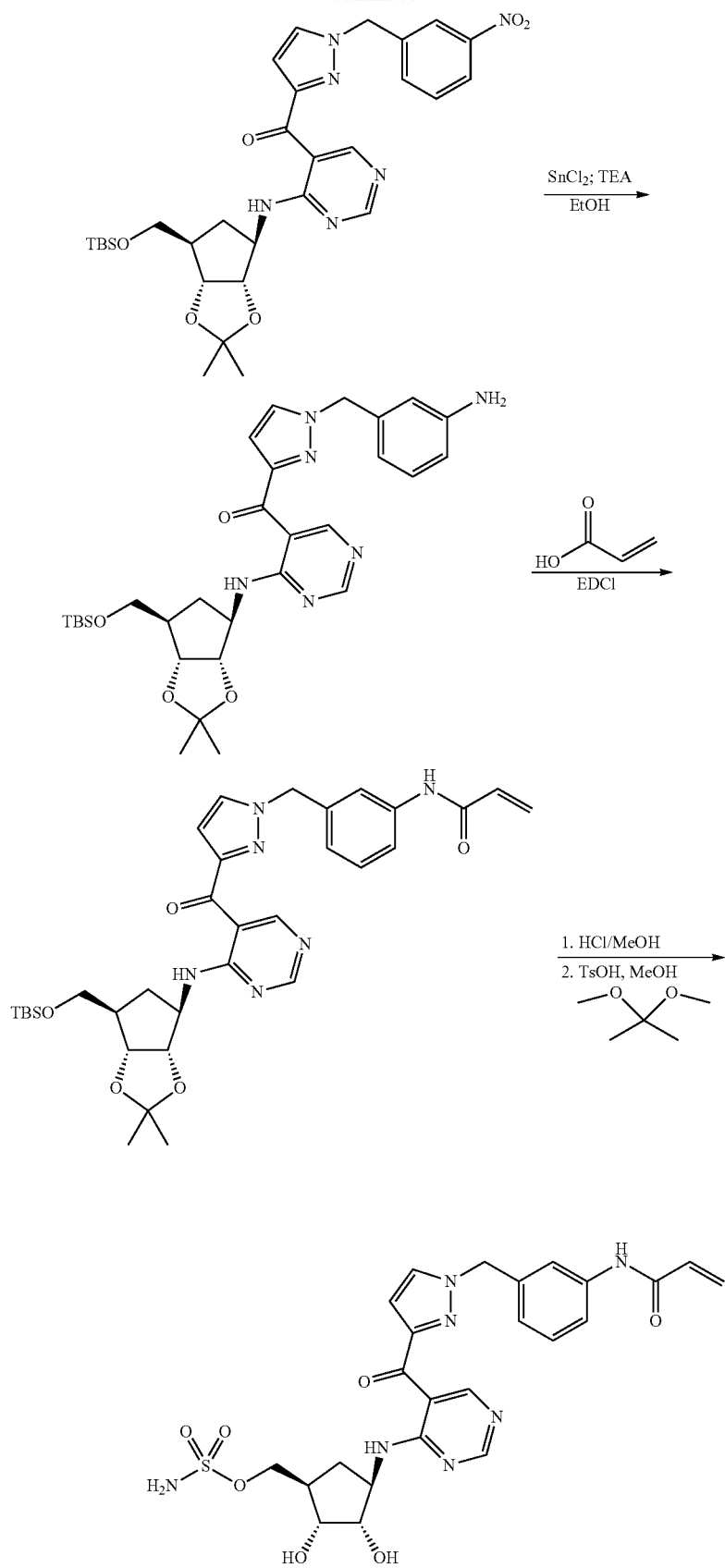

Step 1: (4-{[(3aS,4R,6R,6aR)-6-({[tert-Butyl(dimethyl)silyl]oxy}methyl)-2,2-dimethyltetrahydro-3aH-cyclopenta[d][1,3]dioxol-4-yl]amino}pyrimidin-5-yl)[1-(3-nitrobenzyl)-1H-pyrazol-3-yl]methanone Sodium hydride (0.030 g, 1.3 mmol) was added to a solution of (4-{[(3aS,4R,6R,6aR)-6-({[tert-butyl(dimethyl)silyl]oxy}methyl)-2,2-dimethyltetrahydro-3aH-cyclopenta[d][1,3]dioxol-4-yl]amino}pyrimidin-5-yl)(1H-pyrazol-3-yl)methanone (0.18 g, 0.39 mmol) in THF (15 mL) at rt. This mixture was allowed to stir at rt for 1 h, then 1-(bromomethyl)-3-nitro-benzene (0.14 g, 0.65 mmol) was added. The resulting mixture was stirred at rt for 16 h. A solution of acetic acid (1 mL) and methanol (2 mL) was added to quench and the resulting solution was concentrated. The residue was purified on silica gel to yield (4-{[(3aS,4R,6R,6aR)-6-({[tert-butyl(dimethyl)silyl]oxy}methyl)-2,2-dimethyltetrahydro-3aH-cyclopenta[d][1,3]dioxol-4-yl]amino}pyrimidin-5-yl)[1-(3-nitrobenzyl)-H-pyrazol-3-yl]methanone (192 mg, 81%). LCMS (FA): m/z=609.3 (M+H).

Step 2: [1-(3-Aminobenzyl)-1H-pyrazol-3-yl](4-{[(3aS,4R,6R,6aR)-6-({[tert-butyl(dimethyl)silyl]oxy}methyl)-2,2-dimethyltetrahydro-3aH-cyclopenta[d][1,3]dioxol-4-yl]amino}pyrimidin-5-yl)methanone (4-{[(3aS,4R,6R,6aR)-6-({[tert-Butyl(dimethyl)silyl]oxy}methyl)-2,2-dimethyltetrahydro-3aH-cyclopenta[d][1,3]dioxol-4-yl]amino}pyrimidin-5-yl)[1-(3-nitrobenzyl)-1H-pyrazol-3-yl]methanone (0.20 g, 0.33 mmol) was dissolved in absolute ethanol (20 mL). Tin dichloride (0.63 g, 3.3 mmol) was added to this solution and the resulting mixture was allowed to stir at rt for 16 h. TEA (1 mL) was added and the resulting solid was filtered and washed with methanol. The filtrate was concentrated to give [1-(3-aminobenzyl)-1H-pyrazol-3-yl](4-{[(3aS,4R,6R,6aR)-6-({[tert-butyl(dimethyl)silyl]oxy}methyl)-2,2-dimethyltetrahydro-3aH-cyclopenta[d][1,3]dioxol-4-yl]amino}pyrimidin-5-yl)methanone (0.16 g, 80%). LCMS (FA); m/z=579.5 (M+H).

Step 3: N-[3-({3-[(4-{[(3aS,4R,6R,6aR)-6-({[tert-butyl(dimethyl)silyl]oxy}methyl)-2,2-dimethyltetrahydro-3aH-cyclopenta[d][1,3]dioxol-4-yl]amino}pyrimidin-5-yl)carbonyl]-1H-pyrazol-1-yl}methyl)phenyl]acrylamide

[1-(3-Aminobenzyl)-1H-pyrazol-3-yl](4-{[(3aS,4R,6aR)-6-({[tert-butyl(dimethyl)silyl]oxy}methyl)-2,2-dimethyltetrahydro-3 aH-cyclopenta[d][1,3]dioxol-4-yl]amino}pyrimidin-5-yl)methanone (0.053 g, 0.092 mmol) and N-(3-dimethylaminopropyl)-N'-ethylcarbodiimide hydrochloride (0.053 g, 0.28 mmol) were stirred as a solution in THF (10 mL). TEA (0.047 g, 0.46 mmol) and acrylic acid (0.013 g, 0.18 mmol) were added to this solution and it was allowed to stir at rt for 3 h. The reaction was concentrated and the residue was purified on silica gel to afford N-[3-({3-[(4-{[(3aS,4R,6R,6aR)-6-({[tert-butyl(dimethyl)silyl]oxy}methyl)-2,2-dimethyltetrahydro-3aH-cyclopenta[d][1,3]dioxol-4-yl]amino}pyrimidin-5-yl)carbonyl]-H-pyrazol-1-yl}methyl)phenyl]acrylamide (38 mg, 65%). LCMS (FA): m/z=633.5 (M+H).

Step 4: N-[3-({3-[(4-{[(3aS,4R,6R,6aR)-6-(Hydroxymethyl)-2,2-dimethyltetrahydro-3aH-cyclopenta[d][1,3]dioxol-4-yl]amino}pyrimidin-5-yl)carbonyl]-1H-pyrazol-1-yl}methyl)phenyl]acrylamide N-[3-({3-[(4-{[(3aS,4R,6R,6aR)-6-({[tert-Butyl(dimethyl)silyl]oxy}methyl)-2,2-dimethyltetrahydro-3aH-cyclopenta[d][1,3]dioxol-4-yl]amino}pyrimidin-5-yl)carbonyl]-1H-pyrazol-1-yl}methyl)phenyl]acrylamide (0.037 g, 0.058 mmol) was added to a solution of 0.05 M HCl in methanol (8.0 mL, 0.40 mmol) and the resulting solution was allowed to stir at rt for 1 h. At this point LCMS analysis showed that TBS group removal was complete, but the acetonide protecting group was also removed. The reaction mixture was concentrated and methanol (10 mL), 2,2-dimethoxypropane (0.069 g, 0.66 mmol), and p-toluenesulfonic acid (0.017 g, 0.099 mmol) were added. The resulting mixture was allowed to stir at rt for 1 h. The reaction mixture was concentrated and the residue was purified on silica gel to give N-[3-({3-[(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)carbonyl]-1H-pyrazol-1-yl}methyl)phenyl]acrylamide (18 mg, 60%). LCMS (FA): m/z=519.5 (M+H).

Step 5: [(1R,2R,3S,4R)-4-{[5-({1-[3-(Acryloylamino)benzyl]-1H-pyrazol-3-yl}carbonyl)pyrimidin-4-yl]amino}-2,3-dihydroxycyclopentyl]methyl sulfamate I-313

To a solution of N-[3-({3-[(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)carbonyl]-1H-pyrazol-1-yl}methyl)phenyl]acrylamide (0.015 g, 0.028 mmol) in DMF (3 mL) was added chlorosulfonamide (10 mL), 0.084 mmol) at rt, and the mixture was stirred for 2 h. To the reaction mixture was added TFA (1 mL) and water (1 mL) and allowed to stir at rt for 1 h. The reaction mixture was then quenched by addition of NaHCO$_3$ and water. The mixture was extracted with EtOAc (2×). The combined organic layers were dried over MgSO$_4$, filtered, and concentrated. The crude was purified on silica gel to afford [(1R,2R,3S,4R)-4-{[5-({1-[3-(acryloylamino)benzyl]-1H-pyrazol-3-yl}carbonyl)pyrimidin-4-yl]amino}-2,3-dihydroxycyclopentyl]methyl sulfamate (7 mg, 43%). $^1$H NMR (MeOD) δ 9.66 (s, 1H), 8.57 (s, 1H), 7.82 (d, J=2.4 Hz, 1H), 7.61 (d, J=6.7 Hz, 1H), 7.59 (s, 1H), 7.34 (t, J=8.1 Hz, 1H), 7.08 (d, J=7.8 Hz, 1H), 6.96 (d, J=2.4 Hz, 1H), 6.46-6.29 (m, 2H), 5.75 (dd, J=9.2, 2.7 Hz, 1H), 5.47 (s, 2H), 4.65-4.53 (m, 1H), 4.27-4.14 (m, 2H), 4.00-3.85 (m, 2H), 2.57-2.46 (m, 1H), 2.42-2.27 (m, 1H), 1.43-1.32 (m, 1H). LCMS (FA): m/z=558.2 (M+H).

The compound listed in the table below was prepared using an analogous method to that described above starting from the listed starting material in step 3.

| Starting material | Compound No. | LCMS Data |
|---|---|---|
| 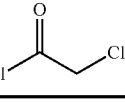 | I-67 | LCMS (FA): m/z = 580.1 (M + H). |

Example 43: {(1R,2R,3S,4R)-2,3-Dihydroxy-4-[(5-{([1-(2-oxo-2-phenylethyl)-1H-pyrazol-3-yl]carbonyl}pyrimidin-4-yl)amino]cyclopentyl}methyl sulfamate I-125

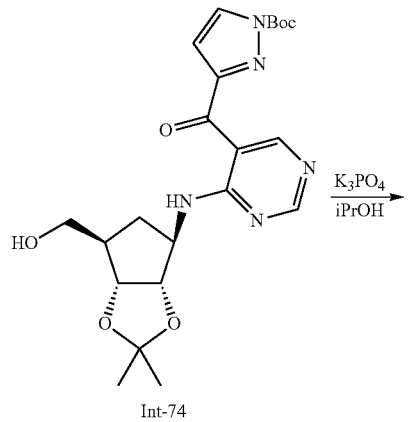

Int-74

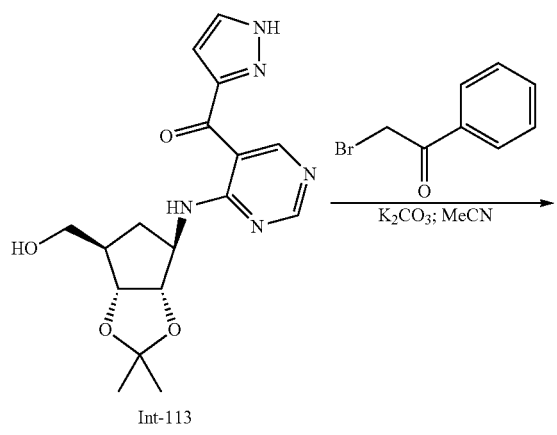

Int-113

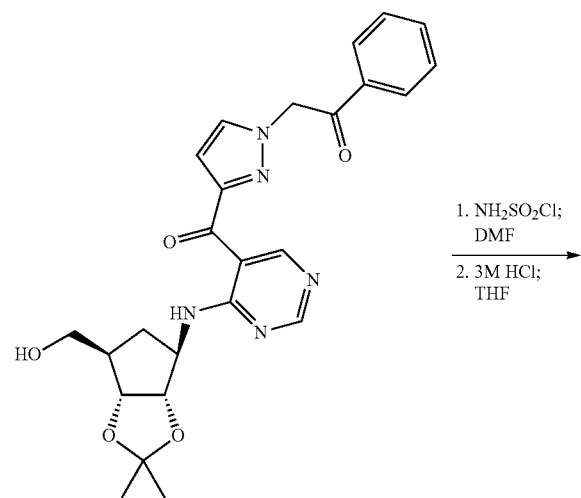

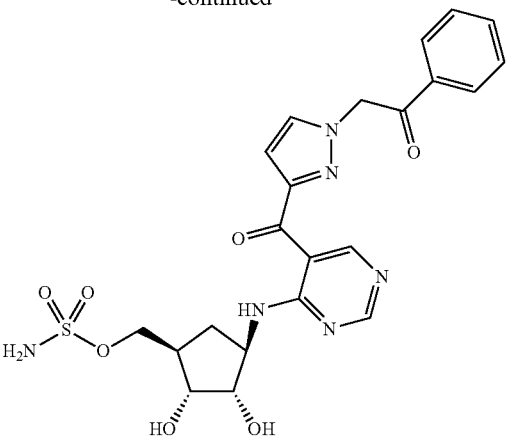

Step 1: (4-{[(3aS,4R,6R,6aR)-6-(Hydroxymethyl)-2,2-dimethyltetrahydro-3aH-cyclopenta[d][1,3]dioxol-4-yl]amino}pyrimidin-5-yl)(1H-pyrazol-3-yl)methanone Int-113 tert-Butyl 3-[(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)carbonyl]-1H-pyrazole-1-carboxylate (1.3 g, 2.9 mmol) was dissolved in 2-propanol (50 mL) and a solution of potassium phosphate (1.2 g, 5.7 mmol) in water (5 mL) was added. It was allowed to stir at rt for 3 h. Then, water (20 mL) was added to the reaction and it was extracted with DCM (2×). The combined organic layers were dried over MgSO₄, filtered, and concentrated to yield (4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)(1H-pyrazol-3-yl)methanone (0.82 g, 80%). LCMS (FA): nm/z=360.2 (M+H).

Step 2: 2-{3-[(4-{[(3aS,4R,6R,6aR)-6-(Hydroxymethyl)-2,2-dimethyltetrahydro 3aH-cyclopenta[d][1,3]dioxol-4-yl]amino}pyrimidin-5-yl)carbonyl]-1H-pyrazol-1yl}-1-phenylethanone A mixture of (4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)(1H-pyrazol-3-yl)methanone (0.10 g, 0.28 mmol), 2-bromoacetophenone (68 mg, 0.34 mmol), and potassium carbonate (48 mg, 0.35 mmol) were stirred in acetonitrile (4 mL) at rt for 30 min. Water was added to the reaction mixture and it was extracted with EtOAc (3×). The combined organic layers were washed with brine, dried over magnesium sulfate, filtered and concentrated. The residue was purified on silica gel to give 2-{3-[(4-{[(3aS,4R,6R,6aR)-6-(hydroxymethyl)-2,2-dimethyltetrahydro3aH-cyclopenta[d][1,3]dioxol-4-yl]amino}pyrimidin-5-yl)carbonyl]-1H-pyrazol-1yl}1-phenylethanone (0.075 g, 56%). LCMS (FA): m/z=476.5 (M+H).

Step 3: {(1R,2R,3S,4R)-2,3-Dihydroxy-4-[(5-{[1-(2-oxo-2-phenylethyl)-1H-pyrazol-3-yl]carbonyl}pyrimidin-4-yl)amino]cyclopentyl}methyl sulfamate I-125

To a solution of 2-{3-[(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)carbonyl]-1H-pyrazol- 1-yl}-1-phenylethanone (0.075 g, 0.16 mmol) and TEA (0.066 mL, 0.47 mmol) in DMF (1.2 mL) was added chlorosulfonamide (54 mg, 0.47 mmol) at rt, and the mixture was stirred for 2 h. The reaction was quenched by addition of a saturated solution of NaHCO$_3$ and diluted with water. The mixture was extracted with EtOAc (4×). The combined organic layers were dried over MgSO$_4$, filtered, and concentrated. The crude sulfamate intermediate was dissolved in DMF (2 mL) and HCl (3.0 M in water; 2 mL, 6 mmol) was added to the solution. The reaction was stirred for 1 h at rt. The reaction was quenched by the addition of a saturated solution of NaHCO$_3$ and extracted with EtOAc (4×). The combined organic layers were dried over MgSO$_4$, filtered, and concentrated. The residue was purified on silica gel to afford {(1R,2R,3S,4R)-2,3-dihydroxy-4-[(5-{[1-(2-oxo-2-phenylethyl)-1H-pyrazol-3-yl]carbonyl}pyrimidin-4-yl)amino]cyclopentyl}methyl sulfamate (41 mg, 50%). $^1$H NMR (DMSO) δ 9.49 (s, 1H), 9.11 (d, J=7.2 Hz, 1H), 8.62 (s, 1H), 8.07 (d, J=7.3 Hz, 2H), 7.96 (d, J=2.4 Hz, 1H), 7.74 (t, J=7.4 Hz, 1H), 7.62 (t, J=7.7 Hz, 2H), 7.47 (s, 2H), 6.96 (s, 1H), 6.10 (s, 2H), 4.95 (d, J=6.0 Hz, 1H), 4.77-4.71 (m, 1H), 4.52-4.40 (m, 1H), 4.12-4.05 (m, 1H), 4.04-3.94 (m, 1H), 3.86-3.77 (m, 1H), 3.77-3.66 (m, 1H), 2.38-2.31 (m, 1H), 2.27-2.14 (m, 1H), 1.22-1.11 (m, 1H); LCMS (FA): m/z=517.2 (M+H).

The compounds listed in the table below were prepared in an analogous fashion to that described above starting from the listed starting materials used in step 2. DMF and THF are also acceptable solvents for use in step 2 instead of acetonitrile.

| Starting material | Compound No. | LCMS Data |
|---|---|---|
| (3-chlorophenacyl bromide) | I-283 | LCMS (FA): m/z = 551.4 (M + H). |
| (3-bromophenacyl bromide) | I-96 | LCMS (FA): m/z = 597.1 (M + H). |
| Int-7 | I-51 | LCMS (FA): m/z = 504.5 (M + H). |
| Int-110 | I-324 | LCMS (FA): m/z = 570.3 (M + H). |
| Int-111 | I-70 | LCMS (FA): m/z = 524.5 (M + H). |
| (2-bromo-6-(bromomethyl)pyridine) | I-284 | LCMS (FA): m/z = 570.4 (M + H). |

Example 44: [(1R,2R,3S,4R)-2,3-Dihydroxy-4-{[5-({1-[3-(vinylsulfonyl)benzyl]-1H-pyrazol-3-yl}carbonyl)pyrimidin-4-yl]amino}cyclopentyl] methyl sulfamate I-321

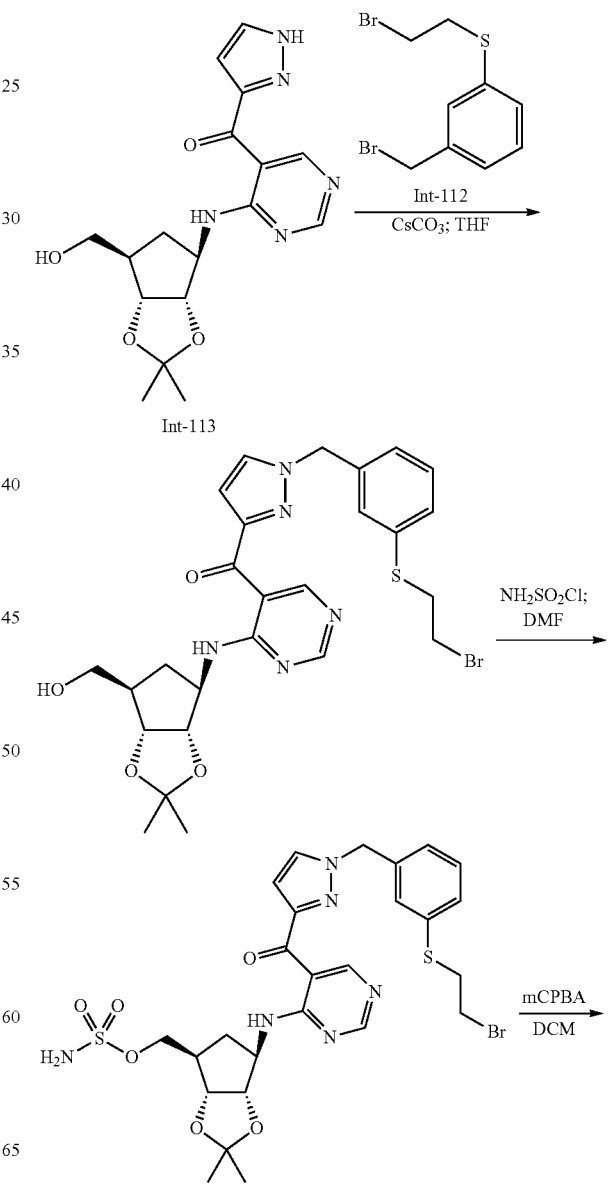

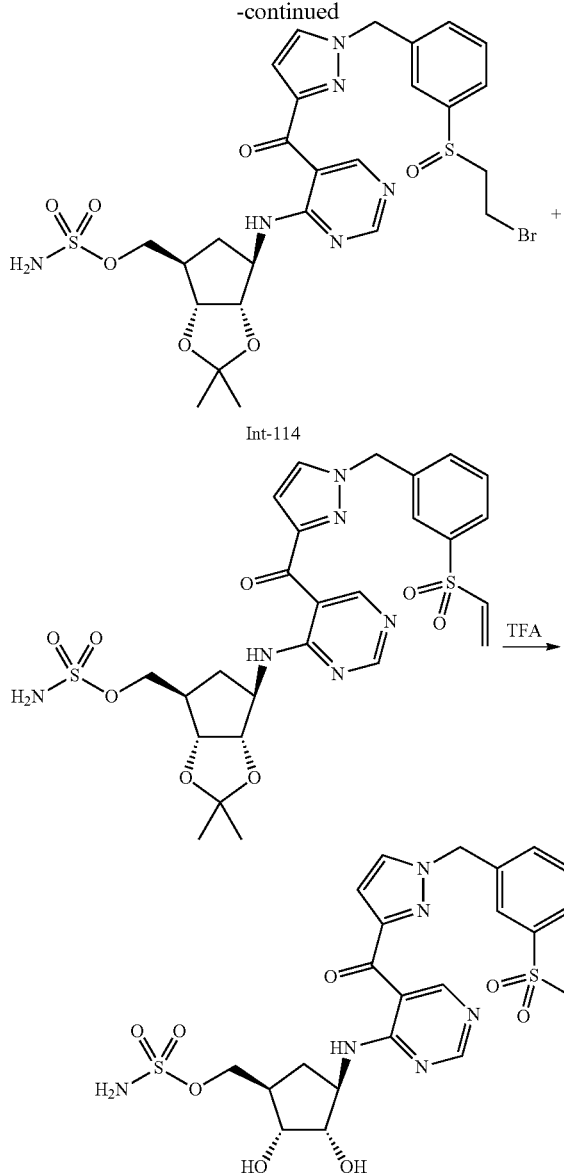

Int-114

Step 1: (1-{3-[(2-Bromoethyl)sulfanyl]benzyl}-1H-pyrazol-3-yl)(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)methanone To a round bottomed flask with stirbar was added (4-{[(3aS,4R,6R,6aR)-6-(hydroxymethyl)-2,2-dimethyltetrahydro-3 aH-cyclopenta[d][1,3]dioxol-4-yl]amino}pyrimidin-5-yl)(1H-pyrazol-3-yl)methanone (0.12 g, 0.35 mmol), 1-[(2-bromoethyl)sulfanyl]-3-(bromomethyl)benzene2-bromoethyl 3-(bromomethyl)phenyl sulfide (0.16 g, 0.52 mmol), cesium carbonate (0.23 g, 0.69 mmol), and THF (10 mL). The resulting reaction mixture was stirred 4 h at rt. The mixture was filtered to remove cesium carbonate and the filtrate concentrated. The residue was purified on silica gel to yield (1-{3-[(2-bromoethyl)sulfanyl]benzyl}-1H-pyrazol-3-yl)(4-{[(3  aS,4R,6R,6aR)-6-(hydroxymethyl)-2,2-dimethyltetrahydro-3aH-cyclopenta[d][1,3]dioxol-4-yl]amino}pyrimidin-5-yl)methanone (0.15 g, 73%). LCMS (FA): m/z=590.5 (M+H).

Step 2: [(3aR,4R,6R,6aS)-6-({5-[(1-{3-[(2-Bromoethyl)sulfanyl]benzyl}-1H-pyrazol-3-yl)carbonyl]pyrimidin-4-yl}amino)-2,2-dimethyltetrahydro-3aH-cyclopenta[d][1,3]dioxol-4-yl]methyl sulfamate To a solution of (1-{3-[(2-bromoethyl)sulfanyl]benzyl}-1H-pyrazol-3-yl)(4-{[(3  aS,4R,6R,6aR)-6-(hydroxymethyl)-2,2-dimethyltetrahydro-3 aH-cyclopenta[d][1,3]dioxol-4-yl]amino}pyrimidin-5-yl)methanone (0.081 g, 0.14 mmol) and DIEA (0.071 g, 0.55 mmol) in DMF (8 mL) was added chlorosulfonamide (0.032 g, 0.28 mmol) at 0° C. and the reaction was allowed to stir for 30 min at that temperature. The reaction mixture was purified directly on silica gel to give [(3aR,4R,6R,6aS)-6-({5-[(1-{3-[(2-bromoethyl)sulfanyl]benzyl}-1H-pyrazol-3-yl)carbonyl]pyrimidin-4-yl}amino)-2,2-dimethyltetrahydro-3aH-cyclopenta[d][1,3]dioxol-4-yl]methyl sulfamate (60 mg, 66%). LCMS (FA): m/z=669.5 (M+H).

Step 3: [(3aR,4R,6R,6aS)-2,2-Dimethyl-6-{[5-({1-[3-(vinylsulfonyl)benzyl]-1H-pyrazol-3-yl}carbonyl)pyrimidin-4-yl]amino}tetrahydro-3aH-cyclopenta[d][1,3]dioxol-4-yl]methyl sulfamate and [(3aR,4R,6R,6aS)-6-({5-[(1-{3-[(2-Bromoethyl)sulfinyl]benzyl}-1H-pyrazol-3-yl)carbonyl]pyrimidin-4-yl}amino)-2,2-dimethyltetrahydro-3aH-cyclopenta[d][1,3]dioxol-4-yl]methyl sulfamate Int-114 m-Chloroperbenzoic acid (0.051 g, 0.30 mmol) was added to a solution of [(3aR,4R,6R,6aS)-6-({5-[(1-{3-[(2-bromoethyl)sulfanyl]benzyl}-1H-pyrazol-3-yl)carbonyl]pyrimidin-4-yl}amino)-2,2-dimethyltetrahydro-3aH-cyclopenta[d][1,3]dioxol-4-yl]methyl sulfamate (0.13 g, 0.19 mmol) in DCM (10 mL) at rt. The reaction mixture was stirred at rt for 6 h. DIEA (0.098 g, 0.76 mmol) was then added to this solution and the resulting mixture was allowed to stir for 4 h. The reaction mixture was concentrated and the residue was purified on silica gel to afford [(3aR,4R,6R,6aS)-2,2-dimethyl-6-{[5-({1-[3-(vinylsulfonyl)benzyl]-1H-pyrazol-3-yl}carbonyl)pyrimidin-4-yl]amino}tetrahydro-3aH-cyclopenta[d][1,3]dioxol-4-yl]methyl sulfamate (13 mg, 11%). LCMS (FA): m/z=619.5 (M+H) and [(3 aR,4R,6R,6aS)-6-({5-[(1-{3-[(2-bromoethyl)sulfinyl]benzyl}-1H-pyrazol-3-yl)carbonyl]pyrimidin-4-yl}amino)-2,2-dimethyltetrahydro-3aH-cyclopenta[d][1,3]dioxol-4-yl]methyl sulfamate Int-x (29 mg, 23%). LCMS (FA): m/z=683.3 (M+H).

Step 4: [(1R,2R,3S,4R)-2,3-Dihydroxy-4-{[5-({1-[3-(vinylsulfonyl)benzyl]-1H-pyrazol-3-yl}carbonyl)pyrimidin-4-yl]amino}cyclopentyl]methyl sulfamate I-321

A solution of [(3aR,4R,6R,6aS)-2,2-dimethyl-6-({[5-({-[3-(vinylsulfonyl)benzyl]-1H-pyrazol-3-yl}carbonyl)pyrimidin-4-yl]amino}tetrahydro-3aH-cyclopenta[d][1,3]dioxol-4-yl]methyl sulfamate (0.014 g, 0.023 mmol) in TFA (4.5 mL) and water (0.50 mL) was stirred at room temperature for 1 h. The reaction mixture was concentrated and the crude product was purified by prep HPLC to afford [(1R,2R,3S,4R)-2,3-dihydroxy-4-{[5-({1-[3-(vinylsulfonyl)benzyl]-1H-pyrazol-3-yl}carbonyl)pyrimidin-4-yl]amino}cyclopentyl]methyl sulfamate I-number (6 mg, 47%). $^1$H NMR (MeOD) δ 9.53 (s, 1H), 8.53 (d, J=19.2 Hz, 1H), 7.88 (s, 1H), 7.87-7.82 (m, 1H), 7.82 (s, 1H), 7.64-7.60 (m, 1H), 6.96 (d, J=2.4 Hz, 1H), 6.86 (m, J=30.5, 15.3 Hz, 1H), 6.37 (d, J=15.1 Hz, 1H), 6.09 (d, J=10.9 Hz, 1H), 5.56

(s, 2H), 4.60-4.49 (m, 1H), 4.27-4.06 (m, 2H), 3.98-3.83 (m, 2H), 2.55-2.45 (m, 1H), 2.41-2.31 (m, 1H), 1.42-1.31 (m, 1H). LCMS (AA): m/z=579.1 (M+H).

Example 45: [(1R,2R,3S,4R)-2,3-Dihydroxy-4-{[5-({1-[3-((R)-vinylsulfinyl)benzyl]-1H-pyrazol-3-yl}carbonyl)pyrimidin-4-yl]amino}cyclopentyl]methyl sulfamate and [(1R,2R,3S,4R)-2,3-dihydroxy-4-{[5-({1-[3-((S)-vinyl)benzyl]-1H-pyrazol-3-yl}carbonyl)pyrimidin-4-yl]amino}cyclopentyl]methyl sulfamate I-74

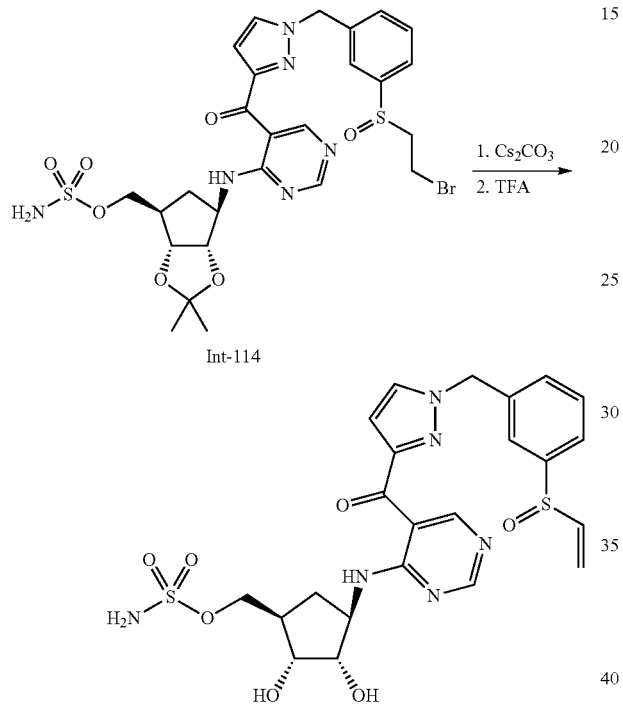

Step 1: [(1R,2R,3S,4R)-2,3-Dihydroxy-4-{[5-({1-[3-((R)-vinylsulfinyl)benzyl]-1H-pyrazol-3-yl}carbonyl)pyrimidin-4-yl]amino}cyclopentyl]methyl sulfamate and [(1R,2R,3S,4R)-2,3-dihydroxy-4-{[5-({1-[3-((S)-vinylsulfinyl)benzyl]-1H-pyrazol-3-yl}carbonyl)pyrimidin-4-yl]amino}cyclopentyl]methyl sulfamate I-74

Cesium carbonate (0.14 g, 0.43 mmol) was added to a solution of [(3aR,4R,6R,6aS)-6-({5-[(1-{3-[(2-bromoethyl)sulfinyl]benzyl}-1H-pyrazol-3-yl)carbonyl]pyrimidin-4-yl}amino)-2,2-dimethyltetrahydro-3aH-cyclopenta[d][1,3]dioxol-4-yl]methyl sulfamate (0.029 g, 0.043 mmol) in methanol (5 mL) at rt. The resulting mixture was allowed to stir at rt for 1 hr and then concentrated. Water (10 ml) was added and this mixture was then extracted with DCM (2×). The combined organic layers were dried over MgSO₄, filtered, and concentrated. The crude intermediate was dissolved in a mixture of TFA (4.5 mL) and water (0.5 mL). After stirring 1 h at rt the reaction mixture was concentrated and the crude product was purified by prep HPLC to yield [(1R,2R,3S,4R)-2,3-dihydroxy-4-{[5-({1-[3-((R)-vinylsulfinyl)benzyl]-1H-pyrazol-3-yl}carbonyl)pyrimidin-4-yl]amino}cyclopentyl]methyl sulfamate and [(1R,2R,3S,4R)-2,3-dihydroxy-4-{[5-({1-[3-((S)-vinylsulfinyl)benzyl]-1H-pyrazol-3-yl}carbonyl)pyrimidin-4-yl]amino}cyclopentyl]methyl sulfamate as a mixture of diastereomers (5 mg, 21%). ¹H NMR (MeOD) δ 9.60 (s, 1H), 8.55 (s, 1H), 7.91-7.83 (m, 1H), 7.68-7.54 (m, 3H), 7.54-7.45 (m, 1H), 6.97 (d, J=2.4 Hz, 1H), 6.79 (dd, J=16.4, 9.6 Hz, 1H), 6.16 (d, 1H), 5.97 (d, 1H), 5.56 (s, 2H), 4.63-4.50 (m, 1H), 4.24-4.12 (m, 2H), 3.97-3.90 (m, 2H), 2.59-2.44 (m, 1H), 2.42-2.31 (m, 1H), 1.43-1.33 (m, 1H). LCMS (AA): m/z=563.1 (M+H).

Example 46: ((1R,2R,3S,4R)-4-((5-(1-(2-Chlorobenzyl)-1H-pyrazole-3-carbonyl)pyrimidin-4-yl)amino)-2,3-dihydroxycyclopentyl)methyl sulfamate I-193

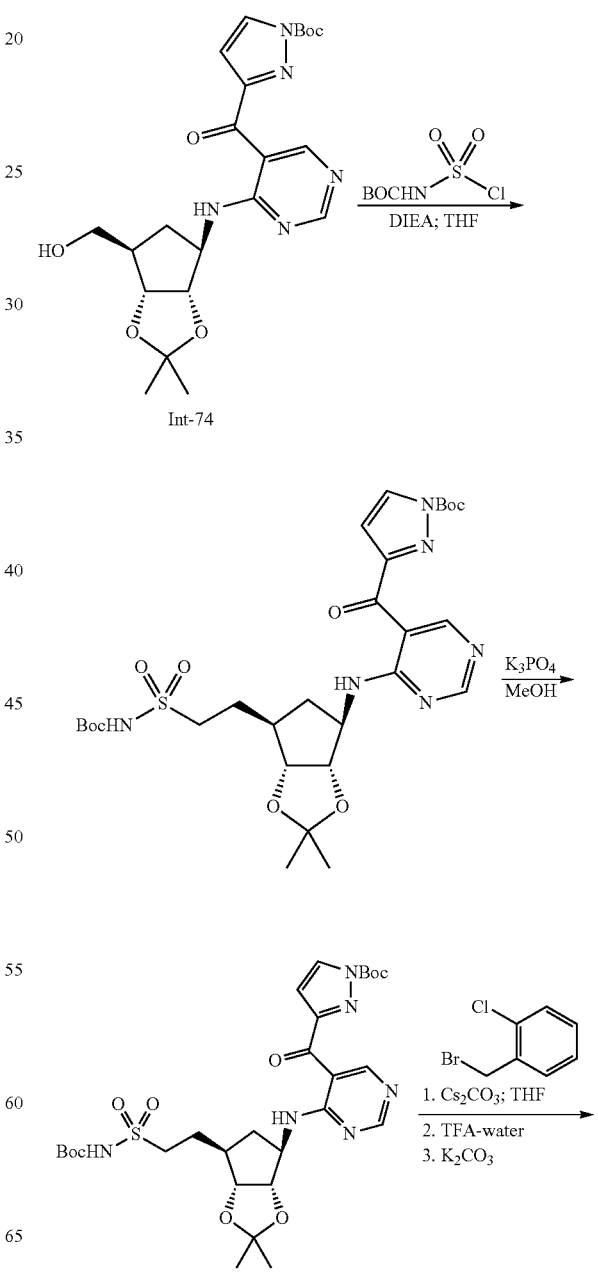

-continued

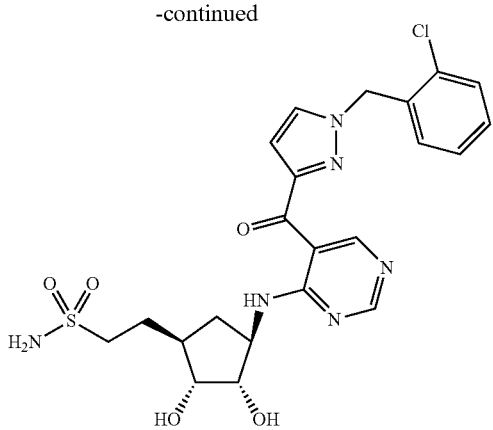

Step 1: tert-Butyl 3-[(4-{[(3aS,4R,6R,6aR)-6-(7,7-dimethyl-3,3-dioxido-5-oxo-2,6-dioxa-3lambda~6~-thia-4-azaoct-1-yl)-2,2-dimethyltetrahydro-3aH-cyclopenta[d][1,3]dioxol-4-yl]amino}pyrimidin-5-yl)carbonyl]-1H-pyrazole-1-carboxylate To a solution of tert-butyl 3-[(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)carbonyl]-1H-pyrazole-1-carboxylate (2.8 g, 6.0 mmol) in THF (40 mL) was added DIEA (1.8 g, 14 mmol). The solution was cooled to 0° C. and tert-butyl (chlorosulfonyl)carbamate (1.5 g, 6.9 mmol) was added. The resulting mixture was then stirred at 0° C. for 4 h. The reaction mixture was then concentrated and the crude product purified on silica gel to give tert-butyl 3-[(4-{[(3aS,4R,6R,6aR)-6-(7,7-dimethyl-3,3-dioxido-5-oxo-2,6-dioxa-3lambda~6~-thia-4-azaoct-1-yl)-2,2-dimethyltetrahydro-3aH-cyclopenta[d][1,3]dioxol-4-yl]amino}pyrimidin-5-yl)carbonyl]-1H-pyrazole-1-carboxylate (2.9 g, 75%). LCMS (AA): m/z=639 (M+H).

Step 2: [tert-Butyl ({[(3aR,4R,6R,6aS)-2,2-dimethyl-6-{[5-(1H-pyrazol-3-ylcarbonyl)pyrimidin-4-yl]amino}tetrahydro-3aH-cyclopenta[d][1,3]dioxol-4-yl]methoxy}sulfonyl)carbamate]

tert-Butyl 3-[(4-{[(3aS,4R,6R,6aR)-6-(7,7-dimethyl-3,3-dioxido-5-oxo-2,6-dioxa-3 lambda~-6~-thia-4-azaoct-1-yl)-2,2-dimethyltetrahydro-3 aH-cyclopenta[d][1,3]dioxol-4-yl]amino}pyrimidin-5-yl)carbonyl]-1H-pyrazole-1-carboxylate (2.9 g, 4.5 mmol) was dissolved in methanol (80 mL), and a solution of potassium phosphate (1.3 g, 6.0 mmol) in water (15 mL) was added. The reaction was allowed to stir at rt for 1 h. The reaction mixture was concentrated and purified by prep HPLC to provide [tert-butyl ({[(3aR,4R,6R,6aS)-2,2-dimethyl-6-{[5-(1H-pyrazol-3-ylcarbonyl)pyrimidin-4-yl]amino}tetrahydro-3 aH-cyclopenta[d][1,3]dioxol-4-yl]methoxy}sulfonyl)carbamate] (1.9 g, 77%). LCMS (AA): m/z=539 (M+H).

Step 3: ((1R,2R,3S,4R)-4-((5-(1-(2-chlorobenzyl)-1H-pyrazole-3-carbonyl)pyrimidin-4-yl)amino)-2,3-dihydroxycyclopentyl)methyl sulfamate I-193

To a 3-dram vial was added tert-butyl ({[(3aR,4R,6R,6aS)-2,2-dimethyl-6-{[5-(1H-pyrazol-3-ylcarbonyl)pyrimidin-4-yl]amino}tetrahydro-3H-cyclopenta[1,3]dioxol-4-yl]methoxy}sulfonyl) carbamate (0.022 g, 0.041 mmol), THF (1.5 mL), 2-chlorobenzyl bromide (0.017 g, 0.082 mmol) and cesium carbonate (0.13 g, 0.41 mmol). The reaction was shaken at rt for 6 h then filtered through a syringe pad to remove solids. To the crude THF solution was added TFA (3.0 mL) and water (0.2 mL). After the reaction was then stirred at rt for 4 h, solvent was completely evaporated. To the crude product was added DMSO (1.2 mL), potassium carbonate (0.07 g, 0.50 mmol) and water (3 drops). This mixture was shaken at rt for 1 h, filtered to remove solids then purified by prep HPLC to give ((1R,2R,3S,4R)-4-((5-(1-(2-chlorobenzyl)-1-pyrazole-3-carbonyl)pyrimidin-4-yl) amino)-2,3-dihydroxycyclopentyl)methyl sulfamate (6.0 mg, 27%). LCMS (AA): m/z=523 (M+H).

The compounds listed in the table below were prepared in a similar fashion to that described above starting from the listed starting materials used in step 3:

| Starting material | Compound No. | LCMS Data |
|---|---|---|
| Br–CH2–C6H4–OMe (3-methoxy) | I-325 | LCMS (FA): m/z = 519 (M + H). |
| Br–CH2–C6H4–CF3 (3-CF3) | I-119 | LCMS (FA): m/z = 557.6 (M + H). |
| Br–CH2CH2–O–CH2CH3 | I-28 | LCMS (FA): m/z = 471.5 (M + H). |
| Br–CH2–cyclopropyl | I-30 | LCMS (FA): m/z = 453.5 (M + H). |

-continued

| Starting material | Compound No. | LCMS Data |
|---|---|---|
| (2-bromoethyl-3-methylpyrazole) | I-4 | LCMS (FA): m/z = 507.5 (M + H). |
| (2-(bromomethyl)naphthalene) | I-103 | LCMS (FA): m/z = 539.6 (M + H). |
| (3-(bromomethyl)-5-methylisoxazole) | I-169 | LCMS (FA): m/z = 494.5 (M + H). |
| (1-(bromomethyl)-3-(trifluoromethoxy)benzene) | I-349 | LCMS (FA): m/z = 573.5 (M + H). |
| (1-(bromomethyl)-4-(trifluoromethoxy)benzene) | I-265 | LCMS (FA): m/z = 573.4 (M + H). |
| (1-(bromomethyl)-2-(trifluoromethyl)benzene) | I-182 | LCMS (FA): m/z = 557.5 (M + H). |
| (1-(bromomethyl)-2-(trifluoromethoxy)benzene) | I-98 | LCMS (FA): m/z = 573.5 (M + H). |
| (2-(bromomethyl)-1,3,5-trifluorobenzene) | I-88 | LCMS (FA): m/z = 543.6 (M + H). |
| (2-(bromomethyl)-1,4-difluorobenzene) | I-91 | LCMS (FA): m/z = 525.6 (M + H). |
| (4-(bromomethyl)-2-fluoro-1-methylbenzene) | I-198 | LCMS (FA): m/z = 521.6 (M + H). |

-continued
| Starting material | Compound No. | LCMS Data |
|---|---|---|
| 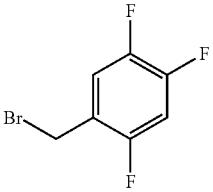 [SMILES: Fc1cc(F)c(CBr)cc1F] | I-314 | LCMS (FA): m/z = 543.6 (M + H). |
| 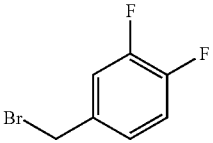 | I-190 | LCMS (FA): m/z = 525.6 (M + H). |
| 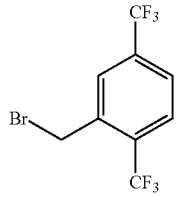 | I-267 | LCMS (FA): m/z = 625.6 (M + H). |
| 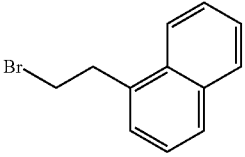 [SMILES: BrCCc1cccc2ccccc12] | I-118 | LCMS (FA): m/z = 553.6 (M + H). |
| 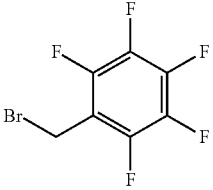 [SMILES: Fc1c(F)c(F)c(CBr)c(F)c1F] | I-318 | LCMS (FA): m/z = 579.6 (M + H). |
| 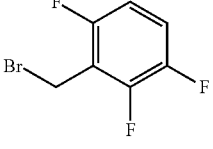 | I-225 | LCMS (FA): m/z = 543.6 (M + H). |
|  | I-249 | LCMS (FA): m/z = 514.6 (M + H). |
| 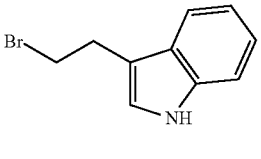 | I-33 | LCMS (FA): m/z = 541.5 (M + H). |
|  | I-146 | LCMS (FA): m/z = 541.5 (M + H). |

| Starting material | Compound No. | LCMS Data |
|---|---|---|
| 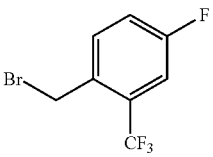 | I-121 | LCMS (FA): m/z = 575.6 (M + H). |
| 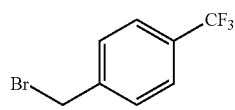 [SMILES: FC(F)(F)c1ccc(CBr)cc1] | I-167 | LCMS (FA): m/z = 557.6 (M + H). |
| 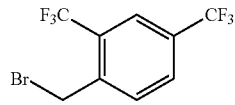 | I-266 | LCMS (FA): m/z = 625.6 (M + H). |
| 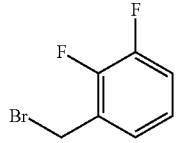 | I-327 | LCMS (FA): m/z = 525.6 (M + H). |
| 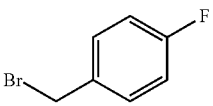 | I-106 | LCMS (FA): m/z = 507.6 (M + H). |
| 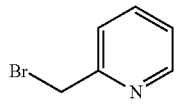 | I-150 | LCMS (FA): m/z = 490.6 (M + H). |
| 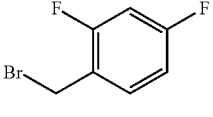 | I-336 | LCMS (FA): m/z = 525.6 (M + H). |
| 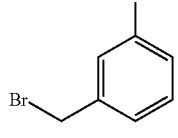 | I-123 | LCMS (FA): m/z = 507.6 (M + H). |
| 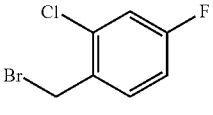 | I-194 | LCMS (FA): m/z = 541.5 (M + H). |
| 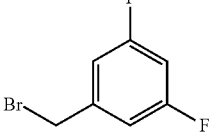 | I-269 | LCMS (FA): m/z = 525.6 (M + H). |
| 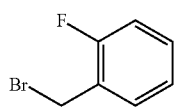 | I-338 | LCMS (FA): m/z = 507.6 (M + H). |

| Starting material | Compound No. | LCMS Data |
|---|---|---|
| 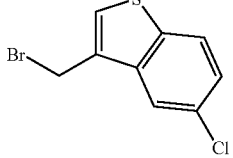 | I-285 | LCMS (FA): m/z = 579.5 (M + H). |
| 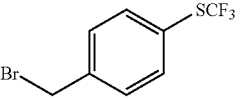 | I-259 | LCMS (FA): m/z = 589.5 (M + H). |
| 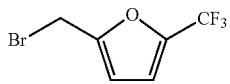 | I-130 | LCMS (FA): m/z = 547.6 (M + H). |
| 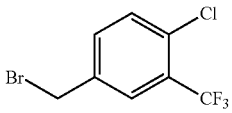 | I-34 | LCMS (FA): m/z = 591.6 (M + H). |
|  | I-230 | LCMS (FA): m/z = 575.5 (M + H). |
| 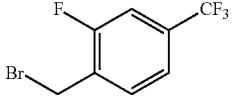 | I-112 | LCMS (FA): m/z = 541.5 (M + H). |
| 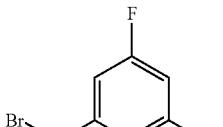 | I-258 | LCMS (FA): m/z = 575.5 (M + H). |
| 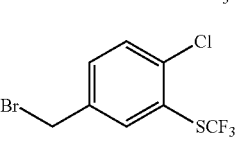 | I-126 | LCMS (FA): m/z = 623.5 (M + H). |
| 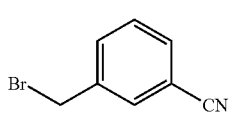 | I-25 | LCMS (FA): m/z = 514.6 (M + H). |
| 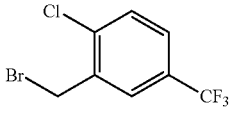 | I-268 | LCMS (FA): m/z = 591.5 (M + H). |
| 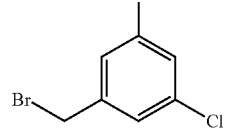 | I-334 | LCMS (FA): m/z = 541.5 (M + H). |
| 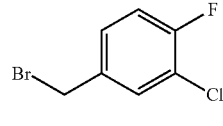 | I-89 | LCMS (FA): m/z = 541.5 (M + H). |

-continued
| Starting material | Compound No. | LCMS Data |
|---|---|---|
| 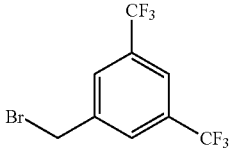 [SMILES: FC(F)(F)c1cc(CBr)cc(C(F)(F)F)c1] | I-155 | LCMS (FA): m/z = 625.5 (M + H). |
| 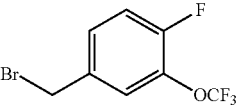 | I-134 | LCMS (FA): m/z = 591.6 (M + H). |
| 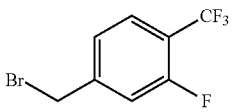 [SMILES: Fc1cc(CBr)ccc1C(F)(F)F] | I-146 | LCMS (FA): m/z = 575.5 (M + H). |
| 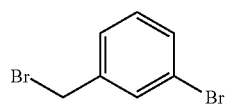 | I-240 | LCMS (FA): m/z = 567.5 (M + H). |
| 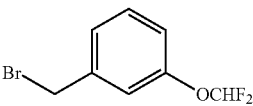 | I-256 | LCMS (FA): m/z = 555.6 (M + H). |
| 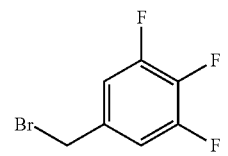 | I-326 | LCMS (FA): m/z = 543.5 (M + H). |
| 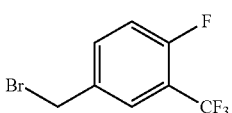 | I-343 | LCMS (FA): m/z = 575.5 (M + H). |
| 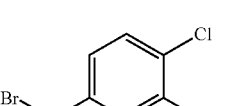 | I-100 | LCMS (FA): m/z = 607 (M + H). |
| 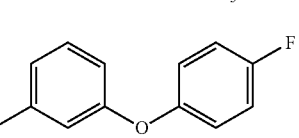 | I-229 | LCMS (FA): m/z = 599.4 (M + H). |
| 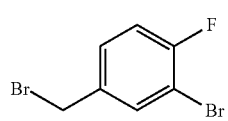 | I-290 | LCMS (FA): m/z = 585.3 (M + H). |
| 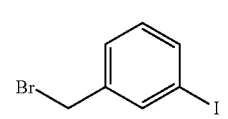 | I-221 | LCMS (FA): m/z = 615.3 (M + H). |
| 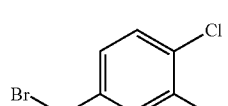 | I-204 | LCMS (FA): m/z = 601.2 (M + H). |

-continued
| Starting material | Compound No. | LCMS Data |
|---|---|---|
| 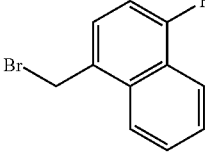 | I-273 | LCMS (FA): m/z = 557.3 (M + H). |
| 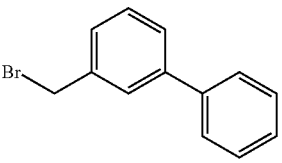 [SMILES: BrCc1cccc(-c2ccccc2)c1] | I-278 | LCMS (FA): m/z = 566 (M + H). |
Example 47: [(1R,2R,3S,4R)-2,3-Dihydroxy-4-({5-[(5-methyl-1-{[5-(trifluoromethyl)-2-furyl]methyl}-1H-pyrazol-3-yl)carbonyl]pyrimidin-4-yl}amino)cyclopentyl]methyl sulfamate I-138
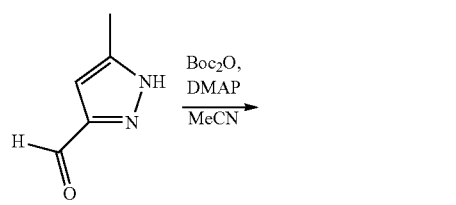
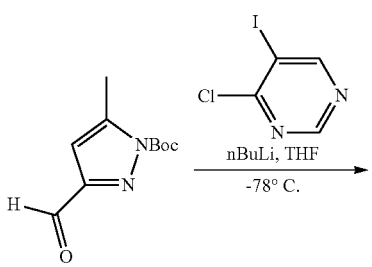
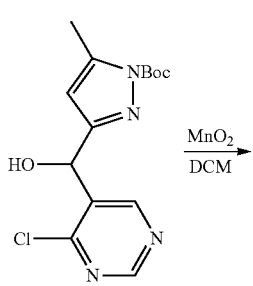
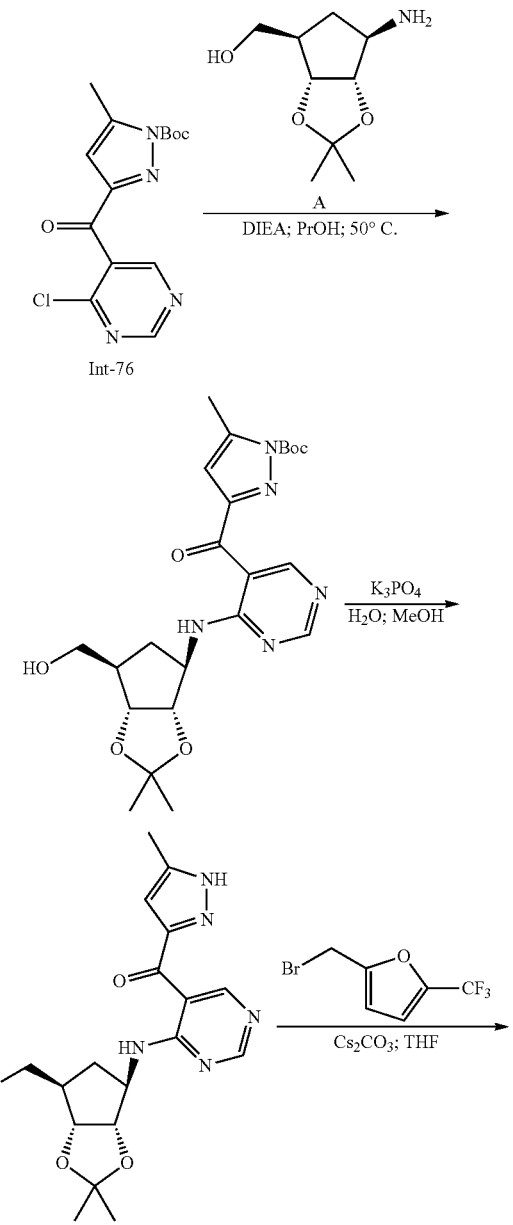

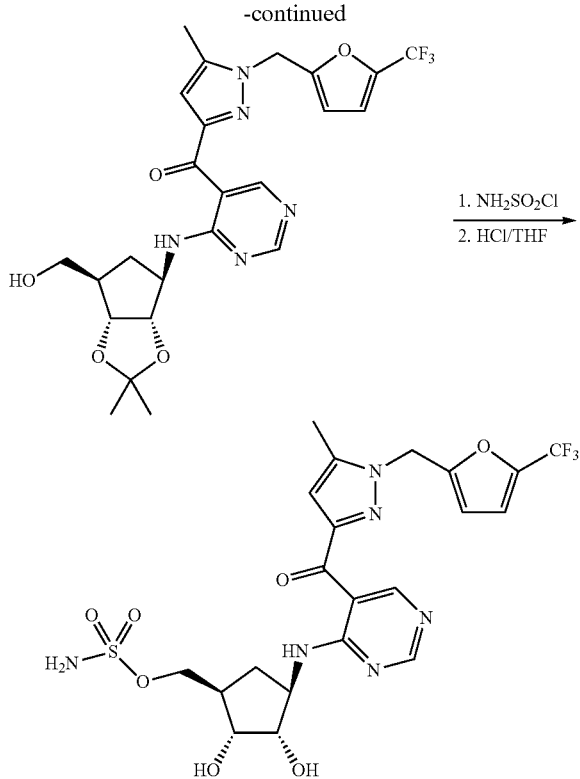

Step 1: tert-Butyl 3-formyl-5-methyl-1H-pyrazole-1-carboxylate

5-Methyl-1H-pyrazole-3-carbaldehyde (5.4 g, 49 mmol) was dissolved in acetonitrile (200 mL) and cooled to 0° C. with stirring. DMAP (0.60 g, 4.9 mmol) and di-tert-butyl-dicarbonate (12.9 g, 59 q mmol) were added and the solution was allowed to warm to rt and stir for 16 h. The reaction was diluted with EtOAc (200 mL). Then the mixture was washed with 1N HCl (aq.) (2×100 mL), saturated aq NaHCO$_3$ (2×100 mL), dried over magnesium sulfate, filtered and concentrated. The residue was purified on silica gel to give tert-butyl 3-formyl-5-methyl-1H-pyrazole-1-carboxylate (3.9 g, 38%) as a clear oil. $^1$H NMR (CDCl$_3$) δ 10.10 (s, 1H), 6.65 (s, 1H), 2.60 (s, 3H), 1.72 (s, 9H).

Step 2: tert-Butyl 3-[(4-chloropyrimidin-5-yl)(hydroxy)methyl]-5-methyl-1H-pyrazole-1-carboxylate Into a flame dried RBF with stirbar was added 4-chloro-5-iodopyrimidine (4.9 g, 20 mmol) dissolved in THF (40 mL). The flask was purged with argon and cooled to −78° C. To this solution was added dropwise n-butyllithium (2.5 M in hexane; 17.1 mL, 42.8 mmol) at −78° C. and the mixture was stirred for 30 min. To this mixture was added tert-butyl 3-formyl-5-methyl-1H-pyrazole-1-carboxylate (3.9 g, 18.6 mmol) dissolved in THF (15 mL) dropwise. The reaction was stirred at −78° C. for 2 h. The reaction was quenched with a solution of acetic acid (3.2 mL) in THF (10 mL). Water was added to the mixture and then extracted with EtOAc (3×). The combined organic layers were then washed with water and brine, dried over Na$_2$SO$_4$, filtered and concentrated. The crude product was purified on silica gel to give tert-butyl 3-[(4-chloropyrimidin-5-yl)(hydroxy) methyl]-5-methyl-1H-pyrazole-1-carboxylate (1.0 g, 16%). LCMS (FA): m/z=325.2 (M+H).

Step 3: tert-Butyl 3-[(4-chloropyrimidin-5-yl)carbonyl]-5-methyl-1H-pyrazole-1-carboxylate Int-76

To a solution of tert-butyl 3-[(4-chloropyrimidin-5-yl)(hydroxy)methyl]-5-methyl-1H-pyrazole-1-carboxylate (1.0 g, 3.0 mmol) in DCM (20 mL) was added manganese(IV) oxide (2.6 g, 30 mmol). The suspension was stirred for 19 h at rt. The reaction was then filtered through a celite pad and the residual solid was washed with DCM several times. The filtrate was then concentrated in vacuo and the residue was purified on silica gel to afford tert-butyl 3-[(4-chloropyrimidin-5-yl)carbonyl]-1H-pyrrole-1-carboxylate (0.81 g, 83%). LCMS (FA): m/z=323.3 (M+H).

Step 4: tert-Butyl 3-[(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)carbonyl]-5-methyl-1H-pyrazole-1-carboxylate A (0.069 g, 0.31 mmol) and tert-butyl 3-[(4-chloropyrimidin-5-yl)carbonyl]-5-methyl-1H-pyrazole-1-carboxylate (0.090 g, 0.28 mmol) were weighed into a 20 mL reaction vessel. To this mixture was added 1-propanol (4 mL) and DIEA (0.10 mL, 0.56 mmol). The resulting mixture was sealed and the vessel allowed to stir while heating at 50° C. for 3 h. The reaction was then cooled to rt and the reaction was concentrated. The crude product was purified on silica gel to afford tert-butyl 3-[(4-{[(3 aS,4R,6R,6aR)-6-(hydroxymethyl)-2,2-dimethyltetrahydro-3aH-cyclopenta[d][1,3]dioxol-4-yl]amino}pyrimidin-5-yl)carbonyl]-5-methyl-1H-pyrazole-1-carboxylate (0.13 g, 98%). LCMS (FA): m/z=474 (M+H).

Step 5: (4-{[(3aS,4R,6R,6aR)-6-(Hydroxymethyl)-2,2-dimethyltetrahydro-3aH-cyclopenta[d][1,3]dioxol-4-yl]amino}pyrimidin-5-yl)(5-methyl-1H-pyrazol-3-yl)methanone tert-Butyl 3-[(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)carbonyl]-5-methyl-1H-pyrazole-1-carboxylate (0.13 g, 0.27 mmol) was dissolved in methanol (2 mL) and a solution of potassium phosphate (29 mg, 0.14 mmol) in water (0.20 mL) was added. It was allowed to stir at rt for 15 h. Then, the reaction was concentrated and diluted with EtOAc and water. The aqueous layer was extracted with EtOAc (3×). The combined organic layers were dried over MgSO$_4$, filtered, and concentrated to yield (4-{[(3 aS,4R,6R,6aR)-6-(hydroxymethyl)-2,2-dimethyltetrahydro-3 aH-cyclopenta[d][1,3]dioxol-4-yl] amino}pyrimidin-5-yl)(5-methyl-1H-pyrazol-3-yl)methanone (91 mg, 89%). LCMS (FA): m/z=374 (M+H).

Step 6: (4-{[(3aS,4R,6R,6aR)-6-(Hydroxymethyl)-2,2-dimethyltetrahydro-3aH-cyclopenta[d][1,3]dioxol-4-yl]amino}pyrimidin-5-yl)(5-methyl-1-{[5-(trifluoromethyl)-2-furyl]methyl}-1H-pyrazol-3-yl)methanone (4-{[(3 aS,4R,6R,6aR)-6-(Hydroxymethyl)-2,2-dimethyltetrahydro-3 aH-cyclopenta[d][1,3]dioxol-4-yl] amino}pyrimidin-5-yl)(5-methyl-1H-pyrazol-3-yl)methanone (90 mg, 0.24 mmol) was dissolved in THF (10 mL). To this solution was added cesium carbonate (0.16 g, 0.48 mmol) and 2-(bromomethyl)-5-(trifluoromethyl)furan (0.063 g, 0.28 mmol) and the reaction was stirred at rt for 45 h. The reaction was then quenched by addition of water and the mixture extracted with EtOAc (3×). The combined organic layers were washed with brine, dried over MgSO$_4$, filtered, and concentrated. The residue was purified on silica gel to give (4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)(5-methyl-1-{[5-(trifluoromethyl)-2-furyl]methyl}-1H-pyrazol-3-yl)methanone (110 mg, 88%). LCMS (FA): m/z=523 (M+H).

Step 7: [(1R,2R,3S,4R)-2,3-Dihydroxy-4-({5-[(5-methyl-1-{[5-(trifluoromethyl)-2-furyl]methyl}-1H-pyrazol-3-yl)carbonyl]pyrimidin-4-yl}amino)cyclopentyl]methyl sulfamate I-138

To a solution of (4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)(5-methyl-1-{[5-(trifluoromethyl)-2-furyl]methyl}-1H-pyrazol-3-yl)methanone (0.11 g, 0.21 mmol) and TEA (0.09 mL, 0.63 mmol) in DMF (3.3 mL) was added chlorosulfonamide (61 mg, 0.53 mmol) at rt, and the mixture was stirred for 1 h. The reaction was quenched by addition of a saturated solution of NaHCO$_3$ and diluted with water. The mixture was extracted with EtOAc (4×). The combined organic layers were dried over MgSO$_4$, filtered, and concentrated. The crude sulfamate intermediate was dissolved in THF (3.1 mL). Water (3.1 mL) and conc. HCl (0.54 mL, 6.5 mmol) was added to the solution. The reaction was stirred for 4 h at rt. The reaction was quenched by the addition of a saturated solution of NaHCO$_3$ and extracted with EtOAc (4×). The combined organic layers were dried over MgSO$_4$, filtered, and concentrated. The residue was triturated with DCM and filtered to afford [(1R,2R,3S,4R)-2,3-dihydroxy-4-({5-[(5-methyl-1-{[5-(trifluoromethyl)-2-furyl]methyl}-1H-pyrazol-3-yl)carbonyl]pyrimidin-4-yl}amino)cyclopentyl]methyl sulfamate (65 mg, 54%). $^1$H NMR (DMSO) δ 9.45 (s, 1H), 9.09 (d, J=7.4 Hz, 1H), 8.62 (s, 1H), 7.46 (s, 2H), 7.23 (s, 1H), 6.71 (s, 2H), 5.61 (s, 2H), 4.93 (d, J=5.8 Hz, 1H), 4.75 (d, J=4.5 Hz, 1H), 4.53-4.39 (m, 1H), 4.14-4.04 (m, 1H), 4.04-3.93 (m, 1H), 3.85-3.76 (m, 1H), 3.76-3.65 (m, 1H), 2.40 (s, 3H), 2.37-2.26 (m, 1H), 2.26-2.14 (m, 1H), 1.23-1.05 (m, 1H); LCMS (AA): m/z=561.4 (M+H).

Example 48: N-({(1R,2R,3S,4R)-4-[((5-{[1-(3-Chlorobenzyl)-1H-pyrazol-3-yl]carbonyl}pyrimidin-4-yl)amino]-2,3-dihydroxycyclopentyl}methyl)sulfuric diamide I-136

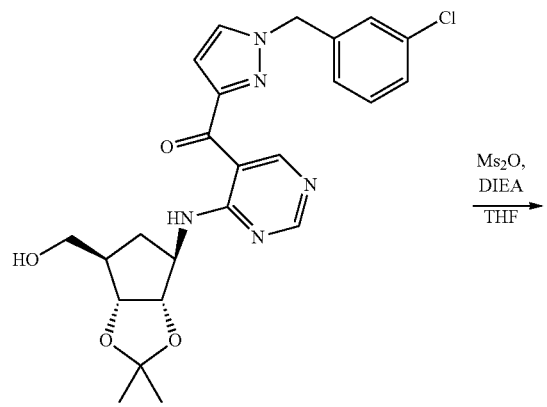

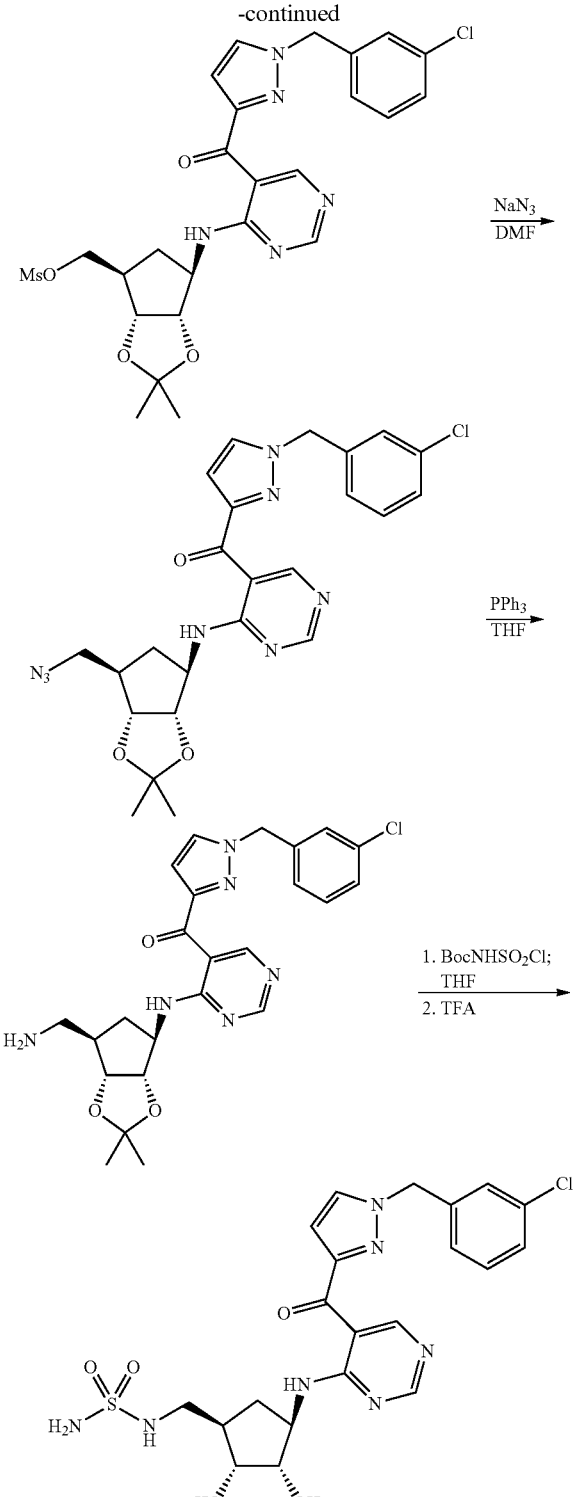

Step 1: {(3aR,4R,6R,6aS)-6-[(5-{[1-(3-Chlorobenzyl)-1H-pyrazol-3-yl]carbonyl}pyrimidin-4-yl)amino]-2,2-dimethyltetrahydro-3aH-cyclopenta[d][1,3]dioxol-4-yl}methyl methanesulfonate

[1-(3-Chlorobenzyl)-1H-pyrazol-3-yl](4-{[(3 aS,4R,6R,6aR)-6-(hydroxymethyl)-2,2-dimethyltetrahydro-3aH-cyclopenta[d][1,3]dioxol-4-yl]amino}pyrimidin-5-yl)methanone (see example 41 for synthesis) (0.26 g, 0.55 mmol) was dissolved in THF (15 mL). DIEA (0.28 g, 2.2 mmol) and methanesulfonic anhydride (0.19 g, 1.1 mmol) were then added and the reaction mixture was allowed to stir at rt for 30 min. DCM (50 mL) was added and the mixture was washed with water (2x). The organic layer was dried over MgSO$_4$, filtered, and concentrated to yield {(3aR,4R,6R,6aS)-6-[(5-{[1-(3-chlorobenzyl)-1H-pyrazol-3-yl]carbonyl}pyrimidin-4-yl)amino]-2,2-dimethyltetrahydro-3 aH-cyclopenta[d][1,3]dioxol-4-yl}methyl methanesulfonate (0.30 g, 97%). LCMS (AA): m/z=561 (M+H).

Step 2: (4-{[(3aS,4R,6R,6aR)-6-(Azidomethyl)-2,2-dimethyltetrahydro-3aH-cyclopenta[d][1,3]dioxol-4-yl]amino}pyrimidin-5-yl)[1-(3-chlorobenzyl)-1H-pyrazol-3-yl]methanone {(3aR,4R,6R,6aS)-6-[(5-{[1-(3-Chlorobenzyl)-1H-pyrazol-3-yl]carbonyl}pyrimidin-4-yl)amino]-2,2-dimethyltetrahydro-3aH-cyclopenta[d][1,3]dioxol-4-yl}methyl methanesulfonate (0.30 g, 0.54 mmol) was dissolved in DMF (10 mL). Sodium azide (0.14 g, 2.1 mmol) was added and the reaction mixture was allowed to stir at 40° C. for 16 h. Water (60 mL) was added and the mixture was extracted with DCM (2x). The organic layer was concentrated and purified on silica gel to afford (4-{[(3aS,4R,6R,6aR)-6-(azidomethyl)-2,2-dimethyltetrahydro-3aH-cyclopenta[d][1,3]dioxol-4-yl]amino}pyrimidin-5-yl)[1-(3-chlorobenzyl)-1H-pyrazol-3-yl]methanone. The eluent was 40-90% EtOAc in hexane (0.17 g, 63%). LCMS (AA): m/z=509 (M+H).

Step 3: (4-{[(3aS,4R,6R,6aR)-6-(Aminomethyl)-2,2-dimethyltetrahydro-3aH-cyclopenta[d][1,3]dioxol-4-yl]amino}pyrimidin-5-yl)[1-(3-chlorobenzyl)-1H-pyrazol-3-yl]methanone (4-{[(3aS,4R,6R,6aR)-6-(Azidomethyl)-2,2-dimethyltetrahydro-3 aH-cyclopenta[d][1,3]dioxol-4-yl] amino}pyrimidin-5-yl)[1-(3-chlorobenzyl)-1H-pyrazol-3-yl]methanone (0.17 g, 0.34 mmol) was dissolved in a solution of THF (15 mL) and water (1.0 mL). Triphenylphosphine (0.18 g, 0.68 mmol) was added and the solution was stirred at rt for 3 days. The reaction solvent was evaporated in vacuo and the crude material was purified on silica gel to give (4-{[(3aS,4R,6R,6aR)-6-(azidomethyl)-2, 2-dimethyltetrahydro-3 aH-cyclopenta[d][1,3]dioxol-4-yl] amino}pyrimidin-5-yl)[1-(3-chlorobenzyl)-1H-pyrazol-3-yl]methanone (0.12 g, 74%). LCMS (AA): m/z=483 (M+H).

Step 4: N-({(1R,2R,3S,4R)-4-[(5-{[1-(3-Chlorobenzyl)-1H-pyrazol-3-yl]carbonyl}pyrimidin-4-yl)amino]-2,3-dihydroxycyclopentyl}methyl)sulfuric diamide I-136

(4-{[(3aS,4R,6R,6aR)-6-(Aminomethyl)-2,2-dimethyltetrahydro-3aH-cyclopenta[d][1,3]dioxol-4-yl]amino}pyrimidin-5-yl)[1-(3-chlorobenzyl)-1H-pyrazol-3-yl]methanone (0.12 g, 0.25 mmol) was dissolved in THF (20 mL). DIEA (0.10 g, 0.76 mmol) and tert-butyl (chlorosulfonyl)carbamate (0.11 g, 0.51 mmol) were then added to the solution at rt. The reaction mixture was allowed to stir at rt for 30 min. The reaction mixture was concentrated and purified on silica gel to give the Boc-protected intermediate [52 mg, 66%; LCMS (AA): m/z=662 (M+H).] which was then dissolved in a solution of TFA (7.2 mL) and water (0.80 mL). It was allowed to stir at rt for 30 min. Solvent was then evaporated and the residue was dissolved in methanol (5 mL). TEA (0.5 mL) was added to neutralize the solution and the resulting mixture was concentrated and subsequently dissolved in EtOAc (20 mL). This mixture was washed with water (2x). The organic layer was concentrated to yield N-({(1R,2R,3S,4R)-4-[(5-{[1-(3-chlorobenzyl)-1H-pyrazol-3-yl]carbonyl}pyrimidin-4-yl}amino]-2,3-dihydroxycyclopentyl)methyl)sulfuric diamide (0.025 g, 61%). $^1$H NMR (MeOD) δ 9.64 (s, 1H), 8.58 (s, 1H), 7.86 (d, J=2.4 Hz, 1H), 7.44-7.29 (m, 3H), 7.29-7.20 (m, 1H), 6.98 (d, J=2.4 Hz, 1H), 5.49 (s, 2H), 4.58 (dd, J=15.3, 8.2 Hz, 1H), 4.00-3.93 (m, 1H), 3.90 (t, J=5.3 Hz, 1H), 3.28-3.17 (m, 1H), 3.10 (dd, J=12.8, 7.2 Hz, 1H), 2.52 (dt, J=13.3, 8.3 Hz, 1H), 2.32-2.16 (m, 1H), 1.31-1.25 (m, 1H). LCMS (AA): m/z=522.2 (M+H).

Example 49: [(1R,2R,3R,4R)-4-({5-[(1-Benzyl-1H-pyrazol-3-yl)carbonyl]pyrimidin-4-yl}amino)-2,3-dihydroxycyclopentyl]methyl sulfamate I-135

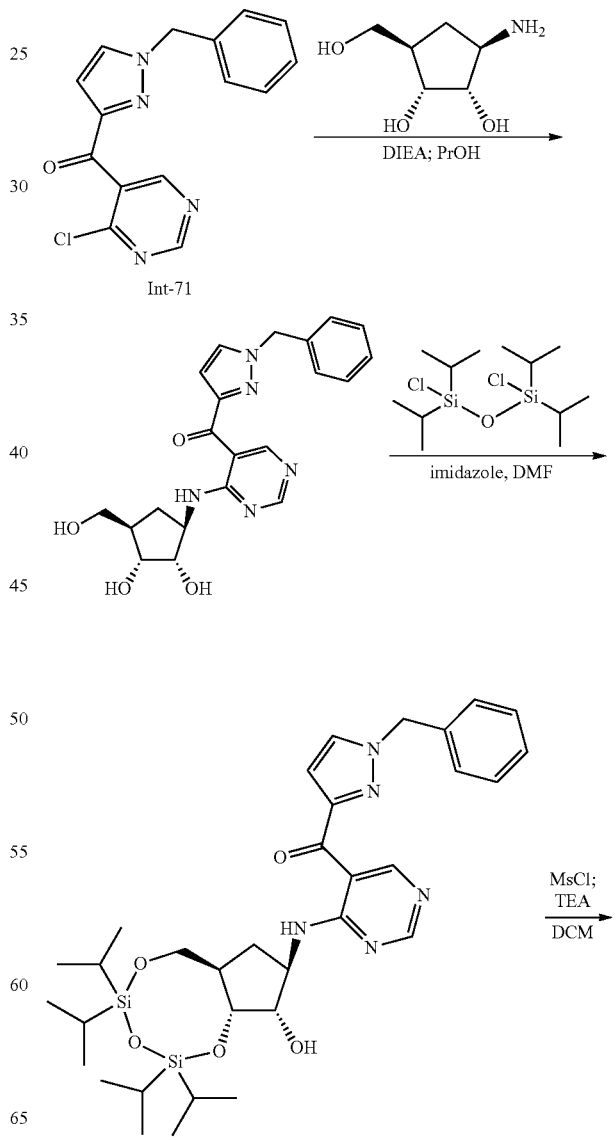

251
-continued

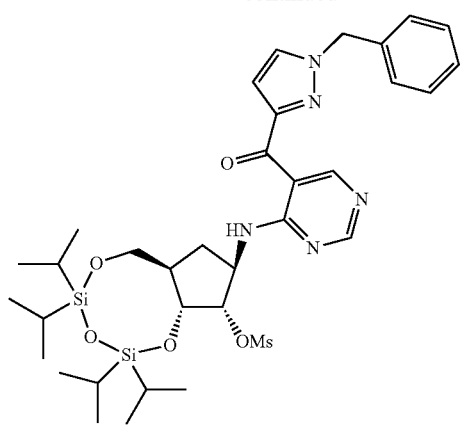

Cs₂OAc
benzene

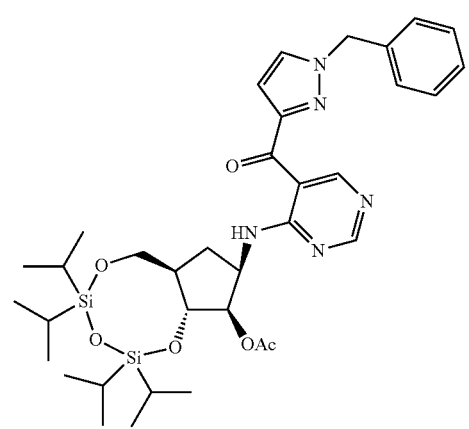

K₂CO₃
MeOH

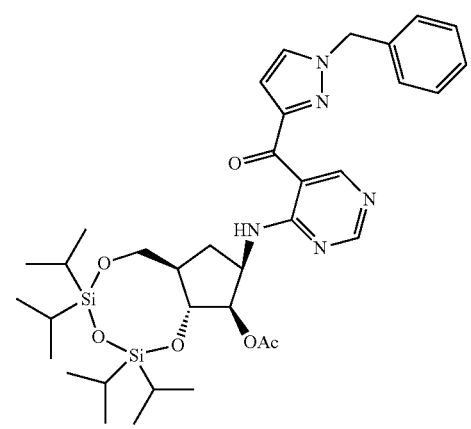

TBAF
THF

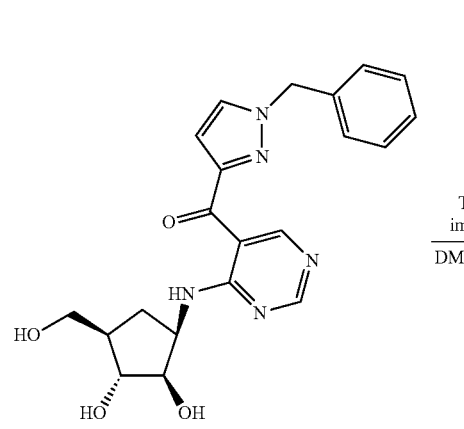

TBSCl,
imidazole
—————
DMAP; DMF

252
-continued

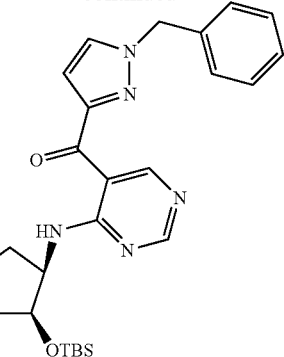

1% HCl/
EtOH

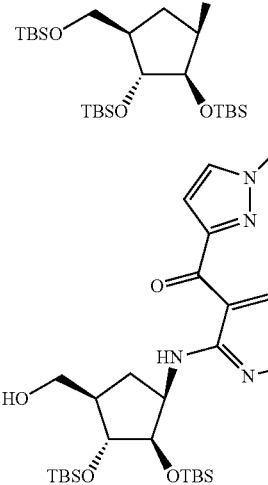

1. SO₂NH₂Cl;
DMF 2. 3M HCl;
THF

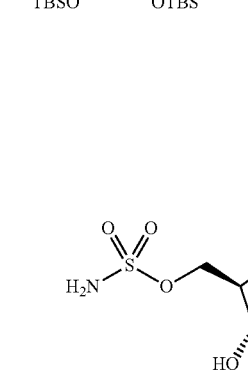

Step 1: (1-Benzyl-1H-pyrazol-3-yl)(4-{[(1R,2S,3R,4R)-2,3-dihydroxy-4-(hydroxymethyl)cyclopentyl]amino}pyrimidin-5-yl)methanone (1-Benzyl-1H-pyrazol-3-yl)(4-chloropyrimidin-5-yl)methanone (1.00 g, 3.35 mmol) and (1R,2S,3R,5R)-3-amino-5-(hydroxymethyl)cyclopentane-1,2-diol hydrochloride (0.68 g, 3.68 mmol) were weighed into a 250 ml RBF fitted with a reflux condenser. To this mixture was added 1-propanol (48 mL) and DIEA (1.75 mL, 10.0 mmol). The resulting mixture was stirred at 50° C. for 18 h. The reaction was allowed to cool to rt and the solution was concentrated. The residue was purified on silica gel to yield (1-benzyl-1H-pyrazol-3-yl)(4-{[(1R,2S,3R,4R)-2,3-dihydroxy-4-(hydroxymethyl)cyclopentyl]amino}pyrimidin-5-yl)methanone (1.3 g, 100%).

Step 2: (1-Benzyl-1H-pyrazol-3-yl)(4-{[(6aR,8R,9S,9aR)-9-hydroxy-2,2,4,4-tetraisopropylhexahydrocyclopenta[f][1,3,5,2,4]trioxadisilocin-8-yl]amino}pyrimidin-5-yl)methanone A 100 mL RBF under nitrogen was charged with (1-benzyl-1H-pyrazol-3-yl)(4-{[(1R,2S,3R,4R)-2,3-dihydroxy-4-

(hydroxymethyl)cyclopentyl]amino}pyrimidin-5-yl)methanone (1.3 g, 3.2 mmol), DMF (13 mL), and imidazole (0.87 g, 12.7 mmol). A solution of 1,3-dichloro-1,1,3,3-tetraisopropyldisiloxane (1.1 mL, 3.5 mmol) in DMF (10 mL) was added dropwise over 1 h. The resulting mixture was allowed to stir at rt overnight. After 16 h reaction was poured into a saturated NaHCO$_3$ solution and the mixture was extracted with EtOAc (3×). The combined organic portions were washed with brine, dried over MgSO$_4$, filtered, and concentrated. The crude product was purified on silica gel to give (1-benzyl-1H-pyrazol-3-yl)(4-{[(6aR,8R,9S,9aR)-9-hydroxy-2,2,4,4-tetraisopropylhexahydrocyclopenta[f][1,3,5,2,4]trioxadisilocin-8-yl]amino}pyrimidin-5-yl)methanone (1.9 g, 92%). LCMS (FA): m/z=652 (M+H).

Step 3: (6aR,8R,9S,9aR)-8-({5-[(1-Benzyl-1H-pyrazol-3-yl)carbonyl]pyrimidin-4-yl}amino)-2,2,4,4-tetraisopropylhexahydrocyclopenta[f][1,3,5,2,4]trioxadisilocin-9-yl methanesulfonate A 500 mL RBF under nitrogen was charged with (1-benzyl-1H-pyrazol-3-yl)(4-{[(6aR,8R,9S,9aR)-9-hydroxy-2,2,4,4-tetraisopropylhexahydrocyclopenta[f][1,3,5,2,4]trioxadisilocin-8-yl]amino}pyrimidin-5-yl)methanone (1.8 g, 2.8 mmol), DCM (8 mL), TEA (0.42 mL, 3.0 mmol) and DMAP (0.37 g, 3.0 mmol). The reaction was cooled in an ice bath and a solution of methanesulfonyl chloride (0.24 mL, 3.0 mmol) in DCM (6 mL) was added dropwise. The reaction was then allowed to slowly warm to rt and stir overnight. After stirring 15 h, the reaction was quenched by the addition of water. The mixture was extracted with EtOAc (3×). The combined organic layers were dried over MgSO$_4$, filtered, and concentrated to give (6aR,8R,9S,9aR)-8-({5-[(1-benzyl-1H-pyrazol-3-yl)carbonyl]pyrimidin-4-yl}amino)-2,2,4,4-tetraisopropylhexahydrocyclopenta[f][1,3,5,2,4]trioxadisilocin-9-yl methanesulfonate (2 g, 100%). LCMS (FA): m/z=731 (M+H).

Step 4: (6aR,8R,9R,9aR)-8-({5-[(1-Benzyl-1H-pyrazol-3-yl)carbonyl]pyrimidin-4-yl}amino)-2,2,4,4-tetraisopropylhexahydrocyclopenta[f][1,3,5,2,4]trioxadisilocin-9-yl acetate A 500 mL RBF under nitrogen was charged with (6aR,8R,9S,9aR)-8-({5-[(1-benzyl-1H-pyrazol-3-yl)carbonyl]pyrimidin-4-yl}amino)-2,2,4,4-tetraisopropylhexahydrocyclopenta[f][1,3,5,2,4]trioxadisilocin-9-yl methanesulfonate (1.1 g, 1.5 mmol), benzene (20 mL), 1,4,7,10,13,16-hexaoxacyclooctadecane (0.21 g, 0.78 mmol), and cesium acetate (0.91 g, 4.7 mmol). The reaction was then heated at 80° C. while stirring. After 7 h, additional cesium acetate (0.91 g, 4.7 mmol) was added and the reaction continued to stir overnight at 80° C. LCMS then showed a mixture of desired product, starting material and more polar byproducts. The reaction was subsequently quenched by the addition of water then extracted with EtOAc (3×). The combined extracts were concentrated and the crude material purified on silica gel to provide (6aR,8R,9R,9aR)-8-({5-[(1-benzyl-1H-pyrazol-3-yl)carbonyl]pyrimidin-4-yl}amino)-2,2,4,4-tetraisopropylhexahydrocyclopenta[f][1,3,5,2,4]trioxadisilocin-9-yl acetate (0.25 g, 24%). LCMS (FA): m/z=694 (M+H).

Step 5: (1-Benzyl-1H-pyrazol-3-yl)(4-{[(6aR,8R,9R,9aR)-9-hydroxy-2,2,4,4-tetraisopropylhexahydrocyclopenta[f][1,3,5,2,4]trioxadisilocin-8-yl]amino}pyrimidin-5-yl)methanone (6aR,8R,9R,9aR)-8-({5-[(1-Benzyl-1H-pyrazol-3-yl)carbonyl]pyrimidin-4-yl}amino)-2,2,4,4-tetraisopropylhexahydrocyclopenta[f][1,3,5,2,4]trioxadisilocin-9-yl acetate (0.15 g, 0.22 mmol), methanol (7 mL), and potassium carbonate (90 mg, 0.6 mmol) were stirred in a 20 mL scintillation vial at rt for 20 h. The reaction mixture was then concentrated and a solution of saturated sodium bicarbonate (aq.) (20 mL) was added. The resulting mixture was extracted with EtOAc (3×). The combined organic layers were dried over MgSO$_4$, filtered, and concentrated to yield (1-benzyl-1H-pyrazol-3-yl)(4-{[(6aR,8R,9R,9aR)-9-hydroxy-2,2,4,4-tetraisopropylhexahydrocyclopenta[f][1,3,5,2,4]trioxadisilocin-8-yl]amino}pyrimidin-5-yl)methanone (0.14 g, 99%). LCMS (FA): m/z=652 (M+H).

Step 6: (1-Benzyl-1H-pyrazol-3-yl)(4-{[(1R,2R,3R,4R)-2,3-dihydroxy-4-(hydroxymethyl)cyclopentyl]amino}pyrimidin-5-yl)methanone (1-Benzyl-1H-pyrazol-3-yl)(4-{[(6aR,8R,9R,9aR)-9-hydroxy-2,2,4,4-tetraisopropylhexahydrocyclopenta[f][1,3,5,2,4]trioxadisilocin-8-yl]amino}pyrimidin-5-yl)methanone (0.36 g, 0.55 mmol) was dissolved in THF (5 mL). TBAF (1.0 M solution in THF; 0.58 mL, 0.58 mmol) was added and the solution was allowed to stir at rt. After stirring for 1 h, additional TBAF (1.0 M solution in THF; 0.2 mL, 0.2 mmol) was added and the reaction stirred an additional 4 h. The reaction mixture was concentrated and purified on silica gel to afford (1-benzyl-1H-pyrazol-3-yl)(4-{[(1R,2R,3R,4R)-2,3-dihydroxy-4-(hydroxymethyl)cyclopentyl]amino}pyrimidin-5-yl)methanone (0.19 g, 84%). LCMS (FA): m/z=410 (M+H).

Step 7: (1-Benzyl-1H-pyrazol-3-yl)(4-{[(1R,2R,3R,4R)-2,3-bis{[tert-butyl(dimethyl)silyl]oxy}-4-({[tert-butyl(dimethyl)silyl]oxy}methyl)cyclopentyl]amino}pyrimidin-5-yl)methanone To a solution of (1-benzyl-1H-pyrazol-3-yl)(4-{[(1R,2R,3R,4R)-2,3-dihydroxy-4-(hydroxymethyl)cyclopentyl]amino}pyrimidin-5-yl)methanone (0.19 g, 0.45 mmol) in DMF (8.0 mL) was added imidazole (0.22 g, 3.2 mmol) and DMAP (0.0055 g, 0.045 mmol) followed by tert-butyldimethylsilyl chloride (0.34 g, 2.3 mmol) at rt, and the mixture was stirred for 3 days. Additional Imidazole (0.092 g, 1.4 mmol) and tert-butyldimethylsilyl chloride (0.14 g, 0.90 mmol) were added and the reaction was allowed to continue to stir at rt. After 5 h, TLC and LCMS showed no starting material, but a mixture of the bis-silylated and tris-silylated desired products. The reaction was quenched by addition of water and extracted with EtOAc (3×). The combined organic layers were dried over MgSO$_4$, filtered, and concentrated in vacuo. The residue was purified on silica gel to give 1-benzyl-1H-pyrazol-3-yl)(4-{[(1R,2R,3R,4R)-2R,3R,4R)-2,3-bis {[tert-butyl(dimethyl)silyl]oxy}-4-({[tert-butyl(dimethyl)silyl]oxy}methyl)cyclopentyl]amino}pyrimidin-5-yl) methanone (0.090 g, 26%). LCMS (FA): m/z=752 (M+H).

Step 8: (1-Benzyl-1H-pyrazol-3-yl)(4-{[(1R,2R,3R,4R)-2,3-bis{[tert-butyl(dimethyl)silyl]oxy}-4-(hydroxymethyl)cyclopentyl]amino}pyrimidin-5-yl)methanone To a solution of 1-benzyl-1H-pyrazol-3-yl)(4-{[(1R,2R,3R,4R)-2,3-bis {[tert-butyl(dimethyl)silyl]oxy}-4-({[tert-butyl(dimethyl)silyl]oxy}methyl)cyclopentyl] amino}pyrimidin-5-yl)methanone (0.090 g, 0.12 mmol) in EtOH (3.0 mL) was added a solution of 1% HCl in EtOH (3.0 mL, 0.36 mmol) at rt. The reaction mixture was sealed and placed in a refrigerator (4° C.) for 2 h then moved to a −20° C. freezer for 60 h. The reaction was then quenched by the addition of aq. saturated NaHCO₃ (10 mL). To the residue was added water (20 mL) and it was extracted with EtOAc (4×). The combined organic layers were dried over MgSO₄, filtered, and concentrated. The residue was purified on silica gel to yield (1-benzyl-1H-pyrazol-3-yl)(4-{[(1R, 2R,3R,4R)-2,3-bis{[tert-butyl(dimethyl)silyl]oxy}-4-(hydroxymethyl)cyclopentyl]amino}pyrimidin-5-yl)methanone (0.06 g, 79%).

Step 9: [(1R,2R,3R,4R)-4-({5-[(1-Benzyl-1H-pyrazol-3-yl)carbonyl]pyrimidin-4-yl}amino)-2,3-dihydroxycyclopentyl]methyl sulfamate I-135

To a solution of (1-benzyl-1H-pyrazol-3-yl)(4-{[(1R,2R, 3R,4R)-2,3-bis {[tert-butyl(dimethyl)silyl]oxy}-4-(hydroxymethyl)cyclopentyl]amino}pyrimidin-5-yl)methanone (0.060 g, 0.094 mmol) in DMF (1.5 mL) and TEA (0.079 mL, 0.56 mmol) was added chlorosulfonamide (0.049 g, 0.42 mmol) at rt, and the mixture was allowed to stir for 1 h. Additional chlorosulfonamide (0.025 g, 0.21 mmol) was then added and the reaction stirred at rt an additional 1 h. The reaction was quenched with sat NaHCO₃, and then extracted with EtOAc (4×). The combined organic layers were dried over MgSO₄, filtered and concentrated to give the crude sulfamate intermediate which was immediately dissolved in THF (4 mL). HCl (3.0 M solution in water; 1 mL, 3 mmol) was added to the solution. The reaction flask was fitted with a reflux condenser and the reaction stirred at 60° C. for 7 h. The reaction was then quenched with sat NaHCO₃, and then extracted with EtOAc (4×). The combined organic layers were dried over MgSO₄, filtered and concentrated. The crude product was triturated with DCM and collected as a white solid to provide [(1R, 2R,3R,4R)-4-({5-[(1-benzyl-1H-pyrazol-3-yl)carbonyl]pyrimidin-4-yl}amino)-2,3-dihydroxycyclopentyl]methyl sulfamate (40 mg, 61%). ¹H NMR (DMSO) δ 9.50 (s, 1H), 9.39 (d, J=7.5 Hz, 1H), 8.62 (s, 1H), 8.07 (d, J=2.4 Hz, 1H), 7.43 (s, 2H), 7.41-7.27 (m, 5H), 6.91 (d, J=2.4 Hz, 1H), 5.59 (d, J=4.4 Hz, 1H), 5.51 (s, 2H), 5.12 (d, J=4.7 Hz, 1H), 4.67-4.53 (m, 1H), 4.13 (dd, J=9.4, 6.5 Hz, 1H), 4.01-3.92 (m, 1H), 3.87-3.79 (m, 1H), 3.66 (dd, J=6.7, 4.4 Hz, 1H), 2.38-2.28 (m, 1H), 2.14-2.03 (m, 1H), 1.40-1.25 (m, 1H). LCMS (FA): m/z=489 (M+H).

Example 50: {(1R,2S,4R)-4-Amino-2-[(triisopropylsilyl)oxy]cyclopentyl}methanol.CF₃CO₂H Int-79

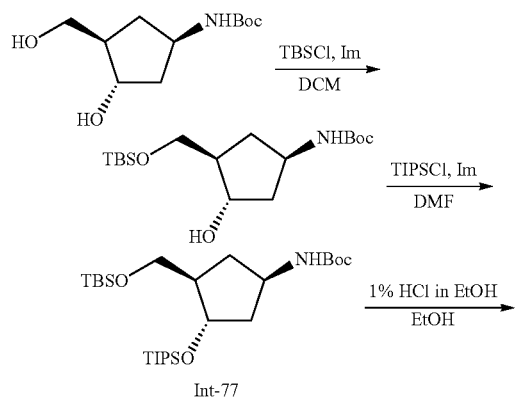

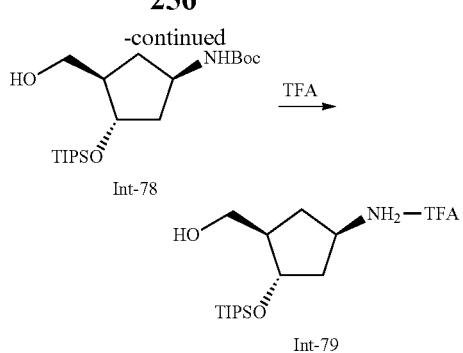

Step 1: tert-Butyl [(1R,3R,4S)-3-({[tert-butyl(dimethyl)silyl]oxy}methyl)-4-hydroxycyclopentyl]carbamate A solution of tert-butyl [(1R,3S,4R)-3-hydroxy-4-(hydroxymethyl)cyclopentyl]carbamate (4.0 g, 17 mmol) (for synthesis of starting material see: Ober, M. et. al. J. Am. Chem. Soc. 2005, 127, 18143-18149.) and imidazole (1.4 g, 21 mmol) in DMF (40 mL) was diluted with DCM (200 mL) and cooled in an ice/water bath. tert-Butyldimethylsilylchloride (2.9 g, 19 mmol) was added as a solution in DCM (40 mL). The reaction was allowed to warm to ambient temperature and stirred overnight. The reaction was quenched by addition of water (150 mL) and the mixture was transferred to separatory funnel. The organic layer was collected and the residual water layer was extracted with DCM (150 mL×2). The combined organic layers were dried over Na₂SO₄, filtered, and concentrated. The residue was purified on silica gel to provide tert-butyl [(1R,3R,4S)-3-({[tert-butyl (dimethyl)silyl]oxy}methyl)-4-hydroxycyclopentyl]carbamate (5.21 g, 87%). ¹H NMR (CDCl₃) δ 4.73 (s, 1H), 4.20-4.05 (m, 2H), 3.81 (dd, J=9.8, 4.2 Hz, 1H), 3.54 (dd, J=9.7, 7.1 Hz, 1H), 2.33-2.10 (m, 2H), 2.05-1.79 (m, 3H), 1.43 (s, 9H), 1.20-1.08 (m, 1H), 0.90 (s, 9H), 0.08 (s, 6H).

Step 2: tert-Butyl {(1R,3R,4S)-3-({[tert-butyl(dimethyl)silyl]oxy}methyl)-4-[(triisopropylsilyl)oxy]cyclopentyl}carbamate Int-77

To a solution of tert-butyl [(1R,3R,4S)-3-({[tert-butyl (dimethyl)silyl]oxy}methyl)-4-hydroxycyclopentyl]carbamate (3.8 g, 11 mmol) in DMF (57 mL) under an atmosphere of argon was added imidazole (2.25 g, 33 mmol) followed by triisopropylchlorosilane (4.7 mL, 22 mmol) at rt, and the mixture was stirred for 61 h. The reaction was quenched by addition of saturated NH₄Cl (150 mL) and extracted with EtOAc (200 mL×5). The combined organic layers were washed with brine, dried over Na₂SO₄, filtered, and concentrated in vacuo. The residue was purified on silica gel to afford tert-butyl {(1R,3R,4S)-3-({[tert-butyl(dimethyl)silyl]oxy}methyl)-4-[(triisopropylsilyl)oxy] cyclopentyl}carbamate (5.13 g, 93%) as a colorless oil. ¹H NMR (CDCl₃) δ 4.90 (s, 1H), 4.35-4.20 (m, 1H), 4.19-3.99 (m, 1H), 3.75-3.44 (m, 2H), 2.37-2.17 (m, 1H), 2.03 (s, 1H), 1.96-1.69 (m, 2H), 1.43 (s, 9H), 1.31-1.13 (m, 1H), 1.04 (s, 2H), 0.90 (s, 9H), 0.06 (s, 6H).

Step 3: tert-Butyl {(1R,3R,4S)-3-(hydroxymethyl)-4-[(triisopropylsilyl)oxy]cyclopentyl}carbamate Int-78

To a solution of tert-butyl {(1R,3R,4S)-3-({[tert-butyl (dimethyl)silyl]oxy}methyl)-4-[(triisopropylsilyl)oxy]

cyclopentyl}carbamate (535 mg, 0.91 mmol) in EtOH (9.7 mL) was added 1% HCl in EtOH (9.7 mL, 1.2 mmol) at rt, and the mixture was allowed to stand at 4° C. for 13 h. The reaction was then stirred for 4 h at rt. The reaction was quenched by addition of saturated NaHCO$_3$ (50 mL) and extracted with DCM (50 mL×3). The combined organic layers were dried over Na$_2$SO$_4$, filtered, and concentrated in vacuo. The residue was purified on silica gel to give tert-butyl {(1R,3R,4S)-3-(hydroxymethyl)-4-[(triisopropylsilyl)oxy]cyclopentyl}carbamate (327 mg, 93%) as a colorless oil. $^1$H NMR (CDCl$_3$) δ 4.65 (s, 1H), 4.22 (dd, J=10.9, 5.1 Hz, 1H), 4.19-4.05 (m, 1H), 3.72-3.58 (m, 2H), 2.41-2.27 (m, 1H), 2.13-2.04 (m, 1H), 2.00 (m, 1H), 1.80-1.63 (m, 2H), 1.44 (s, 9H), 1.23-1.09 (m, 1H), 1.06 (s, 21H).

Step 4: {(1R,2S,4R)-4-Amino-2-[(triisopropylsilyl)oxy]cyclopentyl}methanol.CF$_3$CO$_2$H Int-79

A 250 mL RBF was charged with tert-butyl {(1R,3R,4S)-3-(hydroxymethyl)-4-[(triisopropylsilyl)oxy]cyclopentyl}carbamate (1.0 g, 2.6 mmol). To the reaction vessel was added TFA (6.5 mL, 84 mmol) at rt, and the mixture was stirred for 5 min. To the mixture was added toluene (50 mL) and the mixture was concentrated in vacuo. This was repeated twice more to remove water and the resulting residue was dried under high vacuum to give {(1R,2S,4R)-4-amino-2-[(triisopropylsilyl)oxy]cyclopentyl}methanol.CF$_3$CO$_2$H (1.31 g, 100%) as colorless oil. LCMS (FA): m/z=288.6 (M+H).

Example 51: (1R,3R,4S)-3-({[tert-Butyl(dimethyl)silyl]oxy}methyl)-4-[(triisopropylsilyl)oxy]cyclopentanamine Int-80

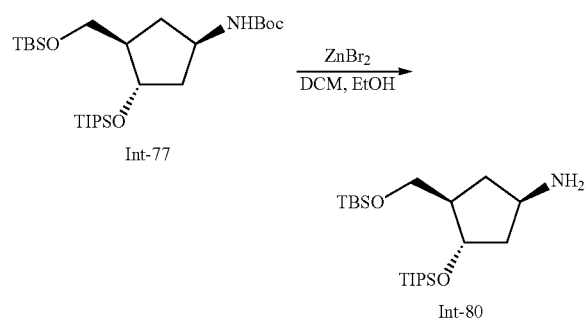

Int-77

Int-80

Step 1: (1R,3R,4S)-3-({[tert-Butyl(dimethyl)silyl]oxy}methyl)-4-[(triisopropylsilyl)oxy]cyclopentanamine To solution of tert-butyl {(1R,3R,4S)-3-({[tert-butyl(dimethyl)silyl]oxy}methyl)-4-[(triisopropylsilyl)oxy]cyclopentyl}carbamate (1.5 g, 3.0 mmol) in DCM (100 mL) was added EtOH (0.38 mL, 6.6 mmol) followed by zinc bromide (5.4 g, 24 mmol) at rt, and the mixture was stirred for 37 h. The reaction was quenched by addition of 1N NaOH (100 mL) and extracted with DCM (100 mL×5). The combined organic layers were washed with brine and then dried over Na$_2$SO$_4$. After filtration, the filtrate was concentrated in vacuo. The residue was purified on silica gel to give (1R,3R,4S)-3-({[tert-butyl(dimethyl)silyl]oxy}methyl)-4-[(triisopropylsilyl)oxy]cyclopentanamine (1.09 g, 91%) as a colorless oil. LCMS (FA): m/z=402.6 (M+H).

Example 52: (1S,2R,4R)-4-Amino-2-(hydroxymethyl)cyclopentanol Int-81

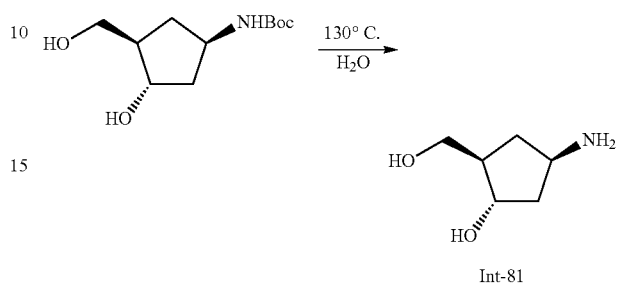

Int-81

Step 1: (1S,2R,4R)-4-Amino-2-(hydroxymethyl)cyclopentanol Int-81 tert-Butyl [(1R,3S,4R)-3-hydroxy-4-(hydroxymethyl)cyclopentyl]carbamate (450 mg, 1.90 mmol) (for synthesis see: Ober, M. et al. J. Am. Chem. Soc. 2005, 127, 18143-18149.) was weighed into a 100 mL RBF and water (10 mL) was added. This mixture was stirred for 48 h at 100° C. The reaction mixture was concentrated in vacuo and the residue was azeototroped with toluene twice. The resulting residue was dried under high vacuum for 16 h to give (1S,2R,4R)-4-amino-2-(hydroxymethyl)cyclopentanol (268 mg, 99%) as a colorless oil. LCMS (FA): m/z=132.2 (M+H).

Example 53: 2-{(1R,2S,4R)-4-Amino-2-[(triisopropylsilyl)oxy]cyclopentyl}ethanesulfonamide-CF$_3$CO$_2$H Int-82

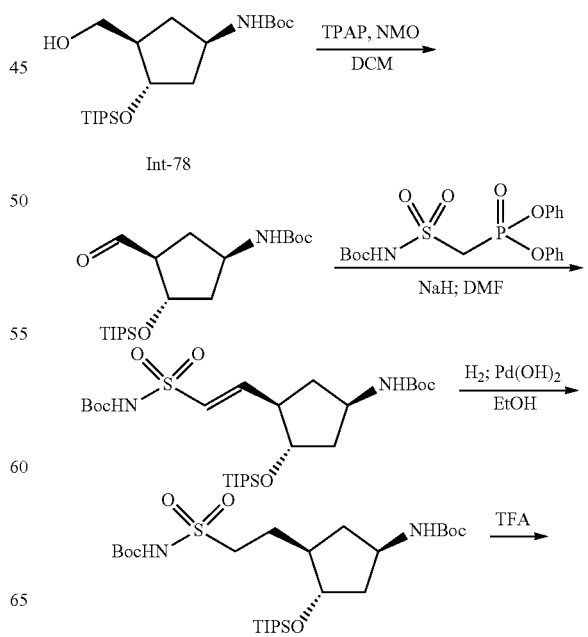

Int-78

-continued

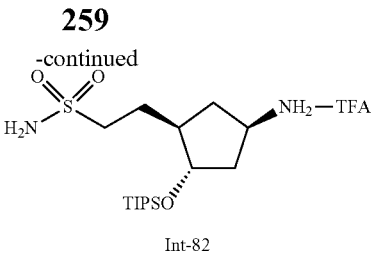

Int-82

Step 1: tert-Butyl {(1R,3S,4S)-3-formyl-4-[(triisopropylsilyl)oxy]cyclopentyl}carbamate A 100 mL RBF was charged with tert-butyl {(1R,3R,4S)-3-(hydroxymethyl)-4-[(triisopropylsilyl)oxy]cyclopentyl}carbamate (550 mg, 1.4 mmol), N-methylmorpholine N-oxide (332 mg, 2.8 mmol), and 3 angstrom molecular sieves (activated at 220° C. under high vac for 2 h). The flask was then purged with argon. DCM (22 mL) was added and the mixture was stirred for 10 min. To this mixture was added tetrapropylammonium perruthenate (TPAP) (50 mg, 0.14 mmol), and the resulting mixture was stirred for 30 min at rt. The reaction was diluted with EtOAc and the mixture was filtered through a silica gel pad over Celite pad (two layers; Celite is bottom and silica gel on the top). The residual molecular sieves were rinsed with EtOAc several times. The organic layer was concentrated in vacuo and the residue was purified on silica gel to give tert-butyl {(1R,3S,4S)-3-formyl-4-[(triisopropylsilyl)oxy]cyclopentyl}carbamate (380 mg, 69%) as colorless oil. $^1$H NMR (CDCl$_3$) δ 9.81 (s, 1H), 4.70-4.42 (m, 2H), 4.36-4.20 (m, 1H), 3.01-2.89 (m, 1H), 2.44-2.31 (m, 1H), 2.14-2.03 (m, 1H), 1.77-1.64 (m, 1H), 1.62-1.53 (m, 1H), 1.44 (s, 9H), 1.14-0.96 (m, 21H).

Step 2: tert-Butyl {[(E)-2-{(1R,2S,4R)-4-[(tert-butoxycarbonyl)amino]-2-[(triisopropylsilyl)oxy]cyclopentyl}vinyl]sulfonyl}carbamate To a solution of tert-butyl {[(diphenylphosphoryl)methyl]sulfonyl}carbamate (1.8 g, 4.5 mmol) in DMF (9.3 mL) was added NaH (60% in mineral oil) (363.0 mg, 9.1 mmol) at rt, and the mixture was stirred for 90 min. To the light yellow solution was added a solution of tert-butyl {(1R,3S,4S)-3-formyl-4-[(triisopropylsilyl)oxy]cyclopentyl}carbamate (700 mg, 1.82 mmol) in DMF and the resulting mixture was stirred for 1 h at rt. The reaction was cooled to 0° C. and then quenched by addition of water (150 mL). The mixture was extracted with EtOAc:Hexanes (1:1) (50 mL×3). The combined organic layers were dried over Na$_2$SO$_4$, filtered, and concentrated in vacuo. The residue was purified on silica gel to give tert-butyl {[(E)-2-{(1R,2S,4R)-4-[(tert-butoxycarbonyl)amino]-2-[(triisopropylsilyl)oxy]cyclopentyl}vinyl]sulfonyl}carbamate (565 mg, 53%) as colorless oil. $^1$H NMR (CDCl$_3$) δ 7.06-6.94 (m, 1H), 6.93 (dd, J=15.1, 8.3 Hz, 1H), 6.48 (dd, J=15.1, 1.0 Hz, 1H), 4.60-4.40 (m, 1H), 4.30-4.14 (m, 2H), 2.75-2.65 (m, 1H), 2.52-2.39 (m, 1H), 2.16-2.05 (m, 1H), 1.73 (dt, J=13.7, 7.0 Hz, 1H), 1.48 (s, 9H), 1.44 (s, 9H), 1.37-1.26 (m, 1H), 1.03 (m, 21H).

Step 3: tert-Butyl [(2-{(1R,2S,4R)-4-[(tert-butoxycarbonyl)amino]-2-[(triisopropylsilyl)oxy]cyclopentyl}ethyl)sulfonyl]carbamate To a solution of tert-butyl {[(E)-2-{(1R,2S,4R)-4-[(tert-butoxycarbonyl)amino]-2-[(triisopropylsilyl)oxy]cyclopentyl}vinyl]sulfonyl}carbamate (520 mg, 0.92 mmol) in EtOH (50 mL) in a parr shaker flask was added 10% palladium hydroxide on carbon (50 mg, 0.36 mmol), and the mixture was stirred for 4 h under an atmosphere of hydrogen (50 psi). The reaction was filtered through a celite pad and the residual solid was rinsed with MeOH several times. The filtrate was concentrated in vacuo and the residue was purified on silica gel to give tert-butyl [(2-{(1R,2S,4R)-4-[(tert-butoxycarbonyl)amino]-2-[(triisopropylsilyl)oxy]cyclopentyl}ethyl)sulfonyl]carbamate (443 mg, 85%) as a colorless amorphous solid. LCMS (FA): m/z=565.5 (M+H).

Step 4: 2-{(1R,2S,4R)-4-Amino-2-[(triisopropylsilyl)oxy]cyclopentyl}ethanesulfonamide.CF$_3$CO$_2$H Int-82 tert-Butyl [(2-{(1R,2S,4R)-4-[(tert-butoxycarbonyl)amino]-2-[(triisopropylsilyl)oxy]cyclopentyl}ethyl)sulfonyl]carbamate (150 mg, 0.27 mmol) was weighed into a 100 mL RBF and TFA (2.0 mL, 26 mmol) was added to the reaction vessel. The mixture was stirred for 15 min then diluted with toluene and concentrated in vacuo. The residue was azeotroped with toluene twice and then dried under high vacuum for 18 h to give 2-{(1R,2S,4R)-4-amino-2-[(triisopropylsilyl)oxy]cyclopentyl}ethanesulfonamide.CF$_3$CO$_2$H (127 mg, 100%) as a colorless oil. LCMS (FA): m/z=365.4 (M+H).

Example 54: [(1R,2S,4R)-4-({5-[(1-Benzyl-1H-pyrazol-3-yl)carbonyl]pyrimidin-4-yl}amino)-2-hydroxycyclopentyl]methyl sulfamate I-158

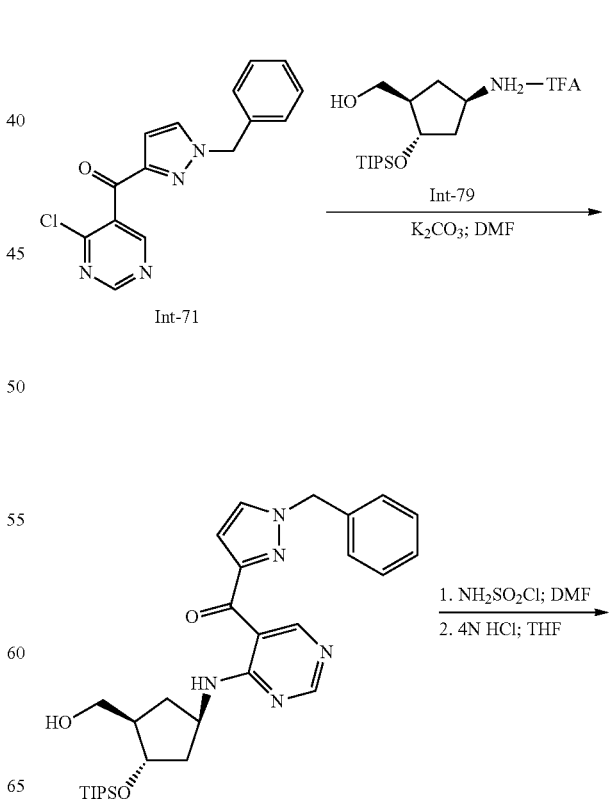

-continued

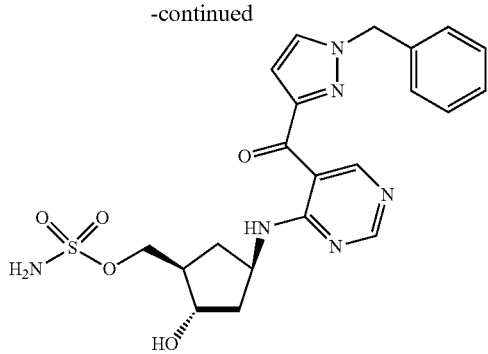

Step 1: (1-Benzyl-1H-pyrazol-3-yl)[4-({(1R,3R,4S)-3-(hydroxymethyl)-4-[(triisopropylsilyl)oxy]cyclopentyl}amino)pyrimidin-5-yl]methanone To a solution of {(1R,2S,4R)-4-amino-2-[(triisopropylsilyl)oxy]cyclopentyl}methanol.CF$_3$CO$_2$H (1.04 g, 2.58 mmol) in DMF (20 mL) was added K$_2$CO$_3$ (1.1 g, 7.7 mmol) followed by (1-benzyl-1H-pyrazol-3-yl)(4-chloropyrimidin-5-yl)methanone (0.85 g, 2.8 mmol) at rt, and the mixture was stirred for 13 h. The reaction was then concentrated in vacuo. To the residue was added water (100 mL) and then the mixture was extracted with EtOAc (100 mL×3). The combined organic layers were washed with brine, dried over Na$_2$SO$_4$, filtered, and concentrated in vacuo. The residue was purified on silica gel to give (1-benzyl-1H-pyrazol-3-yl)[4-({(1R,3R,4S)-3-(hydroxymethyl)-4-[(triisopropylsilyl)oxy]cyclopentyl}amino)pyrimidin-5-yl]methanone (1.08 g, 75%) as a colorless oil. LCMS (FA): m/z=550.7 (M+H).

Step 2: [(1R,2S,4R)-4-({5-[(1-Benzyl-1H-pyrazol-3-yl)carbonyl]pyrimidin-4-yl}amino)-2-hydroxycyclopentyl]methyl sulfamate I-158

To a solution of (1-benzyl-1H-pyrazol-3-yl)[4-({(1R,3R,4S)-3-(hydroxymethyl)-4-[(triisopropylsilyl)oxy]cyclopentyl}amino)pyrimidin-5-yl]methanone (1.0 g, 1.8 mmol) in DMF (30 mL) was added chlorosulfonamide (650 mg, 5.6 mmol) at rt, and the mixture was stirred for 20 min. The reaction was quenched by addition of saturated NaHCO$_3$ (100 mL) and water (50 mL). The mixture was extracted with EtOAc (150 mL×3), and the combined organic layers were dried over Na$_2$SO$_4$, filtered, and concentrated in vacuo. The residue was purified on silica gel to give the sulfamate intermediate [(0.91 g, 80%); LCMS (FA): m/z=629.7 (M+H).] which was then dissolved in THF (20 mL) and HCl (4 M in water; 20 mL, 80 mmol) was added at rt. This mixture was stirred for 1 h and then quenched by addition of saturated NaHCO$_3$ (150 mL) and extracted with EtOAc (200 mL×4). The combined organic layers were dried over Na$_2$SO$_4$, filtered, and concentrated in vacuo. To the residue was added DCM and the resulting suspension was filtered through a glass frit funnel and the residual solid was washed with DCM twice. The filtrate was concentrated in vacuo and the residue was purified on silica gel. The purification product and solid from filtration were combined to give [(1R,2S,4R)-4-({5-[(1-benzyl-1H-pyrazol-3-yl)carbonyl]pyrimidin-4-yl}amino)-2-hydroxycyclopentyl]methyl sulfamate (652 mg, 95%) as a colorless solid. $^1$H NMR (DMSO) δ 9.46 (s, 1H), 9.00 (d, J=7.5 Hz, 1H), 8.62 (s, 1H), 8.07 (d, J=2.4 Hz, 1H), 7.45 (s, 2H), 7.41-7.25 (m, 5H), 6.90 (d, J=2.4 Hz, 1H), 5.50 (s, 2H), 4.92 (d, J=4.6 Hz, 1H), 4.76-4.64 (m, 1H), 4.10 (dd, J=9.7, 5.9 Hz, 1H), 4.01-3.92 (m, 2H), 2.41-2.30 (m, 1H), 2.19-2.07 (m, 1H), 2.00 (ddd, J=11.7, 7.7, 3.8 Hz, 1H), 1.83-1.72 (m, 1H), 1.28 (dt, J=12.9, 9.2 Hz, 1H); LCMS (FA): m/z=473.5 (M+H).

The compounds listed in the table below were prepared in an analogous fashion to that described above starting from the appropriate starting materials used in step 1. I-133 and I-360 were made as a diastereomeric mixture (benzylic methyl stereocenter) and then separated via HPLC (chiral column). Absolute configurations of the undefined stereocenters are unknown.

| Starting material | Compound No. | LCMS Data |
|---|---|---|
| Int-66 | I-93 | LCMS (FA): m/z = 479.6 (M + H). |
| Int-67 | I-133 | LCMS (FA): m/z = 521.0 (M + H). |
| | I-360 | LCMS (FA): m/z = 521.1 (M + H). |

Example 55: {(1R,2S,4R)-4-[(5-{[1-(3-Fluoro-4-methylbenzyl)-1H-pyrazol-3-yl]carbonyl}pyrimidin-4-yl)amino]-2-hydroxycyclopentyl}methyl sulfamate I-210

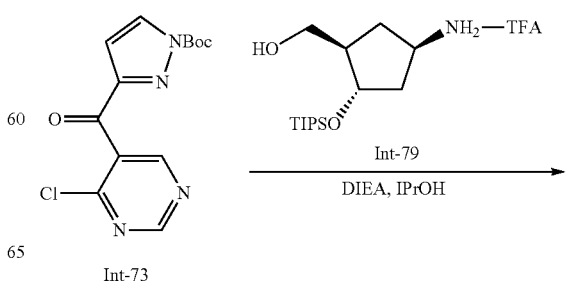

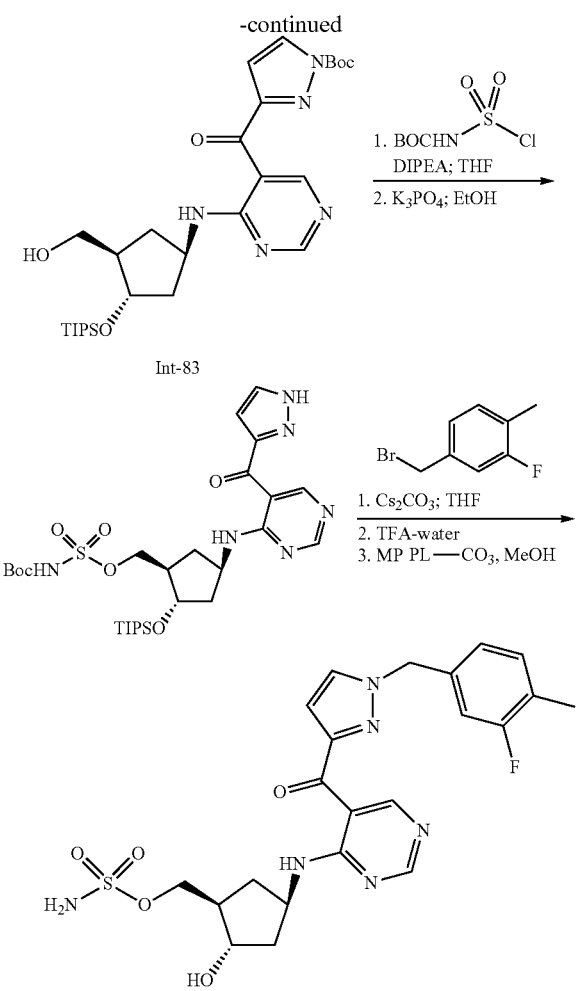

Step 1: tert-Butyl 3-{[4-({(1R,3R,4S)-3-(hydroxymethyl)-4-[(triisopropylsilyl)oxy]cyclopentyl}amino)pyrimidin-5-yl]carbonyl}-1H-pyrazole-1-carboxylate Int-83 tert-Butyl 3-[(4-chloropyrimidin-5-yl)carbonyl]-1H-pyrazole-1-carboxylate (2.2 g, 7.1 mmol) was dissolved in isopropyl alcohol (80 mL). DIEA (2.8 g, 21 mmol) and {(1R,2S,4R)-4-amino-2-[(triisopropylsilyl)oxy]cyclopentyl}methanol.TFA (2.9 g, 7.1 mmol) dissolved iPrOH (20 mL) was added to the solution and it was stirred at rt for 16 h. The reaction mixture was concentrated and the crude product was purified on silica gel to produce tert-butyl 3-{[4-({(1R,3R,4S)-3-(hydroxymethyl)-4-[(triisopropylsilyl)oxy]cyclopentyl}amino)pyrimidin-5-yl]carbonyl}-H-pyrazole-1-carboxylate (2.5 g, 625). LCMS (AA): m/z=560 (M+H).

Step 2: tert-Butyl [({(1R,2S,4R)-4-{[5-(1H-pyrazol-3-ylcarbonyl)pyrimidin-4-yl]amino}-2-[(triisopropylsilyl)oxy]cyclopentyl}methoxy)sulfonyl]carbamate To a solution of tert-butyl 3-{[4-({(1R,3R,4S)-3-(hydroxymethyl)-4-[(triisopropylsilyl)oxy]cyclopentyl}amino)pyrimidin-5-yl]carbonyl}-1H-pyrazole-1-carboxylate (2.5 g, 4.4 mmol) and DIEA (2.3 g, 18 mmol) in THF (40 mL) was added tert-butyl (chlorosulfonyl)carbamate (1.9 g, 8.8 mmol) at 0° C. It was then stirred at 0° C. for 4 h. The reaction solvent was evaporated and the residue was dissolved in EtOH (60 mL). A solution of potassium phosphate (0.47 g, 2.2 mmol) in water (4 mL) was then added and the resulting mixture stirred at rt for 2 h. The reaction solvent was evaporated and the crude product was purified on silica gel to provide [tert-butyl [({(1R,2S,4R)-4-{[5-(1H-pyrazol-3-ylcarbonyl)pyrimidin-4-yl]amino}-2-[(triisopropylsilyl)oxy]cyclopentyl}methoxy)sulfonyl]carbamate](1.6 g, 56%). LCMS (AA): m/z=639 (M+H).

Step 3: {(1R,2S,4R)-4-[(5-{[1-(3-fluoro-4-methylbenzyl)-1H-pyrazol-3-yl]carbonyl}pyrimidin-4-yl)amino]-2-hydroxycyclopentyl}methyl sulfamate I-210

To a 3-dram vial was added 3-fluoro-4-methyl benzyl bromide (0.020 g, 0.10 mmol), tert-butyl [({(1R,2S,4R)-4-{[5-(1H-pyrazol-3-ylcarbonyl)pyrimidin-4-yl]amino}-2-[(triisopropylsilyl) oxy]cyclopentyl}methoxy)sulfonyl]carbamate (0.032 g, 0.050 mmol) in THF (1.00 mL) followed by cesium carbonate (0.16 g, 0.50 mmol). The mixture was shaken at rt for 4 h then the mixture was filtered to remove solids. To the clear THF solution was added TFA (3.0 mL), water (0.30 mL). This mixture was then shaken at rt for 16 h. Solvent was then evaporated and to the residue was added DMSO (1.2 mL), potassium carbonate (0.069 g, 0.50 mmol) and water (3 drops). After shaking at rt for 1 h, the solution was filtered and purified by prep-HPLC to give {(1R,2S,4R)-4-[(5-{[1-(3-fluoro-4-methylbenzyl)-1H-pyrazol-3-yl]carbonyl}pyrimidin-4-yl)amino]-2-hydroxycyclopentyl}methyl sulfamate (2.1 mg, 8%). LCMS (FA): m/z=505.6 (M+H).

The compounds listed in the table below were prepared in an analogous fashion to that described above starting from the listed starting materials used in step 3:

| Starting material | Compound No. | LCMS Data |
|---|---|---|
| Br-CH2-C6H3(F)(Cl) | I-185 | LCMS (FA): m/z = 525.5 (M + H). |
| Br-CH2-C6H3(F)(F) | I-219 | LCMS (FA): m/z = 509.6 (M + H). |
| Br-CH2-C6H4(CN) | I-253 | LCMS (FA): m/z = 498.6 (M + H). |
| Br-CH2-C6H4(Cl) | I-47 | LCMS (FA): m/z = 507.6 (M + H). |

-continued

| Starting material | Compound No. | LCMS Data |
|---|---|---|
| 2,4,6-trifluorobenzyl bromide | I-286 | LCMS (FA): m/z = 527.6 (M + H). |
| 2-(trifluoromethyl)benzyl bromide | I-226 | LCMS (FA): m/z = 541.6 (M + H). |
| 2,4-bis(trifluoromethyl)benzyl bromide | I-261 | LCMS (FA): m/z = 609.6 (M + H). |
| 2,4,5-trifluorobenzyl bromide | I-329 | LCMS (FA): m/z = 527.6 (M + H). |
| 2,4-difluorobenzyl bromide | I-62 | LCMS (FA): m/z = 509.5 (M + H). |
| 2-chlorobenzyl bromide | I-206 | LCMS (FA): m/z = 507.6 (M + H). |
| pentafluorobenzyl bromide | I-202 | LCMS (FA): m/z = 563.5 (M + H). |
| 3,5-difluorobenzyl bromide | I-260 | LCMS (FA): m/z = 509.5 (M + H). |
| 2,3,6-trifluorobenzyl bromide | I-16 | LCMS (FA): m/z = 527.5 (M + H). |
| 2,5-difluorobenzyl bromide | I-35 | LCMS (FA): m/z = 509.5 (M + H). |
| 3-(trifluoromethyl)benzyl bromide | I-140 | LCMS (FA): m/z = 541 (M + H). |

-continued

| Starting material | Compound No. | LCMS Data |
|---|---|---|
| 4-chloro-2-fluorobenzyl bromide | I-191 | LCMS (FA): m/z = 525.5 (M + H). |
| 3-(trifluoromethoxy)benzyl bromide | I-20 | LCMS (FA): m/z = 557 (M + H). |
| 3,4-difluorobenzyl bromide | I-212 | LCMS (FA): m/z = 509.5 (M + H). |
| 4-fluorobenzyl bromide | I-161 | LCMS (FA): m/z = 491.5 (M + H). |
| 3,5-bis(trifluoromethyl)benzyl bromide | I-69 | LCMS (FA): m/z = 609.6 (M + H). |
| 4-(trifluoromethoxy)benzyl bromide | I-276 | LCMS (FA): m/z = 557.6 (M + H). |
| 2-(bromomethyl)naphthalene | I-48 | LCMS (FA): m/z = 523.6 (M + H). |
| 3-fluorobenzyl bromide | I-165 | LCMS (FA): m/z = 491.5 (M + H). |
| 2-(trifluoromethoxy)benzyl bromide | I-39 | LCMS (FA): m/z = 557.5 (M + H). |
| 2,4-dichlorobenzyl bromide | I-289 | LCMS (FA): m/z = 541.5 (M + H). |
| 4-fluoro-2-(trifluoromethyl)benzyl bromide | I-328 | LCMS (FA): m/z = 559.6 (M + H). |

Example 56: [(1R,2S,4R)-4-{[5-({1-[4-Chloro-3-(trifluoromethoxy)benzyl]-1H-pyrazol-3-yl}carbonyl)pyrimidin-4-yl]amino}-2-hydroxycyclopentyl]methyl sulfamate I-152

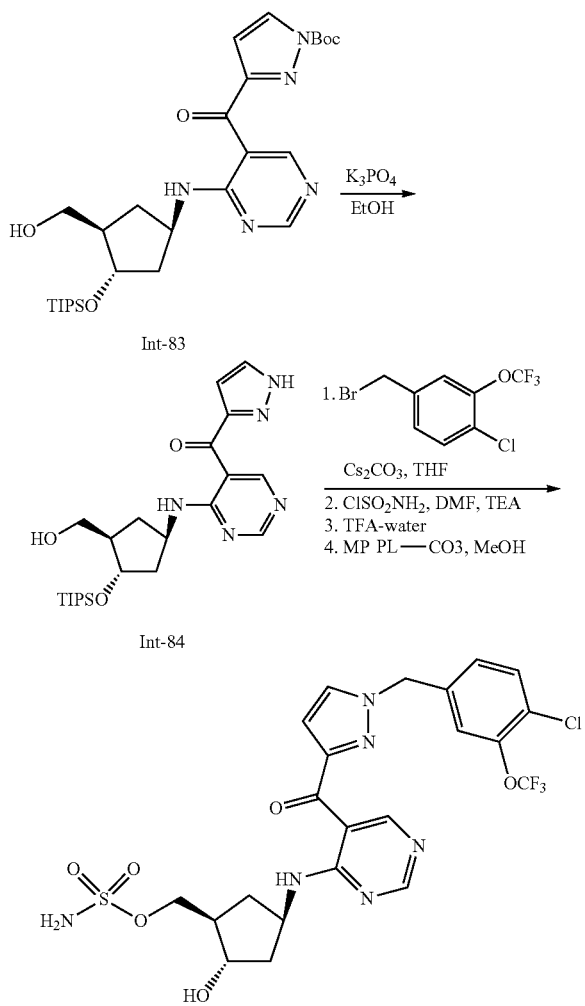

Int-83

Int-84

Step 1: [4-({(1R,3R,4S)-3-(Hydroxymethyl)-4-[(triisopropylsilyl)oxy]cyclopentyl}amino)pyrimidin-5-yl](1H-pyrazol-3-yl)methanone Int-84

To a solution of tert-butyl 3-{[4-({(1R,3R,4S)-3-(hydroxymethyl)-4-[(triisopropylsilyl)oxy]cyclopentyl}amino)pyrimidin-5-yl]carbonyl}-1H-pyrazole-1-carboxylate (1.7 g, 3.1 mmol) in EtOH (30 mL) was added a solution of potassium phosphate (1.4 g, 6.5 mmol) in water (4.5 mL). This mixture was stirred at rt for 2 h. Water was added to the mixture and it was extracted with DCM (2×50 mL). The combined extracts were dried over MgSO$_4$, filtered, and concentrated. The residue was purified on silica gel to give [4-({(1R,3R,4S)-3-(hydroxymethyl)-4-[(triisopropylsilyl)oxy]cyclopentyl}amino)pyrimidin-5-yl](1H-pyrazol-3-yl)methanone (1.13 g, 79%). LCMS (FA): m/z=460.4 (M+H).

Step 2: [(1R,2S,4R)-4-{[5-({1-[4-Chloro-3-(trifluoromethoxy)benzyl]-1H-pyrazol-3-yl}carbonyl)pyrimidin-4-yl]amino}-2-hydroxycyclopentyl]methyl sulfamate I-152

To a 50 mL reaction vial was added [4-({(1R,3R,4S)-3-(hydroxymethyl)-4-[(triisopropylsilyl)oxy]cyclopentyl}amino)pyrimidin-5-yl](1H-pyrazol-3-yl)methanone (0.14 g, 0.31 mmol), 4-chloro-3-(trifluoromethoxy)benzylbromide (0.11 g, 0.39 mmol), cesium carbonate (0.41 g, 1.25 mmol), and THF (4.0 mL). The mixture was stirred at rt for 2 h. To the vial was added brine (1 mL), water (1 mL) and EtOAc (20 mL). After separation, the aqueous layer was extracted with EtOAc (5 mL). The combined organic phases were concentrated. To the vial was then added chlorosulfonamide (0.15 g, 1.25 mmol), TEA (0.17 mL, 1.25 mmol), and acetonitrile (2 mL). After the reaction stirred at rt for 1 h, saturated NaHCO$_3$ (2 mL) and EtOAc (20 mL) were added. After separation of the phases, the aqueous layer was extracted with EtOAc (5 mL). The combined organic phases were then concentrated. To the resulting solid in the reaction vial was added TFA (5.0 mL) and water (0.5 mL). After this mixture was stirred at rt for 16 h, solvent was completely evaporated. This residue was dissolved in MeOH (10 mL) and to it was added MP PL-CO3 resin (3 g). After this mixture was stirred at rt for 2 h, the resin was filtered and rinsed with MeOH (10 mL). The filtrate was then evaporated and the resulting residue was purified by prep-HPLC to give [(1R,2S,4R)-4-{[5-({1-[4-chloro-3-(trifluoromethoxy)benzyl]-1H-pyrazol-3-yl}carbonyl)pyrimidin-4-yl]amino}-2-hydroxycyclopentyl]methyl sulfamate (0.122 g, 66%). $^1$H NMR (MeOD) δ 9.61 (s, 1H), 8.57 (s, 1H), 7.88 (d, J=2.4 Hz, 1H), 7.59 (d, J=8.4 Hz, 1H), 7.38 (s, 1H), 7.30 (d, J=8.4, 1H), 6.98 (s, 1H), 5.53 (s, 2H), 4.82 (m, 1H), 4.21 (m, 3H), 2.55 (m, 1H), 2.31 (m, 1H), 2.17 (m, 1H), 1.92 (m, 1H), 1.45 (m, 1H). LCMS (FA): m/z=592 (M+H).

The compounds listed in the table below were prepared in an analogous fashion to that described above starting from the listed starting materials used in step 2:

| Starting material | Compound No. | LCMS Data |
|---|---|---|
| Br—CH$_2$—C$_6$H$_3$(Cl)(Cl) | I-58 | LCMS (FA): m/z = 541.1 (M + H). |
| Br—CH$_2$—C$_6$H$_4$—OCHF$_2$ | I-117 | LCMS (FA): m/z = 540 (M + H). |

-continued
| Starting material | Compound No. | LCMS Data |
|---|---|---|
| 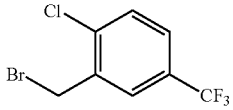 | I-50 | LCMS (FA): m/z = 576 (M + H). |
| 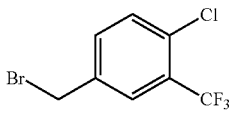 | I-288 | LCMS (FA): m/z = 575 (M + H). |
| 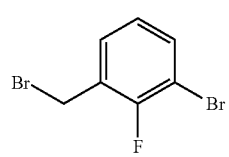 | I-282 | LCMS (FA): m/z = 570.7 (M + H). |
| 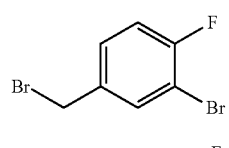 | I-72 | LCMS (FA): m/z = 570.8 (M + H). |
| 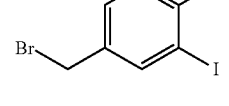 | I-245 | LCMS (FA): m/z = 616.8 (M + H). |
| 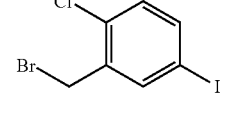 | I-104 | LCMS (FA): m/z = 632.8 (M + H). |
| 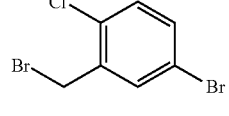 | I-239 | LCMS (FA): m/z = 584.7 (M + H). |
| 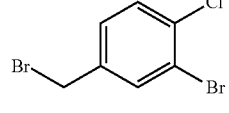 | I-179 | LCMS (FA): m/z = 584.8 (M + H). |
| 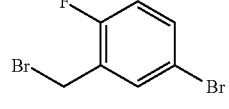 | I-346 | LCMS (FA): m/z = 569 (M + H). |
| 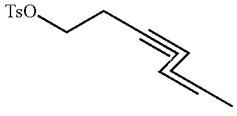<br>Fang, F. et al. *Org. Biomol. Chem.* 2012, 10, 3080-3091. | I-115 | LCMS (FA): m/z = 449.8 (M + H). |
| 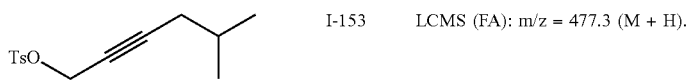<br>Hasting, C. J. et al. *J. Am. Chem. Soc.* 2008, 130, 10977-10983. | I-153 | LCMS (FA): m/z = 477.3 (M + H). |

-continued
| Starting material | Compound No. | LCMS Data |
|---|---|---|
| 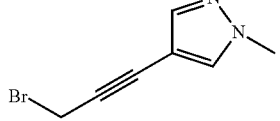<br>Int-48 | I-308 | LCMS (FA): m/z = 501.3 (M + H). |
| 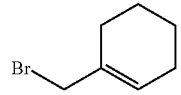<br>Int-60 | I-252 | LCMS (FA): m/z = 477.8 (M + H). |
| 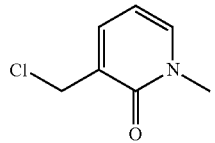<br>Int-35 | I-80 | LCMS (FA): m/z = 504.3 (M + H). |
| 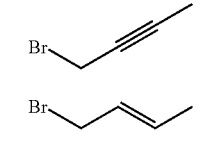 | I-228 | LCMS (FA): m/z = 435.2 (M + H). |
| 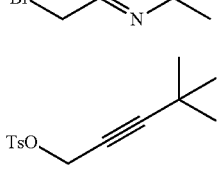 | I-107 | LCMS (FA): m/z = 437.3 (M + H). |
| 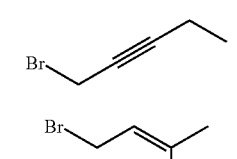 | I-298 | LCMS (FA): m/z = 488.4 (M + H). |
| 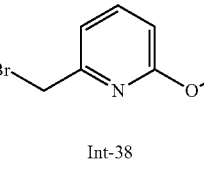<br>Int-55 | I-113 | LCMS (FA): m/z = 477.3 (M + H). |
| 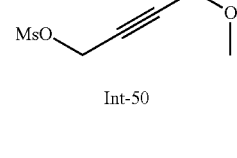 | I-234 | LCMS (FA): m/z = 449.3 (M + H). |
|  | I-344 | LCMS (FA): m/z = 451 (M + H). |
| 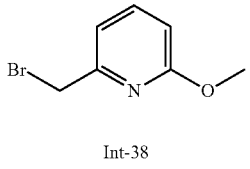<br>Int-38 | I-295 | LCMS (FA): m/z = 504 (M + H). |
| 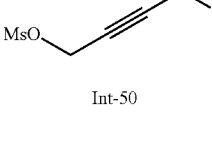<br>Int-50 | I-151 | LCMS (FA): m/z = 494 (M + H). |

-continued
| Starting material | Compound No. | LCMS Data |
|---|---|---|
| Int-18 | I-251 | LCMS (FA): m/z = 558.2 (M + H). |
| Int-12 | I-137 | LCMS (FA): m/z = 545.1 (M + H). |
| Int-20 | I-232 | LCMS (FA): m/z = 513.0 (M + H). |
| Int-19 | I-280 | LCMS (FA): m/z = 513.0 (M + H). |
| Int-11 | I-64 | LCMS (FA): m/z = 529.1 (M + H). |
Example 57: [{(1R,2S,4R)-2-Hydroxy-4-[(5-{[1-(3-iodobenzyl)-1H-pyrazol-3-yl]carbonyl}pyrimidin-4-yl)amino]cyclopentyl}methyl sulfamate] I-292
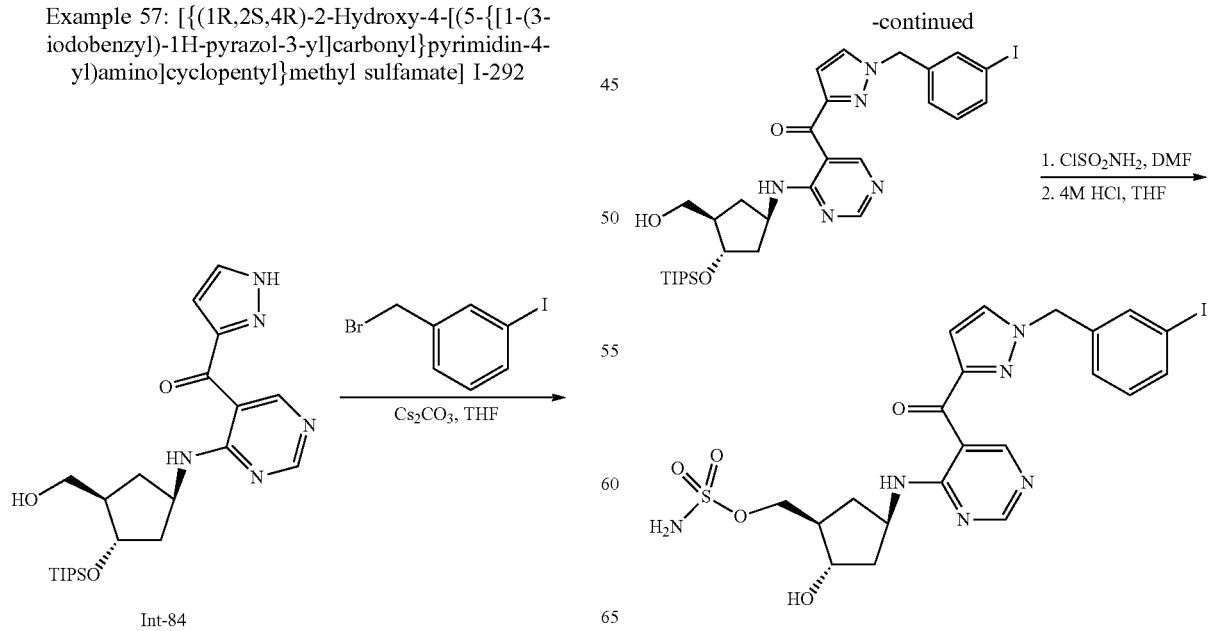

Step 1: [4-({(1R,3R,4S)-3-(Hydroxymethyl)-[(triisopropylsilyl)oxy]cyclopentyl}amino)pyrimidin-5-yl][1-(3-iodobenzyl)-1H-pyrazol-3-yl]methanone

[4-({(1R,3R,4S)-3-(hydroxymethyl)-4-[(triisopropylsilyl)oxy]cyclopentyl}amino)pyrimidin-5-yl](1H-pyrazol-3-yl)methanone (0.64 g, 1.4 mmol) was dissolved in THF (25 mL). To this solution was added cesium carbonate (1.6 g, 4.9 mmol) and 3-iodobenzyl bromide (0.62 g, 2.1 mmol) and the reaction was stirred at rt for 20 h. The reaction was filtered and the filtrate concentrated. The residue was purified on silica gel to give [4-({(1R,3R,4S)-3-(hydroxymethyl)-4-[(triisopropylsilyl)oxy]cyclopentyl}amino)pyrimidin-5-yl][1-(3-iodobenzyl)-1H-pyrazol-3-yl]methanone (0.79 g, 83%). LCMS (FA): m/z=677.3 (M+H).

Step 2: {(1R,2S,4R)-2-Hydroxy-4-[(5-{[1-(3-iodobenzyl)-1H-pyrazol-3-yl]carbonyl}pyrimidin-4-yl)amino]cyclopentyl}methyl sulfamate I-292

To a solution of [4-({(1R,3R,4S)-3-(hydroxymethyl)-4-[(triisopropylsilyl)oxy]cyclopentyl}amino)pyrimidin-5-yl][1-(3-iodobenzyl)-1H-pyrazol-3-yl]methanone (0.79 g, 1.16 mmol) and TEA (0.5 mL, 2.4 mmol) in DMF (10 mL) was added chlorosulfonamide (400 mg, 3.3 mmol) at rt, and the mixture was stirred for 2 h. The reaction was quenched by addition of a saturated solution of NaHCO$_3$ and diluted with water. The mixture was extracted with EtOAc (4×). The combined organic layers were dried over MgSO$_4$, filtered, and concentrated. The residue was purified on silica gel to give the sulfamate intermediate [(830 mg, 95%); LCMS (FA): m/z=755.2 (M+H).] which was dissolved in THF (7 mL) and HCl (4.0 M in water; 7 mL, 28 mmol) was added to the solution. The reaction was stirred for 5 h at 40° C. The reaction was cooled to rt and quenched by the addition of a saturated solution of NaHCO$_3$ and extracted with EtOAc (4×). The combined organic layers were dried over MgSO$_4$, filtered, and concentrated. The residue was triturated with the addition of DCM. A white solid was collected as {(1R,2S,4R)-2-hydroxy-4-[(5-{[1-(3-iodobenzyl)-1H-pyrazol-3-yl]carbonyl}pyrimidin-4-yl)amino]cyclopentyl}methyl sulfamate (0.40 g, 61%). $^1$H NMR (DMSO) δ 9.45 (s, 1H), 9.01 (d, J=7.4 Hz, 1H), 8.63 (s, 1H), 8.09 (d, J=2.4 Hz, 1H), 7.73-7.66 (m, 2H), 7.45 (s, 2H), 7.29 (d, J=7.7 Hz, 1H), 7.18 (t, J=7.7 Hz, 1H), 6.91 (d, J=2.4 Hz, 1H), 5.49 (s, 2H), 4.92 (d, J=4.5 Hz, 1H), 4.76-4.63 (m, 1H), 4.14-4.06 (m, 1H), 4.00-3.93 (m, 2H), 2.42-2.32 (m, 1H), 2.18-2.09 (m, 1H), 2.06-1.96 (m, 1H), 1.85-1.73 (m, 1H), 1.34-1.21 (m, 1H); LCMS (FA): m/z=599.3 (M+H).

The compounds listed in the table below were prepared using a similar method to that described above starting from the listed starting materials. The following alternative conditions could be employed in the described reaction steps. Step 1: K$_2$CO$_3$ instead of Cs$_2$CO$_3$; DMF instead of THF. Step 3: aq. TFA and aq. H$_3$PO$_4$ instead of aq. HCl. I-55 was made as a diastereomeric mixture (trans cyclopropyl). The following sets were made as diastereomeric mixtures and then separated via HPLC (chiral column): I-315/I-358 (benzylic methyl), I-86/I-362 (propargylic methyl); I-79/I-354 (furylic methyl); I-65/I-366 (pyridyl methyl). Absolute configurations of the undefined stereocenters are unknown.

| Starting material | Compound No. | LCMS Data |
|---|---|---|
| Br–CH$_2$–(2-CF$_3$-pyridin-6-yl) | I-3 | LCMS (FA): m/z = 542.3 (M + H). |
| Br–CH$_2$–CN | I-108 | LCMS (FA): m/z = 422.0 (M + H). |
| Br–CH$_2$–(2-CF$_3$-pyridin-4-yl) Int-17 | I-53 | LCMS (FA): m/z = 542.5 (M + H). |
| Br–CH$_2$–C≡C–(furan-2-yl) Int-47 | I-199 | LCMS (FA): m/z = 487.1 (M + H). |
| Br–CH$_2$–(trans-cyclopropyl) diastereomers Int-4 | I-55 | LCMS (FA): m/z = 451.4 (M + H). |

-continued

| Starting material | Compound No. | LCMS Data |
|---|---|---|
| TsO—\—≡—\—(tetrahydropyran)  Int-52 | I-12 | LCMS (FA): m/z = 519.3 (M + H). |
| Cl-CH₂-S-CH₃ | I-281 | LCMS (FA): m/z = 443.0 (M + H). |
| Cl-CH₂CH₂-S-CH₃ | I-37 | LCMS (FA): m/z = 456.6 (M + H). |
| Br-CH₂CH₂-O-CH₃ | I-305 | LCMS (FA): m/z = 441.5 (M + H). |
| 1-(1-bromoethyl)-3-bromobenzene  Int-3 | I-315 | LCMS (FA): m/z = 564.9 (M + H). |
| 1-(1-bromoethyl)-3-bromobenzene  Int-3 | I-358 | LCMS (FA): m/z = 564.9 (M + H). |
| 2-(bromomethyl)-4-methylpyridine  Int-7 | I-162 | LCMS (FA): m/z = 488.0 (M + H). |
| 2-(bromomethyl)-6-chloropyridine  Int-8 | I-95 | LCMS (FA): m/z = 508.0 (M + H). |
| 3-(bromomethyl)tetrahydrofuran  Int-5 | I-332 | LCMS (FA): m/z = 467.4 (M + H). |
| 3-bromopent-1-yne derivative  Int-2 | I-86 | LCMS (FA): m/z = 449.5 (M + H). |
| 3-bromopent-1-yne derivative  Int-2 | I-362 | LCMS (FA): m/z = 449.5 (M + H). |

-continued
| Starting material | Compound No. | LCMS Data |
|---|---|---|
| 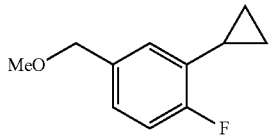<br>Int-46 | I-301 | LCMS (FA): m/z = 531.5 (M + H). |
| 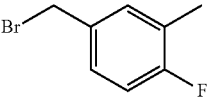 | I-14 | LCMS (FA): m/z = 505.5 (M + H). |
| 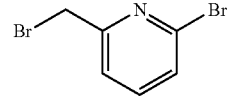 | I-352 | LCMS (FA): m/z = 554.4 (M + H). |
| 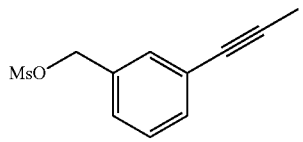<br>Int-45 | I-84 | LCMS (FA): m/z = 511.5 (M + H). |
| 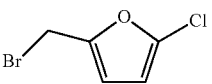<br>Int-23 | I-180 | LCMS (FA): m/z = 497.3 (M + H). |
| 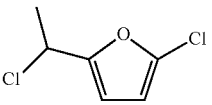<br>Int-25 | I-79 | LCMS (FA): m/z = 511.4 (M + H). |
| 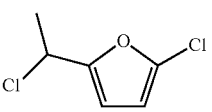<br>Int-25 | I-354 | LCMS (FA): m/z = 511.4 (M + H). |
| 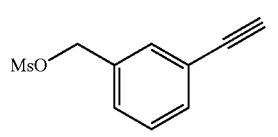<br>Int-44 | I-85 | LCMS (FA): m/z = 497 (M + H). |
| 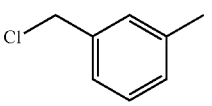 | I-128 | LCMS (FA): m/z = 487 (M + H). |
| 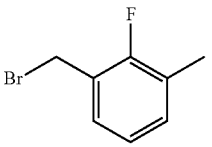 | I-22 | LCMS (FA): m/z = 505 (M + H). |

-continued
| Starting material | Compound No. | LCMS Data |
|---|---|---|
| 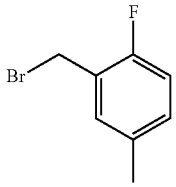 | I-32 | LCMS (FA): m/z = 505 (M + H). |
| 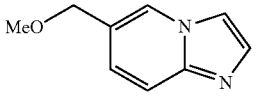<br>Int-39 | I-144 | LCMS (FA): m/z = 513.0 (M + H). |
| 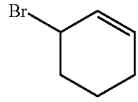 | I-302 | LCMS (FA): m/z = 463.0 (M + H). |
| 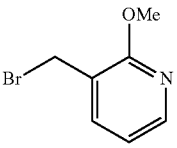<br>Int-37 | I-63 | LCMS (FA): m/z = 504.0 (M + H). |
| 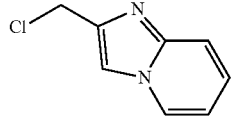 | I-214 | LCMS (FA): m/z = 513.0 (M + H). |
| 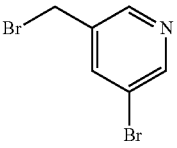 | I-29 | LCMS (FA): m/z = 552.3 (M + H). |
| 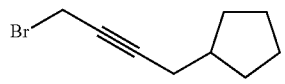<br>Int-53 | I-59 | LCMS (FA): m/z = 503.4 (M + H). |
| 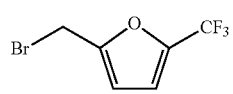 | I-163 | LCMS (FA): m/z = 531.4 (M + H). |
| 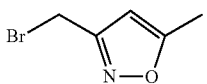 | I-348 | LCMS (FA): m/z = 478.4 (M + H). |
| 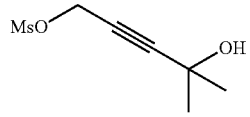<br>Int-51 | I-154 | LCMS (FA): m/z = 479.3 (M + H). |

-continued
| Starting material | Compound No. | LCMS Data |
|---|---|---|
| 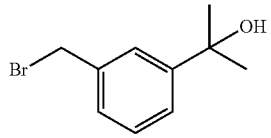<br>Int-13 | I-60 | LCMS (AA): m/z = 531.2 (M + H). |
| 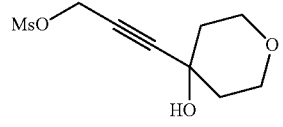<br>Int-29 | I-27 | LCMS (AA): m/z = 521.2 (M + H). |
| 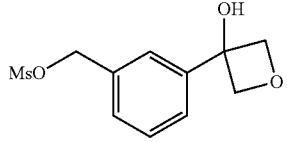<br>Int-30 | I-270 | LCMS (AA): m/z = 543.2 (M + H). |
| 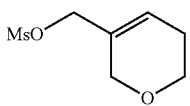<br>Int-32 | I-145 | LCMS (AA): m/z = 479.2 (M + H). |
| 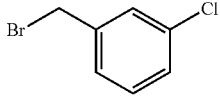 | I-215 | LCMS (FA): m/z = 507.1 (M + H). |
| 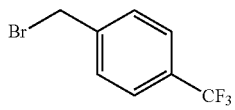 | I-171 | LCMS (FA): mz = 541.1 (M + H). |
| 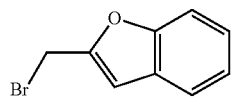<br>Pelcman, B. et al. PCT Application Publication WO 2008/110793 | I-17 | LCMS (AA): m/z = 513.2 (M + H). |
| 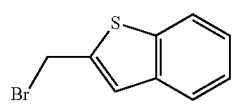<br>Kong, X. et al. PCT Application Publication WO 2006/085149 | I-241 | LCMS (AA): m/z = 529.1 (M + H). |
| 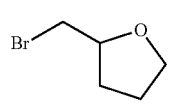<br>Int-5 | I-293 | LCMS (AA): m/z = 467.2 (M + H). |

-continued
| Starting material | Compound No. | LCMS Data |
|---|---|---|
| 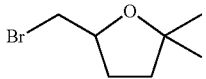<br>Florjancic, A. S. etal.<br>US Application Publication 2010/0093814 | I-77 | LCMS (AA): m/z = 495.2 (M + H). |
| 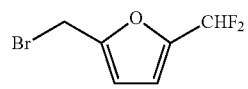<br>Int-26 | I-235 | LCMS (AA): m/z = 513.1 (M + H). |
| 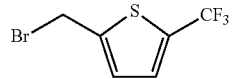<br>Int-16 | I-183 | LCMS (AA): m/z = 547.1 (M + H). |
| 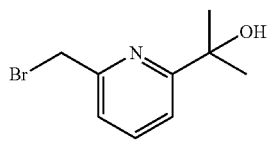<br>Int-14 | I-109 | LCMS (AA): m/z = 532.2 (M + H). |
| 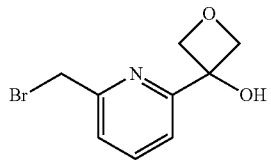<br>Int-27 | I-120 | LCMS (AA): m/z = 544.2 (M + H). |
| 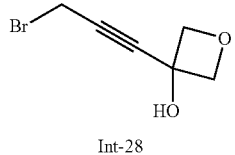<br>Int-28 | I-275 | LCMS (FA): m/z = 493.1 (M + H). |
| 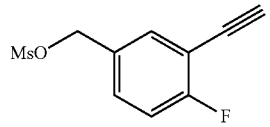<br>Int-43 | I-166 | LCMS (FA): m/z = 515.4 (M + H). |
| <br>Int-54 | I-287 | LCMS (FA): m/z = 461.4 (M + H). |

| Starting material | Compound No. | LCMS Data |
|---|---|---|
| 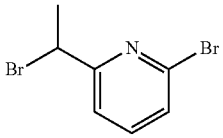 Int-109 | I-65 | LCMS (FA): m/z = 568.2 (M + H). |
| 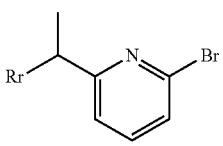 Int-109 | I-366 | LCMS (FA): m/z = 568.2 (M + H). |
Example 58: {(1R,2S,4R)-4-[(5-{[1-(3-Bromobenzyl)-1H-pyrazol-3-yl]carbonyl}pyrimidin-4-yl)amino]-2-hydroxycyclopentyl}methyl sulfamate I-11
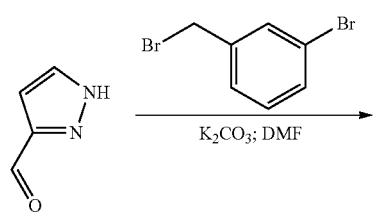
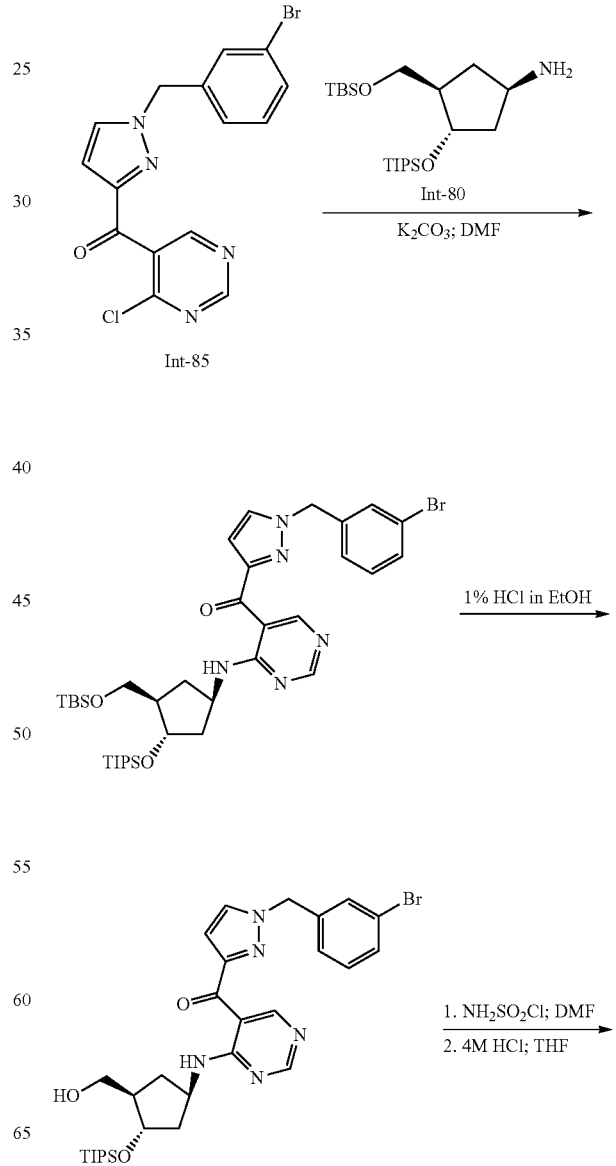

-continued

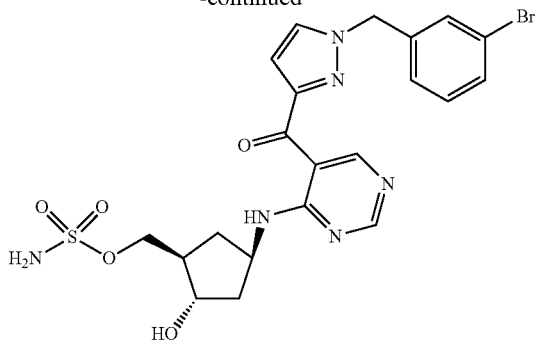

Step 1:
1-(3-Bromobenzyl)-1H-pyrazole-3-carbaldehyde

To a solution of pyrazol-3-carbaldehyde (10.0 g, 104 mmol) in DMF (333 mL) was added $K_2CO_3$ (43 g, 312 mmol) followed by 3-bromobenzyl bromide (27.3 g, 109 mmol) at rt, and the mixture was stirred for 14 h. The reaction was filtered through a celite pad and the residual solid was rinsed with EtOAc. The filtrate was concentrated in vacuo. To the residue was added water (200 mL) and the mixture was extracted with Hexane:EtOAc (1:1, 200 mL×3). The combined organic layers were dried over $Na_2SO_4$, filtered, and concentrated in vacuo. The residue was purified on silica to provide 1-(3-bromobenzyl)-1H-pyrazole-3-carbaldehyde (21.1 g, 76%) as a colorless solid. LCMS (FA): m/z=267.1 (M+H).

Step 2: [1-(3-Bromobenzyl)-1H-pyrazol-3-yl](4-chloropyrimidin-5-yl)methanol

4-Chloro-5-iodopyrimidine (20.0 g, 83.0 mmol) was added to a 3-neck RBF, which was equipped with additional funnel, three way stop cock, septum, and internal temperature probe. The reaction vessel was purged with argon. The content was dissolved in THF (500 mL), and the solution was cooled to −78° C. with a dry ice bath. To the solution was added dropwise n-Butyllithium (2.50 M in hexane; 66.4 mL, 166 mmol), and the mixture was stirred for 30 min. A solution of 1-(3-bromobenzyl)-1H-pyrazole-3-carbaldehyde (20.0 g, 75 mmol) in THF (80 mL) was added dropwise to the mixture at −78° C., and the reaction was stirred for 30 min at the same temperature. The reaction was quenched by addition of saturated $NH_4Cl$ (300 mL) and extracted with EtOAc (300 mL×3). The combined organic layers were dried over $Na_2SO_4$, filtered, and concentrated in vacuo. The residue was purified on silica gel to give [1-(3-bromobenzyl)-1H-pyrazol-3-yl](4-chloropyrimidin-5-yl)methanol (20.4 g, 71%) as an orange oil. LCMS (FA): m/z=381.0 (M+H).

Step 3: [1-(3-Bromobenzyl)-1H-pyrazol-3-yl](4-chloropyrimidin-5-yl)methanone Int-85

To a solution of [1-(3-bromobenzyl)-1H-pyrazol-3-yl](4-chloropyrimidin-5-yl)methanol (20.4 g, 53.7 mmol) in DCM (474 mL) was added manganese(IV) oxide (46.7 g, 537 mmol) and the mixture was stirred for 12 h at rt. The reaction was then filtered through a celite pad and the residual solid was washed with DCM and EtOAc several times. The filtrate was concentrated in vacuo and the residue was purified on silica gel to give [1-(3-bromobenzyl)-1H-pyrazol-3-yl](4-chloropyrimidin-5-yl)methanone (16.7 g, 82%) as an off-white solid. LCMS (FA): m/z=379.1 (M+H).

Step 4: [1-(3-Bromobenzyl)-1H-pyrazol-3-yl][4-({(1R,3R,4S)-3-({[tert-butyl(dimethyl)silyl]oxy}methyl)-4-[(triisopropylsilyl)oxy]cyclopentyl}amino)pyrimidin-5-yl]methanone (1R,3R,4S)-3-({[tert-Butyl(dimethyl)silyl]oxy}methyl)-4-[(triisopropylsilyl)oxy]cyclopentanamine (40.0 g, 100 mmol) and [1-(3-bromobenzyl)-1H-pyrazol-3-yl](4-chloropyrimidin-5-yl)methanone (34.2 g, 90.5 mmol) were weighed into a reaction vessel and the contents were dissolved in DMF (400 mL). To the solution was added $K_2CO_3$ (37.5 g, 271 mmol) at rt, and the resulting mixture was stirred for overnight. The reaction was concentrated in vacuo. To the residue was added water and then the mixture was extracted with EtOAc (3×). The combined organic layers were then washed with brine, dried over $Na_2SO_4$, filtered and concentrated in vacuo. The residue was purified on silica gel to give [1-(3-bromobenzyl)-1H-pyrazol-3-yl][4-({(1R,3R,4S)-3-({[tert-butyl(dimethyl)silyl]oxy}methyl)-4-[(triisopropylsilyl)oxy]cyclopentyl}amino)pyrimidin-5-yl]methanone (63.2 g, 94%) as a light brown oil. LCMS (FA): m/z=744.2 (M+H).

Step 5: [1-(3-Bromobenzyl)-1H-pyrazol-3-yl][4-({(1R,3R,4S)-3-(hydroxymethyl)-4-[(triisopropylsilyl)oxy]cyclopentyl}amino)pyrimidin-5-yl]methanone To a solution of [1-(3-bromobenzyl)-1H-pyrazol-3-yl][4-({(1R,3R,4S)-3-({[tert-butyl(dimethyl)silyl]oxy}methyl)-4-[(triisopropylsilyl)oxy]cyclopentyl}amino)pyrimidin-5-yl]methanone (63.0 g, 80.6 mmol) in EtOH (630 mL) cooled to 0° C. was added 1% HCl in EtOH (1.33 L, 161.1 mmol). The reaction was sealed and allowed to stand at rt for 6 h then at 4° C. for 14 h. The mixture was then warmed to rt and stirred for 9 h. The reaction was quenched by addition of saturated $NaHCO_3$ (200 mL) and the mixture was concentrated to remove EtOH. To the residue was added water (150 mL) and then the mixture was extracted with EtOAc (400 mL×4). The combined organic layers were dried over $Na_2SO_4$, filtered, and concentrated in vacuo. The residue was purified on silica gel to give [1-(3-bromobenzyl)-1H-pyrazol-3-yl][4-({(1R,3R,4S)-3-(hydroxymethyl)-4-[(triisopropylsilyl)oxy]cyclopentyl}amino)pyrimidin-5-yl]methanone (45.6 g, 90%) as a light yellow oil. LCMS (FA): m/z=630.5 (M+H).

Step 6: {(1R,2S,4R)-4-[(5-{[1-(3-Bromobenzyl)-1H-pyrazol-3-yl]carbonyl}pyrimidin-4-yl)amino]-2-hydroxycyclopentyl}methyl sulfamate I-11

To a solution of [1-(3-bromobenzyl)-1H-pyrazol-3-yl][4-({(1R,3R,4S)-3-(hydroxymethyl)-4-[(triisopropylsilyl)oxy]cyclopentyl}amino)pyrimidin-5-yl]methanone (45.5 g, 69 mmol) in DMF (396 mL) was added chlorosulfonamide (12.7 g, 110 mmol) at 0° C., and the mixture was stirred for 20 min at the same temperature. The reaction was quenched by addition of a saturated aqueous solution of $NaHCO_3$ (600 mL) and the resulting mixture was extracted with EtOAc (400 mL×4). The combined organic layers were dried over $Na_2SO_4$, filtered, and concentrated in vacuo. The residue was purified on silica gel to give the sulfamate intermediate [(42.0 g, 86%); LCMS (FA): m/z=630.5 (M+H).] which was then dissolved in THF (200 mL). To this solution was added HCl (4.0 M in water; 200 mL, 800 mmol) at rt, and the mixture was stirred for 14 h. The reaction was quenched by the addition of saturated NaHCO₃ and the mixture was extracted with EtOAc (4×). The combined organic layers were dried over Na₂SO₄, filtered, and concentrated in vacuo. To the residue was added a small volume of DCM and the suspension was filtered through a glass frit funnel. The residual solid was rinsed with Et₂O and dried under high vacuum for 16 h to give {(1R,2S,4R)-4-[(5-{[1-(3-bromobenzyl)-1H-pyrazol-3-yl]carbonyl}pyrimidin-4-yl) amino]-2-hydroxycyclopentyl}methyl sulfamate (29.6 g, 90%). ¹H NMR (DMSO) δ 9.44 (s, 1H), 9.00 (d, J=7.4 Hz, 1H), 8.63 (s, 1H), 8.09 (d, J=2.4 Hz, 1H), 7.56-7.50 (m, 2H), 7.43 (s, 2H), 7.37-7.31 (m, 1H), 7.28 (d, J=7.7 Hz, 1H), 6.91 (d, J=2.4 Hz, 1H), 5.52 (s, 2H), 4.91 (d, J=4.3 Hz, 1H), 4.77-4.65 (m, 1H), 4.10 (dd, J=9.7, 5.9 Hz, 1H), 4.01-3.93 (m, 2H), 2.41-2.31 (m, 1H), 2.18-2.08 (m, 1H), 2.05-1.95 (m, 1H), 1.78 (ddd, J=13.2, 8.4, 6.9 Hz, 1H), 1.28 (dt, J=12.8, 9.2 Hz, 1H); LCMS (FA): m/z=553.3 (M+H).

Example 59: 2-{(1R,2S,4R)-4-[(5-{[1-(3-Bromobenzyl)-H-pyrazol-3-yl]carbonyl}pyrimidin-4-yl) amino]-2-hydroxycyclopentyl}ethanesulfonamide I-38

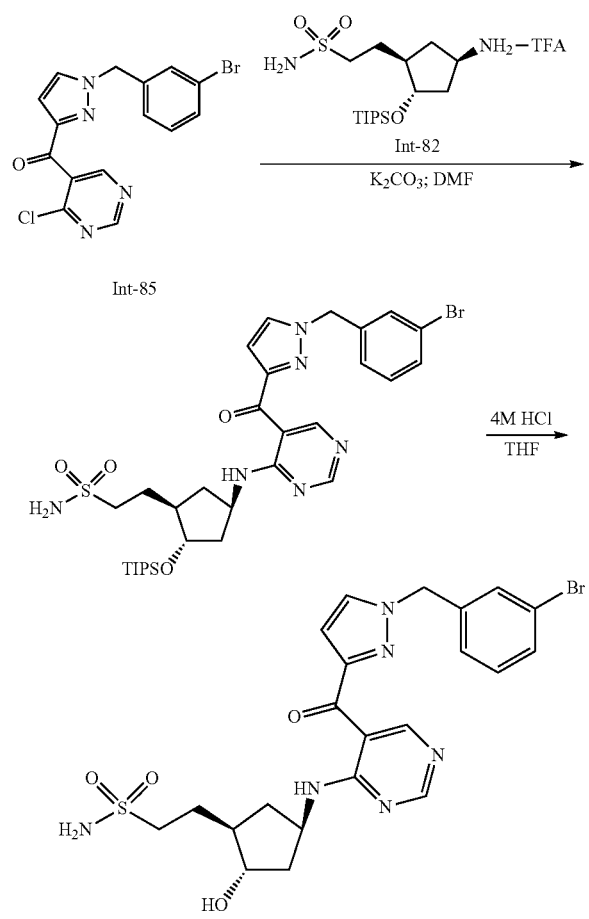

Step 1: 2-{(1R,2S,4R)-4-[(5-{[1-(3-Bromobenzyl)-1H-pyrazol-3-yl]carbonyl}pyrimidin-4-yl)amino]-2-[(triisopropylsilyl)oxy] cyclopentyl}ethanesulfonamide To a flask containing 2-{(1R,2S,4R)-4-amino-2-[(triisopropylsilyl)oxy]cyclopentyl}ethanesulfonamide·CF₃CO₂H (127 mg, 0.27 mmol) was added DMF (2 mL), K₂CO₃ (110 mg, 0.80 mmol) and [1-(3-bromobenzyl)-1H-pyrazol-3-yl](4-chloropyrimidin-5-yl)methanone (120 mg, 0.32 mmol) at rt. The mixture was stirred for 1 h and then quenched by addition of water (50 mL). The mixture was then extracted with EtOAc (60 mL×3). The combined organic layers were dried over Na₂SO₄, filtered, and concentrated. The residue was purified on silica gel to give 2-{(1R,2S,4R)-4-[(5-{[1-(3-bromobenzyl)-1H-pyrazol-3-yl]carbonyl}pyrimidin-4-yl)amino]-2-[(triisopropylsilyl)oxy] cyclopentyl}ethanesulfonamide (164 mg, 83%) as a colorless solid. %). LCMS (AA): m/z=707.4 (M+H).

Step 2: 2-{(1R,2S,4R)-4-[(5-{[1-(3-Bromobenzyl)-1H-pyrazol-3-yl]carbonyl}pyrimidin-4-yl)amino]-2-hydroxycyclopentyl}ethanesulfonamide I-38

To a solution of 2-{(1R,2S,4R)-4-[(5-{[1-(3-bromobenzyl)-1H-pyrazol-3-yl]carbonyl}pyrimidin-4-yl)amino]-2-[(triisopropylsilyl)oxy]cyclopentyl}ethanesulfonamide (155 mg, 0.22 mmol) in THF (2.0 mL) was added HCl (4 M solution in water; 2.0 mL, 8.9 mmol) at rt, and the mixture was stirred for 1 h at 45° C. The reaction was quenched by addition of saturated NaHCO₃ and extracted with EtOAc (×3). The combined organic layers were dried over Na₂SO₄, filtered, and concentrated in vacuo. To the residual solid was added Et₂O and the resulting suspension was filtered through a glass frit funnel. The residual white solid was rinsed with Et₂O and dried under high vacuum to give 2-{(1R,2S,4R)-4-[(5-{[1-(3-bromobenzyl)-1H-pyrazol-3-yl]carbonyl}pyrimidin-4-yl)amino]-2-hydroxycyclopentyl}ethanesulfonamide (114 mg, 95%) as a colorless solid. ¹H NMR (DMSO) δ 9.44 (s, 1H), 9.00 (d, J=7.4 Hz, 1H), 8.62 (s, 1H), 8.09 (d, J=2.4 Hz, 1H), 7.55-7.49 (m, 2H), 7.37-7.31 (m, 1H), 7.30-7.25 (m, 1H), 6.91 (d, J=2.4 Hz, 1H), 6.73 (s, 2H), 5.52 (s, 2H), 4.83 (d, J=5.0 Hz, 1H), 4.69-4.57 (m, 1H), 3.84-3.76 (m, 1H), 3.10-2.91 (m, 2H), 2.39-2.29 (m, 1H), 2.00-1.89 (m, 2H), 1.85-1.61 (m, 3H), 1.20-1.10 (m, 1H); LCMS (FA): m/z=551.3 (M+H).

Example 60: {(1S,2S,4R)-4-[(5-{[1-(3-Bromobenzyl)-1H-pyrazol-3-yl]carbonyl}pyrimidin-4-yl) amino]-2-hydroxycyclopentyl}methyl sulfamate I-2

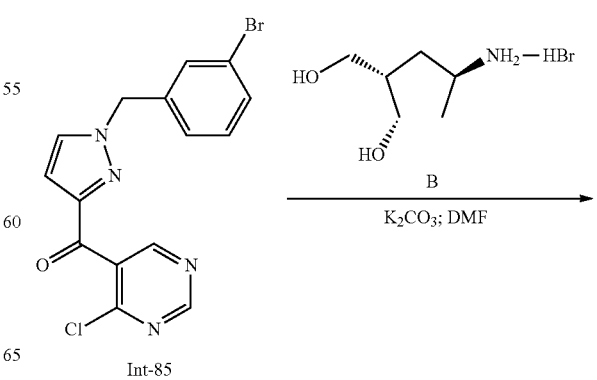

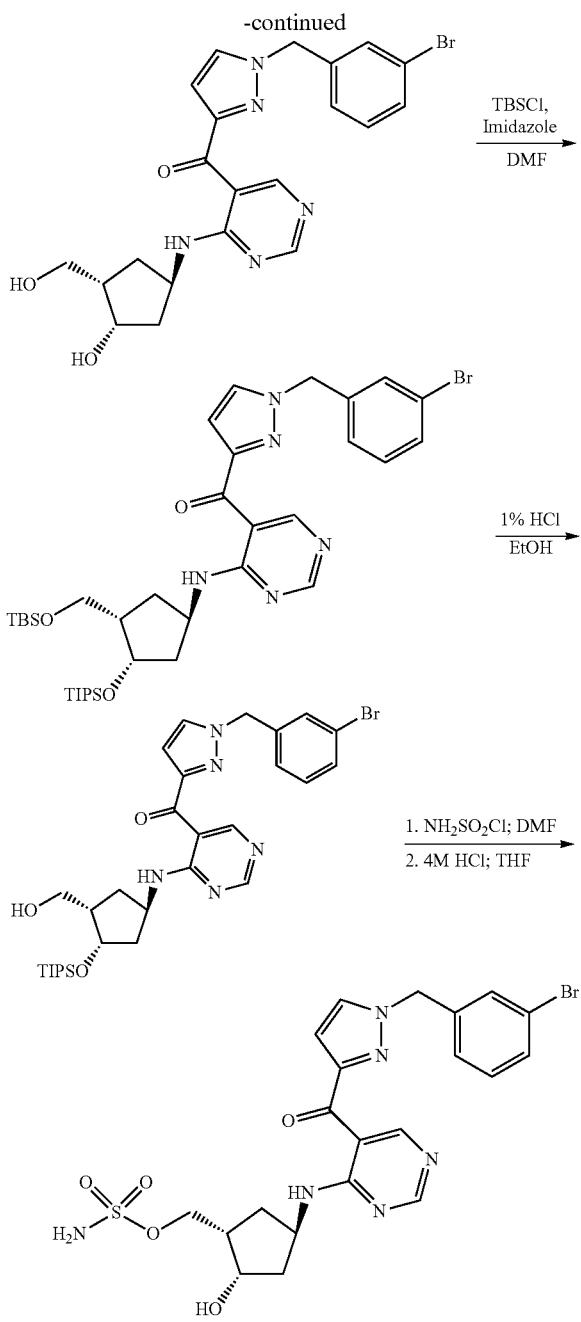

Step 1: [1-(3-Bromobenzyl)-1H-pyrazol-3-yl](4-{[(1R,3S,4S)-3-hydroxy-4-(hydroxymethyl)cyclopentyl]amino}pyrimidin-5-yl)methanone A RBF was charged with [1-(3-bromobenzyl)-1H-pyrazol-3-yl](4-chloropyrimidin-5-yl)methanone (200 mg, 0.53 mmol), (1S,2S,4R)-4-amino-2-(hydroxymethyl)cyclopentanol hydrobromide (B) (135 mg, 0.64 mmol) (for synthesis see: Armitage, I. et al. US Application Publication 2009/0036678), and K$_2$CO$_3$ (183 mg, 1.32 mmol). The contents were dissolved in DMF (4 mL) and the mixture was stirred for 1 h at 80° C. The reaction was then cooled to rt and diluted with EtOAc. The suspension was filtered through a celite pad and the residual solid was rinsed with EtOAc several times. The filtrate was concentrated in vacuo and the residue was dissolved in EtOAc (80 mL) which was then washed with water (30 mL) followed by brine. The organic layer was dried over Na$_2$SO$_4$, filtered, and concentrated. The residue was purified on silica gel to give [1-(3-bromobenzyl)-1H-pyrazol-3-yl](4-{[(1R,3S,4S)-3-hydroxy-4-(hydroxymethyl)cyclopentyl]amino}pyrimidin-5-yl)methanone (167 mg, 60%) as a colorless solid. LCMS (FA): m/z=474.3 (M+H).

Step 2: [1-(3-Bromobenzyl)-1H-pyrazol-3-yl](4-{[(1R,3S,4S)-3-{[tert-butyl(dimethyl)silyl]oxy}-4-({[tert-butyl(dimethyl)silyl]oxy}methyl)cyclopentyl]amino}pyrimidin-5-yl)methanone To a solution of [1-(3-bromobenzyl)-1H-pyrazol-3-yl](4-{[(1R,3S,4S)-3-hydroxy-4-(hydroxymethyl)cyclopentyl]amino}pyrimidin-5-yl)methanone (144 mg, 0.31 mmol) in DMF (5 mL) was added DMAP (1.9 mg, 0.02 mmol), imidazole (100 mg, 1.5 mmol), and TBSCl (115 mg, 0.76 mmol) at rt. The resulting mixture was stirred for 12 h. The reaction was then concentrated in vacuo. To the residue was added water (40 mL) and the mixture was extracted with EtOAc (50 mL×3). The combined organic layers were dried over Na$_2$SO$_4$, filtered, and concentrated in vacuo. The residue was purified on silica gel to give [1-(3-bromobenzyl)-1H-pyrazol-3-yl](4-{[(1R,3S,4S)-3-{[tert-butyl(dimethyl)silyl]oxy}-4-({[tert-butyl(dimethyl)silyl]oxy}methyl)cyclopentyl]amino}pyrimidin-5-yl)methanone (168 mg, 79%) as a colorless oil. LCMS (FA): m/z=702.4 (M+H).

Step 3: [1-(3-Bromobenzyl)-1H-pyrazol-3-yl](4-{([(1R,3S,4S)-3-{[tert-butyl(dimethyl)silyl]oxy}-4-(hydroxymethyl)cyclopentyl]amino}pyrimidin-5-yl)methanone To a solution of [1-(3-bromobenzyl)-1H-pyrazol-3-yl](4-{[(1R,3S,4S)-3-{[tert-butyl(dimethyl)silyl]oxy}-4-({[tert-butyl(dimethyl)silyl]oxy}methyl)cyclopentyl]amino}pyrimidin-5-yl)methanone (160 mg, 0.23 mmol) in EtOH (3.0 mL) was added 1% HCl in EtOH (3.0 mL, 0.36 mmol) and the mixture was stirred for 2 h at rt. The reaction was quenched by addition of saturated NaHCO$_3$ (30 mL) and the mixture was concentrated to remove EtOH. To the residue was added water (20 mL) and the mixture was extracted with EtOAc (50 mL×4). The combined organic layers were dried over Na$_2$SO$_4$, filtered, and concentrated in vacuo. The residue was purified on silica gel to give [1-(3-bromobenzyl)-1H-pyrazol-3-yl](4-{[(1R,3S,4S)-3-{[tert-butyl(dimethyl)silyl]oxy}-4-(hydroxymethyl)cyclopentyl]amino}pyrimidin-5-yl)methanone (113 mg, 84%). LCMS (FA): m/z=588.4 (M+H).

Step 4: {(1S,2S,4R)-4-[(5-{[1-(3-Bromobenzyl)-1H-pyrazol-3-yl]carbonyl}pyrimidin-4-yl)amino]-2-hydroxycyclopentyl}methyl sulfamate I-2

To a solution of [1-(3-bromobenzyl)-1H-pyrazol-3-yl](4-{[(1R,3S,4S)-3-{[tert-butyl(dimethyl)silyl]oxy}-4-(hydroxymethyl)cyclopentyl]amino}pyrimidin-5-yl)methanone (105 mg, 0.18 mmol) in DMF (2.0 mL) was added chlorosulfonamide (41 mg, 0.36 mmol) at rt, and the mixture was stirred for 20 min. The reaction mixture was quenched by addition of saturated NaHCO$_3$ and then the mixture extracted with EtOAc (×3). The combined organic layers were dried over Na$_2$SO$_4$, filtered, and concentrated. The residue was purified on silica gel to give the sulfamate intermediate [(91 mg, 76%); LCMS (FA): m/z=667.4

(M+H).] which was dissolved in THF (2.0 mL). To this solution was added HCl (4 M solution in water; 2.0 mL, 8.9 mmol), and the mixture was stirred for 14 h at rt. The reaction was quenched by addition of saturated NaHCO₃ (30 mL) and the resulting mixture extracted with EtOAc (50 mL×4). The combined organic layers were dried over Na₂SO₄, filtered, and concentrated in vacuo. The residue was purified on silica gel to afford {(1S,2S,4R)-4-[(5-{[1-(3-bromobenzyl)-1H-pyrazol-3-yl]carbonyl}pyrimidin-4-yl)amino]-2-hydroxycyclopentyl}methyl sulfamate (69 mg, 94%). ¹H NMR (DMSO) δ 9.45 (s, 1H), 9.05 (d, J=6.9 Hz, 1H), 8.63 (s, 1H), 8.10 (s, 1H), 7.53 (s, 2H), 7.48-7.19 (m, 4H), 6.92 (s, 1H), 5.53 (s, 2H), 4.97-4.56 (m, 2H), 4.29-4.15 (m, 2H), 4.05-3.95 (m, 1H), 2.47-2.37 (m, 1H), 2.23-2.10 (m, 1H), 2.06-1.93 (m, 1H), 1.85-1.61 (m, 2H); LCMS (FA): m/z=553.3 (M+H).

Example 61: {(1R,2S,4R)-4-[(5-{[1-(3-Bromobenzyl)-1H-pyrazol-3-yl]carbonyl}pyrimidin-4-yl)(methyl)amino]-2-hydroxycyclopentyl}methyl sulfamate I-157

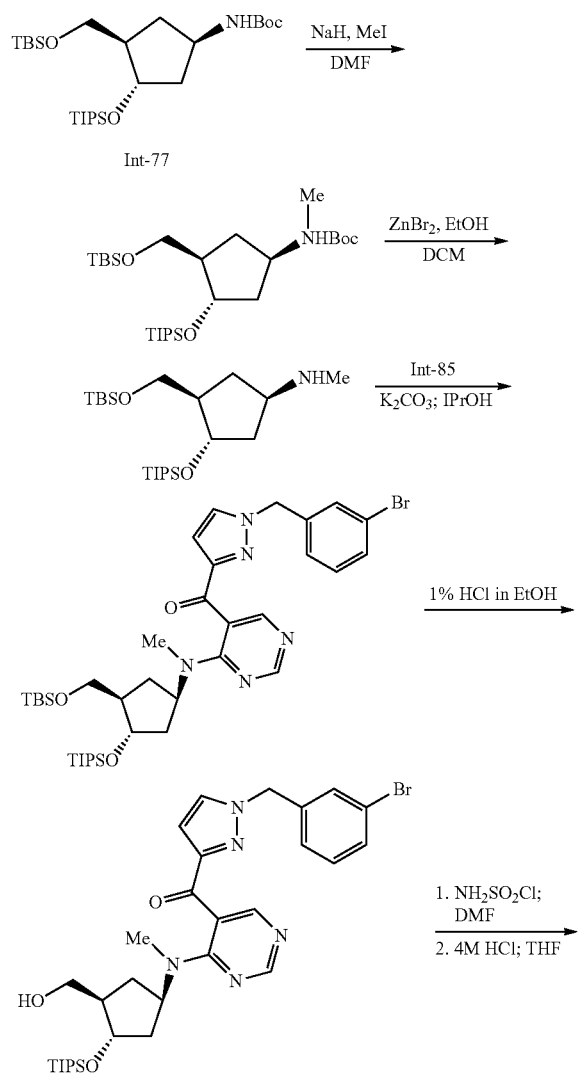

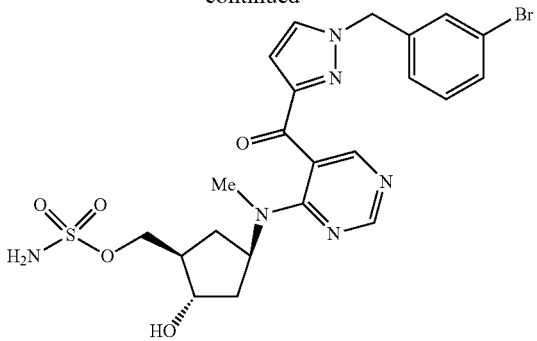

Step 1: tert-Butyl {(1R,3R,4S)-3-({[tert-butyl(dimethyl)silyl]oxy}methyl)-4-[(triisopropylsilyl)oxy]cyclopentyl}methylcarbamate To a solution of tert-butyl {(1R,3R,4S)-3-({[tert-butyl(dimethyl)silyl]oxy}methyl)-4-[(triisopropylsilyl)oxy]cyclopentyl}carbamate (150 mg, 0.30 mmol) in DMF (2.0 mL) was added NaH (60% in mineral oil) (35.9 mg, 0.90 mmol) followed by MeI (55.8 uL, 0.90 mmol) at rt, and the mixture was stirred for 14 h. The reaction was quenched by addition of water (40 mL) and extracted with hexane (50 mL×3). The combined organic layers were dried over Na₂SO₄, filtered, and concentrated in vacuo. The residue was purified by ISCO silica gel column chromatography to give tert-butyl {(1R,3R,4S)-3-({[tert-butyl(dimethyl)silyl]oxy}methyl)-4-[(triisopropylsilyl)oxy]cyclopentyl}methylcarbamate (145 mg, 80%). ¹H NMR (CDCl₃) δ 4.87-4.66 (m, 1H), 4.23-4.15 (m, 1H), 3.62 (dd, J=9.9, 4.8 Hz, 1H), 3.57-3.49 (m, 1H), 2.71 (s, 3H), 2.07-1.86 (m, 2H), 1.79-1.70 (m, 2H), 1.46 (s, 9H), 1.41-1.31 (m, 1H), 1.10-0.99 (m, 21H), 0.89 (s, 9H), 0.03 (s, 6H).

Step 2: (1R,3R,4S)-3-({[tert-Butyl(dimethyl)silyl]oxy}methyl)-N-methyl-4-[(triisopropylsilyl)oxy]cyclopentanamine To a solution of tert-butyl {(1R,3R,4S)-3-({[tert-butyl(dimethyl)silyl]oxy}methyl)-4-[(triisopropylsilyl)oxy]cyclopentyl}methylcarbamate (123 mg, 0.24 mmol) in DCM (5.0 mL) was added EtOH (0.07 mL, 1.19 mmol) followed by ZnBr₂ (538 mg, 2.39 mmol) at rt, and the mixture was stirred for 63 h. The reaction was quenched by addition of saturated 1 M NaOH and extracted with DCM (×3). The combined organic layers were dried over Na₂SO₄, filtered, and concentrated in vacuo. The residue was purified by silica gel column chromatography to give (1R,3R,4S)-3-({[tert-butyl(dimethyl)silyl]oxy}methyl)-N-methyl-4-[(triisopropylsilyl)oxy]cyclopentanamine (82 mg, 82%) as light brown oil. LCMS (FA): m/z=416.6 (M+H).

Step 3: [1-(3-Bromobenzyl)-1H-pyrazol-3-yl]{4-[{(1R,3R,4S)-3-({[tert-butyl(dimethyl)silyl]oxy}methyl)-4-[(triisopropylsilyl)oxy]cyclopentyl}(methyl)amino]pyrimidin-5-yl}methanone To a solution of (1R,3R,4S)-3-({([tert-butyl(dimethyl)silyl]oxy}methyl)-N-methyl-4-[(triisopropylsilyl)oxy]cyclopentanamine (80 mg, 0.19 mmol) in DMF (2.0 mL) was added K₂CO₃ (80 mg, 0.58 mmol) followed by [1-(3-bromobenzyl)-1H-pyrazol-3-yl](4-chloropyrimidin-5-yl)methanone (73 mg, 0.19 mmol) at rt, and the mixture was stirred for 1 h. The reaction was quenched by addition of water (50 mL) and extracted with EtOAc:Hexane (1:1) (50 mL×4). The combined organic layers were dried over Na₂SO₄, filtered, and concentrated in vacuo. The residue was purified on silica gel to give [1-(3-bromobenzyl)-1H-pyrazol-3-yl]{4-[{(1R,3R,4S)-3-({[tert-butyl(dimethyl)silyl]oxy}methyl)-4-[(triisopropylsilyl)oxy]cyclopentyl}(methyl)amino]pyrimidin-5-yl}methanone (121 mg, 83%) as a colorless oil. LCMS (FA): m/z=758.6 (M+H).

Step 4: [1-(3-Bromobenzyl)-1H-pyrazol-3-yl]{4-[{(1R,3R,4S)-3-(hydroxymethyl)-4-[(triisopropylsilyl)oxy]cyclopentyl}(methyl)amino]pyrimidin-5-yl}methanone To a solution of [1-(3-bromobenzyl)-1H-pyrazol-3-yl]{4-[{(1R,3R,4S)-3-({[tert-butyl(dimethyl)silyl]oxy}methyl)-4-[(triisopropylsilyl)oxy]cyclopentyl}(methyl)amino]pyrimidin-5-yl}methanone (115 mg, 0.15 mmol) in EtOH (4 mL) was added 1% HCl in EtOH (4.0 mL, 0.32 mmol) at rt, and the mixture was allowed to stand at 4° C. for 16 h. The reaction was quenched by addition of saturated NaHCO₃ (50 mL) and extracted with EtOAc (50 mL×3). The combined organic layers were dried over Na₂SO₄, filtered, and concentrated in vacuo. The residue was purified on silica gel to give [1-(3-bromobenzyl)-1H-pyrazol-3-yl]{4-[{(1R,3R,4S)-3-(hydroxymethyl)-4-[(triisopropylsilyl)oxy]cyclopentyl}(methyl)amino]pyrimidin-5-yl}methanone (91 mg, 93%). LCMS (FA): m/z=644.6 (M+H).

Step 5: {(1R,2S,4R)-4-[(5-{[1-(3-Bromobenzyl)-1H-pyrazol-3-yl]carbonyl}pyrimidin-4-yl)(methyl)amino]-2-hydroxycyclopentyl}methyl sulfamate I-157

To a solution of [1-(3-bromobenzyl)-1H-pyrazol-3-yl]{4-[{(1R,3R,4S)-3-(hydroxymethyl)-4-[(triisopropylsilyl)oxy]cyclopentyl}(methyl)amino]pyrimidin-5-yl}methanone (88.0 mg, 0.14 mmol) in DMF (2.0 mL) was added chlorosulfonamide (31.6 mg, 0.27 mmol) at rt, and the mixture was stirred for 10 min. The reaction was quenched by addition of saturated NaHCO₃ (40 mL) and extracted with EtOAc (50 mL×3). The combined organic layers were dried over Na₂SO₄, filtered, and concentrated in vacuo. The residue was purified on silica gel to give the sulfamate intermediate [(95 mg, 91%); LCMS (FA): m/z=723.6 (M+H).] which was dissolved in THF (2 mL). To this solution was added HCl (4.0 M solution in water; 2.0 mL, 8.0 mmol) at rt, and the mixture was allowed to stand at 4° C. for 14 h and then warmed to room temp for 4 h. The reaction was quenched by addition of saturated NaHCO₃ (60 mL) and the mixture was extracted with EtOAc (50 mL×3). The combined organic layers were dried over Na₂SO₄, filtered, and concentrated in vacuo. The residue was purified on silica gel to give {(1R,2S,4R)-4-[(5-{[1-(3-bromobenzyl)-1H-pyrazol-3-yl]carbonyl}pyrimidin-4-yl)(methyl)amino]-2-hydroxycyclopentyl}methyl sulfamate (59 mg, 86%). ¹H NMR (DMSO) δ 8.57 (s, 1H), 8.39 (s, 1H), 8.09 (d, J=2.4 Hz, 1H), 7.52 (d, J=7.9 Hz, 1H), 7.48 (s, 1H), 7.43 (s, 2H), 7.33 (t, J=7.8 Hz, 1H), 7.22 (d, J=7.7 Hz, 1H), 6.94 (d, J=2.4 Hz, 1H), 5.47 (s, 2H), 5.23-5.09 (m, 1H), 4.88 (d, J=4.5 Hz, 1H), 4.12-4.04 (m, 1H), 3.99-3.85 (m, 2H), 2.09-1.98 (m, 1H), 1.96-1.75 (m, 3H), 1.70-1.59 (m, 1H), 1.35-1.22 (m, 1H); LCMS (FA): m/z=567.3 (M+H).

Example 62: {(1R,2S,4R)-4-[(5-{[1-(3-Chlorobenzyl)-5-(trifluoromethyl)-1H-pyrazol-3-yl]carbonyl}pyrimidin-4-yl)amino]-2-hydroxycyclopentyl}methyl sulfamate I-170

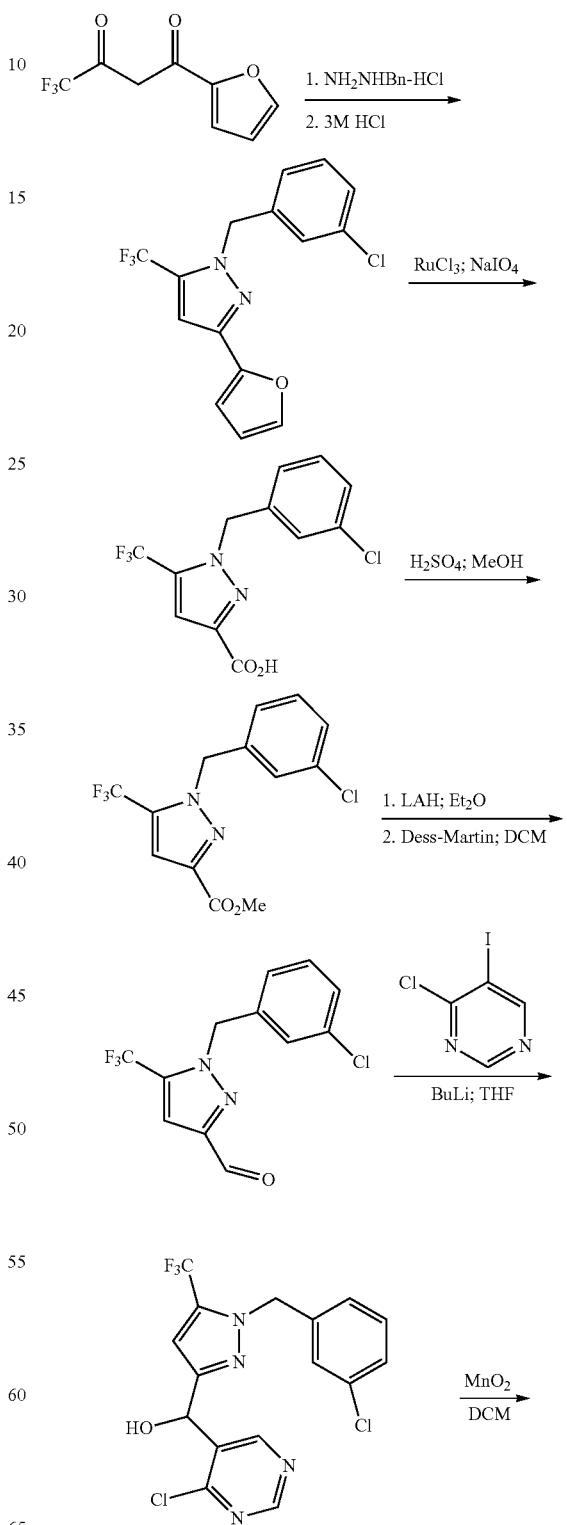

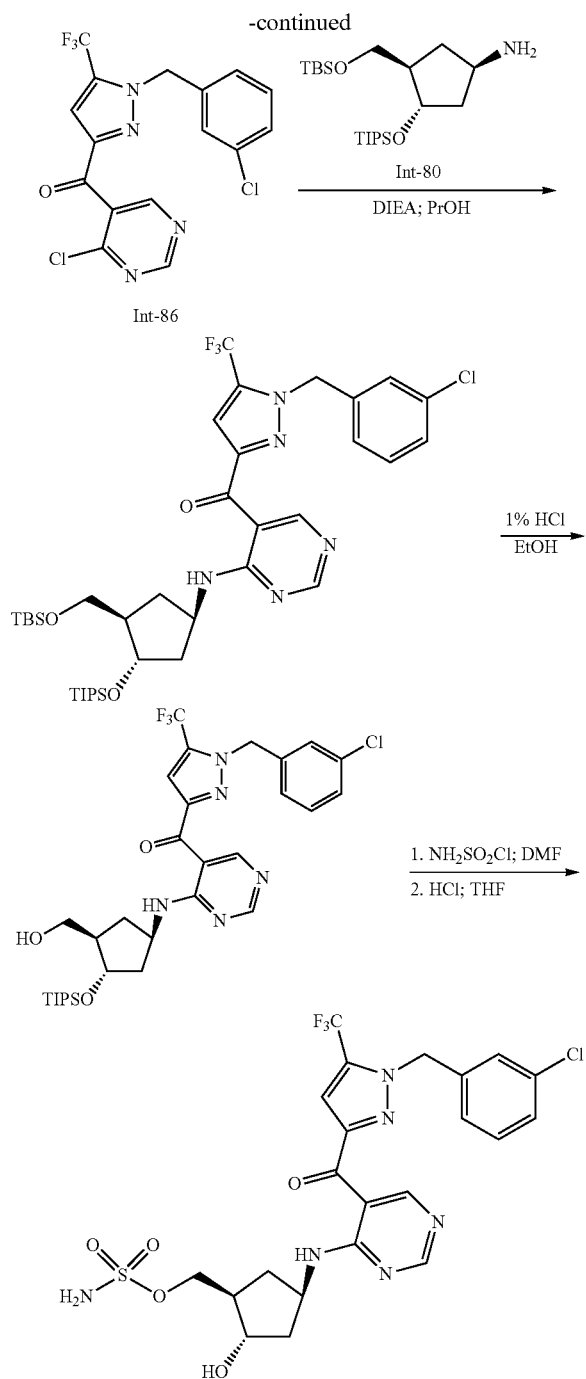

Step 1: 1-(3-Chlorobenzyl)-3-(2-furyl)-5-(trifluoromethyl)-1H-pyrazole

DIEA (0.90 mL, 5.2 mmol) was added to a solution of 2-furoyltrifluoroacetone (0.71 g, 3.4 mmol) in EtOH (6 mL) at rt. (3-Chlorobenzyl)hydrazine hydrochloride (1.0 g, 5.2 mmol) was then added in portions. The resulting light orange solution was allowed to stir at rt for 14 h. The reaction mixture was then concentrated and the residue dissolved in EtOAc. This solution was then washed with water and brine. The organic layer was dried over MgSO$_4$, filtered, and concentrated. The crude product was purified on silica gel to give the pyrazolinol intermediate (0.90 g, 76%).

LCMS (FA): m/z=345 (M+H). The pyrazolinol intermediate was dissolved in THF (11 mL) and HCl (3.0 M solution in water; 2.6 mL, 7.8 mmol) was added. The resulting solution was heated to reflux with stirring. After 45 min LCMS showed the reaction to be complete. The reaction was allowed to cool to rt and quenched by the addition of a saturated NaHCO$_3$ solution. The mixture was extracted with EtOAc (2×). The combined organic extracts were dried over MgSO$_4$, filtered, and concentrated to give 1-(3-chlorobenzyl)-3-(2-furyl)-5-(trifluoromethyl)-1H-pyrazole (0.76 g, 89%). LCMS (FA): m/z=327 (M+H).

Step 2: 1-(3-Chlorobenzyl)-5-(trifluoromethyl)-1H-pyrazole-3-carboxylic acid

To a solution of 1-(3-chlorobenzyl)-3-(2-furyl)-5-(trifluoromethyl)-1H-pyrazole (0.75 g, 2.3 mmol) in acetonitrile (7 mL) was added carbon tetrachloride (7 mL) and water (9.8 mL). Sodium metaperiodate (2.7 g, 12 mmol) and ruthenium (III) chloride hydrate (0.052 g, 0.23 mmol) were added to this mixture. After stirring 20 min at rt TLC showed the reaction was complete. 1N NaOH (10 mL) was added to the reaction mixture which was extracted with EtOAc (2×). The organic extracts were discarded. The aqueous layer was acidified and extracted with EtOAc (3×). The combined organic extracts were dried over MgSO$_4$, filtered, and concentrated to yield 1-(3-chlorobenzyl)-5-(trifluoromethyl)-1H-pyrazole-3-carboxylic acid (0.37 g, 53%). LCMS (FA): m/z=182 (M+H).

Step 3: Methyl 1-(3-chlorobenzyl)-5-(trifluoromethyl)-1H-pyrazole-3-carboxylate

Concentrated sulfuric acid (0.1 mL, 2 mmol) was added to a solution of 1-(3-chlorobenzyl)-5-(trifluoromethyl)-1H-pyrazole-3-carboxylic acid (0.36 g, 1.2 mmol) in methanol (10 mL). The resulting solution was heated at 60° C. with stirring for 3 h. The reaction mixture was then concentrated and purified on silica gel to afford methyl 1-(3-chlorobenzyl)-5-(trifluoromethyl)-1H-pyrazole-3-carboxylate (0.30 g, 80%). LCMS (FA): m/z=319 (M+H).

Step 4: 1-(3-Chlorobenzyl)-5-(trifluoromethyl)-1H-pyrazole-3-carbaldehyde

Lithium aluminum hydride (1.0 M solution in THF; 0.94 mL, 0.94 mmol) was added to an ice-bath cooled solution of 1-(3-chlorobenzyl)-5-(trifluoromethyl)-1H-pyrazole-3-carboxylate (0.30 g, 0.94 mmol) in ether (4.9 mL). The resulting solution was stirred at 0° C. for 30 min. The reaction was quenched with water (~1 mL) at 0° C. Na$_2$SO$_4$ dodecahydrate (~2 g) was added along with EtOAc (15 mL) and the mixture was allowed to warm to rt and stir 18 h. The mixture was filtered and the solid washed with EtOAc. The filtrate was concentrated to give the alcohol intermediate [LCMS (FA): m/z=291 (M+H).] which was then dissolved in DCM (15 mL). Dess-Martin periodinane (0.73 g, 1.72 mmol) was added and the reaction was allowed to stir at rt for 1 h. The reaction mixture was then concentrated and the crude material purified on silica gel to provide 1-(3-chlorobenzyl)-5-(trifluoromethyl)-1H-pyrazole-3-carbaldehyde (226 mg, 83%). LCMS (FA): m/z=289 (M+H).

Step 5: [1-(3-Chlorobenzyl)-5-(trifluoromethyl)-1H-pyrazol-3-yl](4-chloropyrimidin-5-yl)methanol 4-Chloro-5-iodopyrimidine (167 mg, 0.69 mmol) was weighed into a 100 mL flame dried RBF under argon. The solid was dissolved in THF (4.9 mL) and the solution was cooled to −78° C. in a dry ice-acetone bath. To this solution was added dropwise n-butyllithium (2.5 M solution in hexanes; 0.55 mL, 1.39 mmol) and the resulting mixture was stirred for 45 min at −78° C. To the mixture was added dropwise a solution of 1-(3-chlorobenzyl)-5-(trifluoromethyl)-1H-pyrazole-3-carbaldehyde (0.22 g, 0.76 mmol) in THF (2.4 mL) at −78° C., and the resulting mixture was stirred for 30 min. The reaction was warmed to rt and subsequently quenched by the addition of saturated NH₄Cl (10 mL). After dilution with water, the mixture was extracted with EtOAc (3×). The combined organic layers were dried over MgSO₄, filtered, and concentrated. The residue was purified on silica gel to yield [1-(3-chlorobenzyl)-5-(trifluoromethyl)-1H-pyrazol-3-yl](4-chloropyrimidin-5-yl)methanol (240 mg, 86%). LCMS (FA): m/z=403 (M+H).

Step 6: [1-(3-Chlorobenzyl)-5-(trifluoromethyl)-1H-pyrazol-3-yl](4-chloropyrimidin-5-yl)methanone To a solution of [1-(3-chlorobenzyl)-5-(trifluoromethyl)-1H-pyrazol-3-yl](4-chloropyrimidin-5-yl)methanol (0.24 g, 0.60 mmol) in DCM (7.2 mL) was added manganese(IV) oxide (0.62 g, 7.1 mmol), and the mixture was stirred at rt for 16 h. Additional manganese(IV) oxide (0.21 g, 2.4 mmol) was then added and the mixture continued to stir at rt an additional 24 h. The reaction mixture was then filtered through a celite pad and the residual solid was washed with DCM and EtOAc several times. The filtrate was concentrated to give [1-(3-chlorobenzyl)-5-(trifluoromethyl)-1H-pyrazol-3-yl](4-chloropyrimidin-5-yl)methanone (220 mg, 92%). LCMS (FA): m/z=401 (M+H).

Step 7: [4-({(1R,3R,4S)-3-({[tert-Butyl(dimethyl)silyl]oxy}methyl)-4-[(triisopropylsilyl)oxy]cyclopentyl}amino)pyrimidin-5-yl][1-(3-chlorobenzyl)-5-(trifluoromethyl)-1H-pyrazol-3-yl]methanone Int-86

[1-(3-chlorobenzyl)-5-(trifluoromethyl)-1H-pyrazol-3-yl](4-chloropyrimidin-5-yl)methanone (110 mg, 0.27 mmol) and (1R,3R,4S)-3-({[tert-butyl(dimethyl)silyl]oxy}methyl)-4-[(triisopropylsilyl)oxy]cyclopentanamine (0.13 g, 0.33 mmol) were weighed into a reaction vessel with stirbar. To this mixture was added 1-propanol (3.3 mL) and DIEA (0.14 mL, 0.82 mmol). The resulting mixture was sealed and the vessel allowed to stir while heating at 35° C. After 16 h the reaction was cooled to rt and the reaction was concentrated. The crude product was purified on silica gel to afford [4-({(1R,3R,4S)-3-({[tert-butyl(dimethyl)silyl]oxy}methyl)-4-[(triisopropylsilyl)oxy]cyclopentyl}amino)pyrimidin-5-yl][1-(3-chlorobenzyl)-5-(trifluoromethyl)-1H-pyrazol-3-yl]methanone (0.15 g, 73%).

Step 8: [1-(3-Chlorobenzyl)-5-(trifluoromethyl)-1H-pyrazol-3-yl][4-({(1R,3R,4S)-3-(hydroxymethyl)-4-[(triisopropylsilyl)oxy]cyclopentyl}amino)pyrimidin-5-yl]methanone To a solution of [4-({(1R,3R,4S)-3-({[tert-butyl(dimethyl)silyl]oxy}methyl)-4-[(triisopropylsilyl)oxy]cyclopentyl}amino)pyrimidin-5-yl][1-(3-chlorobenzyl)-5-(trifluoromethyl)-1H-pyrazol-3-yl]methanone (0.15 g, 0.20 mmol) in EtOH (4.7 mL) was added 1% HCl in EtOH (4.9 mL, 0.59 mmol) at rt. The reaction vessel was sealed and placed in a refrigerator (4° C.) for 22 h. The reaction was quenched by addition of a saturated aq. solution of NaHCO₃. To the residue was added water which was extracted with EtOAc (4×). The combined organic layers were dried over MgSO₄, filtered, and concentrated. The residue was purified on silica gel to give [1-(3-chlorobenzyl)-5-(trifluoromethyl)-1H-pyrazol-3-yl][4-({(1R,3R,4S)-3-(hydroxymethyl)-4-[(triisopropylsilyl)oxy]cyclopentyl}amino)pyrimidin-5-yl]methanone (0.12 g, 94%). LCMS (FA): m/z=653 (M+H).

Step 9: {(1R,2S,4R)-4-[(5-{[1-(3-Chlorobenzyl)-5-(trifluoromethyl)-1H-pyrazol-3-yl]carbonyl}pyrimidin-4-yl)amino]-2-hydroxycyclopentyl}methyl sulfamate I-170

To a solution of [1-(3-chlorobenzyl)-5-(trifluoromethyl)-1H-pyrazol-3-yl][4-({(1R,3R,4S)-3-(hydroxymethyl)-4-[(triisopropylsilyl)oxy]cyclopentyl}amino)pyrimidin-5-yl]methanone (0.11 g, 0.17 mmol) in DMF (2.6 mL) and TEA (0.071 mL, 0.51 mmol) was added chlorosulfonamide (0.049 g, 0.42 mmol) at rt, and the mixture was allowed to stir for 10 min. The reaction was quenched with sat NaHCO₃, and then extracted with EtOAc (4×). The combined organic layers were dried over MgSO₄, filtered and concentrated to give the crude sulfamate intermediate which was immediately dissolved in THF (5.5 mL). HCl (3.0 M solution in water; 1.1 mL, 3.2 mmol) was added to the solution. The reaction was allowed to stir for 15 h at rt then at 40-45° C. for 6 h. The reaction was then quenched with sat NaHCO₃, and extracted with EtOAc (4×). The combined organic layers were dried over MgSO₄, filtered and concentrated. The crude product was purified on silica gel to afford {(1R,2S,4R)-4-[(5-{[1-(3-chlorobenzyl)-5-(trifluoromethyl)-1H-pyrazol-3-yl]carbonyl}pyrimidin-4-yl)amino]-2-hydroxycyclopentyl}methyl sulfamate I-number (68 mg, 72%). ¹H NMR (DMSO) δ 9.36 (d, J=4.9 Hz, 1H), 8.96 (d, J=7.4 Hz, 1H), 8:67 (s, 1H), 7.54 (s, 1H), 7.45 (s, 2H), 7.43-7.40 (m, 2H), 7.34 (s, 1H), 7.18-7.08 (m, 1H), 5.70 (s, 2H), 4.93 (d, J=4.5 Hz, 1H), 4.82-4.67 (m, 1H), 4.12 (dd, J=9.7, 5.9 Hz, 1H), 4.04-3.93 (m, 2H), 2.43-2.31 (m, 1H), 2.20-2.09 (m, 1H), 2.08-1.99 (m, 1H), 1.86-1.72 (m, 1H), 1.37-1.25 (m, 1H); LCMS (FA): m/z=575.5 (M+H).

Example 63: {(1R,2S,4R)-4-[(5-{[1-(3-Bromobenzyl)-5-methyl-1H-pyrazol-3-yl]carbonyl}pyrimidin-4-yl)amino]-2-hydroxycyclopentyl}methyl sulfamate I-309

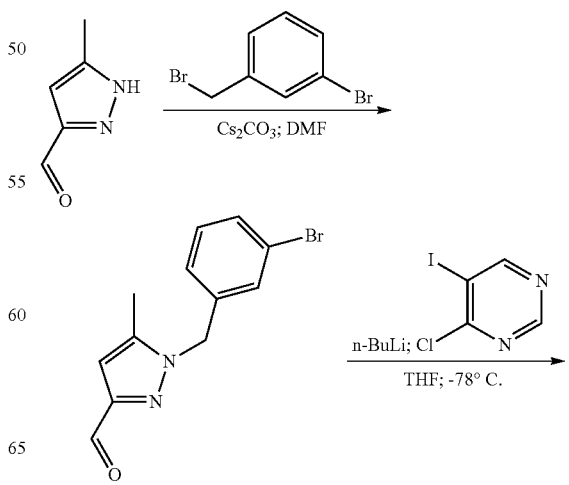

-continued

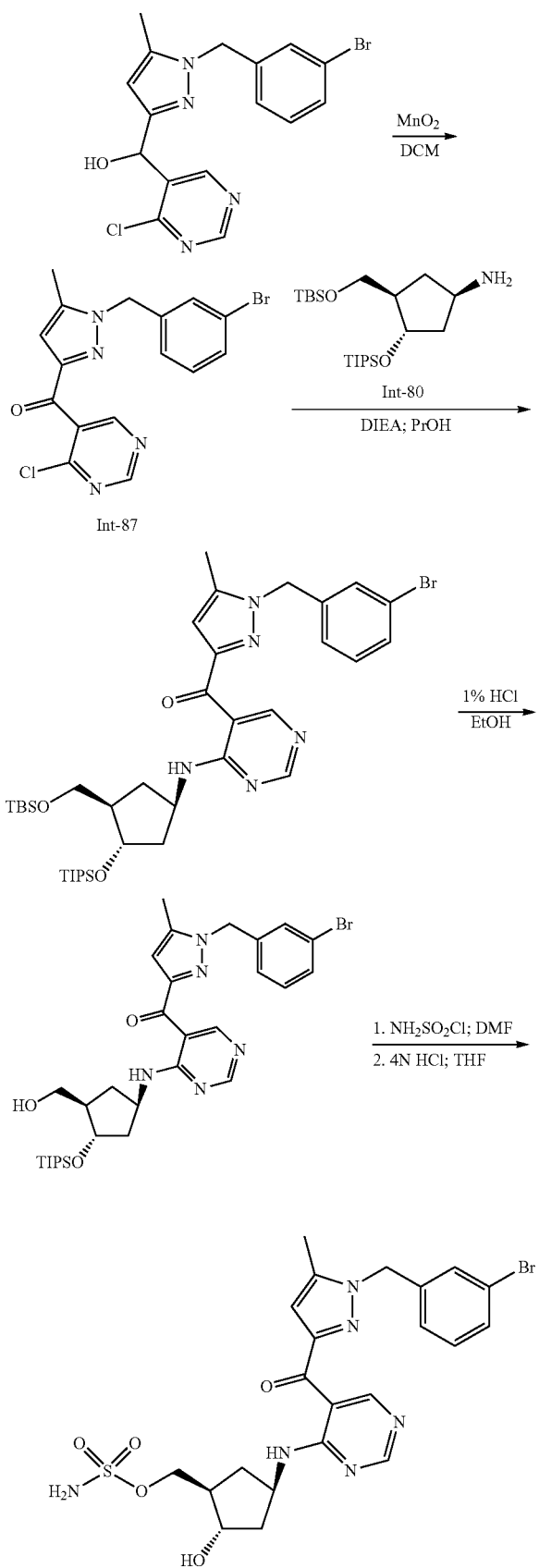

Int-87

Step 1: 1-(3-Bromobenzyl)-5-methyl-1H-pyrazole-3-carbaldehyde

5-Methyl-2H-pyrazole-3-carbaldehyde (0.99 g, 9.0 mmol) was dissolved in DMF (35 mL). To this solution was added cesium carbonate (7.3 g, 22.5 mmol) and 3-bromobenzyl bromide (2.5 g, 9.9 mmol) and the reaction was stirred at rt for 1 h. The reaction was quenched by addition of water. This mixture was then extracted with EtOAc (3×). The combined organic layers were dried over $MgSO_4$, filtered and concentrated. The residue was purified on silica gel to give 1-(3-bromobenzyl)-5-methyl-1H-pyrazole-3-carbaldehyde (1.7 g, 68%). LCMS (FA): m/z=281.0 (M+H).

Step 2: [1-(3-Bromobenzyl)-5-methyl-1H-pyrazol-3-yl](4-chloropyrimidin-5-yl)methanol Into a flame dried RBF with stirbar was added 4-chloro-5-iodopyrimidine (1.6 g, 6.7 mmol) dissolved in THF (23 mL). The flask was purged with argon and cooled to −78° C. To this solution was added dropwise n-butyllithium (2.5 M in hexane; 5.6 mL, 14.0 mmol) at −78° C. and the mixture was stirred for 30 min. To this mixture was added 1-(3-bromobenzyl)-5-methyl-1H-pyrazole-3-carbaldehyde (1.7 g, 6.1 mmol) dissolved in THF (4.3 mL) dropwise. The reaction was stirred at −78° C. for 2 h. The reaction was quenched with a saturated solution of $NH_4Cl$ and then extracted with EtOAc (3×). The combined organic layers were then washed with wafer and brine, dried over $Na_2SO_4$, filtered and concentrated. The crude product was purified on silica gel to give [1-(3-bromobenzyl)-5-methyl-1H-pyrazol-3-yl](4-chloropyrimidin-5-yl)methanol (2.0 g, 82%). LCMS (FA): m/z=395.2 (M+H).

Step 3: [1-(3-Bromobenzyl)-5-methyl-1H-pyrazol-3-yl](4-chloropyrimidin-5-yl)methanone Int-87

To a solution of [1-(3-bromobenzyl)-5-methyl-1H-pyrazol-3-yl](4-chloropyrimidin-5-yl)methanol (2.0 g, 5.0 mmol) in DCM (32 mL) was added manganese(IV) oxide (4.34 g, 50 mmol). The suspension was stirred for 19 h at rt. The reaction was then filtered through a celite pad and the residual solid was washed with DCM several times. The filtrate was then concentrated in vacuo and the residue was purified on silica gel to afford [1-(3-bromobenzyl)-5-methyl-1H-pyrazol-3-yl](4-chloropyrimidin-5-yl)methanone (1.44 g, 74%). LCMS (FA): m/z=393.1 (M+H).

Step 4: [1-(3-Bromobenzyl)-5-methyl-1H-pyrazol-3-yl][4-({(1R,3R,4S)-3-({[tert-butyl(dimethyl)silyl]oxy}methyl)-4-[(triisopropylsilyl)oxy]cyclopentyl}amino)pyrimidin-5-yl]methanone

[1-(3-bromobenzyl)-5-methyl-1H-pyrazol-3-yl](4-chloropyrimidin-5-yl)methanone (0.77 g, 2.0 mmol) and (1R,3R,4S)-3-({[tert-butyl(dimethyl)silyl]oxy}methyl)-4-[(triisopropylsilyl)oxy]cyclopentanamine (0.79 g, 2.0 mmol) were stirred as a mixture in 2-propanol (22 mL) and DIEA (1.0 mL, 5.9 mmol) at rt for 18 h. The reaction was then concentrated and the crude product was purified on silica gel to afford [1-(3-bromobenzyl)-5-methyl-1H-pyrazol-3-yl][4-({(1R,3R,4S)-3-({[tert-butyl(dimethyl)silyl]oxy}methyl)-4-[(triisopropylsilyl)oxy]cyclopentyl}amino)pyrimidin-5-yl]methanone (1.17 g, 78%).

Step 5: [1-(3-Bromobenzyl)-5-methyl-1H-pyrazol-3-yl][4-({(1R,3R,4S)-3-(hydroxymethyl)-4-[(triisopropylsilyl)oxy]cyclopentyl}amino)pyrimidin-5-yl]methanone To a solution of [1-(3-bromobenzyl)-5-methyl-1H-pyrazol-3-yl][4-({(1R,3R,4S)-3-({[tert-butyl(dimethyl)silyl]

oxy}methyl)-4-[(triisopropylsilyl)oxy]cyclopentyl}amino)pyrimidin-5-yl]methanone (1.17 g, 1.5 mmol) in EtOH (11 mL) was added 1% HCl in EtOH (15.3 mL, 1.9 mmol) at rt. The solution was stirred at rt for 3 h. The reaction was quenched by addition of a saturated aq. solution of NaHCO$_3$. To the residue was added water which was extracted with EtOAc (4×). The combined organic layers were dried over MgSO$_4$, filtered, and concentrated. The residue was purified on silica gel to give [1-(3-bromobenzyl)-5-methyl-1H-pyrazol-3-yl][4-({(1R,3R,4S)-3-(hydroxymethyl)-4-[(triisopropylsilyl)oxy]cyclopentyl}amino)pyrimidin-5-yl]methanone (0.68 g, 69%). LCMS (FA): m/z=644.5 (M+H).

Step 6: {(1R,2S,4R)-4-[(5-{[1-(3-Bromobenzyl)-5-methyl-1H-pyrazol-3-yl]carbonyl}pyrimidin-4-yl)amino]-2-hydroxycyclopentyl}methyl sulfamate I-309

To a solution of [1-(3-bromobenzyl)-5-methyl-1H-pyrazol-3-yl][4-({(1R,3R,4S)-3-(hydroxymethyl)-4-[(triisopropylsilyl)oxy]cyclopentyl}amino)pyrimidin-5-yl]methanone (0.68 g, 1.1 mmol) and TEA (0.44 mL, 3.2 mmol) in DMF (8 mL) was added chlorosulfonamide (0.36 g, 3.2 mmol) at rt, and the mixture was stirred for 2 h. HCl (3.0 M in water; 10 mL, 30 mmol) was then added to the solution. The reaction was stirred for 30 min at rt and then quenched by the addition of a saturated solution of NaHCO$_3$ and extracted with EtOAc (4×). The combined organic layers were dried over MgSO$_4$, filtered, and concentrated. The residue was purified on silica gel to afford {(1R,2S,4R)-4-[(5-{[1-(3-bromobenzyl)-5-methyl-1H-pyrazol-3-yl]carbonyl}pyrimidin-4-yl)amino]-2-hydroxycyclopentyl}methyl sulfamate (0.35 g, 59%). $^1$H NMR (DMSO) δ 9.48 (s, 1H), 9.02 (d, J=7.3 Hz, 1H), 8.63 (s, 1H), 7.52 (d, J=8.0 Hz, 1H), 7.45 (s, 2H), 7.41 (s, 1H), 7.34 (t, J=7.9 Hz, 1H), 7.13 (d, J=8.2 Hz, 1H), 6.73 (d, J=0.7 Hz, 1H), 5.50 (s, 2H), 4.92 (d, J=4.6 Hz, 1H), 4.78-4.63 (m, 1H), 4.14-4.05 (m, 1H), 4.04-3.91 (m, 2H), 2.42-2.33 (m, 1H), 2.30 (s, 3H), 2.18-2.06 (m, 1H), 2.04-1.94 (m, 1H), 1.86-1.71 (m, 1H), 1.34-1.24 (m, 1H); LCMS (FA): m/z=568.1 (M+H).

The compounds listed in the table below were prepared using a similar method to that described above starting from the appropriate starting materials. The following alternative conditions could be employed in the described reaction steps. Step 1: K$_2$CO$_3$ instead of Cs$_2$CO$_3$; THF instead of DMF. Step 3: Dess-Martin oxidation instead of manganese dioxide. Step 4: K$_2$CO$_3$/DMF; DIEA/2-propanol instead of DIEA/1-propanol. Step 5: aq. TFA and aq. H$_3$PO$_4$ instead of aq. HCl. I-172 and I-365 were made as a mixture of diastereomers (benzylic methyl) then separated via HPLC (chiral column). Absolute configuration of the undefined stereocenter is unknown.

| Starting material | Compound No. | LCMS Data |
|---|---|---|
| 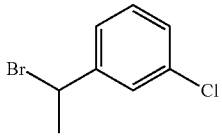 | I-347 | LCMS (FA): m/z = 613.4 (M + H). |
| 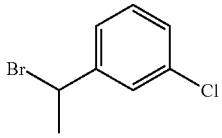 Int-1 | I-172 | LCMS (FA): m/z = 535.0 (M + H). |
| 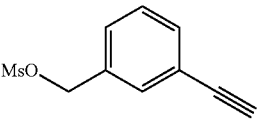 Int-1 | I-365 | LCMS (FA): m/z = 535.0 (M + H). |
| 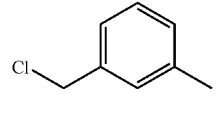 Int-44 | I-164 | LCMS (FA): m/z = 511 (M + H). |
| 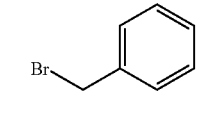 | I-248 | LCMS (FA): m/z = 501 (M + H). |
| 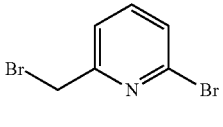 | I-66 | LCMS (FA): m/z = 487.5 (M + H). |
| 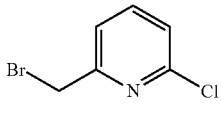 | I-238 | LCMS (FA): m/z = 568.4 (M + H). |
| 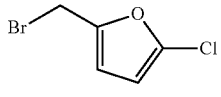 | I-99 | LCMS (FA): m/z = 522.3 (M + H). |
|  | I-101 | LCMS (FA): m/z = 511.4 (M + H). |

Example 64: [(1S,2S,4R)-4-[(5-{[1-(3-Bromobenzyl)-5-methyl-1H-pyrazol-3-yl]carbonyl}pyrimidin-4-yl)amino]-2-{[tert-butyl(dimethyl)silyl]oxy}cyclopentyl]methyl sulfamate I-6

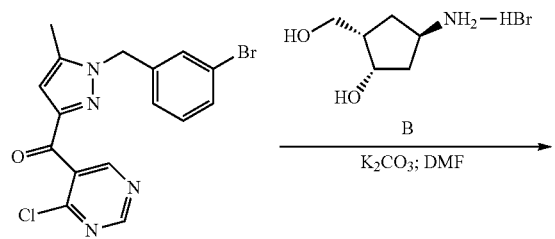

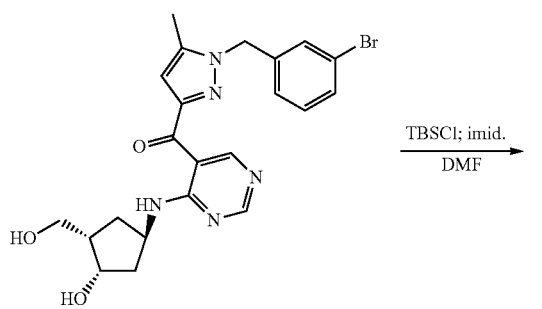

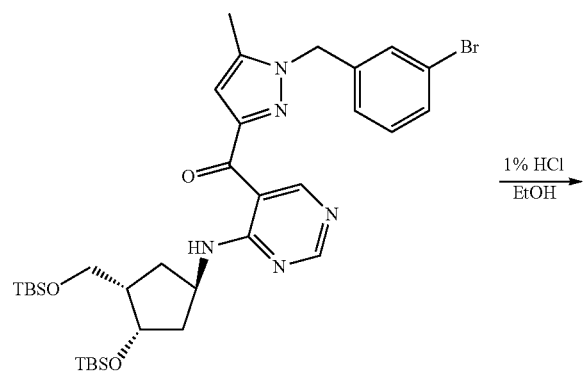

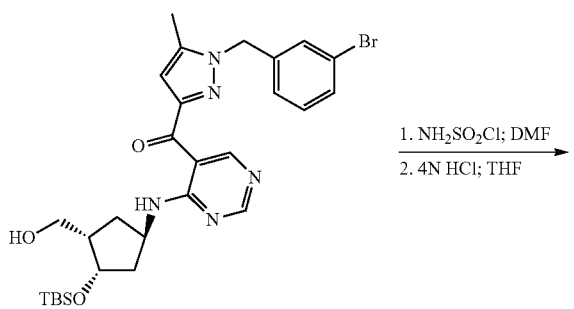

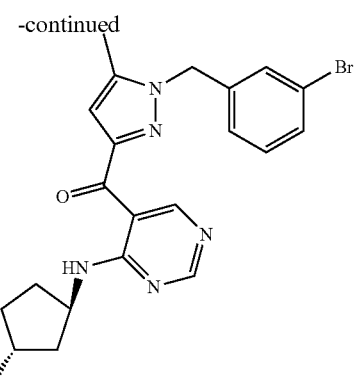

Step 1: [1-(3-Bromobenzyl)-5-methyl-1H-pyrazol-3-yl](4-{[(1R,3S,4S)-3-hydroxy-4-(hydroxymethyl)cyclopentyl]amino}pyrimidin-5-yl)methanone B (0.14 g, 0.68 mmol) and [1-(3-bromobenzyl)-5-methyl-1H-pyrazol-3-yl](4-chloropyrimidin-5-yl)methanone (0.22 g, 0.56 mmol) were weighed into a round bottomed flask with stirbar. The mixture was dissolved in DMF (4 mL). Potassium carbonate (0.2 g, 1.4 mmol) was added to the reaction vessel at rt and the resulting mixture was stirred at 80° C. for 1 h. The reaction was then diluted with EtOAc and filtered through a pad of celite. The filtrate was concentrated. The resulting residue was dissolved in EtOAc and the mixture was washed with water and brine, dried over $Na_2SO_4$, filtered and concentrated. The crude product was purified on silica gel to provide [1-(3-bromobenzyl)-5-methyl-1H-pyrazol-3-yl](4-{[(1R,3S,4S)-3-hydroxy-4-(hydroxymethyl)cyclopentyl]amino}pyrimidin-5-yl)methanone (0.17 g, 63%). LCMS (FA): m/z=488 (M+H).

Step 2: [1-(3-Bromobenzyl)-5-methyl-1H-pyrazol-3-yl](4-{[(1R,3S,4S)-3-{[tert-butyl(dimethyl)silyl]oxy}-4-({[tert-butyl(dimethyl)silyl]oxy}methyl)cyclopentyl]amino}pyrimidin-5-yl)methanone To a solution of [1-(3-bromobenzyl)-5-methyl-1H-pyrazol-3-yl](4-{[(1R,3S,4S)-3-hydroxy-4-(hydroxymethyl)cyclopentyl]amino}pyrimidin-5-yl)methanone (170 mg, 0.35 mmol) in DMF (6 mL) was added DMAP (2.2 mg, 0.02 mmol), imidazole (0.12 g, 1.8 mmol) followed by tert-butyldimethylsilyl chloride (0.13 g, 0.88 mmol) at rt, and the mixture was stirred for 12 h. The reaction was then quenched by addition of water and extracted with EtOAc (3×). The combined organic layers were washed with brine, dried over $MgSO_4$, filtered, and concentrated. The residue was purified on silica gel to give [1-(3-bromobenzyl)-5-methyl-1H-pyrazol-3-yl](4-{[(1R,3S,4S)-3-{[tert-butyl(dimethyl)silyl]oxy}-4-({[tert-butyl(dimethyl)silyl]oxy}methyl)cyclopentyl]amino}pyrimidin-5-yl)methanone (0.20 g, 79%). LCMS (FA): m/z=716 (M+H).

Step 3: [1-(3-Bromobenzyl)-5-methyl-1H-pyrazol-3-yl](4-{[(1R,3S,4S)-3-{[tert-butyl(dimethyl)silyl]oxy}-4-(hydroxymethyl)cyclopentyl]amino}pyrimidin-5-yl)methanone To a solution of [1-(3-bromobenzyl)-5-methyl-1H-pyrazol-3-yl](4-{[(1R,3S,4S)-3-{[tert-butyl(dimethyl)silyl]oxy}-4-({[tert-butyl(dimethyl)silyl]oxy}methyl)cyclopentyl]amino}pyrimidin-5-yl)methanone (0.20 g, 0.28 mmol) in EtOH (3.5 mL) was added 1% HCl in EtOH (4.6 mL, 0.56 mmol) at rt. The reaction vessel was sealed and allowed to stand in a refrigerator (4° C.) for 16 h. The reaction was quenched by addition of a saturated aq. solution of NaHCO₃. To the residue was added water which was extracted with EtOAc (4×). The combined organic layers were dried over MgSO₄, filtered, and concentrated. The residue was purified on silica gel to give [1-(3-bromobenzyl)-5-methyl-1H-pyrazol-3-yl](4-{[(1R,3S,4S)-3-{[tert-butyl(dimethyl)silyl]oxy}-4-(hydroxymethyl)cyclopentyl]amino}pyrimidin-5-yl)methanone (136 mg, 81%). LCMS (FA): m/z=602 (M+H).

Step 4: {(1S,2S,4R)-4-[(5-{([1-(3-Bromobenzyl)-5-methyl-1H-pyrazol-3-yl]carbonyl}pyrimidin-4-yl)amino]-2-hydroxycyclopentyl}methyl sulfamate I-6

To a solution of [1-(3-bromobenzyl)-5-methyl-1H-pyrazol-3-yl](4-{[(1R,3S,4S)-3-{[tert-butyl(dimethyl)silyl]oxy}-4-(hydroxymethyl)cyclopentyl]amino}pyrimidin-5-yl)methanone (136 mg, 0.23 mmol) in DMF (2 mL) was added chlorosulfonamide (39 mg, 0.34 mmol) at rt, and the mixture was stirred for 30 min. The reaction was quenched by addition of a saturated solution of NaHCO₃ and diluted with water. The mixture was extracted with EtOAc (4×). The combined organic layers were dried over MgSO₄, filtered, and concentrated. The crude sulfamate intermediate was dissolved in THF (4 mL) and HCl (4.0 M in water; 1 mL, 4 mmol) was added to the solution. The reaction was stirred for 16 h at rt. The reaction was quenched by the addition of a saturated solution of NaHCO₃ and extracted with EtOAc (4×). The combined organic layers were dried over MgSO₄, filtered, and concentrated. The residue was purified by prep HPLC to afford {(1S,2S,4R)-4-[(5-{[1-(3-bromobenzyl)-5-methyl-1H-pyrazol-3-yl]carbonyl}pyrimidin-4-yl)amino]-2-hydroxycyclopentyl}methyl sulfamate (89 mg, 74%). ¹H NMR (MeOD) δ 9.63 (s, 1H), 8.57 (s, 1H), 7.48 (d, J=8.0 Hz, 1H), 7.37 (s, 1H), 7.30 (t, J=7.9 Hz, 1H), 7.17 (d, J=7.7 Hz, 1H), 6.77 (d, J=0.7 Hz, 1H), 5.47 (s, 2H), 4.46-4.39 (m, 1H), 4.35 (dd, J=9.7, 7.7 Hz, 1H), 4.18 (dd, J=9.7, 7.3 Hz, 1H), 2.69-2.50 (m, 1H), 2.41-2.34 (m, 1H), 2.33 (s, 3H), 2.23-2.08 (m, 1H), 1.96-1.75 (m, 2H). LCMS (FA): m/z=567.1 (M+H).

Example 65: [(1R,2S,4R)-4-{[5-({1-[(1R)-1-(3-Ethynylphenyl)ethyl]-1H-pyrazol-3-yl}carbonyl)pyrimidin-4-yl]amino}-2-hydroxycyclopentyl]methyl sulfamate and [(1R,2S,4R)-4-{[5-({1-[(1S)-1-(3-Ethynylphenyl)ethyl]-1H-pyrazol-3-yl}carbonyl)pyrimidin-4-yl]amino}-2-hydroxycyclopentyl]methyl sulfamate I-10/I-355

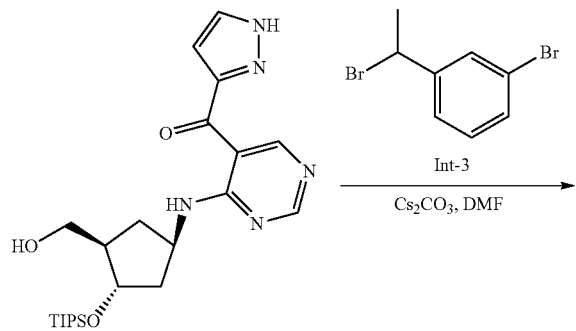

Int-84

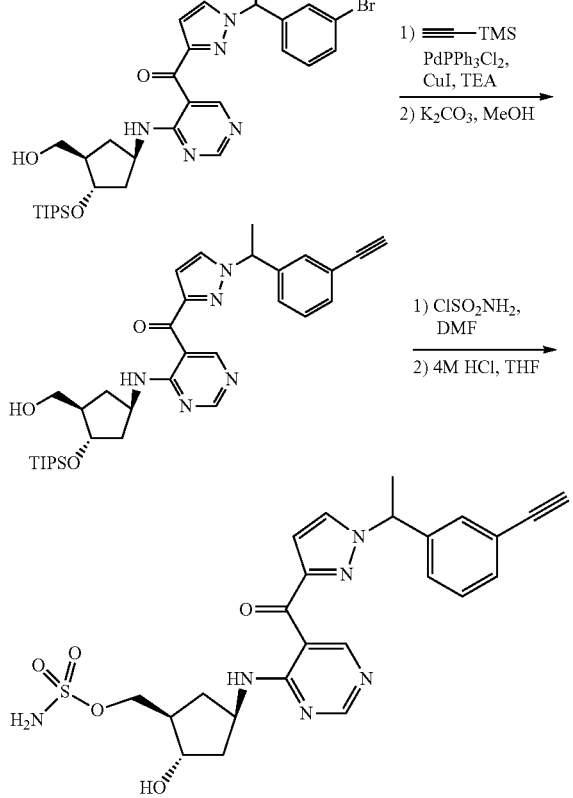

Step 1: {1-[1-(3-Bromophenyl)ethyl]-1H-pyrazol-3-yl}[4-({(1R,3R,4S)-3-(hydroxymethyl)-4-[(triisopropylsilyl)oxy]cyclopentyl}amino)pyrimidin-5-yl]methanone Into a flask was added [4-({(1R,3R,4S)-3-(hydroxymethyl)-4-[(triisopropylsilyl)oxy]cyclopentyl}amino)pyrimidin-5-yl](1H-pyrazol-3-yl)methanone (0.32 g, 0.70 mmol) and DMF (12 mL). To this solution was added cesium carbonate (0.68 g, 2.1 mmol) followed by 1-bromo-3-(1-bromoethyl)benzene (0.28 g, 1.04 mmol). The reaction was allowed to stir at rt for 18 h. The reaction was quenched with water and extracted with EtOAc (3×). The combined organic layers were then washed with water and brine, dried over Na₂SO₄, filtered and concentrated. The crude product was purified on silica gel to give {1-[1-(3-bromophenyl)ethyl]-1H-pyrazol-3-yl}[4-({(1R,3R,4S)-3-(hydroxymethyl)-4-[(triisopropylsilyl)oxy]cyclopentyl}amino)pyrimidin-5-yl]methanone (467 mg, 100%). LCMS (FA); m/z=644.3 (M+H).

Step 2: {1-[1-(3-Ethynylphenyl)ethyl]-1H-pyrazol-3-yl}[4-({(1R,3R,4S)-3-(hydroxymethyl)-4-[(triisopropylsilyl)oxy]cyclopentyl}amino)pyrimidin-5-yl]methanone To a solution of rel-{1-[1-(3-bromophenyl)ethyl]-1H-pyrazol-3-yl}[4-({(1R,3R,4S)-3-(hydroxymethyl)-4-[(triisopropylsilyl)oxy]cyclopentyl}amino)pyrimidin-5-yl]methanone (500 mg, 0.78 mmol) in TEA (2.0 mL) was added bis(triphenylphosphine)palladium(II) chloride (27 mg, 0.039 mmol) and copper(I) iodide (59 mg, 0.31 mmol), followed by (trimethylsilyl)acetylene (660 uL, 4.7 mmol). The reaction was heated at 100° C. for 3 h. Bis(triphenylphosphine)palladium(II) chloride (27 mg, 0.039 mmol), copper(I) iodide (59 mg, 0.31 mmol), and (trimethylsilyl)acetylene (660 uL, 4.7 mmol) were each added again and the reaction heated 18 h at 100° C. Bis(triphenylphosphine)palladium(II) chloride (27 mg, 0.039 mmol), copper(I) iodide (59 mg, 0.31 mmol), and (trimethylsilyl)acetylene (660 uL, 4.7 mmol) were each added a third time and the reaction heated an additional 24 h at 100° C. The reaction mixture was allowed to cool and filtered through celite, washing with EtOAc. This filtrate was washed with 0.1N HCl (aq.) and brine. The organic layer was dried over Na$_2$SO$_4$, filtered and concentrated. The crude product was purified on silica gel to afford the silyl intermediate (150 mg, 29%) [LCMS (FA): m/z=660.6 (M+H).] which was next dissolved in methanol (1.0 mL). Potassium carbonate (150 mg, 1.1 mmol) was added and the reaction stirred for 15 min. The reaction was filtered and the filtrate concentrated. Purification on silica gel gave {(1-[1-(3-Ethynylphenyl)ethyl]-1H-pyrazol-3-yl}[4-({(1R,3R,4S)-3-(hydroxymethyl)-4-[(triisopropylsilyl)oxy]cyclopentyl}amino)pyrimidin-5-yl]methanone (100 mg, 77%). LCMS (FA): m/z=588.6 (M+H).

Step 3: [(1R,2S,4R)-4-{[5-({1-[(1R)-1-(3-Ethynylphenyl)ethyl]-1H-pyrazol-3-yl}carbonyl)pyrimidin-4-yl]amino}-2-hydroxycyclopentyl]methyl sulfamate and [(1R,2S,4R)-4-{[5-({1-[(1S)-1-(3-ethynylphenyl)ethyl]-1H-pyrazol-3-yl}carbonyl)pyrimidin-4-yl]amino}-2-hydroxycyclopentyl]methyl sulfamate I-10/I-355

To a solution of rel-{1-[1-(3-ethynylphenyl)ethyl]-1H-pyrazol-3-yl}[4-({(1R,3R,4S)-3-(hydroxymethyl)-4-[(triisopropylsilyl)oxy]cyclopentyl}amino)pyrimidin-5-yl]methanone (100 mg, 0.17 mmol) in DMF (1.5 mL) was added chlorosulfonamide (39 mg, 0.34 mmol) and the reaction stirred for 30 min at rt. The reaction was quenched with a satd. sodium bicarbonate solution (2 mL) and then the mixture was extracted with EtOAc. The organic layers were dried (Na$_2$SO$_4$), filtered, and evaporated [LCMS (FA): m/z=667.2 (M+H).]. The crude sulfamate intermediate was next dissolved in THF (1.0 mL). Water (1.0 mL) was added followed by conc. HCl (0.4 mL, 5 mmol) and the reaction was allowed to stir for 3 h. It was then quenched with satd. sodium bicarbonate solution and the resulting mixture was extracted with EtOAc. The combined organic layers were washed with water then concentrated. The crude product was purified using prep HPLC (chiral column) to separate diastereomers and give [(1R,2S,4R)-4-{[5-({1-[(1R)-1-(3-ethynylphenyl)ethyl]-1H-pyrazol-3-yl}carbonyl)pyrimidin-4-yl]amino}-2-hydroxycyclopentyl]methyl sulfamate and [(1R,2S,4R)-4-{[5-({1-[(1S)-1-(3-ethynylphenyl)ethyl]-1H-pyrazol-3-yl}carbonyl)pyrimidin-4-yl]amino}-2-hydroxycyclopentyl]methyl sulfamate as equal amounts of each diastereomer (20 mg, 20%). Absolute configuration of the benzylic methyl group for each particular isolated diastereomer is unknown. First eluting peak: $^1$H NMR (MeOD) δ 9.56 (s, 1H), 8.46 (s, 1H), 7.75 (d, J=2.4 Hz, 1H), 7.35-7.14 (m, 4H), 6.85 (d, J=2.4 Hz, 1H), 5.63 (q, J=7.0 Hz, 1H), 4.76-4.65 (m, 1H), 4.16-4.00 (m, 3H), 3.40 (s, 1H), 2.49-2.37 (m, 1H), 2.24-2.12 (m, 1H), 2.12-2.02 (m, 1H), 1.84 (d, J=7.1 Hz, 3H), 1.82-1.75 (m, 1H), 1.41-1.27 (m, 1H). LCMS (FA): m/z=511.2 (M+H); Second eluting peak: $^1$H NMR (MeOD) δ 9.56 (s, 1H), 8.46 (s, 1H), 7.75 (d, J=2.4 Hz, 1H), 7.35-7.16 (m, 4H), 6.85 (d, J=2.4 Hz, 1H), 5.63 (q, J=7.0 Hz, 1H), 4.74-4.65 (m, 1H), 4.17-3.95 (m, 3H), 3.40 (s, 1H), 2.49-2.35 (m, 1H), 2.23-2.13 (m, 1H), 2.13-2.03 (m, 1H), 1.84 (d, J=7.1 Hz, 3H), 1.82-1.76 (m, 1H), 1.41-1.25 (m, 1H). LCMS (FA): m/z=511.2 (M+H).

Example 66: {(1R,2S,4R)-4-[(5-{[1-(3-Bromobenzyl)-4-chloro-1H-pyrazol-3-yl]carbonyl}pyrimidin-4-yl)amino]-2-[(triisopropylsilyl)oxy]cyclopentyl}methyl sulfamate I-111

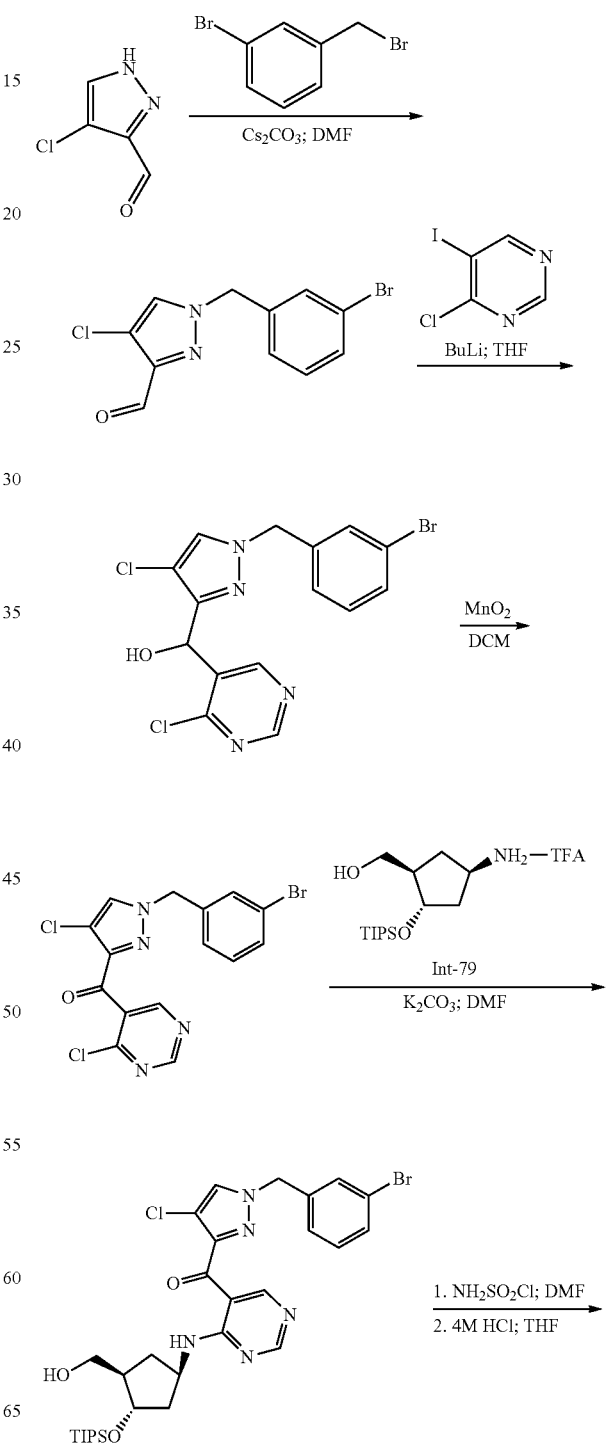

313

-continued

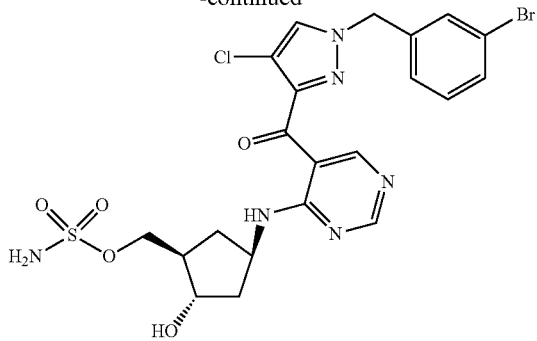

Step 1: 1-(3-Bromobenzyl)-4-chloro-1H-pyrazole-3-carbaldehyde

To a solution of 4-chloro-3-formylpyrazole (300 mg, 2.3 mmol) in DMF (20 mL) was added $Cs_2CO_3$ (1.9 g, 5.8 mmol) followed by 3-bromobenzyl bromide (630 mg, 2.5 mmol) at rt, and the mixture was stirred for 15 h. The reaction was quenched by addition of water (100 mL) and extracted with 1:1 EtOAc:hexanes (100 mL×3). The combined organic layers were dried over $Na_2SO_4$, filtered, and concentrated in vacuo. The residue was purified on silica gel to give 1-(3-bromobenzyl)-4-chloro-1H-pyrazole-3-carbaldehyde (314 mg, 46%) as a colorless solid. $^1H$ NMR ($CDCl_3$) δ 10.00 (s, 1H), 7.56-7.47 (m, 1H), 7.46-7.38 (m, 2H), 7.31-7.22 (m, 1H), 7.20 (d, J=7.7 Hz, 1H), 5.30 (s, 2H).

Step 2: [1-(3-Bromobenzyl)-4-chloro-1H-pyrazol-3-yl](4-chloropyrimidin-5-yl)methanol A 100 mL 2-necked RBF, equipped with septum and 3-way stopcock with an argon balloon, was charged with 4-chloro-5-iodopyrimidine (279 mg, 1.16 mmol), and the reaction vessel was purged with argon. The contents were dissolved in THF (8 mL) and the solution was cooled to −78° C. To the solution was added dropwise n-Butyllithium (2.50 M solution in hexane; 0.93 mL, 2.3 mmol), and the mixture was stirred for 30 min. To the mixture was added dropwise a solution of 1-(3-bromobenzyl)-4-chloro-1H-pyrazole-3-carbaldehyde (290 mg, 0.97 mmol) in THF (4 mL) at −78° C. and the resulting mixture was stirred for 30 min. The reaction was quenched by addition of saturated $NH_4Cl$ (40 mL) and extracted with EtOAc (50 mL×3). The combined organic layers were dried over $Na_2SO_4$, filtered, and concentrated in vacuo. The residue was purified on silica gel to give [1-(3-bromobenzyl)-4-chloro-1H-pyrazol-3-yl](4-chloropyrimidin-5-yl)methanol (175 mg, 44%). LCMS (FA): m/z=414.8 (M+H).

Step 3: [1-(3-Bromobenzyl)-4-chloro-1H-pyrazol-3-yl](4-chloropyrimidin-5-yl)methanone To a solution of [1-(3-bromobenzyl)-4-chloro-1H-pyrazol-3-yl](4-chloropyrimidin-5-yl)methanol (170 mg, 0.41 mmol) in DCM (10 mL) was added manganese(IV) oxide (360 mg, 4.1 mmol), and the mixture was stirred for 16 h at rt. The reaction was filtered through a Celite pad and the residual solid was rinsed with DCM several times. The filtrate was concentrated in vacuo and the residue was purified on silica gel to give [1-(3-bromobenzyl)-4-chloro-1H-pyrazol-3-yl](4-chloropyrimidin-5-yl)methanone (135 mg, 76%) as a colorless solid. LCMS (FA): m/z=412.8 (M+H).

Step 4: [1-(3-Bromobenzyl)-4-chloro-1H-pyrazol-3-yl][4-({(1R,3R,4S)-3-(hydroxymethyl)-4-[(triisopropylsilyl)oxy]cyclopentyl}amino)pyrimidin-5-yl]methanone A 100 mL reaction vessel was charged with {(1R,2S,4R)-4-amino-2-[(triisopropylsilyl)oxy]cyclopentyl}methanol.$CF_3CO_2H$ (150 mg, 0.38 mmol) and $K_2CO_3$ (130 mg, 0.95 mmol). To the mixture was added a solution of [1-(3-bromobenzyl)-4-chloro-1H-pyrazol-3-yl](4-chloropyrimidin-5-yl)methanone (130 mg, 0.32 mmol) in DMF (3 mL) at it and the resulting mixture was stirred for 18 h at rt. The reaction was quenched by addition of water (50 mL) and extracted with EtOAc (50 mL×3). The combined organic layers were dried over $Na_2SO_4$, filtered, and concentrated in vacuo. The residue was purified on silica gel to give [1-(3-bromobenzyl)-4-chloro-1H-pyrazol-3-yl][4-({(1R,3R,4S)-3-(hydroxymethyl)-4-[(triisopropylsilyl)oxy]cyclopentyl}amino)pyrimidin-5-yl]methanone (185 mg, 88%). LCMS (FA): m/z=664.1 (M+H).

Step 5: {(1R,2S,4R)-4-[(5-{[1-(3-Bromobenzyl)-4-chloro-1H-pyrazol-3-yl]carbonyl}pyrimidin-4-yl)amino]-2-hydroxycyclopentyl}methyl sulfamate I-111

To a solution of [1-(3-bromobenzyl)-4-chloro-1H-pyrazol-3-yl][4-({(1R,3R,4S)-3-(hydroxymethyl)-4-[(triisopropylsilyl)oxy]cyclopentyl}amino)pyrimidin-5-yl]methanone (130 mg, 0.20 mmol) in DMF (3.00 mL) was added chlorosulfonamide (45.3 mg, 0.39 mmol) at rt, and the mixture was stirred for 15 min. The reaction was quenched by addition of saturated $NaHCO_3$ (50 mL) and extracted with EtOAc (50 mL×3). The combined organic layers were dried over $Na_2SO_4$, filtered, and concentrated in vacuo. The residue was purified on silica gel to give the sulfamate intermediate [(155 mg, 96%); LCMS (FA): m/z=743.0 (M+H).] which was dissolved in THF (2 mL). To this solution was added HCl (4.0 M in $H_2O$; 3.0 mL, 12 mmol) at rt, and the mixture was stirred for 3 h. The reaction was quenched by addition of saturated $NaHCO_3$ (50 mL) and extracted with EtOAc (50 mL×3). The combined organic layers were dried over $Na_2SO_4$, filtered, and concentrated in vacuo. The residue was purified by ISCO silica gel column chromatography to give {(1R,2S,4R)-4-[(5-{[1-(3-bromobenzyl)-4-chloro-1H-pyrazol-3-yl]carbonyl}pyrimidin-4-yl)amino]-2-hydroxycyclopentyl}methyl sulfamate (102 mg, 93%). $^1H$ NMR (DMSO) δ 9.00 (s, 1H), 8.90 (d, J=7.4 Hz, 1H), 8.63 (s, 1H), 8.38 (s, 1H), 7.60-7.50 (m, 2H), 7.43 (s, 2H), 7.35 (t, J=7.7 Hz, 1H), 7.29 (d, J=7.7 Hz, 1H), 5.46 (s, 2H), 4.91 (d, J=4.5 Hz, 1H), 4.79-4.67 (m, 1H), 4.10 (dt, J=8.3, 5.7 Hz, 1H), 4.03-3.93 (m, 2H), 2.41-2.28 (m, 1H), 2.20-2.07 (m, 1H), 2.06-1.93 (m, 1H), 1.87-1.73 (m, 1H), 1.30 (dt, J=12.5, 9.3 Hz, 1H); LCMS (FA): m/z=587.2 (M+H).

Example 67: {(1R,2S,4R)-4-[(6-Chloro-5-{[1-(3-chlorobenzyl)-1H-pyrazol-3-yl]carbonyl}pyrimidin-4-yl)amino]-2-hydroxycyclopentyl}methyl sulfamate I-54

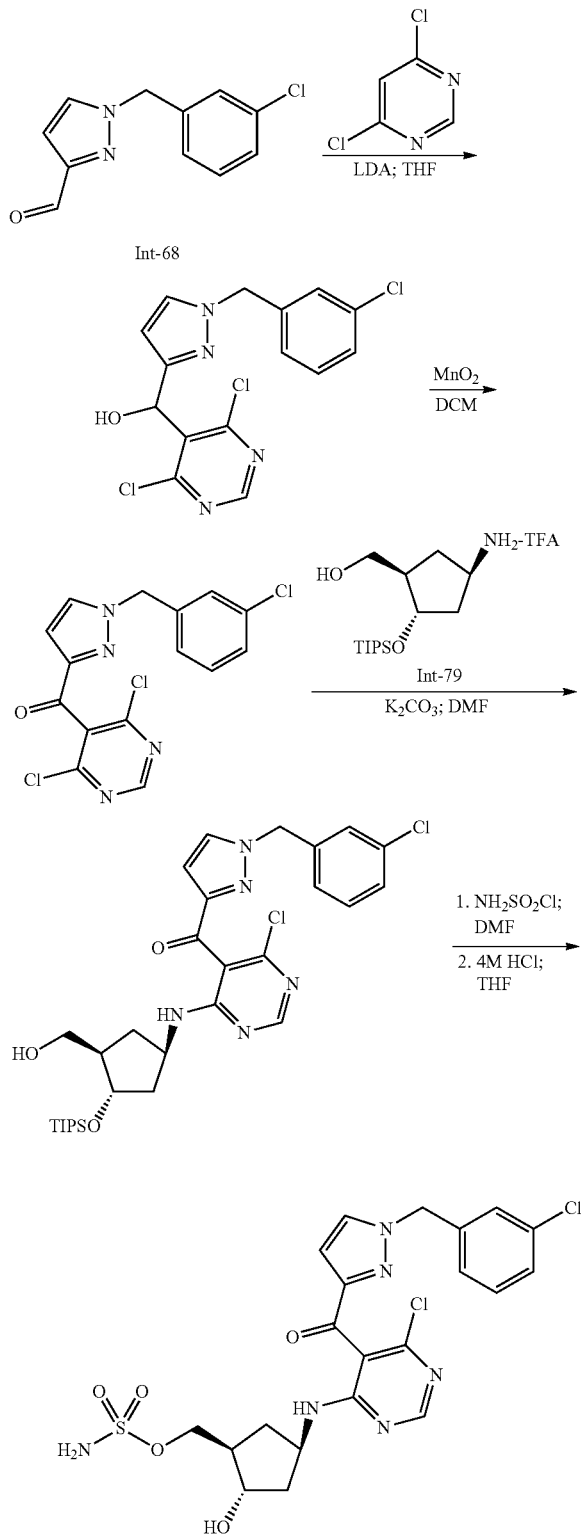

Step 1: [1-(3-Chlorobenzyl)-1H-pyrazol-3-yl](4,6-dichloropyrimidin-5-yl)methanol A solution of N,N-diisopropylamine (0.36 mL, 2.6 mmol) in THF (10 mL) was cooled to −78° C. under an atmosphere of argon. To this solution was added dropwise n-butyl-lithium (2.50 M solution in hexane; 1.0 mL, 2.5 mmol), and the mixture was stirred for 30 min at 0° C. This LDA solution was cooled to −78° C. and then a solution of 4,6-dichloropyrimidine (350 mg, 2.35 mmol) in THF (3 mL) was added dropwise to the LDA solution. The dark red brown solution was stirred for 30 min. To this mixture was added a solution of 1-(3-chlorobenzyl)-1H-pyrazole-3-carbaldehyde (518 mg, 2.35 mmol) in THF (3 mL) at −78° C., and the resulting mixture was stirred for 30 min. The reaction was quenched by addition of saturated NH$_4$Cl (50 mL) and extracted with EtOAc (50 mL×3). The combined organic layers were dried over Na$_2$SO$_4$, filtered, and concentrated in vacuo. The residue was purified on silica gel to give [1-(3-chlorobenzyl)-1H-pyrazol-3-yl](4,6-dichloropyrimidin-5-yl)methanol (174 mg, 16%). $^1$H NMR (CDCl$_3$) δ 8.72 (s, 1H), 7.38 (d, J=2.3 Hz, 1H), 7.31-7.22 (m, 2H), 7.12 (s, 1H), 7.06-7.03 (m, 1H), 6.54 (d, J=8.4 Hz, 1H), 6.17 (d, J=2.1 Hz, 1H), 5.25 (s, 2H), 3.71 (d, J=8.4 Hz, 1H).

Step 2: [1-(3-Chlorobenzyl)-1H-pyrazol-3-yl](4,6-dichloropyrimidin-5-yl)methanone To a solution of [1-(3-chlorobenzyl)-1H-pyrazol-3-yl](4,6-dichloropyrimidin-5-yl)methanol (140 mg, 0.37 mmol) in DCM (4.4 mL) was added manganese(IV) oxide (0.32 g, 3.7 mmol) and the mixture was stirred for 12 h at rt. The reaction was filtered through a celite pad and the residual solid was rinsed with DCM several times. The filtrate was concentrated in vacuo and the residue was purified on silica gel to give [1-(3-chlorobenzyl)-1H-pyrazol-3-yl](4,6-dichloropyrimidin-5-yl)methanone (86 mg, 64%) as a colorless solid. LCMS (FA): m/z=368.9 (M+H).

Step 3: [1-(3-Chlorobenzyl)-1H-pyrazol-3-yl][4-chloro-6-({(1R,3R,4S)-3-(hydroxymethyl)-4-[(triisopropylsilyl)oxy]cyclopentyl}amino)pyrimidin-5-yl]methanone A 100 mL reaction vessel was charged with {(1R,2S,4R)-4-amino-2-[(triisopropylsilyl)oxy]cyclopentyl}methanol.CF$_3$CO$_2$H (96 mg, 0.24 mmol) and K$_2$CO$_3$ (0.10 g, 0.69 mmol). To the mixture was added a solution of [1-(3-chlorobenzyl)-1H-pyrazol-3-yl](4,6-dichloropyrimidin-5-yl)methanone (85 mg, 0.23 mmol) in DMF (3 mL) and the resulting mixture was stirred for 2 h at rt. The reaction was quenched by the addition of water (40 mL) and extracted with EtOAc (50 mL×3). The combined organic layers were dried over Na$_2$SO$_4$, filtered, and concentrated in vacuo. The residue was purified on silica gel to give [1-(3-chlorobenzyl)-1H-pyrazol-3-yl][4-chloro-6-({(1R,3R,4S)-3-(hydroxymethyl)-4-[(triisopropylsilyl)oxy]cyclopentyl}amino)pyrimidin-5-yl]methanone (132 mg, 88%) as a colorless solid. LCMS (FA): m/z=618.1 (M+H).

Step 4: {(1R,2S,4R)-4-[(6-Chloro-5-{[1-(3-chlorobenzyl)-1H-pyrazol-3-yl]carbonyl}pyrimidin-4-yl)amino]-2-hydroxycyclopentyl}methyl sulfamate I-54

To a solution of [1-(3-chlorobenzyl)-1H-pyrazol-3-yl][4-chloro-6-({(1R,3R,4S)-3-(hydroxymethyl)-4-[(triisopropylsilyl)oxy]cyclopentyl}amino)pyrimidin-5-yl]methanone (120 mg, 0.20 mmol) in DMF (2 mL) was added chlorosulfonamide (45 mg, 0.39 mmol) at rt, and the mixture was stirred for 10 min. The reaction was quenched by addition of saturated NaHCO$_3$ (50 mL) and extracted with EtOAc (50 mL×3). The combined organic layers were dried over Na$_2$SO$_4$, filtered, and concentrated in vacuo. The residue was purified on silica gel to give the sulfamate intermediate [(116 mg, 80%); LCMS (FA): m/z=697.5 (M+H).] which was dissolved in THF (2 mL). To this solution was added HCl (4.0 M solution in water; 2.0 mL, 8.0 mmol) at rt, and the mixture was stirred for 5 h. The reaction was quenched by addition of saturated NaHCO$_3$ (50 mL) and extracted with EtOAc (50 mL×3). The combined organic layers were dried over Na$_2$SO$_4$, filtered, and concentrated in vacuo. The residue was purified by ISCO silica gel column chromatography to give {(1R,2S,4R)-4-[(6-chloro-5-{[1-(3-chlorobenzyl)-1H-pyrazol-3-yl]carbonyl}pyrimidin-4-yl)amino]-2-hydroxycyclopentyl}methyl sulfamate (65 mg, 77%) as a colorless solid. $^1$H NMR (DMSO) δ 8.34 (s, 1H), 8.05 (d, J=2.3 Hz, 1H), 7.45-7.38 (m, 2H), 7.38-7.30 (m, 3H), 7.22 (s, 1H), 7.17-7.10 (m, 1H), 6.94 (d, J=2.3 Hz, 1H), 5.48 (s, 2H), 4.78 (d, J=4.5 Hz, 1H), 4.71-4.59 (m, 1H), 4.02 (dd, J=9.6, 5.9 Hz, 1H), 3.92-3.80 (m, 2H), 2.14-1.96 (m, 2H), 1.81-1.71 (m, 1H), 1.70-1.60 (m, 1H), 1.20 (m, 1H); LCMS (FA): m/z=541.2 (M+H).

Example 68: [(1R,2S,4R)-2-Hydroxy-4-({5-[(1-phenyl-1H-pyrazol-3-yl)carbonyl]pyrimidin-4-yl}amino)cyclopentyl]methyl sulfamate I-205

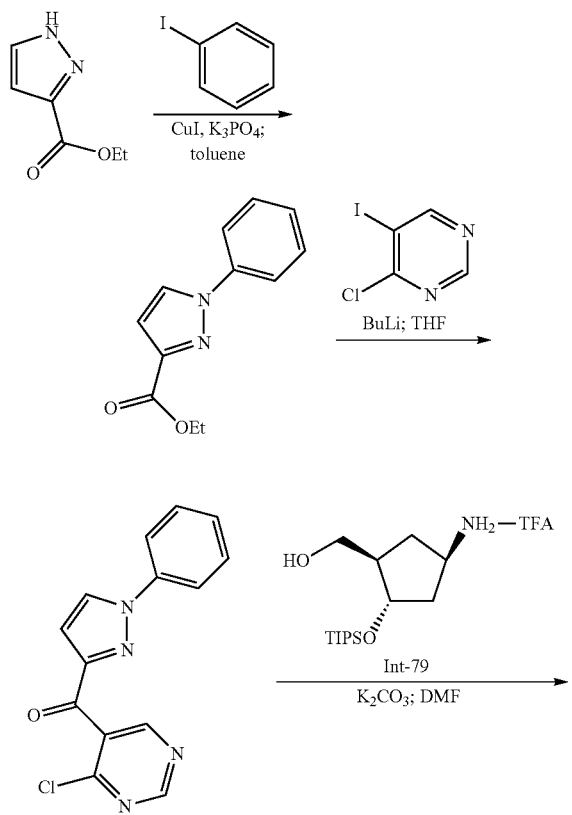

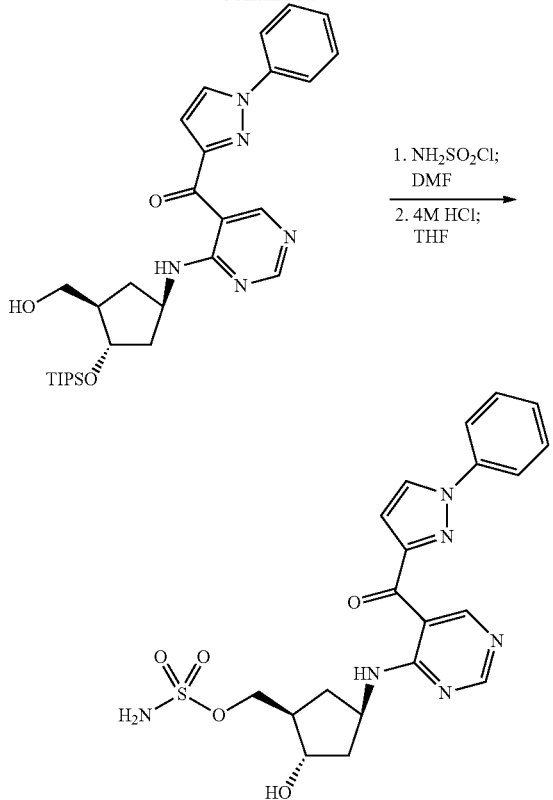

Step 1: Ethyl 1-phenyl-1H-pyrazole-3-carboxylate

A large sealable reaction vessel was charged with ethyl 1H-pyrazole-3-carboxylate (300 mg, 2.1 mmol), iodobenzene (0.57 g, 2.8 mmol), copper(I) iodide (20 mg, 0.10 mmol), trans-1,2-bis(methylamino)cyclohexane (0.06 g, 0.42 mmol), and potassium phosphate (0.96 g, 4.5 mmol). To the reaction vessel was added toluene (10 mL) and the mixture was purged with nitrogen for 5 min. The vessel was sealed and heated at 110° C. for 16 h. The reaction was cooled to rt and filtered through a celite pad. The residual solid was rinsed with EtOAc several times. The filtrate was concentrated in vacuo and the residue was purified on silica gel to give ethyl 1-phenyl-1H-pyrazole-3-carboxylate (320 mg, 69%) as colorless oil. LCMS (FA): m/z=217.1 (M+H).

Step 2: (4-Chloropyrimidin-5-yl)(1-phenyl-1H-pyrazol-3-yl)methanone

A round bottomed flask was charged with 4-chloro-5-iodopyrimidine (360 mg, 1.5 mmol) and the reaction vessel was purged with argon. The content was dissolved in THF (12 mL) and the solution was cooled to −78° C. To the solution was added dropwise n-butyllithium (2.50 M solution in hexane; 1.2 mL, 3.0 mmol), and the mixture was stirred for 30 min at −78° C. To this mixture was added dropwise a solution of ethyl 1-phenyl-1H-pyrazole-3-carboxylate (300 mg, 1.4 mmol) in THF (6 mL), and the resulting mixture was stirred for 30 min. The reaction was quenched by addition of saturated NH$_4$Cl (50 mL) and extracted with EtOAc (50 mL×4). The combined organic layers were dried over Na$_2$SO$_4$, filtered, and concentrated in vacuo. The residue was purified on silica gel to give (4-chloropyrimidin-5-yl)(1-phenyl-1H-pyrazol-3-yl)methanone (210 mg, 54%) as a colorless solid. LCMS (FA): m/z=285.1 (M+H).

Step 3: [4-({(1R,3R,4S)-3-(Hydroxymethyl)-4-[(triisopropylsilyl)oxy]cyclopentyl}amino)pyrimidin-5-yl](1-phenyl-1H-pyrazol-3-yl)methanone A reaction vessel was charged with {(1R,2S,4R)-4-amino-2-[(triisopropylsilyl)oxy]cyclopentyl}methanol.CF$_3$CO$_2$H (293 mg, 0.73 mmol) and K$_2$CO$_3$ (277 mg, 2.00 mmol). To the mixture was added a solution of (4-chloropyrimidin-5-yl)(1-phenyl-1H-pyrazol-3-yl)methanone (190 mg, 0.67 mmol) in DMF (6 mL), and the resulting mixture was stirred for 2 h at rt. The reaction was concentrated in vacuo. To the residue was added water (40 mL) and the mixture was extracted with EtOAc (50 mL×3). The combined organic layers were dried over Na$_2$SO$_4$, filtered, and concentrated in vacuo. The residue was purified on silica gel to give [4-({(1R,3R,4S)-3-(hydroxymethyl)-4-[(triisopropylsilyl)oxy]cyclopentyl}amino)pyrimidin-5-yl](1-phenyl-1H-pyrazol-3-yl)methanone (311 mg, 83%) as a yellow sticky oil. LCMS (FA): m/z=536.4 (M+H).

Step 4: [(1R,2S,4R)-2-Hydroxy-4-({5-[(1-phenyl-1H-pyrazol-3-yl)carbonyl]pyrimidin-4-yl}amino)cyclopentyl]methyl sulfamate I-205

To a solution of [4-({(1R,3R,4S)-3-(hydroxymethyl)-4-[(triisopropylsilyl)oxy]cyclopentyl}amino)pyrimidin-5-yl](1-phenyl-1H-pyrazol-3-yl)methanone (300 mg, 0.56 mmol) in DMF (2.0 mL) was added chlorosulfonamide (129 mg, 1.12 mmol) at rt, and the mixture was stirred for 30 min. LC/MS showed reaction completed. The reaction was quenched by addition of saturated NaHCO$_3$ (50 mL) and extracted with EtOAc (60 mL×3). The combined organic layers were dried over Na$_2$SO$_4$, filtered, and concentrated in vacuo. The residue was purified on silica gel to give the sulfamate intermediate [(267 mg, 78%); LCMS (FA): m/z=615.2 (M+H).] which was dissolved in THF (2 mL). To this solution was added HCl (4.0 M solution in water; 2.0 mL, 8.0 mmol) at rt and the mixture was stirred for 5 h at rt. The reaction was quenched by addition of saturated NaHCO$_3$ and solid NaCl. The mixture was extracted with a 9:1 EtOAc:MeOH solution (60 mL×3). The combined organic layers were dried over Na$_2$SO$_4$, filtered, and concentrated in vacuo. To the residue was added a small amount of DCM and the resulting suspension was filtered through a glass frit funnel. The residual solid was rinsed with DCM twice and dried under high vacuum overnight to give [(1R,2S,4R)-2-hydroxy-4-({5-[(1-phenyl-1H-pyrazol-3-yl)carbonyl]pyrimidin-4-yl}amino)cyclopentyl]methyl sulfamate (168 mg, 88%) as a colorless solid. $^1$H NMR (DMSO) δ 9.61 (s, 1H), 9.05 (d, J=7.3 Hz, 1H), 8.69 (m, 2H), 7.98-7.89 (m, 2H), 7.63-7.54 (m, 2H), 7.47-7.39 (m, 3H), 7.14 (s, 1H), 4.91 (d, J=4.5 Hz, 1H), 4.81-4.69 (m, 1H), 4.12 (dd, J=9.5, 6.0 Hz, 1H), 4.03-3.95 (m, 2H), 2.44-2.34 (m, 1H), 2.21-2.10 (m, 1H), 2.08-1.99 (m, 1H), 1.86-1.76 (m, 1H), 1.32 (dd, J=21.8, 9.3 Hz, 1H); LCMS (FA): m/z=459.2 (M+H).

Example 69: {(1R,2S,4R)-4-[(3-{[1-(3-Chlorobenzyl)-1H-pyrazol-3-yl]carbonyl}pyridin-4-yl)amino]-2-hydroxycyclopentyl}methyl sulfamate I-52

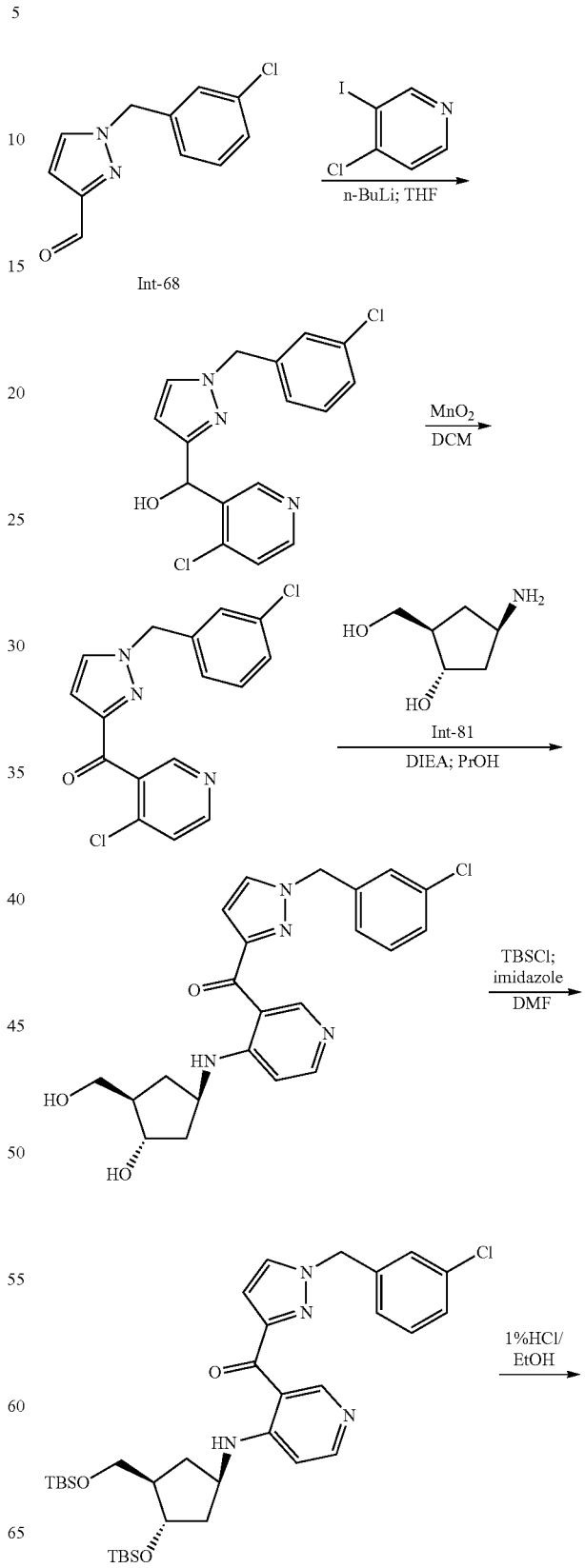

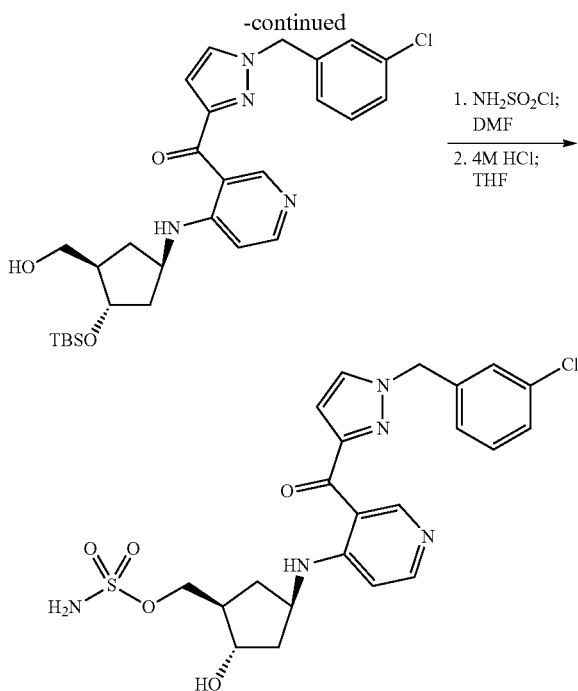

Step 1: [1-(3-Chlorobenzyl)-1H-pyrazol-3-yl](4-chloropyridin-3-yl)methanol

Into a flame dried RBF with stirbar was added 4-chloro-5-iodopyrimidine (0.72 g, 3.0 mmol) dissolved in THF (15 mL). The flask was purged with argon and cooled to −78° C. To this solution was added dropwise n-butyllithium (2.5 M in hexane; 2.39 mL, 5.78 mmol) at −78° C. and the mixture was stirred for 30 min. To this mixture was added 1-(3-chlorobenzyl)-1H-pyrazole-3-carbaldehyde (0.60 g, 2.7 mmol) dissolved hi THF (6 mL) dropwise. The reaction was stirred at −78° C. for 2 h then allowed to warm slowly to rt and stir an additional 12 h. The reaction was quenched with a saturated solution of NH₄Cl and then extracted with EtOAc (3×). The combined organic layers were then washed with water and brine, dried over Na₂SO₄, filtered and concentrated. The crude product was purified on silica gel to give [1-(3-chlorobenzyl)-1H-pyrazol-3-yl](4-chloropyridin-3-yl)methanol (0.44 g, 46%); LCMS (FA): m/z=334.4 (M+H).

Step 2: [1-(3-Chlorobenzyl)-1H-pyrazol-3-yl](4-chloropyridin-3-yl)methanone

To a solution of [1-(3-chlorobenzyl)-1H-pyrazol-3-yl](4-chloropyridin-3-yl)methanol (0.42 g, 1.3 mmol) in DCM (12 mL) was added manganese(IV) oxide (1.1 g, 12.6 mmol). The suspension was stirred for 19 h at rt. The reaction was then filtered through a celite pad and the residual solid was washed with DCM several times. The filtrate was then concentrated in vacuo and the residue was purified on silica gel to afford [1-(3-chlorobenzyl)-1H-pyrazol-3-yl](4-chloropyridin-3-yl)methanone (0.39 g, 91%). LCMS (FA): m/z=332.4 (M+H).

Step 3: [1-(3-Chlorobenzyl)-1H-pyrazol-3-yl](4-{[(1R,3S,4R)-3-hydroxy-4-(hydroxymethyl)cyclopentyl]amino}pyridin-3-yl)methanone

[1-(3-Chlorobenzyl)-1H-pyrazol-3-yl](4-chloropyridin-3-yl)methanone (0.38 g, 1.1 mmol) and (1S,2R,4R)-4-amino-2-(hydroxymethyl)cyclopentanol (0.18 g, 1.4 mmol) were weighed into a 20 mL reaction vessel. To this mixture was added 1-propanol (5 mL) and DIEA (0.40 mL, 2.3 mmol). The resulting mixture was sealed and the vessel heated at 180° C. for 2 h in a microwave reactor. It was then cooled to rt and quenched with water. The reaction was then extracted with EtOAc (3×). The combined organic layers were washed with brine, dried over Na₂SO₄, filtered, and concentrated in vacuo. The crude product was purified on silica gel to afford [1-(3-chlorobenzyl)-1H-pyrazol-3-yl](4-{[(1R,3S,4R)-3-hydroxy-4-(hydroxymethyl)cyclopentyl]amino}pyridin-3-yl)methanone (0.18 g, 39%). LCMS (FA): m/z 427.5 (M+H).

Step 4: (4-{[(1R,3S,4R)-3-{[tert-Butyl(dimethyl)silyl]oxy}-4-({[tert-butyl(dimethyl)silyl]oxy}methyl)cyclopentyl]amino}pyridin-3-yl) [1-(3-chlorobenzyl)-1H-pyrazol-3-yl]methanone To a solution of [1-(3-chlorobenzyl)-1H-pyrazol-3-yl](4-{[(1R,3S,4R)-3-hydroxy-4-(hydroxymethyl)cyclopentyl]amino}pyridin-3-yl)methanone (0.18 g, 0.43 mmol) in DMF (7 mL) was added imidazole (0.12 g, 1.7 mmol) followed by tert-butyldimethylsilyl chloride (0.16 g, 1.1 mmol) at rt, and the mixture was stirred for 2 days. The reaction was then quenched by addition of water and extracted with EtOAc (3×). The combined organic layers were washed with brine, dried over MgSO₄, filtered, and concentrated. The residue was purified on silica gel column to give (4-{[(1R,3S,4R)-3-{[tert-butyl(dimethyl)silyl]oxy}-4-({[tert-butyl(dimethyl)silyl]oxy}methyl)cyclopentyl]amino}pyridin-3-yl)[1-(3-chlorobenzyl)-1H-pyrazol-3-yl]methanone (0.23 g, 81%). LCMS (FA): m/z=655.7 (M+H).

Step 5: (4-{[(1R,3S,4R)-3-{[tert-Butyl(dimethyl)silyl]oxy}-4-(hydroxymethyl)cyclopentyl]amino}pyridin-3-yl) [1-(3-chlorobenzyl)-1H-pyrazol-3-yl]methanone To a solution of (4-{[(1R,3S,4R)-3-{[tert-butyl(dimethyl)silyl]oxy}-4-({[tert-butyl(dimethyl)silyl]oxy}methyl)cyclopentyl]amino}pyridin-3-yl)[1-(3-chlorobenzyl)-1H-pyrazol-3-yl]methanone (0.23 g, 0.35 mmol) in EtOH (16 mL) was added 1% HCl in EtOH (11.5 mL, 1.4 mmol) at rt. The reaction vessel was sealed and placed in a refrigerator (4° C.) for 5 h and then allowed to stand at −20° C. for 16 h. The reaction was quenched by addition of a saturated aq. solution of NaHCO₃. To the residue was added water which was extracted with EtOAc (4×). The combined organic layers were dried over MgSO₄, filtered, and concentrated. The residue was purified on silica gel to give (4-{[(1R,3S,4R)-3-{[tert-butyl(dimethyl)silyl]oxy}-4-(hydroxymethyl)cyclopentyl]amino}pyridin-3-yl)[1-(3-chlorobenzyl)-1H-pyrazol-3-yl]methanone (0.072 g, 38%). LCMS (FA): m/z=541.6 (M+H).

Step 6: {(1R,2S,4R)-4-[(3-{[1-(3-Chlorobenzyl)-1H-pyrazol-3-yl]carbonyl}pyridin-4-yl)amino]-2-hydroxycyclopentyl}methyl sulfamate I-52

To a solution of (4-{[(1R,3S,4R)-3-{[tert-Butyl(dimethyl)silyl]oxy}-4-(hydroxymethyl)cyclopentyl]amino}pyridin-3-yl)[1-(3-chlorobenzyl)-1H-pyrazol-3-yl]methanone (0.072 g, 0.13 mmol) in DMF (2 mL) was added chlorosulfonamide (31 mg, 0.27 mmol) at rt, and the mixture was stirred for 1 h. The reaction was quenched by addition of a saturated solution of NaHCO₃ and diluted with water. The mixture was extracted with EtOAc (4×). The combined organic layers were dried over MgSO$_4$, filtered, and concentrated. The crude sulfamate intermediate was dissolved in THF (3 mL) and HCl (3.0 M in water; 1.5 mL, 4.5 mmol) was added to the solution. The reaction was stirred for 2 h at rt. The reaction was quenched by the addition of a saturated solution of NaHCO$_3$ and extracted with EtOAc (4×). The combined organic layers were dried over MgSO$_4$, filtered, and concentrated. The residue was purified by prep HPLC to afford {(1R,2S,4R)-4-[(3-{[1-(3-chlorobenzyl)-1H-pyrazol-3-yl]carbonyl}pyridin-4-yl)amino]-2-hydroxycyclopentyl}methyl sulfamate (0.018 g, 27%). $^1$H NMR (DMSO) δ 9.31 (s, 1H), 8.89 (d, J=6.9 Hz, 1H), 8.20 (d, J=6.1 Hz, 1H), 8.16 (s, 1H), 8.06 (d, J=2.3 Hz, 1H), 7.45-7.34 (m, 4H), 7.26-7.19 (m, 1H), 6.87 (d, J=2.3 Hz, 1H), 6.78 (d, J=6.2 Hz, 1H), 5.51 (s, 2H), 4.97 (s, 1H), 4.20-4.08 (m, 2H), 4.02-3.93 (m, 2H), 2.49-2.41 (m, 1H), 2.21-2.10 (m, 1H), 2.11-2.01 (m, 1H), 1.81-1.70 (m, 1H), 1.31-1.17 (m, 1H); LCMS (FA): m/z=506.5 (M+H).

Example 70: {(1R,2S,4R)-4-[(3-{[1-(3-Chloro-4-fluorobenzyl)-1H-pyrazol-3-yl]carbonyl}pyridin-4yl)amino]-2-hydroxycyclopentyl}methyl sulfamate I-97

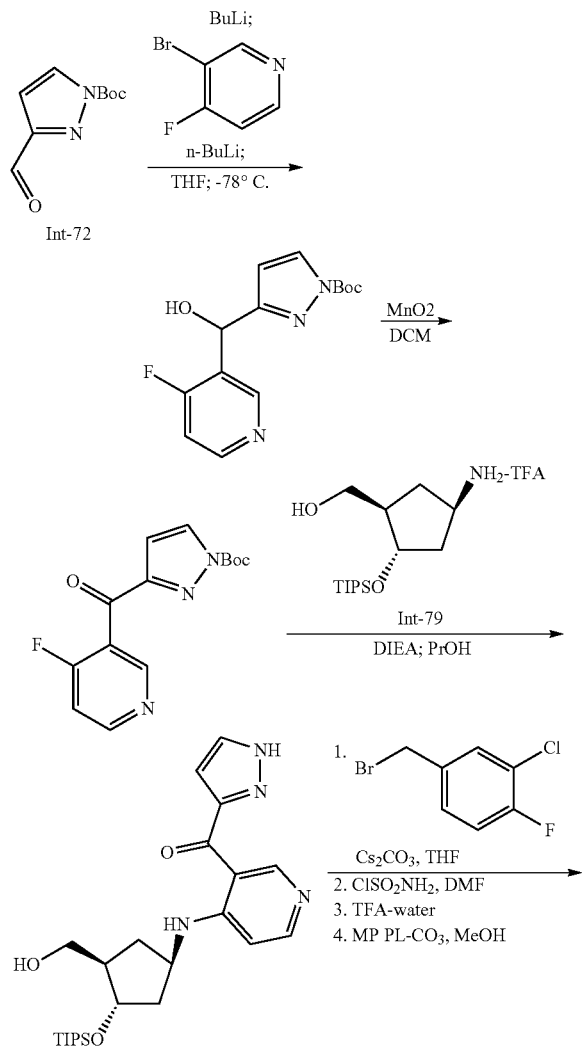

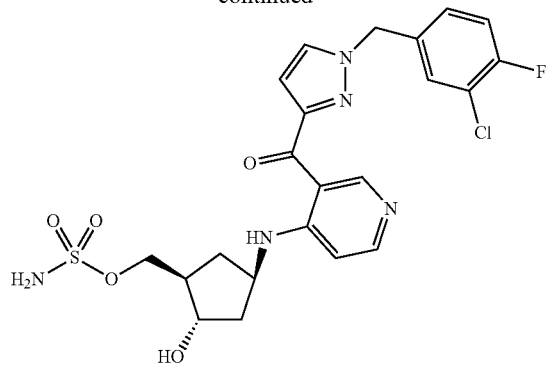

Step 1: tert-Butyl 3-[(4-fluoropyridin-3-yl)(hydroxy)methyl]-1H-pyrazole-1-carboxylate Into a flame dried RBF with stirbar was added 3-bromo-4-fluoropyridine (4.5 g, 25 mmol) dissolved in THF (200 mL). The flask was purged with argon and cooled to −95° C. To this solution was added dropwise n-butyllithium (2.5 M in hexane; 23 mL, 58 mmol) at −95° C. and the mixture was stirred for 15 min. To this mixture was added tert-butyl 3-formyl-1H-pyrazole-1-carboxylate (4.8 g, 25 mmol) dissolved in THF (35 mL) dropwise at −90° C. The reaction was stirred at −90° C. for 30 min then allowed to warm to −60° C. The reaction was then quenched with a solution of acetic acid (4.3 mL) in THF (20 mL) and allowed to warm to rt. The mixture was concentrated and the crude product was purified on silica gel to give tert-butyl 3-[(4-fluoropyridin-3-yl)(hydroxy)methyl]-1H-pyrazole-1-carboxylate (2.1 g, 29%). LCMS (AA): m/z=294 (M+H).

Step 2: tert-Butyl 3-[(4-fluoropyridin-3-yl)carbonyl]-1H-pyrazole-1-carboxylate

To a solution of tert-butyl 3-[(4-fluoropyridin-3-yl)(hydroxy)methyl]-1H-pyrazole-1-carboxylate (0.48 g, 1.6 mmol) in DCM (20 mL) was added manganese(IV) oxide (2.0 g, 23 mmol). The suspension was stirred for 3 h at rt. The reaction was then filtered through a celite pad and the residual solid was washed with DCM several times. The filtrate was then concentrated in vacuo and the residue was purified on silica gel to afford tert-butyl 3-[(4-fluoropyridin-3-yl)carbonyl]-1H-pyrazole-1-carboxylate (0.36 g, 76%). LCMS (AA): m/z=292 (M+H).

Step 3: [4-({(1R,3R,4S)-3-(Hydroxymethyl)-4-[(triisopropylsilyl)oxy]cyclopentyl}amino)pyridin-3-yl](1H-pyrazol-3-yl)methanone tert-Butyl {(1 R,3R,4S)-3-(hydroxymethyl)-4-[(triisopropylsilyl)oxy]cyclopentyl}carbamate (0.48 g, 1.2 mmol) was dissolved in TFA (10.0 mL) and then the mixture was immediately concentrated. A solution of DIEA (1.7 mL, 9.9 mmol) in 1-propanol (10.0 mL) was then added and the solution was transferred to a microwave reaction vessel. tert-Butyl 3-[(4-fluoropyridin-3-yl)carbonyl]-1H-pyrazole-1-carboxylate (0.36 g, 1.2 mmol) was added to the reaction mixture and it was heated at 120° C. for 90 min in a microwave reactor. The reaction mixture was concentrated and the crude product was purified on silica gel to give [4-({(1R,3R,4S)-3-(hydroxymethyl)-4-[(triisopropylsilyl)

oxy]cyclopentyl}amino)pyridin-3-yl](1H-pyrazol-3-yl)methanone (0.17 g, 31%). LCMS (AA): m/z=459 (M+H).

Step 4: {(1R,2S,4R)-4-[(3-{[1-(3-Chloro-4-fluorobenzyl)-1H-pyrazol-3-yl]carbonyl}pyridin-4-yl)amino]-2-hydroxycyclopentyl}methyl sulfamate
I-97

To a 3-dram vial was added 3-chloro-4-fluorobenzylbromide (0.024 g, 0.11 mmol) and cesium carbonate (0.17 g, 0.52 mmol), followed by [4-({(1R,3R,4S)-3-(hydroxymethyl)-4 [(triisopropylsilyl)oxy]cyclopentyl}amino)pyridin-3-yl](1H-pyrazol-3-yl)methanone (0.04 g, 0.087 mmol) in THF (1.0 mL). The solution was shaken at rt for 1 h. The solid carbonate was filtered and rinsed with THF (1 mL). To the combined THF clear solution (~2 mL) in another 3-dram vial was added DMF (0.50 mL) followed by chlorosulfonamide (0.040 g, 0.35 mmol). The solution was shaken at rt for 1 h, then saturated NaHCO$_3$ solution (0.5 ml), water (1 mL), and EtOAc (3 mL) were added. After the layers were separated, the aqueous layer was extracted with EtOAc (3 mL). The combined organic phases were concentrated to a solid residue. To the residue in a 20-mL vial was added TFA (2.0 mL) and water (0.2 mL). The mixture was shaken at rt for 2 h and then the solvent was evaporated. To the residue was added methanol (2.0 mL) and MP PL-CO3 resin (0.5 g). After shaking at rt for 1 h, the solid was filtered and the resin was rinsed with MeOH (5 mL). The MeOH solution was concentrated to a solid residue which was purified by prep HPLC to provide {(1R,2S,4R)-4-[(3-{[1-(3-chloro-4-fluorobenzyl)-1H-pyrazol-3-yl]carbonyl}pyridin-4yl)amino]-2-hydroxycyclopentyl}methyl sulfamate (7 mg, 15%). LCMS (FA): m/z=524.4 (M+H).

The compounds listed in the table below were prepared in an analogous fashion to that described above starting from the listed starting materials used in step 4:

| Starting material | Compound No. | LCMS Data |
|---|---|---|
| 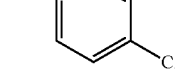 | I-78 | LCMS (FA): m/z = 540.4 (M + H). |
| 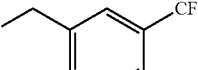 | I-263 | LCMS (FA): m/z = 558.4 (M + H). |
| 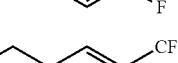 | I-174 | LCMS (FA): m/z = 574.4 (M + H). |
| 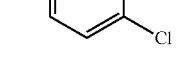 | I-223 | LCMS (FA): m/z = 550.4 (M + H). |
| 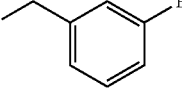 | I-246 | LCMS (FA): m/z = 538.4 (M + H). |
| 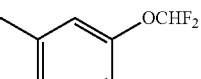 | I-18 | LCMS (FA): m/z = 556.9 (M + H). |
| 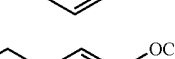 | I-262 | LCMS (FA): m/z = 540 (M + H). |

Example 71: [(1R,2R,3R,4R)-4-({5-[(1-Benzyl-1H-pyrazol-3-yl)carbonyl]pyrimidin-4-yl}amino)-3-fluoro-2-hydroxycyclopentyl]methyl sulfamate
I-317

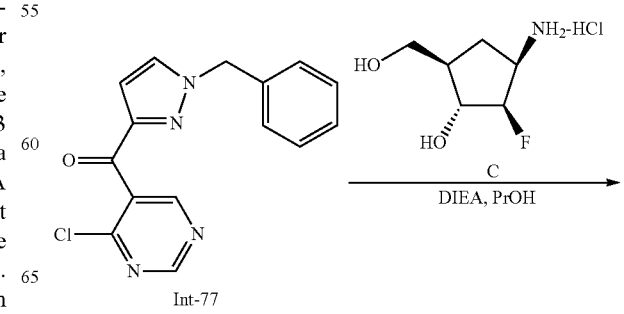

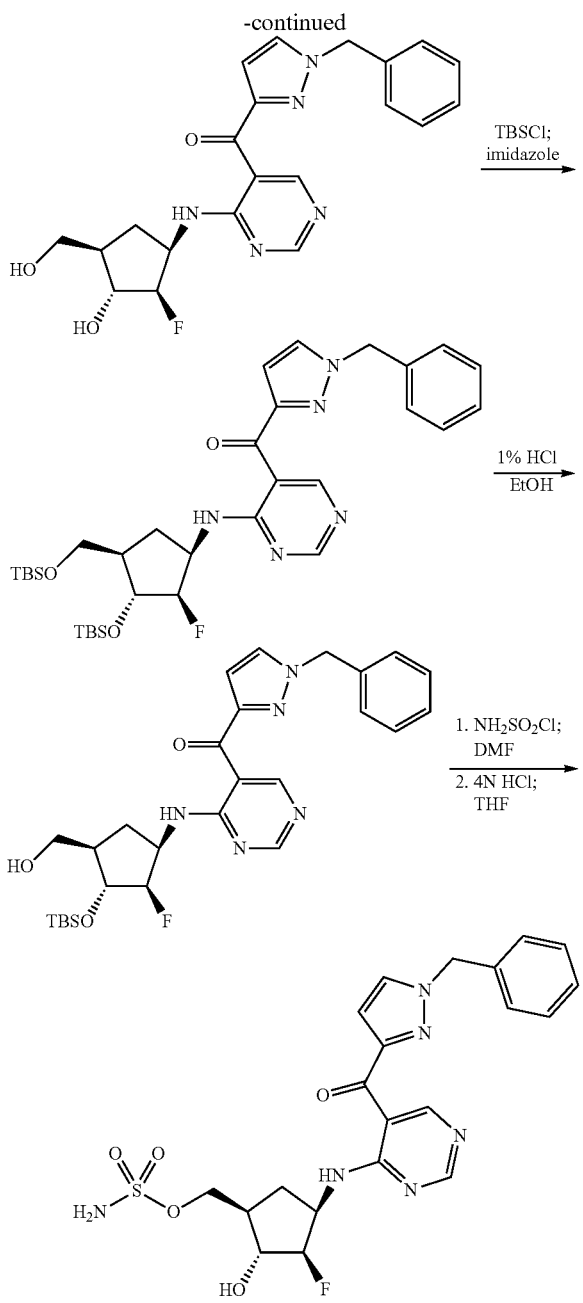

Step 1: (1-Benzyl-1H-pyrazol-3-yl)(4-{[(1R,2R,3R,4R)-2-fluoro-3-hydroxy-4-(hydroxymethyl)cyclopentyl]amino}pyrimidin-5-yl)methanone (1-Benzyl-1H-pyrazol-3-yl)(4-chloropyrimidin-5-yl)methanone (0.30 g, 1.0 mmol) and (1R,2R,3R,5R)-3-amino-2-fluoro-5-(hydroxymethyl)cyclopentanol hydrochloride (C) (0.21 g, 1.11 mmol) (for synthesis see: Biggadike, K. et al. *J. Chem. Soc. Perkin Trans.* 1988, 3, 549-554; Borthwick, A. D. et al. *J. Med. Chem.* 1990, 33, 179-186.) were weighed into a 20 mL reaction vessel. To this mixture was added 1-propanol (14 mL) and DIEA (0.52 mL, 3.0 mmol). The resulting mixture was sealed and the vessel allowed to stir while heating at 50° C. for 2 h. The reaction was then cooled to rt and the reaction was concentrated. The crude product was purified on silica gel to afford (1-benzyl-1H-pyrazol-3-yl)(4-{[(1R,2R,3R,4R)-2-fluoro-3-hydroxy-4-(hydroxymethyl)cyclopentyl]amino}pyrimidin-5-yl)methanone (0.38 g, 94%). LCMS (FA): m/z=412 (M+H).

Step 2: (1-Benzyl-1H-pyrazol-3-yl)(4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)methanone To a solution of (1-benzyl-1H-pyrazol-3-yl)(4-{[(1R,2R,3R,4R)-2-fluoro-3-hydroxy-4-(hydroxymethyl)cyclopentyl]amino}pyrimidin-5-yl)methanone (0.37 g, 0.90 mmol) in DMF (14.8 mL) was added imidazole (0.24 g, 3.6 mmol) followed by tert-butyldimethylsilyl chloride (0.34 g, 2.2 mmol) at rt, and the mixture was stirred for 3 days. The reaction was then quenched by addition of water and extracted with EtOAc (3×). The combined organic layers were washed with brine, dried over MgSO$_4$, filtered, and concentrated. The residue was purified on silica gel column to give (1-benzyl-1H-pyrazol-3-yl)(4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)methanone (0.53 g, 92%).

Step 3: (1-Benzyl-1H-pyrazol-3-yl)(4-{[(1R,2R,3R,4R)-3-{[tert-butyl(dimethyl)silyl]oxy}-2-fluoro-4-(hydroxymethyl)cyclopentyl]amino}pyrimidin-5-yl)methanone To a solution of [A] (1-benzyl-1H-pyrazol-3-yl)(4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)methanone (0.50 g, 0.78 mmol) in EtOH (51 mL) was added 1% HCl in EtOH (25.9 mL, 3.12 mmol) at rt. The reaction vessel was sealed and placed in a refrigerator (4° C.) for 22 h. The reaction was quenched by addition of a saturated aq. solution of NaHCO$_3$. To the residue was added water which was extracted with EtOAc (4×). The combined organic layers were dried over MgSO$_4$, filtered, and concentrated. The residue was purified on silica gel to give (1-benzyl-1H-pyrazol-3-yl)(4-{[(1R,2R,3R,4R)-3-{[tert-butyl(dimethyl)silyl]oxy}-2-fluoro-4-(hydroxymethyl)cyclopentyl]amino}pyrimidin-5-yl)methanone (0.29 g, 71%). LCMS (FA): m/z=412 (M+H).

Step 4: [(1R,2R,3R,4R)-4-({5-[(1-Benzyl-1H-pyrazol-3-yl)carbonyl]pyrimidin-4-yl}amino)-3-fluoro-2-hydroxycyclopentyl]methyl sulfamate I 317

To a solution of (1-benzyl-1H-pyrazol-3-yl)(4-{[(1R,2R,3R,4R)-3-{[tert-butyl(dimethyl)silyl]oxy}-2-fluoro-4-(hydroxymethyl)cyclopentyl]amino}pyrimidin-5-yl)methanone (0.28 g, 0.53 mmol) in DMF (4.1 mL) was added chlorosulfonamide (123 mg, 1.1 mmol) at rt, and the mixture was stirred for 1 h. The reaction was quenched by addition of a saturated solution of NaHCO$_3$ and diluted with water. The mixture was extracted with EtOAc (4×). The combined organic layers were dried over MgSO$_4$, filtered, and concentrated. The crude sulfamate intermediate was dissolved in THF (11 mL) and HCl (3.0 M in water; 5.50 mL, 16.5 mmol) was added to the solution. The reaction was stirred for 3 h at rt. The reaction was quenched by the addition of a saturated solution of NaHCO$_3$ (30 mL) and extracted with EtOAc (4×). The combined organic layers were dried over MgSO$_4$, filtered, and concentrated. The residue was purified by prep HPLC to afford [(1R,2R,3R,4R)-4-({5-[(1-benzyl-1H-pyrazol-3-yl)carbonyl]pyrimidin-4-yl}amino)-3-fluoro-2-hydroxycyclopentyl]methyl sulfamate (115 mg, 44%). $^1$H NMR (DMSO) δ 9.56 (d, J=1.1 Hz, 1H), 9.23 (d, J=7.6 Hz, 1H), 8.68 (s, 1H), 8.07 (dd, J=2.3, 1.2 Hz, 1H), 7.50 (s, 2H), 7.43-7.22 (m, 5H), 6.93 (d, J=2.4 Hz, 1H), 5.57 (s, 1H), 5.51 (s, 2H), 4.93-4.70 (m, 2H), 4.12 (dd, J=9.8, 6.0 Hz, 1H), 4.03 (dd, J=9.8, 6.9 Hz, 1H), 3.94 (dd, J=21.9, 4.7 Hz, 1H), 2.41-2.28 (m, 1H), 2.25-2.12 (m, 1H), 1.47 (dd, J=22.4, 11.4 Hz, 1H); LCMS (FA): m/z=491.5 (M+H).

The compounds listed in the table below were prepared in an analogous fashion to that described above starting from the listed starting materials: (for synthesis of C, D, and E in this table see Biggadike, K. et al. *J. Chem. Soc. Perkin Trans.* 1988, 3, 549-554.; Borthwick, A. D. et al. *J. Med. Chem.* 1990, 33, 179-186 respectively)

| Starting material | Starting material | Compound No. | LCMS Data |
|---|---|---|---|
| Int-71 | B | I-342 | LCMS (FA): m/z = 471 (M + H). |
| Int-71 | D | I-227 | LCMS (FA): m/z = 491 (M + H). |
| Int-71 | E | I-203 | LCMS (FA): m/z = 509.4 (M + H). |
| See Ex. 38; prepared in a similar manner to Int-71 | C | I-242 | LCMS (FA): m/z = 524 (M + H). |

331

Example 72: ((1R,2R,3R,4R)-4-((5-(1-(3-Bromo-2-fluorobenzyl)-1H-pyrazole-3 carbonyl) pyrimidin-4-yl)amino)-3-fluoro-2-hydroxycyclopentyl)methyl sulfamate I-177

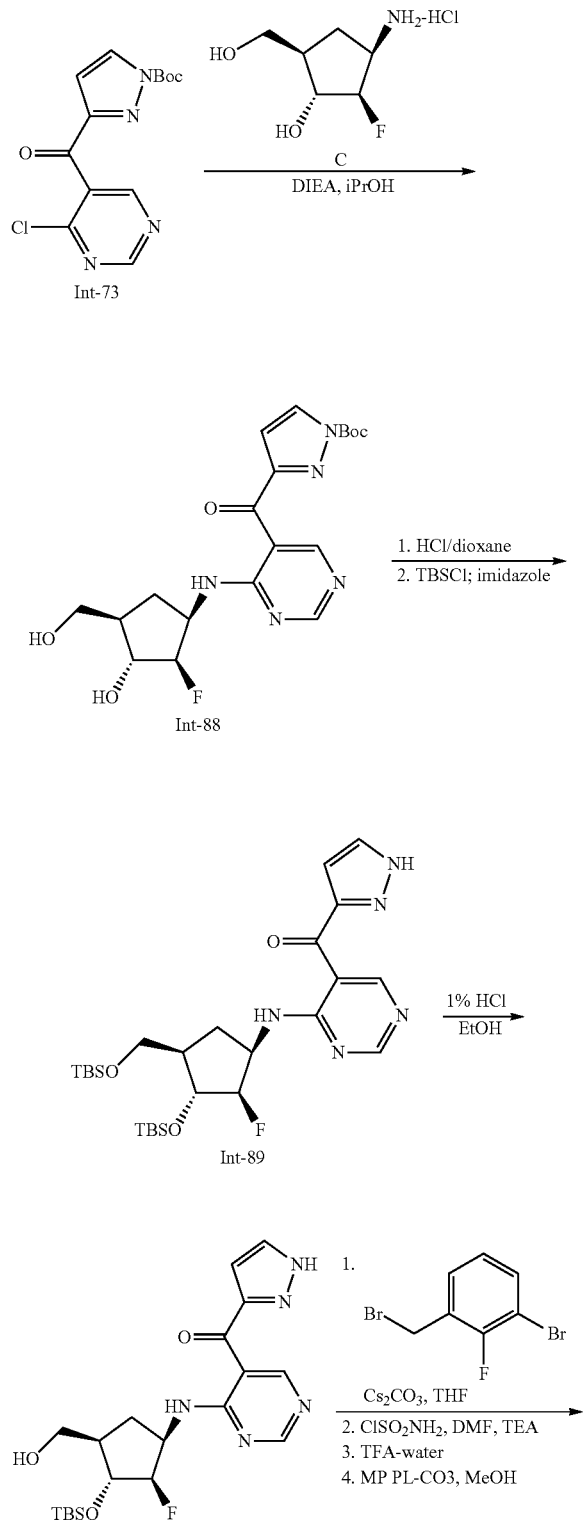

332

-continued

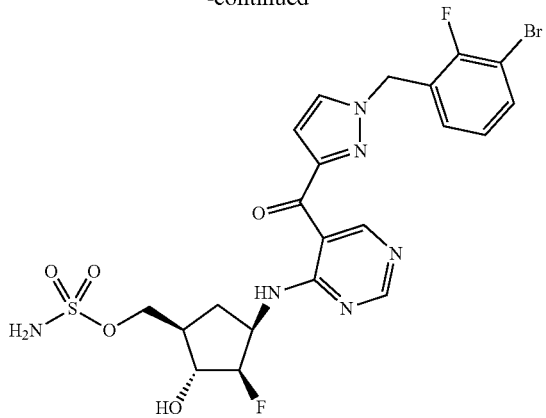

Step 1: tert-Butyl 3-[(4-{[(1R,2R,3R,4R)-2-fluoro-3-hydroxy-4-(hydroxymethyl)cyclopentyl]amino}pyrimidin-5-yl)carbonyl]-1H-pyrazole-1-carboxylate Int-88 tert-Butyl 3-[(4-chloropyrimidin-5-yl)carbonyl]-1H-pyrazole-1-carboxylate (1.5 g, 4.9 mmol) and (1R,2R,3R,5R)-3-amino-2-fluoro-5-(hydroxymethyl)cyclopentanol hydrochloride (1.08 g, 5.83 mmol) were weighed into a reaction vessel with stirbar. To this mixture was added 2-propanol (20 mL) and DIEA (3 mL, 17 mmol). The resulting mixture was sealed and the vessel allowed to stir at rt for 18 h. The reaction was then concentrated to afford tert-butyl 3-[(4-{[(1R,2R,3R,4R)-2-fluoro-3-hydroxy-4-(hydroxymethyl)cyclopentyl]amino}pyrimidin-5-yl)carbonyl]-1H-pyrazole-1-carboxylate (2.1 g, 100%). LCMS (AA): m/z=422.5 (M+H).

Step 2: (4-{[(1R,2R,3R,4R)-3-{[tert-Butyl(dimethyl)silyl]oxy}-4-({[tert-butyl(dimethyl)silyl]oxy}methyl)-2-fluorocyclopentyl]amino}pyrimidin-5-yl)(1H-pyrazol-3-yl)methanone Int-89

To a RBF was added tert-butyl 3-[(4-{[(1R,2R,3R,4R)-2-fluoro-3-hydroxy-4-(hydroxymethyl)cyclopentyl]amino}pyrimidin-5-yl)carbonyl]-1H-pyrazole-1-carboxylate (0.47 g, 1.1 mmol), DCM (6 mL), and HCl (4.0 M solution in dioxane; 10 mL, 40 mmol). The resulting reaction mixture was stirred at rt for 16 hr. The reaction mixture was then concentrated and imidazole (0.38 g, 5.6 mmol), tert-butyldimethylsilyl chloride (0.5 g, 3.3 mmol), and DCM (10 mL) were added. The mixture was then stirred for 16 h at rt. The mixture was filtered and the filtrate was concentrated. The resulting residue was purified on silica gel to afford (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)(1H-pyrazol-3-yl)methanone (0.13 g, 20%). LCMS (AA): m/z=550.7 (M+H).

Step 3: (4-{[(1R,2R,3R,4R)-3-{[tert-Butyl(dimethyl)silyl]oxy}-2-fluoro-4-(hydroxymethyl)cyclopentyl]amino}pyrimidin-5-yl)(1H-pyrazol-3-yl)methanone To (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)(1H-pyrazol-3-yl)methanone (0.50 g, 0.73 mmol) was added 1% HCl in EtOH

333

(30 mL, 3.6 mmol) at rt. The reaction vessel was sealed and placed in a refrigerator (4° C.) for 14 h. The reaction was quenched by addition of a saturated aq. solution of NaHCO$_3$. To the residue was added water which was extracted with EtOAc (4×). The combined organic layers were dried over MgSO$_4$, filtered, and concentrated. The residue was purified on silica gel to give (4-{[(1R,2R,3R,4R)-3-{[tert-butyl(dimethyl)silyl]oxy}-2-fluoro-4-(hydroxymethyl)cyclopentyl]amino}pyrimidin-5-yl)(1H-pyrazol-3-yl)methanone (0.20 g, 63%). LCMS (FA): m/z=436 (M+H).

Step 4: ((1R,2R,3R,4R)-4-((5-(1-(3-Bromo-2-fluorobenzyl)-1H-pyrazole-3 carbonyl) pyrimidin-4-yl)amino)-3-fluoro-2-hydroxycyclopentyl)methyl sulfamate I-177

To a 2-dram vial pre-weighed with 1-bromo-3-(bromomethyl)-2-fluorobenzene (0.022 g, 0.080 mmol) was added (4-{[(1R,2R,3R,4R)-3-{[tert-butyl(dimethyl)silyl]oxy}-2-fluoro-4 (hydroxymethyl)cyclopentyl]amino}pyrimidin-5-yl)(1H-pyrazol-3-yl)methanone (0.028 g, 0.064 mmol) in DMF (1.0 mL) followed by cesium carbonate (0.084 g, 0.26 mmol). The mixture was shaken at rt for 1 h. Dimethylamine (2.0 M in THF; 0.016 mL, 0.032 mmol) was then added to quench excess benzyl bromide. The solids were then filtered and rinsed with DMF (1 mL). To the filtrate solution in a 3-dram vial was added TEA (0.036 mL, 0.26 mmol) and chlorosulfonamide (0.030 g, 0.26 mmol). The solution was shaken at rt for 1 h. To the vial was then added EtOAc (5 mL) and water (2 mL). After separation of the phases, the aqueous layer was extracted with EtOAc (5 mL). The combined organic phases were concentrated. To the resulting residue in a 20-mL vial was added TFA (1.8 mL) and water (0.2 mL). After shaking at rt for 2 h, solvent was completed evaporated. To this residue was added MeOH (5.0 mL) and MP PL-CO3 (0.50 g). After shaking at rt for 30 min, the resin was filtered and rinsed with MeOH (5 mL). This filtrate solution was then concentrated and the solid residue was purified by prep-HPLC to provide ((1R,2R,3R,4R)-4-((5-(1-(3-bromo-2-fluorobenzyl)-1H-pyrazole-3 carbonyl) pyrimidin-4-yl)amino)-3-fluoro-2-hydroxycyclopentyl)methyl sulfamate (4 mg, 11%). LCMS (FA): m/z=587.1 (M+H).

The compounds listed in the table below were prepared in an analogous fashion to that described above starting from the listed starting materials:

| Starting material | Compound No. | LCMS Data |
|---|---|---|
| (4-F, 3-Br, benzyl-Br) | I-92 | LCMS (FA): m/z = 587.1 (M + H). |
| (4-F, 3-Cl, benzyl-Br) | I-122 | LCMS (FA): m/z = 543.1 (M + H). |
| (4-Cl, 3-Br, benzyl-Br) | I-207 | LCMS (FA): m/z = 603.1 (M + H). |
| (4-Cl, 3-Br, benzyl-Br) | I-127 | LCMS (FA): m/z = 603.0 (M + H). |
| (4-F, 3-I, benzyl-Br) | I-178 | LCMS (FA): m/z = 635.4 (M + H). |
| (3-I, benzyl-Br) | I-42 | LCMS (FA): m/z = 617.0 (M + H). |

Example 73: [(1R,2R,3R,4R)-3-Fluoro-2-hydroxy-4-{[5-({1-[3-(trifluoromethoxy)benzyl]-1H-pyrazol-3-yl}carbonyl)pyrimidin-4-yl]amino}cyclopentyl]methyl sulfamate I-23

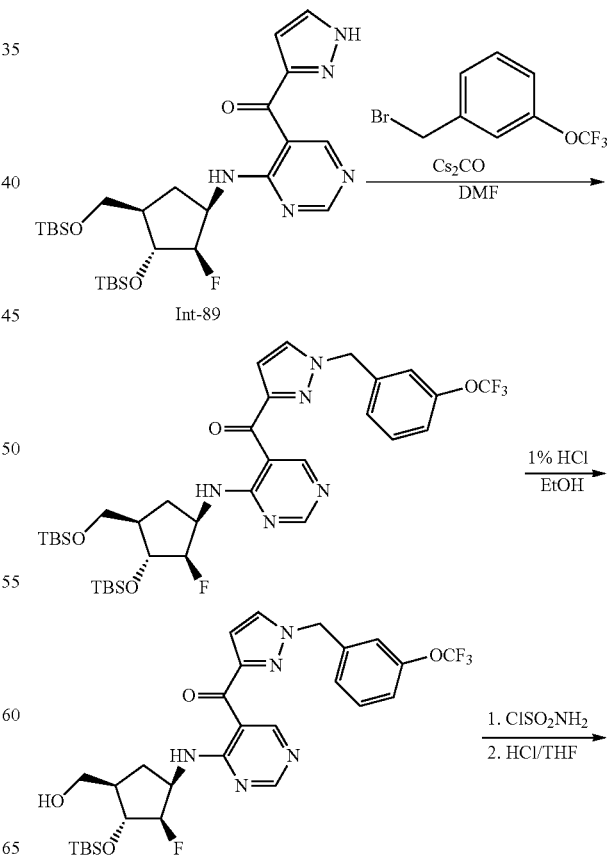

335

-continued

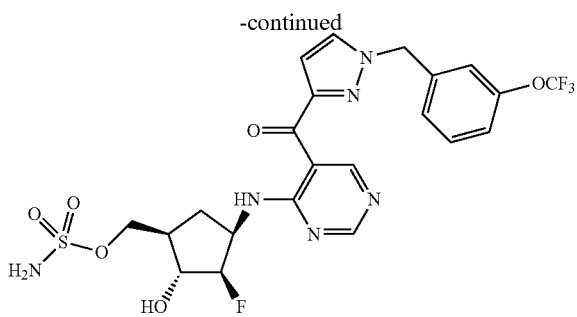

Step 1: (4-{[(1R,2R,3R,4R)-3-([tert-Butyl(dimethyl) silyl]oxy}-4-({[tert-butyl(dimethyl)silyl]oxy) methyl)-2-fluorocyclopentyl]amino}pyridin-5-yl){1-[3-(trifluoromethoxy)benzyl]-1H-pyrazol-3-yl}methanone To a round bottomed flask with stirbar was added (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)(1H-pyrazol-3-yl)methanone (0.25 g, 0.46 mmol), 3-(trifluoromethoxy)benzyl bromide (0.10 mL, 0.64 mmol), cesium carbonate (0.74 g, 2.3 mmol), and THF (10 mL). The resulting reaction mixture was stirred at rt overnight. The mixture was filtered to remove cesium carbonate and the filtrate concentrated. The residue was purified on silica gel to yield (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl){1-[3-(trifluoromethoxy)benzyl]-1H-pyrazol-3-yl}methanone (0.29 g, 88%).

Step 2: (4-{[(1R,2R,3R,4R)-3-{[tert-Butyl(dimethyl)silyl]oxy}-2-fluoro-4-(hydroxymethyl)cyclopentyl]amino}pyrimidin-5-yl){1-[3-(trifluoromethoxy)benzyl]-1H-pyrazol-3-yl}methanone To a solution of (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl){1-[3-(trifluoromethoxy)benzyl]-1H-pyrazol-3-yl}methanone (0.28 g, 0.40 mmol) in EtOH (9.6 mL) was added 1% HCl in EtOH (9.6 mL, 1.2 mmol) at rt. The reaction vessel was sealed and placed in a refrigerator (4° C.) for 23 h. The reaction was quenched by addition of a saturated aq. solution of NaHCO₃. To the residue was added water which was then extracted with EtOAc (4×). The combined organic layers were dried over MgSO₄, filtered, and concentrated. The residue was purified on silica gel to give (4-{[(1R,2R,3R,4R)-3-{[tert-butyl(dimethyl)silyl]oxy}-2-fluoro-4-(hydroxymethyl)cyclopentyl]amino}pyrimidin-5-yl) {1-[3-(trifluoromethoxy)benzyl]-1H-pyrazol-3-yl}methanone (0.17 g, 71%). LCMS (FA): m/z=611 (M+H).

Step 3: [(1R,2R,3R,4R)-3-Fluoro-2-hydroxy-4-{[5-({1-[3-(trifluoromethoxy)benzyl]-1H-pyrazol-3-yl}carbonyl)pyrimidin-4-yl]amino}cyclopentyl]methyl sulfamate I-23

To a solution of (4-{[(1R,2R,3R,4R)-3-{[tert-butyl(dimethyl)silyl]oxy}-2-fluoro-4-(hydroxymethyl)cyclopentyl]amino}pyrimidin-5-yl){1-[3-(trifluoromethoxy)benzyl]-1H-pyrazol-3-yl}methanone (0.17 g, 0.28 mmol) in DMF (2 mL) was added chlorosulfonamide (60 mg, 0.52 mmol) at rt, and the mixture was stirred for 1.25 h. Additional chlorosulfonamide (15 mg, 0.13 mmol) was added and the reaction stirred 16 h. The reaction was then quenched by addition of a saturated solution of NaHCO₃ and diluted with water. The mixture was extracted with EtOAc (4×). The combined organic layers were dried over MgSO₄, filtered, and concentrated. The crude sulfamate intermediate was dissolved in THF (4.4 mL) and HCl (3.0 M in water; 2.6 mL, 7.9 mmol) was added to the solution. The reaction was stirred for 2 h at rt. The reaction was quenched by the addition of a saturated solution of NaHCO₃ and extracted with EtOAc (4×). The combined organic layers were dried over MgSO₄, filtered, and concentrated. The residue was purified on silica gel to afford [(1R,2R,3R,4R)-3-fluoro-2-hydroxy-4-{[5-({1-[3-(trifluoromethoxy)benzyl]-1H-pyrazol-3-yl}carbonyl)pyrimidin-4-yl]amino}cyclopentyl]methyl sulfamate (100 mg, 67%). ¹H NMR (DMSO) δ 9.56 (s, 1H), 9.24 (d, J=7.5 Hz, 1H), 8.69 (s, 1H), 8.13 (d, J=2.4 Hz, 1H), 7.59-7.39 (m, 3H), 7.39-7.24 (m, 3H), 6.96 (d, J=2.4 Hz, 1H), 5.60 (s, 2H), 5.56 (s, 1H), 4.94-4.71 (m, 2H), 4.13 (dd, J=9.8, 6.0 Hz, 1H), 4.04 (dd, J=9.5, 6.7 Hz, 1H), 4.02-3.87 (m, 1H), 2.42-2.30 (m, 1H), 2.27-2.05 (m, 1H), 1.58-1.41 (m, 1H); LCMS (FA): m/z=575.4 (M+H).

The compounds listed in the table below were prepared using a similar method to that described above starting from the listed starting materials:

| Starting material | Compound No. | LCMS Data |
| --- | --- | --- |
| Br—⌬—OCHF₂ | I-303 | LCMS (FA): m/z = 557.3 (M + H). |
| Cl—⌬—Cl with Br | I-307 | LCMS (AA): m/z = 559.5 (M + H). |
| Br—⌬—Cl,Cl | I-311 | LCMS (FA): m/z = 559.5 (M + H). |

337
-continued
| Starting material | Compound No. | LCMS Data |
|---|---|---|
| 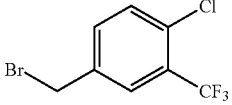 | I-156 | LCMS (FA): m/z = 593.6 (M + H). |
| 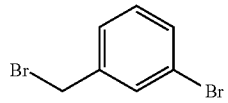 | I-15 | LCMS (FA): m/z = 571.0 (M + H). |
| 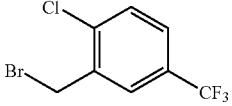 | I-181 | LCMS (FA): m/z = 514.3 (M + H). |
| 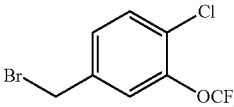 | I-218 | LCMS (FA): m/z = 609.6 (M + H). |
Example 74: [(1R,2R,3R,4R)-4-({5-[(1-{3-[Acryloyl(methyl)amino]benzyl}-1H-pyrazol-3-yl)carbonyl]pyrimidin-4-yl}amino)-3-fluoro-2-hydroxycyclopentyl]methyl sulfamate I-116
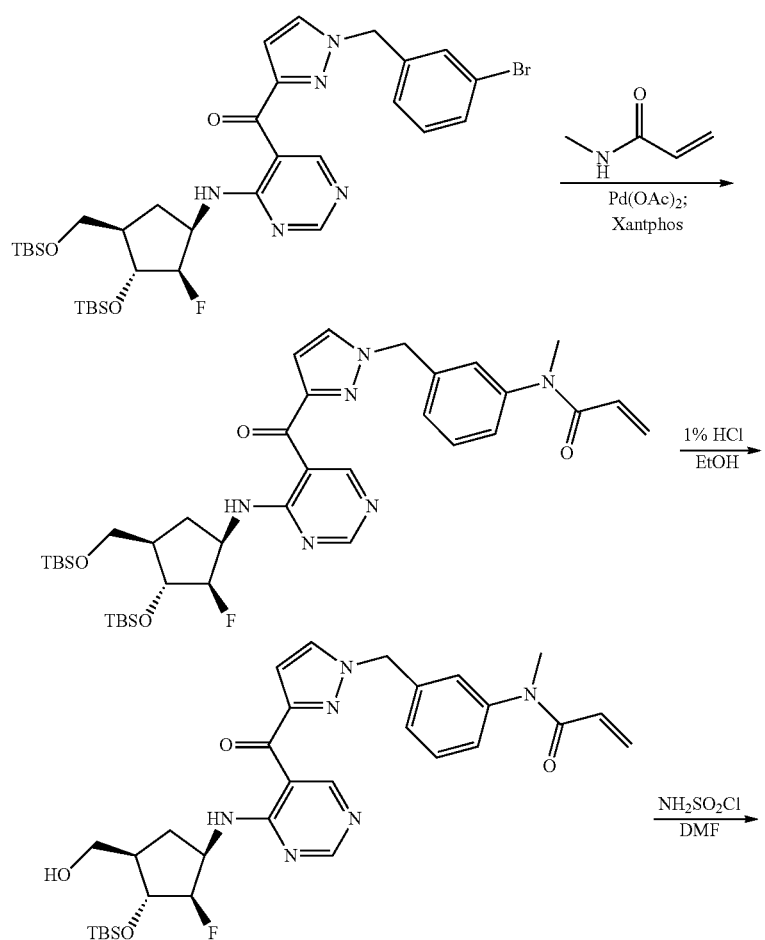

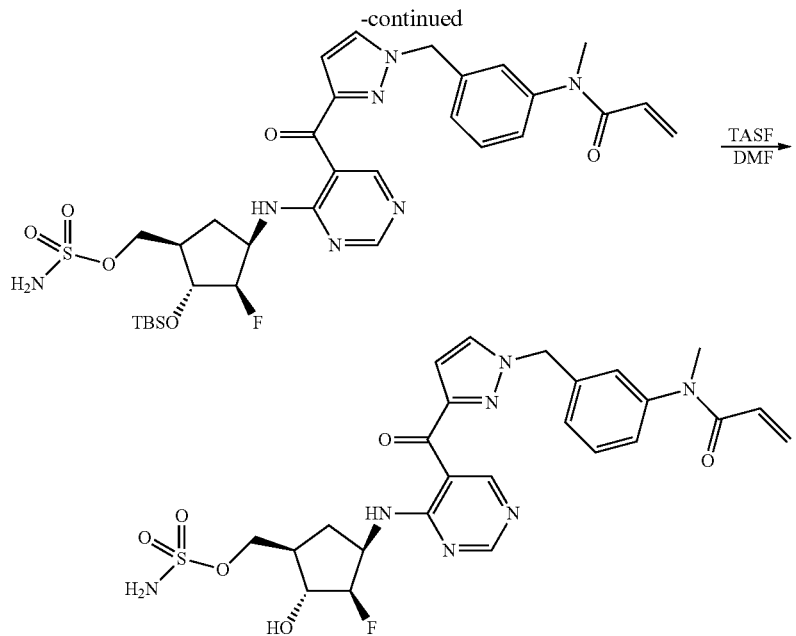

Step 1: N-[3-({3-[(4-{[(1R,2R,3R,4R)-3-{[tert-Butyl(dimethyl)silyl]oxy}-4-({[tert-butyl(dimethyl)silyl]oxy}methyl)-2-fluorocyclopentyl]amino}pyrimidin-5-yl)carbonyl]-1H-pyrazol-1-yl}methyl)phenyl]-N-methylacrylamide A solution of [1-(3-bromobenzyl)-1H-pyrazol-3-yl](4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)methanone (400 mg, 0.56 mmol; see example 73 for analagous synthesis) in 1,4-dioxane (17 mL) was degassed by bubbling through argon. N-Methylacrylamide (142 mg, 1.7 mmol) and cesium carbonate (540 mg, 1.7 mmol) were added and the mixture stirred under an atmosphere of argon. Separately, a solution of 4,5-bis(diphenylphosphino)-9,9-dimethylxanthene (29.0 mg, 0.050 mmol) and tris(dibenzylideneacetone)dipalladium(0) (15.3 mg, 0.017 mmol) was prepared in 1,4-dioxane (5.7 mL). This solution was degassed by bubbling through argon and then heated to 60° C. It was subsequently added to the above solution and the resulting mixture was heated at 90° C. for 18 h. The reaction was allowed to cool, filtered through celite, and concentrated. The residue was purified on silica gel to yield N-[3-({3-[(4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)carbonyl]-1H-pyrazol-1-yl}methyl)phenyl]-N-methylacrylamide (320 mg, 80%). LCMS (FA): m/z=723.3 (M+H).

Step 2: N-[3-({3-[(4-{[(1R,2R,3R,4R)-3-{[tert-Butyl(dimethyl)silyl]oxy}-2-fluoro-4-(hydroxymethyl)cyclopentyl]amino}pyrimidin-5-yl)carbonyl]-1H-pyrazol-1-yl}methyl)phenyl]-N-methylacrylamide A solution of HCl (0.10 M solution in EtOH; 1.0 mL, 0.10 mmol) was added to N-[3-({3-[(4-{[(1R,2R,3R,4R)-3-{[tert-butyl(dimethyl)silyl]oxy}methyl)-2-fluorocyclopentyl]amino}pyrimidin-5-yl)carbonyl]-1H-pyrazol-1-yl}methyl)phenyl]-N-methylacrylamide (90.0 mg, 0.124 mmol) and the solution was stirred for 3 h at rt. The reaction was quenched by addition of a saturated aq. solution of NaHCO₃. To the residue was added water which was then extracted with EtOAc (3×). The combined organic layers were dried over MgSO₄, filtered, and concentrated. The residue was purified on silica gel to give N-[3-({3-[(4-{[(1R,2R,3R,4R)-3-{[tert-butyl(dimethyl)silyl]oxy}-2-fluoro-4-(hydroxymethyl)cyclopentyl]amino}pyrimidin-5-yl)carbonyl]-1H-pyrazol-1-yl}methyl)phenyl]-N-methylacrylamide (49 mg, 65%). LCMS (FA): m/z=609.2 (M+H).

Step 3: [(1R,2R,3R,4R)-4-({5-[(1-{3-[Acryloyl(methyl)amino]benzyl}-1H-pyrazol-3-yl)carbonyl]pyrimidin-4-yl}amino)-2-{[tert-butyl(dimethyl)silyl]oxy}-3-fluorocyclopentyl]methyl sulfamate To a solution of N-[3-({3-[(4-{[(1R,2R,3R,4R)-3-{[tert-butyl(dimethyl)silyl]oxy}-2-fluoro-4-(hydroxymethyl)cyclopentyl]amino}pyrimidin-5-yl)carbonyl]-1H-pyrazol-1-yl}methyl)phenyl]-N-methylacrylamide (100 mg, 0.16 mmol) and TEA (0.10 mL, 0.72 mmol) in DMF (2 mL) was added chlorosulfonamide (57 mg, 0.49 mmol) at rt, and the mixture was stirred for 3 h. The reaction was then quenched by addition of a saturated solution of NaHCO₃ and diluted with water. The mixture was extracted with EtOAc (3×). The combined organic layers were dried over MgSO₄, filtered, and concentrated. The crude product was purified on silica gel to give [(1R,2R,3R,4R)-4-({5-[(1-{3-[acryloyl(methyl)amino]benzyl}-1H-pyrazol-3-yl)carbonyl]pyrimidin-4-yl}amino)-2-{[tert-butyl(dimethyl)silyl]oxy}-3-fluorocyclopentyl]methyl sulfamate (63 mg, 56%). LCMS (FA): m/z=689.3 (M+H).

Step 4: [(1R,2R,3R,4R)-4-({5-[(1-{3-[Acryloyl(methyl)amino]benzyl}-1H-pyrazol-3-yl)carbonyl]pyrimidin-4-yl}amino)-3-fluoro-2-hydroxycyclopentyl]methyl sulfamate I-116

TASF (24 mg, 0.087 mmol) was added to a solution of [(1R,2R,3R,4R)-4-({5-[(1-{3-[acryloyl(methyl)amino]benzyl}-1H-pyrazol-3-yl)carbonyl]pyrimidin-4-yl}amino)-2-{[tert-butyl(dimethyl)silyl]oxy}-3-fluorocyclopentyl]methyl sulfamate (30 mg, 0.044 mmol) in DMF (1 mL) at rt. The reaction mixture was stirred for 16 h at rt. The reaction was diluted with EtOAc and washed with water. The organic layer was dried over MgSO₄, filtered, and concentrated. The residue was purified by prep HPLC to afford [(1R,2R,3R,4R)-4-({5-[(1-{3-[acryloyl(methyl)amino]benzyl}-1H-pyrazol-3-yl)carbonyl]pyrimidin-4-yl}amino)-3-fluoro-2-hydroxycyclopentyl]methyl sulfamate (21 mg, 84%). ¹H NMR (DMSO) δ 9.56 (s, 1H), 9.23 (d, J=7.3 Hz, 1H), 8.69 (s, 1H), 8.09 (s, 1H), 7.52 (s, 2H), 7.47-7.34 (m, 3H), 7.28 (m, 2H), 6.94 (s, 1H), 6.60 (s, 1H), 6.56 (s, 1H), 5.54 (s, 2H), 4.97-4.69 (m, 2H), 4.16-4.08 (m, 1H), 4.08-4.00 (m, 1H), 3.94 (m, 1H), 2.70 (s, 3H), 2.41-2.29 (m, 1H), 2.25-2.12 (m, 1H), 1.55-1.39 (m, 1H). LCMS (FA): m/z=574.3 (M+H).

Example 75: [(1R,2R,3R,4R)-3-Fluoro-2-hydroxy-4-{[5-({1-[2-oxo-2-(pyrrolidin-1-yl)ethyl]-1H-pyrazol-3-yl}carbonyl)pyrimidin-4-yl]amino}cyclopentyl]methyl sulfamate I-19

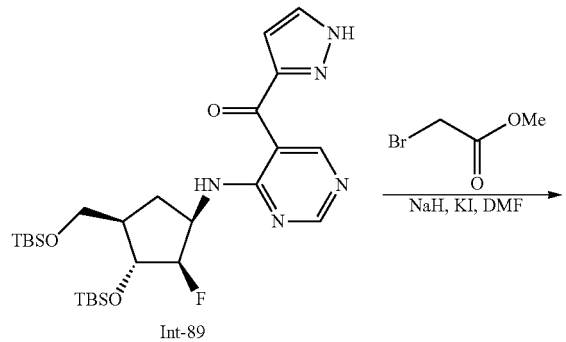

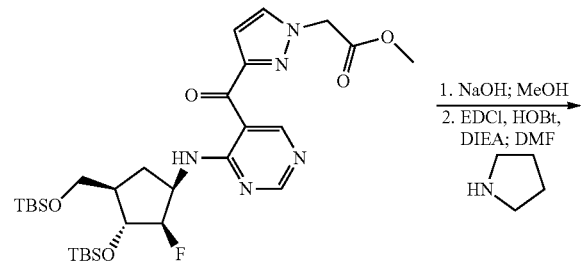

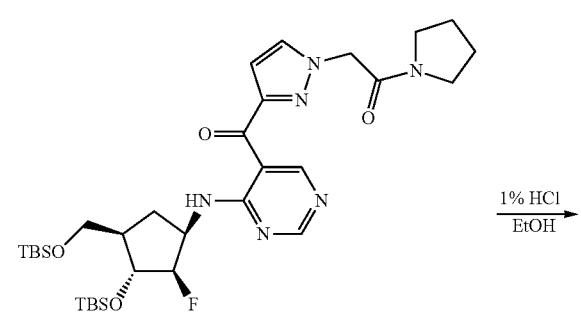

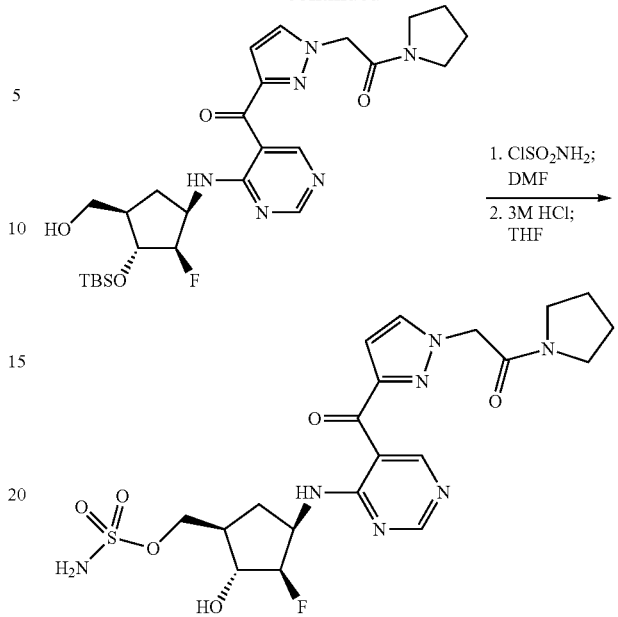

Step 1: Methyl {3-[(4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)carbonyl]-1H-pyrazol-1-yl}acetate Sodium hydride (60% in mineral oil; 0.038 g, 0.94 mmol) was added to a solution of (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)(1H-pyrazol-3-yl)methanone (0.35 g, 0.63 mmol) in DMF (13 mL) at 0° C. The suspension was stirred at that temperature for 1 h. Potassium iodide (0.11 g, 0.69 mmol) was added followed by a solution of methyl bromoacetate (0.15 mL, 1.6 mmol) in DMF (2 mL). The reaction mixture was allowed to warm to rt and stirred for 2 h. A saturated solution of NaHCO₃ was added to the reaction mixture and it was extracted with EtOAc (3×). The combined organic layers were washed with brine, dried over magnesium sulfate, filtered and concentrated. The residue was purified on silica gel to give methyl {3-[(4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)carbonyl]-1H-pyrazol-1-yl}acetate (0.39 g, 99%). LCMS (FA): m/z=622.5 (M+H).

Step 2: 2-{3-[(4-{[(1R,2R,3R,4R)-3-{[tert-Butyl(dimethyl)silyl]oxy}-4-({[tert-butyl(dimethyl)silyl]oxy}methyl)-2-fluorocyclopentyl]amino}pyrimidin-5-yl)carbonyl]-1H-pyrazol-1-yl}-1-(pyrrolidin-1-yl)ethanone A mixture of {3-[(4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)carbonyl]-1H-pyrazol-1-yl}acetate (0.39 g, 0.62 mmol) and sodium hydroxide (0.5 g, 12.4 mmol) were stirred in methanol (10 mL) at rt for 18 h. The mixture was concentrated to remove the solvent then diluted with water. The mixture was extracted with EtOAc, washed with brine, dried over magnesium sulfate, filtered and concentrated to give the carboxylic acid intermediate (0.18 g, 47%) which was dissolved in DMF (2.0 mL). N-(3-Dimethylaminopropyl)-N'-ethylcarbodiimide hydrochloride (42 mg, 0.22 mmol), 1-hydroxybenzotriazole (29 mg, 0.22 mmol), pyrrolidine (0.02 mL, 0.3 mmol), and DIEA (0.04 mL, 0.2 mmol) were added to the solution and the resulting mixture was stirred at rt for 24 h. A saturated solution of NaHCO$_3$ was added to the reaction mixture and it was extracted with EtOAc (3×). The combined organic layers were washed with brine, dried over magnesium sulfate, filtered and concentrated to give 2-{3-[(4-{[(1R,2R,3R,4R)-3-{[tert-butyl(dimethyl)silyl]oxy}methyl)-2-fluorocyclopentyl]amino}pyrimidin-5-yl)carbonyl]-1H-pyrazol-1-yl}-1-(pyrrolidin-1-yl)ethanone (58 mg, 61%). LCMS (FA): m/z=661.6 (M+H).

Step 3: 2-{3-[(4-{[(1R,2R,3R,4R)-3-{[tert-Butyl(dimethyl)silyl]oxy}-2-fluoro-4-(hydroxymethyl)cyclopentyl]amino}pyrimidin-5-yl)carbonyl]-1H-pyrazol-1-yl}-1-(pyrrolidin-1-yl)ethanone To a solution of 2-{3-[(4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)carbonyl]-1H-pyrazol-1-yl}-1-(pyrrolidin-1-yl)ethanone (50 mg, 0.076 mmol) in EtOH (1.8 mL) was added 1% HCl in EtOH (3.3 mL, 0.40 mmol) at it. The reaction vessel was sealed and allowed to stand in a refrigerator (4° C.) for 15 h. The reaction was quenched by addition of a saturated aq. solution of NaHCO$_3$. To the residue was added water which was extracted with EtOAc (4×). The combined organic layers were dried over MgSO$_4$, filtered, and concentrated to give 2-{3-[(4-{[(1R,2R,3R,4R)-3-{[tert-butyl(dimethyl)silyl]oxy}-2-fluoro-4-(hydroxymethyl)cyclopentyl]amino}pyrimidin-5-yl)carbonyl]-1H-pyrazol-1-yl}-1-(pyrrolidin-1-yl)ethanone (53 mg, 100%). LCMS (FA): m/z=547.5 (M+H).

Step 4: [(1R,2R,3R,4R)-3-Fluoro-2-hydroxy-4-{[5-({1-[2-oxo-2-(pyrrolidin-1-yl)ethyl]-1H-pyrazol-3-yl}carbonyl)pyrimidin-4-yl]amino}cyclopentyl]methyl sulfamate I-19

To a solution of 2-{3-[(4-{[(1R,2R,3R,4R)-3-({[tert-butyl(dimethyl)silyl]oxy}-2-fluoro-4-(hydroxymethyl)cyclopentyl]amino}pyrimidin-5-yl)carbonyl]-1H-pyrazol-1-yl}-1-(pyrrolidin-1-yl)ethanone (53 mg, 0.097 mmol) and TEA (0.040 mL, 0.29 mmol) in DMF (0.7 mL) was added chlorosulfonamide (34 mg, 0.29 mmol) at rt, and the mixture was stirred for 1 h. HCl (3.0 M in water, 1.3 mL, 3.9 mmol) was added to the solution. The reaction was stirred for 30 min at rt. The reaction was quenched by the addition of a saturated solution of NaHCO$_3$ and extracted with EtOAc (4×). The combined organic layers were dried over MgSO$_4$, filtered, and concentrated. The residue was purified by prep HPLC to afford [(1R,2R,3R,4R)-3-fluoro-2-hydroxy-4-{[5-({-[2-oxo-2-(pyrrolidin-1-yl)ethyl]-1H-pyrazol-3-yl}carbonyl)pyrimidin-4-yl]amino}cyclopentyl]methyl sulfamate (4 mg, 7%). $^1$H NMR (DMSO) δ 9.60 (s, 1H), 9.26 (d, J=7.3 Hz, 1H), 8.70 (s, 1H), 7.88 (s, 1H), 7.50 (s, 2H), 6.92 (s, 1H), 5.57 (d, J=5.1 Hz, 1H), 5.25 (s, 2H), 4.96-4.86 (m, 1H), 4.80-4.75 (m, 1H), 4.15-4.10 (m, 1H), 4.06-4.01 (m, 1H), 3.57 (s, 4H), 3.52 (t, J=6.8 Hz, 2H), 2.42-2.28 (m, 2H), 1.96-1.88 (m, 2H), 1.85-1.75 (m, 2H); LCMS (FA): m/z=512.3 (M+H).

Example 76: [(1R,2R,3R,4R)-3-fluoro-2-hydroxy-4-{[5-({1-[3-(trifluoromethyl)benzyl]-1H-pyrazol-3-yl}carbonyl)pyrimidin-4-yl]amino}cyclopentyl] methyl sulfamate I-102

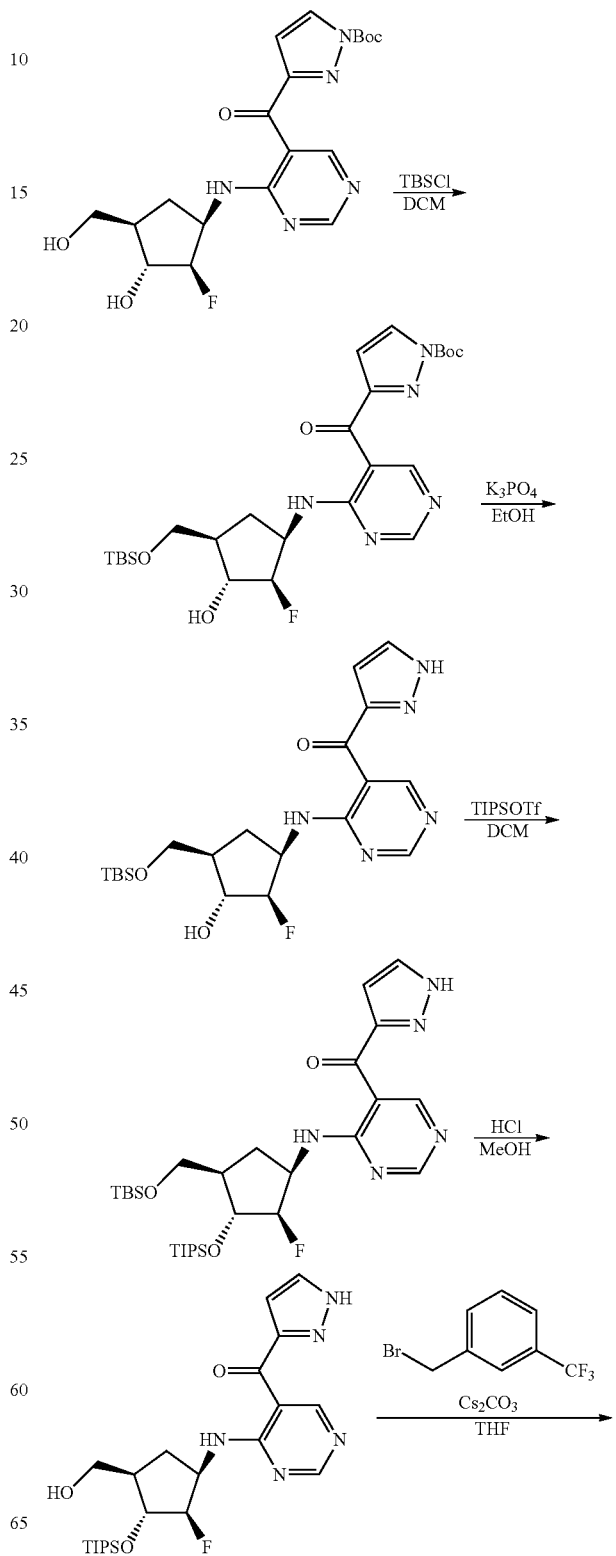

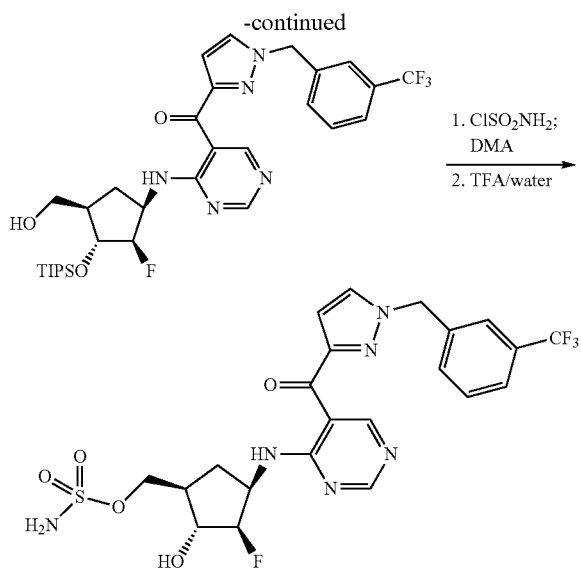

Step 1: tert-Butyl 3-[(4-{[(1R,2R,3R,4R)-4-({[tert-butyl(dimethyl)silyl]oxy}methyl)-2-fluoro-3-hydroxycyclopentyl]amino}pyrimidin-5-yl)carbonyl]-1H-pyrazole-1-carboxylate A solution of tert-butyl 3-[(4-{[(1R,2R,3R,4R)-2-fluoro-3-hydroxy-4-(hydroxymethyl)cyclopentyl]amino}pyrimidin-5-yl)carbonyl]-1H-pyrazole-1-carboxylate (0.57 g, 1.4 mmol) and 1H-imidazole (0.277 g, 4.07 mmol) in DCM (25 mL) was cooled in an ice/water bath. tert-Butyldimethylsilyl chloride (0.23 g, 1.5 mmol) was added and the reaction was stirred at 0° C. for 2 h. The reaction was then quenched by addition of water (350 mL) and the mixture was extracted with DCM (2×). The combined organic layers were concentrated and the crude product was purified on silica gel to afford [tert-butyl 3-[(4-{[(1R,2R,3R,4R)-4-({[tert-butyl(dimethyl)silyl]oxy}methyl)-2-fluoro-3-hydroxycyclopentyl]amino}pyrimidin-5-yl)carbonyl]-1H-pyrazole-1-carboxylate] (0.58 g, 72%). LCMS (AA): m/z=536 (M+H).

Step 2: (4-{[(1R,2R,3R,4R)-4-({[tert-Butyl(dimethyl)silyl]oxy}methyl)-2-fluoro-3-hydroxycyclopentyl]amino}pyrimidin-5-yl)(1H-pyrazol-3-yl)methanone tert-Butyl 3-[(4-{[(1R,2R,3R,4R)-4-({[tert-butyl(dimethyl)silyl]oxy}methyl)-2-fluoro-3-hydroxycyclopentyl]amino}pyrimidin-5-yl)carbonyl]-1H-pyrazole-1-carboxylate (0.58 g, 1.08 mmol) was dissolved in methanol (20 mL) and a solution of potassium phosphate (0.23 g, 1.08 mmol) in water (3 mL) was added. This mixture was allowed to stir at rt for 3 h. The reaction solvent was evaporated and DCM (100 mL) was added to the residue. This solution was washed with water (2×) and the organic layer was concentrated to yield (4-{[(1R,2R,3R,4R)-4-({[tert-butyl(dimethyl)silyl]oxy}methyl)-2-fluoro-3-hydroxycyclopentyl]amino}pyrimidin-5-yl)(1H-pyrazol-3-yl)methanone (0.47 g, 100%). LCMS (AA): m/z=436 (M+H).

Step 3: [4-({(1R,2R,3R,4R)-4-({[tert-butyl(dimethyl)silyl]oxy}methyl)-2-fluoro-3-[(triisopropylsilyl)oxy]cyclopentyl}amino)pyrimidin-5-yl](1H-pyrazol-3-yl)methanone (4-{[(1R,2R,3R,4R)-4-({[tert-Butyl(dimethyl)silyl]oxy}methyl)-2-fluoro-3-hydroxycyclopentyl]amino}pyrimidin-5-yl)(1H-pyrazol-3-yl)methanone (0.86 g, 2.0 mmol) and 2,6-lutidine (0.64 g, 5.9 mmol) were dissolved in DCM (30 mL) and triisopropylsilyl triflate (0.91 g, 3.0 mmol) was added to this solution. The reaction mixture was allowed to stir at rt for 4 h. The reaction mixture was concentrated and the resulting residue was purified on silica gel to produce [4-({(1R,2R,3R,4R)-4-({[tert-butyl(dimethyl)silyl]oxy}methyl)-2-fluoro-3-[(triisopropylsilyl)oxy]cyclopentyl}amino)pyrimidin-5-yl](1H-pyrazol-3-yl)methanone (0.92 g, 79%). LCMS (AA): m/z=592 (M+H).

Step 4: [4-({(1R,2R,3R,4R)-2-fluoro-4-(hydroxymethyl)-3-[(triisopropylsilyl)oxy]cyclopentyl}amino)pyrimidin-5-yl](1H-pyrazol-3-yl)methanone

[4-({(1R,2R,3R,4R)-4-({[tert-Butyl(dimethyl)silyl]oxy}methyl)-2-fluoro-3-[(triisopropylsilyl)oxy]cyclopentyl}amino)pyrimidin-5-yl](1H-pyrazol-3-yl)methanone (0.42 g, 0.71 mmol) was dissolved in methanol (20 mL) and HCl (0.05 M solution in methanol; 20 mL, 1.0 mmol) was added to this solution. The reaction mixture was allowed to stir at rt for 15 min. The reaction mixture was concentrated and the residue was dissolved in MeOH (20 mL). TEA (1 mL) was added to this solution and the solvent was subsequently removed in vacuo and the resulting residue was purified on silica gel to produce [4-({(1R,2R,3R,4R)-2-fluoro-4-(hydroxymethyl)-3-[(triisopropylsilyl)oxy]cyclopentyl}amino)pyrimidin-5-yl](1H-pyrazol-3-yl)methanone (0.22 g, 82%). LCMS (AA): m/z=478.6 (M+H).

Step 5: {(1R,2R,3R,4R)-3-fluoro-4-{[5-({1-[3-(trifluoromethyl)benzyl]-1H-pyrazol-3-yl}carbonyl)pyrimidin-4-yl]amino}-2-[(triisopropylsilyl)oxy]cyclopentyl}methyl sulfamate

[4-({(1R,2R,3R,4R)-2-Fluoro-4-(hydroxymethyl)-3-[(triisopropylsilyl)oxy]cyclopentyl}amino)pyrimidin-5-yl](1H-pyrazol-3-yl)methanone (0.051 g, 0.11 mmol) was dissolved in THF (50 mL) and cesium carbonate (0.11 g, 0.32 mmol) was added to this solution. 3-(trifluoromethyl)benzyl bromide (0.027 g, 0.11 mmol) was added and the reaction was allowed to stir for 16 h at rt. The solids were removed via filtration and DMA (4 mL) was added to the filtrate. Chlorosulfonamide (0.037 g, 0.32 mmol) was then added and the mixture stirred at rt for 30 min. The reaction mixture was then concentrated and the resulting residue was purified on silica gel to afford {(1R,2R,3R,4R)-3-fluoro-4-{[5-({1-[3-(trifluoromethyl)benzyl]-1H-pyrazol-3-yl}carbonyl)pyrimidin-4-yl]amino}-2-[(triisopropylsilyl)oxy]cyclopentyl}methyl sulfamate (0.058 g, 73%). LCMS (AA): m/z=636 (M+H).

Step 6: [(1R,2R,3R,4R)-3-fluoro-2-hydroxy-4-{[5-({1-[3-(trifluoromethyl)benzyl]-1H-pyrazol-3-yl}carbonyl)pyrimidin-4-yl]amino}cyclopentyl] methyl sulfamate I-102

{(1R,2R,3R,4R)-3-Fluoro-4-{[5-({1-[3-(trifluoromethyl)benzyl]-1H-pyrazol-3-yl}carbonyl)pyrimidin-4-yl]amino}-2-[(triisopropylsilyl)oxy]cyclopentyl}methyl sulfamate (0.058 g, 0.081 mmol) was dissolved in a solution of TFA (3.6 mL) and water (0.40 mL). The reaction was allowed to stir for 1 h at rt. TLC and LCMS indicated no desired reaction had occurred. HCl (4.0 M in EtOH; 2.0 mL, 8.0 mmol) was subsequently added and the resulting solution was stirred for 1 h at rt. The reaction mixture was then concentrated and the resulting residue dissolved in MeOH (5 mL) and DIEA (1 mL). This mixture was concentrated and purified by prep HPLC to provide [(1R,2R,3R,4R)-3-fluoro-2-hydroxy-4-{[5-({1-[3-(trifluoromethyl)benzyl]-1H-pyrazol-3-yl}carbonyl)pyrimidin-4-yl]amino}cyclopentyl]methyl sulfamate (13 mg, 28%). ¹H NMR (MeOD) δ 9.68 (s, 1H), 8.61 (s, 1H), 7.89 (d, J=2.4 Hz, 1H), 7.63 (d, J=11.3 Hz, 2H), 7.60-7.53 (m, 2H), 7.00 (d, J=2.4 Hz, 1H), 5.59 (s, 2H), 5.02-4.96 (m, 1H), 4.23 (ddd, 2H), 4.12 (dd, 1H), 2.58-2.42 (m, 1H), 2.37-2.22 (m, 1H), 1.74-1.51 (m, 1H). LCMS (AA): m/z=559.1 (M+H).

The compound listed in the table below was prepared in an analogous fashion to that described above starting from the listed starting material used in step 5.

| Starting material | Compound No. | LCMS Data |
|---|---|---|
| 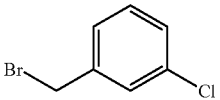 | I-176 | LCMS (FA): m/z = 525.1 (M + H). |

Example 77: {(1R,2R,3R,4R)-4-[(5-{[1-(3-Bromobenzyl)-5-methyl-1H-pyrazol-3-yl]carbonyl}pyrimidin-4-yl)amino]-3-fluoro-2-hydroxycyclopentyl}methyl sulfamate I-186

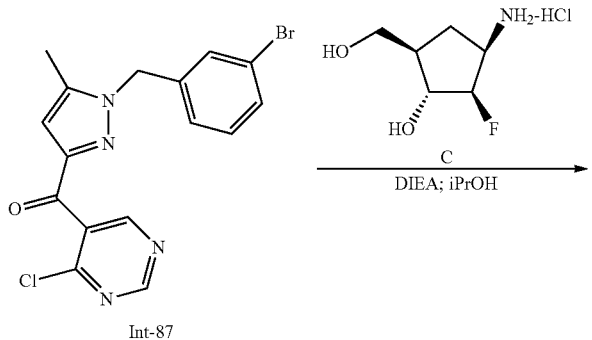

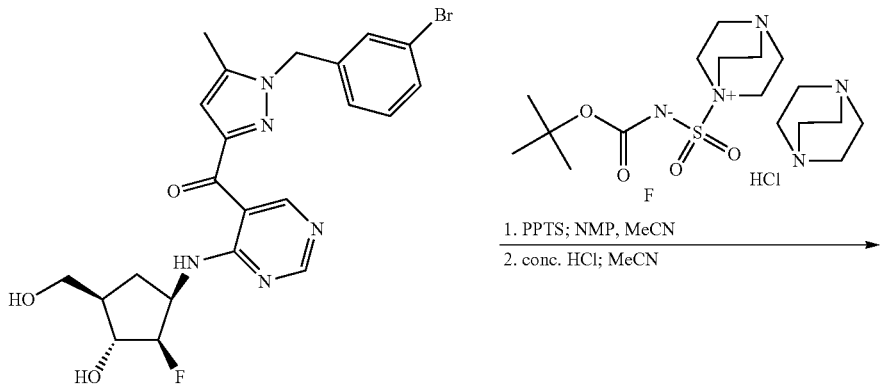

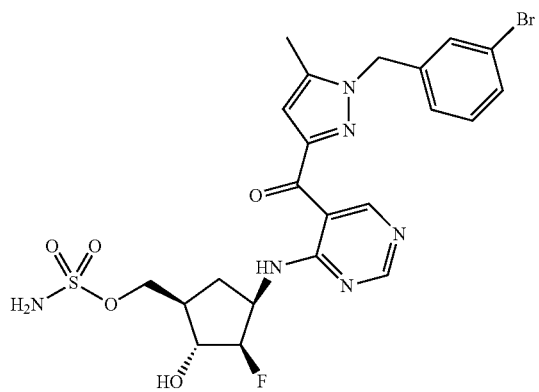

Step 1: [1-(3-Bromobenzyl)-5-methyl-1H-pyrazol-3-yl](4-{[(1R,2R,3R,4R)-2-fluoro-3-hydroxy-4-(hydroxymethyl)cyclopentyl]amino}pyrimidin-5-yl)methanone

[1-(3-bromobenzyl)-5-methyl-1H-pyrazol-3-yl](4-chloropyrimidin-5-yl)methanone (0.54 g, 1.4 mmol) and (1R,2R,3R,5R)-3-amino-2-fluoro-5-(hydroxymethyl)cyclopentanol.HCl (0.29 g, 1.6 mmol) were weighed into a reaction vessel. To this mixture was added 2-propanol (21 mL) and DIEA (0.7 mL, 4.1 mmol). The resulting mixture was stirred at rt for 3.5 h. The reaction was then concentrated. The crude product was purified on silica gel to afford [1-(3-bromobenzyl)-5-methyl-1H-pyrazol-3-yl](4-{[(1R,2R,3R,4R)-2-fluoro-3-hydroxy-4-(hydroxymethyl)cyclopentyl]amino}pyrimidin-5-yl)methanone (0.20 g, 28%). LCMS (FA): m/z=506.4 (M+H).

Step 2: {(1R,2R,3R,4R)-4-[(5-{[1-(3-Bromobenzyl)-5-methyl-1H-pyrazol-3-yl]carbonyl}pyrimidin-4-yl)amino]-3-fluoro-2-hydroxycyclopentyl}methyl sulfamate I-186

[1-(3-Bromobenzyl)-5-methyl-1H-pyrazol-3-yl](4-{[(1R,2R,3R,4R)-2-fluoro-3-hydroxy-4-(hydroxymethyl)cyclopentyl]amino}pyrimidin-5-yl)methanone (0.20 g, 0.39 mmol) was dissolved in NMP (1.9 mL) and acetonitrile (0.95 mL). To this solution was added in one portion PPTS (98 mg, 0.39 mmol) followed by the addition of (4-aza-1-azoniabicyclo[2.2.2]oct-1-ylsulfonyl)(tert-butoxycarbonyl)azanide-1,4-diazabicyclo[2.2.2]octane (1:1) hydrochloride (F) (see: Armitage, I. et al. Org. Lett. 2012, 14, 2626-2629.) (0.43 g, 0.97 mmol). After stirring 2 h at rt, additional (4-aza-1-azoniabicyclo[2.2.2]oct-1-ylsulfonyl)(tert-butoxycarbonyl)azanide-1,4-diazabicyclo[2.2.2]octane (1:1) hydrochloride (F) (80 mg, 0.18 mmol) was added and continued to stir at rt an additional 2 h. Upon reaction completion, the reaction was quenched by the addition of water. The mixture was extracted with EtOAc (3×). The combined organic layers were dried over MgSO$_4$, filtered and concentrated. The crude product was purified on silica gel to give the Boc-protected sulfamate intermediate [(0.22 g, 84%); LCMS (FA): m/z=685.5 (M+H).] which was then dissolved in acetonitrile (1.0 mL) at rt. Concentrated HCl (0.50 mL, 6.0 mmol) was added at 0° C. The mixture was then allowed to stir at rt for 18 h. The reaction was quenched by the addition of a saturated solution of NaHCO$_3$ in water. After diluting the mixture with water it was extracted with EtOAc (4×). The combined organic layers were dried over MgSO$_4$, filtered, and concentrated. The crude product was purified on silica gel to give {(1R,2R,3R,4R)-4-[(5-{[1-(3-bromobenzyl)-5-methyl-1H-pyrazol-3-yl]carbonyl}pyrimidin-4-yl)amino]-3-fluoro-2-hydroxycyclopentyl}methyl sulfamate (82 mg, 43%). $^1$H NMR (DMSO) δ 9.58 (s, 1H), 9.24 (d, J=7.9 Hz, 1H), 8.69 (s, 1H), 7.54-7.48 (m, 3H), 7.42 (s, 1H), 7.34 (t, J=7.9 Hz, 1H), 7.16-7.10 (m, 1H), 6.76 (s, 1H), 5.56 (d, J=5.2 Hz, 1H), 5.51 (s, 2H), 4.93-4.73 (m, 2H), 4.16-4.08 (m, 1H), 4.07-3.99 (m, 1H), 3.99-3.87 (m, 1H), 2.40-2.32 (m, 1H), 2.30 (s, 3H), 2.24-2.14 (m, 1H), 1.57-1.39 (m, 1H); LCMS (FA): m/z=585.2 (M+H).

The compound listed in the table below was prepared in an analogous fashion to that described above starting from the listed starting material:

| Starting material | Compound No. | LCMS Data |
|---|---|---|
| (structure with iodine-substituted benzyl pyrazole pyrimidine) | I-294 | LCMS (FA): m/z = 631.3 (M + H). |
| See Ex. 63; prepared in a similar manner to Int-87 | | |

Example 78: [(1R,2R,3R,4R)-3-Fluoro-2-hydroxy-4-({5-[(5-methyl-1-{[5-(trifluoromethyl)-2-furyl]methyl-1H-pyrazol-3-yl}-1-pyrazol-3-yl)carbonyl]pyrimidin-4-yl}amino)cyclopentyl]methyl sulfamate I-197

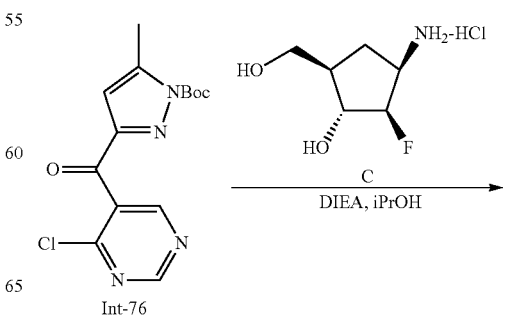

Int-76

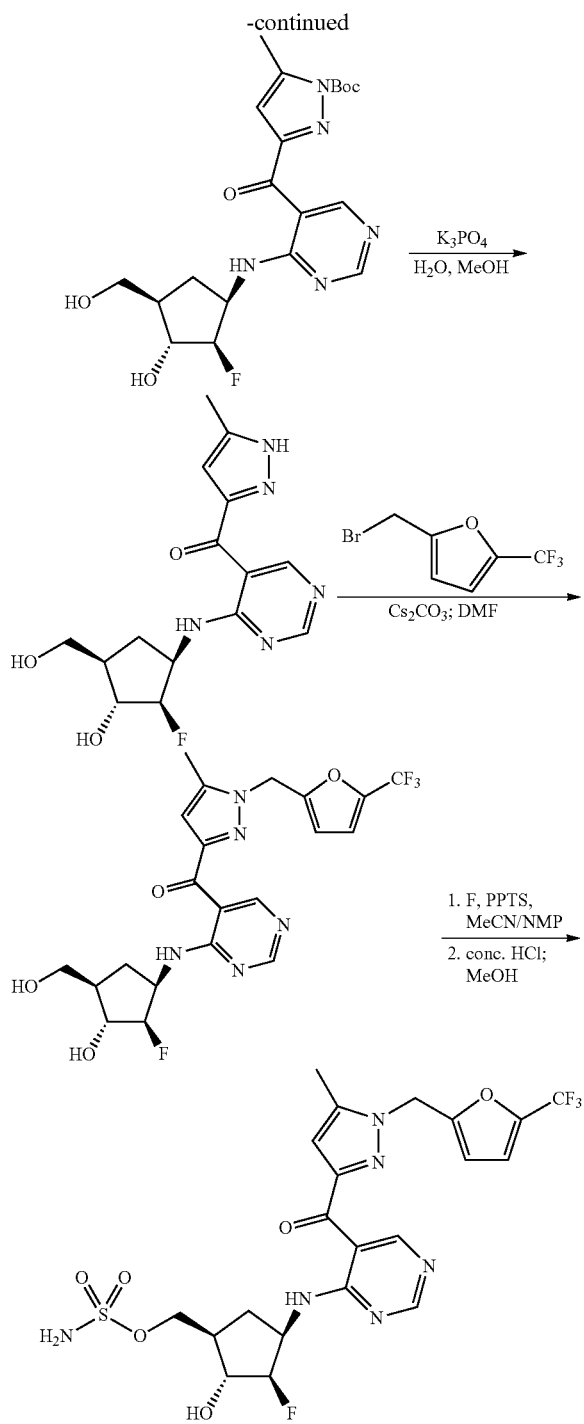

was stirred at rt for 5 h. The reaction was then concentrated. The crude product was purified on silica gel to afford tert-butyl 3-[(4-{[(1R,2R,3R,4R)-2-fluoro-3-hydroxy-4-(hydroxymethyl)cyclopentyl]amino}pyrimidin-5-yl)carbonyl]-5-methyl-1H-pyrazole-1-carboxylate (0.46 g, 100%). LCMS (FA): m/z=436.5 (M+H).

Step 2: (4-{[(1R,2R,3R,4R)-2-Fluoro-3-hydroxy-4-(hydroxymethyl) cyclopentyl]amino}pyrimidin-5-yl) (5-methyl-1H-pyrazol-3-yl)methanone To a solution of tert-butyl 3-[(4-{[(1R,2R,3R,4R)-2-fluoro-3-hydroxy-4-(hydroxymethyl)cyclopentyl]amino}pyrimidin-5-yl)carbonyl]-5-methyl-1H-pyrazole-1-carboxylate (0.46 g, 1.1 mmol) in EtOH (10 mL) was added a solution of potassium phosphate (0.47 g, 2.2 mmol) in water (1.5 mL). This mixture was stirred at rt for 16 h. The mixture was concentrated to remove the EtOH. Water was added to the mixture and it was extracted with EtOAc (3×). The combined extracts were dried over MgSO$_4$, filtered, and concentrated. To the resulting residue was added ether and a white solid formed. The white solid was filtered off and the filtrate concentrated to give (4-{[(1R,2R,3R,4R)-2-fluoro-3-hydroxy-4-(hydroxymethyl) cyclopentyl]amino}pyrimidin-5-yl)(5-methyl-1H-pyrazol-3-yl)methanone (0.35 g, 98%). LCMS (FA): m/z=336.4 (M+H).

Step 3: (4-{[(1R,2R,3R,4R)-2-Fluoro-3-hydroxy-4-(hydroxymethyl) cyclopentyl]amino}pyrimidin-5-yl) (5-methyl-1-{[5-(trifluoromethyl)-2-furyl]methyl}-1H-pyrazol-3-yl)methanone (4-{[(1R,2R,3R,4R)-2-Fluoro-3-hydroxy-4-(hydroxymethyl) cyclopentyl]amino}pyrimidin-5-yl)(5-methyl-1H-pyrazol-3-yl)methanone (0.35 g, 1.0 mmol) was dissolved in DMF (10 mL). To this solution was added cesium carbonate (0.67 g, 2.1 mmol) and 2-(bromomethyl)-5-(trifluoromethyl)furan (0.28 g, 1.2 mmol) and the reaction was stirred at rt for 2 h. The reaction was quenched by addition of water. This mixture was then extracted with EtOAc (3×). The combined organic layers were dried over MgSO$_4$, filtered and concentrated. The residue was purified on silica gel to give (4-{[(1R,2R,3R,4R)-2-fluoro-3-hydroxy-4-(hydroxymethyl) cyclopentyl]amino}pyrimidin-5-yl)(5-methyl-1-{[5-(trifluoromethyl)-2-furyl]methyl}-1H-pyrazol-3-yl)methanone (0.15 g, 29%). LCMS (FA): m/z=485.5 (M+H).

Step 4: [(1R,2R,3R,4R)-3-Fluoro-2-hydroxy-4-({5-[(5-methyl-1-{[5-(trifluoromethyl)-2-furyl]methyl}-1H-pyrazol-3-yl)carbonyl]pyrimidin-4-yl}amino) cyclopentyl]methyl sulfamate I-197

(4-{[(1R,2R,3R,4R)-2-Fluoro-3-hydroxy-4-(hydroxymethyl)cyclopentyl]amino}pyrimidin-5-yl)(5-methyl-1-{[5-(trifluoromethyl)-2-furyl]methyl}-1H-pyrazol-3-yl)methanone (0.14 g, 0.30 mmol) was dissolved in NMP (2.0 mL) and acetonitrile (1.0 mL). To this solution was added in one portion PPTS (74 mg, 0.30 mmol) followed by the addition of (4-aza-1-azoniabicyclo[2.2.2]oct-1-ylsulfonyl)(tert-butoxycarbonyl)azanide-1,4-diazabicyclo[2.2.2]octane (1:1) hydrochloride (F) (0.39 g, 0.89 mmol). After stirring 1 h at rt, additional (4-aza-1-azoniabicyclo[2.2.2]oct-1-ylsulfonyl)(tert-butoxycarbonyl)azanide-1,4-diazabicyclo[2.2.2]octane (1:1) hydrochloride (F) (60 mg, 0.14 mmol) was added and continued to stir at rt an additional 2 h. Upon reaction completion, the reaction was quenched by the addition of Step 1: tert-Butyl 3-[(4-{[(1R,2R,3R,4R)-2-fluoro-3-hydroxy-4-(hydroxymethyl)cyclopentyl]amino}pyrimidin-5-yl)carbonyl]-5-methyl-1H-pyrazole-1-carboxylate tert-Butyl 3-[(4-chloropyrimidin-5-yl)carbonyl]-5-methyl-1H-pyrazole-1-carboxylate (0.31 g, 0.95 mmol) and (1R,2R,3R,5R)-3-amino-2-fluoro-5-(hydroxymethyl)cyclopentanol.HCl (0.26 g, 1.4 mmol) were weighed into a reaction vessel. To this mixture was added 2-propanol (14 mL) and DIEA (0.5 mL, 2.9 mmol). The resulting mixture water. The mixture was extracted with EtOAc (3×). The combined organic layers were dried over MgSO₄, filtered and concentrated. The crude Boc-protected sulfamate intermediate was then dissolved in acetonitrile (1.0 mL) at rt. Concentrated HCl (0.50 mL, 6.0 mmol) was added at 0° C. The mixture was then allowed to stir at rt for 18 h. The reaction was quenched by the addition of a saturated solution of NaHCO₃ in water. After diluting the mixture with water it was extracted with EtOAc (4×). The combined organic layers were dried over MgSO₄, filtered, and concentrated. The crude product was purified by prep HPLC to give [(1R,2R,3R,4R)-3-fluoro-2-hydroxy-4-({5-[(5-methyl-1-{[5-(trifluoromethyl)-2-furyl]methyl}-1H-pyrazol-3-yl)carbonyl]pyrimidin-4-yl}amino)cyclopentyl]methyl sulfamate (50 mg, 27%). ¹H NMR (DMSO) δ 9.55 (s, 1H), 9.23 (d, J=7.3 Hz, 1H), 8.70 (s, 1H), 7.50 (s, 2H), 7.23 (s, 1H), 6.74-6.67 (m, 2H), 5.61 (s, 2H), 5.56 (d, J=5.0 Hz, 1H), 4.92-4.71 (m, 2H), 4.16-4.07 (m, 1H), 4.07-3.99 (m, 1H), 3.99-3.88 (m, 1H), 2.40 (s, 3H), 2.38-2.30 (m, 1H), 2.25-2.14 (m, 1H), 1.54-1.43 (m, 1H); LCMS (FA): m/z=485.5 (M+H).

Example 79: {(1R,2R,3R,4R)-4-[(5-{[1-(3-Chlorobenzyl)-5-(trifluoromethyl)-1H-pyrazol-3-yl]carbonyl}pyrimidin-4-yl)amino]-3-fluoro-2-hydroxycyclopentyl}methyl sulfamate I-316

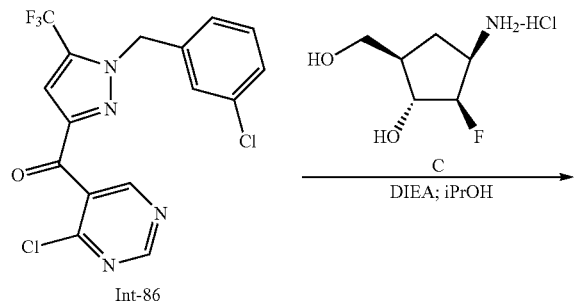

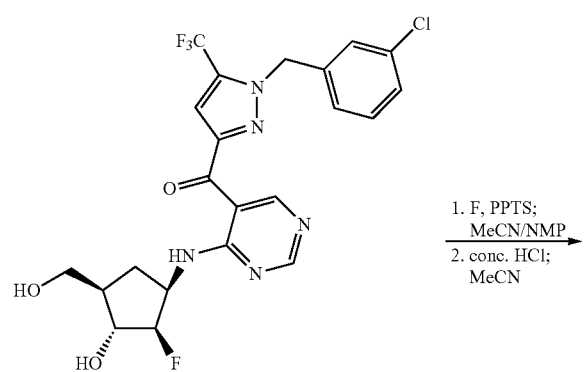

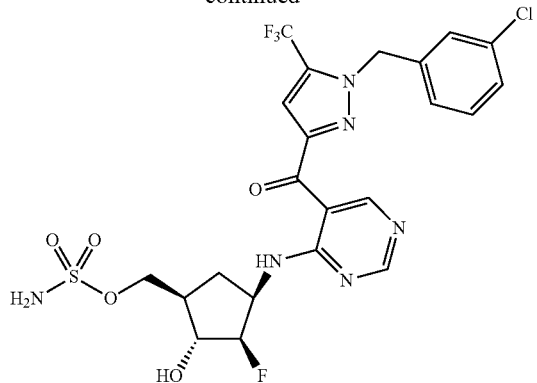

Step 1: [1-(3-Chlorobenzyl)-5-(trifluoromethyl)-1H-pyrazol-3-yl](4-{[(1R,2R,3R,4R)-2-fluoro-3-hydroxy-4-(hydroxymethyl)cyclopentyl]amino}pyrimidin-5-yl)methanone

[1-(3-Chlorobenzyl)-5-(trifluoromethyl)-1H-pyrazol-3-yl](4-chloropyrimidin-5-yl)methanone (0.11 g, 0.27 mmol) and (1R,2R,3R,5R)-3-amino-2-fluoro-5-(hydroxymethyl)cyclopentanol hydrochloride (61 mg, 0.33 mmol) were weighed into a 20 mL reaction vessel. To this mixture was added 1-propanol (3.3 mL) and DIEA (0.14 mL, 0.82 mmol). The resulting mixture was sealed and the vessel allowed to stir while heating at 35° C. for 16 h. The reaction was then cooled to rt and the reaction was concentrated. The crude product was purified on silica gel to afford [1-(3-chlorobenzyl)-5-(trifluoromethyl)-1H-pyrazol-3-yl](4-{[(1R,2R,3R,4R)-2-fluoro-3-hydroxy-4-(hydroxymethyl)cyclopentyl]amino}pyrimidin-5-yl)methanone (0.12 g, 85%). LCMS (FA): m/z=514 (M+H).

Step 2: {(1R,2R,3R,4R)-4-[(5-{[1-(3-Chlorobenzyl)-5-(trifluoromethyl)-1H-pyrazol-3-yl]carbonyl}pyrimidin-4-yl)amino]-3-fluoro-2-hydroxycyclopentyl}methyl sulfamate I-316

[1-(3-chlorobenzyl)-5-(trifluoromethyl)-1H-pyrazol-3-yl](4-{[(1R,2R,3R,4R)-2-fluoro-3-hydroxy-4-(hydroxymethyl)cyclopentyl]amino}pyrimidin-5-yl)methanone (0.12 g, 0.23 mmol) was dissolved in NMP (1.1 mL) and acetonitrile (0.57 mL). To this solution was added in one portion PPTS (59 mg, 0.23 mmol) followed by the addition of (4-aza-1-azoniabicyclo[2.2.2]oct-1-ylsulfonyl)(tert-butoxycarbonyl)azanide-1,4-diazabicyclo[2.2.2]octane (1:1) hydrochloride (F) (0.21 g, 0.47 mmol). After 1 h, additional (4-aza-1-azoniabicyclo[2.2.2]oct-1-ylsulfonyl)(tert-butoxycarbonyl)azanide-1,4-diazabicyclo[2.2.2]octane (1:1) hydrochloride (F) (40 mg, 0.09 mmol) was added and continued to stir at rt an additional 2 h. Upon completion, the reaction was quenched by the addition of water. The mixture was extracted with EtOAc (3×). The combined organic layers were dried over MgSO₄, filtered and concentrated. The crude product was purified on silica gel to give the Boc-protected sulfamate intermediate which was then dissolved in acetonitrile (1.0 mL) at rt. Concentrated HCl (0.50 mL, 6.0 mmol) was added at 0° C. The mixture was then allowed to stir at rt for 18 h. The reaction was quenched by the addition of a saturated solution of NaHCO₃ in water. After diluting the mixture with water it was extracted with EtOAc (4×). The combined organic layers were dried over MgSO$_4$, filtered, and concentrated. The crude product was purified by prep HPLC to give {(1R,2R,3R,4R)-4-[(5-{[1-(3-chlorobenzyl)-5-(trifluoromethyl)-1H-pyrazol-3-yl]carbonyl}pyrimidin-4-yl)amino]-3-fluoro-2-hydroxycyclopentyl}methyl sulfamate (65 mg, 51%). $^1$H NMR (DMSO) δ 9.45 (s, 1H), 9.18 (d, J=7.6 Hz, 1H), 8.72 (s, 1H), 7.57 (s, 1H), 7.49 (s, 2H), 7.44-7.37 (m, 2H), 7.34 (s, 1H), 7.20-7.08 (m, 1H), 5.70 (s, 2H), 5.57 (s, 1H), 4.95-4.71 (m, 2H), 4.12 (dd, J=9.7, 5.9 Hz, 1H), 4.03 (dd, J=9.7, 6.9 Hz, 1H), 3.95 (dd, J=22.1, 4.1 Hz, 1H), 2.41-2.31 (m, 1H), 2.25-2.12 (m, 1H), 1.50 (dd, J=22.5, 11.2 Hz, 1H); LCMS (FA): m/z=593.5 (M+H).

Example 80: [(1R,2S,4R)-4-{[5-({1-[3,5-Bis(trifluoromethyl)benzyl]-1H-pyrrol-3-yl}carbonyl) pyrimidin-4-yl]amino}-2-hydroxycyclopentyl]methylsulfamate I-168

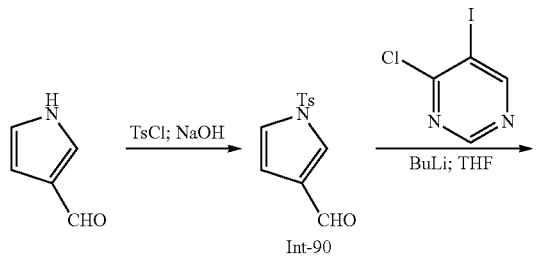

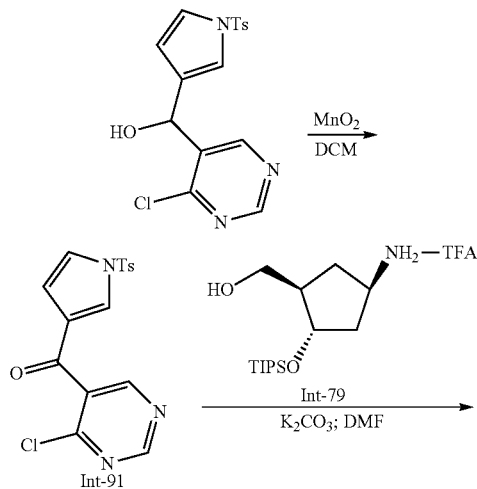

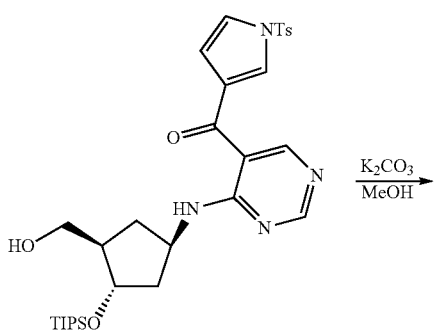

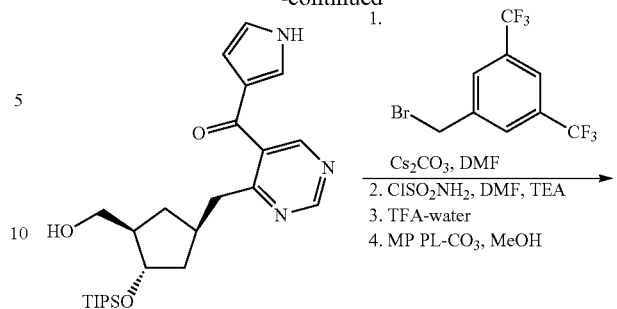

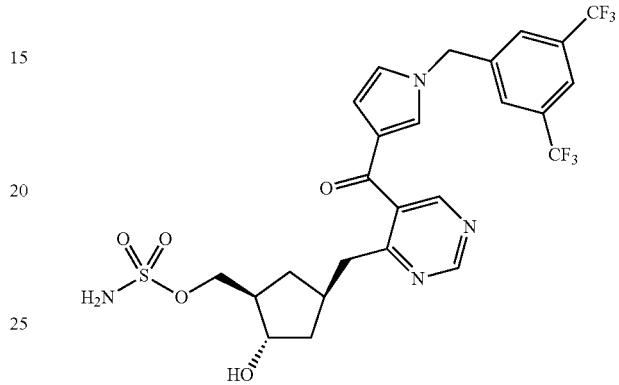

Step 1: 1-[(4-Methylphenyl)sulfonyl]-1H-pyrrole-3-carbaldehyde

1H-Pyrrole-3-carbaldehyde (4.5 g, 47 mmol) was dissolved in DCM (400 mL) and the solution was cooled to 0° C. in an ice bath. Sodium hydroxide (2.3 g, 57 mmol) was added and the mixture stirred for 10 min at 0° C. The reaction mixture was kept cool and p-toluenesulfonyl chloride (18.0 g, 95 mmol) was added in 2 portions (10 min apart). The reaction mixture was allowed to stir at 0° C. and then slowly warm to rt and stir for 19 h. The reaction was then diluted with DCM (100 mL) and the mixture washed with water (2×). The organic layer was dried over MgSO$_4$, filtered, and concentrated. The crude product was purified on silica gel to yield 1-[(4-methylphenyl)sulfonyl]-1H-pyrrole-3-carbaldehyde (10.4 g, 88%). LCMS (FA): m/z=250.1 (M+H).

Step 2: (4-Chloropyrimidin-5-yl){1-[(4-methylphenyl)sulfonyl]-1H-pyrrol-3-yl}methanol Into a flame dried RBF with stirbar was added 4-chloro-5-iodopyrimidine (2.3 g, 9.5 mmol) dissolved in THF (20 mL). The flask was purged with argon and cooled to −78° C. To this solution was added dropwise n-butyllithium (2.5 M in hexane; 7.9 mL, 19.8 mmol) at −78° C. and the mixture was stirred for 30 min. To this mixture was added 1-[(4-methylphenyl)sulfonyl]-1H-pyrrole-3-carbaldehyde (2.15 g, 8.6 mmol) dissolved in THF (10 mL) dropwise. The reaction was stirred at −78° C. for 3 h. The reaction was quenched with a saturated solution of NH$_4$Cl and then extracted with EtOAc (3×). The combined organic layers were then washed with water and brine, dried over Na$_2$SO$_4$, filtered and concentrated. The crude product was purified on silica gel to give (4-chloropyrimidin-5-yl){1-[(4-methylphenyl)sulfonyl]-1H-pyrrol-3-yl}methanol (2.2 g, 69%); LCMS (FA): m/z=364.0 (M+H).

Step 3: (4-Chloropyrimidin-5-yl){1-[(4-methylphenyl)sulfonyl]-1H-pyrrol-3-yl}methanone To a solution of (4-chloropyrimidin-5-yl) {I-[(4-methylphenyl)sulfonyl}-1H-pyrrol-3-yl}methanol (2.2 g, 6.0 mmol) in DCM (60 mL) was added manganese(IV) oxide (5.2 g, 60 mmol). The suspension was stirred for 19 h at rt. The reaction was then filtered through a celite pad and the residual solid was washed with DCM several times. The filtrate was then concentrated in vacuo and the residue was purified on silica gel to afford (4-chloropyrimidin-5-yl){1-[(4-methylphenyl)sulfonyl]-1H-pyrrol-3-yl}methanone (2.1 g, 97%). LCMS (FA): m/z=362.0 (M+H).

Step 4: [4-({(1R,3R,4S)-3-(Hydroxymethyl)-4-[(triisopropylsilyl)oxy]cyclopentyl}amino)pyrimidin-5-yl]{1-[(4-methylphenyl)sulfonyl]-1H-pyrrol-3-yl}methanone Into a RBF was added tert-butyl {(1R,3R,4S)-3-(hydroxymethyl)-4-[(triisopropylsilyl)oxy]cyclopentyl}carbamate (0.75 g, 1.9 mmol), DCM (2 mL), and TFA (2.0 mL, 26 mmol). The mixture was stirred for 10 min at rt. The reaction was concentrated and azeotroped with toluene (3×) to remove water. The crude material was then dried under high vacuum, dissolved in DMF (3 mL), and added to a solution of (4-chloropyrimidin-5-yl){1-[(4-methylphenyl)sulfonyl]-1H-pyrrol-3-yl}methanone (0.59 g, 1.6 mmol) in DMF (8 mL). Potassium carbonate (0.67 g, 4.9 mmol) was added to the reaction vessel and the resulting mixture was stirred at rt for 24 h. The reaction was then quenched by addition of water and the mixture extracted with EtOAc (3×). The combined organic layers were then washed with water and brine, dried over $Na_2SO_4$, filtered and concentrated. The crude product was purified on silica gel to provide [4-({(1R,3R,4S)-3-(hydroxymethyl)-4-[(triisopropylsilyl)oxy]cyclopentyl}amino)pyrimidin-5-yl]{-[(4-methylphenyl)sulfonyl]-1H-pyrrol-3-yl}methanone (0.80 g, 81%). LCMS (FA): m/z=613.2 (M+H).

Step 5: [4-({(1R,3R,4S)-3-(Hydroxymethyl)-4-[(triisopropylsilyl)oxy]cyclopentyl}amino)pyrimidin-5-yl](1H-pyrrol-3-yl)methanone Into a RBF with stirbar was added [4-({(1R,3R,4S)-3-(hydroxymethyl)-4-[(triisopropylsilyl)oxy]cyclopentyl}amino)pyrimidin-5-yl]{1-[(4-methylphenyl)sulfonyl]-1H-pyrrol-3-yl}methanone (0.80 g, 1.3 mmol), methanol (20 mL) and potassium carbonate (0.54 g, 3.9 mmol) and the mixture was stirred at rt for 3 h. The reaction was then quenched by addition of water and the mixture extracted with EtOAc (3×). The combined organic layers were then washed with water and brine, dried over $Na_2SO_4$, filtered and concentrated. The crude product was purified on silica gel to provide [4-({(1R,3R,4S)-3-(hydroxymethyl)-4-[(triisopropylsilyl)oxy]cyclopentyl}amino)pyrimidin-5-yl](1H-pyrrol-3-yl)methanone (0.38 g, 64%). LCMS (FA): m/z=459.2 (M+H).

Step 6: [(1R,2S,4R)-4-{[5-({1-[3,5-Bis(trifluoromethyl)benzyl]-1H-pyrrol-3-yl}carbonyl) pyrimidin-4-yl]amino}-2-hydroxycyclopentyl]methylsulfamate I-168

To a 3-dram vial with 1-(bromomethyl)-3,5-bis(trifluoromethyl)benzene (0.025 g, 0.082 mmol) was added [4-({(1R,3R,4S)-3-(hydroxymethyl)-4-[(triisopropylsilyl)oxy]cyclopentyl}amino)pyrimidin-5-yl](1H-pyrrol-3-yl)methanone (0.029 g, 0.063 mmol) in DMF (1.0 mL) followed by cesium carbonate (0.082 g, 0.25 mmol). The mixture was shaken at rt for 2 h. The solid $Cs_2CO_3$ was filtered and rinsed with DMF (1 mL). To the combined clear DMF solution was added chlorosulfonamide (0.0292 g, 0.253 mmol). The solution was shaken at rt for 1 h, then saturated $NaHCO_3$ (2 mL) and EtOAc (5 mL) were added. After separation, the aqueous layer was extracted with EtOAc (5 mL). The combined organic phases were then concentrated. To the resulting solid in a 20-mL vial was added TFA (2.0 mL) and water (0.2 mL) and then shaken at rt for 2 h. The solvent was then evaporated and to the resulting residue was added MeOH (3.0 mL) and MP PL-CO3 resin. After shaking at rt for 30 min, the resin was filtered off and rinsed with MeOH (10 mL). The filtrate was concentrated and the residue purified by prep-HPLC to provide [(1R,2S,4R)-4-{[5-({1-[3,5-bis(trifluoromethyl)benzyl]-1H-pyrrol-3-yl}carbonyl) pyrimidin-4-yl]amino}-2-hydroxycyclopentyl]methylsulfamate (3 mg, 8%). LCMS (FA): m/z=608.4 (M+H).

The compounds listed in the table below were prepared in an analogous fashion to that described above starting from the list class of starting materials in step 6.

| Starting material | Compound No. or Name | LCMS Data |
|---|---|---|
| 3-bromobenzyl bromide | I-333 | LCMS (FA): m/z = 540 (M + H). |
| 5-bromomethyl-2-fluoro-(trifluoromethoxy)benzene | I-211 | LCMS (FA): m/z = 574.4 (M + H). |
| 4-bromomethyl-2-bromo-1-chlorobenzene | I-43 | LCMS (FA): m/z = 584.3 (M + H). |
| 4-bromomethyl-2-bromo-1-fluorobenzene | I-279 | LCMS (FA): m/z = 568.3 (M + H). |
| 4-bromomethyl-1-fluoro-2-(trifluoromethyl)benzene | I-21 | LCMS (FA): m/z = 558.3 (M + H). |
| 3-bromomethyl-5-chlorobenzothiophene | I-341 | LCMS (FA): m/z = 562.4 (M + H). |
| 2-bromomethyl-5-(trifluoromethyl)furan | I-274 | LCMS (FA): m/z = 530.8 (M + H). |

359
-continued

| Starting material | Compound No. or Name | LCMS Data |
|---|---|---|
| Br-CH2-C6H3(CF3)(F) | I-213 | LCMS (FA): m/z = 558.4 (M + H). |
| Br-CH2-C6H4-OCF3 | I-271 | LCMS (FA): m/z = 556.3 (M + H). |
| Br-CH2-C6H4-I | I-68 | LCMS (FA): m/z = 598.3 (M + H). |
| Br-CH2-C6H4-CF3 | I-129 | LCMS (FA): m/z = 540.3 (M + H). |

Example 81: [(1R,2S,4R)-4-{[5-({1-[(5-Bromopyridin-3-yl)methyl]-1H-pyrrol-3-yl}carbonyl)pyrimidin-4-yl]amino}-2-hydroxycyclopentyl]methyl sulfamate I-299

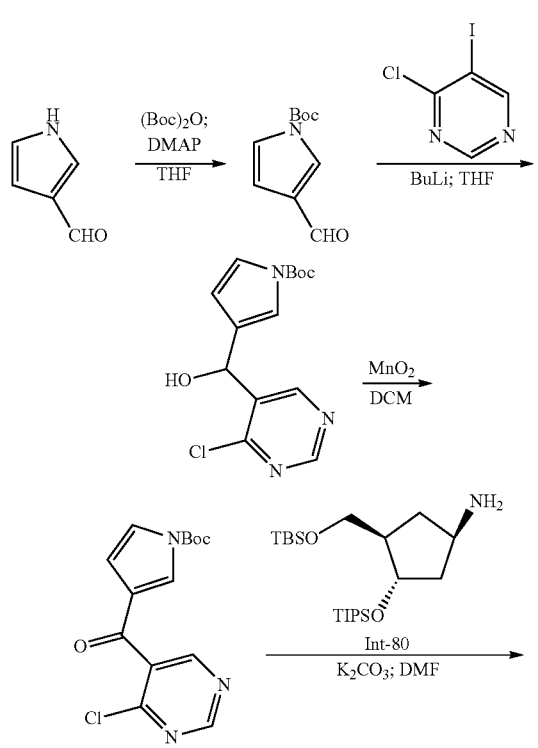

360
-continued

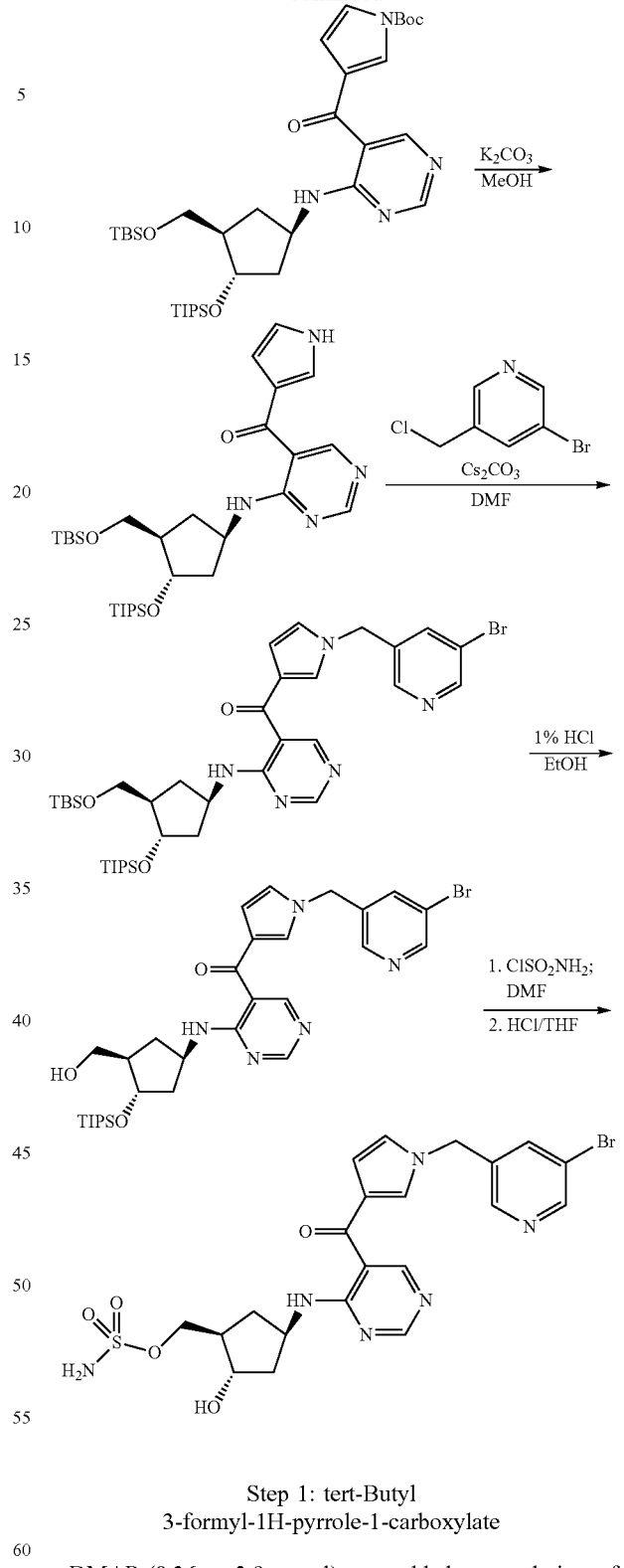

Step 1: tert-Butyl 3-formyl-1H-pyrrole-1-carboxylate

DMAP (0.36 g, 2.9 mmol) was added to a solution of 1H-pyrrole-3-carbaldehyde (2.8 g, 29 mmol) and di-tert-butyldicarbonate (6.8 g, 31 mmol) in acetonitrile (20 mL) and the mixture was stirred at rt overnight. The mixture was concentrated and the residue was purified on silica gel to afford tert-butyl 3-formyl-1H-pyrrole-1-carboxylate (5.4 g, 94%) as a yellow oil. LCMS (FA): m/z=196 (M+H).

Step 2: tert-Butyl 3-[(4-chloropyrimidin-5-yl)(hydroxy)methyl]-1H-pyrrole-1-carboxylate Into a RBF with stirbar was added 4-chloro-5-iodopyrimidine (3.7 g, 15.4 mmol) dissolved in THF (60 mL). The flask was purged with argon and cooled to −78° C. To this solution was added dropwise n-butyllithium (2.5 M in hexane; 11.3 mL, 28.2 mmol) at −78° C. and the mixture was stirred for 30 min. To this mixture was added tert-butyl 3-formyl-1H-pyrrole-1-carboxylate (2.50 g, 12.8 mmol) dissolved in THF (20 mL) dropwise. The reaction was stirred at −78° C. for 2 h. The reaction was quenched with a saturated solution of $NH_4Cl$ and then extracted with EtOAc (3×). The combined organic layers were then washed with water and brine, dried over $Na_2SO_4$, filtered and concentrated. The crude product was purified on silica gel to give tert-butyl 3-[(4-chloropyrimidin-5-yl)(hydroxy)methyl]-1H-pyrrole-1-carboxylate (2.98 g, 75%). LCMS (FA): m/z=310 (M+H).

Step 3: tert-Butyl 3-[(4-chloropyrimidin-5-yl)carbonyl]-1H-pyrrole-1-carboxylate To a solution of 3-[(4-chloropyrimidin-5-yl)(hydroxy)methyl]-1H-pyrrole-1-carboxylate (3.0 g, 9.6 mmol) in DCM (90 mL) was added manganese(IV) oxide (8.34 g, 96 mmol). The suspension was stirred for 19 h at rt. The reaction was then filtered through a celite pad and the residual solid was washed with DCM several times. The filtrate was then concentrated in vacuo and the residue was purified on silica gel to afford tert-butyl 3-[(4-chloropyrimidin-5-yl)carbonyl]-1H-pyrrole-1-carboxylate (2.6 g, 88%). LCMS (FA): m/z=308 (M+H).

Step 4: tert-Butyl 3-{[4-({(1R,3R,4S)-3-({[tert-butyl(dimethyl)silyl]oxy}methyl)-4-[(triisopropylsilyl)oxy]cyclopentyl}amino)pyrimidin-5-yl]carbonyl}-1H-pyrrole-1-carboxylate (1R,3R,4S)-3-({[tert-Butyl(dimethyl)silyl]oxy}methyl)-4-[(triisopropylsilyl)oxy]cyclopentanamine (3.8 g, 9.4 mmol) and tert-butyl 3-[(4-chloropyrimidin-5-yl)carbonyl]-1H-pyrrole-1-carboxylate (2.5 g, 8.2 mmol) were weighed into a RBF with stirbar. The mixture was dissolved in DMF (40 mL). Potassium carbonate (3.4 g, 25 mmol) was added to the reaction vessel at rt and the resulting mixture was stirred at rt overnight. The reaction was then quenched by addition of water and the mixture extracted with EtOAc (3×). The combined organic layers were then washed with water and brine, dried over $Na_2SO_4$, filtered and concentrated. The crude product was purified on silica gel to provide tert-butyl 3-{[4-({(1R,3R,4S)-3-({[tert-butyl(dimethyl)silyl]oxy}methyl)-4-[(triisopropylsilyl)oxy]cyclopentyl}amino)pyrimidin-5-yl]carbonyl}-1H-pyrrole-1-carboxylate (4.3 g; 78%). LCMS (FA): m/z=674 (M+H).

Step 5: [4-({(1R,3R,4S)-3-({[tert-Butyl(dimethyl)silyl]oxy}methyl)-4-[(triisopropylsilyl)oxy]cyclopentyl}amino)pyrimidin-5-yl](1H-pyrrol-3-yl)methanone tert-Butyl 3-{[4-({(1R,3R,4S)-3-({[tert-butyl(dimethyl)silyl]oxy}methyl)-4-[(triisopropylsilyl)oxy]cyclopentyl}amino)pyrimidin-5-yl]carbonyl}-1H-pyrrole-1-carboxylate (4.14 g, 6.15 mmol) was dissolved in methanol (20 mL). Potassium carbonate (2.1 g, 15.4 mmol) was added to the reaction vessel at rt and the resulting mixture was stirred at rt for 2 h. The reaction was quenched by the addition of water and extracted with EtOAc (3×). The combined organic layers were then washed with water and brine, dried over $Na_2SO4$, filtered and concentrated. The crude product was purified on silica gel to afford [4-({(1R,3R,4S)-3-({[tert-butyl(dimethyl)silyl]oxy}methyl)-4-[(triisopropylsilyl)oxy]cyclopentyl}amino)pyrimidin-5-yl](1H-pyrrol-3-yl)methanone (3.07 g, 87.0%). LCMS (FA): m/z=574 (M+H).

Step 6: {1-[(5-Bromopyridin-3-yl)methyl]-1H-pyrrol-3-yl}[4-({(1R,3R,4S)-3-({[tert-butyl(dimethyl)silyl]oxy}methyl)-4-[(triisopropylsilyl)oxy]cyclopentyl}amino)pyrimidin-5-yl]methanone

[4-({(1R,3R,4S)-3-({[tert-Butyl(dimethyl)silyl]oxy}methyl)-4-[(triisopropylsilyl)oxy]cyclopentyl}amino)pyrimidin-5-yl](1H-pyrrol-3-yl)methanone (160 mg, 0.28 mmol) was dissolved in DMF (6 mL) and cesium carbonate (0.27 g, 0.84 mmol) was added. The mixture was stirred at rt for 10 min and 3-bromo-5-(chloromethyl)pyridine-HCl (108 mg, 0.44 mmol) was added. The mixture was then stirred at rt overnight and then quenched with aq. $NH_4Cl$ and extracted with EtOAc. The organic layer was washed with brine, dried over $Na_2SO4$ and filtered. The residue was purified on silica gel to yield {1-[(5-bromopyridin-3-yl)methyl]-1H-pyrrol-3-yl}[4-({(1R,3R,4S)-3-({[tert-butyl(dimethyl)silyl]oxy}methyl)-4-[(triisopropylsilyl)oxy]cyclopentyl}amino)pyrimidin-5-yl]methanone (177 mg, 85%) as yellow gum. LCMS (FA): m/z=745 (M+H).

Step 7: {1-[(5-Bromopyridin-3-yl)methyl]-1H-pyrrol-3-yl)}[4-({(1R,3R,4S)-3-(hydroxymethyl)-4-[(triisopropylsilyl)oxy]cyclopentyl}amino)pyrimidin-5-yl]methanone To a solution of {1-[(5-bromopyridin-3-yl)methyl]-1H-pyrrol-3-yl}[4-({(1R,3R,4S)-3-({[tert-butyl(dimethyl)silyl]oxy}methyl)-4-[(triisopropylsilyl)oxy]cyclopentyl}amino)pyrimidin-5-yl]methanone (165 mg, 0.22 mmol) in EtOH (2.3 mL) was added 1% HCl in EtOH (2.3 mL, 0.28 mmol) at rt. The reaction vessel was sealed and stirred at rt for 16 h. The reaction was quenched by addition of a saturated aq. solution of $NaHCO_3$. To the residue was added water which was extracted with EtOAc (4×). The combined organic layers were dried over $MgSO_4$, filtered, and concentrated. The residue was purified on silica gel to obtain {1-[(5-bromopyridin-3-yl)methyl]-1H-pyrrol-3-yl}[4-({(1R,3R,4S)-3-(hydroxymethyl)-4-[(triisopropylsilyl)oxy]cyclopentyl}amino)pyrimidin-5-yl]methanone (121 mg, 87%). LCMS (FA): m/z=631 (M+H).

Step 8: [(1R,2S,4R)-4-{[5-({1-[(5-Bromopyridin-3-yl)methyl]-1H-pyrrol-3-yl}carbonyl)pyrimidin-4-yl]amino}-2-hydroxycyclopentyl]methyl sulfamate I-299

To a solution of {1-[(5-bromopyridin-3-yl)methyl]-1H-pyrrol-3-yl}[4-({(1R,3R,4S)-3-(hydroxymethyl)-4-[(triisopropylsilyl)oxy]cyclopentyl}amino)pyrimidin-5-yl]methanone (120 mg, 0.19 mmol) in DMF (1 mL) was added chlorosulfonamide (66 mg, 0.57 mmol) at rt, and the mixture was stirred for 30 min. The reaction was quenched by addition of a saturated solution of $NaHCO_3$ and diluted with water. The mixture was extracted with EtOAc (3×). The combined organic layers were dried over $MgSO_4$, filtered, and concentrated. The crude product was purified on silica gel to give the sulfamate intermediate [90 mg, 67%; LCMS (FA): m/z=709 (M+H).] which was dissolved in THF (1.7 mL) and HCl (4.0 M in water; 1.7 mL, 6.9 mmol) was added to the solution. The reaction was stirred for 3 h at rt. The reaction was quenched by the addition of a saturated solution of NaHCO$_3$ and extracted with EtOAc (4×). The combined organic layers were dried over MgSO$_4$, filtered, and concentrated. The residue was purified by prep HPLC to afford [(1R,2S,4R)-4-{[5-({1-[(5-bromopyridin-3-yl)methyl]-1H-pyrrol-3-yl}carbonyl)pyrimidin-4-yl]amino}-2-hydroxycyclopentyl]methyl sulfamate (70 mg, 87%). $^1$H NMR (MeOD) δ 8.70 (s, 1H), 8.61 (d, J=2.2 Hz, 1H), 8.54 (s, 1H), 8.44 (d, J=1.9 Hz, 1H), 7.89 (t, J=2.0 Hz, 1H), 7.56 (t, J=1.9 Hz, 1H), 6.95 (dd, J=3.0, 2.1 Hz, 1H), 6.65 (dd, J=3.0, 1.7 Hz, 1H), 5.29 (s, 2H), 4.83-4.69 (m, 1H), 4.26-4.12 (m, 3H), 2.58-2.43 (m, 1H), 2.32-2.20 (m, 1H), 2.20-2.07 (m, 1H), 1.95-1.82 (m, 1H), 1.47-1.34 (m, 1H); LCMS (FA): m/z=551.3 (M+H).

The compounds listed in the table below were prepared in an analogous method to that described above starting from the listed starting materials used in step 6. I-339 was made as a mixture of diastereomers (trans cyclopropyl).

| Starting material | Compound No. | LCMS Data |
|---|---|---|
| Br—⧸≡—Me | I-340 | LCMS (FA): m/z = 434.4 (M + H). |
| Br—CH$_2$—cyclopropyl—Ph | I-339 | LCMS (FA): m/z = 512.5 (M + H). |
| Br—CH$_2$—cyclopropyl—Ph (Int-6) | | |
| MsO—pyrazole—CF$_3$ (Int-33) | I-45 | LCMS (FA): m/z = 544.4 (M + H). |
| Br—allyl | I-291 | LCMS (FA): m/z = 422.3 (M + H). |
| Br—propargyl | I-330 | LCMS (FA): m/z = 420.4 (M + H). |
| MsO—pyrazole—CF$_3$ (Int-34) | I-306 | LCMS (FA): m/z = 544.4 (M + H). |
| MsO—thiazole—CF$_3$ | I-73 | LCMS (FA): m/z = 547.4 (M + H). |

Ito, M. et al. PCT Application Publication WO 2007/145349

| Starting material | Compound No. | LCMS Data |
|---|---|---|
| Cl—SO$_2$—C$_6$H$_4$—Br | I-255 | LCMS (FA): m/z = 599.8 (M + H). |

Example 82: (1-Benzyl-1H-pyrrol-3-yl)(4-chloropyrimidin-5-yl)methanone Int-92

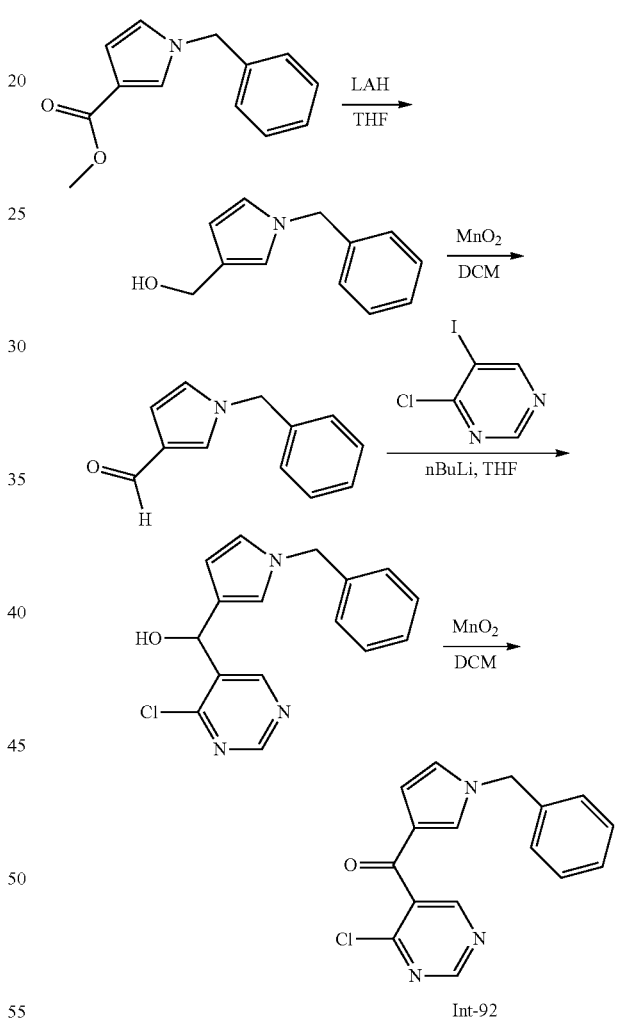

Step 1: (1-Benzyl-1H-pyrrol-3-yl)methanol

A solution of lithium aluminum hydride (0.66 g, 17 mmol) in THF (100 mL) was stirred at 0° C. A solution of 1-benzylpyrrole-3-carboxylic acid ethyl ester (2.0 g, 8.7 mmol) in THF (10 mL) was added dropwise. The resulting reaction mixture was heated at 50° C. for 3 h. Additional lithium aluminum hydride (0.75 g, 20 mmol) was added and the reaction continued to stir at 50° C. for 1 h. The reaction mixture was then cooled to 0° C., and sodium sulfate decahydrate (8 g) was added and the mixture was stirred for 16 h. EtOAc was added and the mixture was filtered over a pad of celite, then washed with additional EtOAc. The filtrate was concentrated and the crude residue purified on silica gel to give (1-benzyl-1H-pyrrol-3-yl)methanol (1.4 g, 88%). LCMS (FA): m/z=188.4 (M+H).

Step 2: 1-Benzyl-1H-pyrrole-3-carbaldehyde

To a solution of (1-benzyl-1H-pyrrol-3-yl)methanol (1.4 g, 7.7 mmol) in DCM (39 mL) was added manganese(IV) oxide (6.7 g, 77 mmol). The suspension was stirred for 19 h at rt. The reaction was then filtered through a celite pad and the residual solid was washed with DCM several times. The filtrate was then concentrated in vacuo and the residue was purified on silica gel to afford 1-benzyl-1H-pyrrole-3-carbaldehyde (1.2 g, 83%). LCMS (AA): m/z=186.1 (M+H).

Step 3: (1-Benzyl-1H-pyrrol-3-yl)(4-chloropyrimidin-5-yl)methanol

Into a flame dried RBF with stirbar was added 4-chloro-5-iodopyrimidine (1.4 g, 5.8 mmol) dissolved in THF (40 mL). The flask was purged with argon and cooled to −78° C. To this solution was added dropwise n-butyllithium (2.5 M in hexane; 4.6 mL, 11.5 mmol) at −78° C. and the mixture was stirred for 30 min. To this mixture was added 1-benzyl-1H-pyrrole-3-carbaldehyde (1.2 g, 6.3 mmol) dissolved in THF (10 mL) dropwise. The reaction was stirred at −78° C. for 2 h. The reaction was quenched with a saturated solution of NH$_4$Cl and then extracted with EtOAc (3×). The combined organic layers were then washed with water and brine, dried over Na$_2$SO$_4$, filtered and concentrated. The crude product was purified on silica gel to give (1-benzyl-1H-pyrrol-3-yl)(4-chloropyrimidin-5-yl)methanol (0.70 g, 41%). LCMS (AA): m/z=300.2 (M+H).

Step 4: (1-Benzyl-1H-pyrrol-3-yl)(4-chloropyrimidin-5-yl)methanone Int-92

To a solution of (1-benzyl-1H-pyrrol-3-yl)(4-chloropyrimidin-5-yl)methanol (0.70 g, 2.4 mmol) in DCM (23 mL) was added manganese(IV) oxide (2.0 g, 23 mmol). The suspension was stirred for 19 h at rt. The reaction was then filtered through a celite pad and the residual solid was washed with DCM several times. The filtrate was then concentrated in vacuo and the residue was purified on silica gel to afford (1-benzyl-1H-pyrrol-3-yl)(4-chloropyrimidin-5-yl)methanone (1.2 g, 83%). LCMS (FA): m/z=298.4 (M+H).

The compounds listed in the table below were prepared in an analogous method to that described above starting from the listed starting materials:

| Starting material | Compound Name/No. | LCMS Data |
|---|---|---|
| Br—CH$_2$—C$_6$H$_4$—Cl | [1-(3-Chlorobenzyl)-1H-pyrrol-3-yl](4-chloropyrimidin-5-yl)methanone/Int-93 | LCMS (FA): m/z = 332.1 (M + H). |
| Br—CH$_2$—C$_6$H$_4$—Br | [1-(3-Bromobenzyl)-1H-pyrrol-3-yl](4-chloropyrimidin-5-yl)methanone/Int-94 | LCMS (FA): m/z = 376 (M + H). |

Example 83: [(1R,2S,4R)-4-({5-[(1-Benzyl-1H-pyrrol-3-yl)carbonyl]pyrimidin-4-yl}amino)-2-hydroxycyclopentyl]methyl sulfamate I-300

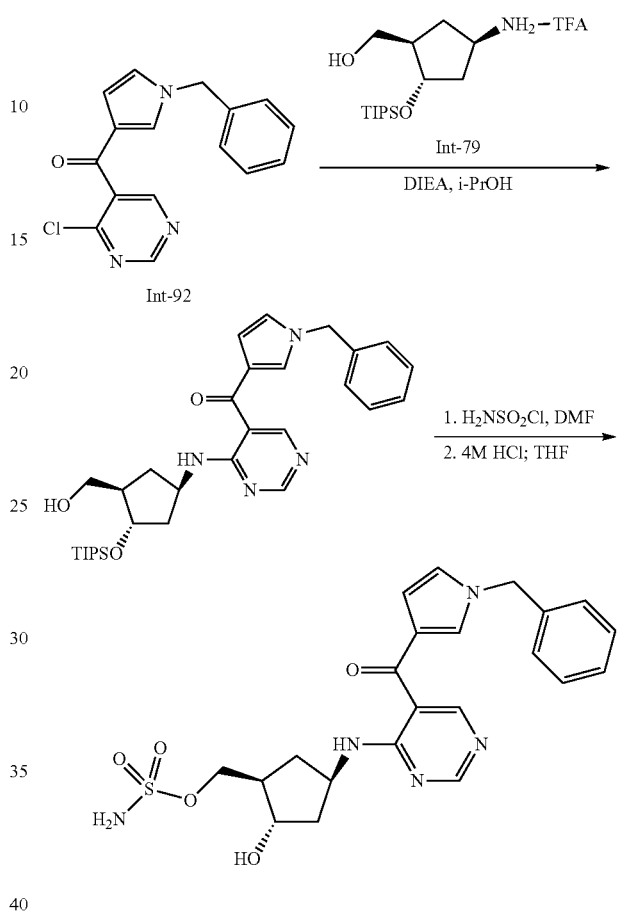

Step 1: (1-Benzyl-1H-pyrrol-3-yl)[4-({(1R,3R,4S)-3-(hydroxymethyl)-4-[(triisopropylsilyl)oxy]cyclopentyl}amino)pyrimidin-5-yl]methanone (1-Benzyl-1H-pyrrol-3-yl)(4-chloropyrimidin-5-yl)methanone (0.049 g, 0.16 mmol) and {(1R,2S,4R)-4-amino-2-[(triisopropylsilyl)oxy]cyclopentyl}methanol.C$_2$HO$_2$F$_3$ (0.086 g, 0.21 mmol) were weighed into a reaction vessel with stirbar. To this mixture was added 2-propanol (2 mL) and DIEA (0.086 mL, 0.50 mmol). The resulting mixture was allowed to stir at rt for 18 h. The reaction was then concentrated and the crude product was purified on silica gel to afford (1-benzyl-1H-pyrrol-3-yl)[4-({(1R,3R,4S)-3-(hydroxymethyl)-4-[(triisopropylsilyl)oxy]cyclopentyl}amino)pyrimidin-5-yl]methanone (13 mg, 14%). LCMS (FA): m/z=549.7 (M+H).

Step 2: [(1R,2S,4R)-4-({5-[(1-Benzyl-1H-pyrrol-3-yl)carbonyl]pyrimidin-4-yl}amino)-2-hydroxycyclopentyl]methyl sulfamate I-300

To a solution of (1-benzyl-1H-pyrrol-3-yl)[4-({(1R,3R,4S)-3-(hydroxymethyl)-4-[(triisopropylsilyl)oxy]cyclopentyl}amino)pyrimidin-5-yl]methanone (0.12 g, 0.21 mmol) in DMF (4 mL) was added chlorosulfonamide (74 mg, 0.64 mmol) at rt, and the mixture was stirred for 1 h. The reaction was quenched by addition of a saturated solution of NaHCO₃ and diluted with water. The mixture was extracted with EtOAc (4×). The combined organic layers were dried over MgSO₄, filtered, and concentrated. The crude sulfamate intermediate was dissolved in THF (2 mL) and HCl (4.0 M in water; 2.1 mL, 8.4 mmol) was added to the solution. The reaction was stirred for 3 h at rt. The reaction was quenched by the addition of a saturated solution of NaHCO₃ and extracted with EtOAc (4×). The combined organic layers were dried over MgSO₄, filtered, and concentrated. The residue was purified by prep HPLC to afford [(1R,2S,4R)-4-({5-[(1-benzyl-1H-pyrrol-3-yl)carbonyl]pyrimidin-4-yl}amino)-2-hydroxycyclopentyl]methyl sulfamate (26 mg, 36%). $^1$H NMR (DMSO) δ 8.66 (s, 1H), 8.60 (s, 1H), 8.44 (d, J=7.4 Hz, 1H), 7.67 (s, 1H), 7.50-7.33 (m, 3H), 7.30 (t, J=6.3 Hz, 3H), 7.00 (s, 1H), 6.54 (s, 1H), 5.21 (s, 2H), 5.05-4.75 (m, 1H), 4.74-4.57 (m, 1H), 4.15-4.03 (m, 1H), 4.03-3.88 (m, 2H), 2.96-2.52 (m, 1H), 2.40-2.25 (m, 1H), 2.20-2.05 (m, 1H), 2.03-1.90 (m, 1H), 1.79-1.66 (m, 1H), 1.31-1.18 (m, 1H); LCMS (FA): m/z=472.5 (M+H).

Example 84: {(1S,2S,4R)-4-[(5-{[1-(3-Bromobenzyl)-1H-pyrrol-3-yl]carbonyl}pyrimidin-4-yl)amino]-2-hydroxycyclopentyl}methyl sulfamate I-319

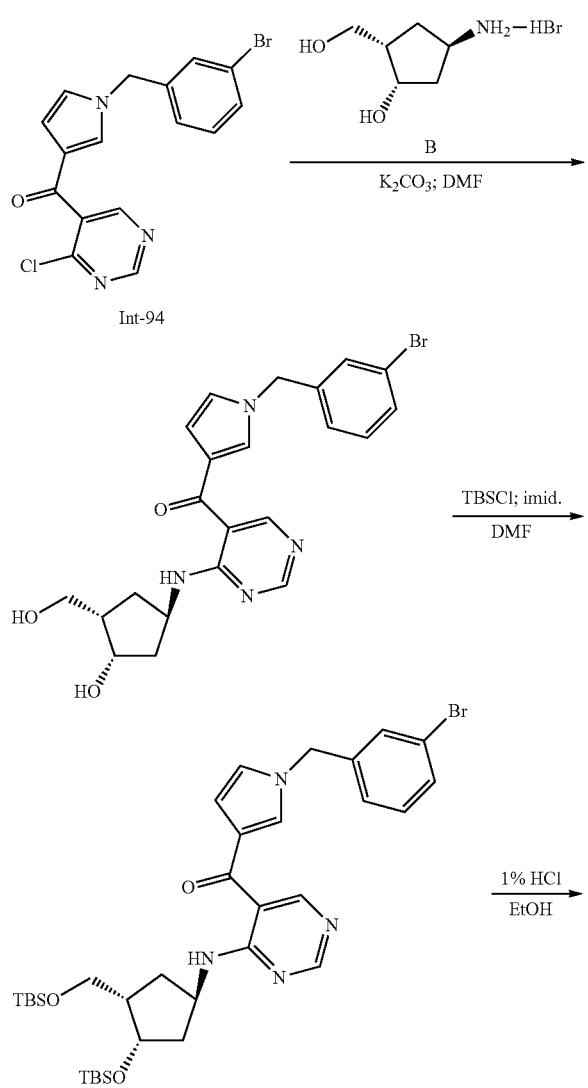

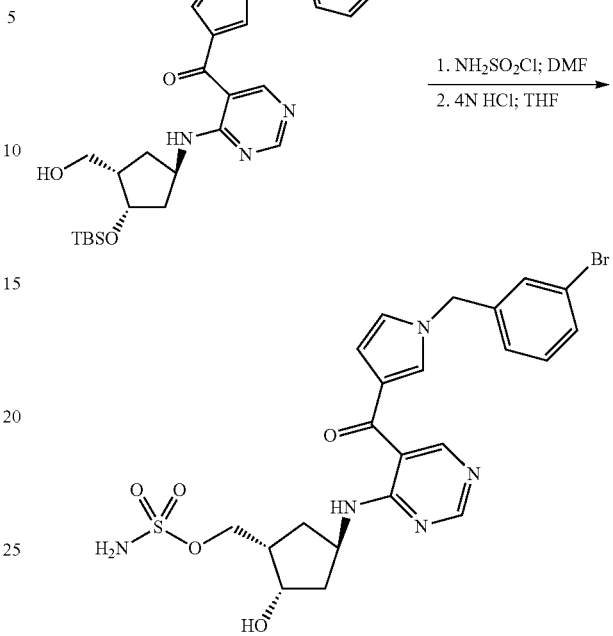

Step 1: [1-(3-Bromobenzyl)-1H-pyrrol-3-yl](4-{[(1R,3S,4S)-3-hydroxy-4-(hydroxymethyl)cyclopentyl]amino}pyrimidin-5-yl)methanone

[1-(3-Bromobenzyl)-1H-pyrrol-3-yl](4-chloropyrimidin-5-yl)methanone (360 mg, 0.95 mmol) and (1S,2S,4R)-4-amino-2-(hydroxymethyl)cyclopentanol hydrobromide (240 mg, 1.1 mmol) were weighed into a round bottomed flask with stirbar. The mixture was dissolved in DMF (7.5 mL). Potassium carbonate (0.33 g, 2.4 mmol) was added to the reaction vessel at rt and the resulting mixture was stirred at 80° C. for 1 h. The reaction was then diluted with EtOAc and filtered through a pad of celite. The filtrate was concentrated. The resulting residue was dissolved in EtOAc and the mixture was washed with water and brine, dried over Na₂SO₄, filtered and concentrated. The crude product was purified on silica gel to provide [1-(3-bromobenzyl)-1H-pyrrol-3-yl](4-{[(1R,3S,4S)-3-hydroxy-4-(hydroxymethyl)cyclopentyl]amino}pyrimidin-5-yl)methanone (295 mg, 66%). LCMS (FA): m/z=473 (M+H).

Step 2: [1-(3-Bromobenzyl)-1H-pyrrol-3-yl](4-{[(1R,3S,4S)-3-{[tert-butyl(dimethyl)silyl]oxy}-4-({[tert-butyl(dimethyl)silyl]oxy}methyl)cyclopentyl]amino}pyrimidin-5-yl)methanone To a solution of [1-(3-bromobenzyl)-1H-pyrrol-3-yl](4-{[(1R,3S,4S)-3-hydroxy-4-(hydroxymethyl)cyclopentyl]amino}pyrimidin-5-yl)methanone (295 mg, 0.63 mmol) in DMF (10 mL) was added DMAP (3.8 mg, 0.03 mmol), imidazole (0.3 g, 4.5 mmol) followed by tert-butyldimethylsilyl chloride (0.28 g, 1.9 mmol) at rt, and the mixture was stirred for 12 h. Additional imidazole (0.17 g, 2.5 mmol) and tert-butyldimethylsilyl chloride (0.19 g, 1.3 mmol) were added and the reaction was stirred for 16 h. The reaction was then quenched by addition of water and extracted with EtOAc (3×). The combined organic layers were washed with brine, dried over MgSO₄, filtered, and concentrated. The residue was purified on silica gel to give [1-(3-bromobenzyl)-1H-pyrrol-3-yl](4-{[(1R,3S,4S)-3-{[tert-butyl(dimethyl)silyl]oxy}-4-({[tert-butyl(dimethyl)silyl]oxy}methyl)cyclopentyl]amino}pyrimidin-5-yl)methanone (0.31 g, 71%). LCMS (FA): m/z=701.4 (M+H).

Step 3: [1-(3-Bromobenzyl)-1H-pyrrol-3-yl](4-{[(1R,3S,4S)-3-{[tert-butyl(dimethyl)silyl]oxy}-4-(hydroxymethyl)cyclopentyl]amino}pyrimidin-5-yl)methanone To a solution of [1-(3-bromobenzyl)-1H-pyrrol-3-yl](4-{[(1R,3S,4S)-3-{[tert-butyl(dimethyl)silyl]oxy}-4-({[tert-butyl(dimethyl)silyl]oxy}methyl)cyclopentyl]amino}pyrimidin-5-yl)methanone (0.31 g, 0.45 mmol) in EtOH (5.5 mL) was added 1% HCl in EtOH (7.5 mL, 0.91 mmol) at rt. The reaction vessel was sealed and allowed to stand in a refrigerator (4° C.) for 24 h. The reaction was quenched by addition of a saturated aq. solution of NaHCO₃. To the residue was added water which was extracted with EtOAc (4×). The combined organic layers were dried over MgSO₄, filtered, and concentrated. The residue was purified on silica gel to give [1-(3-bromobenzyl)-1H-pyrrol-3-yl](4-{[(1R,3S,4S)-3-{[tert-butyl(dimethyl)silyl]oxy}-4-(hydroxymethyl)cyclopentyl]amino}pyrimidin-5-yl)methanone (233 mg, 89%). LCMS (FA): m/z=587.3 (M+H).

Step 4: {(1S,2S,4R)-4-[(5-{[1-(3-Bromobenzyl)-1H-pyrrol-3-yl]carbonyl}pyrimidin-4-yl)amino]-2-hydroxycyclopentyl}methyl sulfamate I-319

To a solution of [1-(3-bromobenzyl)-1H-pyrrol-3-yl](4-{[(1R,3S,4S)-3-{[tert-butyl(dimethyl)silyl]oxy}-4-(hydroxymethyl)cyclopentyl]amino}pyrimidin-5-yl)methanone (233 mg, 0.40 mmol) in DMF (4 mL) was added chlorosulfonamide (69 mg, 0.60 mmol) at rt, and the mixture was stirred for 30 min. The reaction was quenched by addition of a saturated solution of NaHCO₃ and diluted with water. The mixture was extracted with EtOAc (4×). The combined organic layers were dried over MgSO₄, filtered, and concentrated. The crude sulfamate intermediate was dissolved in THF (6 mL) and HCl (4.0 M in water; 1 mL, 4 mmol) was added to the solution. The reaction was stirred for 16 h at rt. The reaction was quenched by the addition of a saturated solution of NaHCO₃ and extracted with EtOAc (4×). The combined organic layers were dried over MgSO₄, filtered, and concentrated. The residue was purified by prep HPLC to afford {(1S,2S,4R)-4-[(5-{[1-(3-bromobenzyl)-1H-pyrrol-3-yl]carbonyl}pyrimidin-4-yl)amino]-2-hydroxycyclopentyl}methyl sulfamate (127 mg, 58%). ¹H NMR (MeOD) δ 8.62 (s, 1H), 8.48 (s, 1H), 7.46-7.39 (m, 2H), 7.36 (s, 1H), 7.23 (t, J=7.7 Hz, 1H), 7.16 (d, J=8.0 Hz, 1H), 6.87-6.81 (m, 1H), 6.60-6.53 (m, 1H), 5.15 (s, 2H), 4.38-4.30 (m, 1H), 4.27 (dd, J=9.7, 7.7 Hz, 1H), 4.10 (dd, J=9.7, 7.3 Hz, 1H), 2.57-2.42 (m, 1H), 2.32-2.17 (m, 1H), 2.13-2.00 (m, 1H), 1.86-1.65 (m, 2H), LCMS (FA): m/z=552.0 (M+H)

Example 85: [(1R,2S,4R)-4-{[5-({1-[1-(3-Chlorophenyl)cyclopropyl]-1H-pyrrol-3-yl}carbonyl)pyrimidin-4-yl]amino}-2-hydroxycyclopentyl]methyl sulfamate I-264

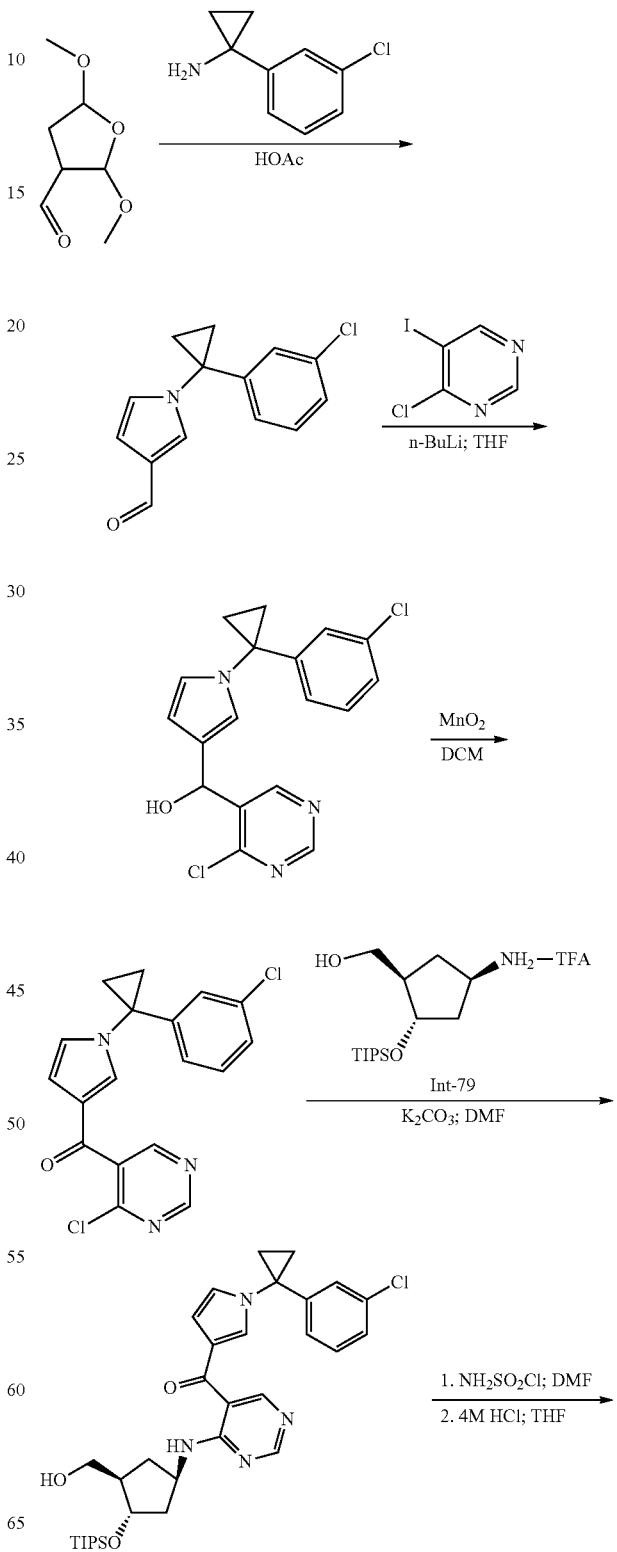

-continued

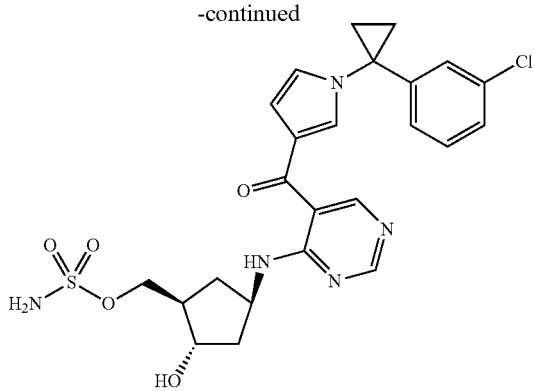

Step 1: 1-[1-(3-Chlorophenyl)cyclopropyl]-1H-pyrrole-3-carbaldehyde 1-(3-Chlorophenyl)cyclopropanaminehydrochloride (300 mg, 1.5 mmol) was weighed into a 50 mL RBF and water (3 mL) was added to the flask. The solution was filtered through a syringe filter and rinsed with a small amount of water. To the filtrate was added NaOH (1.0 M solution in water; 1.5 mL, 1.5 mmol) to neutralize and brine (10 mL) was added to the mixture. The mixture was extracted with Et$_2$O (30 mL) and the organic layer was dried over Na$_2$SO$_4$, filtered, concentrated in vacuo. To the residue was added 2,5-dimethoxy-3-tetrahydrofurancarboxaldehyde (0.19 mL, 1.3 mmol) followed by HOAc (2.0 mL, 35 mmol) at rt, and the resulting mixture was heated at 85° C. for 2 h. The reaction was cooled to room temp and concentrated in vacuo. To the mixture was added saturated NaHCO$_3$ (50 mL) and the mixture was extracted with EtOAc (60 mL×3). The organic layers were dried over Na$_2$SO$_4$, filtered through a celite pad, and concentrated in vacuo. The residue was purified on silica gel to give 1-[1-(3-chlorophenyl)cyclopropyl]-1H-pyrrole-3-carbaldehyde (300 mg, 82%) as a yellow oil. LCMS (FA): m/z=246.2 (M+H).

Step 2: {-[1-(3-Chlorophenyl)cyclopropyl]-1H-pyrrol-3-yl}(4-chloropyrimidin-5-yl)methanol 4-Chloro-5-iodopyrimidine (290 mg, 1.2 mmol) was weighed into a 100 mL 2 necked round bottomed flask and the flask was purged with argon. The contents were dissolved in THF (8 mL) and the solution was cooled to −78° C. To the solution was added dropwise n-Butyllithium (2.50 M solution in hexane; 0.95 mL, 2.4 mmol) at −78° C., and the mixture was stirred for 30 min. To the mixture was added a solution of 1-[1-(3-chlorophenyl)cyclopropyl]-1H-pyrrole-3-carbaldehyde (270 mg, 1.1 mmol) in THF (4 mL) at −78° C., and the resulting mixture was stirred for 30 min at the same temperature. The reaction was quenched by the addition of saturated NH$_4$Cl (40 mL) and extracted with EtOAc (50 mL×3). The combined organic layers were dried over Na$_2$SO$_4$, filtered, and concentrated in vacuo. The residue was purified on silica gel to give {1-[1-(3-chlorophenyl)cyclopropyl]-1H-pyrrol-3-yl}(4-chloropyrimidin-5-yl)methanol (351 mg, 86%). LCMS (FA): m/z=360.2 (M+H).

Step 3: {1-[1-(3-Chlorophenyl)cyclopropyl]-1H-pyrrol-3-yl}(4-chloropyrimidin-5-yl)methanone To a solution of {1-[1-(3-chlorophenyl)cyclopropyl]-1H-pyrrol-3-yl}(4-chloropyrimidin-5-yl)methanol (330 mg, 0.91 mmol) in DCM (10 mL) was added manganese(IV) oxide (790 mg, 9.1 mmol) at rt, and the mixture was stirred for 21 h. The reaction was filtered through a celite pad and the residual solid was rinsed with DCM and EtOAc several times. The filtrate was concentrated in vacuo. The residue was purified on silica gel to give {1-[1-(3-chlorophenyl)cyclopropyl]-1H-pyrrol-3-yl}(4-chloropyrimidin-5-yl)methanone (315 mg, 92%) as a colorless solid. LCMS (FA): m/z=358.2 (M+H).

Step 4: {1-[1-(3-Chlorophenyl)cyclopropyl]-1H-pyrrol-3-yl}[4-({(1R,3R,4S)-3-(hydroxymethyl)-4-[(triisopropylsilyl)oxy]cyclopentyl}amino)pyrimidin-5-yl]methanone A 100 mL reaction vessel was charged with {(1R,2S,4R)-4-amino-2-[(triisopropylsilyl)oxy]cyclopentyl}methanol.CF$_3$CO$_2$H (382 mg, 0.95 mmol) and K$_2$CO$_3$ (340 mg, 2.5 mmol). To the mixture was added a solution of {1-[1-(3-chlorophenyl)cyclopropyl]-1H-pyrrol-3-yl}(4-chloropyrimidin-5-yl)methanone (295 mg, 0.82 mmol) in DMF (5 mL) and the resulting mixture was stirred for 3 h at rt. The reaction was quenched by addition of water (50 mL) and extracted with EtOAc (60 mL×3). The combined organic layers were dried over Na$_2$SO$_4$, filtered, and concentrated in vacuo. The residue was purified on silica gel to give {1-[1-(3-chlorophenyl)cyclopropyl]-1H-pyrrol-3-yl}[4-({(1R,3R,4S)-3-(hydroxymethyl)-4-[(triisopropylsilyl)oxy]cyclopentyl}amino)pyrimidin-5-yl]methanone (460 mg, 87%) as a colorless amorphous solid. LCMS (FA): m/z=609.4 (M+H).

Step 5: [(1R,2S,4R)-4-{[5-({1-[1-(3-Chlorophenyl)cyclopropyl]-1H-pyrrol-3-yl}carbonyl)pyrimidin-4-yl]amino}-2-hydroxycyclopentyl]methyl sulfamate I-264

To a solution of {1-[1-(3-chlorophenyl)cyclopropyl]-1H-pyrrol-3-yl}[4-({(1R,3R,4S)-3-(hydroxymethyl)-4-[(triisopropylsilyl)oxy]cyclopentyl}amino)pyrimidin-5-yl]methanone (460 mg, 0.75 mmol) in DMF (4 mL) was added chlorosulfonamide (170 mg, 1.5 mmol) at rt, and the mixture was stirred for 30 min. The reaction was quenched by addition of saturated NaHCO$_3$ (70 mL) and the resulting suspension was filtered through a Celite pad. The residual solid was washed with water several times and dried under vacuum. To the residual solid in the glass frit filter was added EtOAc. The resulting solution was filtered and the Celite pad was washed with EtOAc several times. The filtrate was concentrated in vacuo and the residue was purified on silica gel to give the sulfamate intermediate [(375 mg, 72%); LCMS (FA): m/z=688.3 (M+H).] which was dissolved in THF (3 mL). To this solution was added HCl (4.0 M solution in water, 4.0 mL, 16 mmol) at rt, and the mixture was stirred for 2 h at 40° C. The reaction was quenched by addition of saturated NaHCO$_3$ (60 mL) and extracted with EtOAc (60 mL×3). The combined organic layers were dried over Na$_2$SO$_4$, filtered, and concentrated in vacuo. To the residue was added a small volume of DCM and colorless solids were appeared. The suspension was filtered through a glass frit funnel with some DCM to rinse the flask. The resulting colorless solid was dried to give [(1R,2S,4R)-4-{[5-({1-[1-(3-chlorophenyl)cyclopropyl]-1H-pyrrol-3-yl}carbonyl)pyrimidin-4-yl]amino}-2-hydroxycyclopentyl]methyl sulfamate (254 mg, 87%) as a colorless amorphous solid. $^1$H NMR (DMSO) δ 8.70 (s, 1H), 8.60 (s, 1H), 8.50 (d, J=7.5 Hz, 1H), 7.72 (s, 1H), 7.42 (s, 2H), 7.36-7.26 (m, 2H), 7.17-7.12 (m, 1H), 7.00 (s, 1H), 6.91 (d, J=7.5 Hz, 1H), 6.61-6.56 (m, 1H), 4.88 (d, J=4.3 Hz, 1H), 4.74-4.61 (m, 1H), 4.10 (dd, J=9.7, 5.9 Hz, 1H), 3.97 (dd, J=9.6, 7.1 Hz, 2H), 2.39-2.28 (m, 1H), 2.17-2.06 (m, 1H), 2.03-1.92 (m, 1H), 1.80-1.65 (m, 3H), 1.52 (t, J=6.6 Hz, 2H), 1.25 (dt, J=12.6, 9.1 Hz, 1H). LCMS (FA): m/z=532.3 (M+H).

The compound listed in the table below was prepared in an analogous method to that described above starting from the listed starting material:

| Starting material | Compound No. | LCMS Data |
|---|---|---|
|  | I-76 | LCMS (FA): m/z = 500.3 (M + H). |

Example 86: [(1R,2S,4R)-2-Hydroxy-4-{[5-({1-[(Z)-2-phenylvinyl]-1H-pyrrol-3-yl}carbonyl)pyrimidin-4-yl]amino}cyclopentyl]methyl sulfamate I-200

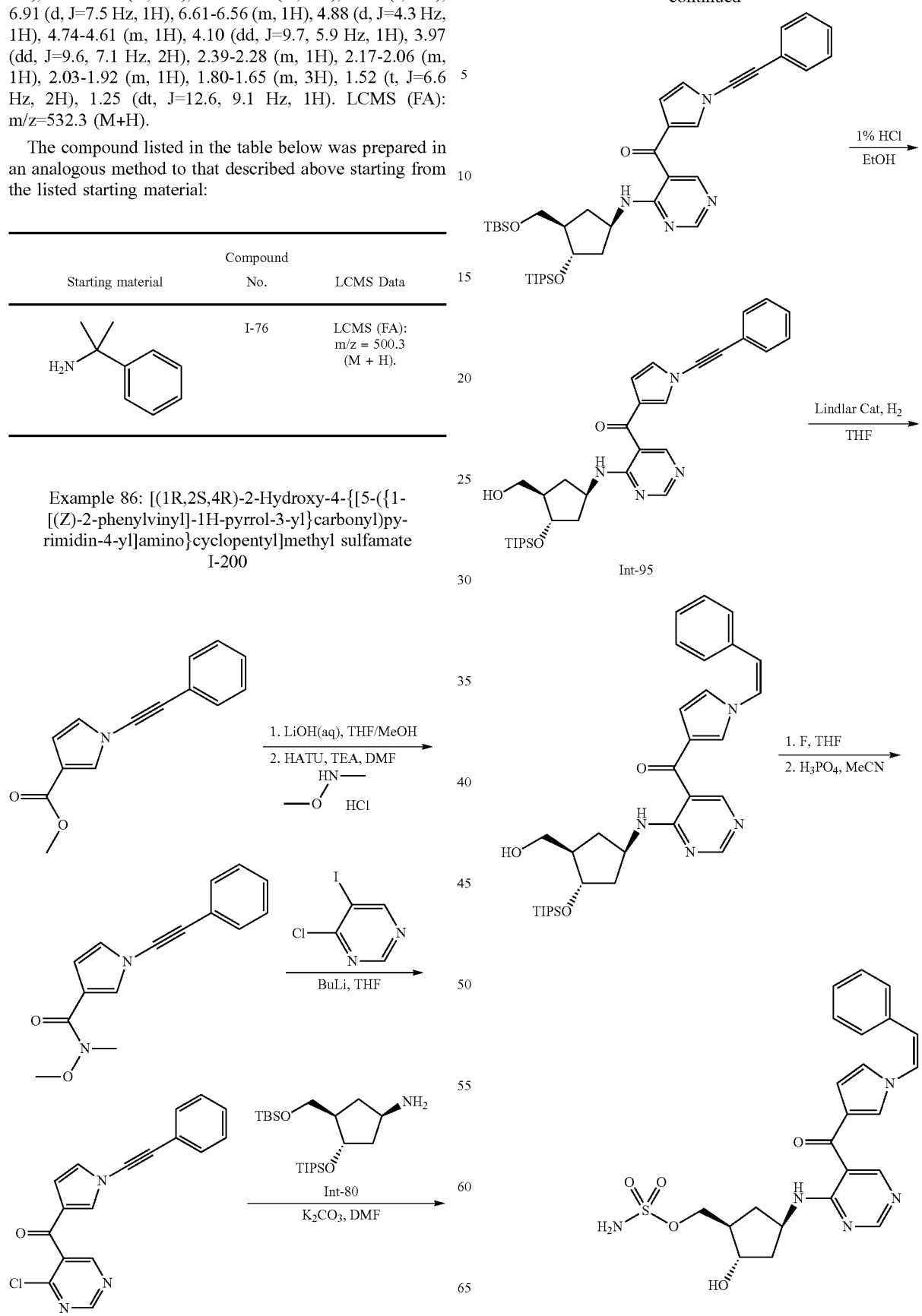

Step 1: N-Methoxy-N-methyl-1-(phenylethynyl)-1H-pyrrole-3-carboxamide

A round bottomed flask was charged with methyl 1-(phenylethynyl)-1H-pyrrole-3-carboxylate (1.5 g, 6.7 mmol) and methanol (10 mL). Lithium hydroxide (1.0 M solution in water; 13.3 mL, 13.3 mmol) was added followed by addition of THF (10 mL). The resulting solution was stirred at rt for 18 h. The organic solvents were removed under reduced pressure and 5% potassium bisulfate was added to the remaining aqueous solution. The mixture was extracted with EtOAc (3×). The combined organic layers were washed with brine, dried over sodium sulfate, filtered, and concentrated to give the carboxylic acid intermediate [(1.39 g); (FA): m/z=212 (M+H).]. The carboxylic acid was then placed in a 50 mL RBF under nitrogen. DMF (20 mL), N,O-dimethylhydroxylamine hydrochloride (1.1 g, 11 mmol), HATU (4.1 g, 11 mmol), and TEA (2.3 mL, 16 mmol) were all added and the resulting suspension was allowed to stir for 18 h. The reaction mixture was then poured into a saturated NaHCO$_3$ solution. The mixture was extracted with EtOAc (3×). The combined organic layers were washed with brine, dried over sodium sulfate, filtered, and concentrated. The crude residue was purified on silica gel to afford N-methoxy-N-methyl-1-(phenylethynyl)-1H-pyrrole-3-carboxamide (1.3 g, 76%). LCMS (FA): m/z=255 (M+H).

Step 2: (4-Chloropyrimidin-5-yl)[1-(phenylethynyl)-1H-pyrrol-3-yl]methanone

An oven-dried 250 mL 2-neck RBF under nitrogen was charged with 4-chloro-5-iodopyrimidine (1.2 g, 5.1 mmol) and THF (30 mL) and then cooled to −70° C. n-Butyllithium (2.5 M solution in hexane; 4.1 mL, 10.2 mmol) was added dropwise over 10 min keeping the internal temperature less than −65 deg C. A deep yellow solution resulted which was stirred an additional 10 min. A solution of N-methoxy-N-methyl-1-(phenylethynyl)-1H-pyrrole-3-carboxamide (865 mg, 3.4 mmol) in THF (20 mL) was then added at a rate to keep the internal temperature less than −60° C. This solution was allowed to warm to 0° C. and then quenched with a saturated NH$_4$Cl solution. The mixture was extracted with EtOAc (3×). The combined organic layers were washed with brine, dried over sodium sulfate, filtered, and concentrated. The crude residue was purified on silica gel to afford (4-chloropyrimidin-5-yl)[1-(phenylethynyl)-1H-pyrrol-3-yl]methanone (235 mg, 15%). LCMS (FA): m/z=308 (M+H).

Step 3: [4-({(1R,3R,4S)-3-({[tert-Butyl(dimethyl)silyl]oxy}methyl)-4-[(triisopropylsilyl)oxy]cyclopentyl}amino)pyrimidin-5-yl][1-(phenylethynyl)-1H-pyrrol-3-yl]methanone (1R,3R,4S)-3-({[tert-butyl(dimethyl)silyl]oxy}methyl)-4-[(triisopropylsilyl)oxy]cyclopentanamine (370 mg, 0.92 mmol) and (4-chloropyrimidin-5-yl)[1-(phenylethynyl)-1H-pyrrol-3-yl]methanone (0.24 g, 0.76 mmol) were weighed into a RBF with stirbar. The mixture was dissolved in DMF (5 mL). Potassium carbonate (320 mg, 2.3 mmol) was added to the reaction vessel at rt and the resulting mixture was stirred at rt for 3 days. The reaction was then quenched by addition of water and the mixture extracted with EtOAc (3×). The combined organic layers were then washed with water and brine, dried over Na$_2$SO$_4$, filtered and concentrated. The crude product was purified on silica gel to give [4-({(1R,3R,4S)-3-({[tert-butyl(dimethyl)silyl]oxy}methyl)-4-[(triisopropylsilyl)oxy]cyclopentyl}amino)pyrimidin-5-yl][1-(phenylethynyl)-1H-pyrrol-3-yl]methanone (413 mg, 79%). LCMS (FA): m/z=674 (M+H).

Step 4: [4-({(1R,3R,4S)-3-(Hydroxymethyl)-4-[(triisopropylsilyl)oxy]cyclopentyl}amino)pyrimidin-5-yl][1-(phenylethynyl)-1H-pyrrol-3-yl]methanone Int-95

A solution of [4-({(1R,3R,4S)-3-({[tert-butyl(dimethyl)silyl]oxy}methyl)-4-[(triisopropylsilyl)oxy]cyclopentyl}amino)pyrimidin-5-yl][1-(phenylethynyl)-1H-pyrrol-3-yl]methanone (0.40 g, 0.60 mmol) in EtOH (1.0 mL) was cooled in an ice bath. To the solution was added HCl (0.3 M solution in EtOH; 4.0 mL, 1.2 mmol) via syringe and this solution was allowed to stir at rt for 5 h. The reaction was then quenched by addition of a saturated NaHCO$_3$ solution. Water was added to solubilize the salts and the mixture was concentrated to remove EtOH. The aqueous mixture was extracted with EtOAc (3×). The combined organic layers were then washed with water and brine, dried over Na$_2$SO$_4$, filtered and concentrated. The crude product was purified on silica gel to give [4-({(1R,3R,4S)-3-(hydroxymethyl)-4-[(triisopropylsilyl)oxy]cyclopentyl}amino)pyrimidin-5-yl][1-(phenylethynyl)-1H-pyrrol-3-yl]methanone (290 mg, 86%). LCMS (FA): m/z=559 (M+H).

Step 5: [4-({(1R,3R,4S)-3-(Hydroxymethyl)-4-[(triisopropylsilyl)oxy]cyclopentyl}amino)pyrimidin-5-yl](1-[(Z)-2-phenylvinyl]-1H-pyrrol-3-yl}methanone A 100 mL RBF was charged with [4-({(1R,3R,4S)-3-(hydroxymethyl)-4-[(triisopropylsilyl)oxy]cyclopentyl}amino)pyrimidin-5-yl][1-(phenylethynyl)-1H-pyrrol-3-yl]methanone (0.12 g, 0.22 mmol), THF (5 mL), and 5% palladium on calcium carbonate (0.05 g, 0.19 mmol). The suspension was stirred under an atmosphere of hydrogen for 4 h. The mixture was filtered through a celite pad and the filtrate was concentrated then purified on silica gel to produce [4-({(1R,3R,4S)-3-(Hydroxymethyl)-4-[(triisopropylsilyl)oxy]cyclopentyl}amino)pyrimidin-5-yl]{1-[(Z)-2-phenylvinyl]-1H-pyrrol-3-yl}methanone (54 mg, 44%). LCMS (FA): m/z=561 (M+H).

Step 6: [(1R,2S,4R)-2-Hydroxy-4-{[5-({1-[(Z)-2-phenylvinyl]-1H-pyrrol-3-yl}carbonyl)pyrimidin-4-yl]amino}cyclopentyl]methyl sulfamate I 200

[4-({(1R,3R,4S)-3-(Hydroxymethyl)-4-[(triisopropylsilyl)oxy]cyclopentyl}amino)pyrimidin-5-yl]{1-[(Z)-2-phenylvinyl]-1H-pyrrol-3-yl}methanone (0.054 g, 0.096 mmol) was dissolved in THF (2.3 mL). To this solution was added in one portion PPTS (48 mg, 0.19 mmol) followed by the addition of (4-aza-1-azoniabicyclo[2.2.2]oct-1-ylsulfonyl)(tert-butoxycarbonyl)azanide-1,4-diazabicyclo[2.2.2]octane (1:1) hydrochloride (F) (0.13 g, 0.29 mmol). After stirring 4 h at rt, additional (4 aza 1 azoniabicyclo[2.2.2]oct-1-ylsulfonyl)(tert-butoxycarbonyl)azanide-1,4-diazabicyclo[2.2.2]octane (1:1) hydrochloride (F) (0.10 g, 0.23 mmol) was added and continued to stir at rt an additional 2 h. The reaction was then diluted with DCM and filtered to remove solids. The filtrate was purified on silica gel to give the Boc-protected sulfamate intermediate [34 mg; LCMS (FA): m/z=740 (M+H).] which was then dissolved in acetonitrile (1.0 mL) and cooled to 0° C. Phosphoric acid (1.0 mL, 17 mmol) was added and the mixture was then allowed to stir at rt for 3 h. The reaction was quenched by the addition of a 1.0 M solution of Na$_2$CO$_3$ in water. After diluting the mixture with water it was extracted with EtOAc (3×). The combined organic layers were dried over MgSO$_4$, filtered, and concentrated. The crude product was purified by prep HPLC to give [(1R,2S,4R)-2-hydroxy-4-{[5-({1-[(Z)-2-phenylvinyl]-1H-pyrrol-3-yl}carbonyl)pyrimidin-4-yl]amino}cyclopentyl]methyl sulfamate (8 mg, 17%). $^1$H NMR (MeOD) δ 8.53 (s, 2H), 7.39-7.28 (m, 3H), 7.26 (s, 1H), 7.22-7.16 (m, 2H), 6.95 (d, J=9.3 Hz, 1H), 6.84-6.80 (m, 1H), 6.66-6.61 (m, 1H), 6.48 (d, J=9.3 Hz, 1H), 4.83-4.72 (m, 1H), 4.26-4.13 (m, 3H), 2.57-2.48 (m, 1H), 2.32-2.23 (m, 1H), 2.20-2.11 (m, 1H), 1.95-1.85 (m, 1H), 1.47-1.37 (m, 1H); LCMS (FA): m/z=484.4 (M+H).

Example 87: {(1R,2S,4R)-2-Hydroxy-4-[(5-{[(1-(phenylethynyl)-1H-pyrrol-3-yl]carbonyl}pyrimidin-4-yl)amino]cyclopentyl}methyl sulfamate I-196

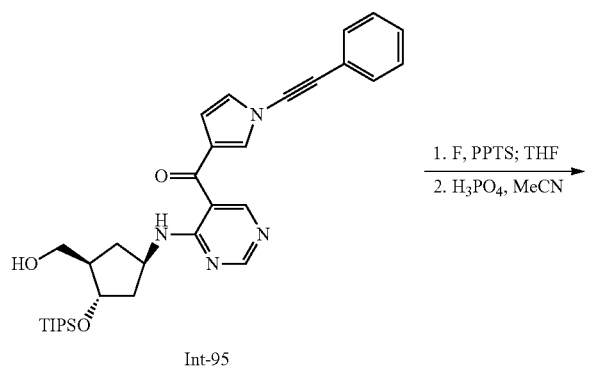

Int-95

1. F, PPTS; THF
2. H$_3$PO$_4$, MeCN

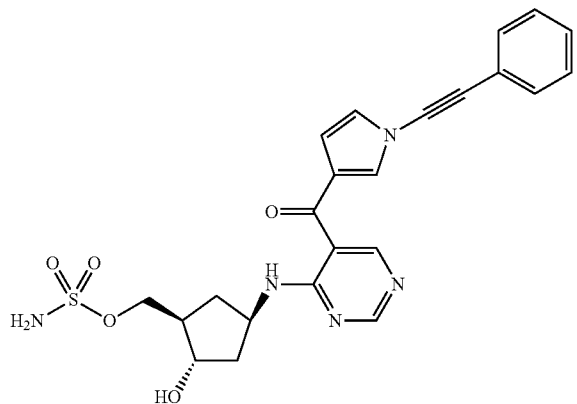

Step 1: {(1R,2S,4R)-2-Hydroxy-4-[(5-{[1-(phenylethynyl)-1H-pyrrol-3-yl]carbonyl}pyrimidin-4-yl)amino]cyclopentyl}methyl sulfamate I-196

[4-({(1R,3R,4S)-3-(Hydroxymethyl)-4-[(triisopropylsilyl)oxy]cyclopentyl}amino)pyrimidin-5-yl][1-(phenylethynyl)-1H-pyrrol-3-yl]methanone (100 mg, 0.18 mmol) was dissolved in THF (4 mL). To this solution was added in one portion PPTS (48 mg, 0.19 mmol) followed by the addition of (4-aza-1-azoniabicyclo[2.2.2]oct-1-ylsulfonyl)(tert-butoxycarbonyl)azanide-1,4-diazabicyclo[2.2.2]octane (1:1) hydrochloride (F) (0.24 g, 0.54 mmol). After stirring 1 h at rt, the reaction was quenched by the addition of water. The mixture was extracted with EtOAc (3×). The combined organic layers were dried over MgSO$_4$, filtered and concentrated to give the Boc-protected sulfamate intermediate [140 mg; LCMS (FA): m/z=738 (M+H).] which was then dissolved in acetonitrile (1.0 mL) and cooled to 0° C. Phosphoric acid (1.0 mL, 17 mmol) was added and the mixture was then allowed to stir at rt for 3 h. The reaction was quenched by the addition of a 1.0 M solution of Na$_2$CO$_3$ in water. After diluting the mixture with water it was extracted with EtOAc (3×). The combined organic layers were dried over MgSO$_4$, filtered, and concentrated. The crude product was purified by prep HPLC to give {(1R,2S,4R)-2-hydroxy-4-[(5-{[1-(phenylethynyl)-1H-pyrrol-3-yl]carbonyl}pyrimidin-4-yl)amino]cyclopentyl}methyl sulfamate (26 mg, 30%). $^1$H NMR (MeOD) δ 8.79 (s, 1H), 8.60 (s, 1H), 7.78-7.72 (m, 1H), 7.59-7.52 (m, 2H), 7.46-7.37 (m, 3H), 7.24-7.19 (m, 1H), 6.77-6.72 (m, 1H), 4.85-4.77 (m, 1H), 4.27-4.15 (m, 3H), 2.60-2.49 (m, 1H), 2.35-2.24 (m, 1H), 2.23-2.14 (m, 1H), 1.99-1.88 (m, 1H), 1.52-1.40 (m, 1H); LCMS (FA): m/z=484.2 (M+H).

Example 88: [(1R,2S,4R)-2-Hydroxy-4-{[3-({1-[3-(trifluoromethoxy) benzyl]-1H-pyrrol-3-yl}carbonyl)pyridin-4-yl]amino}cyclopentyl]methyl sulfamate I-83

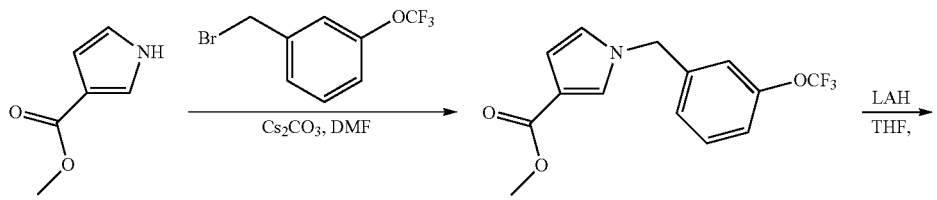

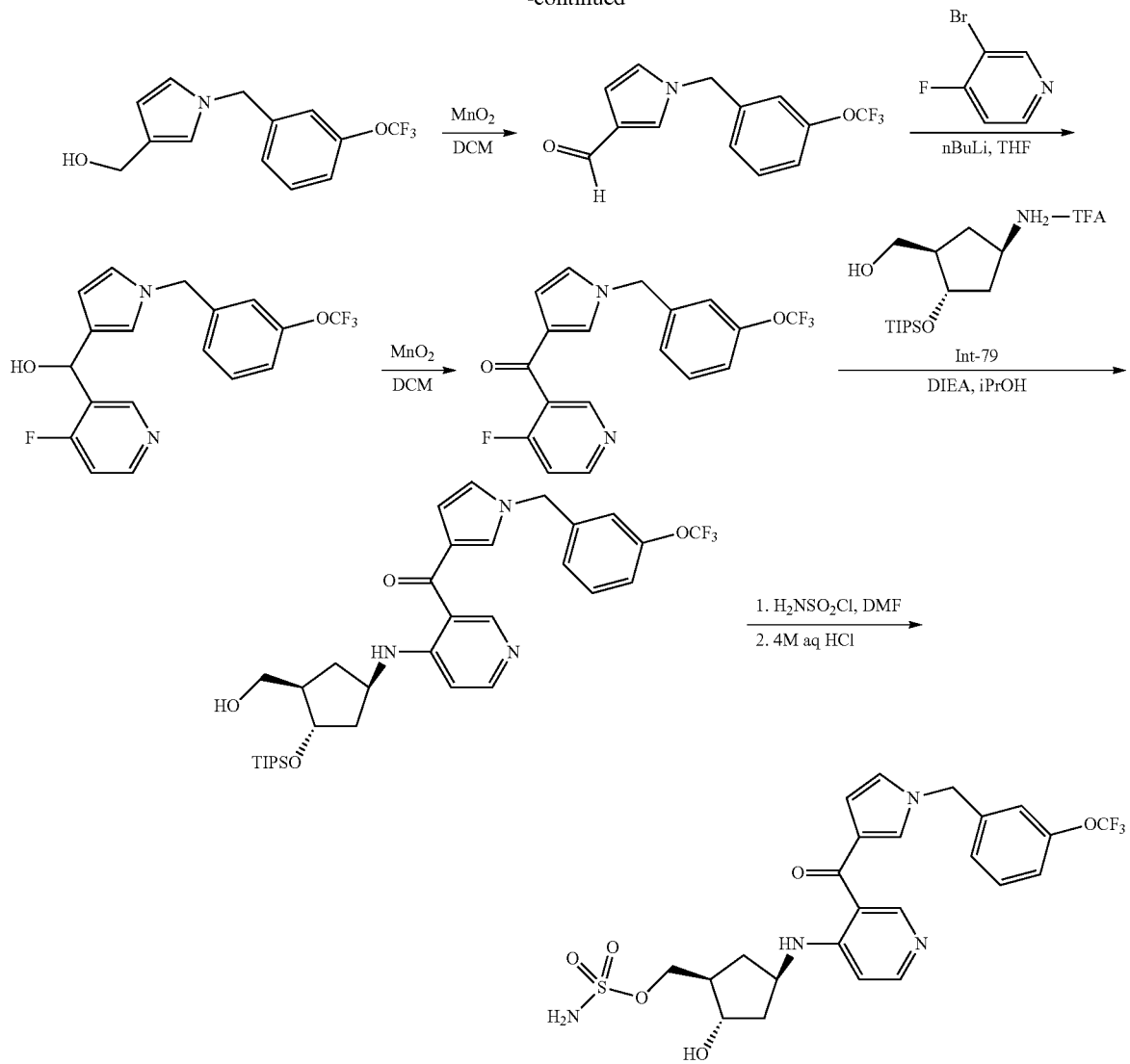

Step 1: Methyl 1-[3-(trifluoromethoxy)benzyl]-1H-pyrrole-3-carboxylate

Methyl 1H-pyrrole-3-carboxylate (0.50 g, 4.0 mmol) was dissolved in DMF (14 mL). To this solution was added cesium carbonate (3.3 g, 10.0 mmol) and 3-(trifluoromethoxy)benzyl bromide (0.78 mL, 4.8 mmol) and the reaction was stirred at rt for 4 h. The reaction was quenched by addition of water. This mixture was then extracted with EtOAc (3×). The combined organic layers were dried over $MgSO_4$, filtered and concentrated. The residue was purified on silica gel to give methyl 1-[3-(trifluoromethoxy)benzyl]-1H-pyrrole-3-carboxylate (1.17 g, 98%). LCMS (FA): m/z=300.2 (M+H).

Step 2: {1-[3-(Trifluoromethoxy)benzyl]-1H-pyrrol-3-yl}methanol

A solution of lithium aluminum hydride (2.0 M solution in THF; 3.9 mL, 7.8 mmol) was added to THF (25 mL) and stirred at 0° C. A solution of methyl 1-[3-(trifluoromethoxy)benzyl]-1H-pyrrole-3-carboxylate (1.17 g, 3.9 mmol) in THF (5 mL) was added dropwise: The resulting reaction mixture was heated at 60° C. for 2 h. The reaction mixture was then diluted with EtOAc, sodium sulfate decahydrate (1 g) was added and the mixture was stirred for 2 h. The mixture was filtered over a pad of celite, and then washed with additional EtOAc. The filtrate was concentrated and the crude residue purified on silica gel to give {1-[3-(trifluoromethoxy)benzyl]-1H-pyrrol-3-yl}methanol (0.54 g, 51%). LCMS (FA): m/z=272.4 (M+H).

Step 3: 1-[3-(Trifluoromethoxy)benzyl]-1H-pyrrole-3-carbaldehyde

To a solution of {1-[3-(trifluoromethoxy)benzyl]-1H-pyrrol-3-yl}methanol (1.4 g, 7.7 mmol) in DCM (17 mL) was added manganese(IV) oxide (1.7 g, 11 mmol). The suspension was stirred for 19 h at rt. The reaction was then filtered through a celite pad and the residual solid was washed with DCM several times. The filtrate was then concentrated in vacuo and the residue was purified on silica gel to afford 1-[3-(trifluoromethoxy)benzyl]-1H-pyrrole-3-carbaldehyde (0.36 g, 67%). LCMS (FA): m/z=270.2 (M+H).

Step 4: (4-Fluoropyridin-3-yl){1-[3-(trifluoromethoxy)benzyl]-1H-pyrrol-3-yl}methanol Into a flame dried RBF with stirbar was added 3-bromo-4-fluoropyridine (0.20 g, 1.1 mmol) dissolved in THF (6 mL). The flask was purged with argon and cooled to −78° C. To this solution was added dropwise n-butyllithium (2.5 M in hexane; 1.1 mL, 2.8 mmol) at −78° C. and the mixture was stirred for 30 min. To this mixture was added 1-[3-(trifluoromethoxy)benzyl]-1H-pyrrole-3-carbaldehyde (0.36 g, 1.3 mmol) dissolved in THF (4 mL) dropwise. The reaction was stirred at −78° C. for 2 h. The reaction was quenched with a saturated solution of NH$_4$Cl and then extracted with EtOAc (3×). The combined organic layers were then washed with water and brine, dried over Na$_2$SO$_4$, filtered and concentrated. The crude product was purified on silica gel to give (1-benzyl-1H-pyrrol-3-yl)(4-chloropyrimidin-5-yl)methanol (0.135 g, 33%). LCMS (FA): m/z=367.2 (M+H).

Step 5: (4-Fluoropyridin-3-yl){1-[3-(trifluoromethoxy)benzyl]-1H-pyrrol-3-yl}methanone To a solution of (1-benzyl-1H-pyrrol-3-yl)(4-chloropyrimidin-5-yl)methanol (0.14 g, 0.37 mmol) in DCM (3.9 mL) was added manganese(IV) oxide (0.32 g, 3.7 mmol). The suspension was stirred for 16 h at rt. The reaction was then filtered through a celite pad and the residual solid was washed with DCM several times. The filtrate was then concentrated in vacuo and the residue was purified on silica gel to afford (4-fluoropyridin-3-yl) {1-[3-(trifluoromethoxy)benzyl]-1H-pyrrol-3-yl}methanone (0.125 g, 93%). LCMS (FA): m/z=365.2 (M+H).

Step 6: [4-({(1R,3R,4S)-3-(Hydroxymethyl)-4-[(triisopropylsilyl)oxy]cyclopentyl}amino)pyridin-3-yl]{1-[3-(trifluoromethoxy)benzyl]-1H-pyrrol-3-yl}methanone (4-Fluoropyridin-3-yl) {1-[3-(trifluoromethoxy)benzyl]-1H-pyrrol-3-yl}methanone (0.125 g, 0.34 mmol) and {(1R,2S,4R)-4-amino-2-[(triisopropylsilyl)oxy]cyclopentyl}methanol.C$_2$HO$_2$F$_3$ (0.34 g, 0.86 mmol) were weighed into a reaction vessel with stirbar. To this mixture was added 2-propanol (3.9 mL) and DIEA (0.30 mL, 1.7 mmol). The resulting mixture was allowed to stir at 90° C. for 4 h. The reaction was then concentrated and the crude product was purified on silica gel to afford [4-({(1R,3R,4S)-3-(hydroxymethyl)-4-[(triisopropylsilyl)oxy]cyclopentyl}amino)pyridin-3-yl]{1-[3-(trifluoromethoxy)benzyl]-1H-pyrrol-3-yl}methanone (66 mg, 30%). LCMS (FA): m/z=632.2 (M+H).

Step 7: [(1R,2S,4R)-2-Hydroxy-4-{[3-({(1-[3-(trifluoromethoxy) benzyl]-1H-pyrrol-3-yl}carbonyl)pyridin-4-yl]amino}cyclopentyl]methyl sulfamate I-83

To a solution of [4-({(1R,3R,4S)-3-(hydroxymethyl)-4-[(triisopropylsilyl)oxy]cyclopentyl}amino)pyridin-3-yl]{1-[3-(trifluoromethoxy)benzyl]-1H-pyrrol-3-yl}methanone (0.066 g, 0.10 mmol) and TEA (0.72 mL, 0.52 mmol) in DMF (1.6 mL) was added chlorosulfonamide (36 mg, 0.31 mmol) at rt, and the mixture was stirred for 2 h. HCl (3.0 M in water; 1.5 mL, 3.9 mmol) was added to the solution. The reaction was stirred for 15 h at rt. The reaction was quenched by the addition of a saturated solution of NaHCO$_3$ and extracted with EtOAc (3×). The combined organic layers were dried over MgSO$_4$, filtered, and concentrated. The residue was purified on silica gel to afford [(1R,2S,4R)-2-hydroxy-4-{[3-({1-[3-(trifluoromethoxy) benzyl]-1H-pyrrol-3-yl}carbonyl)pyridin-4-yl]amino}cyclopentyl]methyl sulfamate (16 mg, 26%). $^1$H NMR (DMSO) δ 8.92-8.83 (m, 1H), 8.62 (s, 1H), 8.34-8.27 (m, 1H), 7.83 (s, 1H), 7.54-7.48 (m, 1H), 7.46 (s, 2H), 7.37-7.28 (m, 3H), 7.20-7.13 (m, 1H), 7.12 (s, 1H), 6.62 (s, 1H), 5.28 (s, 2H), 5.05 (s, 1H), 4.39-4.23 (m, 1H), 4.15-4.05 (m, 1H), 4.01-3.90 (m, 2H), 2.43-2.33 (m, 1H), 2.20-2.07 (m, 1H), 2.06-1.95 (m, 1H), 1.92-1.75 (m, 1H), 1.41-1.27 (m, 1H); LCMS (FA): m/z=555.2 (M+H).

The compounds listed in the table below were prepared in an analogous method to that described above starting from the listed starting materials:

| Starting material | Compound No. | LCMS Data |
|---|---|---|
| 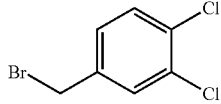 | I-233 | LCMS (FA): m/z = 539.1 (M + H). |
| 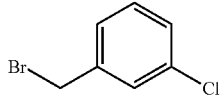 | I-201 | LCMS (FA): m/z = 505.3 (M + H). |

Example 89: [(1R,2R,3S,4R)-4-({5-[(1-Benzyl-1H-pyrrol-3-yl)carbonyl]pyrimidin-4-yl}amino)-2,3-dihydroxycyclopentyl]methyl sulfamate I-217

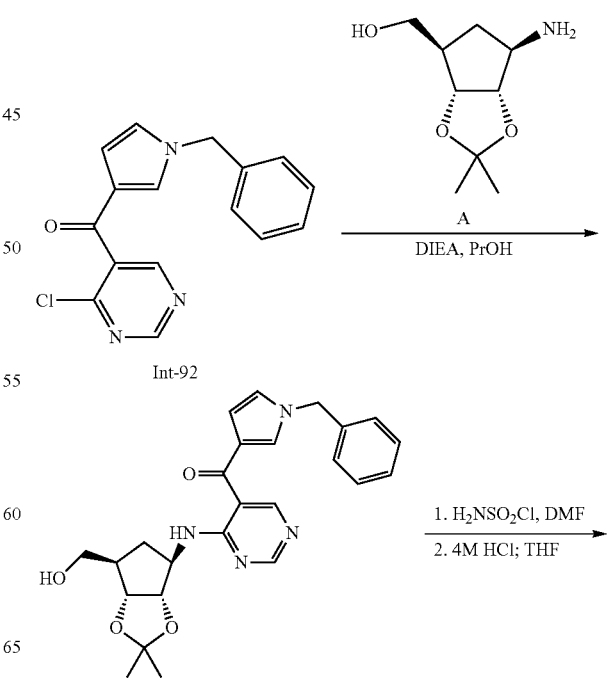

-continued

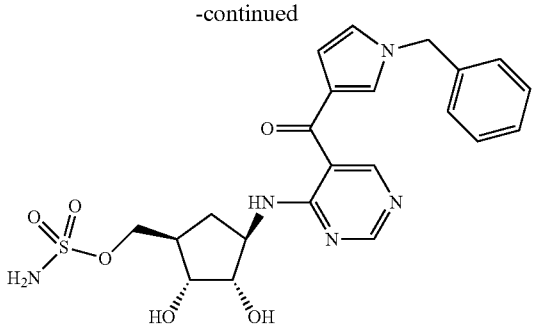

Step 1: (1-Benzyl-1H-pyrrol-3-yl)(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)methanone (1-Benzyl-1H-pyrrol-3-yl)(4-chloropyrimidin-5-yl)methanone (95 mg, 0.32 mmol) and (1R,2S,3R,4R)-1-amino-2,3-(isoproplydenyl)dihydroxy-4-hydroxymethyl cyclopentane (66 mg, 0.35 mmol) were weighed into a reaction vessel and dissolved in n-PrOH (3 mL). DIEA (0.11 mL, 0.64 mmol) was added to the solution and the reaction tube was sealed under an atmosphere of argon. The mixture was heated at 105° C. with stirring for 2 h. The reaction was then concentrated in vacuo. To the residue was added water (30 mL) and the mixture was extracted with EtOAc (50 mL×3). The combined organic layers were washed with brine, dried over $Na_2SO_4$, filtered, and concentrated in vacuo. The residue was purified on silica gel to give (1-benzyl-1H-pyrrol-3-yl)(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)methanone (138 mg, 92%) as a colorless amorphous solid. LCMS (FA): m/z=449.0 (M+H).

Step 2: [(1R,2R,3S,4R)-4-({5-[(1-Benzyl-1H-pyrrol-3-yl)carbonyl]pyrimidin-4-yl}amino)-2,3-dihydroxycyclopentyl]methyl sulfamate I-217

To a solution of (1-benzyl-1H-pyrrol-3-yl)(4-{[(3aS,4R,6R,6aR)-6-(hydroxymethyl)-2,2-dimethyltetrahydro-3aH-cyclopenta[d][1,3]dioxol-4-yl]amino}pyrimidin-5-yl)methanone (135 mg, 0.29 mmol) in DMF (2 mL) was added chlorosulfonamide (66 mg, 0.57 mmol) at rt, and the mixture was stirred for 15 min. The reaction was quenched by addition of saturated $NaHCO_3$ (30 mL) and extracted with EtOAc (50 mL×3). The combined organic layers were dried over $Na_2SO_4$, filtered, and concentrated in vacuo. The residue was purified on silica gel to give the sulfamate intermediate [(151 mg, 90%); LCMS (FA): m/z=528.0 (M+H).] which was dissolved in THF (2 mL). To this solution was added water (2 mL) followed by concentrated HCl (0.22 mL, 2.6 mmol) at rt, and the mixture was stirred for 3 h. The reaction was quenched by addition of saturated $NaHCO_3$ (30 mL) and extracted with EtOAc (50 mL×4). The combined organic layers were dried over $Na_2SO_4$, filtered, and concentrated in vacuo. To the residue was added small volumes of EtOAc and DCM, and then the resulting suspension was filtered through a glass frit funnel. The residual white solid was rinsed with DCM and dried under high vacuum to give [(1R,2R,3S,4R)-4-({5-[(1-benzyl-1H-pyrrol-3-yl)carbonyl]pyrimidin-4-yl}amino)-2,3-dihydroxycyclopentyl]methyl sulfamate (99 mg, 74%) as a colorless solid. $^1$H NMR (DMSO) δ 8.67 (s, 1H), 8.59 (s, 1H), 8.50 (d, J=7.4 Hz, 1H), 7.69 (s, 1H), 7.44 (s, 2H), 7.39-7.33 (m, 2H), 7.30 (dd, J=6.9, 4.6 Hz, 3H), 7.02-6.98 (m, 1H), 6.55 (dd, J=2.9, 1.8 Hz, 1H), 5.21 (s, 2H), 4.87 (d, J=5.9 Hz, 1H), 4.71 (br s, 1H), 4.45-4.33 (m, 1H), 4.06 (dd, J=9.7, 6.0 Hz, 1H), 3.96 (dd, J=9.7, 6.7 Hz, 1H), 3.75 (dd, J=12.7, 5.8 Hz, 1H), 3.69 (s, 1H), 2.37-2.26 (m, 1H), 2.18 (d, J=4.5 Hz, 1H), 1.11 (dt, J=12.9, 8.8 Hz, 1H); LCMS (FA): m/z=488.0 (M+H).

Example 90: [(1R,2R,3R,4R)-3-Fluoro-2-hydroxy-4-{[5-({1-[3-(trifluoromethoxy)benzyl]-1H-pyrrol-3-yl}carbonyl)pyrimidin-4-yl]amino}cyclopentyl]methyl sulfamate I-131

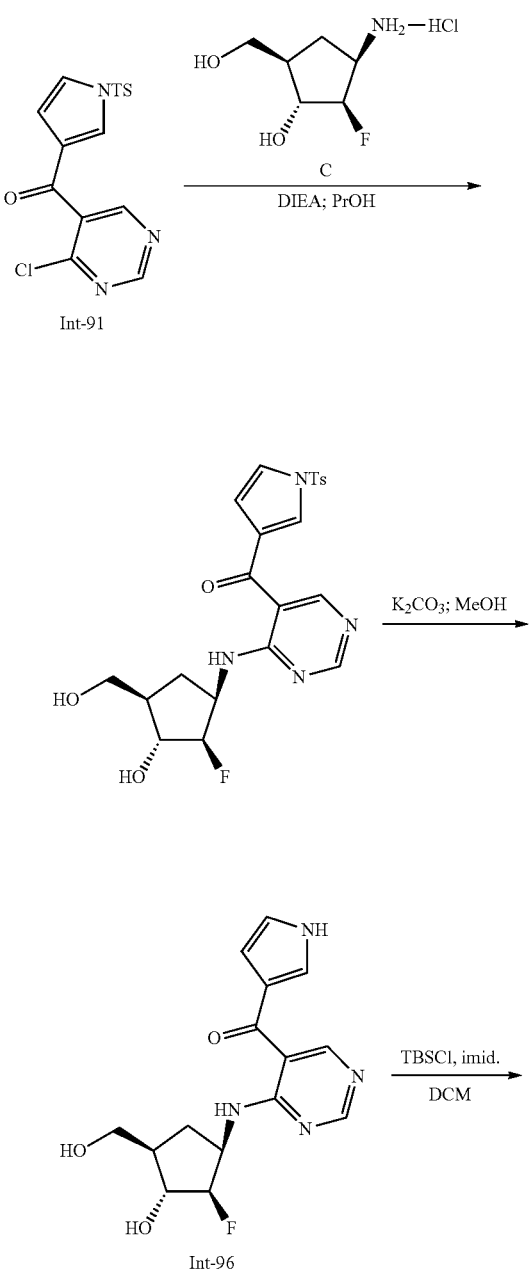

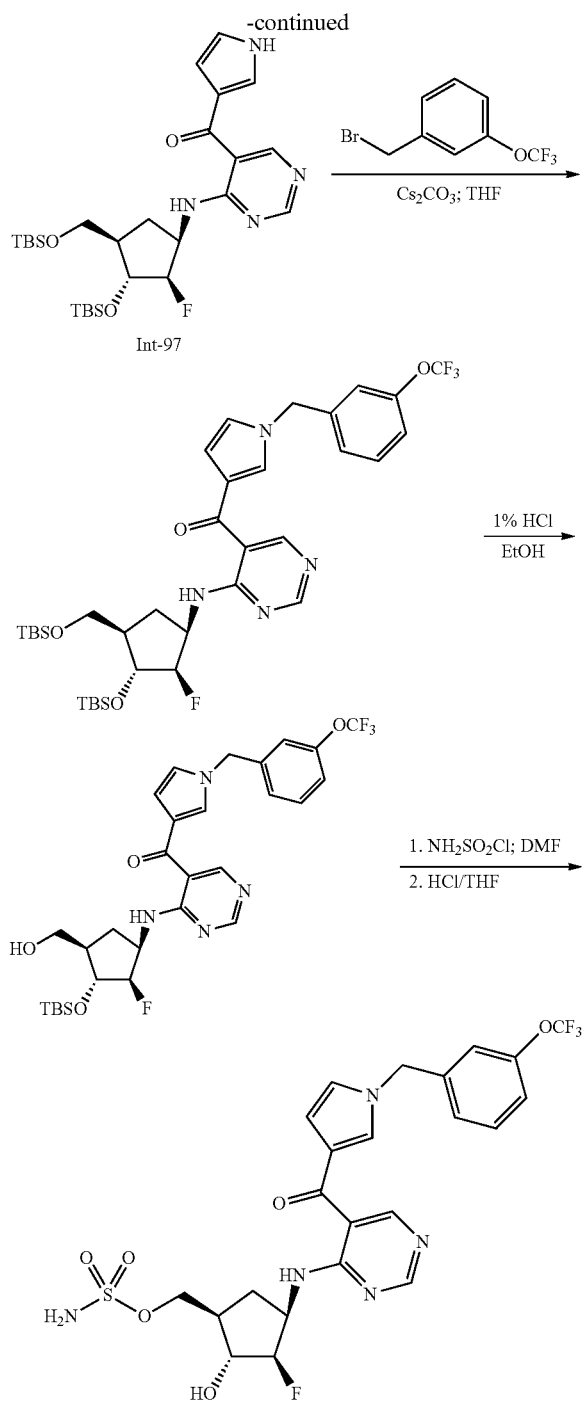

Step 1: (4-{[(1R,2R,3R,4R)-2-Fluoro-3-hydroxy-4-(hydroxymethyl)cyclopentyl]amino}pyrimidin-5-yl) {1-[(4-methylphenyl)sulfonyl]-1H-pyrrol-3-yl}methanone (4-Chloropyrimidin-5-yl) {-[(4-methylphenyl)sulfonyl]-1H-pyrrol-3-yl}methanone (12.90 g, 35.65 mmol) and (1R,2R,3R,5R)-3-amino-2-fluoro-5-(hydroxymethyl)cyclopentanol hydrochloride (7.28 g, 39.2 mmol) were weighed into a RBF with stirbar. To this mixture was added 2-propanol (300 mL) and DIEA (23 mL, 132 mmol). The resulting mixture was stirred at rt for 16 h. The reaction mixture was then concentrated and the crude product was purified on silica gel to afford (4-{[(1R,2R,3R,4R)-2-Fluoro-3-hydroxy-4-(hydroxymethyl)cyclopentyl]amino}pyrimidin-5-yl) {1-[(4-methylphenyl)sulfonyl]-H-pyrrol-3-yl}methanone (16.1 g, 95%) LCMS (AA): m/z=475.3 (M+H).

Step 2: (4-{[(1R,2R,3R,4R)-2-Fluoro-3-hydroxy-4-(hydroxymethyl)cyclopentyl]amino}pyrimidin-5-yl) (1H-pyrrol-3-yl)methanone Int-96

Into a round-bottom flask was added (4-{[(1R,2R,3R,4R)-2-fluoro-3-hydroxy-4-(hydroxymethyl)cyclopentyl]amino}pyrimidin-5-yl) {1-[(4-methylphenyl)sulfonyl]-1H-pyrrol-3-yl}methanone (16.1 g, 33.9 mmol) dissolved in methanol (500 mL). Potassium carbonate (14.1 g, 102 mmol) was added and the mixture was stirred at rt for 18 h. The resulting suspension was filtered and the filtrate was concentrated. The crude residue was purified on silica gel to give (4-{[(1R,2R,3R,4R)-2-fluoro-3-hydroxy-4-(hydroxymethyl)cyclopentyl]amino}pyrimidin-5-yl)(1H-pyrrol-3-yl)methanone (5.8 g, 53%). LCMS (AA): m/z=321.0 (M+H).

Step 3: (4-{[(1R,2R,3R,4R)-3-{[tert-Butyl(dimethyl)silyl]oxy}-4-({[tert-butyl(dimethyl)silyl]oxy}methyl)-2-fluorocyclopentyl]amino}pyrimidin-5-yl)(1H-pyrrol-3-yl)methanone Int-97

To a RBF was added (4-{[(1R,2R,3R,4R)-2-fluoro-3-hydroxy-4-(hydroxymethyl)cyclopentyl]amino}pyrimidin-5-yl)(1H-pyrrol-3-yl)methanone (0.14 g, 0.44 mmol), tert-Butyldimethylsilyl chloride (0.41 g, 2.7 mmol), DCM (20 mL), and imidazole (0.18 g, 2.7 mmol). The resulting reaction mixture was stirred at rt for 18 h. The mixture was then filtered through celite and the filtrate was concentrated. The crude residue was purified on silica gel to provide (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)(1H-pyrrol-3-yl)methanone (0.20 g, 82%). LCMS (AA): m/z=549.3 (M+H).

Step 4: (4-{[(1R,2R,3R,4R)-3-{[tert-Butyl(dimethyl)silyl]oxy}-4-({[tert-butyl(dimethyl)silyl]oxy}methyl)-2-fluorocyclopentyl]amino}pyrimidin-5-yl) {1-[3-(trifluoromethoxy)benzyl]-1H-pyrrol-3-yl}methanone To a RBF was added (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)(1H-pyrrol-3-yl)methanone (0.080 g, 0.14 mmol), 3-(trifluoromethoxy)benzyl bromide (0.074 g, 0.29 mmol), cesium carbonate (0.24 g, 0.73 mmol), and THF (3.20 mL). The resulting reaction mixture was stirred at rt for 3 days. The mixture was then filtered through celite and the filtrate was concentrated. The crude residue was purified on silica gel to give (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl) {1-[3-(trifluoromethoxy)benzyl]-1H-pyrrol-3-yl}methanone (0.086 g, 82%).

Step 5: (4-{[(1R,2R,3R,4R)-3-{[tert-Butyl(dimethyl)silyl]oxy}-2-fluoro-4-(hydroxymethyl)cyclopentyl]amino}pyrimidin-5-yl){1-[3-(trifluoromethoxy)benzyl]-1H-pyrrol-3-yl}methanone To a solution of (4-{[(1R,2R,3R,4R)-3-{[tert-butyl(dimethyl)silyl]oxy}-4-({[tert-butyl(dimethyl)silyl]

oxy}methyl)-2-fluorocyclopentyl]amino}pyrimidin-5-yl) {1-[3-(trifluoromethoxy)benzyl]-1H-pyrrol-3-yl}methanone (86 mg, 0.12 mmol) in EtOH (6 mL) was added 1% HCl in EtOH (7.5 mL, 0.91 mmol) at rt. The solution was allowed to stand at −20° C. for 40 h. The reaction was quenched by addition of a saturated aq. solution of NaHCO₃. To the residue was added water which was extracted with EtOAc (4×). The combined organic layers were dried over MgSO₄, filtered, and concentrated to give (4-{[(1R,2R,3R,4R)-3-{[tert-butyl(dimethyl)silyl]oxy}-2-fluoro-4-(hydroxymethyl)cyclopentyl]amino}pyrimidin-5-yl){1-[3-(trifluoromethoxy)benzyl]-1H-pyrrol-3-yl}methanone (0.060 g, 83%). LCMS (AA): m/z=609.2 (M+H).

Step 6: [(1R,2R,3R,4R)-3-Fluoro-2-hydroxy-4-{[5-({1-[3-(trifluoromethoxy)benzyl]-1H-pyrrol-3-yl}carbonyl)pyrimidin-4-yl]amino}cyclopentyl] methyl sulfamate I-131

To a solution of (4-{[(1R,2R,3R,4R)-3-{[tert-butyl(dimethyl)silyl]oxy}-2-fluoro-4-(hydroxymethyl)cyclopentyl]amino}pyrimidin-5-yl) {1-[3-(trifluoromethoxy)benzyl]-1H-pyrrol-3-yl}methanone (0.060 g, 0.10 mmol) and TEA (0.041 mL, 0.30 mmol) in DMF (4 mL) was added chlorosulfonamide (23 mg, 0.20 mmol) at rt, and the mixture was stirred for 30 min. The reaction was concentrated and the crude sulfamate intermediate was dissolved in THF (0.42 mL) and HCl (3.0 M in water; 0.43 mL, 1.3 mmol) was added to the solution. The reaction was stirred for 4 h at rt. The reaction was then quenched by the addition of a saturated solution of NaHCO₃ and extracted with DCM (3×). The combined organic layers were dried over MgSO₄, filtered, and concentrated. The residue was purified by prep HPLC to afford [(1R,2R,3R,4R)-3-fluoro-2-hydroxy-4-{[5-({1-[3-(trifluoromethoxy)benzyl]-1H-pyrrol-3-yl}carbonyl)pyrimidin-4-yl]amino}cyclopentyl]methyl sulfamate (26 mg, 46%). ¹H NMR (CDCl₃) δ 8.76 (s, 1H), 8.72 (d, J=7.7 Hz, 1H), 8.66 (d, J=5.2 Hz, 1H), 7.76 (t, J=1.8 Hz, 1H), 7.56-7.43 (m, 2H), 7.32 (dd, J=7.3, 5.9 Hz, 3H), 7.05 (dd, J=2.8, 2.1 Hz, 1H), 6.57 (dd, J=2.9, 1.8 Hz, 1H), 5.27 (s, 2H), 4.93-4.62 (m, 2H), 4.16-4.06 (m, 1H), 4.05-3.98 (m, 1H), 3.97-3.86 (m, 1H), 2.39-2.25 (m, 1H), 2.23-2.10 (m, 1H), 1.53-1.36 (m, 1H). LCMS (AA): m/z=574.2 (M+H).

The compounds listed in the table below were prepared in an analogous method to that described above starting from the listed starting materials used in step 4. The following alternative conditions could be employed in the described reaction steps. Step 4: K₂CO₃ is an acceptable replacement for Cs₂CO₃; DMF is an acceptable replacement for THF. I-175/I-356 (benzylic ethyl) and I-192/I-363 (benzylic methyl) were made as diastereomeric mixtures and then separated via HPLC (chiral column). Absolute configurations of the undefined stereocenters are unknown.

| Starting material | Compound No. or Name | LCMS Data |
|---|---|---|
| (Br-CH₂-phenyl-Br, 3-bromobenzyl bromide) | I-312 | LCMS (FA): m/z = 568.0 (M + H). |
| (Br-CH₂-phenyl with 2 Cl) | I-331 | LCMS (FA): m/z = 558.3 (M + H). |
| (Br-CH₂-furan-CF₃) | I-209 | LCMS (FA): m/z = 546 (M + H). |
| (Br-CH₂CH₂-phenyl-Br) | I-243 | LCMS (FA): m/z = 582.1 (M + H). |
| (Br-CH(Et)-phenyl) | I-175 | LCMS (FA): m/z = 596.5 (M + H). |
| (Br-CH(Et)-phenyl) | I-356 | LCMS (FA): m/z = 596.5 (M + H). |
| (Br-CH(Me)-phenyl) | I-192 | LCMS (FA): m/z = 582.1 (M + H). |
| (Br-CH(Me)-phenyl) | I-363 | LCMS (FA): m/z = 582.1 (M + H). |

Example 91: {(1R,2R,3R,4R)-3-Fluoro-4-[(5-{[1-(4-fluoro-3-methoxybenzyl)-1H-pyrrol-3-yl]carbonyl}pyrimidin-4-yl)amino]-2-hydroxycyclopentyl}methyl sulfamate I-57

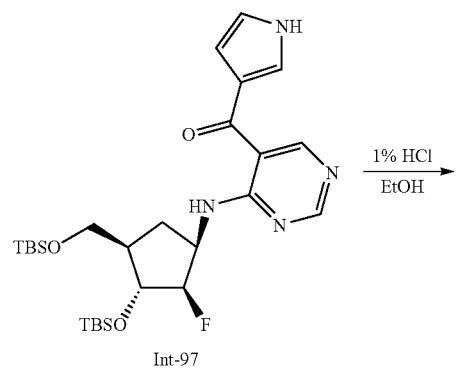

Int-97

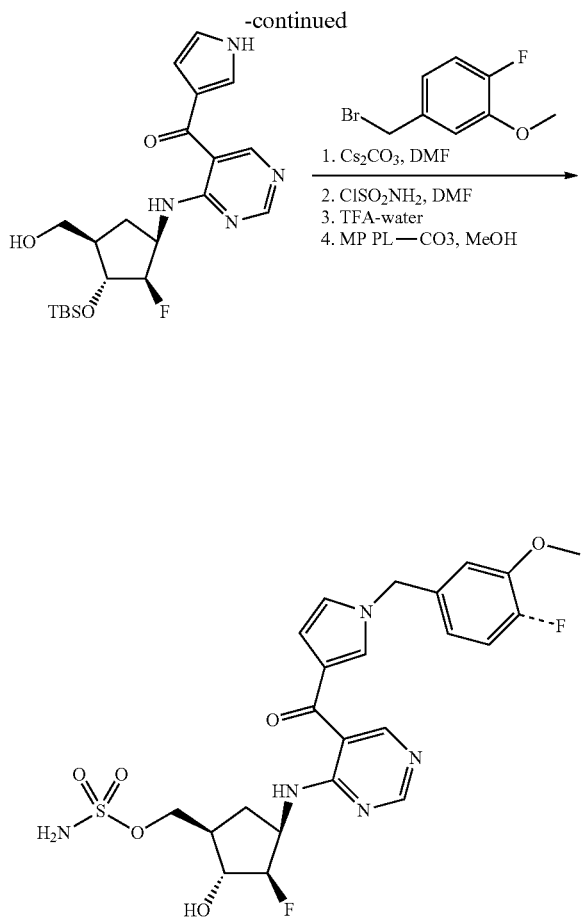

Step 1: (4-{[(1R,2R,3R,4R)-3-{[tert-butyl(dimethyl)silyl]oxy}-2-fluoro-4-(hydroxymethyl)cyclopentyl]amino}pyrimidin-5-yl)(1H-pyrrol-3-yl)methanone To a solution of (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)(1H-pyrrol-3-yl)methanone (0.56 g, 1.0 mmol) in EtOH (42 mL) was added 1% HCl in EtOH (30 mL, 3.6 mmol) at rt. The reaction vessel was sealed and allowed to stand in a refrigerator (4° C.) for 18 h. The reaction was quenched by addition of a saturated aq. solution of NaHCO₃. To the residue was added water which was extracted with EtOAc (4×). The combined organic layers were dried over MgSO₄, filtered, and concentrated. The residue was purified on silica gel to give (4-{[(1R,2R,3R,4R)-3-{[tert-butyl(dimethyl)silyl]oxy}-2-fluoro-4-(hydroxymethyl)cyclopentyl]amino}pyrimidin-5-yl)(1H-pyrrol-3-yl)methanone (0.34 g, 76%).

Step 2: {(1R,2R,3R,4R)-3-Fluoro-4-[(5-{[1-(4-fluoro-3-methoxybenzyl)-1H-pyrrol-3-yl]carbonyl}pyrimidin-4-yl)amino]-2-hydroxycyclopentyl}methyl sulfamate I-57

To a 3-dram vial with 4-fluoro-3-methoxybenzyl bromide (0.020 g, 0.090 mmol) was added (4-{[(1R,2R,3R,4R)-3-{[tert-butyl(dimethyl)silyl]oxy}-2-fluoro-4-(hydroxymethyl)cyclopentyl]amino}pyrimidin-5-yl)(1H-pyrrol-3-yl)methanone (0.030 g, 0.069 mmol) in DMF (1.0 mL) followed by cesium carbonate (0.090 g, 0.28 mmol). The mixture was shaken at rt for 2 h, then dimethylamine (2.0 M solution in THF; 0.017 mL, 0.035 mmol) was added to quench excess benzyl bromide. The solid Cs₂CO₃ was filtered and rinsed with DMF (1 mL). To the filtrate in another 3-dram vial was added chlorosulfonamide (0.032 g, 0.28 mmol). The solution was shaken at rt for 1 h, then saturated NaHCO₃ (2 mL) and EtOAc (5 mL) were added. After separation of the phases, the aqueous layer was extracted with EtOAc (5 mL). The combined organic phases were concentrated to give a solid residue. To the solid in a 20 mL vial was added TFA (1.8 mL) and water (0.2 mL). After shaking at rt for 2 h, the solvent was evaporated. To the residue was added MeOH (3.0 mL) and MP PL-CO3 resin. The mixture was then shaken at rt for 30 min, and the resin was subsequently filtered and rinsed with MeOH (10 mL). The filtrate was concentrated and the residue was purified by prep HPLC to give {(1R,2R,3R,4R)-3-fluoro-4-[(5-{[1-(4-fluoro-3-methoxybenzyl)-1H-pyrrol-3-yl]carbonyl}pyrimidin-4-yl)amino]-2-hydroxycyclopentyl}methyl sulfamate (8 mg, 22%). LCMS (FA): m/z=538.8 (M+H).

The compounds listed in the table below were prepared in an analogous method to that described above starting from the listed starting materials:

| Starting material | Compound No. | LCMS Data |
|---|---|---|
| Br-CH₂-C₆H₃(Br)(F) (3-Br, 4-F) | I-143 | LCMS (FA): m/z = 588.0 (M + H). |
| Br-CH₂-C₆H₄-I (3-I) | I-13 | LCMS (FA): m/z = 616.1 (M + H). |
| Br-CH₂-C₆H₃(Br)(Cl) (3-Br, 4-Cl) | I-337 | LCMS (FA): m/z = 602.1 (M + H). |
| Br-CH₂-C₆H₄-CF₃ (3-CF₃) | I-7 | LCMS (FA): m/z = 558.2 (M + H). |
| Br-CH₂-C₆H₄-OCHF₂ (3-OCHF₂) | I-224 | LCMS (FA): m/z = 556.2 (M + H). |
| Br-CH₂-C₆H₃(Cl)(F) (3-Cl, 4-F) | I-141 | LCMS (FA): m/z = 542.2 (M + H). |

Example 92: [(1R,2R,3R,4R)-4-{[5-({1-[(5-Bromo-2-furyl)methyl]-1H-pyrrol-3-yl}carbonyl)pyrimidin-4-yl]amino}-3-fluoro-2-hydroxycyclopentyl]methyl sulfamate I-24

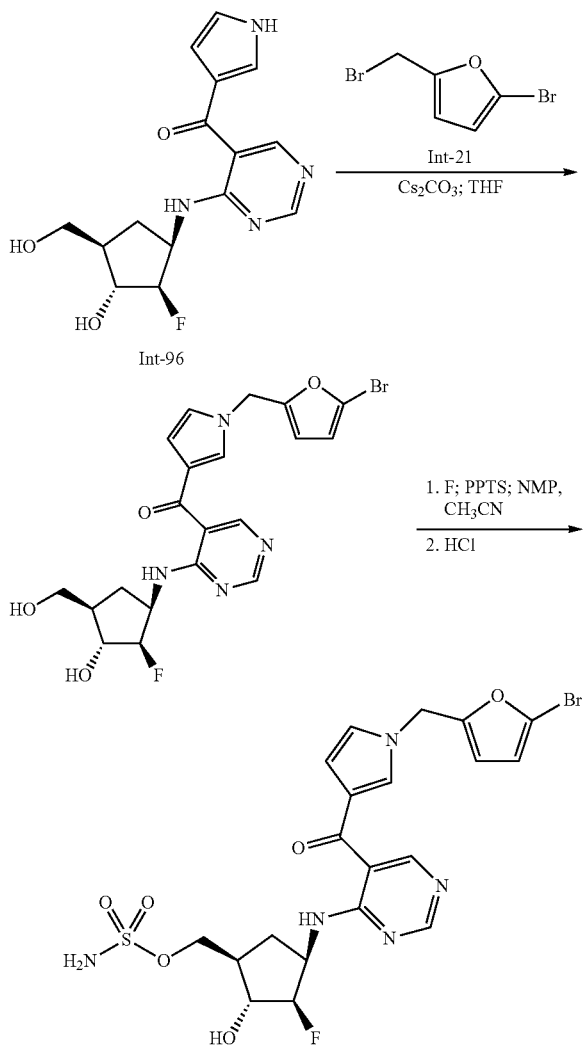

Step 1: {1-[(5-Bromo-2-furyl)methyl]-1H-pyrrol-3-yl}(4-{[(1R,2R,3R,4R)-2-fluoro-3-hydroxy-4-(hydroxymethyl)cyclopentyl]amino}pyrimidin-5-yl)methanone To a RBF was added (4-{[(1R,2R,3R,4R)-2-fluoro-3-hydroxy-4-(hydroxymethyl)cyclopentyl]amino}pyrimidin-5-yl)(1H-pyrrol-3-yl)methanone (0.11 g, 0.33 mmol), 2-bromo-5-(bromomethyl)furan (0.091 g, 0.38 mmol), cesium carbonate (0.22 g, 0.66 mmol), and THF (13 mL). The resulting reaction mixture was stirred at 48° C. for 3 days. The reaction mixture was then concentrated and water (12 mL) was added. The mixture was extracted with EtOAc (2×). The combined organic layers were dried over MgSO₄, filtered, and concentrated. The crude product was purified on silica gel to provide {1-[(5-bromo-2-furyl)methyl]-1H-pyrrol-3-yl}(4-{[(1R,2R,3R,4R)-2-fluoro-3-hydroxy-4-(hydroxymethyl)cyclopentyl]amino}pyrimidin-5-yl)methanone (81 mg, 51%). LCMS (AA): m/z=479.3 (M+H).

Step 2: [(1R,2R,3R,4R)-4-{[5-({1-[(5-Bromo-2-furyl)methyl]-1H-pyrrol-3-yl}carbonyl)pyrimidin-4-yl]amino}-3-fluoro-2-hydroxycyclopentyl]methyl sulfamate I-24

{1-[(5-Bromo-2-furyl)methyl]-1H-pyrrol-3-yl}(4-{[1(1R,2R,3R,4R)-2-fluoro-3-hydroxy-4-(hydroxymethyl)cyclopentyl]amino}pyrimidin-5-yl)methanone (81 mg, 0.17 mmol) was dissolved in NMP (0.8 mL) and acetonitrile (0.4 mL). To this solution was added in one portion PPTS (43 mg, 0.17 mmol) followed by the addition of (4-aza-1-azoniabicyclo[2.2.2]oct-1-ylsulfonyl)(tert-butoxycarbonyl)azanide-1,4-diazabicyclo[2.2.2]octane (1:1) hydrochloride (F) (0.15 g, 0.34 mmol). After stirring for 1 h at rt, additional (4-aza-1-azoniabicyclo[2.2.2]oct-1-ylsulfonyl)(tert-butoxycarbonyl)azanide-1,4-diazabicyclo[2.2.2]octane (1:1) hydrochloride (F) (40 mg, 0.09 mmol) was added and continued to stir at rt an additional 2 h. The reaction was quenched by the addition of water. The mixture was extracted with EtOAc (3×). The combined organic layers were dried over MgSO₄, filtered and concentrated to give the crude Boc-protected sulfamate intermediate which was then dissolved in acetonitrile (1.0 mL) at rt. Concentrated HCl (0.50 mL, 6.0 mmol) was added at 0° C. The mixture was then allowed to stir at rt for 18 h. The reaction was quenched by the addition of a saturated solution of NaHCO₃ in water. After diluting the mixture with water it was extracted with EtOAc (4×). The combined organic layers were dried over MgSO₄, filtered, and concentrated. The crude product was purified by prep HPLC to give [(1R,2R,3R,4R)-4-{[5-({1-[(5-bromo-2-furyl)methyl]1H-pyrrol-3-yl}carbonyl)pyrimidin-4-yl]amino}-3-fluoro-2-hydroxycyclopentyl]methyl sulfamate (29 mg, 24%). ¹H NMR (DMSO) δ 8.75 (s, 1H), 8.73-8.68 (m, 1H), 8.67 (s, 1H), 7.63 (t, J=1.9 Hz, 1H), 6.98 (dd, J=2.9, 2.1 Hz, 1H), 6.65-6.51 (m, 3H), 5.25 (s, 2H), 4.95-4.61 (m, 2H), 4.18-4.07 (m, 1H), 4.07-3.99 (m, 1H), 3.97-3.86 (m, 1H), 2.40-2.26 (m, 1H), 2.24-2.11 (m, 1H), 1.54-1.39 (m, 1H). LCMS (AA): m/z=558.3 (M+H).

The compounds listed in the table below were prepared using a similar method to that described above starting from the listed starting materials in step 1. The following alternative conditions could be employed in the described reaction steps. Step 1: K₂CO₃ is an acceptable replacement for Cs₂CO₃; DMF is an acceptable replacement for THF. Step 3: aq. TFA and aq. H₃PO₄ are acceptable replacements for aq. HCl. I-350 and I-364 were made as a diastereomeric mixture (furylic methyl) and then separated via chiral HPLC. I-9 and I-359 were also made as a diastereomeric mixture (trans cyclopropyl) and separated via HPLC (chiral column) to give the single diastereomers, respectively. Absolute configurations of these stereocenters are unknown.

| Starting material | Compound No. or Name | LCMS Data |
|---|---|---|
| Int-22 | I-41 | LCMS (FA): m/z = 524.4 (M + H). |
| | I-222 | LCMS (FA): m/z = 498.4 (M + H). |

| Starting material | Compound No. or Name | LCMS Data |
|---|---|---|
| 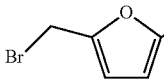<br>Int-23 | I-296 | LCMS (FA): m/z = 514.3 (M + H). |
| 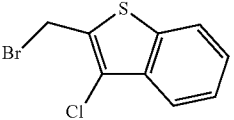 [SMILES: Clc1c(CBr)sc2ccccc12]<br>Int-15 | I-49 | LCMS (FA): m/z = 580.4 (M + H). |
| 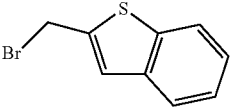 [SMILES: BrCc1cc2ccccc2s1]<br>Kong, X. et al. PCT Application Publication WO 2006/085149 | I-322 | LCMS (FA): m/z = 546.1 (M + H). |
| 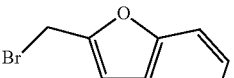<br>Pelcman, B. et al. PCT Application Publication WO 2008/110793 | I-110 | LCMS (FA): m/z = 530.2 (M + H). |
| 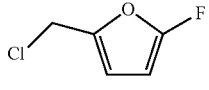<br>Int-58 | I-231 | LCMS (FA): m/z = 498.4 (M + H). |
| 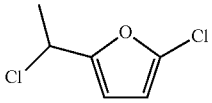<br>Int-25 | I-350 | LCMS (FA): m/z = 528.4 (M + H). |
| 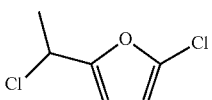<br>Int-25 | I-364 | LCMS (FA): m/z = 528.4 (M + H). |
| 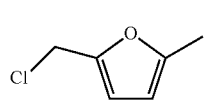<br>Int-24 | I-277 | LCMS (FA): m/z = 494.4 (M + H). |
| 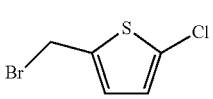<br>Int-19 | I-189 | LCMS (FA): m/z = 530.3 (M + H). |

| Starting material | Compound No. or Name | LCMS Data |
|---|---|---|
| 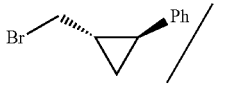<br>Int-6 | I-9 | LCMS (FA): m/z = 530.1 (M + H). |
| 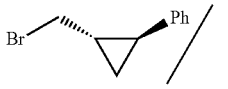<br>Int-6 | I-359 | LCMS (FA): m/z = 530.1 (M + H). |
| 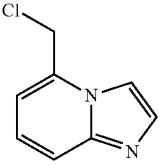 [SMILES: ClCc1cccc2nccn12]<br>Int-36 | I-237 | LCMS (FA): m/z = 530.4 (M + H). |
| 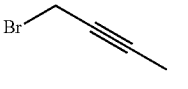 | I-195 | LCMS (FA): m/z = 452.5 (M + H). |
| 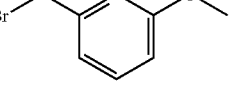 | I-188 | LCMS (FA): m/z = 521.4 (M + H). |
| 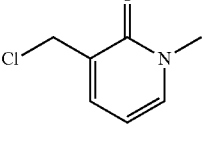<br>Int-35 | I-216 | LCMS (FA): m/z = 521.4 (M + H). |
| 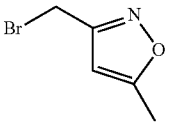 | I-297 | LCMS (FA): m/z = 495.3 (M + H). |
| 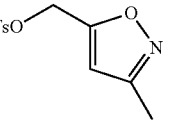<br>Int-40 | I-208 | LCMS (FA): m/z = 495.4 (M + H). |
| <br>Int-50 | I-75 | LCMS (FA): m/z = 510.5 (M + H). |

395
-continued

| Starting material | Compound No. or Name | LCMS Data |
|---|---|---|
| Int-16 | I-257 | LCMS (FA): m/z = 564.1 (M + H). |
| Int-26 | I-87 | LCMS (FA): m/z = 530.1 (M + H). |
| Int-31 | I-114 | LCMS (FA): m/z = 548.1 (M + H). |
| | I-250 | LCMS (FA): m/z = 512.2 (M + H). |

Florjancic, A.S. et al.
US Application Publication
2010/0093814

Example 93: [(1R,2R,3R,4R)-4-{[5-({1-[(6-Chloro-pyridin-2-yl)methyl]-1H-pyrrol-3-yl}carbonyl)py-rimidin-4-yl]amino}-3-fluoro-2-hydroxycyclopentyl] methyl sulfamate I-8

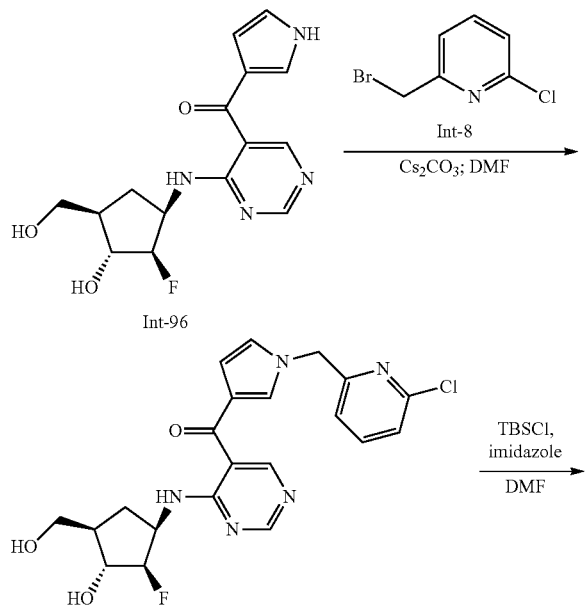

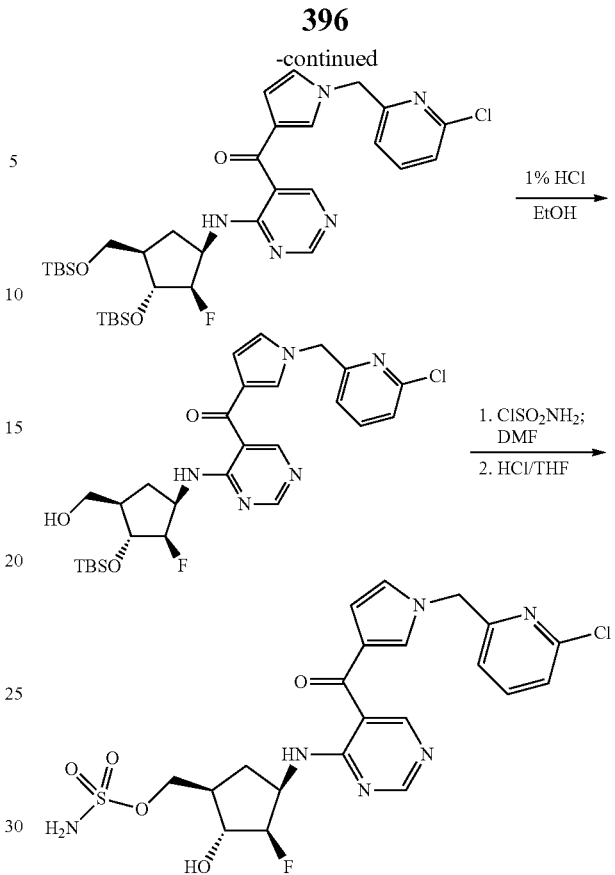

Step 1: {1-[(6-Chloropyridin-2-yl)methyl]-1H-pyr-rol-3-yl}(4-{[(1R,2R,3R,4R)-2-fluoro-3-hydroxy-4-(hydroxymethyl)cyclopentyl]amino}pyrimidin-5-yl) methanone (4-{[(1R,2R,3R,4R)-2-Fluoro-3-hydroxy-4-(hydroxymethyl)cyclopentyl]amino}pyrimidin-5-yl)(1H-pyrrol-3-yl) methanone (0.16 g, 0.50 mmol) was dissolved in DMF (7 mL). To this solution was added cesium carbonate (0.49 g, 1.5 mmol) and 2-(bromomethyl)-6-chloro-pyridine (0.15 g, 0.75 mmol) and the reaction was stirred at rt for 2 h. The reaction was then quenched by addition of water and the mixture extracted with EtOAc (3×). The combined organic layers were washed with brine, dried over MgSO$_4$, filtered, and concentrated. The residue was purified on silica gel to give {1-[(6-chloropyridin-2-yl)methyl]-1H-pyrrol-3-yl}(4-{[(1R,2R,3R,4R)-2-fluoro-3-hydroxy-4-(hydroxymethyl)cy-clopentyl]amino}pyrimidin-5-yl)methanone (0.18 g, 78%). LCMS (FA): m/z=446.0 (M+H).

Step 2: (4-{[(1R,2R,3R,4R)-3-{[tert-Butyl(dim-ethyl)silyl]oxy}-4-({[tert-butyl(dimethyl)silyl] oxy}methyl)-2-fluorocyclopentyl]amino}pyrimidin-5-yl) {1-[(6-chloropyridin-2-yl)methyl]-1H-pyrrol-3-yl}methanone To a solution of {1-[(6-chloropyridin-2-yl)methyl]-1H-pyrrol-3-yl}(4-{[(1R,2R,3R,4R)-2-fluoro-3-hydroxy-4-(hy-droxymethyl)cyclopentyl]amino}pyrimidin-5-yl)metha-none (0.18 g, 0.39 mmol) in DMF (1.5 mL) was added imidazole (0.11 g, 1.6 mmol) followed by tert-butyldimeth-ylsilyl chloride (0.18 g, 1.2 mmol) at rt, and the mixture was stirred for 24 h. The reaction was then quenched by addition of water and extracted with EtOAc (3×). The combined organic layers were washed with brine, dried over MgSO₄, filtered, and concentrated. The residue was purified on silica gel to give (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl) {1-[(6-chloropyridin-2-yl)methyl]-1H-pyrrol-3-yl}methanone (0.23 g, 89%). LCMS (FA): m/z=674.1 (M+H).

Step 3: (4-{[(1R,2R,3R,4R)-3-{[tert-Butyl(dimethyl)silyl]oxy}-2-fluoro-4-(hydroxymethyl)cyclopentyl]amino}pyrimidin-5-yl) {1-[(6-chloropyridin-2-yl)methyl]-1H-pyrrol-3-yl}methanone To a solution of (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl) {1-[(6-chloropyridin-2-yl)methyl]-1H-pyrrol-3-yl}methanone (0.23 g, 0.34 mmol) in EtOH (12 mL) was added 1% HCl in EtOH (10 mL, 1.2 mmol) at rt. The reaction vessel was sealed and placed in a refrigerator (4° C.) for 13 h. The reaction was quenched by addition of a saturated aq. solution of NaHCO₃. To the residue was added water which was extracted with EtOAc (4×). The combined organic layers were dried over MgSO₄, filtered, and concentrated. The residue was purified on silica gel to give (4-{[(1R,2R,3R,4R)-3-{[tert-butyl(dimethyl)silyl]oxy}-2-fluoro-4-(hydroxymethyl)cyclopentyl]amino}pyrimidin-5-yl) {1-[(6-chloropyridin-2-yl)methyl]-1H-pyrrol-3-yl}methanone (0.15 g, 78%). LCMS (FA): m/z=560.1 (M+H).

Step 4: [(1R,2R,3R,4R)-4-{[5-({1-[(6-Chloropyridin-2-yl)methyl]-1H-pyrrol-3-yl}carbonyl)pyrimidin-4-yl]amino}-3-fluoro-2-hydroxycyclopentyl] methyl sulfamate I-8

To a solution of (4-{[(1R,2R,3R,4R)-3-{[tert-butyl(dimethyl)silyl]oxy}-2-fluoro-4-(hydroxymethyl)cyclopentyl]amino}pyrimidin-5-yl) {1-[(6-chloropyridin-2-yl)methyl]-1H-pyrrol-3-yl}methanone (0.15 g, 0.26 mmol) and TEA (0.11 mL, 0.79 mmol) in DMF (5 mL) was added chlorosulfonamide (61 mg, 0.53 mmol) at rt, and the mixture was stirred for 4 h. The reaction was quenched by addition of a saturated solution of NaHCO₃ and diluted with water. The mixture was extracted with EtOAc (4×). The combined organic layers were dried over MgSO₄, filtered, and concentrated. The crude sulfamate intermediate was dissolved in THF (7 mL) and HCl (4.0 M in water; 3 mL, 12 mmol) was added to the solution. The reaction was stirred for 3 h at it. The reaction was quenched by the addition of a saturated solution of NaHCO₃ and extracted with EtOAc (4×). The combined organic layers were dried over MgSO₄, filtered, and concentrated. The residue was purified by prep HPLC to afford [(1R,2R,3R,4R)-4-{[5-({1-[(6-chloropyridin-2-yl)methyl]-1H-pyrrol-3-yl}carbonyl)pyrimidin-4-yl]amino}-3-fluoro-2-hydroxycyclopentyl]methyl sulfamate (0.067 g, 49%). ¹H NMR (DMSO) δ 8.78 (s, 1H), 8.72 (d, J=7.6 Hz, 1H), 8.66 (s, 1H), 7.87 (t, J=7.8 Hz, 1H), 7.71 (t, J=1.8 Hz, 1H), 7.49 (s, 2H), 7.46 (d, J=7.9 Hz, 1H), 7.12 (d, J=7.6 Hz, 1H), 7.04 (dd, J=2.8, 2.0 Hz, 1H), 6.59 (dd, J=2.9, 1.8 Hz, 1H), 5.54 (d, J=5.1 Hz, 1H), 5.33 (s, 2H), 4.92-4.66 (m, 2H), 4.11 (dd, J=9.7, 6.0 Hz, 1H), 4.02 (dd, J=9.7, 6.9 Hz, 1H), 3.92 (dt, J=9.4, 5.0 Hz, 1H), 2.39-2.27 (m, 1H), 2.22-2.11 (m, 1H), 1.46 (dd, J=22.8, 11.2 Hz, 1H); LCMS (FA): m/z=524.9 (M+H).

The compounds listed in the table below were prepared by an analogous method to that described above starting from the listed starting materials used in step 1. I-304 and I-357 were made as a diastereomeric mixture (furylic methyl) and then separated via HPLC (chiral column). Absolute configuration of the undefined stereocenter is unknown.

| Starting material | Compound No. | LCMS Data |
| --- | --- | --- |
| 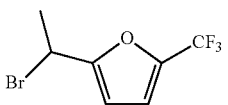 Int-59 | I-304 | LCMS (FA): m/z = 562.5 (M + H). |
|  Int-59 | I-357 | LCMS (FA): m/z = 562.5 (M + H). |
| 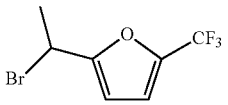 Int-42 | I-5 | LCMS (FA): m/z = 496.4 (M + H). |
|  Int-57 | I-236 | LCMS (FA): m/z = 482.4 (M + H). |
| 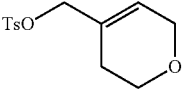 Int-55 | I-26 | LCMS (FA): m/z = 494.4 (M + H). |

Example 94: Methyl 5-chloro-1H-pyrrole-3-carboxylate Int-98 and Methyl 2,5-dichloro-1H-pyrrole-3-carboxylate Int-99

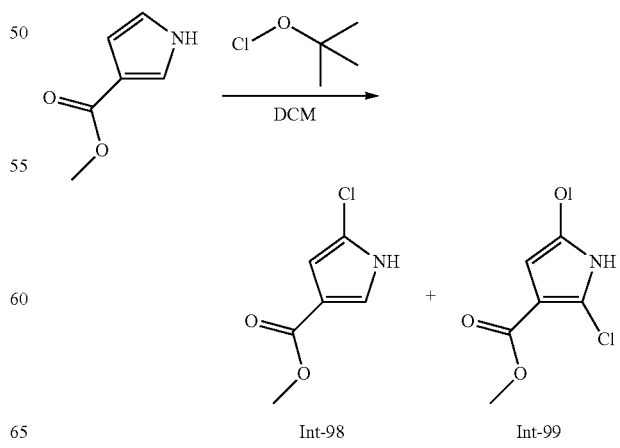

Step 1: Methyl 5-chloro-1H-pyrrole-3-carboxylate Int-98 and Methyl 2,5-dichloro-1H-pyrrole-3-carboxylate Int-99

To a RBF was added methyl 1H-pyrrole-3-carboxylate (2.1 g, 17 mmol) and DCM (80 mL). The resulting reaction mixture was stirred at 0° C. and tert-butyl hypochlorite (1.9 mL, 17 mmol) in DCM (30 mL) was added dropwise. After addition was complete, the mixture was stirred at 0° C. for 20 min, then warmed to rt and stirred 2 h. A saturated solution of NaHCO$_3$ was then added and the phases separated. The organic layer was separated and concentrated. The crude residue was purified on silica gel to give methyl 5-chloro-H-pyrrole-3-carboxylate (1.75 g, 65%). $^1$H NMR (CDCl$_3$) δ 7.32 (dd, J=3.0, 1.8 Hz, 1H), 6.50 (dd, J=2.7, 1.8 Hz, 1H), 3.83 (s, 3H). Also isolated was methyl 2,5-dichloro-1H-pyrrole-3-carboxylate (0.41 g, 12%). LCMS (AA): m/z=194.0 (M+H).

Example 95: [5-Chloro-1-(3-chlorobenzyl)-1H-pyrrol-3-yl](4-chloropyrimidin-5-yl)methanone Int-100

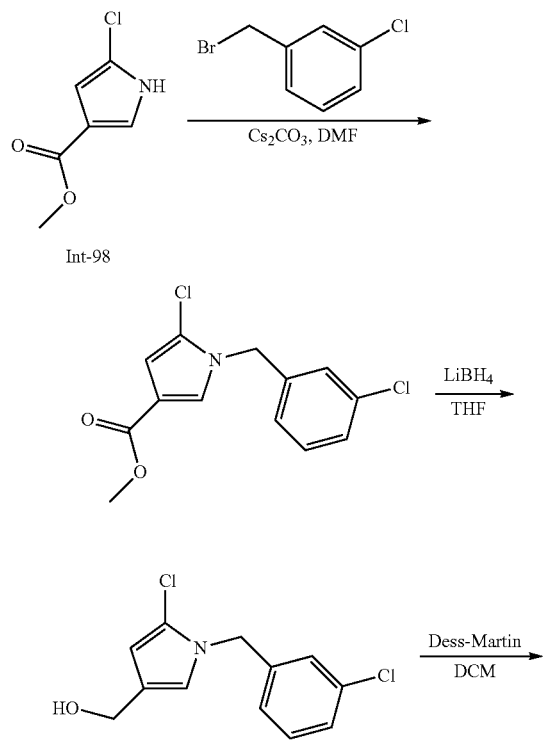

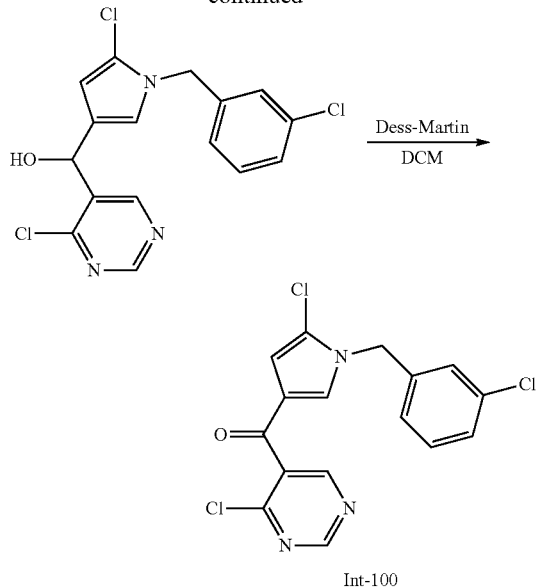

Int-100

Step 1

Methyl 5-chloro-1-(3-chlorobenzyl)-1H-pyrrole-3-carboxylate

To a RBF was added methyl 5-chloro-1H-pyrrole-3-carboxylate (0.42 g, 2.6 mmol), benzene, 1-(bromomethyl)-3-chloro-(0.69 mL, 5.3 mmol), cesium carbonate (4.3 g, 13 mmol), and THF (58 mL). The resulting reaction mixture was stirred at rt for 24 h. The mixture was filtered through celite and the filtrate was concentrated. The crude residue was purified on silica gel to provide methyl 5-chloro-1-(3-chlorobenzyl)-1H-pyrrole-3-carboxylate (0.68 g, 91%). LCMS (AA): m/z=284.1 (M+H).

Step 2: [5-Chloro-1-(3-chlorobenzyl)-1H-pyrrol-3-yl]methanol

To a RBF was added methyl 5-chloro-1-(3-chlorobenzyl)-1H-pyrrole-3-carboxylate (0.68 g, 2.4 mmol), THF (21 mL), and lithium tetrahydroborate (0.78 g, 36 mmol). The resulting reaction mixture was heated at reflux for 3 days. The reaction was then allowed to cool to rt and MeOH (5 mL) was added to quench the reaction. The mixture was then concentrated and water was added. The mixture was extracted with DCM (2×) and the combined extracts were dried over MgSO$_4$, filtered, and concentrated to give [5-chloro-1-(3-chlorobenzyl)-1H-pyrrol-3-yl]methanol (0.57 g, 93%). LCMS (AA): m/z=256.1 (M+H).

Step 3: 5-Chloro-1-(3-chlorobenzyl)-1H-pyrrole-3-carbaldehyde

To a RBF was added [5-chloro-1-(3-chlorobenzyl)-1H-pyrrol-3-yl]methanol (0.57 g, 2.2 mmol), DCM (24 mL), and Dess-Martin periodinane (1.9 g, 4.5 mmol). The resulting reaction mixture was stirred at rt for 3 h. The mixture was then filtered through celite and the filtrate was concentrated. The crude residue was purified on silica gel to give 5-chloro-1-(3-chlorobenzyl)-1H-pyrrole-3-carbaldehyde (0.28 g, 50%). LCMS (AA): m/z=254.1 (M+H).

Step 4: [5-Chloro-1-(3-chlorobenzyl)-1H-pyrrol-3-yl](4-chloropyrimidin-5-yl)methanol Into a flame dried RBF with stirbar was added 4-chloro-5-iodopyrimidine (0.29 g, 1.2 mmol) dissolved in THF (4.2 mL). The flask was purged with argon and cooled to −78° C. To this solution was added dropwise n-butyllithium (2.5 M in hexane; 1.0 mL, 2.5 mmol) at −78° C. and the mixture was stirred for 10 min. To this mixture was added 5-chloro-1-(3-chlorobenzyl)-1H-pyrrole-3-carbaldehyde (0.28 g, 1.1 mmol) dissolved in THF (0.8 mL) dropwise. The reaction was stirred at −78° C. for 2 h. The reaction was quenched with a solution of acetic acid (0.2 mL) in THF (15 mL) at −78° C. After warming to rt, water was added to the mixture and then it was extracted with EtOAc (3×). The combined organic layers were then washed with water and brine, dried over Na$_2$SO$_4$, filtered and concentrated. The crude product was purified on silica gel to [5-chloro-1-(3-chlorobenzyl)-1H-pyrrol-3-yl](4-chloropyrimidin-5-yl)methanol (0.25 g, 62%). LCMS (AA): m/z=368.0 (M+H).

Step 5: [5-Chloro-1-(3-chlorobenzyl)-1H-pyrrol-3-yl](4-chloropyrimidin-5-yl)methanone Int-100

To a RBF was added [5-chloro-1-(3-chlorobenzyl)-1H-pyrrol-3-yl](4-chloropyrimidin-5-yl)methanol (0.25 g, 0.68 mmol), DCM (4.4 mL), and Dess-Martin periodinane (0.35 g, 0.8 mmol). The resulting reaction mixture was stirred at rt for 3 h. The mixture was filtered through celite and the filtrate was concentrated. The crude residue was purified on silica gel to afford [5-chloro-1-(3-chlorobenzyl)-1H-pyrrol-3-yl](4-chloropyrimidin-5-yl)methanone (0.22 g, 88%). LCMS (AA): m/z=365.9 (M+H).

The compounds listed in the table below were prepared using an analogous method to that described above starting from the listed starting materials:

| Starting material | Starting material | Compound Name/No. | LCMS Data |
|---|---|---|---|
| Int-98 | | {5-Chloro-1-[(4-methylphenyl)sulfonyl]-1H-pyrrol-3-yl}(4-chloropyrimidin-5-yl)methanone/Int-101 | LCMS (FA): m/z = 396.1 (M + H). |
| Int-99 | | [1-(3-Bromobenzyl)-2,5-dichloro-1H-pyrrol-3-yl](4-chloropyrimidin-5-yl)methanone/Int-102 | — |
| Menear, K.A. WO 2009093032 | | (4-Chloropyrimidin-5-yl){5-methyl-1-[(4-methylphenyl)sulfonyl]-1H-pyrrol-3-yl}methanone/Int-103 | LCMS (FA): m/z = 376.3 (M + H). |
| | | (4-Chloropyrimidin-5-yl){4-methyl-1-[(4-methylphenyl)sulfonyl]-1H-pyrrol-3-yl}methanone/Int-104 | LCMS (FA): m/z = 376.3 (M + H). |

Example 96: {(1R,2R,3R,4R)-4-[(5-{[2-Chloro-1-(3-chlorobenzyl)-1H-pyrrol-3-yl]carbonyl}pyrimidin-4-yl)amino]-3-fluoro-2-hydroxycyclopentyl}methyl sulfamate I-61

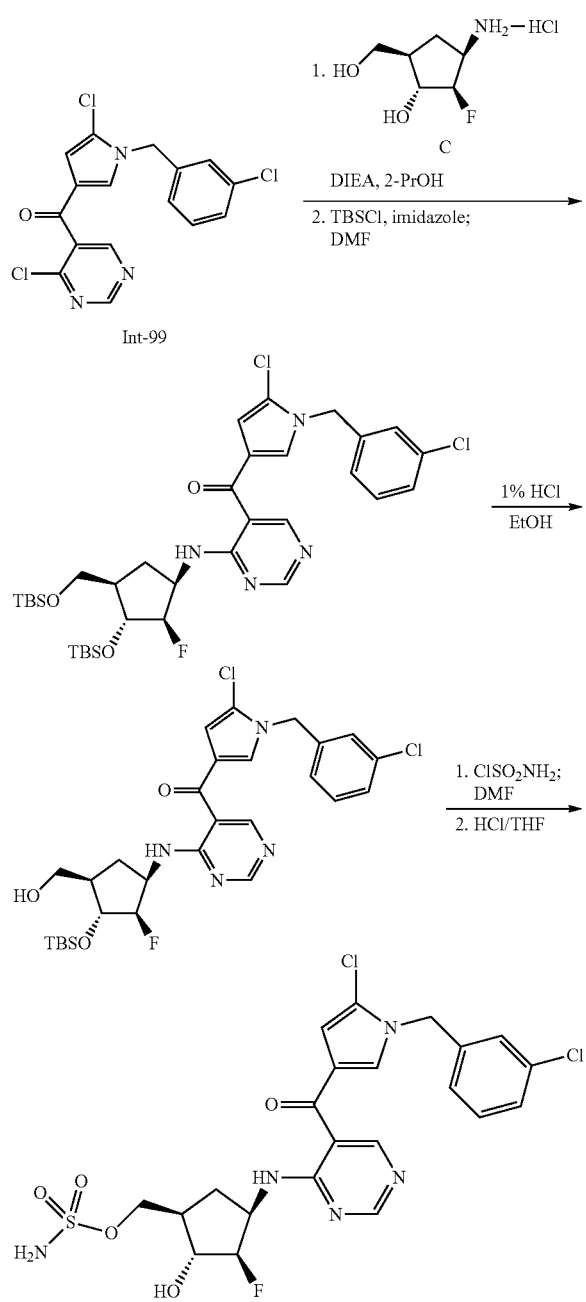

Step 1: (4-{[(1R,2R,3R,4R)-3-{[tert-Butyl(dimethyl)silyl]oxy}-4-({[tert-butyl(dimethyl)silyl]oxy}methyl)-2-fluorocyclopentyl]amino}pyrimidin-5-yl) [5-chloro-1-(3-chlorobenzyl)-1H-pyrrol-3-yl]methanone

[5-Chloro-1-(3-chlorobenzyl)-1H-pyrrol-3-yl](4-chloro-pyrimidin-5-yl)methanone (0.22 g, 0.60 mmol) and (1R,2R,3R,5R)-3-amino-2-fluoro-5-(hydroxymethyl)cyclopentanol hydrochloride (0.13 g, 0.72 mmol) were weighed into a reaction vessel. To this mixture was added 2-propanol (2.5 mL) and DIEA (0.37 mL, 2.1 mmol). The resulting mixture was allowed to stir at rt for 18 h. The reaction was then concentrated. The crude product was dissolved in DMF (25 mL). To this solution was added imidazole (0.33 g, 4.8 mmol) followed by tert-butyldimethylsilyl chloride (0.54 g, 3.6 mmol) at rt, and the mixture was stirred for 20 h. The reaction was then filtered to remove solids and the filtrate was concentrated. The residue was purified on silica gel to give (4-{[(1R,2R,3R,4R)-3-{[tert-butyl(dimethyl)silyl]oxy}-4-({[tert-butyl(dimethyl)silyl]oxy}methyl)-2-fluoro-cyclopentyl]amino}pyrimidin-5-yl)[5-chloro-1-(3-chlorobenzyl)-1H-pyrrol-3-yl]methanone (0.24 g, 56%).

Step 2: (4-{[(1R,2R,3R,4R)-3-{[tert-Butyl(dimethyl)silyl]oxy}-2-fluoro-4-(hydroxymethyl)cyclopentyl]amino}pyrimidin-5-yl)[5-chloro-1-(3-chlorobenzyl)-1H-pyrrol-3-yl]methanone To a solution of (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)[5-chloro-1-(3-chlorobenzyl)-1H-pyrrol-3-yl]methanone (0.24 g, 0.34 mmol) in EtOH (22 mL) was added 1% HCl in EtOH (11.2 mL, 1.4 mmol) at rt. The reaction vessel was sealed and allowed to stand in a freezer (−20° C.) for 40 h. The reaction was quenched by addition of a saturated aq. solution of NaHCO$_3$. To the residue was added water which was extracted with EtOAc (4×). The combined organic layers were dried over MgSO$_4$, filtered, and concentrated. The residue was dried on high vacuum to give (4-{[(1R,2R,3R,4R)-3-{[tert-butyl(dimethyl)silyl]oxy}-2-fluoro-4-(hydroxymethyl)cyclopentyl]amino}pyrimidin-5-yl)[5-chloro-1-(3-chlorobenzyl)-1H-pyrrol-3-yl]methanone (0.19 g, 94%). LCMS (FA): m/z=593.0 (M+H).

Step 3: {(1R,2R,3R,4R)-4-[(5-{[2-Chloro-1-(3-chlorobenzyl)-1H-pyrrol-3-yl]carbonyl}pyrimidin-4-yl)amino]-3-fluoro-2-hydroxycyclopentyl}methyl sulfamate I-61

To a solution of (4-{[(1R,2R,3R,4R)-3-{[tert-butyl(dimethyl)silyl]oxy}-2-fluoro-4-(hydroxymethyl)cyclopentyl]amino}pyrimidin-5-yl)[5-chloro-1-(3-chlorobenzyl)-1H-pyrrol-3-yl]methanone (0.19 g, 0.32 mmol) and TEA (0.13 mL, 0.96 mmol) in DMF (4 mL) was added chlorosulfonamide (74 mg, 0.64 mmol) at rt, and the mixture was stirred for 1 h. The reaction was quenched by addition of a saturated solution of NaHCO$_3$ and diluted with water. The mixture was extracted with EtOAc (4×). The combined organic layers were dried over MgSO$_4$, filtered, and concentrated. The crude sulfamate intermediate was dissolved in THF (1.4 mL). Water (1.0 mL) and concentrated HCl (0.42 mL, 5.1 mmol) were added to the solution. The reaction was stirred for 4 h at rt. The reaction was quenched by the addition of a saturated solution of NaHCO$_3$ and extracted with DCM (3×). The combined organic layers were dried over MgSO$_4$, filtered, and concentrated. The residue was purified by prep HPLC to afford {(1R,2R,3R,4R)-4-[(5-{[2-chloro-1-(3-chlorobenzyl)-1H-pyrrol-3-yl]carbonyl}pyrimidin-4-yl)amino]-3-fluoro-2-hydroxycyclopentyl}methyl sulfamate (61 mg, 34%). $^1$H NMR (DMSO) δ 8.81 (s, 1H), 8.73 (d, J=7.6 Hz, 1H), 8.69 (s, 1H), 7.92 (d, J=2.1 Hz, 1H), 7.47-7.35 (m, 2H), 7.32 (d, J=1.8 Hz, 1H), 7.21-7.06 (m, 1H), 6.67 (d, J=2.1 Hz, 1H), 5.30 (s, 2H), 4.96-4.62 (m, 2H), 4.17-4.08 (m, 1H), 4.07-3.99 (m, 1H), 3.98-3.87 (m, 1H), 2.40-2.26 (m, 1H), 2.25-2.10 (m, 1H), 1.55-1.39 (m, 1H). LCMS (FA): m/z=558.2 (M+H).

The compounds listed in the table below were prepared using a similar method to that described above starting from the listed starting materials:

| Starting material | Compound No. | LCMS Data |
|---|---|---|
| Int-102 | I-105 | LCMS (FA): m/z = 638.0 (M + H). |
| Int-93 | I-147 | LCMS (FA): m/z = 524.4 (M + H). |

Example 97: {(1R,2R,3R,4R)-4-[(5-{[1-(3-Bromobenzyl)-5-chloro-1H-pyrrol-3-yl]carbonyl}pyrimidin-4-yl)amino]-3-fluoro-2-hydroxycyclopentyl)methyl sulfamate I-244

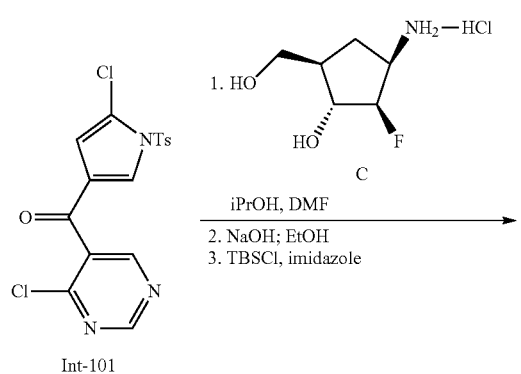

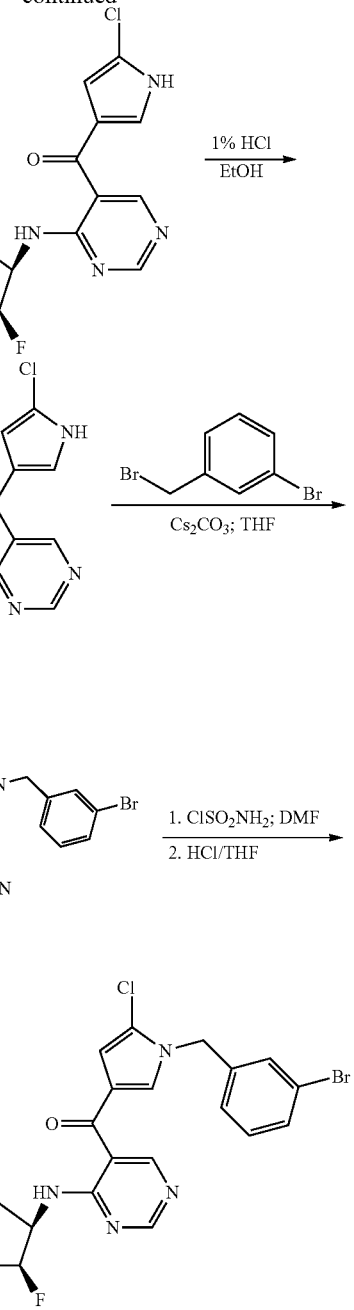

Step 1: (4-{[(1R,2R,3R,4R)-3-{[tert-Butyl(diethyl)silyl]oxy}-4-({[tert-butyl(dimethyl)silyl]oxy}methyl)-2-fluorocyclopentyl]amino}pyrimidin-5-yl) (5-chloro-1H-pyrrol-3-yl)methanone To a RBF was added (5-chloro-1-[(4-methylphenyl)sulfonyl]-1H-pyrrol-3-yl}(4-chloropyrimidin-5-yl)methanone (2.25 g, 5.7 mmol), (1R,2R,3R,5R)-3-amino-2-fluoro-5-(hydroxymethyl)cyclopentanol hydrochloride (1.26 g, 6.8 mmol), isopropyl alcohol (40 mL), and DIEA (3.5 mL). The resulting reaction mixture was stirred at rt for 15 h. The mixture was then concentrated. The crude product was dissolved in EtOH (30 ml) and sodium hydroxide (0.86 g, 21 mmol) was added. The resulting reaction mixture was stirred at rt for 70 h. The mixture was then concentrated and DCM (60 mL), imidazole (2.9 g, 42 mmol), and tert-butyldimethylsilyl chloride (5.6 g, 37 mmol) were added. The subsequent mixture was then stirred 16 h at rt. The mixture was filtered and the filtrate was concentrated. The crude residue was purified on silica gel to give (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)(5-chloro-1H-pyrrol-3-yl)methanone (2.0 g, 64%). LCMS (AA): m/z=583.2 (M+H).

Step 2: (4-{[(1R,2R,3R,4R)-3-{[tert-Butyl(dimethyl)silyl]oxy}-2-fluoro-4-(hydroxymethyl)cyclopentyl]amino}pyrimidin-5-yl)(5-chloro-1H-pyrrol-3-yl)methanone To a solution of (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyrimidin-5-yl)(5-chloro-1H-pyrrol-3-yl)methanone (1.4 g, 2.4 mmol) in EtOH (40 mL) was added 1% HCl in EtOH (350 mL, 42 mmol) at rt. The reaction vessel was sealed and allowed to stand in a freezer (−20° C.) for 40 h. The reaction was quenched by addition of a saturated aq. solution of NaHCO₃ and then the mixture concentrated. To the residue was added water which was then extracted with DCM 3×). The combined organic layers were dried over MgSO₄, filtered, and concentrated. The residue was purified on silica gel to give (4-{[(1R,2R,3R,4R)-3-{[tert-butyl(dimethyl)silyl]oxy}-2-fluoro-4-(hydroxymethyl)cyclopentyl]amino}pyrimidin-5-yl)(5-chloro-1H-pyrrol-3-yl)methanone (0.53 g, 47%). LCMS (AA): m/z=469.1 (M+H).

Step 3: [1-(3-Bromobenzyl)-5-chloro-1H-pyrrol-3-yl](4-{[(1R,2R,3R,4R)-3-{[tert-butyl(dimethyl)silyl]oxy}-2-fluoro-4-(hydroxymethyl)cyclopentyl]amino}pyrimidin-5-yl)methanone To a RBF was added (4-{[(1R,2R,3R,4R)-3-{[tert-butyl(dimethyl)silyl]oxy}-2-fluoro-4-(hydroxymethyl)cyclopentyl]amino}pyrimidin-5-yl)(5-chloro-1H-pyrrol-3-yl)methanone (0.26 g, 0.55 mmol), 3-bromobenzyl bromide (0.25 g, 1.0 mmol), cesium carbonate (0.9 g, 2.8 mmol), and THF (12 mL). The resulting reaction mixture was stirred at rt for 4 h. The mixture was filtered through celite and the filtrate was concentrated. The crude residue was purified on silica gel to afford [1-(3-bromobenzyl)-5-chloro-1H-pyrrol-3-yl](4-{[(1R,2R,3R,4R)-3-{[tert-butyl(dimethyl)silyl]oxy}-2-fluoro-4-(hydroxymethyl)cyclopentyl]amino}pyrimidin-5-yl)methanone (0.34 g, 96%). LCMS (AA): m/z=639.2 (M+H).

Step 4: {(1R,2R,3R,4R)-4-[(5-{[1-(3-Bromobenzyl)-5-chloro-1H-pyrrol-3-yl]carbonyl}pyrimidin-4-yl)amino]-3-fluoro-2-hydroxycyclopentyl}methyl sulfamate I-244

To a solution of [1-(3-bromobenzyl)-5-chloro-1H-pyrrol-3-yl](4-{[(1R,2R,3R,4R)-3-{[tert-butyl(dimethyl)silyl]oxy}-2-fluoro-4-(hydroxymethyl)cyclopentyl]amino}pyrimidin-5-yl)methanone (0.26 mg, 0.55 mmol) and TEA (0.2 mL, 1.6 mmol) in DMF (4 mL) was added chlorosulfonamide (0.12 mg, 1.1 mmol) at rt, and the mixture was stirred for 1 h. The reaction mixture was then concentrated. The crude sulfamate intermediate was dissolved in THF (2.3 mL). Water (1.7 mL) and conc. HCl (0.7 mL, 8.4 mmol) were added to the solution. The reaction was stirred for 4 h at it. It was then quenched by the addition of a saturated solution of NaHCO₃ and extracted with DCM (3×). The combined organic layers were dried over MgSO₄, filtered, and concentrated. The residue was purified on silica gel to afford {(1R,2R,3R,4R)-4-[(5-{[1-(3-bromobenzyl)-5-chloro-1H-pyrrol-3-yl]carbonyl}pyrimidin-4-yl)amino]-3-fluoro-2-hydroxycyclopentyl}methyl sulfamate (0.28 g, 87%). ¹H NMR (DMSO) δ 8.81 (s, 1H), 8.72 (t, J=7.3 Hz, 1H), 8.69 (s, 1H), 7.96 (s, 1H), 7.92 (d, J=2.1 Hz, 1H), 7.60-7.43 (m, 4H), 7.34 (t, J=7.8 Hz, 1H), 7.21 (dd, J=17.6, 5.8 Hz, 1H), 6.67 (d, J=2.1 Hz, 1H), 5.55 (d, J=5.1 Hz, 1H), 5.29 (s, 2H), 4.95-4.61 (m, 2H), 4.17-4.08 (m, 1H), 4.07-4.00 (m, 1H), 3.99-3.87 (m, 1H), 2.40-2.27 (m, 1H), 2.26-2.08 (m, 1H), 1.56-1.38 (m, 1H). LCMS (AA): m/z=602.2 (M+H).

The compounds listed in the table below were prepared using a similar method to that described above starting from the listed starting materials used in step 3. The following alternative conditions could be employed in the described reaction steps. Step 3: K₂CO₃ instead of Cs₂CO₃; DMF instead of THF. Step 4: aq. TFA instead of aq. HCl:

| Starting material | Compound No. | LCMS Data |
|---|---|---|
| Br—⌬—Br, F | I-320 | LCMS (FA): m/z = 620.0 (M + H). |
| Br—isoxazole—CF₃ | I-148 | LCMS (FA): m/z = 583.0 (M + H). |
| Br—furan—CF₃ | I-36 | LCMS (FA): m/z = 582.0 (M + H). |
| Br—⌬—CF₃ | I-184 | LCMS (FA): m/z = 592.1 (M + H). |
| Br—⌬—I | I-310 | LCMS (FA): m/z = 649.9 (M + H). |
| Br—furan—Cl | I-254 | LCMS (FA): m/z = 549.9 (M + H). |
| Int-23 | | |

Example 98: 5-Ethyl-1H-pyrrole-3-carbaldehyde Int-115

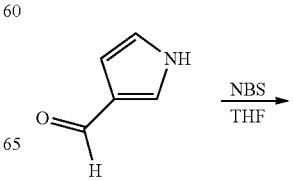

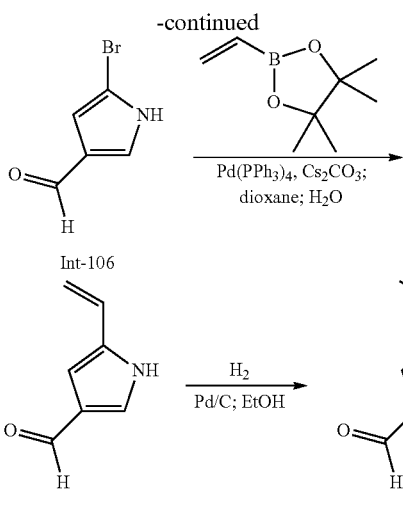

Step 1: 5-Bromo-1H-pyrrole-3-carbaldehyde Int-106

A solution of 1H-pyrrole-3-carbaldehyde (0.63 g, 6.6 mmol) in THF (15 mL) was cooled to −78° C. N-Bromosuccinimide (1.2 g, 6.7 mmol) and pyridine (~1 drop) were added, and the mixture was stirred at the same temperature for 5 min. The mixture was then warmed to 0° C. and stirred for 2 h. The mixture was subsequently cooled to −78° C. and additional N-bromosuccinimide (0.9 g, 5.0 mmol) was added. This mixture was stirred for 10 min at −78° C. then warmed to 0° C. and stirred for 2 h. Water was added to the reaction mixture, and the mixture was extracted with EtOAc. The extract was washed with saturated aqueous NaHCO$_3$ and water, dried over MgSO$_4$, filtered and concentrated under reduced pressure. The residue was then purified on silica gel to give 5-bromo-1H-pyrrole-3-carbaldehyde (0.51 g, 44%). $^1$H NMR (MeOD) δ 9.59 (s, 1H), 7.57 (d, J=1.8 Hz, 1H), 6.56 (d, J=1.7 Hz, 1H).

Step 2: 5 Vinyl 1H pyrrole-3-carbaldehyde

To a reaction vessel was added 5-bromo-1H-pyrrole-3-carbaldehyde (0.47 g, 2.7 mmol), vinylboronic acid pinacol ester (1.0 mL, 5.4 mmol), tetrakis(triphenylphosphine)palladium(0) (0.62 g, 0.54 mmol), cesium carbonate (3.5 g, 10.8 mmol), 1,4-dioxane (25 mL), and water (2.1 mL). The mixture was sealed and heated at 145° C. for 60 min in a microwave reactor. The reaction mixture was filtered and the filtrate concentrated. The crude residue was purified on silica gel to provide 5-vinyl-1H-pyrrole-3-carbaldehyde (0.32 g, 98%). $^1$H NMR (CDCl$_3$) δ 9.80 (d, J=8.1 Hz, 1H), 7.41 (dd, J=3.1, 1.6 Hz, 1H), 6.66 (s, 1H), 6.57 (dd, J=17.8, 11.2 Hz, 1H), 5.44 (d, J=17.8 Hz, 1H), 5.19 (d, J=11.3 Hz, 1H).

Step 3: 5-Ethyl-1H-pyrrole-3-carbaldehyde Int-115

To a RBF was added 5-vinyl-1H-pyrrole-3-carbaldehyde (0.55 g, 4.5 mmol), EtOH (15.0 mL, 257 mmol), and palladium on carbon (10% on carbon; 0.12 g). The resulting suspension was stirred at rt for 4 h under an atmosphere of hydrogen. The mixture was filtered through celite and the filtrate was concentrated to give 5-ethyl-1H-pyrrole-3-carbaldehyde (0.50 g, 89%).

Example 99: (4-Chloropyrimidin-5-yl){5-ethyl-1-[(4-methylphenyl)sulfonyl]-1H-pyrrol-3-yl}methanone Int-107

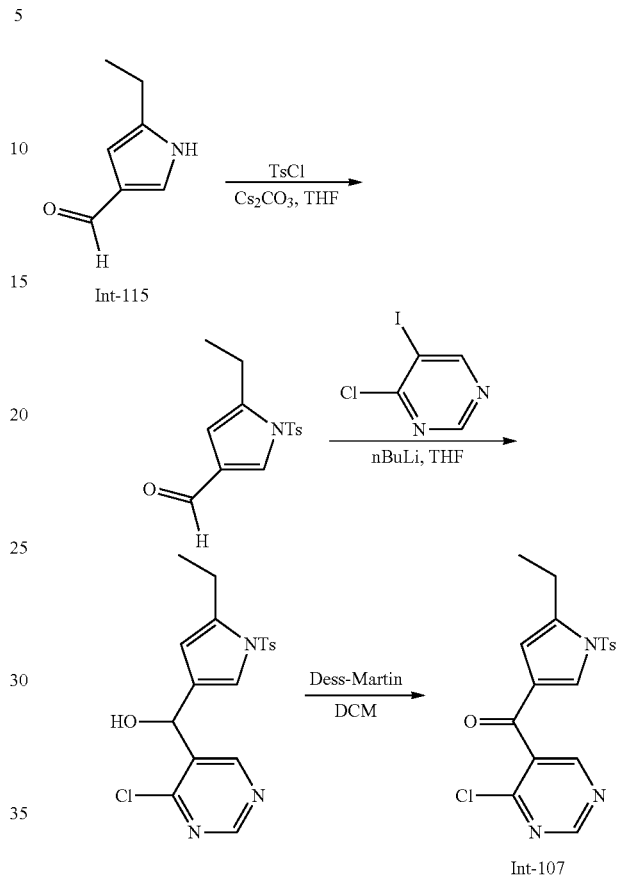

Step 1: 5-Ethyl-1-[(4-methylphenyl)sulfonyl]-1H-pyrrole-3-carbaldehyde

To a RBF was added p-toluenesulfonyl chloride (0.77 g, 4.1 mmol), 5-ethyl-1H-pyrrole-3-carbaldehyde (0.50 g, 4.1 mmol), cesium carbonate (4.6 g, 14 mmol), and THF (8.8 mL). The resulting reaction mixture was stirred at rt for 16 h. The mixture was then filtered and the filtrate diluted with EtOAc, washed with water and concentrated. The crude residue was purified on silica gel to provide 5-ethyl-1-[(4-methylphenyl)sulfonyl]-1H-pyrrole-3-carbaldehyde (0.10 g, 9%). $^1$H NMR (CDCl$_3$) δ 9.83-9.76 (m, 1H), 7.96 (d, J=1.9 Hz, 1H), 7.75-7.70 (m, 2H), 7.35 (dd, J=8.6, 0.6 Hz, 2H), 6.42 (d, J=1.5 Hz, 1H), 2.65 (qd, J=7.4, 1.2 Hz, 2H), 2.43 (s, 3H), 1.16 (t, J=7.4 Hz, 3H).

Step 2: (4-Chloropyrimidin-5-yl){5-ethyl-1-[(4-methylphenyl)sulfonyl]-1H-pyrrol-3-yl}methanol Into a flame dried RBF with stirbar was added 4-chloro-5-iodopyrimidine (0.095 g, 0.4 mmol) dissolved in THF (10 mL). The flask was purged with argon and cooled to −78° C. To this solution was added dropwise n-butyllithium (2.5 M in hexane; 0.33 mL, 0.83 mmol) at −78° C. and the mixture was stirred for 5 min. To this mixture was added 5-ethyl-1-[(4-methylphenyl)sulfonyl]-1H-pyrrole-3-carbaldehyde (0.10 g, 0.36 mmol) dissolved in THF (1.4 mL) dropwise.

The reaction was stirred at −78° C. for 2 h. The reaction was quenched with a solution of acetic acid (0.06 mL) in THF (15 mL) then allowed to warm to rt. The mixture was diluted with water and then extracted with EtOAc (3×). The combined organic layers were then washed with water and brine, dried over Na$_2$SO$_4$, filtered and concentrated. The crude product was purified on silica gel to give (4-chloropyrimidin-5-yl){5-ethyl-1-[(4-methylphenyl)sulfonyl]-1H-pyrrol-3-yl}methanol (0.090 g, 64%). LCMS (AA): m/z=391.9 (M+H).

Step 3: (4-Chloropyrimidin-5-yl){5-ethyl-1-[(4-methylphenyl)sulfonyl]-1H-pyrrol-3-yl}methanone Int-107

To a RBF was added (4-chloropyrimidin-5-yl) {5-ethyl-1-[(4-methylphenyl)sulfonyl]-1H-pyrrol-3-yl}methanol (0.090 g, 0.23 mmol), DCM (5.9 mL), and Dess-Martin periodinane (0.10 g, 0.24 mmol). The resulting reaction mixture was stirred at rt for 2 h. The mixture was filtered through celite and the filtrate was concentrated. The crude residue was purified on silica gel to provide (4-chloropyrimidin-5-yl){5-ethyl-1-[(4-methylphenyl)sulfonyl]-1H-pyrrol-3-yl}methanone (0.076 g, 85%). LCMS (AA): m/z=389.9 (M+H).

The compound listed in the table below was prepared using an analogous method to that described above starting from the listed starting material in step 1:

| Starting material | Compound No. or Name | LCMS Data |
|---|---|---|
| Int-106 | {5-Bromo-1-[(4-methylphenyl)sulfonyl]-1H-pyrrol-3-yl}(4-chloropyrimidin-5-yl)methanone/Int-108 | LCMS (FA): m/z = 442.2 (M + H). |

Example 100: {(1R,2R,3R,4R)-4-[(5-{[1-(3-Bromobenzyl)-5-ethyl-1H-pyrrol-3-yl]carbonyl}pyrimidin-4-yl)amino]-3-fluoro-2-hydroxycyclopentyl}methyl sulfamate I-187

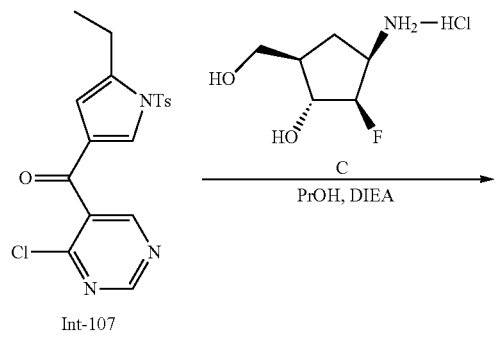

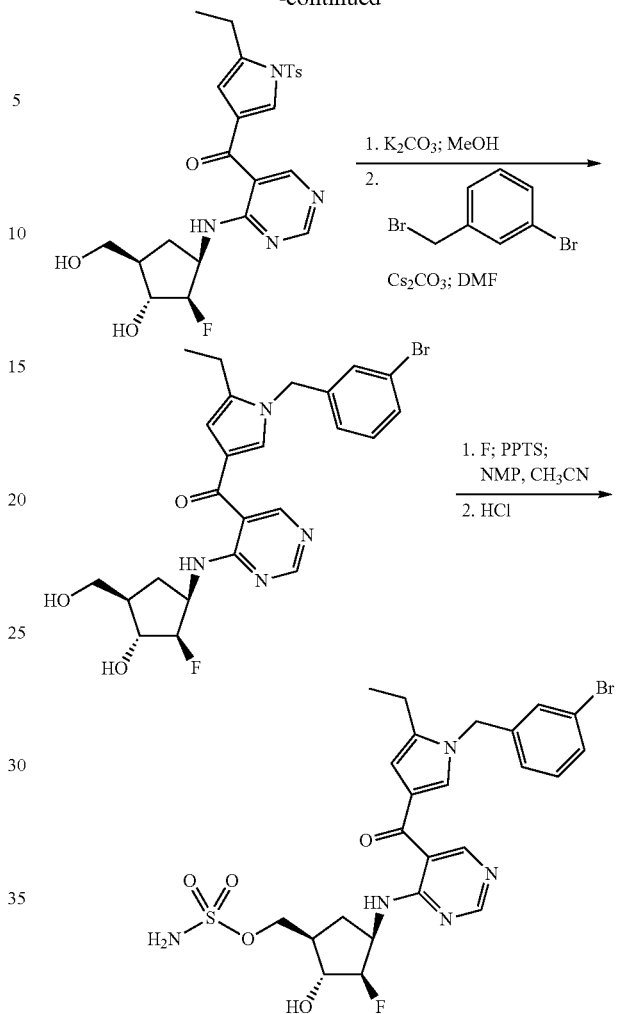

Step 1: {5-Ethyl-1-[(4-methylphenyl)sulfonyl]-1H-pyrrol-3-yl}(4-{[(1R,2R,3R,4R)-2-fluoro-3-hydroxy-4-(hydroxymethyl)cyclopentyl]amino}pyrimidin-5-yl)methanone (4-Chloropyrimidin-5-yl){5-ethyl-1-[(4-methylphenyl)sulfonyl]-1H-pyrrol-3-yl}methanone (0.076 g, 0.19 mmol) and (1R,2R,3R,5R)-3-amino-2-fluoro-5-(hydroxymethyl)cyclopentanol hydrochloride (0.0398 g, 0.214 mmol) were weighed into a 20 mL reaction vessel. To this mixture was added 2-propanol (2 mL) and DIEA (0.13 mL, 0.72 mmol). The resulting mixture was sealed and the vessel allowed to stir at rt for 18 h. The reaction was then concentrated and the crude product was purified on silica gel to afford {5-ethyl-1-[(4-methylphenyl)sulfonyl]-1H-pyrrol-3-yl}(4-{[(1R,2R,3R,4R)-2-fluoro-3-hydroxy-4-(hydroxymethyl)cyclopentyl]amino}pyrimidin-5-yl)methanone (0.095 g, 97%). LCMS (AA): m/z=503.3 (M+H).

Step 2: 1-(3-Bromobenzyl)-5-ethyl-1H-pyrrol-3-yl](4-{[(1R,2R,3R,4R)-2-fluoro-3-hydroxy-4-(hydroxymethyl)cyclopentyl]amino}pyrimidin-5-yl)methanone Into a RBF was added {5-ethyl-1-[(4-methylphenyl)sulfonyl]-1H-pyrrol-3-yl}(4-{[(1R,2R,3R,4R)-2-fluoro-3-hydroxy-4-(hydroxymethyl)cyclopentyl]amino}pyrimidin-5-yl)methanone (0.095 g, 0.19 mmol) dissolved in methanol (3 mL). Potassium carbonate (0.13 g, 0.95 mmol) was added and the mixture was stirred at rt for 3 h. The mixture was then concentrated and the resulting crude detosylated pyrrole [LCMS (AA): m/z=349.0 (M+H).] was dissolved in THF (25 mL). 3-bromobenzyl bromide (0.057 g, 0.23 mmol) was added and the mixture was stirred at rt for 18 h. The reaction mixture was then concentrated and water and EtOAc were added. The organic layer was separated, dried over $MgSO_4$, filtered and concentrated. The crude product was purified on silica gel to afford 1-(3-bromobenzyl)-5-ethyl-1H-pyrrol-3-yl](4-{[(1R,2R,3R,4R)-2-fluoro-3-hydroxy-4-(hydroxymethyl)cyclopentyl]amino}pyrimidin-5-yl)methanone (0.038 g, 39%). LCMS (AA): m/z=517.2 (M+H).

Step 3: {(1R,2R,3R,4R)-4-[(5-{[1-(3-Bromobenzyl)-5-ethyl-1H-pyrrol-3-yl]carbonyl}pyrimidin-4-yl)amino]-3-fluoro-2-hydroxycyclopentyl}methyl sulfamate I-187

1-(3-Bromobenzyl)-5-ethyl-1H-pyrrol-3-yl](4-{[(1R,2R,3R,4R)-2-fluoro-3-hydroxy-4-(hydroxymethyl)cyclopentyl]amino}pyrimidin-5-yl)methanone (0.038 g, 0.073 mmol) was dissolved in NMP (0.7 mL) and acetonitrile (0.3 mL). To this solution was added in one portion PPTS (18 mg, 0.07 mmol) followed by the addition of (4-aza-1-azoniabicyclo[2.2.2]oct-1-ylsulfonyl)(tert-butoxycarbonyl)azanide-1,4-diazabicyclo[2.2.2]octane (1:1) hydrochloride (F) (0.065 g, 0.15 mmol). Upon reaction completion, water (3 mL) and conc. HCl (2 mL, 24 mmol) were added at 0° C. The mixture was then allowed to stir at rt for 18 h. The reaction was quenched by the addition of a saturated solution of $NaHCO_3$ in water. After diluting the mixture with water it was extracted with EtOAc (4×). The combined organic layers were dried over $MgSO_4$, filtered, and concentrated. The crude product was purified by prep HPLC to give {(1R,2R,3R,4R)-4-[(5-{[1-(3-bromobenzyl)-5-ethyl-1H-pyrrol-3-yl]carbonyl}pyrimidin-4-yl)amino]-3-fluoro-2-hydroxycyclopentyl}methyl sulfamate (9 mg, 20%). $^1$H NMR (MeOD) δ 8.78 (s, 1H), 8.60 (s, 1H), 7.51-7.43 (m, 2H), 7.33-7.24 (m, 2H), 7.12-7.03 (m, 1H), 6.45 (d, J=10.6 Hz, 1H), 5.23 (s, 2H), 4.89 (m, 2H), 4.30-4.05 (m, 3H), 2.49 (dd, J=15.4, 7.0 Hz, 2H), 2.38-2.24 (m, 1H), 1.71-1.33 (m, 2H), 1.22 (t, J=7.5 Hz, 3H). LCMS (AA): m/z=596.4 (M+H).

The compounds listed in the table below were prepared using an analogous method to that described above starting from the listed starting materials:

| Starting material | Compound No. or Name | LCMS Data |
|---|---|---|
| 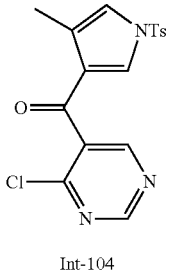 Int-104 | I-149 | LCMS (FA): m/z = 582.4 (M + H). |

-continued

| Starting material | Compound No. or Name | LCMS Data |
|---|---|---|
| Int-108 | I-272 | LCMS (FA): m/z = 648.1 (M + H). |
| Int-103 | I-71 | LCMS (FA): m/z = 582.3 (M + H). |

Example 101: {(1R,2R,3R,4R)-4-[(5-{[1-(3-Bromobenzyl)-5-fluoro-1H-pyrrol-3-yl]carbonyl}pyrimidin-4-yl)amino]-3-fluoro-2-hydroxycyclopentyl}methyl sulfamate I-44

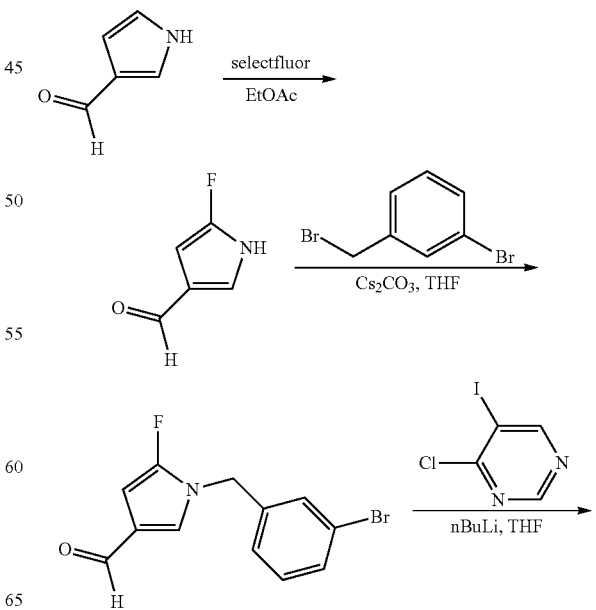

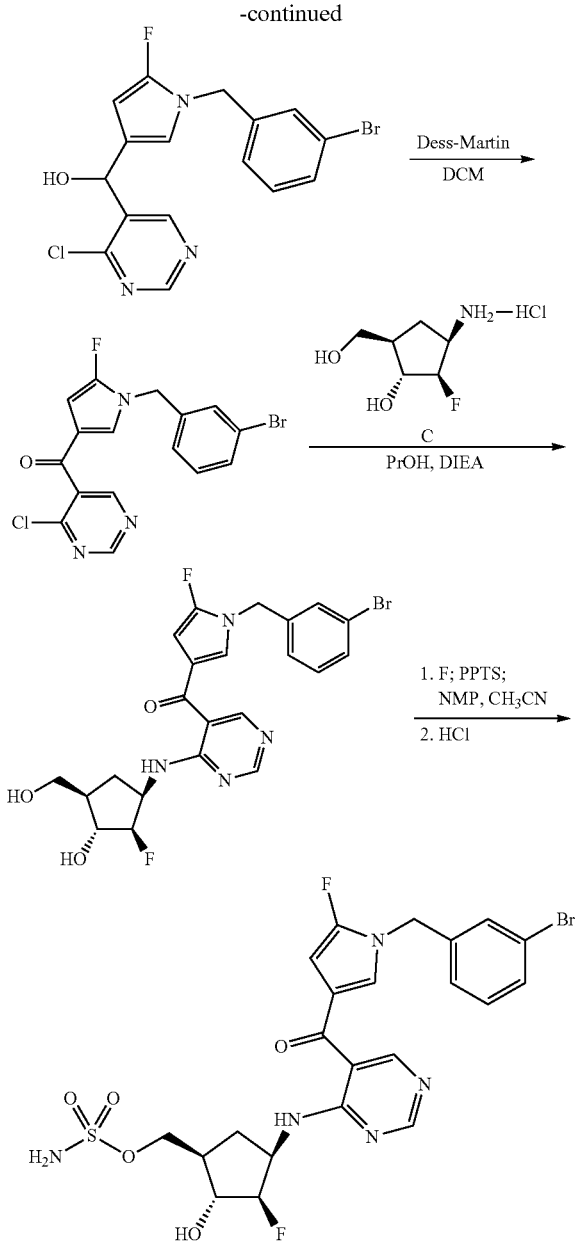

Step 1: 5-Fluoro-1H-pyrrole-3-carbaldehyde

To a RBF was added 1H-pyrrole-3-carbaldehyde (0.96 g, 10 mmol), 1-chloromethyl-4-fluoro-1,4-diazoniabicyclo[2.2.2]octane bis(tetrafluoroborate) (12.5 g, 35 mmol), and EtOAc (80 mL). The resulting reaction mixture was stirred at 65° C. for 18 h. Additional 1-chloromethyl-4-fluoro-1,4-diazoniabicyclo[2.2.2]octane bis(tetrafluoroborate) (9.6 g, 27 mmol) was added and the mixture was stirred at 65° C. for an additional 24 h. The mixture was then filtered through celite and the filtrate was washed with water. The organic layer was separated and concentrated. The crude product was then purified on silica gel to give 5-fluoro-1H-pyrrole-3-carbaldehyde (0.19 g, 17%). $^1$H NMR (DMSO) δ 12.37 (s, 1H), 9.61-9.54 (m, 1H), 7.34 (dt, J=3.0, 2.1 Hz, 1H), 5.86 (dt, J=4.2, 2.2 Hz, 1H).

Step 2: 1-(3-Bromobenzyl)-5-fluoro-1H-pyrrole-3-carbaldehyde

To a RBF was added 5-fluoro-1H-pyrrole-3-carbaldehyde (0.19 g, 1.7 mmol), 3-bromobenzyl bromide (0.85 g, 3.4 mmol), cesium carbonate (1.7 g, 5.1 mmol), and THF (26 mL). The resulting reaction mixture was stirred at rt for 4 h. The mixture was then filtered through celite and the filtrate concentrated. The crude product was then purified on silica gel to afford 1-(3-bromobenzyl)-5-fluoro-1H-pyrrole-3-carbaldehyde (0.38 g, 79%). LCMS (AA): m/z=282.2 (M+H).

Step 3: [1-(3-Bromobenzyl)-5-fluoro-1H-pyrrol-3-yl](4-chloropyrimidin-5-yl)methanol Into a flame dried RBF with stirbar was added 4-chloro-5-iodopyrimidine (0.19 g, 0.78 mmol) dissolved in THF (20 mL). The flask was purged with argon and cooled to −78° C. To this solution was added dropwise n-butyllithium (2.5 M in hexane; 0.65 mL, 1.6 mmol) at −78° C. and the mixture was stirred for 5 min. To this mixture was added 1-(3-bromobenzyl)-5-fluoro-1H-pyrrole-3-carbaldehyde (0.20 g, 0.71 mmol) dissolved in THF (2.7 mL) dropwise. The reaction was stirred at −78° C. for 5 min followed by quenching with a solution of acetic acid (0.12 mL) in THF (15 mL). It was then allowed to warm to rt and the mixture was diluted with water and then extracted with EtOAc (3×). The combined organic layers were then washed with water and brine, dried over $Na_2SO_4$, filtered and concentrated. The crude product was purified on silica gel to make [1-(3-bromobenzyl)-5-fluoro-1H-pyrrol-3-yl](4-chloropyrimidin-5-yl)methanol (0.21 g, 75%). LCMS (AA): m/z=398.2 (M+H).

Step 4: [1-(3-Bromobenzyl)-5-fluoro-1H-pyrrol-3-yl](4-chloropyrimidin-5-yl)methanone To a RBF was added [1-(3-bromobenzyl)-5-fluoro-1H-pyrrol-3-yl](4-chloropyrimidin-5-yl)methanol (0.21 g, 0.53 mmol), DCM (3.5 mL) and Dess-Martin periodinane (0.24 g, 0.55 mmol). The resulting reaction mixture was stirred at rt for 3 h then filtered through celite and concentrated. The residue was purified on silica gel to afford [1-(3-bromobenzyl)-5-fluoro-1H-pyrrol-3-yl](4-chloropyrimidin-5-yl)methanone. (0.18 g, 86%). LCMS (AA): m/z=396.2 (M+H).

Step 5: [1-(2-Bromobenzyl)-5-fluoro-1H-pyrrol-3-yl](4-{[(1R,2R,3R,4R)-2-fluoro-3-hydroxy-4-(hydroxymethyl)cyclopentyl]amino}pyrimidin-5-yl)methanone

[1-(3-Bromobenzyl)-5-fluoro-1H-pyrrol-3-yl](4-chloropyrimidin-5-yl)methanone (0.18 g, 0.46 mmol) and (1R,2R,3R,5R)-3-amino-2-fluoro-5-(hydroxymethyl)cyclopentanol hydrochloride (0.0931 g, 0.502 mmol) were weighed into a 20 mL reaction vessel. To this mixture was added 2-propanol (3.2 mL) and DIEA (0.28 mL, 1.6 mmol). The resulting mixture was stirred at rt for 18 h. The reaction was then concentrated and the crude product was purified on silica gel to afford [1-(2-bromobenzyl)-5-fluoro-1H-pyrrol-3-yl](4-{[(1R,2R,3R,4R)-2-fluoro-3-hydroxy-4-(hydroxymethyl)cyclopentyl]amino}pyrimidin-5-yl)methanone (0.17 g, 73%). LCMS (AA): m/z=509.2 (M+H).

Step 6: {(1R,2R,3R,4R)-4-[(5-{[1-(3-Bromobenzyl)-5-fluoro-1H-pyrrol-3-yl]carbonyl}pyrimidin-4-yl)amino]-3-fluoro-2-hydroxycyclopentyl)}methyl sulfamate I-44

[1-(2-Bromobenzyl)-5-fluoro-1H-pyrrol-3-yl](4-{[(1R,2R,3R,4R)-2-fluoro-3-hydroxy-4-(hydroxymethyl)cyclopentyl]amino}pyrimidin-5-yl)methanone (0.17 g, 0.34 mmol) was dissolved in NMP (3 mL) and acetonitrile (1.5 mL). To this solution was added in one portion PPTS (84 mg, 0.34 mmol) followed by the addition of (4-aza-1-azoniabicyclo[2.2.2]oct-1-ylsulfonyl)(tert-butoxycarbonyl)azanide-1,4-diazabicyclo[2.2.2]octane (1:1) hydrochloride (F) (0.37 g, 0.84 mmol). After stirring 2 h at rt water (3 mL) and conc. HCl (2 mL, 24 mmol) were added and the reaction was stirred for 18 h at rt. The reaction was quenched by the addition of a saturated solution of NaHCO$_3$ in water. After diluting the mixture with water it was extracted with EtOAc (4×). The combined organic layers were dried over MgSO$_4$, filtered, and concentrated. The crude product was purified by prep HPLC to give {(1R,2R,3R,4R)-4-[(5-{[1-(3-bromobenzyl)-5-fluoro-1H-pyrrol-3-yl]carbonyl}pyrimidin-4-yl)amino]-3-fluoro-2-hydroxycyclopentyl}methyl sulfamate (40 mg, 20%). $^1$H NMR (DMSO) δ 8.80 (s, 1H), 8.68 (s, 1H), 8.64 (d, J=7.6 Hz, 1H), 7.59-7.47 (m, 3H), 7.39-7.31 (m, 1H), 7.26 (d, J=7.7 Hz, 1H), 6.16-6.07 (m, 1H), 5.21 (s, 2H), 4.91-4.63 (m, 2H), 4.17-4.07 (m, 1H), 4.06-3.99 (m, 1H), 3.98-3.85 (m, 1H), 2.38-2.26 (m, 1H), 2.25-2.10 (m, 1H), 1.56-1.33 (m, 1H). LCMS (AA): m/z=586.2 (M+H).

Example 102: {(1R,2R,3R,4R)-4-[(5-{[1-Benzyl-5-(trifluoromethyl)-1H-pyrrol-3-yl]carbonyl}pyrimidin-4-yl)amino]-3-fluoro-2-hydroxycyclopentyl}methyl sulfamate I-94

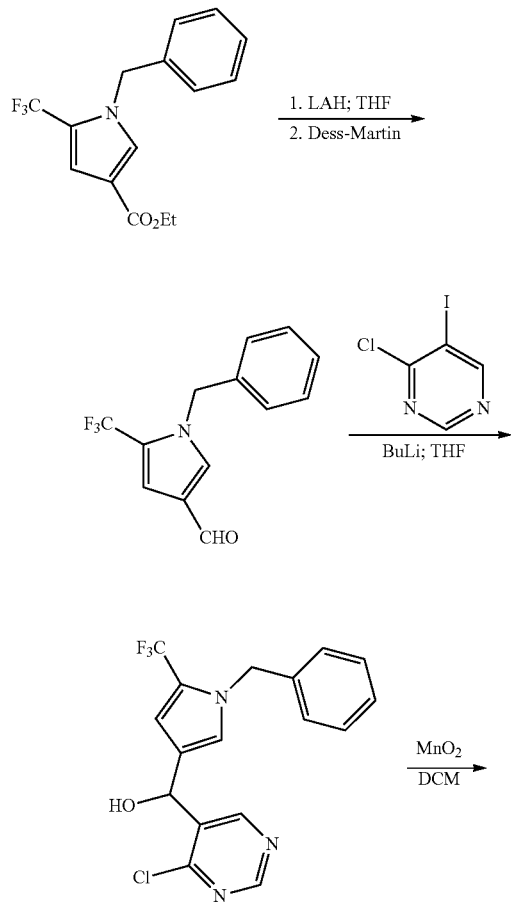

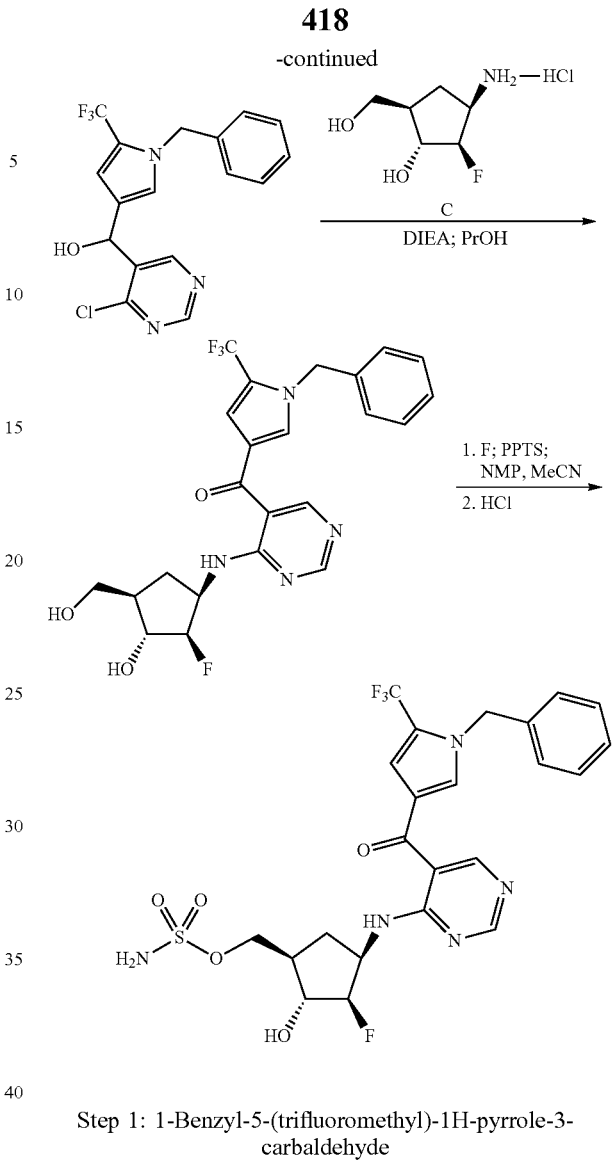

Step 1: 1-Benzyl-5-(trifluoromethyl)-1H-pyrrole-3-carbaldehyde

Lithium aluminum hydride (1.0 M in THF; 3.2 mL, 3.2 mmol) was added to an ice-bath cooled solution of ethyl 1-benzyl-5-(trifluoromethyl)-1H-pyrrole-3-carboxylate (for synthesis see: Padwa, et al. *J. Org. Chem.* 1982, 786.) in ether (30 mL). The resulting solution was stirred at 0° C. for 45 min. The reaction was then quenched with water (~3 mL) at 0° C. Na$_2$SO$_4$ dodecahydrate (5 g) was added along with ~30 mL EtOAc and the mixture allowed to warm to rt and stirred overnight. The mixture was filtered and the solid washed with EtOAc. The filtrate was then concentrated and the crude product was dissolved in DCM (37 mL). Dess-Martin periodinane (2.66 g, 6.3 mmol) was added to this solution and the resulting suspension was allowed to stir at rt for 1 h. The reaction was concentrated and the crude material purified on silica gel to yield 1-benzyl-5-(trifluoromethyl)-1H-pyrrole-3-carbaldehyde (288 mg, 36%). LCMS (FA): m/z=255 (M+H).

Step 2: [1-Benzyl-5-(trifluoromethyl)-1H-pyrrol-3-yl](4-chloropyrimidin-5-yl)methanol Into a flame dried RBF with stirbar under argon was added 4-chloro-5-iodopyrimidine (242 mg, 1.0 mmol) and it was dissolved in THF (7 mL). The flask cooled to −78° C.

To this solution was added dropwise n-butyllithium (2.5 M in hexane; 0.80 mL, 2.0 mmol) at −78° C. and the mixture was stirred for 30 min. To this mixture was added 1-benzyl-5-(trifluoromethyl)-1H-pyrrole-3-carbaldehyde (0.28 g, 1.1 mmol) dissolved in THF (3.5 mL) dropwise. The reaction was stirred at −78° C. for 30 min. The reaction was quenched with a saturated solution of NH$_4$Cl and then extracted with EtOAc (3×). The combined organic layers were then washed with water and brine, dried over Na$_2$SO$_4$, filtered and concentrated. The crude product was purified on silica gel to give [1-benzyl-5-(trifluoromethyl)-1H-pyrrol-3-yl](4-chloropyrimidin-5-yl)methanol (330 mg, 89%). LCMS (FA): m/z=368 (M+H).

Step 3: [1-Benzyl-5-(trifluoromethyl)-1H-pyrrol-3-yl](4-chloropyrimidin-5-yl)methanone To a solution of [1-benzyl-5-(trifluoromethyl)-1H-pyrrol-3-yl](4-chloropyrimidin-5-yl)methanol (0.30 g, 0.82 mmol) in DCM (10 mL) was added manganese(IV) oxide (0.85 g, 9.8 mmol). The suspension was stirred for 24 h at rt. The reaction was then filtered through a celite pad and the residual solid was washed with DCM several times. The filtrate was then concentrated in vacuo and the residue was purified on silica gel to afford [1-benzyl-5-(trifluoromethyl)-1H-pyrrol-3-yl](4-chloropyrimidin-5-yl)methanone (290 mg, 92%). LCMS (FA): m/z=366 (M+H).

Step 4: [1-Benzyl-5-(trifluoromethyl)-1H-pyrrol-3-yl](4-{[(1R,2R,3R,4R)-2-fluoro-3-hydroxy-4-(hydroxymethyl)cyclopentyl]amino}pyrimidin-5-yl)methanone

[1-Benzyl-5-(trifluoromethyl)-1H-pyrrol-3-yl](4-chloropyrimidin-5-yl)methanone (290 mg, 0.86 mmol) and (1R,2R,3R,5R)-3-amino-2-fluoro-5-(hydroxymethyl)cyclopentanol hydrochloride (0.18 g, 0.95 mmol) were weighed into a 20 mL reaction vessel. To this mixture was added 1-propanol (9.5 mL) and DIEA (0.41 mL, 2.4 mmol). The resulting mixture was sealed and the vessel allowed to stir while heating at 50° C. for 16 h. The reaction was then cooled to rt and the reaction was concentrated. The crude product was purified on silica gel to afford [1-benzyl-5-(trifluoromethyl)-1H-pyrrol-3-yl](4-{[(1R,2R,3R,4R)-2-fluoro-3-hydroxy-4-(hydroxymethyl)cyclopentyl]amino}pyrimidin-5-yl)methanone (0.34 g, 83%) LCMS (FA): m/z=479 (M+H).

Step 5: {(1R,2R,3R,4R)-4-[(5-{[1-Benzyl-5-(trifluoromethyl)-1H-pyrrol-3-yl]carbonyl}pyrimidin-4-yl)amino]-3-fluoro-2-hydroxycyclopentyl}methyl sulfamate I-94

[1-Benzyl-5-(trifluoromethyl)-1H-pyrrol-3-yl](4-{[(1R,2R,3R,4R)-2-fluoro-3-hydroxy-4-(hydroxymethyl)cyclopentyl]amino}pyrimidin-5-yl)methanone (0.15 g, 0.31 mmol) was dissolved in NMP (1.5 mL) and acetonitrile (0.77 mL). To this solution was added in one portion PPTS (79 mg, 0.31 mmol) followed by the addition of (4-aza-1-azoniabicyclo[2.2.2]oct-1-ylsulfonyl)(tert-butoxycarbonyl)azanide-1,4-diazabicyclo[2.2.2]octane (1:1) hydrochloride (F) (0.28 g, 0.63 mmol). After 1 h, additional (4-aza-1-azoniabicyclo[2.2.2]oct-1-ylsulfonyl)(tert-butoxycarbonyl)azanide-1,4-diazabicyclo[2.2.2]octane (1:1) hydrochloride (F) (50 mg, 0.12 mmol) was added and continued to stir at rt an additional 2 h. Upon reaction completion, the rxn was quenched by the addition of water. The mixture was extracted with EtOAc (3×). The combined organic layers were dried over MgSO$_4$, filtered and concentrated. The crude Boc-protected sulfamate intermediate was then dissolved in acetonitrile (1.5 mL) at rt. Concentrated HCl (0.74 mL, 8.8 mmol) was added at 0° C. The mixture was then allowed to stir at rt for 18 h. The reaction was quenched by the addition of a saturated solution of NaHCO$_3$ in water. After diluting the mixture with water it was extracted with EtOAc (4×). The combined organic layers were dried over MgSO$_4$, filtered, and concentrated. The crude product was purified by prep HPLC to give {(1R,2R,3R,4R)-4-[(5-{[1-benzyl-5-(trifluoromethyl)-1H-pyrrol-3-yl]carbonyl}pyrimidin-4-yl)amino]-3-fluoro-2-hydroxycyclopentyl}methyl sulfamate (98 mg, 55%). $^1$H NMR (DMSO) δ 8.84 (s, 1H), 8.80 (d, J=7.6 Hz, 1H), 8.70 (s, 1H), 8.06 (d, J=1.9 Hz, 1H), 7.51 (s, 2H), 7.42-7.24 (m, 3H), 7.21-7.10 (m, 3H), 5.57 (s, 1H), 5.39 (s, 2H), 4.94-4.63 (m, 2H), 4.12 (dd, J=9.8, 6.0 Hz, 1H), 4.03 (dd, J=9.7, 6.9 Hz, 1H), 3.94 (dd, J=21.9, 4.3 Hz, 1H), 2.40-2.27 (m, 1H), 2.24-2.12 (m, 1H), 1.55-1.42 (m, 1H); LCMS (FA): m/z=558.4 (M+H).

Example 103: [(1R,2R,3R,4R)-3-Fluoro-2-hydroxy-4-{[3-({1-[3-(trifluoromethoxy)benzyl]-1H-pyrrol-3-yl}carbonyl)pyridin-4-yl]amino}cyclopentyl]methyl sulfamate I-132

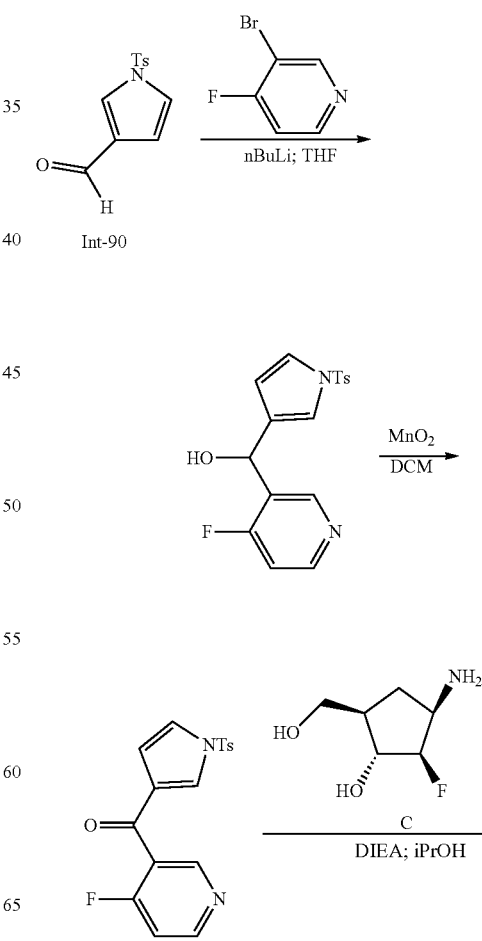

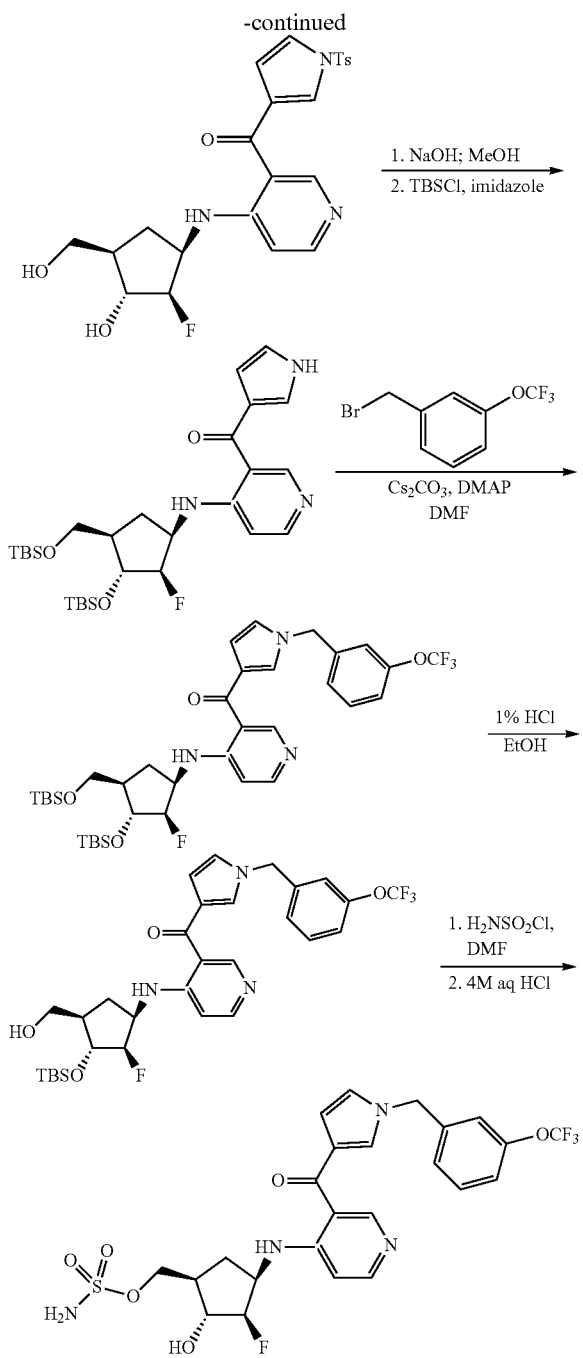

combined organic layers were then washed with water and brine, dried over Na₂SO₄, filtered and concentrated. The crude product was purified on silica gel to give (4-fluoropyridin-3-yl) {1-[(4-methylphenyl)sulfonyl]-1H-pyrrol-3-yl}methanol (1.9 g, 84%). LCMS (FA): m/z=347.2 (M+H).

Step 2: (4-Fluoropyridin-3-yl){1-[(4-methylphenyl) sulfonyl]-1H-pyrrol-3-yl}methanone To a solution of (4-fluoropyridin-3-yl){1-[(4-methylphenyl)sulfonyl]-1H-pyrrol-3-yl}methanol (1.9 g, 5.6 mmol) in DCM (60 mL) was added manganese(IV) oxide (4.8 g, 56 mmol). The suspension was stirred for 20 h at rt. The reaction was then filtered through a celite pad and the residual solid was washed with DCM several times. The filtrate was then concentrated in vacuo and the residue was purified on silica gel to afford (4-fluoropyridin-3-yl){1-[(4-methylphenyl)sulfonyl]-1H-pyrrol-3-yl}methanone (1.28 g, 67%). LCMS (FA): m/z=345.2 (M+H).

Step 3: (4-{[(1R,2R,3R,4R)-2-Fluoro-3-hydroxy-4-(hydroxymethyl)cyclopentyl]amino}pyridin-3-yl) {1-[(4-methylphenyl)sulfonyl]-1H-pyrrol-3-yl}methanone (4-Fluoropyridin-3-yl){1-[(4-methylphenyl)sulfonyl]-1H-pyrrol-3-yl}methanone (1.12 g, 3.3 mmol) and (1R,2R,3R,5R)-3-amino-2-fluoro-5-(hydroxymethyl)cyclopentanol.HCl (0.66 g, 3.6 mmol) were weighed into a reaction vessel. To this mixture was added 2-propanol (30 mL) and DIEA (1.7 mL, 9.8 mmol). The resulting mixture was stirred at 95° C. for 90 min. The reaction was then concentrated. The crude product was purified on silica gel to afford (4-{[(1R,2R,3R,4R)-2-fluoro-3-hydroxy-4-(hydroxymethyl)cyclopentyl]amino}pyridin-3-yl) {1-[(4-methylphenyl)sulfonyl]-1H-pyrrol-3-yl}methanone (0.66 g, 43%). LCMS (FA): m/z=474.3 (M+H).

Step 4: (4-{[(1R,2R,3R,4R)-3-{[tert-Butyl(dimethyl)silyl]oxy}-4-({[tert-butyl(dimethyl)silyl]oxy}methyl)-2-fluorocyclopentyl]amino}pyridin-3-yl)(1H-pyrrol-3-yl)methanone (4-{[(1R,2R,3R,4R)-2-Fluoro-3-hydroxy-4-(hydroxymethyl)cyclopentyl]amino}pyridin-3-yl) {1-[(4-methylphenyl)sulfonyl]-1H-pyrrol-3-yl}methanone (0.45 g, 0.95 mmol) and sodium hydroxide (0.15 g, 3.8 mmol) were dissolved in methanol (10.4 mL) and the mixture was stirred at rt for 4 h. The reaction mixture was concentrated and the crude product was dissolved in DMF (12 mL). To this solution was added imidazole (0.46 g, 6.8 mmol) followed by tert-butyldimethylsilyl chloride (0.67 g, 6.8 mmol) at rt, and the mixture was stirred for 20 h. The reaction was then quenched by addition of water and extracted with EtOAc (3×). The combined organic layers were washed with brine, dried over MgSO₄, filtered, and concentrated. The residue was purified on silica gel to give (4-{[(1R,2R,3R,4R)-3-{[tert-butyl(dimethyl)silyl]oxy}-4-({[tert-butyl(dimethyl)silyl]oxy)}methyl)-2-fluorocyclopentyl]amino}pyridin-3-yl)(1H-pyrrol-3-yl)methanone (0.17 g, 33%). LCMS (FA): m/z=548.2 (M+H).

Step 5: (4-{[(1R,2R,3R,4R)-3-{[tert-Butyl(dimethyl)silyl]oxy}-4-({[tert-butyl(dimethyl)silyl]oxy}methyl)-2-fluorocyclopentyl]amino}pyridin-3-yl) {1-[3-(trifluoromethoxy)benzyl]-1H-pyrrol-3-yl}methanone (4-{[(1R,2R,3R,4R)-3-{[tert-Butyl(dimethyl)silyl]oxy}-4-({[tert-butyl(dimethyl)silyl]oxy}methyl)-2-fluorocyclo- Step 1: (4-Fluoropyridin-3-yl){1-[(4-methylphenyl) sulfonyl]-1H-pyrrol-3-yl}methanol Into a flame dried RBF with stirbar was added n-butyllithium (2.5 M in hexane; 2.9 mL, 7.3 mmol) and THF (35 mL). The reaction flask was cooled to −78° C. A solution of 3-bromo-4-fluoropyridine (1.17 g, 6.6 mmol) in THF (5 mL) was then added dropwise and the resulting mixture allowed to stir for 1 h at −78° C. To this mixture was added 1-[(4-methylphenyl)sulfonyl]-1H-pyrrole-3-carbaldehyde (1.65 g, 6.6 mmol) dissolved in THF (4 mL) dropwise. The reaction was stirred at −78° C. for 1 h and then allowed to warm to rt. The reaction was quenched with a saturated solution of water and then extracted with EtOAc (3×). The pentyl]amino}pyridin-3-yl)(1H-pyrrol-3-yl)methanone (0.093 g, 0.17 mmol) was dissolved in DMF (3.8 mL). To this solution was added cesium carbonate (0.14 g, 0.42 mmol), and DMAP (0.052 g, 0.42 mmol). 3-(Trifluoromethoxy)benzyl bromide (0.055 mL, 0.34 mmol) was then added slowly as a solution in DMF (0.5 mL). After stirring for 18 h at rt, additional 3-(trifluoromethoxy)benzyl bromide (0.040 mL, 0.26 mmol) was added and the reaction was stirred at rt for 4 h. The reaction was then quenched by addition of water. This mixture was then extracted with EtOAc (3×). The combined organic layers were dried over MgSO$_4$, filtered and concentrated. The residue was purified on silica gel to give (4-{[(1R,2R,3R,4R)-3-{[tert-butyl(dimethyl)silyl]oxy}-4-({[tert-butyl(dimethyl)silyl]oxy}methyl)-2-fluorocyclopentyl]amino}pyridin-3-yl) {(1-[3-(trifluoromethoxy)benzyl]-1H-pyrrol-3-yl}methanone (81 mg, 66%). LCMS (FA): m/z=722.3 (M+H).

Step 6: (4-{[(1R,2R,3R,4R)-3-{[tert-Butyl(dimethyl)silyl]oxy}-2-fluoro-4-(hydroxymethyl)cyclopentyl]amino}pyridin-3-yl) {1-[3-(trifluoromethoxy)benzyl]-1H-pyrrol-3-yl}methanone To a solution of (4-{([(1R,2R,3R,4R)-3-{[tert-butyl(dimethyl)silyl]oxy}-4-({[tert-butyl(dimethyl)silyl]oxy}methyl)-2-fluorocyclopentyl]amino}pyridin-3-yl){1-[3-(trifluoromethoxy)benzyl]-1H-pyrrol-3-yl}methanone (41 mg, 0.12 mmol) in EtOH (5.5 mL) was added 1% HCl in EtOH (2.9 mL, 0.35 mmol) at rt. The reaction vessel was sealed and allowed to stand in a refrigerator (4° C.) for 18 h. The reaction was quenched by addition of a saturated aq. solution of NaHCO$_3$. To the residue was added water which was extracted with EtOAc (4×). The combined organic layers were dried over MgSO$_4$, filtered, and concentrated to give (4-{[(1R,2R,3R,4R)-3-{[tert-butyl(dimethyl)silyl] oxy}-2-fluoro-4-(hydroxymethyl)cyclopentyl] amino}pyridin-3-yl){1-[3-(trifluoromethoxy)benzyl]-1H-pyrrol-3-yl}methanone (72 mg, 100%). LCMS (FA): m/z=604.1 (M+H).

Step 7: [(1R,2R,3R,4R)-3-Fluoro-2-hydroxy-4-{[3-({1-[3-(trifluoromethoxy)benzyl]-1H-pyrrol-3-yl}carbonyl)pyridin-4-yl]amino}cyclopentyl]methyl sulfamate I-132

To a solution of (4-{[(1R,2R,3R,4R)-3-{[tert-butyl(dimethyl)silyl]oxy}-2-fluoro-4-(hydroxymethyl)cyclopentyl] amino}pyridin-3-yl) {1-[3-(trifluoromethoxy)benzyl]-1H-pyrrol-3-yl}methanone (0.069 g, 0.11 mmol) in DMF (1.3 mL) was added chlorosulfonamide (21 mg, 0.18 mmol) at rt, and the mixture was stirred for 2 h. HCl (3.0 M in water; 1.4 mL, 4.3 mmol) was then added to the solution and the reaction was stirred for 17 h at rt. The reaction was quenched by the addition of a saturated solution of NaHCO$_3$ and extracted with EtOAc (3×). The combined organic layers were dried over MgSO$_4$, filtered, and concentrated. The residue was purified by prep HPLC to afford [(1R,2R,3R,4R)-3-fluoro-2-hydroxy-4-{[3-({1-[3-(trifluoromethoxy)benzyl]-1H-pyrrol-3-yl}carbonyl)pyridin-4-yl]amino}cyclopentyl]methyl sulfamate (10 mg, 10%). $^1$H NMR (DMSO) δ 8.70 (s, 1H), 8.48-8.40 (m, 1H), 8.26-8.21 (m, 1H), 7.66-7.60 (m, 1H), 7.52-7.45 (m, 3H), 7.34-7.30 (m, 3H), 7.06-7.01 (m, 1H), 6.89 (d, J=6.1 Hz, 1H), 6.57-6.50 (m, 1H), 5.28 (s, 2H), 4.96-4.70 (m, 1H), 4.16-4.05 (m, 1H), 4.06-3.97 (m, 1H), 3.96-3.86 (m, 1H), 2.47-2.30 (m, 2H), 2.23-2.09 (m, 1H), 1.44-1.29 (m, 1H); LCMS (FA): m/z=573.3 (M+H).

The compound listed in the table below was prepared using an analogous method to that described above starting from the listed starting material used in step 5.

| Starting material | Compound No. | LCMS Data |
|---|---|---|
| 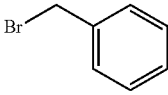 | I-124 | LCMS (FA): m/z = 523.3 (M + H). |

Example 104: {(1R,2S,4R)-4-[(5-{[1-(3-Bromobenzyl)-5-(hydroxymethyl)-1H-pyrazol-3-yl]carbonyl}pyrimidin-4-yl)amino]-2-hydroxycyclopentyl}methyl sulfamate I-90 and {(1R,2S,4R)-4-[(5-{[1-Benzyl-5-(hydroxymethyl)-1H-pyrazol-3-yl]carbonyl}pyrimidin-4-yl)amino]-2-hydroxycyclopentyl}methyl sulfamate I-335

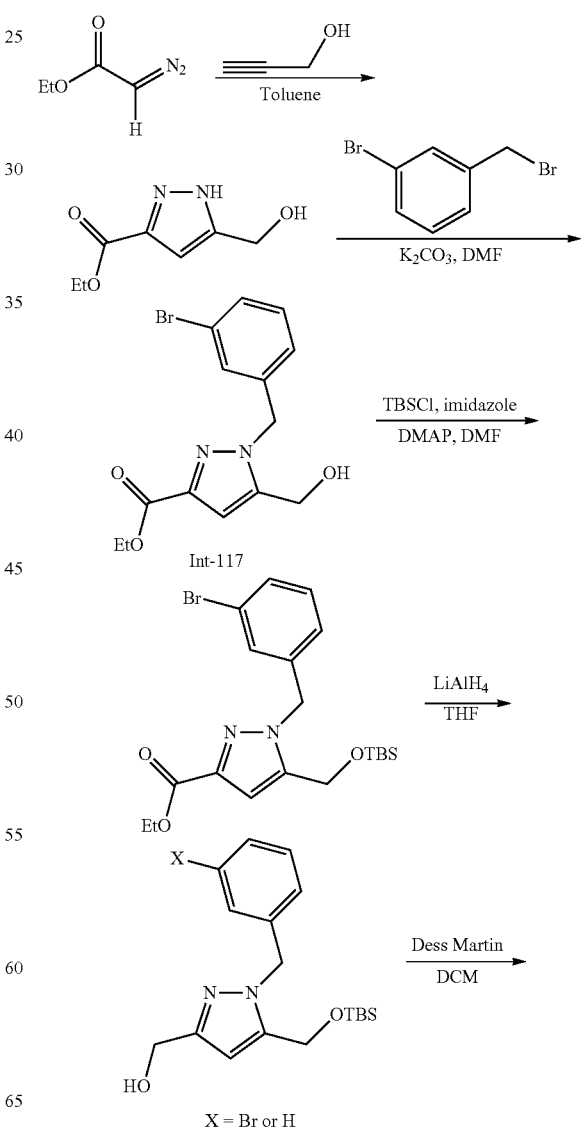

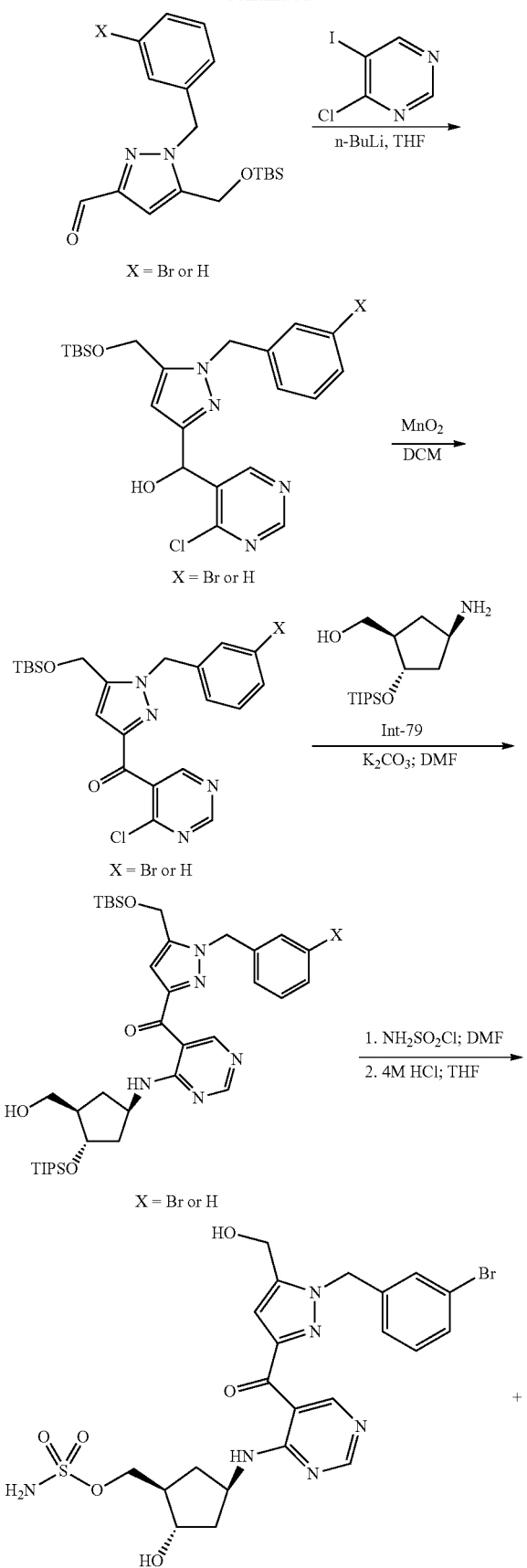

Step 1: Ethyl 5-(hydroxymethyl)-1H-pyrazole-3-carboxylate

Into a microwave vial was added 2-propyn-1-ol (0.50 g, 8.92 mmol) dissolved in toluene (10 mL). The reaction mixture was purged with argon and sealed. To the vial was added ethyl diazoacetate (1.03 mL, 9.81 mmol) via syringe. The mixture was then heated to reflux and stirred for 4 h. The reaction was transferred to a round bottom flask and concentrated to dryness. The residue was purified on silica gel to provide ethyl 5-(hydroxymethyl)-1H-pyrazole-3-carboxylate (0.77 g, 51% as a 9:1 mixture of regioisomers). LCMS (FA): m/z=171.2 (M+H).

Step 2: Ethyl 1-(3-bromobenzyl)-5-(hydroxymethyl)-1H-pyrazole-3-carboxylate

To a solution of ethyl 5-(hydroxymethyl)-1H-pyrazole-3-carboxylate (0.59 g, 3.47 mmol) in DMF (12 mL) was added $K_2CO_3$ (0.72 g, 5.20 mmol) followed by 3-bromobenzyl bromide (0.95 g, 3.81 mmol) at rt, and the mixture was stirred for 3 h. The reaction was diluted with water and extracted with EtOAc (3×). The combined organic layers were washed with water, brine, dried over $Na_2SO_4$, filtered, and concentrated in vacuo. The residue was purified on silica gel to provide ethyl 1-(3-bromobenzyl)-5-(hydroxymethyl)-1H-pyrazole-3-carboxylate (0.42 g, 35%). LCMS (FA): m/z=339.3 (M+H).

Step 3: Ethyl 1-(3-bromobenzyl)-5-({[tert-butyl(dimethyl)silyl]oxy}methyl)-1H-pyrazole-3-carboxylate To a solution of ethyl 1-(3-bromobenzyl)-5-(hydroxymethyl)-1H-pyrazole-3-carboxylate (0.50 g, 1.47 mmol) in DMF (10 mL) was added imidazole (0.25 g, 3.68 mmol) and DMAP (0.018 g, 0.147 mmol) followed by tert-butyldimethylsilyl chloride (0.333 g, 2.21 mmol) at rt, and the mixture was stirred for 1 day. The reaction was quenched by addition of water and extracted with EtOAc (3×). The combined organic layers were washed with water, brine, dried over $MgSO_4$, filtered, and concentrated in vacuo. The residue was purified on silica gel to give ethyl 1-(3-bromobenzyl)-5-({[tert-butyl(dimethyl)silyl]oxy}methyl)-1H-pyrazole-3-carboxylate (0.54 g, 81%). LCMS (FA): m/z=453.4 (M+H).

Step 4: [1-(3-Bromobenzyl)-5-({[tert-butyl(dimethyl)silyl]oxy}methyl)-1H-pyrazol-3-yl]methanol and [1-benzyl-5-({[tert-butyl(dimethyl)silyl]oxy}methyl)-1H-pyrazol-3-yl]methanol To a solution of ethyl 1-(3-bromobenzyl)-5-({[tert-butyl(dimethyl)silyl]oxy}methyl)-1H-pyrazole-3-carboxylate (0.54 g, 1.19 mmol) in THF (5 mL) cooled to 0° C. was added 1.0 M of lithium tetrahydroaluminate in ether (1.55 mL, 1.55 mmol) slowly via a syringe. The mixture was then stirred at 0° C. for 1 h. The reaction was quenched by the slow addition of water (0.5 mL). Solid sodium sulphate was then added and the mixture was stirred at rt for 1 h. The solid was filtered through a pad of celite and the filtrate was concentrated to dryness to provide a mixture of [1-(3-bromobenzyl)-5-({[tert-butyl(dimethyl)silyl]oxy}methyl)-1H-pyrazol-3-yl]methanol (X=Br) and [1-benzyl-5-({[tert-butyl(dimethyl)silyl]oxy}methyl)-1H-pyrazol-3-yl]methanol (X=H) (70:30 ratio). LCMS (FA): m/z=411.3 and 333.5 (M+H).

Step 5: 1-(3-Bromobenzyl)-5-({[tert-butyl(dimethyl)silyl]oxy}methyl)-1H-pyrazole-3-carbaldehyde and 1-benzyl-5-({[tert-butyl(dimethyl)silyl]oxy}methyl)-1H-pyrazole-3-carbaldehyde To a solution of [1-(3-bromobenzyl)-5-({[tert-butyl(dimethyl)silyl]oxy}methyl)-1H-pyrazol-3-yl]methanol and [1-benzyl-5-({[tert-butyl(dimethyl)silyl]oxy}methyl)-1H-pyrazol-3-yl]methanol (70:30 ratio) (0.49 g, 1.19 mmol) in DCM (10 mL) was added sodium bicarbonate (0.30 g, 3.57 mmol) followed by Dess-Martin periodinane (0.606 g, 1.43 mmol) and the mixture was stirred at rt for 1 h. The reaction was quenched by the addition of a saturated solution of sodium thiosulphate (3 mL) and extracted with DCM (3×). The combined organic layers were then washed with a saturated solution of sodium bicarbonate, brine, dried over $Na_2SO_4$, filtered, and concentrated in vacuo. The residue was purified on silica gel to provide a mixture of 1-(3-bromobenzyl)-5-({[tert-butyl(dimethyl)silyl]oxy}methyl)-1H-pyrazole-3-carbaldehyde and 1-benzyl-5-({[tert-butyl(dimethyl)silyl]oxy}methyl)-1H-pyrazole-3-carbaldehyde (70:30 ratio, 0.315 g, 65% over 2 steps). LCMS (FA): m/z=409.4 and 331.5 (M+H).

Step 6: [1-(3-Bromobenzyl)-5-({[tert-butyl(dimethyl)silyl]oxy}methyl)-1H-pyrazol-3-yl](4-chloropyrimidin-5-yl)methanol and [1-benzyl-5-({[tert-butyl(dimethyl)silyl]oxy}methyl)-1H-pyrazol-3-yl](4-chloropyrimidin-5-yl)methanol 4-Chloro-5-iodopyrimidine (0.22 g, 0.92 mmol) was added to a 3-necked RBF, which was equipped with additional funnel, three way stop cock, septum, and internal temperature probe. The reaction vessel was purged with argon. The content was dissolved in THF (4 mL), and the solution was cooled to −78° C. with a dry ice bath. To the solution was added dropwise n-Butyllithium (2.50 M in hexane; 0.739 mL, 1.85 mmol), and the mixture was stirred for 30 min. A solution of 1-(3-bromobenzyl)-5-({[tert-butyl(dimethyl)silyl]oxy}methyl)-1H-pyrazole-3-carbaldehyde and 1-benzyl-5-({[tert-butyl(dimethyl)silyl]oxy}methyl)-1H-pyrazole-3-carbaldehyde (0.315 g, 0.77 mmol) in THF (2 mL) was added dropwise to the mixture at −78° C., and the reaction was stirred for 30 min at the same temperature. The reaction was quenched by addition of saturated $NH_4Cl$ (5 mL) and extracted with EtOAc (3×). The combined organic layers were dried over $Na_2SO_4$, filtered, and concentrated in vacuo. The residue was purified on silica gel to give a mixture of [1-(3-bromobenzyl)-5-({[tert-butyl(dimethyl)silyl]oxy}methyl)-1H-pyrazol-3-yl](4-chloropyrimidin-5-yl)methanol and [1-benzyl-5-({[tert-butyl(dimethyl)silyl]oxy}methyl)-1H-pyrazol-3-yl](4-chloropyrimidin-5-yl)methanol (70:30 ratio, 0.224 g, 56%). LCMS (FA): m/z=523.5 and 445.5 (M+H).

Step 7: [1-(3-Bromobenzyl)-5-({[tert-butyl(dimethyl)silyl]oxy}methyl)-1H-pyrazol-3-yl](4-chloropyrimidin-5-yl)methanone and [1-benzyl-5-({[tert-butyl(dimethyl)silyl]oxy}methyl)-1H-pyrazol-3-yl](4-chloropyrimidin-5-yl)methanone To a solution of [1-(3-bromobenzyl)-5-({[tert-butyl(dimethyl)silyl]oxy}methyl)-1H-pyrazol-3-yl](4-chloropyrimidin-5-yl)methanol and [1-benzyl-5-({[tert-butyl(dimethyl)silyl]oxy}methyl)-1H-pyrazol-3-yl](4-chloropyrimidin-5-yl)methanol (0.22 g, 0.42 mmol) in DCM (5 mL) was added manganese(IV) oxide (0.365 g, 4.2 mmol) and the mixture was stirred for 12 h at rt. The reaction was then filtered through a celite pad and the residual solid was washed with DCM several times. The filtrate was concentrated in vacuo to give a mixture of [1-(3-bromobenzyl)-5-({[tert-butyl(dimethyl)silyl]oxy}methyl)-1H-pyrazol-3-yl](4-chloropyrimidin-5-yl)methanone and [1-benzyl-5-({[tert-butyl(dimethyl)silyl]oxy}methyl)-1H-pyrazol-3-yl](4-chloropyrimidin-5-yl)methanone (70:30 ratio, 0.212 g, 97%). LCMS (FA): m/z=521.1 and 443.2 (M+H).

Step 8: [1-(3-Bromobenzyl)-5-({[tert-butyl(dimethyl)silyl]oxy}methyl)-1H-pyrazol-3-yl][4-({(1R,3R,4S)-3-(hydroxymethyl)-4-[(triisopropylsilyl)oxy]cyclopentyl}amino)pyrimidin-5-yl]methanone and [1-benzyl-5-({[tert-butyl(dimethyl)silyl]oxy}methyl)-1H-pyrazol-3-yl][4-({(1R,3R,4S)-3-(hydroxymethyl)-4-[(triisopropylsilyl)oxy]cyclopentyl}amino)pyrimidin-5-yl]methanone {(1R,2S,4R)-4-Amino-2-[(triisopropylsilyl)oxy]cyclopentyl}methanol (0.175 g, 0.609 mmol) and [1-(3-bromobenzyl)-5-({[tert-butyl(dimethyl)silyl]oxy}methyl)-1H-pyrazol-3-yl](4-chloropyrimidin-5-yl)methanone and [1-benzyl-5-({[tert-butyl(dimethyl)silyl]oxy}methyl)-1H-pyrazol-3-yl](4-chloropyrimidin-5-yl)methanone (0.212 g, 0.406 mmol) were weighed into a reaction vessel and the contents were dissolved in DMF (4 mL). To the solution was added $K_2CO_3$ (0.168 g, 1.22 mmol) at rt, and the resulting mixture was stirred for 2 h. To the residue was added water and then the mixture was extracted with EtOAc (3×). The combined organic layers were then washed with brine, dried over $Na_2SO_4$, filtered and concentrated in vacuo. The residue was purified on silica gel to give a mixture of [1-(3-bromobenzyl)-5-({[tert-butyl(dimethyl)silyl]oxy}methyl)-1H-pyrazol-3-yl][4-({(1R,3R,4S)-3-(hydroxymethyl)-4-[(triisopropylsilyl)oxy]cyclopentyl}amino)pyrimidin-5-yl]methanone and [1-benzyl-5-({[tert-butyl(dimethyl)silyl]oxy}methyl)-1H-pyrazol-3-yl][4-({(1R,3R,4S)-3-(hydroxymethyl)-4-[(triisopropylsilyl)oxy]cyclopentyl}amino)pyrimidin-5-yl]methanone (65:35 ratio, 0.273 g, 87%). LCMS (FA): m/z=772.8 and 694.9 (M+H).

Step 9: {(1R,2S,4R)-4-[(5-{[1-(3-Bromobenzyl)-5-(hydroxymethyl)-1H-pyrazol-3-yl]carbonyl}pyrimidin-4-yl)amino]-2-hydroxycyclopentyl}methyl sulfamate I-90 and {(1R,2S,4R)-4-[(5-{[1-benzyl-5-(hydroxymethyl)-1H-pyrazol-3-yl]carbonyl}pyrimidin-4-yl)amino]-2-hydroxycyclopentyl}methyl sulfamate I-335

To a solution of [1-(3-bromobenzyl)-5-({[tert-butyl(dimethyl)silyl]oxy}methyl)-1H-pyrazol-3-yl][4-({(1R,3R,4S)-3-(hydroxymethyl)-4-[(triisopropylsilyl)oxy]cyclopentyl}amino)pyrimidin-5-yl]methanone and [1-benzyl-5-({[tert-butyl(dimethyl)silyl]oxy}methyl)-1H-pyrazol-3-yl][4-({(1R,3R,4S)-3-(hydroxymethyl)-4-[(triisopropylsilyl)oxy]cyclopentyl}amino)pyrimidin-5-yl]methanone (0.273 g, 0.353 mmol) in DMF (5 mL) was added triethylamine (0.147 mL, 1.06 mmol) followed by chlorosulfonamide (0.082 g, 0.706 mmol) at rt, and the mixture was stirred for 2 h. The reaction was quenched by addition of a saturated aqueous solution of NaHCO$_3$ (5 mL) and the resulting mixture was extracted with EtOAc (3×). The combined organic layers were dried over Na$_2$SO$_4$, filtered, and concentrated in vacuo. The residue was then dissolved in THF (7 mL). To this solution was added HCl (4.0 M in water; 3.5 mL, 14 mmol) at rt, and the mixture was stirred for 14 h. The reaction was quenched by the addition of saturated NaHCO$_3$ and the mixture was extracted with EtOAc (4×). The combined organic layers were dried over Na$_2$SO$_4$, filtered, and concentrated in vacuo. The residue was purified by prep HPLC to give {(1R,2S,4R)-4-[(5-{[1-(3-bromobenzyl)-5-(hydroxymethyl)-1H-pyrazol-3-yl]carbonyl}pyrimidin-4-yl)amino]-2-hydroxycyclopentyl}methyl sulfamate (0.075 g, 37%); $^1$H NMR (DMSO) δ 9.44 (s, 1H), 9.02 (d, J=7.4 Hz, 1H), 8.62 (s, 1H), 7.51 (d, J=8.0 Hz, 1H), 7.48-7.41 (m, 3H), 7.33 (t, J=7.8 Hz, 1H), 7.21 (d, J=7.9 Hz, 1H), 6.84 (s, 1H), 5.56 (t, J=4.9 Hz, 1H), 5.52 (s, 2H), 4.91 (d, J=4.4 Hz, 1H), 4.77-4.66 (m, 1H), 4.56 (d, J=3.9 Hz, 2H), 4.11 (dd, J=9.7, 5.9 Hz, 1H), 4.02-3.94 (m, 2H), 2.41-2.31 (m, 1H), 2.18-2.08 (m, 1H), 2.05-1.96 (m, 1H), 1.84-1.74 (m, 1H), 1.34-1.23 (m, 1H); LCMS (FA): m/z=581.4 (M+H) and {(1R,2S,4R)-4-[(5-{[1-benzyl-5-(hydroxymethyl)-1H-pyrazol-3-yl]carbonyl}pyrimidin-4-yl)amino]-2-hydroxycyclopentyl}methyl sulfamate (0.036 g, 20%); $^1$H NMR (DMSO) δ 9.47 (s, 1H), 9.02 (d, J=7.4 Hz, 1H), 8.62 (s, 1H), 7.44 (s, 2H), 7.39-7.27 (m, 3H), 7.27-7.20 (m, 2H), 6.83 (s, 1H), 5.50 (s, 2H), 4.91 (s, 1H), 4.72 (dq, J=15.9, 7.9 Hz, 1H), 4.54 (s, 2H), 4.11 (dd, J=9.8, 5.9 Hz, 1H), 4.01-3.94 (m, 2H), 2.39-2.31 (m, 1H), 2.18-2.10 (m, 1H), 2.05-1.96 (m, 1H), 1.83-1.74 (m, 1H), 1.29 (dt, J=12.9, 9.2 Hz, 1H); LCMS (FA): m/z=503.5 (M+H).

Example 105: Ethyl 1-(3-bromobenzyl)-3-(hydroxymethyl)-1H-pyrazole-5-carboxylate and ethyl 1-(3-bromobenzyl)-5-(hydroxymethyl)-1H-pyrazole-3-carboxylate Int-116 and Int-117

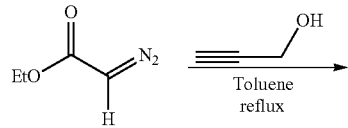

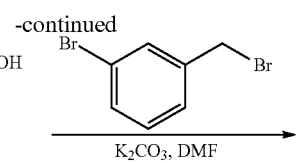

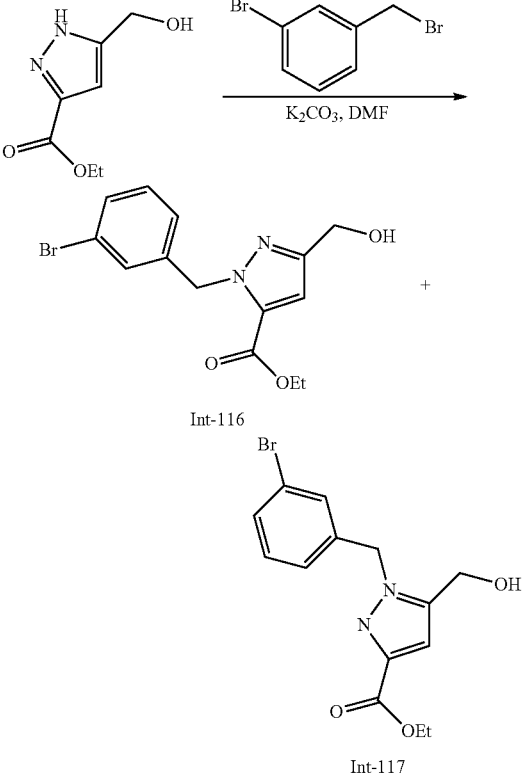

Step 1: Ethyl 5-(hydroxymethyl)-1H-pyrazole-3-carboxylate

Into a 1-neck round-bottom flask was added 2-propyn-1-ol (1.50 g, 26.8 mmol) dissolved in toluene (30.0 mL). The mix was purged with argon and ethyl diazoacetate (3.10 mL, 29.4 mmol) was added via syringe. The mix was heated to reflux and stirred for 4 h. The reaction was then cooled to rt and concentrated to dryness. The residue was purified by ISCO silica gel chromatography (80 g column, eluting with 50-100% EtOAc/Hex over 20 min) to give 2.46 g (54%, as 9:1 mixture of regioisomers) of the title compound. LCMS (FA): m/z=171.2 (M+H).

Step 2: Ethyl 1-(3-bromobenzyl)-3-(hydroxymethyl)-1H-pyrazole-5-carboxylate and ethyl 1-(3-bromobenzyl)-5-(hydroxymethyl)-1H-pyrazole-3-carboxylate Int-116 and Int-117

Into a flask was added ethyl 5-(hydroxymethyl)-1H-pyrazole-3-carboxylate (0.590 g, 3.47 mmol) dissolved in DMF (12.00 mL). Potassium carbonate (0.719 g, 5.20 mmol) was added followed by 3-bromobenzyl bromide (0.953 g, 3.81 mmol) at RT and the reaction was stirred for 3 h. The mixture was then diluted with water and extracted with EtOAc (3×). The combined organic layers were washed with water, brine, dried using Na$_2$SO$_4$, filtered and concentrated. The residue was purified by ISCO silica gel chromatography (40 g column, eluting with 0-50-100% EtOAc/Hex over 20 min) to give 0.544 g (46%) of Int-116 and 0.417 g (35%) of Int-117. Int-116: $^1$H NMR (400 MHz, Chloroform-d) δ 7.42-7.34 (m, 2H), 7.19-7.12 (m, 2H), 6.88 (s, 1H), 5.69 (s, 2H), 4.71 (s, 2H), 4.31 (q, J=7.1 Hz, 2H), 1.93 (s, 1H), 1.34 (t, J=7.2 Hz, 3H). Int-117: $^1$H NMR (400 MHz, Chloroform-d) δ 7.42 (d, J=8.0 Hz, 1H), 7.33 (s, 1H), 7.22-7.16 (m, 1H), 7.10 (d, J=8.1 Hz, 1H), 6.79 (s, 1H), 5.49 (s, 2H), 4.56 (s, 2H), 4.42 (q, J=7.1 Hz, 2H), 1.65 (s, 1H), 1.40 (t, J=7.1 Hz, 3H).

Example 106: 1-(3-Bromobenzyl)-5-{2-[(trimethylsilyl)oxy]propan-2-yl}-1H-pyrazole-3-carbaldehyde Int-118

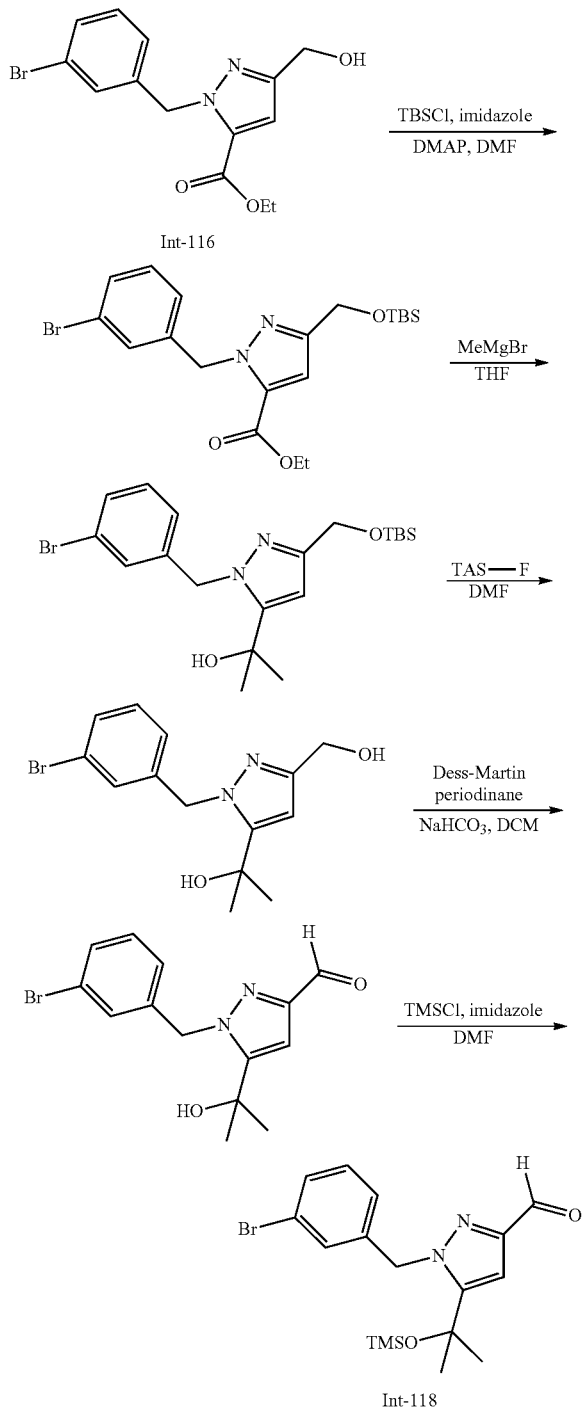

Step 1: Ethyl 1-(3-bromobenzyl)-3-({[tert-butyl(dimethyl)silyl]oxy}methyl)-1H-pyrazole-5-carboxylate Into a 1-neck round-bottom flask was added ethyl 1-(3-bromobenzyl)-3-(hydroxymethyl)-1H-pyrazole-5-carboxylate (0.654 g, 1.93 mmol) dissolved in DMF (12.0 mL). 1H-Imidazole (0.328 g, 4.82 mmol) and N,N-dimethylaminopyridine (23.6 mg, 0.193 mmol) were added followed by tert-butyldimethylsilyl chloride (0.436 g, 2.89 mmol). The reaction was stirred at rt for 3 h. Water was added to the reaction mixture and extracted with EtOAc (3×). The combined organic layers were then washed with water, brine, dried using $Na_2SO_4$, filtered and concentrated. The residue was purified by ISCO silica gel chromatography (24 g column, eluting with 0-50% EtOAc/Hex over 25 min) to give 0.777 g (89%) of the title compound. $^1$H NMR (400 MHz, Chloroform-d) δ 7.40-7.34 (m, 2H), 7.17-7.13 (m, 2H), 6.87 (s, 1H), 5.68 (s, 2H), 4.73 (s, 2H), 4.31 (q, J=7.1 Hz, 2H), 1.34 (t, J=7.1 Hz, 3H), 0.92 (s, 9H), 0.09 (s, 6H).

Step 2: 2-[1-(3-Bromobenzyl)-3-({[tert-butyl(dimethyl)silyl]oxy}methyl)-1H-pyrazol-5-yl]propan-2-ol Into a 1-neck round-bottom flask was added ethyl 1-(3-bromobenzyl)-3-({[tert-butyl(dimethyl)silyl]oxy}methyl)-1H-pyrazole-5-carboxylate (0.775 g, 1.71 mmol) dissolved in THF (10.0 mL). The solution was cooled to 0° C. and a 3.00 M solution of methylmagnesium bromide in ether (2.28 mL, 6.84 mmol) was added dropwise over 15 min. The reaction mixture was stirred at 0° C. for 1 h. The reaction was quenched with saturated $NH_4Cl$ and extracted with EtOAc (3×). The combined organic layers were then washed with water, brine, dried using $Na_2SO_4$, filtered and concentrated. The residue was purified by ISCO silica gel chromatography (24 g column, eluting with 0-50% EtOAc/Hex over 25 min) to give 0.506 g (67%) of the title compound. $^1$H NMR (400 MHz, Chloroform-d) δ 7.39-7.33 (m, 1H), 7.26-7.24 (m, 1H), 7.18-7.11 (m, 1H), 7.03 (d, J=8.2 Hz, 1H), 6.14 (s, 1H), 5.59 (s, 2H), 4.71 (s, 2H), 1.58 (s, 6H), 0.92 (s, 9H), 0.10 (s, 6H).

Step 3: 2-[1-(3-Bromobenzyl)-3-(hydroxymethyl)-1H-pyrazol-5-yl]propan-2-ol

To a solution of 2-[1-(3-bromobenzyl)-3-({[tert-butyl(dimethyl)silyl]oxy}methyl)-1H-pyrazol-5-yl]propan-2-ol (0.506 g, 1.15 mmol) in DMF (15.0 mL) was added tris(dimethylamino)sulfonium trimethylsilyldifluoride (0.634 g, 2.30 mmol) at rt. After stirring overnight under an atmosphere of argon the reaction mixture was poured into a saturated aqueous $NaHCO_3$ solution and extracted with EtOAc (3×). The combined organic layers were then washed with brine, dried over $MgSO_4$, filtered, and concentrated in vacuo to give crude 2-[1-(3-bromobenzyl)-3-(hydroxymethyl)-1H-pyrazol-5-yl]propan-2-ol. LCMS (FA): m/z=325.3 (M+H).

Step 4: 1-(3-Bromobenzyl)-5-(2-hydroxypropan-2-yl)-1H-pyrazole-3-carbaldehyde

Into a 1-neck round-bottom flask was added crude 2-[1-(3-bromobenzyl)-3-(hydroxymethyl)-1H-pyrazol-5-yl]propan-2-ol (0.374 g, 1.15 mmol) dissolved in DCM (10.0 mL) and cooled to 0° C. Sodium bicarbonate (0.290 g, 3.45 mmol) was added followed by Dess-Martin periodinane (0.585 g, 1.38 mmol). The resulting reaction mixture was stirred at 0° C. for 2 h. The reaction was then quenched by the addition of a saturated Na₂S₂O₃ solution and extracted with DCM (3×). The combined organic layers were then washed with water, saturated NaHCO₃, brine, dried using Na₂SO₄, filtered and concentrated to give crude 1-(3-bromobenzyl)-5-(2-hydroxypropan-2-yl)-1H-pyrazole-3-carbaldehyde. LCMS (FA): m/z=323.3 (M+H).

Step 5: 1-(3-Bromobenzyl)-5-{2-[(trimethylsilyl)oxy]propan-2-yl}-1H-pyrazole-3-carbaldehyde Int-118

To a solution of crude 1-(3-bromobenzyl)-5-(2-hydroxypropan-2-yl)-1H-pyrazole-3-carbaldehyde (0.372 g, 1.15 mmol) in DMF (5.00 mL) was added 1H-imidazole (0.235 g, 3.45 mmol) and chlorotrimethylsilane (0.219 mL, 1.735 mmol) at rt. The reaction was stirred for 16 h. The reaction mixture was poured into a saturated aqueous NaHCO₃ solution and extracted with EtOAc (3×). The combined organic layers were then washed with water, brine, dried using Na₂SO₄, filtered and concentrated. The residue was purified by ISCO silica gel chromatography (24 g column, eluting with 0-50% EtOAc/Hex over 20 min) to give 0.30 g (66%, over 3 steps) of Int-118. ¹H NMR (400 MHz, Chloroform-d) δ 9.92 (s, 1H), 7.43-7.38 (m, 1H), 7.22-7.16 (m, 2H), 7.01-6.95 (m, 1H), 6.64 (s, 1H), 5.71 (s, 2H), 1.61 (s, 6H), 0.04 (s, 9H).

Example 107: 1-(3-Bromobenzyl)-5-(methoxymethyl)-1H-pyrazole-3-carbaldehyde Int-119

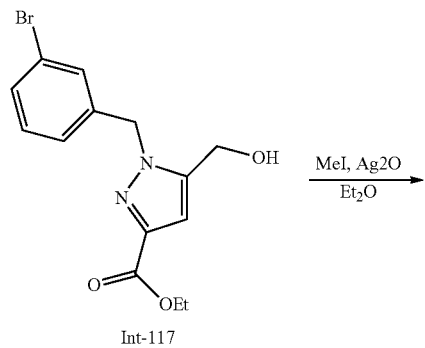

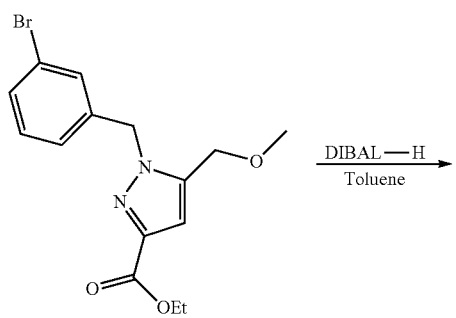

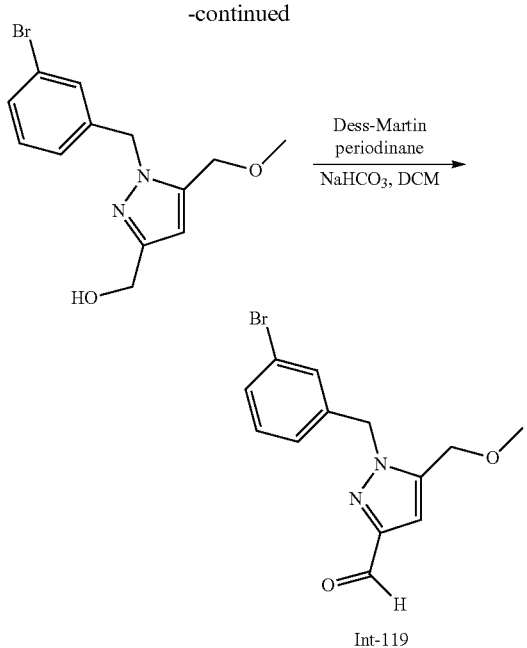

Step 1: Ethyl 1-(3-bromobenzyl)-5-(methoxymethyl)-1H-pyrazole-3-carboxylate

Into a round bottom flask was added ethyl 1-(3-bromobenzyl)-5-(hydroxymethyl)-1H-pyrazole-3-carboxylate (1.13 g, 3.34 mmol) dissolved in diethyl ether (30 mL). Methyl iodide (6.50 mL, 104 mmol) was added followed by silver(I) oxide (1.94 g, 8.35 mmol). The reaction was stirred at rt for 4 days. The reaction mixture was then filtered through celite and the filtrate concentrated to dryness. The residue was purified by ISCO silica gel chromatography (40 g column, eluting with 0-50% EtOAc/Hex over 20 min) to give 0.877 g (74%) of the title compound. ¹H NMR (400 MHz, Chloroform-d) δ 7.41 (d, J=7.9 Hz, 1H), 7.32 (s, 1H), 7.21-7.15 (m, 1H), 7.10 (d, J=7.7 Hz, 1H), 6.80 (s, 1H), 5.45 (s, 2H), 4.42 (q, J=7.1 Hz, 2H), 4.31 (s, 2H), 3.26 (s, 3H), 1.40 (t, J=7.1 Hz, 3H).

Step 2: [1-(3-Bromobenzyl)-5-(methoxymethyl)-1H-pyrazol-3-yl]methanol

To a solution of ethyl 1-(3-bromobenzyl)-5-(methoxymethyl)-1H-pyrazole-3-carboxylate (0.877 g, 2.48 mmol) in toluene (12.0 mL) cooled to −78° C. was added dropwise a 1.00 M solution of diisobutylaluminum hydride in toluene (5.96 mL, 5.96 mmol) over 15 min. The reaction mixture was stirred at −78° C. for 2 h. To the reaction mixture was added saturated aqueous Rochelle's salt and extracted with EtOAc (3×). The combined organic layers were then washed with water, brine, dried using Na₂SO₄, filtered and concentrated to give crude [1-(3-bromobenzyl)-5-(methoxymethyl)-1H-pyrazol-3-yl]methanol. LCMS (FA): m/z=309.0 (M+H).

Step 3: 1-(3-Bromobenzyl)-5-(methoxymethyl)-1H-pyrazole-3-carbaldehyde Int-119

Into a 1-neck round-bottom flask was added crude [1-(3-bromobenzyl)-5-(methoxymethyl)-1H-pyrazol-3-yl]methanol (0.772 g, 2.48 mmol) dissolved in DCM (20.0 mL) and cooled to 0° C. Sodium bicarbonate (0.625 g, 7.44 mmol) was added followed by Dess-Martin periodinane (1.26 g, 2.98 mmol). The resulting reaction mixture was stirred at 0° C. for 2 h. The reaction was quenched by the addition of a saturated Na₂S₂O₃ solution and extracted with DCM (3×). The combined organic layers were washed with water, saturated NaHCO₃, brine, dried using Na₂SO₄, filtered and concentrated. The residue was purified by ISCO silica gel chromatography (24 g column, eluting with 0-30% EtOAc/Hex over 25 min) to give 0.578 g (75%, over 2 steps) of Int-119. ¹H NMR (400 MHz, Chloroform-d) δ 9.97 (s, 1H), 7.45 (d, J=8.0 Hz, 1H), 7.36 (s, 1H), 7.25-7.18 (m, 1H), 7.13 (d, J=7.7 Hz, 1H), 6.78 (s, 1H), 5.43 (s, 2H), 4.37 (s, 2H), 3.30 (s, 3H).

Example 108: 1-(3-Bromobenzyl)-5-(1-methoxyethyl)-1H-pyrazole-3-carbaldehyde Int-120

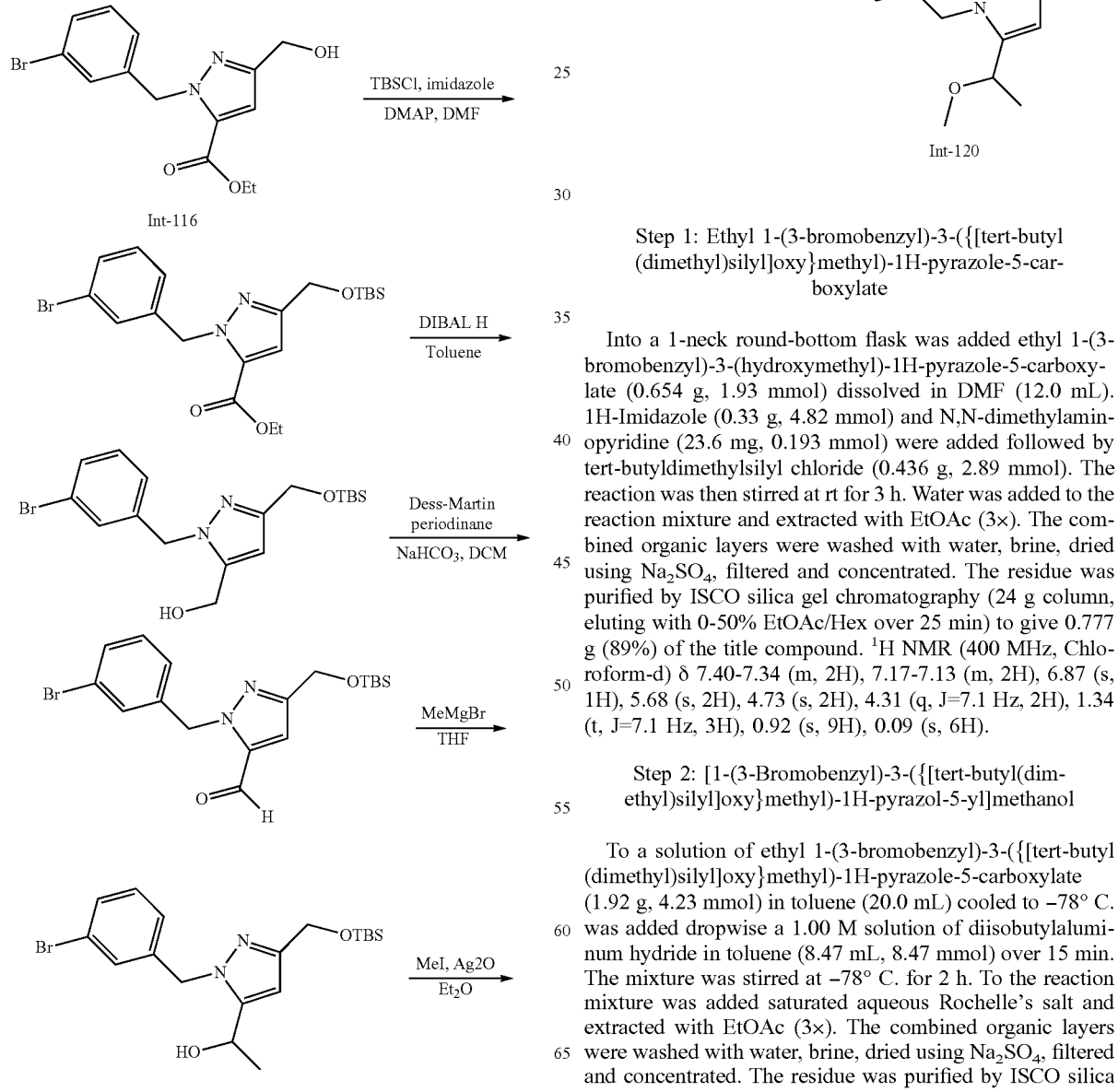

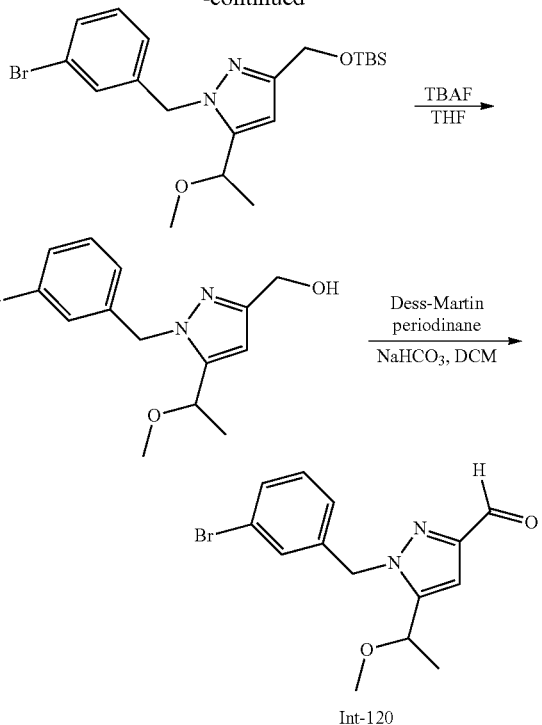

Step 1: Ethyl 1-(3-bromobenzyl)-3-({[tert-butyl(dimethyl)silyl]oxy}methyl)-1H-pyrazole-5-carboxylate Into a 1-neck round-bottom flask was added ethyl 1-(3-bromobenzyl)-3-(hydroxymethyl)-1H-pyrazole-5-carboxylate (0.654 g, 1.93 mmol) dissolved in DMF (12.0 mL). 1H-Imidazole (0.33 g, 4.82 mmol) and N,N-dimethylaminopyridine (23.6 mg, 0.193 mmol) were added followed by tert-butyldimethylsilyl chloride (0.436 g, 2.89 mmol). The reaction was then stirred at rt for 3 h. Water was added to the reaction mixture and extracted with EtOAc (3×). The combined organic layers were washed with water, brine, dried using Na₂SO₄, filtered and concentrated. The residue was purified by ISCO silica gel chromatography (24 g column, eluting with 0-50% EtOAc/Hex over 25 min) to give 0.777 g (89%) of the title compound. ¹H NMR (400 MHz, Chloroform-d) δ 7.40-7.34 (m, 2H), 7.17-7.13 (m, 2H), 6.87 (s, 1H), 5.68 (s, 2H), 4.73 (s, 2H), 4.31 (q, J=7.1 Hz, 2H), 1.34 (t, J=7.1 Hz, 3H), 0.92 (s, 9H), 0.09 (s, 6H).

Step 2: [1-(3-Bromobenzyl)-3-({[tert-butyl(dimethyl)silyl]oxy}methyl)-1H-pyrazol-5-yl]methanol To a solution of ethyl 1-(3-bromobenzyl)-3-({[tert-butyl(dimethyl)silyl]oxy}methyl)-1H-pyrazole-5-carboxylate (1.92 g, 4.23 mmol) in toluene (20.0 mL) cooled to −78° C. was added dropwise a 1.00 M solution of diisobutylaluminum hydride in toluene (8.47 mL, 8.47 mmol) over 15 min. The mixture was stirred at −78° C. for 2 h. To the reaction mixture was added saturated aqueous Rochelle's salt and extracted with EtOAc (3×). The combined organic layers were washed with water, brine, dried using Na₂SO₄, filtered and concentrated. The residue was purified by ISCO silica gel chromatography (40 g column, eluting with 0-20-50%

EtOAc/Hex over 20 mins) to give 1.405 g (80%) of the title compound. LCMS (FA): m/z=411.5 (M+H).

Step 3: 1-(3-Bromobenzyl)-3-({[tert-butyl(dimethyl) silyl]oxy}methyl)-1H-pyrazole-5-carbaldehyde Into a 1-neck round-bottom flask was added [1-(3-bromobenzyl)-3-({[tert-butyl(dimethyl)silyl]oxy}methyl)-1H-pyrazol-5-yl]methanol (1.40 g, 3.40 mmol) dissolved in DCM (30.0 mL) and cooled to 0° C. Sodium bicarbonate (0.858 g, 10.21 mmol) was added followed by Dess-Martin periodinane (1.73 g, 4.08 mmol). The resulting reaction mixture was stirred at 0° C. for 2 h. The reaction was quenched by the addition of a saturated $Na_2S_2O_3$ solution and extracted with DCM (3×). The combined organic layers were then washed with water, saturated $NaHCO_3$, brine, dried using $Na_2SO_4$, filtered and concentrated. The residue was purified by ISCO silica gel chromatography (40 g column, eluting with 0-20% EtOAc/Hex over 25 min) to give 1.08 g (77%) of the title compound. $^1$H NMR (400 MHz, Chloroform-d) δ 9.81 (s, 1H), 7.42-7.35 (m, 2H), 7.22-7.12 (m, 2H), 6.94 (s, 1H), 5.64 (s, 2H), 4.76 (s, 2H), 0.92 (s, 9H), 0.10 (s, 6H).

Step 4: 1-[1-(3-Bromobenzyl)-3-({[tert-butyl(dimethyl)silyl]oxy}methyl)-1H-pyrazol-5-yl]ethanol Into a 1-neck round-bottom flask was added 1-(3-bromobenzyl)-3-({[tert-butyl(dimethyl)silyl]oxy}methyl)-1H-pyrazole-5-carbaldehyde (0.52 g, 1.27 mmol) dissolved in THF (8.00 mL). The solution was cooled to 0° C. and a 3.00 M solution of methylmagnesium bromide in diethylether (1.69 mL, 5.08 mmol) was added dropwise over 5 min. The reaction was stirred at 0° C. for 2 h. The reaction was quenched with saturated $NH_4Cl$ and extracted with EtOAc (3×). The combined organic layers were washed with water, brine, dried using $Na_2SO_4$, filtered and concentrated. The residue was purified by ISCO silica gel chromatography (24 g column, eluting with 0-50% EtOAc/Hex over 25 min) to give 0.498 g (92%) of the title compound. LCMS (FA): m/z=425.5 (M+H).

Step 5: 1-(3-Bromobenzyl)-3-({[tert-butyl(dimethyl) silyl]oxy}methy)-5-(1-methoxyethyl)-1H-pyrazole Into a round bottom flask was added 1-[1-(3-bromobenzyl)-3-({[tert-butyl(dimethyl)silyl]oxy}methyl)-1H-pyrazol-5-yl]ethanol (0.498 g, 1.17 mmol) dissolved in ether (10 mL). Methyl iodide (2.50 mL, 40.2 mmol) was added followed by silver(I) oxide (0.678 g, 2.93 mmol) and the mixture was stirred at rt for 4 days. The reaction mixture was filtered through celite and the filtrate concentrated to dryness. The residue was purified by ISCO silica gel chromatography (24 g column, eluting with 0-50% EtOAc/Hex over 25 min) to give 0.322 g (63%) of the title compound. $^1$H NMR (400 MHz, Chloroform-d) δ 7.38 (d, J=7.9 Hz, 1H), 7.29-7.26 (m, 1H), 7.19-7.13 (m, 1H), 7.04 (d, J=8.1 Hz, 1H), 6.25 (s, 1H), 5.33 (s, 2H), 4.73 (s, 2H), 4.41 (q, J=6.5 Hz, 1H), 3.14 (s, 3H), 1.41 (d, J=6.6 Hz, 3H), 0.92 (s, 9H), 0.09 (s, 6H).

Step 6: [1-(3-Bromobenzyl)-5-(1-methoxyethyl)-1H-pyrazol-3-yl]methanol

Into a 1-neck round-bottom flask was added 1-(3-bromobenzyl)-3-({[tert-butyl(dimethyl)silyl]oxy}methyl)-5-(1-methoxyethyl)-1H-pyrazole (0.322 g, 0.733 mmol) dissolved in THF (10.0 mL). To the solution was added tetrabutylammonium fluoride hydrate (0.307 g, 1.10 mmol) at rt and the reaction was stirred for 1 h. The reaction was quenched with a saturated $NaHCO_3$ solution and extracted with EtOAc (3×). The combined organic layers were washed with water, brine, dried using $Na_2SO_4$, filtered and concentrated to give crude [1-(3-bromobenzyl)-5-(1-methoxyethyl)-1H-pyrazol-3-yl]methanol. LCMS (FA): m/z=327.1 (M+H).

Step 7: 1-(3-Bromobenzyl)-5-(1-methoxyethyl)-1H-pyrazole-3-carbaldehyde Int-120

Into a 1-neck round-bottom flask was added crude [1-(3-bromobenzyl)-5-(1-methoxyethyl)-1H-pyrazol-3-yl]methanol (0.238 g, 0.733 mmol) dissolved in DCM (8.00 mL) and cooled to 0° C. Sodium bicarbonate (0.185 g, 2.20 mmol) was added followed by Dess-Martin periodinane (0.373 g, 0.880 mmol). The resulting reaction mixture was then stirred at 0° C. for 1 h. The reaction was quenched by the addition of a saturated $Na_2S_2O_3$ solution and extracted with DCM (3×). The combined organic layers were washed with water, saturated $NaHCO_3$, brine, dried using $Na_2SO_4$, filtered and concentrated. The residue was purified by ISCO silica gel chromatography (24 g column, eluting with 0-30-50% EtOAc/Hex over 25 min) to give 0.143 g (60%, over 2 steps) of Int-120. $^1$H NMR (400 MHz, Chloroform-d) δ 9.97 (s, 1H), 7.44 (d, J=8.1 Hz, 1H), 7.34 (s, 1H), 7.24-7.18 (m, 1H), 7.10 (d, J=7.8 Hz, 1H), 6.77 (s, 1H), 5.47 (s, 2H), 4.46 (q, J=6.6 Hz, 1H), 3.17 (s, 3H), 1.45 (d, J=6.6 Hz, 3H).

Example 109: {(1R,2S,4R)-4-[(5-{[1-(3-bromobenzyl)-5-(2-hydroxypropan-2-yl)-1H-pyrazol-3-yl] carbonyl}pyrimidin-4-yl)amino]-2-hydroxycyclopentyl}methyl sulfamate I-367

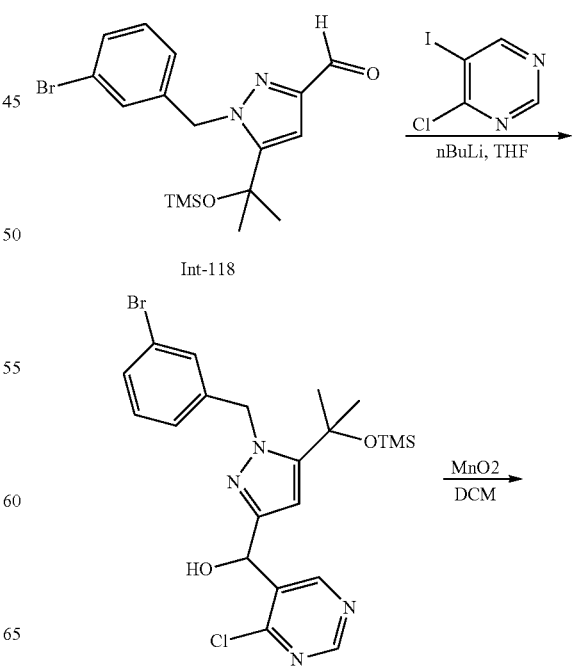

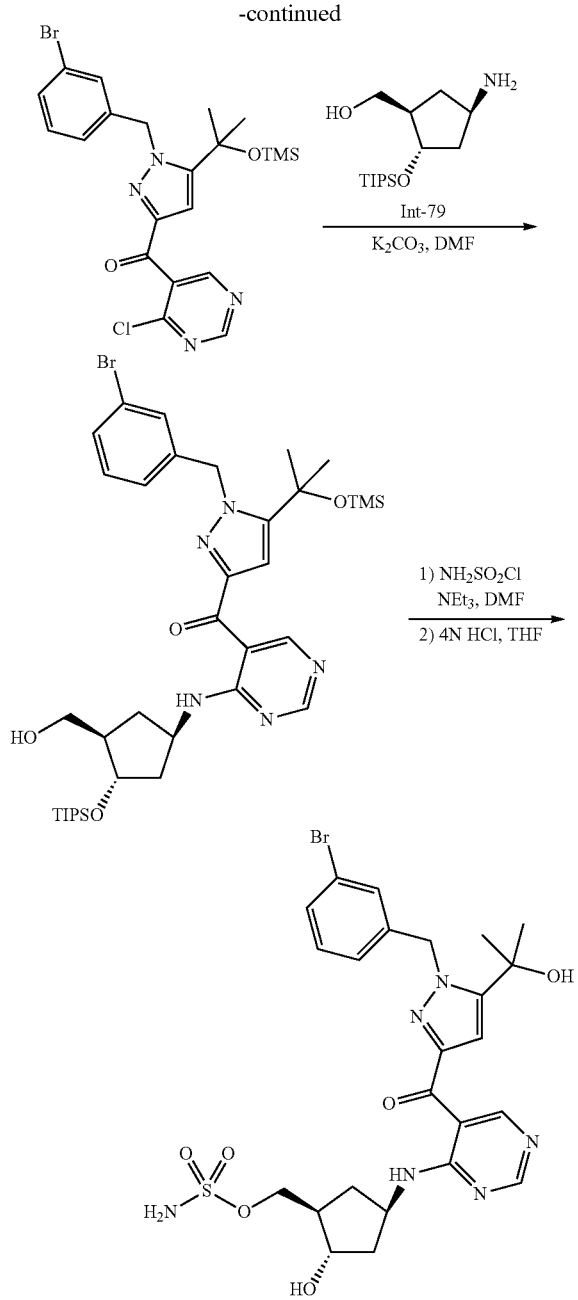

Step 1: [1-(3-Bromobenzyl)-5-{2-[(trimethylsilyl)oxy]propan-2-yl}-1H-pyrazol-3-yl](4-chloropyrimidin-5-yl)methanol Into a 1-neck round-bottom flask was added 4-chloro-5-iodopyrimidine (0.219 g, 0.911 mmol) dissolved in THF (4.0 mL), purged with argon and cooled to −78° C. with a dry-ice bath. To this solution was added dropwise a 2.50 M solution of n-butyllithium in hexane (0.728 mL, 1.82 mmol) at −78° C. and the mixture was stirred for 30 min. To this mixture was added 1-(3-bromobenzyl)-5-{2-[(trimethylsilyl)oxy]propan-2-yl}-1H-pyrazole-3-carbaldehyde (0.30 g, 0.759 mmol) dissolved in THF (2.0 mL) dropwise. The reaction was stirred at −78° C. for 1 h. The reaction was quenched with saturated NH₄Cl and extracted with EtOAc (3×). The combined organic layers were washed with water, brine, dried using Na₂SO₄, filtered and concentrated. The residue was purified by ISCO silica gel chromatography (24 g column, eluting with 0-30-50% EtOAc/Hex over 25 min) to give 0.217 g (56%) of the title compound. LCMS (FA): m/z=509.5 (M+H).

Step 2: [1-(3-Bromobenzyl)-5-{2-[(trimethylsilyl)oxy]propan-2-yl}-1H-pyrazol-3-yl](4-chloropyrimidin-5-yl)methanone To a solution of [1-(3-bromobenzyl)-5-{2-[(trimethylsilyl)oxy]propan-2-yl}-1H-pyrazol-3-yl](4-chloropyrimidin-5-yl)methanol (0.217 g, 0.426 mmol) in DCM (5.00 mL) was added manganese(IV) oxide (0.370 g, 4.26 mmol). The mixture was stirred at rt for 24 h. The reaction was filtered through a celite pad and the residual solid was washed with DCM several times. The filtrate was concentrated to give 0.192 g (89%) of crude [1-(3-bromobenzyl)-5-{2-[(trimethylsilyl)oxy]propan-2-yl}-1H-pyrazol-3-yl](4-chloropyrimidin-5-yl)methanone. LCMS (FA): m/z=507.1 (M+H).

Step 3: [1-(3-bromobenzyl)-5-{2-[(trimethylsilyl)oxy]propan-2-yl}-1H-pyrazol-3-yl][4-({(1R,3R,4S)-3-(hydroxymethyl)-4-[(triisopropylsilyl)oxy]cyclopentyl}amino)pyrimidin-5-yl]methanone Into a round bottom flask was added {(1R,2S,4R)-4-amino-2-[(triisopropylsilyl)oxy]cyclopentyl}methanol (0.163 g, 0.567 mmol) and crude [1-(3-bromobenzyl)-5-{2-[(trimethylsilyl)oxy]propan-2-yl}-1H-pyrazol-3-yl](4-chloropyrimidin-5-yl)methanone (0.192 g, 0.378 mmol). The contents were dissolved in DMF (4.00 mL) and potassium carbonate (0.157 g, 1.13 mmol) was added to the reaction vessel and resulting mixture was stirred at rt for 2 h. The reaction was diluted by addition of water and extracted with EtOAc (3×). The combined organic layers were dried over Na₂SO₄, filtered, and concentrated in vacuo. The residue was purified by ISCO silica gel chromatography (24 g column, eluting with 0-30% EtOAc/Hex over 25 min) to give 0.238 g (83%) of the title compound. ¹H NMR (400 MHz, Chloroform-d) δ 9.62 (s, 1H), 9.43 (s, 1H), 8.62 (s, 1H), 7.39 (d, J=8.1 Hz, 1H), 7.23-7.14 (m, 2H), 7.03-6.96 (m, 1H), 6.72 (s, 1H), 5.71 (s, 2H), 4.89-4.77 (m, 1H), 4.37-4.29 (m, 1H), 3.75-3.66 (m, 2H), 2.57-2.45 (m, 1H), 2.26-2.15 (m, 2H), 1.93-1.83 (m, 1H), 1.74-1.68 (m, 1H), 1.63 (s, 6H), 1.40-1.30 (m, 1H), 1.07 (s, 21H), 0.05 (s, 9H).

Step 4: {(1R,2S,4R)-4-[(5-{[1-(3-bromobenzyl)-5-{2-[(trimethylsilyl)oxy]propan-2-yl}-1H-pyrazol-3-yl]carbonyl}pyrimidin-4-yl)amino]-2-[(triisopropylsilyl)oxy]cyclopentyl}methyl sulfamate To a solution of [1-(3-bromobenzyl)-5-{2-[(trimethylsilyl)oxy]propan-2-yl}-1H-pyrazol-3-yl][4-({(1R,3R,4S)-3-(hydroxymethyl)-4-[(triisopropylsilyl)oxy]cyclopentyl}amino)pyrimidin-5-yl]methanone (0.238 g, 0.314 mmol) in DMF (4.50 mL) and triethylamine (0.131 mL, 0.941 mmol) was added chlorosulfonamide (72.47 mg, 0.627 mmol) at rt and the mixture was stirred for 2 h. The reaction was quenched with saturated NaHCO₃ and extracted with EtOAc (3×). The combined organic layers were washed with water, brine, dried using Na₂SO₄, filtered and concentrated to give crude {(1R,2S,4R)-4-[(5-{[1-(3-bromobenzyl)-5-{2-[(trimethylsilyl)oxy]propan-2-yl}-1H- pyrazol-3-yl]carbonyl}pyrimidin-4-yl)amino]-2-[(triisopropylsilyl)oxy]cyclopentyl}methyl sulfamate. LCMS (FA): m/z=837.9 (M+H).

Step 5: {(1R,2S,4R)-4-[(5-{[1-(3-bromobenzyl)-5-(2-hydroxypropan-2-yl)-1H-pyrazol-3-yl]carbonyl}pyrimidin-4-yl)amino]-2-hydroxycyclopentyl}methyl sulfamate I-367

To a solution of crude {(1R,2S,4R)-4-[(5-{[1-(3-bromobenzyl)-5-{2-[(trimethylsilyl)oxy]propan-2-yl}-1H-pyrazol-3-yl]carbonyl}pyrimidin-4-yl)amino]-2-[(triisopropylsilyl)oxy]cyclopentyl}methyl sulfamate. (0.263 g, 0.314 mmol) in THF (6.00 mL) was added a 4.0 M solution of hydrochloric acid in water (3.00 mL, 12.0 mmol) at rt and the mixture was stirred for 24 h. The reaction was quenched by addition of saturated NaHCO$_3$ and extracted with EtOAc (4×). The combined organic layers were dried over Na$_2$SO$_4$, filtered, and concentrated in vacuo. The residue was purified by ISCO silica gel chromatography (24 g column, eluting with 0-10-20% MeOH/DCM over 20 min) to give 0.142 g (74%, over 2 steps) of product. $^1$H NMR (400 MHz, DMSO-d$_6$) δ 9.37 (s, 1H), 9.00 (d, J=7.3 Hz, 1H), 8.60 (s, 1H), 7.51-7.38 (m, 4H), 7.31 (t, J=7.9 Hz, 1H), 7.15 (d, J=7.7 Hz, 1H), 6.74 (s, 1H), 5.78 (s, 2H), 5.67 (s, 1H), 4.97-4.88 (m, 1H), 4.76-4.63 (m, 1H), 4.10 (dd, J=9.7, 5.9 Hz, 1H), 4.01-3.93 (m, 2H), 2.41-2.31 (m, 1H), 2.17-2.08 (m, 1H), 2.04-1.95 (m, 1H), 1.82-1.72 (m, 1H), 1.51 (s, 6H), 1.27 (dt, J=12.9, 9.1 Hz, 1H); LCMS: (FA) M+1 610.2.

The compounds listed in the table below were prepared using a similar method to that described above starting from the listed starting aldehyde. I-369a and I-369b were made as a diasteromeric mixture (I-369) and then separated via HPLC (chiral chromatography).

| Starting aldehyde | Compound No. | LCMS Data |
|---|---|---|
| Int-119 | I-368 | LCMS (FA): m/z = 595.6 (M + H). |
| Int-120 | I-369 | LCMS (FA): m/z = 609.5 (M + H). |
| Int-120 | I-369a | LCMS (FA): m/z = 609.5 (M + H). |
| Int-120 | I-369b | LCMS (FA): m/z = 609.5 (M + H). |

Example 110: tert-Butyl [(1S,2R,3R,5R)-5-amino-2-hydroxy-3-(hydroxymethyl)cyclopentyl]carbamate Int-121

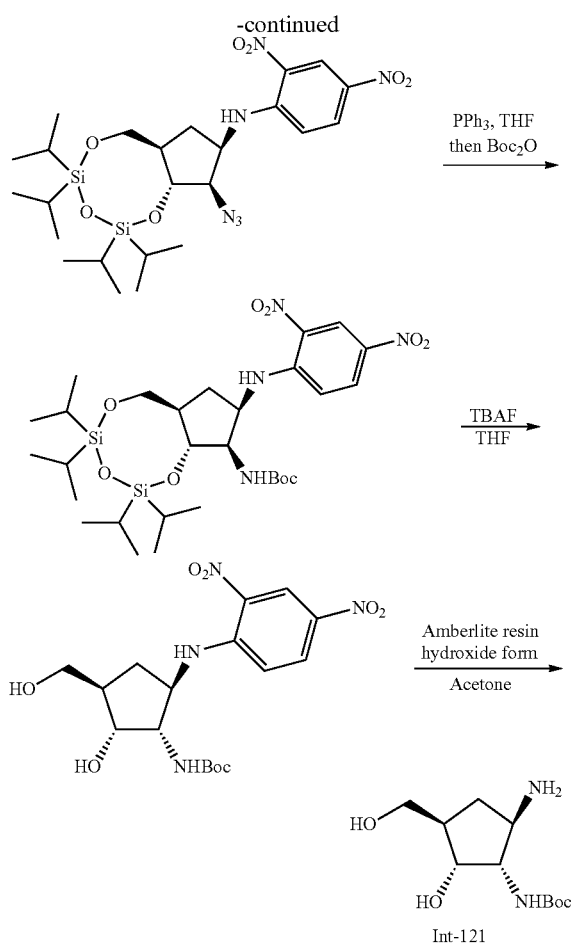

Step 1: (6aR,8R,9R,9aR)-8-[(2,4-Dinitrophenyl)amino]-2,2,4,4-tetraisopropylhexahydrocyclopenta[f][1,3,5,2,4]trioxadisilocin-9-yl methanesulfonate To a solution of (6aR,8R,9R,9aR)-8-[(2,4-dinitrophenyl)amino]-2,2,4,4-tetraisopropylhexahydrocyclopenta[f][1,3,5,2,4]trioxadisilocin-9-ol (G) (1.00 g, 1.80 mmol) (for synthesis see: Biggadike, K. et al. *J. Chem. Soc. Perkin Trans.* 1988, 3, 549-554; Borthwick, A. D. et al. *J. Med. Chem.* 1990, 33, 179-186) in DCM (10.00 mL) was added triethylamine (0.263 mL, 1.89 mmol) and N,N-dimethylaminopyridine (0.231 g, 1.89 mmol). The reaction mixture was cooled (ice water bath) and a solution of methanesulfonyl chloride (216 mg, 1.89 mmol) in DCM (1.0 mL) was added dropwise. The reaction was allowed to warm to rt and was complete after 4 h. Water was added and the mixture was extracted with DCM (3×). The combined organics were dried with anhydrous magnesium sulfate, filtered, and evaporated. The residue was purified by ISCO silica gel chromatography (40 g column, eluting with 10-40% EtOAc/Hex over 20 min) to give 1.12 g (98%) of the title compound. LCMS (FA): m/z=632.2 (M-H).

Step 2: (6aR,8R,9S,9aR)-9-Azido-N-(2,4-dinitrophenyl)-2,2,4,4-tetraisopropylhexahydrocyclopenta[f][1,3,5,2,4]trioxadisilocin-8-amine To a solution of (6aR,8R,9R,9aR)-8-[(2,4-dinitrophenyl)amino]-2,2,4,4-tetraisopropylhexahydrocyclopenta[f][1,3,5,2,4]trioxadisilocin-9-yl methanesulfonate (1.00 g, 1.58 mmol) in DMF (5.0 mL) was added 15-crown-5 (157 uL, 0.789 mmol) followed by sodium azide (0.513 g, 7.89 mmol) and the reaction was heated to 90° C. for 6 h. The reaction was allowed to cool to rt, diluted with water and extracted with EtOAc (3×). The combined organics were dried with anhydrous magnesium sulfate, filtered, and evaporated. The residue was purified by ISCO silica gel chromatography (24 g column, eluting with 10-25% EtOAc/Hex over 20 min) to give 0.38 g (41%) of product. LCMS (FA): m/z=579.2 (M-H)

Step 3: tert-Butyl {(6aR,8R,9S,9aR)-8-[(2,4-dinitrophenyl)amino]-2,2,4,4-tetraisopropylhexahydrocyclopenta[f][1,3,5,2,4]trioxadisilocin-9-yl}carbamate To a solution of (6aR,8R,9S,9aR)-9-azido-N-(2,4-dinitrophenyl)-2,2,4,4-tetraisopropylhexahydrocyclopenta[f][1,3,5,2,4]trioxadisilocin-8-amine (275.0 mg, 0.474 mmol) in THF (4.4 mL) was added triphenylphosphine (149 mg, 0.568 mmol) and the reaction stirred for 1 h. Added water (0.82 mL, 46 mmol) and heated the reaction to 60° C. for 4 h. The reaction was allowed to cool to rt and di-tert-butyldicarbonate (258 mg, 1.18 mmol) was added. The resulting mixture was stirred at rt for 3 days. The reaction mixture was concentrated to dryness and the residue was purified by ISCO silica gel chromatography (24 g column, eluting with 5-25% EtOAc/Hex over 20 min) to give 0.290 g (94%) of the title compound. LCMS (FA): m/z=653.4 (M-H).

Step 4: tert-Butyl [(1S,2R,3R,5R)-5-[(2,4-dinitrophenyl)amino]-2-hydroxy-3-(hydroxymethyl)cyclopentyl]carbamate To a solution of tert-butyl {(6aR,8R,9S,9aR)-8-[(2,4-dinitrophenyl)amino]-2,2,4,4-tetraisopropylhexahydrocyclopenta[f][1,3,5,2,4]trioxadisilocin-9-yl}carbamate (280 mg, 0.43 mmol) in THF (10 mL) was added tetra-n-butylammonium fluoride (224 mg, 0.855 mmol). The reaction was stirred at rt for 2 h. The reaction was quenched with water and extracted with EtOAc (3×). The combined organic layers were dried, filtered, and concentrated. The residue was purified by ISCO silica gel chromatography (24 g column, eluting with 0-10% MeOH/DCM over 20 min) to give 0.170 g (96%) of the title compound. LCMS (FA): m/z=411.2 (M-H).

Step 5: tert-Butyl [(1S,2R,3R,5R)-5-amino-2-hydroxy-3-(hydroxymethyl)cyclopentyl]carbamate Int-121

Amberlite resin (hydroxide form) was freshly prepared by mixing with large excess of 1N sodium hydroxide for 5 min, decanting and washing the resin with water until neutral, followed by washing with acetone. To a solution of tert-butyl [(1S,2R,3R,5R)-5-[(2,4-dinitrophenyl)amino]-2-hydroxy-3-(hydroxymethyl)cyclopentyl]carbamate (75 mg, 0.18 mmol) in acetone (5.0 mL) was added amberlite resin hydroxide form (2.0 g). The reaction was agitated overnight. The reaction was filtered to remove resin, washed resin with acetone and evaporated filtrate to dryness. The crude residue was dissolved in EtOAc and partitioned with 0.05N HCl. The organic layer removed color. Re-extracted organic layer with 0.1N HCl and lyophilized aqueous layer. The residue was purified by reverse phase prep HPLC to give 0.011 g (24%) of Int-121. $^1$H NMR (400 MHz, Methanol-$d_4$) δ 8.54

(s, 2H), 4.01-3.94 (m, 1H), 3.86-3.78 (m, 1H), 3.63-3.53 (m, 2H); 3.53-3.42 (m, 1H), 2.37-2.24 (m, 1H), 2.18-2.07 (m, 1H), 1.47 (s, 9H), 1.47-1.36 (m, 1H).

Example 111: {(1R,2R,3S,4R)-3-amino-4-[(5-{[1-(3-bromobenzyl)-1H-pyrazol-3-yl]carbonyl}pyrimidin-4-yl)amino]-2-hydroxycyclopentyl}methyl sulfamate.2[HCl] I-370

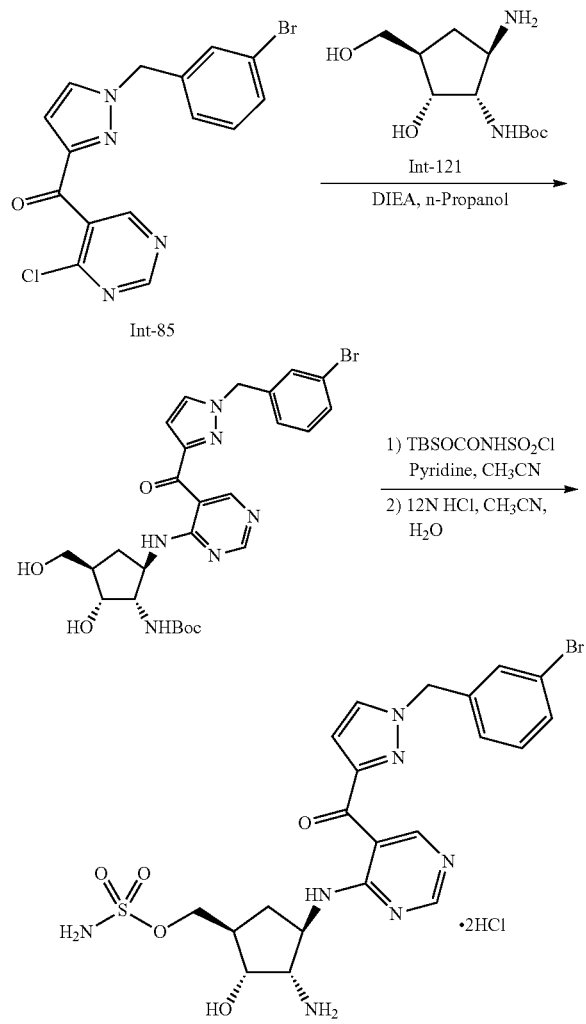

Step 1: tert-Butyl [(1S,2R,3R,5R)-5-[(5-{[1-(3-bromobenzyl)-1H-pyrazol-3-yl]carbonyl}pyrimidin-4-yl)amino]-2-hydroxy-3-(hydroxymethyl)cyclopentyl]carbamate

[1-(3-bromobenzyl)-1H-pyrazol-3-yl](4-chloropyrimidin-5-yl)methanone (184.0 mg, 0.487 mmol) and tert-butyl [(1S,2R,3R,5R)-5-amino-2-hydroxy-3-(hydroxymethyl)cyclopentyl]carbamate (Int-121) (100.0 mg, 0.406 mmol) were weighed into a sealed tube. To this mixture was added n-propanol (4.0 mL) and N,N-diisopropylethylamine (0.177 mL, 1.02 mmol). The resulting mixture was stirred in a sealed vessel at 60° C. for 3 days. The reaction was cooled to rt and the reaction was concentrated in vacuo. The reaction mixture was taken up in EtOAc, washed with 0.1N HCl, brine, and concentrated. The residue was purified by ISCO silica gel chromatography (24 g column, eluting with 40-75-100% EtOAc/Hex over 20 min) to give 0.108 g (45%) of the title compound. LCMS (FA): m/z=589.1 (M+H).

Step 2: tert-Butyl {(1S,2R,3R,5R)-5-[(5-{[1-(3-bromobenzyl)-1H-pyrazol-3-yl]carbonyl}pyrimidin-4-yl)amino]-2-hydroxy-3-[(sulfamoyloxy)methyl]cyclopentyl}carbamate Preparation of a 0.50 M solution of tert-butyl(dimethyl)silyl(chlorosulfonyl)carbamate: To a solution of chlorosulfonyl isocyanate (0.500 mL, 5.74 mmol) in acetonitrile (11.50 mL) at 0° C. was added tert-butyldimethylsilanol (0.940 mL, 5.97 mmol). The addition was dropwise while maintaining the temperature below 10° C. Upon completion of the addition the reaction was stirred at 0° C. for 30 min and the solution was ready for use as a 0.50 M solution. To a suspension of tert-butyl [(1S,2R,3R,5R)-5-[(5-{[1-(3-bromobenzyl)-1H-pyrazol-3-yl]carbonyl}pyrimidin-4-yl)amino]-2-hydroxy-3-(hydroxymethyl)cyclopentyl]carbamate (80.0 mg, 0.136 mmol) in acetonitrile (8.0 mL) and pyridine (13.77 uL, 0.170 mmol) cooled in an ice water bath was added a 0.50 M solution of tert-butyl(dimethyl)silyl(chlorosulfonyl)carbamate (0.34 mL, 0.170 mmol). After stirring for 10 min, the reaction was allowed to warm up to rt. Starting material still remained, thus the reaction was again placed in an ice water bath and an additional 0.50 M solution of tert-butyl(dimethyl)silyl(chlorosulfonyl)carbamate (0.34 mL, 0.170 mmol) was added. The reaction was allowed to warm to rt slowly. The reaction was quenched with a saturated NaHCO$_3$ solution and extracted into EtOAc (3×). The combined organics were washed with brine and concentrated. The residue was purified by ISCO silica gel chromatography (12 g column, eluting with 0-5% MeOH/DCM over 10 min) to give 20 mg of impure product. This material was then purified via reverse phase prep HPLC to give 10 mg (11%) of the title compound. LCMS (FA): m/z=666.1 (M+H).

Step 3: {(1R,2R,3S,4R)-3-Amino-4-[(5-{[1-(3-bromobenzyl)-1H-pyrazol-3-yl]carbonyl}pyrimidin-4-yl)amino]-2-hydroxycyclopentyl}methyl sulfamate.2[HCl] I-370

To water (1.0 mL) was added a 12.0 M solution of hydrochloric acid in water (0.40 mL, 4.8 mmol) and 0.4 mL of this solution was added to a stirred solution of tert-butyl {(1S,2R,3R,5R)-5-[(5-{[1-(3-bromobenzyl)-1H-pyrazol-3-yl]carbonyl}pyrimidin-4-yl)amino]-2-hydroxy-3-[(sulfamoyloxy)methyl]cyclopentyl}carbamate (5.0 mg, 0.008 mmol) in CH$_3$CN (0.20 mL). The reaction was stirred for 1 hr. The crude reaction mixture was lyophilized and purified by reverse phase prep HPLC to give 4.80 mg (100%) of I-370 as the bis-hydrochloride salt. $^1$H NMR (400 MHz, Methanol-d$_4$) δ 9.96 (s, 1H), 8.90 (s, 1H), 7.95 (s, 1H), 7.53-7.42 (m, 2H), 7.35-7.24 (m, 2H), 7.10 (s, 1H), 5.52 (s, 2H), 5.22-5.09 (m, 1H), 4.33-4.20 (m, 2H), 3.85-3.70 (m, 1H), 2.61-2.42 (m, 2H), 2.02-1.71 (m, 2H)); LCMS (FA): m/z=566.4 (M+H)

Example 112: SAE HTRF Enzyme Assay

The SAE enzymatic reaction totals 50 μl and contains 50 mM HEPES Hemisodium (pH 7.5), 0.05% BSA, 5 mM MgCl$_2$, 0.5 μM ATP, 250 μM GSH, 0.01 μM Ubc9-GST, 0.125 μM Sumo-Flag and 0.11 nM recombinant human SAE enzyme. The enzymatic reaction mixture with and without inhibitor, Is incubated at 24° C. for 105 min in a 384-well plate before termination with 25 M of Stop/Detection buffer (0.1M HEPES Hemisodium pH 7.5, 0.05% Tween20, 20 mM EDTA, 410 mM KF, 0.53 nM Europium-Cryptate labeled monoclonal anti-Flag M2 Antibody (CisBio International) and 8.125 µg/ml PHYCOLINK goat anti-GST allophycocyanin (XL-APC) antibody (Prozyme)). After incubation for 2 hours at 24° C., quantification of FRET is performed on the Pherostar™ (BMG Labtech). Percentage inhibition values at a single concentration or enzyme inhibition ($IC_{50}$) values are determined from those curves. One skilled in the art will appreciate that the values generated either as percentage inhibition at a single concentration or $IC_{50}$ values are subject to experimental variation.

Example 113: Cell Viability Assay

The cell viability assay is used to measure the effect of various compounds on cancer cell proliferation. Promega's CellTiter-Glo® Luminescent Cell Viability Assay is used to measure ATP concentration present in all metabolically active cells and the concentration declines rapidly when cells undergo necrosis or apoptosis.

The cancer cell lines of interest are propagated in recommended growth medium (Invitrogen) containing 10% Fetal Bovine Serum (Hyclone or ATCC) and 100 I.U. Penicillin/ 100 µg/mL Streptomycin (Invitrogen) and kept in tissue culture incubator at 37° C. with 5% $CO_2$. On day 1, attached cells are trypsinized with 4.5 mL of 0.25% Trypsin-EDTA (Invitrogen) at 37° C. for 2 minutes or until cells have detached. Suspension cells are collected and washed. Desired number of cells are cultured in 25 µL of media per well in tissue culture-treated black-walled, clear bottom 384-well plates (BD Biosciences) for 16-24 hours. The exact number of cells per well are optimized for each individual cell line. On day 2, 62.5 nL test compounds in DMSO (ranging from 10 mM to 508 uM in 10 point 3-fold dilution series) are directly added to cells in 384-well plate using Echo liquid handler (Labcyte). This results in a final concentration range of 0.0013 to 25 µM in 3-fold dilutions in the cell plates. On day 5 after 72 hour of incubation in tissue culture incubator, 25 µL CellTiter-Glo® (Promega) are added to the compound treated cell plates. The cell plates are incubated at room temperature for 15 min and then read luminescence on Pherastar plate reader (BMG). The test compound concentration versus cell viability curves are generated using percentage of survival calculated from luminescence readout relative to DMSO and media only controls. The percentage growth inhibition values at a single concentration ($LD_{50}$) values are determined from the curves.

Example 114: In Vivo Tumor Efficacy Model

SAE inhibitors are tested for their ability to inhibit tumor growth in standard xenograft tumor models.
For example, HCT-116 cells ($1\times10^6$) in 100 µL of phosphate buffered saline are aseptically injected into the subcutaneous space in the right dorsal flank of female CD-1 nude mice (age 5-8 weeks, Charles River) using a 23-ga needle. Beginning at day 7 after inoculation, tumors are measured twice weekly using a vernier caliper. Tumor volumes are calculated using standard procedures ($0.5 \times length \times width^2$). When the tumors reach a volume of approximately 200 $mm^3$, mice are randomized by tumor volume into treatment groups and injected subcutaneously with test compound (300 µL) at various doses and schedules. All control groups receive vehicle alone. Tumor size and body weight are measured twice a week, and the study is terminated when the control tumors reach approximately 2000 $mm^3$. Analogous procedures are followed for colon (colo205 or HCT-116 cells), AML (THP-1 or HL-60 cells), DLBCL (Ly10 or WSU-DLCL2), melanoma (A375 or A2058 cells) and lung (H460 cells) tumor models.

As detailed above, compounds of the invention inhibit SAE. In certain embodiments, compounds of the invention inhibit SAE with the percent inhibition at the concentrations shown in the table below. In certain embodiments, compounds of the invention inhibit SAE with the $IC_{50}$ values shown in the table below.

| Compound | Concentration (µM) | Percent Inhibition | IC50 (µM) |
|---|---|---|---|
| I-1 | 0.111 | 98 | A |
| I-2 | 0.111 | 99 | A |
| I-3 | 0.111 | 98 | A |
| I-4 | 0.111 | 80 | B |
| I-5 | 0.111 | 89 | B |
| I-6 | 0.111 | 99 | A |
| I-7 | 0.111 | 99 | A |
| I-8 | 0.111 | 99 | A |
| I-9 | 0.111 | 91 | B |
| I-10 | 0.111 | 61 | B |
| I-11 | 0.111 | 100 | A |
| I-12 | 0.111 | 39 | C |
| I-13 | 0.111 | 100 | A |
| I-14 | 0.111 | 98 | A |
| I-15 | 0.111 | 98 | A |
| I-16 | 0.111 | 98 | A |
| I-17 | 0.111 | 99 | A |
| I-18 | 0.111 | 96 | A |
| I-19 | 0.111 | 20 | C |
| I-20 | 0.111 | 96 | A |
| I-21 | 0.111 | 99 | A |
| I-22 | 0.111 | 100 | A |
| I-23 | 0.111 | 98 | A |
| I-24 | 0.111 | 100 | A |
| I-25 | 0.111 | 93 | A |
| I-26 | 0.111 | 90 | B |
| I-27 | 0.111 | 9 | C |
| I-28 | 0.111 | 78 | B |
| I-29 | 0.111 | 94 | B |
| I-30 | 0.111 | 66 | B |
| I-31 | 0.111 | 94 | A |
| I-32 | 0.111 | 98 | A |
| I-33 | 0.111 | 98 | A |
| I-34 | 0.111 | 99 | A |
| I-35 | 0.111 | 95 | A |
| I-36 | 0.111 | 99 | A |
| I-37 | 0.111 | 42 | C |
| I-38 | 0.111 | 51 | C |
| I-39 | 0.111 | 98 | A |
| I-40 | 0.111 | 97 | A |
| I-41 | 0.111 | 94 | A |
| I-42 | 0.111 | 99 | A |
| I-43 | 0.111 | 98 | A |
| I-44 | 0.111 | 99 | A |
| I-45 | 0.111 | 93 | B |
| I-46 | 0.111 | 96 | A |
| I-47 | 0.111 | 98 | A |
| I-48 | 0.111 | 96 | A |
| I-49 | 0.111 | 93 | A |
| I-50 | 0.111 | 99 | A |
| I-51 | 0.111 | 100 | A |
| I-52 | 0.111 | 99 | A |
| I-53 | 0.111 | 79 | B |
| I-54 | 0.111 | 63 | B |
| I-55 | 0.111 | 58 | B |
| I-56 | 0.111 | 100 | A |
| I-57 | 0.111 | 98 | A |
| I-58 | 0.111 | 88 | A |
| I-59 | 0.111 | 70 | B |
| I-60 | 0.111 | 91 | B |

| Compound | Concentration (μM) | Percent Inhibition | IC50 (μM) |
|---|---|---|---|
| I-61 | 0.111 | 99 | A |
| I-62 | 0.111 | 96 | A |
| I-63 | 0.111 | 87 | B |
| I-64 | 0.111 | 91 | B |
| I-65 | 0.111 | 99 | A |
| I-66 | 0.111 | 98 | A |
| I-67 | 0.111 | 94 | A |
| I-68 | 0.111 | 99 | A |
| I-69 | 0.111 | 39 | C |
| I-70 | 0.111 | 99 | A |
| I-71 | 0.111 | 100 | A |
| I-72 | 0.111 | 100 | A |
| I-73 | 0.111 | 94 | A |
| I-74 | 0.111 | 92 | A |
| I-75 | 0.111 | 68 | B |
| I-76 | 0.111 | 80 | B |
| I-77 | 0.111 | 51 | C |
| I-78 | 0.111 | 97 | A |
| I-79 | 0.111 | 98 | A |
| I-80 | 0.111 | 96 | A |
| I-81 | 0.111 | 98 | A |
| I-82 | 0.111 | 96 | A |
| I-83 | 0.111 | 88 | B |
| I-84 | 0.111 | 95 | A |
| I-85 | 0.111 | 98 | A |
| I-86 | 0.111 | 35 | C |
| I-87 | 0.111 | >99 | A |
| I-88 | 0.111 | >99 | A |
| I-89 | 0.111 | 98 | A |
| I-90 | 0.111 | 98 | A |
| I-91 | 0.111 | 98 | A |
| I-92 | 0.111 | 99 | A |
| I-93 | 0.111 | 90 | A |
| I-94 | 0.111 | 97 | A |
| I-95 | 0.111 | 99 | A |
| I-96 | 0.111 | 98 | A |
| I-97 | 0.111 | 96 | A |
| I-98 | 0.111 | 96 | A |
| I-99 | 0.111 | >99 | A |
| I-100 | 0.111 | 98 | A |
| I-101 | 0.111 | 100 | A |
| I-102 | 0.111 | 97 | A |
| I-103 | 0.111 | 97 | A |
| I-104 | 0.111 | 100 | A |
| I-105 | 0.111 | 18 | C |
| I-106 | 0.111 | >99 | A |
| I-107 | 0.111 | 70 | B |
| I-108 | 0.111 | 18 | C |
| I-109 | 0.111 | 76 | B |
| I-110 | 0.111 | 99 | A |
| I-111 | 0.111 | 91 | A |
| I-112 | 0.111 | 97 | A |
| I-113 | 0.111 | 81 | B |
| I-114 | 0.111 | 98 | A |
| I-115 | 0.111 | 33 | C |
| I-116 | 0.111 | 33 | C |
| I-117 | 0.111 | 98 | A |
| I-118 | 0.111 | 99 | A |
| I-119 | 0.111 | 98 | A |
| I-120 | 0.111 | 47 | C |
| I-121 | 0.111 | 94 | A |
| I-122 | 0.111 | 99 | A |
| I-123 | 0.111 | 100 | A |
| I-124 | 0.111 | 97 | A |
| I-125 | 0.111 | 99 | A |
| I-126 | 0.111 | >99 | A |
| I-127 | 0.111 | 99 | A |
| I-128 | 0.111 | 98 | A |
| I-129 | 0.111 | 99 | A |
| I-130 | 0.111 | 98 | A |
| I-131 | 0.111 | 96 | A |
| I-132 | 0.111 | 78 | B |
| I-133 | 0.111 | 61 | B |
| I-134 | 0.111 | 98 | A |
| I-135 | 0.111 | 81 | B |
| I-136 | 0.111 | 88 | B |
| I-137 | 0.111 | 78 | B |
| I-138 | 0.111 | 99 | A |
| I-139 | 0.111 | 86 | A |
| I-140 | 0.111 | 98 | A |
| I-141 | 0.111 | 99 | A |
| I-142 | 0.111 | 99 | A |
| I-143 | 0.111 | 99 | A |
| I-144 | 0.111 | 97 | A |
| I-145 | 0.111 | 65 | B |
| I-146 | 0.111 | 99 | A |
| I-147 | 0.111 | >99 | A |
| I-148 | 0.111 | 85 | B |
| I-149 | 0.111 | 85 | B |
| I-150 | 0.111 | 98 | A |
| I-151 | 0.111 | 54 | B |
| I-152 | 0.111 | 94 | A |
| I-153 | 0.111 | 82 | B |
| I-154 | 0.111 | 39 | C |
| I-155 | 0.111 | 97 | A |
| I-156 | 0.111 | 90 | B |
| I-157 | 0.111 | 67 | B |
| I-158 | 0.111 | 95 | A |
| I-159 | 0.111 | 96 | A |
| I-160 | 0.111 | 81 | B |
| I-161 | 0.111 | 92 | A |
| I-162 | 0.111 | 99 | A |
| I-163 | 0.111 | 98 | A |
| I-164 | 0.111 | >99 | A |
| I-165 | 0.111 | 98 | A |
| I-166 | 0.111 | 98 | A |
| I-167 | 0.111 | 98 | A |
| I-168 | 0.111 | 94 | A |
| I-169 | 0.111 | 97 | A |
| I-170 | 0.111 | 97 | A |
| I-171 | 0.111 | 95 | A |
| I-172 | 0.111 | 83 | B |
| I-173 | 0.111 | 71 | B |
| I-174 | 0.111 | 93 | A |
| I-175 | 0.111 | 99 | A |
| I-176 | 0.111 | 98 | A |
| I-177 | 0.111 | 99 | A |
| I-178 | 0.111 | 99 | A |
| I-179 | 0.111 | >99 | A |
| I-180 | 0.111 | 99 | A |
| I-181 | 0.111 | 94 | A |
| I-182 | 0.111 | 96 | A |
| I-183 | 0.111 | 96 | A |
| I-184 | 0.111 | 97 | A |
| I-185 | 0.111 | 91 | A |
| I-186 | 0.111 | >99 | A |
| I-187 | 0.111 | 99 | A |
| I-188 | 0.111 | 98 | A |
| I-189 | 0.111 | 100 | A |
| I-190 | 0.111 | 98 | A |
| I-191 | 0.111 | 92 | A |
| I-192 | 0.111 | 98 | A |
| I-193 | 0.111 | 99 | A |
| I-194 | 0.111 | 100 | A |
| I-195 | 0.111 | 90 | B |
| I-196 | 0.111 | 33 | C |
| I-197 | 0.111 | 99 | A |
| I-198 | 0.111 | >99 | A |
| I-199 | 0.111 | 94 | A |
| I-200 | 0.111 | 98 | A |
| I-201 | 0.111 | 98 | A |
| I-202 | 0.111 | 83 | B |
| I-203 | 0.111 | 94 | A |
| I-204 | 0.111 | 99 | A |
| I-205 | 0.111 | 60 | B |
| I-206 | 0.111 | 96 | A |
| I-207 | 0.111 | 99 | A |
| I-208 | 0.111 | 95 | A |
| I-209 | 0.111 | 99 | A |
| I-210 | 0.111 | 98 | A |
| I-211 | 0.111 | 97 | A |
| I-212 | 0.111 | 95 | A |

| Compound | Concentration (μM) | Percent Inhibition | IC50 (μM) |
|---|---|---|---|
| I-213 | 0.111 | 97 | A |
| I-214 | 0.111 | 98 | A |
| I-215 | 0.111 | 99 | A |
| I-216 | 0.111 | 97 | A |
| I-217 | 0.111 | 98 | A |
| I-218 | 0.111 | 89 | B |
| I-219 | 0.111 | 99 | A |
| I-220 | 0.111 | 57 | B |
| I-221 | 0.111 | 100 | A |
| I-222 | 0.111 | 63 | B |
| I-223 | 0.111 | 99 | A |
| I-224 | 0.111 | 99 | A |
| I-225 | 0.111 | >99 | A |
| I-226 | 0.111 | 85 | B |
| I-227 | 0.111 | 97 | A |
| I-228 | 0.111 | 72 | B |
| I-229 | 0.111 | 88 | B |
| I-230 | 0.111 | 98 | A |
| I-231 | 0.111 | 99 | A |
| I-232 | 0.111 | 97 | A |
| I-233 | 0.111 | 98 | A |
| I-234 | 0.111 | 91 | B |
| I-235 | 0.111 | 100 | A |
| I-236 | 0.111 | 54 | B |
| I-237 | 0.111 | 85 | B |
| I-238 | 0.111 | 99 | A |
| I-239 | 0.111 | 99 | A |
| I-240 | 0.111 | 100 | A |
| I-241 | 0.111 | 98 | A |
| I-242 | 0.111 | 96 | A |
| I-243 | 0.111 | 99 | A |
| I-244 | 0.111 | 98 | A |
| I-245 | 0.111 | 100 | A |
| I-246 | 0.111 | 97 | A |
| I-247 | 0.111 | 90 | A |
| I-248 | 0.111 | 99 | A |
| I-249 | 0.111 | 97 | A |
| I-250 | 0.111 | 86 | B |
| I-251 | 0.111 | 71 | B |
| I-252 | 0.111 | 97 | A |
| I-253 | 0.111 | 91 | B |
| I-254 | 0.111 | 99 | A |
| I-255 | 0.111 | 97 | A |
| I-256 | 0.111 | 99 | A |
| I-257 | 0.111 | 98 | A |
| I-258 | 0.111 | 97 | A |
| I-259 | 0.111 | 95 | A |
| I-260 | 0.111 | 91 | A |
| I-261 | 0.111 | 97 | A |
| I-262 | 0.111 | 96 | A |
| I-263 | 0.111 | 91 | A |
| I-264 | 0.111 | 90 | B |
| I-265 | 0.111 | 95 | A |
| I-266 | 0.111 | 87 | B |
| I-267 | 0.111 | 97 | A |
| I-268 | 0.111 | 99 | A |
| I-269 | 0.111 | 96 | A |
| I-270 | 0.111 | 87 | B |
| I-271 | 0.111 | 97 | A |
| I-272 | 0.111 | 99 | A |
| I-273 | 0.111 | 98 | A |
| I-274 | 0.111 | 97 | A |
| I-275 | 0.111 | 18 | C |
| I-276 | 0.111 | 82 | B |
| I-277 | 0.111 | 99 | A |
| I-278 | 0.111 | 97 | A |
| I-279 | 0.111 | 98 | A |
| I-280 | 0.111 | 99 | A |
| I-281 | 0.111 | 25 | C |
| I-282 | 0.111 | 100 | A |
| I-283 | 0.111 | 97 | A |
| I-284 | 0.111 | 100 | A |
| I-285 | 0.111 | 99 | A |
| I-286 | 0.111 | 93 | A |
| I-287 | 0.111 | 95 | A |
| I-288 | 0.111 | 97 | A |
| I-289 | 0.111 | 98 | A |
| I-290 | 0.111 | 99 | A |
| I-291 | 0.111 | 79 | B |
| I-292 | 0.111 | 98 | A |
| I-293 | 0.111 | 38 | C |
| I-294 | 0.111 | 100 | A |
| I-295 | 0.111 | 96 | A |
| I-296 | 0.111 | 100 | A |
| I-297 | 0.111 | 97 | A |
| I-298 | 0.111 | 97 | A |
| I-299 | 0.111 | 99 | A |
| I-300 | 0.111 | 97 | A |
| I-301 | 0.111 | 97 | A |
| I-302 | 0.111 | 34 | C |
| I-303 | 0.111 | 99 | A |
| I-304 | 0.111 | 91 | B |
| I-305 | 0.111 | 32 | C |
| I-306 | 0.111 | 99 | A |
| I-307 | 0.111 | 98 | A |
| I-308 | 0.111 | 27 | C |
| I-309 | 0.111 | 100 | A |
| I-310 | 0.111 | 98 | A |
| I-311 | 0.111 | 98 | A |
| I-312 | 0.111 | 99 | A |
| I-313 | 0.111 | 95 | A |
| I-314 | 0.111 | 97 | A |
| I-315 | 0.111 | 99 | A |
| I-316 | 0.111 | 94 | A |
| I-317 | 0.111 | 96 | A |
| I-318 | 0.111 | 95 | A |
| I-319 | 0.111 | 99 | A |
| I-320 | 0.111 | 98 | A |
| I-321 | 0.111 | 89 | B |
| I-322 | 0.111 | 99 | A |
| I-323 | 0.111 | 82 | B |
| I-324 | 0.111 | 100 | A |
| I-325 | 0.111 | 99 | A |
| I-326 | 0.111 | 95 | A |
| I-327 | 0.111 | 99 | A |
| I-328 | 0.111 | 65 | B |
| I-329 | 0.111 | 93 | A |
| I-330 | 0.111 | 82 | B |
| I-331 | 0.111 | 99 | A |
| I-332 | 0.111 | 16 | C |
| I-333 | 0.111 | 99 | A |
| I-334 | 0.111 | 98 | A |
| I-335 | 0.111 | 97 | A |
| I-336 | 0.111 | 97 | A |
| I-337 | 0.111 | 98 | A |
| I-338 | 0.111 | 99 | A |
| I-339 | 0.111 | 93 | A |
| I-340 | 0.111 | 94 | A |
| I-341 | 0.111 | 98 | A |
| I-342 | 0.111 | 79 | B |
| I-343 | 0.111 | 97 | A |
| I-344 | 0.111 | 77 | B |
| I-345 | 0.111 | 54 | C |
| I-346 | 0.111 | 100 | A |
| I-347 | 0.111 | >99 | A |
| I-348 | 0.111 | 94 | A |
| I-349 | 0.111 | 100 | A |
| I-350 | 0.111 | 96 | A |
| I-351 | 0.111 | 97 | A |
| I-352 | 0.111 | 99 | A |
| I-353 | 0.111 | 90 | B |
| I-354 | 0.111 | 79 | B |
| I-355 | 0.111 | 99 | A |
| I-356 | 0.111 | 85 | B |
| I-357 | 0.111 | 100 | A |
| I-358 | 0.111 | 95 | A |
| I-359 | 0.111 | 68 | B |
| I-360 | 0.111 | 99 | A |
| I-361 | 0.111 | 85 | B |
| I-362 | 0.111 | 52 | B |
| I-363 | 0.111 | 100 | A |
| I-364 | 0.111 | 99 | A |

-continued

| Compound | Concentration (µM) | Percent Inhibition | IC50 (µM) |
|---|---|---|---|
| I-365 | 0.111 | 79 | B |
| I-366 | 0.111 | 92 | B |
| I-367 | 0.111 | 99 | A |
| I-368 | 0.111 | 98 | A |
| I-369 | 0.111 | 98 | A |
| I-369a | 0.111 | 98 | A |
| I-369b | 0.111 | 98 | A |
| I-370 | 0.111 | 78 | B |

IC$_{50}$: A) less than 10 nM; B) 10 nM-100 nM, and C) greater than 100 nM and less than 1000 nM

What is claimed is:

1. A compound of formula (I):

(I)

or a pharmaceutically acceptable salt thereof;
wherein:
stereochemical configurations depicted at asterisked positions indicate absolute stereochemistry;

Y is —O—, —CH$_2$—, —N(H)—;

R$^a$ is hydrogen, fluoro, —NH$_2$, or —OH;

R$^{a'}$ is hydrogen, or fluoro; provided that when R$^a$ is —NH$_2$ or —OH, R$^{a'}$ is hydrogen;

R$^c$ is hydrogen or C$_{1-4}$ alkyl;

X$_1$ is C(H), C(F) or N;

X$_2$ is C(R$^d$) or N;

each occurrence of R$^d$ is independently hydrogen, halogen, cyano, C$_{1-4}$ aliphatic, or C$_{1-4}$ fluoroaliphatic;

R$^{d'}$ is hydrogen, halogen, cyano, C$_{1-4}$ aliphatic, C$_{1-4}$fluoroaliphatic, or -T$_2$-R$^3$;

T$_2$ is a C$_1$-C$_2$ alkylene chain optionally substituted with 0-3 independent occurrences of R$^{3c}$;

R$^3$ is —CN, —NO$_2$, —N(R$^{3a}$)$_2$, —OR$^{3a}$, —C(O)R$^{3b}$, —C(O)OR$^{3a}$, —C(O)N(R$^{3a}$)$_2$, or —S(O)$_2$N(R$^{3a}$)$_2$;

each occurrence of R$^{3a}$ is independently hydrogen or C$_{1-4}$alkyl;

R$^{3b}$ is C$_{1-4}$ alkyl;

each occurrence of R$^{3c}$ is independently C$_{1-4}$ alkyl;

R$^e$ is hydrogen or C$_{1-4}$ alkyl;

R$^{e'}$ is hydrogen or C$_{1-4}$ alkyl; or R$^e$ is taken together with R$^{e'}$ to form a 3-6 membered cycloaliphatic ring;

m is 0-2;

R$^f$ is hydrogen, chloro or C$_{1-4}$ alkyl;

G is R$^1$ or -L$_1$-R$^1$;

L$_1$ is

—C(O)—, or —SO$_2$—; provided that when L$_1$ is —SO$_2$—, m is zero;

R$^1$ is an optionally substituted group selected from C$_{1-6}$aliphatic, 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur, wherein R$^1$ is optionally substituted with n occurrences of R$^2$; wherein each occurrence of R$^2$ is independently —R$^{2a}$, -T$_1$-R$^{2d}$, -T$_1$-R$^{2a}$, or —V$_1$-T$_1$-R$^{2d}$;

n is 1-5;

each occurrence of R$^{2a}$ is independently halogen, —CN, —NO$_2$, —R$^{2c}$, —N(R$^{2b}$)$_2$, —OR$^{2b}$, —SR$^{2c}$, —S(O)R$^{2c}$, —S(O)$_2$R$^{2c}$, —C(O)R$^{2b}$, —C(O)OR$^{2b}$, —C(O)N(R$^{2b}$)$_2$, —S(O)$_2$N(R$^{2b}$)$_2$, —OC(O)N(R$^{2b}$)$_2$, —N(R$^{2e}$)C(O)R$^{2b}$, —N(R$^{2e}$)SO$_2$R$^{2c}$, —N(R$^{2e}$)C(O)OR$^{2b}$, —N(R$^{2e}$)C(O)N(R$^{2b}$)$_2$, —N(R$^{2e}$)SO$_2$N(R$^{2b}$)$_2$, or Si(R$^{2c}$)$_3$, or an optionally substituted C$_1$-C$_6$ aliphatic or C$_1$-C$_6$ haloaliphatic;

each occurrence of R$^{2b}$ is independently hydrogen or an optionally substituted group selected from C$_1$-C$_6$ aliphatic, C$_1$-C$_6$ haloaliphatic, 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur, or two occurrences of R$^{2b}$, taken together with a nitrogen atom to which they are bound, form an optionally substituted 4- to -7-membered heterocyclyl ring having 0-1 additional heteroatoms selected from nitrogen, oxygen, and sulfur;

each occurrence of R$^{2c}$ is independently an optionally substituted group selected from C$_1$-C$_6$ aliphatic, C$_1$-C$_6$ haloaliphatic, 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur;

each occurrence of R$^{2d}$ is independently hydrogen or an optionally substituted group selected from 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur;

each occurrence of R$^{2e}$ is independently hydrogen or an optionally substituted C$_{1-6}$ aliphatic group;

each occurrence of V$_1$ is independently —N(R$^{2e}$)—, —O—, —S—, —S(O)—, —S(O)$_2$—, —C(O)—, —C(O)O—, —C(O)N(R$^{2e}$)—, —S(O)$_2$N(R$^{2e}$)—, —OC(O)N($R^{2e}$)—, —N($R^{2e}$)C(O)—, —N($R^{2e}$)SO$_2$—, —N($R^{2e}$)C(O)O—, —N($R^{2e}$)C(O)N($R^{2e}$)—, —N($R^{2e}$)SO$_2$N($R^{2e}$)—, —OC(O)—, or —C(O)N($R^{2e}$)—O—; and T$_1$ is an optionally substituted C$_1$-C$_6$ alkylene chain wherein the alkylene chain optionally is interrupted by —N(R$^4$)—, —O—, —S—, —S(O)—, —S(O)$_2$—, —C(O)—, —C(O)O—, —C(O)N(R$^4$)—, —S(O)$_2$N(R$^4$)—, —OC(O)N(R$^4$)—, —N(R$^4$)C(O)—, —N(R$^4$)SO$_2$—, —N(R$^4$)C(O)O—, —N(R$^4$)C(O)N(R$^4$)—, —N(R$^4$)S(O)$_2$N(R$^4$)—, —OC(O)—, or —C(O)N(R$^4$)—O— or wherein T$_1$ or a portion thereof optionally forms part of an optionally substituted 3- to -7 membered cycloaliphatic or heterocyclyl ring, wherein R$^4$ is hydrogen or an optionally substituted C$_{1-4}$ aliphatic group.

2. The compound of claim 1, wherein Y is —O—.

3. The compound of claim 1, wherein X$_1$ is N.

4. The compound of claim 1, wherein:

m is 1 or 2;

R$^e$ is hydrogen, methyl, or ethyl; and

R$^{e'}$ is hydrogen.

5. The compound of claim 1, represented by formula (III):

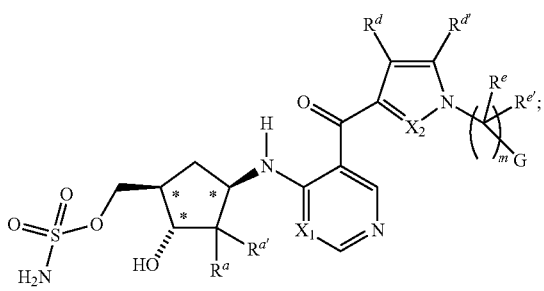

(III)

or a pharmaceutically acceptable salt thereof;

wherein:

stereochemical configurations depicted at asterisked positions indicate absolute stereochemistry.

6. The compound of claim 5, represented by formulas (IV-a)-(IV-c):

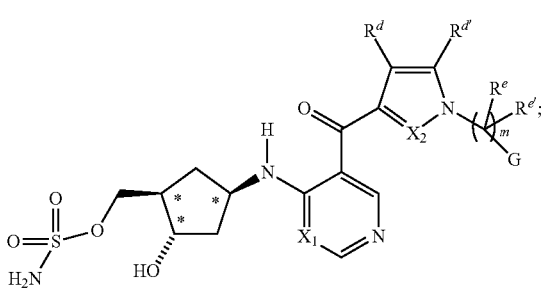

(IV-a)

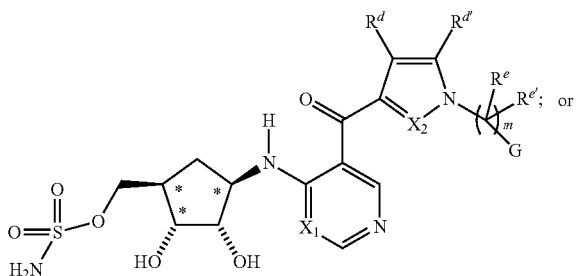

(IV-b)

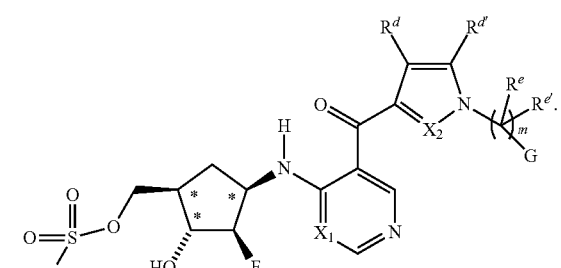

(IV-c)

or a pharmaceutically acceptable salt thereof;

wherein:

stereochemical configurations depicted at asterisked positions indicate absolute stereochemistry.

7. The compound of claim 5, wherein:

X$_1$ is N;

X$_2$ is N; and m is 1 or 2.

8. The compound of claim 5, wherein:

X$_1$ is N;

X$_2$ is C(R$^d$); and m is 1 or 2.

9. The compound of claim 8, wherein m is 1.

10. The compound of claim 5, wherein:

R$^e$ is hydrogen, methyl, or ethyl; and

R$^{e'}$ is hydrogen.

11. The compound of claim 10, wherein R$^e$ is hydrogen.

12. The compound of claim 5, wherein each occurrence of R$^d$ is independently hydrogen, chloro, bromo, fluoro, methyl, ethyl, or trifluoromethyl.

13. The compound of claim 12, wherein R$^d$ is hydrogen.

14. The compound of claim 5, wherein R$^{d'}$ is hydrogen, chloro, bromo, fluoro, methyl, ethyl, or trifluoromethyl.

15. The compound of claim 14, wherein R$^{d'}$ is hydrogen or methyl.

16. The compound of claim 1, wherein G is R$^1$.

17. The compound of claim 16, wherein R$^1$ is 3 to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur, wherein R$^1$ is unsubstituted or substituted with n occurrences of R$^2$.

18. The compound of claim 16, wherein R$^1$ is furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, imidazopyridyl, indolyl, isoindolyl, indazolyl, benzimidazolyl, benzthiazolyl, benzothienyl, benzofuranyl, benzoxazolyl, benzodioxolyl, benzthiadiazolyl, 2,3-dihydrobenzofuranyl, 4H-furo[3,2-b]pyrrolyl, pyrazolopyrimidinyl, purinyl, quinolyl, isoquinolyl, tetrahydroquinolinyl, tetrahydronaphthyridinyl, tetrahydroisoquinolinyl, cinnolinyl, phthalazinyl, quinazolinyl, quinoxalinyl, naphthyridinyl, pteridinyl, tetrahydrofuranyl, tetrahydropyranyl, dihydropyranyl, tetrahydrothienyl, indanyl, tetrahydroindazolyl, pyrrolidinyl, pyrrolidonyl, piperidinyl, pyrrolinyl, decahydroquinolinyl, oxazolidinyl, piperazinyl, dioxanyl, diazepinyl, oxazepinyl, thiazepinyl, morpholinyl, thiomorpholinyl, quinuclidinyl, phenanthridinyl, tetrahydronaphthyl, oxodihydropyridyl, indolinyl, benzodioxanyl, chromanyl, oxetanyl, cyclopropyl, cyclobutyl, cyclopentyl, cyclohexyl, cycloheptyl, cyclooctyl, cyclopentenyl, cyclohexenyl, cycloheptenyl, cyclooctenyl, bicycloheptanyl, azabicyclooctanyl, oxabicyclooctanyl, bicyclononyl, bicyclooctanyl, or adamantyl, wherein $R^1$ is unsubstituted or substituted with n occurrences of $R^2$.

19. The compound of claim 18, wherein $R^1$ is furanyl, thienyl, phenyl, naphthyl, pyridyl, benzothienyl, benzofuranyl, cyclohexyl, or cyclohexenyl, wherein $R^1$ is unsubstituted or substituted with n occurrences of $R^2$.

20. The compound of claim 16, wherein $R^1$ is optionally substituted with 1-3 occurrences of $R^2$, wherein each occurrence of $R^2$ is independently —$R^{2a}$ or $T_1$-$R^{2a}$.

21. The compound of claim 20, wherein:
    each occurrence of $R^2$ is independently halogen, —$R^{2c}$, —$N(R^{2b})_2$, —$OR^{2b}$, —$SR^{2c}$, $C_{1-6}$ aliphatic or $C_{1-6}$ fluoroaliphatic; and
    each occurrence of $R^{2b}$ is independently $C_{1-6}$ aliphatic or $C_{1-6}$ fluoroaliphatic.

22. The compound of claim 21, wherein $R^1$ is optionally substituted with 1-2 occurrences of $R^2$, wherein each occurrence of $R^2$ is independently chloro, bromo, fluoro, iodo, methyl, ethyl, propyl, tert-butyl, methoxy, ethoxy, isopropoxy, tert-butoxy, difluoromethyl, trifluoromethyl, difluoromethoxy, trifluoromethoxy, trifluoromethylthio, dimethylamino, diethylamino, ethyne, cyclopropyl, or phenyl.

23. The compound of claim 21, wherein each occurrence of $R^2$ is independently chloro, bromo, fluoro, iodo, methyl, ethyl, difluoromethoxy, trifluoromethoxy, ethyne, cyclopropyl, or phenyl.

24. The compound of claim 16, wherein $R^1$ is:

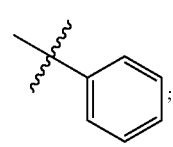
(a-i)

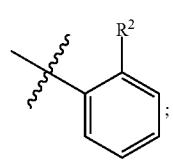
(a-ii)

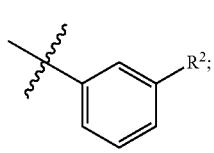
(a-iii)

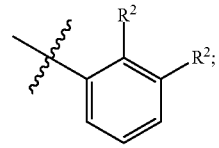
(a-iv)

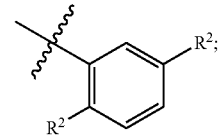
(a-v)

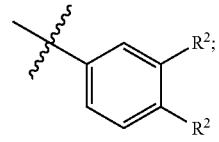
(a-vi)

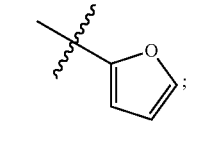
(a-vii)

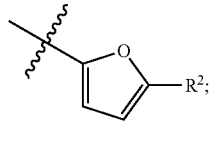
(a-viii)

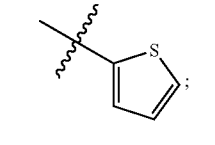
(a-ix)

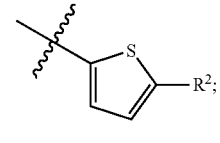
(a-x)

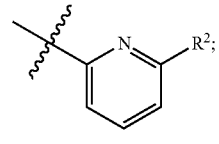
(a-xi)

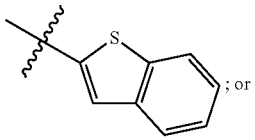
(a-xii)

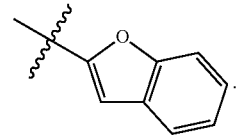
(a-xiii)

25. The compound of claim 24, wherein $R^1$ is (a-i), (a-iii), (a-iv), (a-v), (a-viii), or (a-xi).

26. The compound of claim 24, wherein each occurrence of $R^2$ is independently chloro, bromo, iodo, or methyl.

27. The compound of claim 1, wherein the compound is:

[(1R,2R,3S,4R)-4-{[5-({1-[(3-bromophenyl)sulfonyl]-1H-pyrazol-3-yl}carbonyl)pyrimidin-4-yl]amino}-2,3-dihydroxycyclopentyl]methyl sulfamate;

{(1S,2S,4R)-4-[(5-{[1-(3-bromobenzyl)-1H-pyrazol-3-yl]carbonyl}pyrimidin-4-yl)amino]-2-hydroxycyclopentyl}methyl sulfamate;

[(1R,2S,4R)-2-hydroxy-4-({5-[(1-{[6-(trifluoromethyl)pyridin-2-yl]methyl}-1H-pyrazol-3-yl)carbonyl]pyrimidin-4-yl}amino)cyclopentyl]methyl sulfamate;

[(1R,2R,3S,4R)-2,3-dihydroxy-4-{[5-({1-[2-(3-methyl-1H-pyrazol-1-yl)ethyl]-1H-pyrazol-3-yl}carbonyl)pyrimidin-4-yl]amino}cyclopentyl]methyl sulfamate;

{(1R,2R,3R,4R)-4-[(5-{[1-(3,6-dihydro-2H-pyran-4-ylmethyl)-1H-pyrrol-3-yl]carbonyl}pyrimidin-4-yl)amino]-3-fluoro-2-hydroxycyclopentyl}methyl sulfamate;

((1S,2S,4R)-4-[(5-{[1-(3-bromobenzyl)-5-methyl-1H-pyrazol-3-yl]carbonyl}pyrimidin-4-yl)amino]-2-hydroxycyclopentyl)methyl sulfamate;

[(1R,2R,3R,4R)-3-fluoro-2-hydroxy-4-{[5-({1-[3-(trifluoromethyl)benzyl]-1H-pyrrol-3-yl}carbonyl)pyrimidin-4-yl]amino}cyclopentyl]methyl sulfamate;

[(1R,2R,3R,4R)-4-{[5-({1-[(6-chloropyridin-2-yl)methyl]-1H-pyrrol-3-yl}carbonyl)pyrimidin-4-yl]amino}-3-fluoro-2-hydroxycyclopentyl]methyl sulfamate;

[(1R,2R,3R,4R)-3-fluoro-2-hydroxy-4-{[5-({1-[(1R,2R)-(2-phenylcyclopropyl)methyl]-1H-pyrrol-3-yl}carbonyl)pyrimidin-4-yl]amino}cyclopentyl]methyl sulfamate;

[(1R,2R,3R,4R)-3-fluoro-2-hydroxy-4-{[5-({1-[(1S,2S)-(2-phenylcyclopropyl)methyl]-1H-pyrrol-3-yl}carbonyl)pyrimidin-4-yl]amino}cyclopentyl]methyl sulfamate;

[(1R,2S,4R)-4-{[5-({1-[(1R)-1-(3-ethynylphenyl)ethyl]-1H-pyrazol-3-yl}carbonyl)pyrimidin-4-yl]amino}-2-hydroxycyclopentyl]methyl sulfamate;

[(1R,2S,4R)-4-{[5-({1-[(1S)-1-(3-ethynylphenyl)ethyl]-1H-pyrazol-3-yl}carbonyl)pyrimidin-4-yl]amino}-2-hydroxycyclopentyl]methyl sulfamate;

{(1R,2S,4R)-4-[(5-{[1-(3-bromobenzyl)-1H-pyrazol-3-yl]carbonyl}pyrimidin-4-yl)amino]-2-hydroxycyclopentyl}methyl sulfamate;

[(1R,2S,4R)-2-hydroxy-4-{[5-({1-[4-(tetrahydro-2H-pyran-4-yl)but-2-yn-1-yl]-1H-pyrazol-3-yl}carbonyl)pyrimidin-4-yl]amino}cyclopentyl]methyl sulfamate;

{(1R,2R,3R,4R)-3-fluoro-2-hydroxy-4-[(5-{[1-(3-iodobenzyl)-1H-pyrrol-3-yl]carbonyl}pyrimidin-4-yl)amino]cyclopentyl}methyl sulfamate;

{(1R,2S,4R)-4-[(5-{[1-(4-fluoro-3-methylbenzyl)-1H-pyrazol-3-yl]carbonyl}pyrimidin-4-yl)amino]-2-hydroxycyclopentyl}methyl sulfamate;

{(1R,2R,3R,4R)-4-[(5-{[1-(3-bromobenzyl)-1H-pyrazol-3-yl]carbonyl}pyrimidin-4-yl)amino]-3-fluoro-2-hydroxycyclopentyl}methyl sulfamate;

{(1R,2S,4R)-2-hydroxy-4-[(5-{[1-(2,3,6-trifluorobenzyl)-1H-pyrazol-3-yl]carbonyl}pyrimidin-4-yl)amino]cyclopentyl}methyl sulfamate;

{(1R,2S,4R)-4-[(5-{[1-(1-benzofuran-2-ylmethyl)-1H-pyrazol-3-yl]carbonyl}pyrimidin-4-yl)amino]-2-hydroxycyclopentyl}methyl sulfamate;

[(1R,2S,4R)-2-hydroxy-4-{[3-({1-[3-(trifluoromethoxy)benzyl]-1H-pyrazol-3-yl}carbonyl)pyridin-4-yl]amino}cyclopentyl]methyl sulfamate;

[(1R,2R,3R,4R)-3-fluoro-2-hydroxy-4-{[5-({1-[2-oxo-2-(pyrrolidin-1-yl)ethyl]-1H-pyrazol-3-yl}carbonyl)pyrimidin-4-yl]amino}cyclopentyl]methyl sulfamate;

[(1R,2S,4R)-2-hydroxy-4-{[5-({1-[3-(trifluoromethoxy)benzyl]-1H-pyrazol-3-yl}carbonyl)pyrimidin-4-yl]amino}cyclopentyl]methyl sulfamate;

[(1R,2S,4R)-4-{[5-({1-[4-fluoro-3-(trifluoromethyl)benzyl]-1H-pyrrol-3-yl}carbonyl)pyrimidin-4-yl]amino}-2-hydroxycyclopentyl]methyl sulfamate;

{(1R,2S,4R)-4-[(5-{[1-(2-fluoro-3-methylbenzyl)-1H-pyrazol-3-yl]carbonyl}pyrimidin-4-yl)amino]-2-hydroxycyclopentyl}methyl sulfamate;

[(1R,2R,3R,4R)-3-fluoro-2-hydroxy-4-{[5-((1-[3-(trifluoromethoxy)benzyl]-1H-pyrazol-3-yl}carbonyl)pyrimidin-4-yl]amino}cyclopentyl]methyl sulfamate;

[(1R,2R,3R,4R)-4-{[5-({1-[(5-bromo-2-furyl)methyl]-1H-pyrrol-3-yl}carbonyl)pyrimidin-4-yl]amino}-3-fluoro-2-hydroxycyclopentyl]methyl sulfamate;

{(1R,2R,3S,4R)-4-[(5-{[1-(3-cyanobenzyl)-1H-pyrazol-3-yl]carbonyl}pyrimidin-4-yl)amino]-2,3-dihydroxycyclopentyl}methyl sulfamate;

{(1R,2R,3R,4R)-4-[(5-{[1-(4,4-dimethylpent-2-yn-1-yl)-1H-pyrrol-3-yl]carbonyl}pyrimidin-4yl)amino]3-fluoro-2-hydroxycyclopentyl}methyl sulfamate;

[(1R,2S,4R)-2-hydroxy-4-{[5-({1-[3-(4-hydroxytetrahydro-2H-pyran-4-yl)prop-2-yl-1-yl]-1H-pyrazol-3-yl}carbonyl)pyrimidin-4-yl]amino}cyclopentyl]methyl sulfamate;

{(1R,2R,3S,4R)-4-[(5-{[1-(2-ethoxyethyl)-1H-pyrazol-3-yl]carbonyl}pyrimidin-4-yl)amino]-2,3-dihydroxycyclopentyl}methyl sulfamate;

[(1R,2S,4R)-4-{[5-({1-[(5-bromopyridin-3-yl)methyl]-1H-pyrazol-3-yl}carbonyl)pyrimidin-4-yl]amino}-2-hydroxycyclopentyl]methyl sulfamate;

(1R,2R,3S,4R)-4-[(5-{[1-(cyclopropylmethyl)-1H-pyrazol-3-yl]carbonyl}pyrimidin-4-yl)amino]-2,3-dihydroxycyclopentyl}methyl sulfamate;

[(1R,2R,3S,4R)-4-({5-[(1-benzyl-5-methyl-1H-pyrazol-3-yl)carbonyl]pyrimidin-4-yl}amino)-2,3-dihydroxycyclopentyl]methyl sulfamate;

{(1R,2S,4R)-4-[(5-{[1-(2-fluoro-5-methylbenzyl)-1H-pyrazol-3-yl]carbonyl}pyrimidin-4-yl)amino]-2-hydroxycyclopentyl}methyl sulfamate;

[(1R,2R,3S,4R)-2,3-dihydroxy-4-{[5-({1-[2-(1H-indol-3-yl)ethyl]-1H-pyrazol-3-yl}carbonyl)pyrimidin-4-yl]amino}cyclopentyl]methyl sulfamate;

[(1R,2R,3S,4R)-4-{[5-({1-[4-chloro-3-(trifluoromethyl)benzyl]-1H-pyrazol-3-yl}carbonyl)pyrimidin-4-yl]amino}-2,3-dihydroxycyclopentyl]methyl sulfamate;

{(1R,2S,4R)-4-[(5-{[1-(2,5-difluorobenzyl)-1H-pyrazol-3-yl]carbonyl}pyrimidin-4-yl)amino]-2-hydroxycyclopentyl}methyl sulfamate;

[(1R,2R,3R,4R)-4-({5-[(5-chloro-1-{[5-(trifluoromethyl)-2-furyl]methyl}-1H-pyrrol-3-yl)carbonyl]pyrimidin-4-yl}amino)-3-fluoro-2-hydroxycyclopentyl]methyl sulfamate;

[(1R,2S,4R)-2-hydroxy-4-{[5-({1-[2-(methylsulfanyl)ethyl]-1H-pyrazol-3-yl}carbonyl)pyrimidin-4-yl]amino}cyclopentyl]methyl sulfamate;

2-{(1R,2S,4R)-4-[(5-{[1-(3-bromobenzyl)-1H-pyrazol-3-yl]carbonyl}pyrimidin-4-yl)amino]-2-hydroxycyclopentyl}ethanesulfonamide;

[(1R,2S,4R)-2-hydroxy-4-{[5-({1-[2-(trifluoromethoxy)benzyl]-1H-pyrazol-3-yl}carbonyl)pyrimidin-4-yl]amino}cyclopentyl]methyl sulfamate;

{(1R,2R,3S,4R)-4-[(5-{[1-(3-chlorobenzyl)-1H-pyrazol-3-yl]carbonyl}pyrimidin-4-yl)amino]-2,3-dihydroxycyclopentyl}methyl sulfamate;

[(1R,2R,3R,4R)-3-fluoro-2-hydroxy-4-({5-[(1-{[5-(methoxymethyl)-2-furyl]methyl}-1H-pyrrol-3-yl)carbonyl]pyrimidin-4-yl}amino)cyclopentyl]methyl sulfamate;

{(1R,2R,3R,4R)-3-fluoro-2-hydroxy-4-[(5-{[1-(3-iodobenzyl)-1H-pyrazol-3-yl]carbonyl}pyrimidin-4-yl)amino]cyclopentyl}methyl sulfamate;

{(1R,2S,4R)-4-[(5-{[1-(3-bromo-4-chlorobenzyl)-1H-pyrrol-3-yl]carbonyl}pyrimidin-4-yl)amino]-2-hydroxycyclopentyl}methyl sulfamate;

{(1R,2R,3R,4R)-4-[(5-{[1-(3-bromobenzyl)-5-fluoro-1H-pyrrol-3-yl]carbonyl}pyrimidin-4-yl)amino]-3-fluoro-2-hydroxycyclopentyl}methyl sulfamate;

[(1R,2S,4R)-2-hydroxy-4-({5-[(1-([1-methyl-3-(trifluoromethyl)-1H-pyrazol-5-yl]methyl}-1H-pyrrol-3-yl)carbonyl]pyrimidin-4-yl)amino)cyclopentyl]methyl sulfamate;

[(1R,2R,3S,4R)-4-{[5-({1-[3-fluoro-4-(trifluoromethyl)benzyl]-1H-pyrazol-3-yl}carbonyl)pyrimidin-4-yl]amino}-2,3-dihydroxycyclopentyl]methyl sulfamate;

{(1R,2S,4R)-4-[(5-{[1-(4-chlorobenzyl)-1H-pyrazol-3-yl]carbonyl}pyrimidin-4-yl)amino]-2-hydroxycyclopentyl}methyl sulfamate;

{(1R,2S,4R)-2-hydroxy-4-[(5-{[1-(2-naphthylmethyl)-1H-pyrazol-3-yl]carbonyl}pyrimidin-4-yl)amino]cyclopentyl}methyl sulfamate;

[(1R,2R,3R,4R)-4-{[5-({1-[(3-chloro-1-benzothiophen-2-yl)methyl]-1H-pyrrol-3-yl}carbonyl)pyrimidin-4-yl]amino}-3-fluoro-2-hydroxycyclopentyl]methyl sulfamate;

[(1R,2S,4R)-4-{[5-({1-[2-chloro-5-(trifluoromethyl)benzyl]-1H-pyrazol-3-yl}carbonyl)pyrimidin-4-yl]amino}-2-hydroxycyclopentyl]methyl sulfamate;

[(1R,2R,3S,4R)-2,3-dihydroxy-4-{[5-({1-[(4-methylpyridin-2-yl)methyl]-1H-pyrazol-3-yl}carbonyl)pyrimidin-4-yl]amino}cyclopentyl]methyl sulfamate;

{(1R,2S,4R)-4-[(3-([1-(3-chlorobenzyl)-1H-pyrazol-3-yl]carbonyl}pyridin-4-yl)amino]-2-hydroxycyclopentyl}methyl sulfamate;

[(1R,2S,4R)-2-hydroxy-4-({5-[(1-{[2-(trifluoromethyl)pyridin-4-yl]methyl}-1H-pyrazol-3-yl)carbonyl]pyrimidin-4-yl}amino)cyclopentyl]methyl sulfamate;

{(1R,2S,4R)-4-[(6-chloro-5-{[1-(3-chlorobenzyl)-1H-pyrazol-3-yl]carbonyl}pyrimidin-4-yl)amino]-2-hydroxycyclopentyl}methyl sulfamate;

[(1R,2S,4R)-2-hydroxy-4-{[5-({1-[((1S,2S)-2-methylcyclopropyl)methyl]-1H-pyrazol-3-yl}carbonyl)pyrimidin-4-yl]amino}cyclopentyl]methyl sulfamate;

[(1R,2S,4R)-2-hydroxy-4-{[5-({1-[((1R,2R)-2-methylcyclopropyl)methyl]-1H-pyrazol-3-yl}carbonyl)pyrimidin-4-yl]amino}cyclopentyl]methyl sulfamate;

[(1R,2R,3S,4R)-4-({3-[(1-benzyl-1H-pyrazol-3-yl)carbonyl]pyridin-4-yl}amino)-2,3-dihydroxycyclopentyl]methyl sulfamate;

{(1R,2R,3R,4R)-3-fluoro-2-hydroxy-4-[(5-{[1-(4-fluoro-3-methoxybenzyl)-1H-pyrrol-3-yl]carbonyl}pyrimidin-4-yl)amino]-2-hydroxycyclopentyl}methyl sulfamate;

{(1R,2S,4R)-4-[(5-{[1-(3,4-dichlorobenzyl)-1H-pyrazol-3-yl]carbonyl}pyrimidin-4-yl)amino]-2-hydroxycyclopentyl}methyl sulfamate;

{(1R,2S,4R)-4-[(5-{[1-(4-cyclopentylbut-2-yn-1-yl)-1H-pyrazol-3-yl]carbonyl}pyrimidin-4-yl)amino]-2-hydroxycyclopentyl}methyl sulfamate;

[(1R,2S,4R)-2-hydroxy-4-{[5-({1-[3-(2-hydroxypropan-2-yl)benzyl]-1H-pyrazol-3-yl}carbonyl)pyrimidin-4-yl]amino}cyclopentyl]methyl sulfamate;

{(1R,2R,3R,4R)-4-[(5-{[5-chloro-1-(3-chlorobenzyl)-1H-pyrrol-3-yl]carbonyl}pyrimidin-4-yl)amino]-3-fluoro-2-hydroxycyclopentyl}methyl sulfamate;

{(1R,2S,4R)-4-[(5-{[1-(2,4-difluorobenzyl)-1H-pyrazol-3-yl]carbonyl}pyrimidin-4-yl)amino]-2-hydroxycyclopentyl}methyl sulfamate;

[(1R,2S,4R)-2-hydroxy-4-{[5-({1-[(2-methoxypyridin-3-yl)methyl]-1H-pyrazol-3-yl}carbonyl)pyrimidin-4-yl]amino}cyclopentyl]methyl sulfamate;

{(1R,2S,4R)-4-[(5-{[1-(3-tert-butylbenzyl)-1H-pyrazol-3-yl]carbonyl}pyrimidin-4-yl)amino]-2-hydroxycyclopentyl}methyl sulfamate;

[(1R,2S,4R)-4-{[5-({1-[(1S)-1-(6-bromopyridin-2-yl)ethyl]-1H-pyrazol-3-yl}carbonyl)pyrimidin-4-yl]amino}-2-hydroxycyclopentyl]methyl sulfamate;

[(1R,2S,4R)-4-{[5-({1-[(1R)-1-(6-bromopyridin-2-yl)ethyl]-1H-pyrazol-3-yl}carbonyl)pyrimidin-4-yl]amino}-2-hydroxycyclopentyl]methyl sulfamate;

[(1R,2S,4R)-4-({5-[(1-benzyl-5-methyl-1H-pyrazol-3-yl)carbonyl]pyrimidin-4-yl}amino)-2-hydroxycyclopentyl]methyl sulfamate;

[(1R,2R,3S,4R)-4-({5-[(1-{3-[(chloroacetyl)amino]benzyl}-1H-pyrazol-3-yl)carbonyl]pyrimidin-4-yl}amino)-2,3-dihydroxycyclopentyl]methyl sulfamate;

{(1R,2S,4R)-2-hydroxy-4-[(5-{[1-(3-iodobenzyl)-1H-pyrrol-3-yl]carbonyl}pyrimidin-4-yl)amino]cyclopentyl}methyl sulfamate;

[(1R,2S,4R)-4-{[5-({1-[2,4-bis(trifluoromethyl)benzyl]-1H-pyrazol-3-yl}carbonyl)pyrimidin-4-yl]amino}-2-hydroxycyclopentyl]methyl sulfamate;

[(1R,2R,3S,4R)-4-{[5-({1-[(4-chloropyridin-2-yl)methyl]-1H-pyrazol-3-yl}carbonyl)pyrimidin-4-yl]amino}-2,3-dihydroxycyclopentyl]methyl sulfamate;

{(1R,2R,3R,4R)-4-[(5-{[1-(3-bromobenzyl)-5-methyl-1H-pyrrol-3-yl]carbonyl}pyrimidin-4-yl)amino]-3-fluoro-2-hydroxycyclopentyl}methyl sulfamate;

{(1R,2S,4R)-4-[(5-{[1-(3-bromo-4-fluorobenzyl)-1H-pyrazol-3-yl]carbonyl}pyrimidin-4-yl)amino]-2-hydroxycyclopentyl}methyl sulfamate;

[(1R,2S,4R)-2-hydroxy-4-({5-[(1-{[2-(trifluoromethyl)-1,3-thiazol-5-yl]methyl}-1H-pyrrol-3-yl)carbonyl]pyrimidin-4-yl}amino)cyclopentyl]methyl sulfamate;

[(1R,2R,3S,4R)-2,3-dihydroxy-4-{[5-({1-[3-((R)-vinylsulfinyl)benzyl]-1H-pyrazol-3-yl}carbonyl)pyrimidin-4-yl]amino}cyclopentyl]methyl sulfamate;

[(1R,2R,3S,4R)-2,3-dihydroxy-4-{[5-({1-[3-((S)-vinylsulfinyl)benzyl]-1H-pyrazol-3-yl}carbonyl)pyrimidin-4-yl]amino}cyclopentyl]methyl sulfamate;

{(1R,2R,3R,4R)-3-fluoro-2-hydroxy-4-[(5-{[1-(4-methoxy-4-methylpent-2-yn-1-yl)-1H-pyrrol-3-yl]carbonyl}pyrimidin-4-yl)amino]cyclopentyl}methyl sulfamate;

{(1R,2S,4R)-2-hydroxy-4-[(5-{[1-(2-phenylpropan-2-yl)-1H-pyrrol-3-yl]carbonyl}pyrimidin-4-yl)amino]cyclopentyl}methyl sulfamate;

[(1R,2S,4R)-4-({5-[(1-{[(2R)-5,5-dimethyltetrahydrofuran-2-yl]methyl}-1H-pyrazol-3-yl)carbonyl]pyrimidin-4-yl}amino)-2-hydroxycyclopentyl]methyl sulfamate;

[(1R,2S,4R)-4-({5-[(1-{[(2S)-5,5-dimethyltetrahydrofuran-2-yl]methyl}-1H-pyrazol-3-yl)carbonyl]pyrimidin-4-yl}amino)-2-hydroxycyclopentyl]methyl sulfamate;

{(1R,2S,4R)-4-[(3-{[1-(3,4-dichlorobenzyl)-1H-pyrazol-3-yl]carbonyl}pyridin-4-yl)amino]-2-hydroxycyclopentyl}methyl sulfamate;

[(1R,2S,4R)-4-{[5-({1-[(1S)-1-(5-chloro-2-furyl)ethyl]-1H-pyrazol-3-yl}carbonyl)pyrimidin-4-yl]amino}-2-hydroxycyclopentyl]methyl sulfamate;

[(1R,2S,4R)-4-{[5-(1-[(1R)-1-(5-chloro-2-furyl)ethyl]-1H-pyrazol-3-yl)carbonyl)pyrimidin-4-yl]amino}-2-hydroxycyclopentyl]methyl sulfamate;

[(1R,2S,4R)-2-hydroxy-4-{[5-({1-[(1-methyl-2-oxo-1,2-dihydropyridin-3-yl)methyl]-1H-pyrazol-3-yl}carbonyl)pyrimidin-4-yl]amino}cyclopentyl]methyl sulfamate;

{(1R,2R,3S,4R)-4-[(3-{[1-(3-chlorobenzyl)-1H-pyrazol-3-yl]carbonyl}pyridin-4-yl)amino]-2,3-dihydroxycyclopentyl}methyl sulfamate;

{(1R,2R,3S,4R)-4-[(5-{[1H-pyrazol-3-yl]carbonyl}pyrimidin-4-yl)amino]-2,3-dihydroxycyclopentyl}methyl sulfamate;

[(1R,2S,4R)-2-hydroxy-4-{[3-({1-[3-(trifluoromethoxy)benzyl]-1H-pyrrol-3-yl}carbonyl)pyridin-4-yl]amino}cyclopentyl]methyl sulfamate;

[(1R,2S,4R)-2-hydroxy-4-{[5-({1-[3-(prop-1-yn-1-yl)benzyl]-1H-pyrazol-3-yl}carbonyl)pyrimidin-4-yl]amino}cyclopentyl]methyl sulfamate;

{(1R,2S,4R)-4-[(5-{[1-(3-ethynylbenzyl)-1H-pyrazol-3-yl]carbonyl}pyrimidin-4-yl)amino]-2-hydroxycyclopentyl}methyl sulfamate;

(1R,2S,4R)-2-hydroxy-4-[(5-{[1-(2S)-(pent-3-yn-2-yl)-1H-pyrazol-3-yl]carbonyl}pyrimidin-4-yl)amino]cyclopentyl}methyl sulfamate;

{(1R,2S,4R)-2-hydroxy-4-[(5-{[1-(2R)-(pent-3-yn-2-yl)-1H-pyrazol-3-yl]carbonyl}pyrimidin-4-yl)amino]cyclopentyl}methyl sulfamate;

[(1R,2R,3R,4R)-4-({5-[(1-{[5-(difluoromethyl)-2-furyl]methyl}-1H-pyrrol-3-yl)carbonyl]pyrimidin-4-yl}amino)-3-fluoro-2-hydroxycyclopentyl]methyl sulfamate;

{(1R,2R,3S,4R)-2,3-dihydroxy-4-[(5-{[1-(2,4,6-trifluorobenzyl)-1H-pyrazol-3-yl]carbonyl}pyrimidin-4-yl)amino]cyclopentyl}methyl sulfamate;

{(1R,2R,3S,4R)-4-[(5-{[1-(3-chloro-4-fluorobenzyl)-1H-pyrazol-3-yl]carbonyl}pyrimidin-4-yl)amino]-2,3-dihydroxycyclopentyl}methyl sulfamate;

{(1R,2S,4R)-4-[(5-{[1-(3-bromobenzyl)-5-(hydroxymethyl)-1H-pyrazol-3-yl]carbonyl}pyrimidin-4-yl)amino]-2-hydroxycyclopentyl}methyl sulfamate;

{(1R,2R,3S,4R)-4-[(5-{[1-(2,5-difluorobenzyl)-1H-pyrazol-3-yl]carbonyl}pyrimidin-4-yl)amino]-2,3-dihydroxycyclopentyl}methyl sulfamate;

{(1R,2R,3R,4R)-4-[(5-{[1-(3-bromo-4-fluorobenzyl)-1H-pyrazol-3-yl]carbonyl}pyrimidin-4-yl)amino]-3-fluoro-2-hydroxycyclopentyl}methyl sulfamate;

{(1R,2S,4R)-4-[(5-{[1-(cyclohexylmethyl)-1H-pyrazol-3-yl]carbonyl}pyrimidin-4-yl)amino]-2-hydroxycyclopentyl}methyl sulfamate;

{(1R,2R,3R,4R)-4-[(5-{[1-benzyl-5-(trifluoromethyl)-1H-pyrrol-3-yl]carbonyl}pyrimidin-4-yl)amino]-3-fluoro-2-hydroxycyclopentyl}methyl sulfamate;

[(1R,2S,4R)-4-{[5-({1-[(6-chloropyridin-2-yl)methyl]-1H-pyrazol-3-yl}carbonyl)pyrimidin-4-yl]amino}-2-hydroxycyclopentyl]methyl sulfamate;

[(1R,2R,3S,4R)-4-{[5-({1-[2-(3-bromophenyl)-2-oxoethyl]-1H-pyrazol-3-yl}carbonyl)pyrimidin-4-yl]amino}-2,3-dihydroxycyclopentyl]methyl sulfamate;

{(1R,2S,4R)-4-[(3-{[1-(3-chloro-4-fluorobenzyl)-1H-pyrazol-3-yl]carbonyl}pyridin-4-yl)amino]-2-hydroxycyclopentyl}methyl sulfamate;

[(1R,2R,3S,4R)-2,3-dihydroxy-4-{[5-({1-[2-(trifluoromethoxy)benzyl]-1H-pyrazol-3-yl}carbonyl)pyrimidin-4-yl]amino}cyclopentyl]methyl sulfamate;

[(1R,2S,4R)-4-{[5-({1-[(6-chloropyridin-2-yl)methyl]-5-methyl-1H-pyrazol-3-yl}carbonyl)pyrimidin-4-yl]amino}-2-hydroxycyclopentyl]methyl sulfamate;

[(1R,2R,3S,4R)-4-{[5-({1-[4-chloro-3-(trifluoromethoxy)benzyl]-1H-pyrazol-3-yl}carbonyl)pyrimidin-4-yl]amino}-2,3-dihydroxycyclopentyl]methyl sulfamate;

[(1R,2S,4R)-4-{[5-({1-[(5-chloro-2-furyl)methyl]-5-methyl-1H-pyrazol-3-yl}carbonyl)pyrimidin-4-yl]amino}-2-hydroxycyclopentyl]methyl sulfamate;

[(1R,2R,3R,4R)-3-fluoro-2-hydroxy-4-{[5-({1-[3-(trifluoromethyl)benzyl]-1H-pyrazol-3-yl}carbonyl)pyrimidin-4-yl]amino}cyclopentyl]methyl sulfamate;

{(1R,2R,3S,4R)-2,3-dihydroxy-4-[(5-{[1-(2-naphthylmethyl)-1H-pyrazol-3-yl]carbonyl}pyrimidin-4-yl)amino]cyclopentyl}methyl sulfamate;

{(1R,2S,4R)-4-[(5-{[1-(2-chloro-5-iodobenzyl)-1H-pyrazol-3-yl]carbonyl}pyrimidin-4-yl)amino]-2-hydroxycyclopentyl}methyl sulfamate;

{(1R,2R,3R,4R)-4-[(5-{[1-(3-bromobenzyl)-2,5-dichloro-1H-pyrrol-3-yl]carbonyl}pyrimidin-4-yl)amino]-3-fluoro-2-hydroxycyclopentyl}methyl sulfamate;

{(1R,2R,3S,4R)-4-[(5-{[1-(4-fluorobenzyl)-1H-pyrazol-3-yl]carbonyl}pyrimidin-4-yl)amino]-2,3-dihydroxycyclopentyl}methyl sulfamate;

[(1R,2S,4R)-4-{[5-({1-[(2E)-but-2-en-1-yl]-1H-pyrazol-3-yl}carbonyl)pyrimidin-4-yl]amino}-2-hydroxycyclopentyl]methyl sulfamate;

{(1R,2S,4R)-4-[(5-{[1-(cyanomethyl)-1H-pyrazol-3-yl]carbonyl}pyrimidin-4-yl)amino]-2-hydroxycyclopentyl}methyl sulfamate;

[(1R,2S,4R)-2-hydroxy-4-({5-[(1-{[6-(2-hydroxypropan-2-yl)pyridin-2-yl]methyl}-1H-pyrazol-3-yl)carbonyl]pyrimidin-4-yl}amino)cyclopentyl]methyl sulfamate;

{(1R,2R,3R,4R)-4-[(5-{[1-(1-benzofuran-2-ylmethyl)-1H-pyrrol-3-yl]carbonyl}pyrimidin-4-yl)amino]-3-fluoro-2-hydroxycyclopentyl}methyl sulfamate;

{(1R,2S,4R)-4-[(5-{[1-(3-bromobenzyl)]-4-chloro-1H-pyrazol-3-yl]carbonyl}pyrimidin-4-yl)amino]-2-hydroxycyclopentyl}methyl sulfamate;

{(1R,2R,3S,4R)-4-[(5-{[1-(4-chloro-3-fluorobenzyl)-1H-pyrazol-3-yl]carbonyl}pyrimidin-4-yl)amino]-2,3-dihydroxycyclopentyl}methyl sulfamate;

{(1R,2S,4R)-4-[(5-{[1-(4,4-dimethylpent-2-yn-1-yl)-1H-pyrazol-3-yl]carbonyl}pyrimidin-4-yl)amino]-2-hydroxycyclopentyl}methyl sulfamate;

[(1R,2R,3R,4R)-3-fluoro-2-hydroxy-4-({5-[(1-{[4-(trifluoromethyl)-2-furyl]methyl}-1H-pyrrol-3-yl)carbonyl]pyrimidin-4-yl}amino)cyclopentyl]methyl sulfamate;

{(1R,2S,4R)-2-hydroxy-4-[(5-{[1-(pent-3-yn-1-yl)-1H-pyrazol-3-yl]carbonyl}pyrimidin-4-yl)amino]cyclopentyl}methyl sulfamate;

[(1R,2R,3R,4R)-4-({5-[(1-{3-[acryloyl(methyl)amino]benzyl}-1H-pyrazol-3-yl)carbonyl]pyrimidin-4-yl}amino)-3-fluoro-2-hydroxycyclopentyl]methyl sulfamate;

[(1R,2S,4R)-4-{[5-({1-[3-(difluoromethoxy)benzyl]-1H-pyrazol-3-yl}carbonyl)pyrimidin-4-yl]amino}-2-hydroxycyclopentyl]methyl sulfamate;

[(1R,2R,3S,4R)-2,3-dihydroxy-4-{[5-({1-[2-(1-naphthyl) ethyl]-1H-pyrazol-3-yl}carbonyl)pyrimidin-4-yl] amino}cyclopentyl]methyl sulfamate;

[(1R,2R,3S,4R)-2,3-dihydroxy-4-{[5-({1-[3-(trifluoromethyl)benzyl]-1H-pyrazol-3-yl}carbonyl)pyrimidin-4-yl]amino)cyclopentyl]methyl sulfamate;

[(1R,2S,4R)-2-hydroxy-4-({5-[(1-{[6-(3-hydroxyoxetan-3-yl]pyridin-2-yl]methyl}-1H-pyrazol-3-yl)carbonyl] pyrimidin-4-yl}amino)cyclopentyl]methyl sulfamate;

[(1R,2R,3S,4R)-4-{[5-({1-[4-fluoro-2-(trifluoromethyl) benzyl]-1H-pyrazol-3-yl}carbonyl)pyrimidin-4-yl] amino}-2,3-dihydroxycyclopentyl]methyl sulfamate;

(1R,2R,3R,4R)-4-[(5-{[1-(3-chloro-4-fluorobenzyl)-1H-pyrazol-3-yl]carbonyl}pyrimidin-4-yl)amino]-3-fluoro-2-hydroxycyclopentyl}methyl sulfamate;

{(1R,2R,3S,4R)-4-[(5-{[1-(3-fluorobenzyl)-1H-pyrazol-3-yl]carbonyl}pyrimidin-4-yl)amino]-2,3-dihydroxycyclopentyl}methyl sulfamate;

{(1R,2R,3R,4R)-4-[(3-{[1-(3-chlorobenzyl)-1H-pyrrol-3-yl]carbonyl}pyridin-4-yl)amino]-3-fluoro-2-hydroxycyclopentyl}methyl sulfamate;

{(1R,2R,3S,4R)-2,3-dihydroxy-4-[(5-{[1-(2-oxo-2-phenylethyl)-1H-pyrazol-3-yl]carbonyl}pyrimidin-4-yl) amino]cyclopentyl}methyl sulfamate;

[(1R,2R,3S,4R)-4-({5-[(1-{4-chloro-3-[(trifluoromethyl) sulfanyl]benzyl}-1H-pyrazol-3-yl)carbonyl]pyrimidin-4-yl)amino)-2,3-dihydroxycyclopentyl]methyl sulfamate;

{(1R,2R,3R,4R)-4-[(5-([1-(3-bromo-4-chlorobenzyl)-1H-pyrazol-3-yl]carbonyl}pyrimidin-4-yl)amino]-3-fluoro-2-hydroxycyclopentyl}methyl sulfamate;

{(1R,2S,4R)-2-hydroxy-4-[(5-{[1-(3-methylbenzyl)-1H-pyrazol-3-yl]carbonyl}pyrimidin-4-yl)amino] cyclopentyl}methyl sulfamate;

[(1R,2S,4R)-2-hydroxy-4-{[5-({1-[3-(trifluoromethyl) benzyl]-1H-pyrrol-3-yl}carbonyl)pyrimidin-4-yl] amino}cyclopentyl]methyl sulfamate;

[(1R,2R,3S,4R)-2,3-dihydroxy-4-({5-[(1-{[5-(trifluoromethyl)-2-furyl]methyl}-1H-pyrazol-3-yl)carbonyl] pyrimidin-4-yl}amino)cyclopentyl]methyl sulfamate;

[(1R,2R,3R,4R)-3-fluoro-2-hydroxy-4-{[5-({1-[3-(trifluoromethoxy)benzyl]-1H-pyrrol-3-yl}carbonyl)pyrimidin-4-yl]amino}cyclopentyl]methyl sulfamate;

[(1R,2R,3R,4R)-3-fluoro-2-hydroxy-4-{[3-({1-[3-(trifluoromethoxy)benzyl]-1H-pyrrol-3-yl}carbonyl)pyridin-4-yl]amino}cyclopentyl]methyl sulfamate;

[(1R,2S,4R)-4-{[5-({1-[(1S)-1-(3-chlorophenyl)ethyl]-1H-pyrazol-3-yl}carbonyl)pyrimidin-4-yl]amino}-2-hydroxycyclopentyl]methyl sulfamate;

[(1R,2S,4R)-4-{[5-((1-[(1R)-1-(3-chlorophenyl)ethyl]-1H-pyrazol-3-yl}carbonyl)pyrimidin-4-yl]amino}-2-hydroxycyclopentyl]methyl sulfamate;

[(1R,2R,3S,4R)-4-{[5-({1-[4-fluoro-3-(trifluoromethoxy)benzyl]-1H-pyrazol-3-yl}carbonyl)pyrimidin-4-yl]amino)-2,3-dihydroxycyclopentyl]methyl sulfamate;

[(1R,2R,3R,4R)-4-({5-[(1-benzyl-1H-pyrazol-3-yl)carbonyl]pyrimidin-4-yl}amino)-2,3-dihydroxycyclopentyl]methyl sulfamate;

N-({(1R,2R,3S,4R)-4-[(5-{[1-(3-chlorobenzyl)-1H-pyrazol-3-yl]carbonyl}pyrimidin-4-yl)amino]-2,3-dihydroxycyclopentyl}methyl)sulfuric diamide;

[(1R,2S,4R)-2-hydroxy-4-([5-({1-[3-(trimethylsilyl)benzyl]-1H-pyrazol-3-yl}carbonyl)pyrimidin-4-yl] amino}cyclopentyl]methyl sulfamate;

[(1R,2R,3S,4R)-2,3-dihydroxy-4-({5-[(5-methyl-1-{[5-(trifluoromethyl)-2-furyl]methyl}-1H-pyrazol-3-yl) carbonyl]pyrimidin-4-yl}amino)cyclopentyl]methyl sulfamate;

[(1R,2R,3S,4R)-4-({5-[(1-benzyl-4-chloro-1H-pyrazol-3-yl)carbonyl]pyrimidin-4-yl}amino)-2,3-dihydroxycyclopentyl]methyl sulfamate;

[(1R,2S,4R)-2-hydroxy-4-{[5-({1-[3-(trifluoromethyl) benzyl]-1H-pyrazol-3-yl}carbonyl)pyrimidin-4-yl] amino}cyclopentyl]methyl sulfamate;

{(1R,2R,3R,4R)-4-[(5-{[1-(3-chloro-4-fluorobenzyl)-1H-pyrrol-3-yl]carbonyl}pyrimidin-4-yl)amino-3-fluoro-2-hydroxycyclopentyl}methyl sulfamate;

[(1R,2R,3S,4R)-4-({5-[(1-benzyl-1H-pyrazol-3-yl)carbonyl]pyrimidin-4-yl}amino)-2,3-dihydroxycyclopentyl] methyl sulfamate;

{(1R,2R,3R,4R)-4-[(5-{[1-(3-bromo-4-fluorobenzyl)-1H-pyrrol-3-yl]carbonyl}pyrimidin-4-yl)amino]-3-fluoro-2-hydroxycyclopentyl}methyl sulfamate;

{(1R,2S,4R)-2-hydroxy-4-[(5-{[1-(imidazo[1,2-a]pyridin-6-ylmethyl)-1H-pyrazol-3-yl]carbonyl}pyrimidin-4-yl)amino]cyclopentyl}methyl sulfamate;

{(1R,2S,4R)-4-[(5-([1-(5,6-dihydro-2H-pyran-3-ylmethyl)-1H-pyrazol-3-yl]carbonyl}pyrimidin-4-yl) amino]-2-hydroxycyclopentyl}methyl sulfamate;

{(1R,2R,3S,4R)-4-[(5-{[1-(4-chloro-2-fluorobenzyl)-1H-pyrazol-3-yl]carbonyl}pyrimidin-4-yl)amino]-2,3-dihydroxycyclopentyl}methyl sulfamate;

{(1R,2R,3R,4R)-4-[(5-{[1-(3-chlorobenzyl)-1H-pyrrol-3-yl]carbonyl}pyrimidin-4-yl)amino]-3-fluoro-2-hydroxycyclopentyl}methyl sulfamate;

[(1R,2R,3R,4R)-4-({5-[(5-chloro-1-{[5-(trifluoromethyl) isoxazol-3-yl]methyl}-1H-pyrrol-3-yl)carbonyl]pyrimidin-4-yl}amino)-3-fluoro-2-hydroxycyclopentyl] methyl sulfamate;

{(1R,2R,3R,4R)-4-[(5-{[1-(3-bromobenzyl)-4-methyl-1H-pyrrol-3-yl]carbonyl}pyrimidin-4-yl)amino]-3-fluoro-2-hydroxycyclopentyl}methyl sulfamate;

{(1R,2R,3S,4R)-2,3-dihydroxy-4-[(5-{[1-(pyridin-2-ylmethyl)-1H-pyrazol-3-yl]carbonyl}pyrimidin-4-yl) amino]cyclopentyl}methyl sulfamate;

{(1R,2S,4R)-2-hydroxy-4-[(5-{[1-(4-methoxy-4-methylpent-2-yn-1-yl)-1H-pyrazol-3-yl]carbonyl}pyrimidin-4-yl)amino]cyclopentyl}methyl sulfamate;

[(1R,2S,4R)-4-{[5-({1-[4-chloro-3-(trifluoromethoxy) benzyl]-1H-pyrazol-3-yl}carbonyl)pyrimidin-4-yl] amino}-2-hydroxycyclopentyl]methyl sulfamate;

{(1R,2S,4R)-2-hydroxy-4-[(5-{[1-(5-methylhex-2-yn-1-yl)-1H-pyrazol-3-yl]carbonyl}pyrimidin-4-yl)amino] cyclopentyl}methyl sulfamate;

{(1R,2S,4R)-2-hydroxy-4-[(5-{[1-(4-hydroxy-4-methylpent-2-yn-1-yl)-1H-pyrazol-3-yl]carbonyl}pyrimidin-4-yl)amino]cyclopentyl}methyl sulfamate;

[(1R,2R,3S,4R)-4-{[5-({1-[3,5-bis(trifluoromethyl)benzyl]-1H-pyrazol-3-yl}carbonyl)pyrimidin-4-yl] amino}-2,3-dihydroxycyclopentyl]methyl sulfamate;

[(1R,2R,3R,4R)-4-{[5-({1-[4-chloro-3-(trifluoromethyl) benzyl]-1H-pyrazol-3-yl}carbonyl)pyrimidin-4-yl] amino}-3-fluoro-2-hydroxycyclopentyl]methyl sulfamate;

{(1R,2S,4R)-4-[(5-{[1-(3-bromobenzyl)-1H-pyrazol-3-yl]carbonyl}pyrimidin-4-yl)(methyl)amino]-2-hydroxycyclopentyl}methyl sulfamate;

[(1R,2S,4R)-4-({5-[(1-benzyl-1H-pyrazol-3-yl)carbonyl] pyrimidin-4-yl}amino)-2-hydroxycyclopentyl]methyl sulfamate;

{(1R,2R,3S,4R)-4-[(5-{[1-(3,4-dichlorobenzyl)-1H-pyrazol-3-yl]carbonyl}pyrimidin-4-yl)amino]-2,3-dihydroxycyclopentyl}methyl sulfamate;

{(1R,2R,3S,4R)-2,3-dihydroxy-4-[(5-{[1-(pyridin-4-ylmethyl)-1H-pyrazol-3-yl]carbonyl}pyrimidin-4-yl)amino]cyclopentyl}methyl sulfamate;

{(1R,2S,4R)-4-[(5-{[1-(4-fluorobenzyl)-1H-pyrazol-3-yl]carbonyl}pyrimidin-4-yl)amino]-2-hydroxycyclopentyl}methyl sulfamate;

[(1R,2S,4R)-2-hydroxy-4-{[5-({1-[(4-methylpyridin-2-yl)methyl]-1H-pyrazol-3-yl}carbonyl)pyrimidin-4-yl]amino}cyclopentyl]methyl sulfamate;

[(1R,2S,4R)-2-hydroxy-4-({5-[(1-{[5-(trifluoromethyl)-2-furyl]methyl}-1H-pyrazol-3-yl)carbonyl]pyrimidin-4-yl}amino)cyclopentyl]methyl sulfamate;

{(1R,2S,4R)-4-[(5-{[1-(3-ethynylbenzyl)-5-methyl-1H-pyrazol-3-yl]carbonyl}pyrimidin-4-yl)amino]-2-hydroxycyclopentyl)methyl sulfamate;

{(1R,2S,4R)-4-[(5-{[1-(3-fluorobenzyl)-1H-pyrazol-3-yl]carbonyl}pyrimidin-4-yl)amino]-2-hydroxycyclopentyl}methyl sulfamate;

{(1R,2S,4R)-4-[(5-{[1-(3-ethynyl-4-fluorobenzyl)-1H-pyrazol-3-yl]carbonyl}pyrimidin-4-yl)amino]-2-hydroxycyclopentyl}methyl sulfamate;

[(1R,2R,3S,4R)-2,3-dihydroxy-4-{[5-((1-[4-(trifluoromethyl)benzyl]-1H-pyrazol-3-yl}carbonyl)pyrimidin-4-yl]amino}cyclopentyl]methyl sulfamate;

[(1R,2S,4R)-4-{[5-({1-[3,5-bis(trifluoromethyl)benzyl]-1H-pyrrol-3-yl}carbonyl)pyrimidin-4-yl]amino}-2-hydroxycyclopentyl]methyl sulfamate;

[(1R,2R,3S,4R)-2,3-dihydroxy-4-{[5-({1-[(5-methylisoxazol-3-yl)methyl]-1H-pyrazol-3-yl}carbonyl)pyrimidin-4-yl]amino}cyclopentyl]methyl sulfamate;

{(1R,2S,4R)-4-[(5-{[1-(3-chlorobenzyl)-5-(trifluoromethyl)-1H-pyrazol-3-yl]carbonyl}pyrimidin-4-yl)amino]-2-hydroxycyclopentyl}methyl sulfamate;

[(1R,2S,4R)-2-hydroxy-4-{[5-({1-[4-(trifluoromethyl)benzyl]-1H-pyrazol-3-yl}carbonyl)pyrimidin-4-yl]amino}cyclopentyl]methyl sulfamate;

[(1R,2S,4R)-4-{[5-({1-[(1R)-1-(3-chlorophenyl)ethyl]-5-methyl-1H-pyrazol-3-yl}carbonyl)pyrimidin-4-yl]amino}-2-hydroxycyclopentyl]methyl sulfamate;

[(1R,2S,4R)-4-{[5-({1-[(1S)-1-(3-chlorophenyl)ethyl]-5-methyl-1H-pyrazol-3-yl}carbonyl)pyrimidin-4-yl]amino}-2-hydroxycyclopentyl]methyl sulfamate;

[(1R,2R,3S,4R)-2,3-dihydroxy-4-({5-[(1-isobutyl-1H-pyrazol-3-yl)carbonyl]pyrimidin-4-yl}amino)cyclopentyl]methyl sulfamate;

[(1R,2S,4R)-4-{[3-({1-[4-chloro-3-(trifluoromethyl)benzyl]-1H-pyrazol-3-yl}carbonyl)pyridin-4-yl]amino}-2-hydroxycyclopentyl]methyl sulfamate;

[(1R,2R,3R,4R)-4-{[5-((1-[(1S)-1-(3-bromophenyl)propyl]-1H-pyrrol-3-yl}carbonyl)pyrimidin-4-yl]amino)-3-fluoro-2-hydroxycyclopentyl]methyl sulfamate;

[(1R,2R,3R,4R)-4-{[5-({1-[(1R)-1-(3-bromophenyl)propyl]-1H-pyrrol-3-yl}carbonyl)pyrimidin-4-yl]amino}-3-fluoro-2-hydroxycyclopentyl]methyl sulfamate;

{(1R,2R,3R,4R)-4-[(5-{[1-(3-chlorobenzyl)-1H-pyrazol-3-yl]carbonyl}pyrimidin-4-yl)amino]-3-fluoro-2-hydroxycyclopentyl}methyl sulfamate;

{(1R,2R,3R,4R)-4-[(5-{[1-(3-bromo-2-fluorobenzyl)-1H-pyrazol-3-yl]carbonyl}pyrimidin-4-yl)amino]-3-fluoro-2-hydroxycyclopentyl}methyl sulfamate;

(1R,2R,3R,4R)-3-fluoro-4-[(5-{[1-(4-fluoro-3-iodobenzyl)-1H-pyrazol-3-yl]carbonyl}pyrimidin-4-yl)amino]-2-hydroxycyclopentyl}methyl sulfamate;

{(1R,2S,4R)-4-[(5-{[1-(3-bromo-4-chlorobenzyl)-1H-pyrazol-3-yl]carbonyl}pyrimidin-4-yl)amino]-2-hydroxycyclopentyl}methyl sulfamate;

[(1R,2S,4R)-4-{[5-({1-[(5-chloro-2-furyl)methyl]-1H-pyrazol-3-yl}carbonyl)pyrimidin-4-yl]amino}-2-hydroxycyclopentyl]methyl sulfamate;

[(1R,2R,3R,4R)-4-{[5-({1-[2-chloro-5-(trifluoromethyl)benzyl]-1H-pyrazol-3-yl}carbonyl)pyrimidin-4-yl]amino}-3-fluoro-2-hydroxycyclopentyl]methyl sulfamate;

[(1R,2R,3S,4R)-2,3-dihydroxy-4-{[5-((1-[2-(trifluoromethyl)benzyl]-1H-pyrazol-3-yl}carbonyl)pyrimidin-4-yl]amino}cyclopentyl]methyl sulfamate;

[(1R,2S,4R)-2-hydroxy-4-({5-[(1-{[5-(trifluoromethyl)-2-thienyl]methyl}-1H-pyrazol-3-yl)carbonyl]pyrimidin-4-yl}amino)cyclopentyl]methyl sulfamate;

[(1R,2R,3R,4R)-4-{[5-({5-chloro-1-[3-(trifluoromethyl)benzyl]-1H-pyrrol-3-yl}carbonyl)pyrimidin-4-yl]amino}-3-fluoro-2-hydroxycyclopentyl]methyl sulfamate;

{(1R,2S,4R)-4-[(5-{[1-(2-chloro-4-fluorobenzyl)-1H-pyrazol-3-yl]carbonyl}pyrimidin-4-yl)amino]-2-hydroxycyclopentyl}methyl sulfamate;

{(1R,2R,3R,4R)-4-[(5-{[1-(3-bromobenzyl)-5-methyl-1H-pyrazol-3-yl]carbonyl}pyrimidin-4-yl)amino]-3-fluoro-2-hydroxycyclopentyl}methyl sulfamate;

{(1R,2R,3R,4R)-4-[(5-{[1-(3-bromobenzyl)-5-ethyl-1H-pyrrol-3-yl]carbonyl}pyrimidin-4-yl)amino]-3-fluoro-2-hydroxycyclopentyl}methyl sulfamate;

[(1R,2R,3R,4R)-3-fluoro-2-hydroxy-4-{[5-({1-[(6-methoxypyridin-2-yl)methyl]-1H-pyrrol-3-yl}carbonyl)pyrimidin-4-yl]amino}cyclopentyl]methyl sulfamate;

[(1R,2R,3R,4R)-4-{[5-({1-[(5-chloro-2-thienyl)methyl]-1H-pyrrol-3-yl}carbonyl)pyrimidin-4-yl]amino}-3-fluoro-2-hydroxycyclopentyl]methyl sulfamate;

{(1R,2R,3S,4R)-4-[(5-{[1-(3,4-difluorobenzyl)-1H-pyrazol-3-yl]carbonyl}pyrimidin-4-yl)amino]-2,3-dihydroxycyclopentyl}methyl sulfamate;

{(1R,2S,4R)-4-[(5-{[1-(4-chloro-2-fluorobenzyl)-1H-pyrazol-3-yl]carbonyl}pyrimidin-4-yl)amino]-2-hydroxycyclopentyl}methyl sulfamate;

[(1R,2R,3R,4R)-4-{[5-(1-[(1S)-1-(3-bromophenyl)ethyl]-1H-pyrrol-3-yl}carbonyl)pyrimidin-4-yl]amino}-3-fluoro-2-hydroxycyclopentyl]methyl sulfamate;

[(1R,2R,3R,4R)-4-{[5-({1-[(1R)-1-(3-bromophenyl)ethyl]-1H-pyrrol-3-yl}carbonyl)pyrimidin-4-yl]amino}-3-fluoro-2-hydroxycyclopentyl]methyl sulfamate;

{(1R,2R,3S,4R)-4-[(5-{[1-(2-chlorobenzyl)-1H-pyrazol-3-yl]carbonyl}pyrimidin-4-yl)amino]-2,3-dihydroxycyclopentyl}methyl sulfamate;

{(1R,2R,3S,4R)-4-[(5-{[1-(2-chloro-4-fluorobenzyl)-1H-pyrazol-3-yl]carbonyl}pyrimidin-4-yl)amino]-2,3-dihydroxycyclopentyl}methyl sulfamate;

{(1R,2R,3R,4R)-4-[(5-{[1-(but-2-yn-1-yl)-1H-pyrrol-3-yl]carbonyl}pyrimidin-4-yl)amino]-3-fluoro-2-hydroxycyclopentyl}methyl sulfamate;

{(1R,2S,4R)-2-hydroxy-4-[(5-{[1-(phenylethynyl)-1H-pyrrol-3-yl]carbonyl}pyrimidin-4-yl)amino]cyclopentyl}methyl sulfamate;

[(1R,2R,3R,4R)-3-fluoro-2-hydroxy-4-({5-[(5-methyl-1-{[5-(trifluoromethyl)-2-furyl]methyl}-1H-pyrazol-3-yl)carbonyl]pyrimidin-4-yl}amino)cyclopentyl]methyl sulfamate;

{(1R,2R,3S,4R)-4-[(5-{[1-(3-fluoro-4-methylbenzyl)-1H-pyrazol-3-yl]carbonyl}pyrimidin-4-yl)amino]-2,3-dihydroxycyclopentyl}methyl sulfamate;

[(1R,2S,4R)-4-{[5-({1-[3-(2-furyl)prop-2-yn-1-yl]-1H-pyrazol-3-yl}carbonyl)pyrimidin-4-yl]amino}-2-hydroxycyclopentyl]methyl sulfamate;

[(1R,2S,4R)-2-hydroxy-4-{[5-({1-[(Z)-2-phenylvinyl]-1H-pyrrol-3-yl}carbonyl)pyrimidin-4-yl]amino}cyclopentyl]methyl sulfamate;

{(1R,2S,4R)-4-[(3-{[1-(3-chlorobenzyl)-1H-pyrrol-3-yl]carbonyl}pyridin-4-yl)amino]-2-hydroxycyclopentyl}methyl sulfamate;

{(1R,2S,4R)-2-hydroxy-4-[(5-{[1-(pentafluorobenzyl)-1H-pyrazol-3-yl]carbonyl}pyrimidin-4-yl)amino]cyclopentyl}methyl sulfamate;

[(1R,2R,4R)-4-({5-[(1-benzyl-1H-pyrazol-3-yl)carbonyl]pyrimidin-4-yl}amino)-3,3-difluoro-2-hydroxycyclopentyl]methyl sulfamate;

{(1R,2R,3S,4R)-4-[(5-{[1-(3-bromo-4-chlorobenzyl)-1H-pyrazol-3-yl]carbonyl}pyrimidin-4-yl)amino]-2,3-dihydroxycyclopentyl}methyl sulfamate;

[(1R,2S,4R)-2-hydroxy-4-({5-[(1-phenyl-1H-pyrazol-3-yl)carbonyl]pyrimidin-4-yl}amino)cyclopentyl]methyl sulfamate;

{(1R,2S,4R)-4-[(5-{[1-(2-chlorobenzyl)-1H-pyrazol-3-yl]carbonyl}pyrimidin-4-yl)amino]-2-hydroxycyclopentyl}methyl sulfamate;

{(1R,2R,3R,4R)-4-[(5-{[1-(5-bromo-2-chlorobenzyl)-1H-pyrazol-3-yl]carbonyl}pyrimidin-4-yl)amino-3-fluoro-2-hydroxycyclopentyl}methyl sulfamate;

[(1R,2R,3R,4R)-3-fluoro-2-hydroxy-4-{[5-((1-[(3-methylisoxazol-5-yl)methyl]-1H-pyrrol-3-yl}carbonyl)pyrimidin-4-yl]amino}cyclopentyl]methyl sulfamate;

[(1R,2R,3R,4R)-3-fluoro-2-hydroxy-4-({5-[(1-{[5-(trifluoromethyl)-2-furyl]methyl}-1H-pyrrol-3-yl)carbonyl]pyrimidin-4-yl}amino)cyclopentyl]methyl sulfamate;

{(1R,2S,4R)-4-[(5-{[1-(3-fluoro-4-methylbenzyl)-1H-pyrazol-3-yl]carbonyl}pyrimidin-4-yl)amino]-2-hydroxycyclopentyl}methyl sulfamate;

[(1R,2S,4R)-4-{[5-({1-[4-fluoro-3-(trifluoromethoxy)benzyl]-1H-pyrrol-3-yl}carbonyl)pyrimidin-4-yl]amino}-2-hydroxycyclopentyl]methyl sulfamate;

{(1R,2S,4R)-4-[(5-{[1-(3,4-difluorobenzyl)-1H-pyrazol-3-yl]carbonyl}pyrimidin-4-yl)amino]-2-hydroxycyclopentyl}methyl sulfamate;

[(1R,2S,4R)-4-{[5-({1-[3-fluoro-5-(trifluoromethyl)benzyl]-1H-pyrrol-3-yl}carbonyl)pyrimidin-4-yl]amino}-2-hydroxycyclopentyl]methyl sulfamate;

{(1R,2S,4R)-2-hydroxy-4-[(5-{[1-(imidazo[1,2-a]pyridin-2-ylmethyl)-1H-pyrazol-3-yl]carbonyl}pyrimidin-4-yl)amino]cyclopentyl}methyl sulfamate;

{(1R,2S,4R)-4-[(5-{[1-(3-chlorobenzyl)-1H-pyrazol-3-yl]carbonyl}pyrimidin-4-yl)amino]-2-hydroxycyclopentyl}methyl sulfamate;

[(1R,2R,3R,4R)-3-fluoro-2-hydroxy-4-{[5-({1-[(1-methyl-2-oxo-1,2-dihydropyridin-3-yl)methyl]-1H-pyrrol-3-yl}carbonyl)pyrimidin-4-yl]amino}cyclopentyl]methyl sulfamate;

[(1R,2R,3S,4R)-4-({5-[(1-benzyl-1H-pyrrol-3-yl)carbonyl]pyrimidin-4-yl}amino)-2,3-dihydroxycyclopentyl]methyl sulfamate;

[(1R,2R,3R,4R)-4-{[5-({1-[4-chloro-3-(trifluoromethoxy)benzyl]-1H-pyrazol-3-yl}carbonyl)pyrimidin-4-yl]amino}-3-fluoro-2-hydroxycyclopentyl]methyl sulfamate;

{(1R,2S,4R)-4-[(5-{[1-(2,3-difluorobenzyl)-1H-pyrazol-3-yl]carbonyl}pyrimidin-4-yl)amino]-2-hydroxycyclopentyl}methyl sulfamate;

[(1R,2R,3S,4R)-2,3-dihydroxy-4-({5-[(1-isopropyl-1H-pyrazol-3-yl)carbonyl]pyrimidin-4-yl}amino)cyclopentyl]methyl sulfamate;

{(1R,2R,3S,4R)-2,3-dihydroxy-4-[(5-{[1-(3-iodobenzyl)-1H-pyrazol-3-yl]carbonyl}pyrimidin-4-yl)amino]cyclopentyl}methyl sulfamate;

{(1R,2R,3R,4R)-3-fluoro-2-hydroxy-4-[(5-{[1-(tetrahydro-2H-pyran-4-ylmethyl)-1H-pyrrol-3-yl]carbonyl}pyrimidin-4-yl)amino]cyclopentyl}methyl sulfamate;

{(1R,2S,4R)-4-[(3-{[1-(3-bromobenzyl)-1H-pyrazol-3-yl]carbonyl}pyridin-4-yl)amino]-2-hydroxycyclopentyl}methyl sulfamate;

[(1R,2R,3R,4R)-4-{[5-({1-[3-(difluoromethoxy)benzyl]-1H-pyrrol-3-yl}carbonyl)pyrimidin-4-yl]amino}-3-fluoro-2-hydroxycyclopentyl]methyl sulfamate;

{(1R,2R,3S,4R)-2,3-dihydroxy-4-[(5-{[1-(2,3,6-trifluorobenzyl)-1H-pyrazol-3-yl]carbonyl}pyrimidin-4-yl)amino]cyclopentyl}methyl sulfamate;

[(1R,2S,4R)-2-hydroxy-4-{[5-({1-[2-(trifluoromethyl)benzyl]-1H-pyrazol-3-yl}carbonyl)pyrimidin-4-yl]amino}cyclopentyl]methyl sulfamate;

[(1R,2R,3S,4R)-4-({5-[(1-benzyl-1H-pyrazol-3-yl)carbonyl]pyrimidin-4-yl}amino)-3-fluoro-2-hydroxycyclopentyl]methyl sulfamate;

{(1R,2S,4R)-4-[(5-{[1-(but-2-yn-1-yl)-1H-pyrazol-3-yl]carbonyl}pyrimidin-4-yl)amino]-2-hydroxycyclopentyl)methyl sulfamate;

[(1R,2R,3S,4R)-4-{[5-({1-[3-(4-fluorophenoxy)benzyl]-1H-pyrazol-3-yl}carbonyl)pyrimidin-4-yl]amino}-2,3-dihydroxycyclopentyl]methyl sulfamate;

[(1R,2R,3S,4R)-4-{[5-({1-[2-fluoro-5-(trifluoromethyl)benzyl]-1H-pyrazol-3-yl}carbonyl)pyrimidin-4-yl]amino}-2,3-dihydroxycyclopentyl]methyl sulfamate;

[(1R,2R,3R,4R)-3-fluoro-4-{[5-({1-[(5-fluoro-2-furyl)methyl]-1H-pyrrol-3-yl}carbonyl)pyrimidin-4-yl]amino}-2-hydroxycyclopentyl]methyl sulfamate;

[(1R,2S,4R)-4-{[5-({1-[(3-chloro-2-thienyl)methyl]-1H-pyrazol-3-yl}carbonyl)pyrimidin-4-yl]amino}-2-hydroxycyclopentyl]methyl sulfamate;

{(1R,2S,4R)-4-[(3-{[1-(3,4-dichlorobenzyl)-1H-pyrrol-3-yl]carbonyl}pyridin-4-yl)amino]-2-hydroxycyclopentyl}methyl sulfamate;

{(1R,2S,4R)-2-hydroxy-4-[(5-{[1-(pent-2-yn-1-yl)-1H-pyrazol-3-yl]carbonyl}pyrimidin-4-yl)amino]cyclopentyl}methyl sulfamate;

[(1R,2S,4R)-4-({5-[(1-{[5-(difluoromethyl)-2-furyl]methyl}-1H-pyrazol-3-yl)carbonyl]pyrimidin-4-yl}amino)-2-hydroxycyclopentyl]methyl sulfamate;

{(1R,2R,3R,4R)-3-fluoro-2-hydroxy-4-[(5-{[1-(4-methoxybut-2-yn-1-yl)-1H-pyrrol-3-yl]carbonyl}pyrimidin-4-yl)amino]cyclopentyl}methyl sulfamate;

{(1R,2R,3R,4R)-3-fluoro-2-hydroxy-4-[(5-{[1-(imidazo[1,2-a]pyridin-5-ylmethyl)-1H-pyrrol-3-yl]carbonyl}pyrimidin-4-yl)amino]cyclopentyl}methyl sulfamate;

[(1R,2S,4R)-4-{[5-({1-[(6-bromopyridin-2-yl)methyl]-5-methyl-1H-pyrazol-3-yl}carbonyl)pyrimidin-4-yl]amino}-2-hydroxycyclopentyl]methyl sulfamate;

{(1R,2S,4R)-4-[(5-{[1-(5-bromo-2-chlorobenzyl)-1H-pyrazol-3-yl]carbonyl}pyrimidin-4-yl)amino]-2-hydroxycyclopentyl}methyl sulfamate;

{(1R,2R,3S,4R)-4-[(5-{[1-(3-bromobenzyl)-1H-pyrazol-3-yl]carbonyl}pyrimidin-4-yl)amino]-2,3-dihydroxycyclopentyl}methyl sulfamate;

{(1R,2S,4R)-4-[(5-{[1-(1-benzothiophen-2-ylmethyl)-1H-pyrazol-3-yl]carbonyl}pyrimidin-4-yl)amino]-2-hydroxycyclopentyl)methyl sulfamate;

(1R,2R,3R,4R)-4-[(3-{[1-(3-chlorobenzyl)-1H-pyrazol-3-yl]carbonyl}pyridin-4-yl)amino]-3-fluoro-2-hydroxycyclopentyl}methyl sulfamate;

[(1R,2R,3R,4R)-4-{[5-({1-[2-(3-bromophenyl)ethyl]-1H-pyrrol-3-yl}carbonyl)pyrimidin-4-yl]amino)-3-fluoro-2-hydroxycyclopentyl]methyl sulfamate;

{(1R,2R,3R,4R)-4-[(5-{[1-(3-bromobenzyl)-5-chloro-1H-pyrrol-3-yl]carbonyl}pyrimidin-4-yl)amino]-3-fluoro-2-hydroxycyclopentyl}methyl sulfamate;

{(1R,2S,4R)-4-[(5-{[1-(4-fluoro-3-iodobenzyl)-1H-pyrazol-3-yl]carbonyl}pyrimidin-4-yl)amino]-2-hydroxycyclopentyl}methyl sulfamate;

[(1R,2S,4R)-4-{[3-((1-[3-(difluoromethoxy)benzyl]-1H-pyrazol-3-yl}carbonyl)pyridin-4-yl]amino}-2-hydroxycyclopentyl]methyl sulfamate;

{(1R,2R,3S,4R)-2,3-dihydroxy-4-[(5-{[1-(pyridin-3-ylmethyl)-1H-pyrazol-3-yl]carbonyl}pyrimidin-4-yl)amino]cyclopentyl}methyl sulfamate;

{(1R,2S,4R)-2-hydroxy-4-[(5-{[5-methyl-1-(3-methylbenzyl)-1H-pyrazol-3-yl]carbonyl}pyrimidin-4-yl)amino]cyclopentyl}methyl sulfamate;

{(1R,2R,3S,4R)-4-[(5-{[1-(2-cyanobenzyl)-1H-pyrazol-3-yl]carbonyl}pyrimidin-4-yl)amino]-2,3-dihydroxycyclopentyl}methyl sulfamate;

[(1R,2R,3R,4R)-4-((5-[(1-{[(2R)-5,6-dimethyltetrahydrofuran-2-yl]methyl}-1H-pyrrol-3-yl)carbonyl]pyrimidin-4-yl}amino)-3-fluoro-2-hydroxycyclopentyl]methyl sulfamate;

[(1R,2R,3R,4R)-4-({5-[(1-{[(2S)-5,5-dimethyltetrahydrofuran-2-yl]methyl}-1H-pyrrol-3-yl)carbonyl]pyrimidin-4-yl}amino)-3-fluoro-2-hydroxycyclopentyl]methyl sulfamate;

[(1R,2S,4R)-2-hydroxy-4-{[5-({1-[3-(morpholin-4-yl)benzyl]-1H-pyrazol-3-yl}carbonyl)pyrimidin-4-yl]amino}cyclopentyl]methyl sulfamate;

{(1R,2S,4R)-4-[(5-{[1-(cyclohex-1-en-1-ylmethyl)-1H-pyrazol-3-yl]carbonyl}pyrimidin-4-yl)amino]-2-hydroxycyclopentyl}methyl sulfamate;

{(1R,2S,4R)-4-[(5-{[1-(2-cyanobenzyl)-1H-pyrazol-3-yl]carbonyl}pyrimidin-4-yl)amino]-2-hydroxycyclopentyl}methyl sulfamate;

[(1R,2R,3R,4R)-4-({5-({5-chloro-1-[(5-chloro-2-furyl)methyl]-1H-pyrrol-3-yl}carbonyl)pyrimidin-4-yl]amino)-3-fluoro-2-hydroxycyclopentyl]methyl sulfamate;

[(1R,2S,4R)-4-{[5-({1-[(3-bromophenyl)sulfonyl]-1H-pyrrol-3-yl}carbonyl)pyrimidin-4-yl]amino}-2-hydroxycyclopentyl]methyl sulfamate;

[(1R,2R,3S,4R)-4-{[5-({1-[3-(difluoromethoxy)benzyl]-1H-pyrazol-3-yl}carbonyl)pyrimidin-4-yl]amino}-2,3-dihydroxycyclopentyl]methyl sulfamate;

[(1R,2R,3R,4R)-3-fluoro-2-hydroxy-4-({5-[(1-{[5-(trifluoromethyl)-2-thienyl]methyl}-1H-pyrrol-3-yl)carbonyl]pyrimidin-4-yl}amino)cyclopentyl]methyl sulfamate;

[(1R,2R,3S,4R)-4-{[5-({1-[3-fluoro-5-(trifluoromethyl)benzyl]-1H-pyrazol-3-yl}carbonyl)pyrimidin-4-yl]amino}-2,3-dihydroxycyclopentyl]methyl sulfamate;

[(1R,2R,3S,4R)-2,3-dihydroxy-4-({5-[(1-{4-[(trifluoromethyl)sulfanyl]benzyl}-1H-pyrazol-3-yl)carbonyl]pyrimidin-4-yl}amino)cyclopentyl]methyl sulfamate;

{(1R,2S,4R)-4-[(5-{[1-(3,5-difluorobenzyl)-1H-pyrazol-3-yl]carbonyl}pyrimidin-4-yl)amino]-2-hydroxycyclopentyl}methyl sulfamate;

[(1R,2S,4R)-4-{[5-({1-[2,5-bis(trifluoromethyl)benzyl]-1H-pyrazol-3-yl}carbonyl)pyrimidin-4-yl]amino}-2-hydroxycyclopentyl]methyl sulfamate;

[(1R,2S,4R)-2-hydroxy-4-{[3-({1-[3-(trifluoromethyl)benzyl]-1H-pyrazol-3-yl}carbonyl)pyridin-4-yl]amino}cyclopentyl]methyl sulfamate;

[(1R,2S,4R)-4-{[3-({1-[4-fluoro-3-(trifluoromethyl)benzyl]-1H-pyrazol-3-yl}carbonyl)pyridin-4-yl]amino}-2-hydroxycyclopentyl]methyl sulfamate;

[(1R,2S,4R)-4-{[5-({1-[1-(3-chlorophenyl)cyclopropyl]-1H-pyrrol-3-yl}carbonyl)pyrimidin-4-yl]amino}-2-hydroxycyclopentyl]methyl sulfamate;

[(1R,2R,3S,4R)-2,3-dihydroxy-4-{[5-({1-[4-(trifluoromethoxy)benzyl]-1H-pyrazol-3-yl}carbonyl)pyrimidin-4-yl]amino}cyclopentyl]methyl sulfamate;

[(1R,2R,3S,4R)-4-{[5-({1-[2,4-bis(trifluoromethyl)benzyl]-1H-pyrazol-3-yl}carbonyl)pyrimidin-4-yl]amino}-2,3-dihydroxycyclopentyl]methyl sulfamate;

[(1R,2R,3S,4R)-4-{[5-({1-[2,5-bis(trifluoromethyl)benzyl]-1H-pyrazol-3-yl}carbonyl)pyrimidin-4-yl]amino}-2,3-dihydroxycyclopentyl]methyl sulfamate;

[(1R,2R,3S,4R)-4-{[5-({1-[2-chloro-5-(trifluoromethyl)benzyl]-1H-pyrazol-3-yl}carbonyl)pyrimidin-4-yl]amino}-2,3-dihydroxycyclopentyl]methyl sulfamate;

{(1R,2R,3S,4R)-4-[(5-{[1-(3,5-difluorobenzyl)-1H-pyrazol-3-yl]carbonyl}pyrimidin-4-yl)amino]-2,3-dihydroxycyclopentyl}methyl sulfamate;

[(1R,2S,4R)-2-hydroxy-4-{[5-({1-[3-(3-hydroxyoxetan-3-yl)benzyl]-1H-pyrazol-3-yl}carbonyl)pyrimidin-4-yl]amino}cyclopentyl]methyl sulfamate;

[(1R,2S,4R)-2-hydroxy-4-{[5-({1-[3-(trifluoromethoxy)benzyl]-1H-pyrrol-3-yl}carbonyl)pyrimidin-4-yl]amino}cyclopentyl]methyl sulfamate;

{(1R,2R,3R,4R)-4-[(5-{[5-bromo-1-(3-bromobenzyl)-1H-pyrrol-3-yl]carbonyl}pyrimidin-4-yl)amino]-3-fluoro-2-hydroxycyclopentyl}methyl sulfamate;

[(1R,2R,3S,4R)-4-{[5-({1-[(4-fluoro-1-naphthyl)methyl]-1H-pyrazol-3-yl}carbonyl)pyrimidin-4-yl]amino}-2,3-dihydroxycyclopentyl]methyl sulfamate;

[(1R,2S,4R)-2-hydroxy-4-({5-[(1-{[5-(trifluoromethyl)-2-furyl]methyl}-1H-pyrrol-3-yl)carbonyl]pyrimidin-4-yl}amino)cyclopentyl]methyl sulfamate;

[(1R,2S,4R)-2-hydroxy-4-{[5-({1-[3-(3-hydroxyoxetan-3-yl)prop-2-yn-1-yl]-1H-pyrazol-3-yl}carbonyl)pyrimidin-4-yl]amino}cyclopentyl]methyl sulfamate;

[(1R,2S,4R)-2-hydroxy-4-{[5-({1-[4-(trifluoromethoxy)benzyl]-1H-pyrazol-3-yl}carbonyl)pyrimidin-4-yl]amino}cyclopentyl]methyl sulfamate;

[(1R,2R,3R,4R)-3-fluoro-2-hydroxy-4-{[5-({1-[(5-methyl-2-furyl)methyl]-1H-pyrrol-3-yl}carbonyl)pyrimidin-4-yl]amino}cyclopentyl]methyl sulfamate;

{(1R,2R,3S,4R)-4-[(5-{[1-(biphenyl-3-ylmethyl)-1H-pyrazol-3-yl]carbonyl}pyrimidin-4-yl)amino]-2,3-dihydroxycyclopentyl}methyl sulfamate;

{(1R,2S,4R)-4-[(5-{[1-(3-bromo-4-fluorobenzyl)-1H-pyrrol-3-yl]carbonyl}pyrimidin-4-yl)amino]-2-hydroxycyclopentyl}methyl sulfamate;

[(1R,2S,4R)-4-{[5-({1-[(5-chloro-2-thienyl)methyl]-1H-pyrazol-3-yl}carbonyl)pyrimidin-4-yl]amino}-2-hydroxycyclopentyl]methyl sulfamate;

[(1R,2S,4R)-2-hydroxy-4-{[5-({1-[(methylsulfanyl)methyl]-1H-pyrazol-3-yl}carbonyl)pyrimidin-4-yl]amino}cyclopentyl]methyl sulfamate;

{(1R,2S,4R)-4-[(5-{[1-(3-bromo-2-fluorobenzyl)-1H-pyrazol-3-yl]carbonyl}pyrimidin-4-yl)amino]-2-hydroxycyclopentyl}methyl sulfamate;

[(1R,2R,3S,4R)-4-{[5-({1-[2-(3-chlorophenyl)-2-oxoethyl]-1H-pyrazol-3-yl}carbonyl)pyrimidin-4-yl]amino}-2,3-dihydroxycyclopentyl]methyl sulfamate;

[(1R,2R,3S,4R)-4-{[5-({1-[(6-bromopyridin-2-yl)methyl]-1H-pyrazol-3-yl}carbonyl)pyrimidin-4-yl]amino}-2,3-dihydroxycyclopentyl]methyl sulfamate;

[(1R,2R,3S,4R)-4-{[5-({1-[(5-chloro-1-benzothiophen-3-yl)methyl]-1H-pyrazol-3-yl}carbonyl)pyrimidin-4-yl]amino}-2,3-dihydroxycyclopentyl]methyl sulfamate;

{(1R,2S,4R)-2-hydroxy-4-[(5-{[1-(2,4,6-trifluorobenzyl)-1H-pyrazol-3-yl]carbonyl}pyrimidin-4-yl)amino]cyclopentyl}methyl sulfamate;

{(1R,2S,4R)-4-[(5-{[1-(3-cyclopropylprop-2-yn-1-yl)-1H-pyrazol-3-yl]carbonyl}pyrimidin-4-yl)amino]-2-hydroxycyclopentyl}methyl sulfamate;

{(1R,2S,4R)-4-{[5-({1-[4-chloro-3-(trifluoromethyl)benzyl]-1H-pyrazol-3-yl}carbonyl)pyrimidin-4-yl]amino}-2-hydroxycyclopentyl}methyl sulfamate;

{(1R,2S,4R)-4-[(5-{[1-(2,5-dichlorobenzyl)-1H-pyrazol-3-yl]carbonyl}pyrimidin-4-yl)amino]-2-hydroxycyclopentyl}methyl sulfamate;

{(1R,2R,3S,4R)-4-[(5-{[1-(3-bromo-4-fluorobenzyl)-1H-pyrazol-3-yl]carbonyl}pyrimidin-4-yl)amino]-2,3-dihydroxycyclopentyl}methyl sulfamate;

[(1R,2S,4R)-4-({5-[(1-allyl-1H-pyrrol-3-yl)carbonyl]pyrimidin-4-yl}amino)-2-hydroxycyclopentyl]methyl sulfamate;

{(1R,2S,4R)-2-hydroxy-4-[(5-{[1-(3-iodobenzyl)-1H-pyrazol-3-yl]carbonyl}pyrimidin-4-yl)amino]cyclopentyl}methyl sulfamate;

[(1R,2S,4R)-2-hydroxy-4-{[5-({1-[(2R)-tetrahydrofuran-2-ylmethyl]-1H-pyrazol-3-yl}carbonyl)pyrimidin-4-yl]amino}cyclopentyl]methyl sulfamate;

[(1R,2S,4R)-2-hydroxy-4-{[5-({1-[(2S)-tetrahydrofuran-2-ylmethyl]-1H-pyrazol-3-yl}carbonyl)pyrimidin-4-yl]amino}cyclopentyl]methyl sulfamate;

{(1R,2R,3R,4R)-3-fluoro-2-hydroxy-4-[(5-{[1-(3-iodobenzyl)-5-methyl-1H-pyrazol-3-yl]carbonyl}pyrimidin-4-yl)amino]cyclopentyl}methyl sulfamate;

[(1R,2S,4R)-2-hydroxy-4-{[5-({1-[(6-methoxypyridin-2-yl)methyl]-1H-pyrazol-3-yl}carbonyl)pyrimidin-4-yl]amino}cyclopentyl]methyl sulfamate;

[(1R,2R,3R,4R)-4-{[5-({1-[(5-chloro-2-furyl)methyl]-1H-pyrrol-3-yl}carbonyl)pyrimidin-4-yl]amino}-3-fluoro-2-hydroxycyclopentyl]methyl sulfamate;

[(1R,2R,3R,4R)-3-fluoro-2-hydroxy-4-{[5-({1-[(5-methylisoxazol-3-yl)methyl]-1H-pyrrol-3-yl}carbonyl)pyrimidin-4-yl]amino}cyclopentyl]methyl sulfamate;

[(1R,2S,4R)-2-hydroxy-4-{[5-({1-[(6-methylpyridin-2-yl)methyl]-1H-pyrazol-3-yl}carbonyl)pyrimidin-4-yl]amino}cyclopentyl]methyl sulfamate;

[(1R,2S,4R)-4-{[5-({1-[(5-bromopyridin-3-yl)methyl]-1H-pyrrol-3-yl}carbonyl)pyrimidin-4-yl]amino}-2-hydroxycyclopentyl]methyl sulfamate;

[(1R,2S,4R)-4-({5-[(1-benzyl-1H-pyrrol-3-yl)carbonyl]pyrimidin-4-yl}amino)-2-hydroxycyclopentyl]methyl sulfamate;

{(1R,2S,4R)-4-[(5-{[1-(3-cyclopropyl-4-fluorobenzyl)-1H-pyrazol-3-yl]carbonyl}pyrimidin-4-yl)amino]-2-hydroxycyclopentyl}methyl sulfamate;

[(1R,2S,4R)-4-{[5-({1-[(1R)-cyclohex-2-en-1-yl]-1H-pyrazol-3-yl}carbonyl)pyrimidin-4-yl]amino}-2-hydroxycyclopentyl]methyl sulfamate;

[(1R,2S,4R)-4-{[5-({1-[(1S)-cyclohex-2-en-1-yl]-1H-pyrazol-3-yl}carbonyl)pyrimidin-4-yl]amino}-2-hydroxycyclopentyl]methyl sulfamate;

[(1R,2R,3R,4R)-4-{[5-({1-[3-(difluoromethoxy)benzyl]-1H-pyrazol-3-yl}carbonyl)pyrimidin-4-yl]amino}-3-fluoro-2-hydroxycyclopentyl]methyl sulfamate;

[(1R,2R,3R,4R)-3-fluoro-2-hydroxy-4-({5-[(1-{(1S)-1-[5-(trifluoromethyl)-2-furyl]ethyl}-1H-pyrrol-3-yl)carbonyl]pyrimidin-4-yl}amino)cyclopentyl]methyl sulfamate;

[(1R,2R,3R,4R)-3-fluoro-2-hydroxy-4-((5-[(1-{(1R)-1-[5-(trifluoromethyl)-2-furyl]ethyl}-1H-pyrrol-3-yl)carbonyl]pyrimidin-4-yl}amino)cyclopentyl]methyl sulfamate;

{(1R,2S,4R)-2-hydroxy-4-[(5-{[1-(2-methoxyethyl)-1H-pyrazol-3-yl]carbonyl}pyrimidin-4-yl)amino]cyclopentyl}methyl sulfamate;

[(1R,2S,4R)-2-hydroxy-4-({5-[(1-{[1-methyl-5-(trifluoromethyl)-1H-pyrazol-3-yl]methyl}-1H-pyrrol-3-yl)carbonyl]pyrimidin-4-yl}amino)cyclopentyl]methyl sulfamate;

[(1R,2R,3R,4R)-4-[(5-{[1-(2,5-dichlorobenzyl)-1H-pyrazol-3-yl]carbonyl}pyrimidin-4-yl)amino]-3-fluoro-2-hydroxycyclopentyl]methyl sulfamate;

[(1R,2S,4R)-2-hydroxy-4-{[5-({1-[3-(1-methyl-1H-pyrazol-4-yl)prop-2-yn-1-yl]-1H-pyrazol-3-yl}carbonyl)pyrimidin-4-yl]amino}cyclopentyl]methyl sulfamate;

{(1R,2S,4R)-4-[(5-{[1-(3-bromobenzyl)-5-methyl-1H-pyrazol-3-yl]carbonyl}pyrimidin-4-yl)amino]-2-hydroxycyclopentyl}methyl sulfamate;

{(1R,2R,3R,4R)-4-[(5-{[5-chloro-1-(3-iodobenzyl)-1H-pyrrol-3-yl]carbonyl}pyrimidin-4-yl)amino]-3-fluoro-2-hydroxycyclopentyl}methyl sulfamate;

{(1R,2R,3R,4R)-4-[(5-{[1-(3,4-dichlorobenzyl)-1H-pyrazol-3-yl]carbonyl}pyrimidin-4-yl)amino]-3-fluoro-2-hydroxycyclopentyl}methyl sulfamate;

{(1R,2R,3R,4R)-4-[(5-{[1-(3-bromobenzyl)-1H-pyrrol-3-yl]carbonyl}pyrimidin-4-yl)amino]-3-fluoro-2-hydroxycyclopentyl}methyl sulfamate;

[(1R,2R,3S,4R)-4-{[5-({1-[3-(acryloylamino)benzyl]-1H-pyrazol-3-yl}carbonyl)pyrimidin-4-yl]amino}-2,3-dihydroxycyclopentyl]methyl sulfamate;

{(1R,2R,3S,4R)-2,3-dihydroxy-4-[(5-{[1-(2,4,5-trifluorobenzyl)-1H-pyrazol-3-yl]carbonyl}pyrimidin-4-yl)amino]cyclopentyl}methyl sulfamate;

[(1R,2S,4R)-4-{[5-({1-[(1S)-1-(3-bromophenyl)ethyl]-1H-pyrazol-3-yl}carbonyl)pyrimidin-4-yl]amino}-2-hydroxycyclopentyl]methyl sulfamate;

[(1R,2S,4R)-4-{[5-({1-[(1R)-1-(3-bromophenyl)ethyl]-1H-pyrazol-3-yl}carbonyl)pyrimidin-4-yl]amino}-2-hydroxycyclopentyl]methyl sulfamate;

((1R,2R,3R,4R)-4-[(5-{[1-(3-chlorobenzyl)-5-(trifluoromethyl)-1H-pyrazol-3-yl]carbonyl}pyrimidin-4-yl)amino]-3-fluoro-2-hydroxycyclopentyl}methyl sulfamate;

[(1R,2R,3R,4R)-4-({5-[(1-benzyl-1H-pyrazol-3-yl)carbonyl]pyrimidin-4-yl}amino)-3-fluoro-2-hydroxycyclopentyl]methyl sulfamate;

{(1R,2R,3S,4R)-2,3-dihydroxy-4-[(5-{[1-(pentafluorobenzyl)-1H-pyrazol-3-yl]carbonyl}pyrimidin-4-yl)amino]cyclopentyl}methyl sulfamate;

{(1S,2S,4R)-4-[(5-{[1-(3-bromobenzyl)-1H-pyrrol-3-yl]carbonyl}pyrimidin-4-yl)amino]-2-hydroxycyclopentyl}methyl sulfamate;

{(1R,2R,3R,4R)-4-[(5-{[1-(3-bromo-4-fluorobenzyl)-5-chloro-1H-pyrrol-3-yl]carbonyl}pyrimidin-4-yl)amino]-3-fluoro-2-hydroxycyclopentyl}methyl sulfamate;

[(1R,2R,3S,4R)-2,3-dihydroxy-4-{[5-({1-[3-(vinylsulfonyl)benzyl]-1H-pyrazol-3-yl}carbonyl)pyrimidin-4-yl]amino}cyclopentyl]methyl sulfamate;

{(1R,2R,3R,4R)-4-[(5-{[1-(1-benzothiophen-2-ylmethyl)-1H-pyrrol-3-yl]carbonyl}pyrimidin-4-yl)amino]-3-fluoro-2-hydroxycyclopentyl}methyl sulfamate;

{(1R,2R,3S,4R)-4-[(5-{[1-((1R)-2,3-dihydro-1H-inden-1-yl)-1H-pyrazol-3-yl]carbonyl}pyrimidin-4-yl)amino]-2,3-dihydroxycyclopentyl}methyl sulfamate;

{(1R,2R,3S,4R)-4-[(5-{[1-((1S)-2,3-dihydro-1H-inden-1-yl)-1H-pyrazol-3-yl]carbonyl}pyrimidin-4-yl)amino]-2,3-dihydroxycyclopentyl}methyl sulfamate;

[(1R,2R,3S,4R)-4-{[5-({1-[(4-bromopyridin-2-yl)methyl]-1H-pyrazol-3-yl}carbonyl)pyrimidin-4-yl]amino}-2,3-dihydroxycyclopentyl]methyl sulfamate;

{(1R,2R,3S,4R)-2,3-dihydroxy-4-[(5-({1-[(3-methoxybenzyl)-1H-pyrazol-3-yl]carbonyl)pyrimidin-4-yl)amino]cyclopentyl}methyl sulfamate;

{(1R,2R,3S,4R)-2,3-dihydroxy-4-[(5-{[1-(3,4,5-trifluorobenzyl)-1H-pyrazol-3-yl]carbonyl}pyrimidin-4-yl)amino]cyclopentyl}methyl sulfamate;

{(1R,2R,3S,4R)-4-[(5-{[1-(2,3-difluorobenzyl)-1H-pyrazol-3-yl]carbonyl}pyrimidin-4-yl)amino]-2,3-dihydroxycyclopentyl}methyl sulfamate;

[(1R,2S,4R)-4-{[5-({1-[4-fluoro-2-(trifluoromethyl)benzyl]-1H-pyrazol-3-yl}carbonyl)pyrimidin-4-yl]amino}-2-hydroxycyclopentyl]methyl sulfamate;

{(1R,2S,4R)-2-hydroxy-4-[(5-{[1-(2,4,5-trifluorobenzyl)-1H-pyrazol-3-yl]carbonyl}pyrimidin-4-yl)amino]cyclopentyl}methyl sulfamate;

{(1R,2S,4R)-2-hydroxy-4-[(5-{[1-(prop-2-yn-1-yl)-1H-pyrrol-3-yl]carbonyl}pyrimidin-4-yl)amino]cyclopentyl}methyl sulfamate;

{(1R,2R,3R,4R)-4-[(5-{[1-(3,4-dichlorobenzyl)-1H-pyrrol-3-yl]carbonyl}pyrimidin-4-yl)amino]-3-fluoro-2-hydroxycyclopentyl}methyl sulfamate;

[(1R,2S,4R)-2-hydroxy-4-{[5-({1-[(3R)-tetrahydrofuran-3-ylmethyl]-1H-pyrazol-3-yl}carbonyl)pyrimidin-4-yl]amino}cyclopentyl]methyl sulfamate;

[(1R,2S,4R)-2-hydroxy-4-{[5-({1-[(3S)-tetrahydrofuran-3-ylmethyl]-1H-pyrazol-3-yl}carbonyl)pyrimidin-4-yl]amino}cyclopentyl]methyl sulfamate;

{(1R,2S,4R)-4-[(5-{[1-(3-bromobenzyl)-1H-pyrrol-3-yl]carbonyl}pyrimidin-4-yl)amino]-2-hydroxycyclopentyl}methyl sulfamate;

{(1R,2R,3S,4R)-4-[(5-{[1-(3-chloro-5-fluorobenzyl)-1H-pyrazol-3-yl]carbonyl}pyrimidin-4-yl)amino]-2,3-dihydroxycyclopentyl}methyl sulfamate;

{(1R,2S,4R)-4-[(5-{[1-benzyl-5-(hydroxymethyl)-1H-pyrazol-3-yl]carbonyl}pyrimidin-4-yl)amino]-2-hydroxycyclopentyl}methyl sulfamate;

{(1R,2R,3S,4R)-4-[(5-{[1-(2,4-difluorobenzyl)-1H-pyrazol-3-yl]carbonyl}pyrimidin-4-yl)amino]-2,3-dihydroxycyclopentyl}methyl sulfamate;

{(1R,2R,3R,4R)-4-[(5-{[1-(3-bromo-4-chlorobenzyl)-1H-pyrrol-3-yl]carbonyl}pyrimidin-4-yl)amino-3-fluoro-2-hydroxycyclopentyl}methyl sulfamate;

{(1R,2R,3S,4R)-4-[(5-{[1-(2-fluorobenzyl)-1H-pyrazol-3-yl]carbonyl}pyrimidin-4-yl)amino]-2,3-dihydroxycyclopentyl}methyl sulfamate;

[(1R,2S,4R)-2-hydroxy-4-{[5-({1-[(1S,2S)-(2-phenylcyclopropyl)methyl]-1H-pyrrol-3-yl}carbonyl)pyrimidin-4-yl]amino}cyclopentyl]methyl sulfamate;

[(1R,2S,4R)-2-hydroxy-4-{[5-({1-[(1R,2R)-(2-phenylcyclopropyl)methyl]-1H-pyrrol-3-yl}carbonyl)pyrimidin-4-yl]amino}cyclopentyl]methyl sulfamate;

{(1R,2S,4R)-4-[(5-{[1-(but-2-yn-1-yl)-1H-pyrrol-3-yl]carbonyl}pyrimidin-4-yl)amino]-2-hydroxycyclopentyl}methyl sulfamate;

[(1R,2S,4R)-4-{[5-({1-[(5-chloro-1-benzothiophen-3-yl)methyl]-1H-pyrrol-3-yl}carbonyl)pyrimidin-4-yl]amino}-2-hydroxycyclopentyl]methyl sulfamate;

[(1S,2S,4R)-4-({5-[(1-benzyl-1H-pyrazol-3-yl)carbonyl]pyrimidin-4-yl}amino)-2-hydroxycyclopentyl]methyl sulfamate;

[(1R,2R,3R,4R)-4-{[5-({1-[4-fluoro-3-(trifluoromethyl)benzyl]-1H-pyrazol-3-yl}carbonyl)pyrimidin-4-yl]amino}-2,3-dihydroxycyclopentyl]methyl sulfamate;

{(1R,2S,4R)-2-hydroxy-4-[(5-{[1-(3-methylbut-2-en-1-yl)-1H-pyrazol-3-yl]carbonyl}pyrimidin-4-yl)amino]cyclopentyl}methyl sulfamate;

[(1R,2R,3S,4R)-2,3-dihydroxy-4-({5-[(1-methyl-1H-pyrazol-3-yl)carbonyl]pyrimidin-4-yl}amino)cyclopentyl]methyl sulfamate;

{(1R,2S,4R)-4-[(5-{[1-(5-bromo-2-fluorobenzyl)-1H-pyrazol-3-yl]carbonyl}pyrimidin-4-yl)amino]-2-hydroxycyclopentyl}methyl sulfamate;

{(1R,2S,4R)-2-hydroxy-4-[(5-{[1-(3-iodobenzyl)-5-methyl-1H-pyrazol-3-yl]carbonyl}pyrimidin-4-yl)amino]cyclopentyl}methyl sulfamate;

[(1R,2S,4R)-2-hydroxy-4-{[5-({1-[(5-methylisoxazol-3-yl)methyl]-1H-pyrazol-3-yl}carbonyl)pyrimidin-4-yl]amino}cyclopentyl]methyl sulfamate;

[(1R,2R,3S,4R)-2,3-dihydroxy-4-([5-({1-[3-(trifluoromethoxy)benzyl]-1H-pyrazol-3-yl}carbonyl)pyrimidin-4-yl]amino}cyclopentyl]methyl sulfamate;

[(1R,2R,3R,4R)-4-{[5-((1-[(1S)-1-(5-chloro-2-furyl)ethyl]-1H-pyrrol-3-yl}carbonyl)pyrimidin-4-yl]amino}-3-fluoro-2-hydroxycyclopentyl]methyl sulfamate;

[(1R,2R,3R,4R)-4-{[5-({1-[(1R)-1-(5-chloro-2-furyl)ethyl]-1H-pyrrol-3-yl}carbonyl)pyrimidin-4-yl]amino)-3-fluoro-2-hydroxycyclopentyl]methyl sulfamate;

{(1R,2R,3S,4R)-2,3-dihydroxy-4-[(5-{[1-((1S)-1-phenylethyl)-1H-pyrazol-3-yl]carbonyl}pyrimidin-4-yl)amino]cyclopentyl}methyl sulfamate;

((1R,2R,3S,4R-2,3-dihydroxy-4-[(5-{[1-((1R)-1-phenylethyl)-1H-pyrazol-3-yl]carbonyl}pyrimidin-4-yl)amino]cyclopentyl}methyl sulfamate;

[(1R,2S,4R)-4-{[5-({1-[(6-bromopyridin-2-yl)methyl]-1H-pyrazol-3-yl}carbonyl)pyrimidin-4-yl]amino}-2-hydroxycyclopentyl]methyl sulfamate;

{(1R,2R,3S,4R)-4-[(5-{[1-((1R)-2,3-dihydro-1H-inden-1-yl)-1H-pyrazol-3-yl]carbonyl}pyrimidin-4-yl)amino]-2,3-dihydroxycyclopentyl}methyl sulfamate;

{(1R,2R,3S,4R)-4-[(5-{[1-((1S)-2,3-dihydro-1H-inden-1-yl)-1H-pyrazol-3-yl]carbonyl}pyrimidin-4-yl)amino]-2,3-dihydroxycyclopentyl}methyl sulfamate;

[(1R,2S,4R)-4-{[5-({1-[(1S)-1-(5-chloro-2-furyl)ethyl]-1H-pyrazol-3-yl}carbonyl)pyrimidin-4-yl]amino}-2-hydroxycyclopentyl]methyl sulfamate;

[(1R,2S,4R)-4-{[5-({1-[(1R)-1-(5-chloro-2-furyl)ethyl]-1H-pyrazol-3-yl}carbonyl)pyrimidin-4-yl]amino}-2-hydroxycyclopentyl]methyl sulfamate;

[(1R,2S,4R)-4-{[5-({1-[(1S)-1-(3-ethynylphenyl)ethyl]-1H-pyrazol-3-yl}carbonyl)pyrimidin-4-yl]amino}-2-hydroxycyclopentyl]methyl sulfamate;

[(1R,2S,4R)-4-{[5-({1-[(1R)-1-(3-ethynylphenyl)ethyl]-1H-pyrazol-3-yl}carbonyl)pyrimidin-4-yl]amino}-2-hydroxycyclopentyl]methyl sulfamate;

[(1R,2R,3R,4R)-4-{[5-({1-[(1S)-1-(3-bromophenyl)propyl]-1H-pyrrol-3-yl}carbonyl)pyrimidin-4-yl]amino}-3-fluoro-2-hydroxycyclopentyl]methyl sulfamate;

[(1R,2R,3R,4R)-4-{[5-({1-[(1R)-1-(3-bromophenyl)propyl]-1H-pyrrol-3-yl}carbonyl)pyrimidin-4-yl]amino}-3-fluoro-2-hydroxycyclopentyl]methyl sulfamate;

[(1R,2R,3R,4R)-3-fluoro-2-hydroxy-4-({5-[(1-{(1S)-1-[5-(trifluoromethyl)-2-furyl]ethyl}-1H-pyrrol-3-yl)carbonyl]pyrimidin-4-yl}amino)cyclopentyl]methyl sulfamate;

[(1R,2R,3R,4R)-3-fluoro-2-hydroxy-4-({5-[(1-{(1R)-1-[5-(trifluoromethyl)-2-furyl]ethyl)-1H-pyrrol-3-yl)carbonyl]pyrimidin-4-yl}amino)cyclopentyl]methyl sulfamate;

[(1R,2S,4R)-4-{[5-((1-[(1S)-1-(3-bromophenyl)ethyl]-1H-pyrazol-3-yl}carbonyl)pyrimidin-4-yl]amino}-2-hydroxycyclopentyl]methyl sulfamate;

[(1R,2S,4R)-4-{[5-({1-[(1R)-1-(3-bromophenyl)ethyl]-1H-pyrazol-3-yl}carbonyl)pyrimidin-4-yl]amino}-2-hydroxycyclopentyl]methyl sulfamate;

[(1R,2R,3R,4R)-3-fluoro-2-hydroxy-4-{[5-({1-[(1R,2R)-(2-phenylcyclopropyl)methyl]-1H-pyrrol-3-yl}carbonyl)pyrimidin-4-yl]amino)cyclopentyl]methyl sulfamate;

[(1R,2R,3R,4R)-3-fluoro-2-hydroxy-4-{[5-({1-[(1S,2S)-(2-phenylcyclopropyl)methyl]-1H-pyrrol-3-yl}carbonyl)pyrimidin-4-yl]amino}cyclopentyl]methyl sulfamate;

[(1R,2S,4R)-4-{[5-({1-[(1S)-1-(3-chlorophenyl)ethyl]-1H-pyrazol-3-yl}carbonyl)pyrimidin-4-yl]amino}-2-hydroxycyclopentyl]methyl sulfamate;

[(1R,2S,4R)-4-{[5-((1-[(1R)-1-(3-chlorophenyl)ethyl]-1H-pyrazol-3-yl}carbonyl)pyrimidin-4-yl]amino}-2-hydroxycyclopentyl]methyl sulfamate;

{(1R,2R,3S,4R)-2,3-dihydroxy-4-[(5-{[1-((1S)-1-phenylethyl)-1H-pyrazol-3-yl]carbonyl}pyrimidin-4-yl)amino]cyclopentyl}methyl sulfamate;

{(1R,2R,3S,4R)-2,3-dihydroxy-4-[(5-{[1-((1R)-1-phenylethyl)-1H-pyrazol-3-yl]carbonyl}pyrimidin-4-yl)amino]cyclopentyl}methyl sulfamate;

{(1R,2S,4R)-2-hydroxy-4-[(5-{[[(1S)-1-(pent-3-yn-2-yl)-1H-pyrazol-3-yl]carbonyl}pyrimidin-4-yl)amino]cyclopentyl}methyl sulfamate;

{(1R,2S,4R)-2-hydroxy-4-[(5-{[[(1R)-1-(pent-3-yn-2-yl)-1H-pyrazol-3-yl]carbonyl}pyrimidin-4-yl)amino]cyclopentyl}methyl sulfamate;

[(1R,2R,3R,4R)-4-{[5-({1-[(1S)-1-(3-bromophenyl)ethyl]-1H-pyrrol-3-yl}carbonyl)pyrimidin-4-yl]amino}-3-fluoro-2-hydroxycyclopentyl]methyl sulfamate;

[(1R,2R,3R,4R)-4-{[5-({1-[(1R)-1-(3-bromophenyl)ethyl]-1H-pyrrol-3-yl}carbonyl)pyrimidin-4-yl]amino}-3-fluoro-2-hydroxycyclopentyl]methyl sulfamate;

[(1R,2R,3R,4R)-4-{[5-({1-[(1S)-1-(5-chloro-2-furyl)ethyl]-1H-pyrrol-3-yl}carbonyl)pyrimidin-4-yl]amino}-3-fluoro-2-hydroxycyclopentyl]methyl sulfamate;

[(1R,2R,3R,4R)-4-{[5-({1-[(1R)-1-(5-chloro-2-furyl)ethyl]-1H-pyrrol-3-yl}carbonyl)pyrimidin-4-yl]amino}-3-fluoro-2-hydroxycyclopentyl]methyl sulfamate;

[(1R,2S,4R)-4-{[5-({1-[(1S)-1-(3-chlorophenyl)ethyl]-5-methyl-1H-pyrazol-3-yl}carbonyl)pyrimidin-4-yl]amino}-2-hydroxycyclopentyl]methyl sulfamate;

[(1R,2S,4R)-4-{[5-({1-[(1R)-1-(3-chlorophenyl)ethyl]-5-methyl-1H-pyrazol-3-yl}carbonyl)pyrimidin-4-yl]amino}-2-hydroxycyclopentyl]methyl sulfamate;

[(1R,2S,4R)-4-{[5-({1-[(1S)-1-(6-bromopyridin-2-yl)ethyl]-1H-pyrazol-3-yl}carbonyl)pyrimidin-4-yl]amino}-2-hydroxycyclopentyl]methyl sulfamate;

[(1R,2S,4R)-4-{[5-({1-[(1R)-1-(6-bromopyridin-2-yl)ethyl]-1H-pyrazol-3-yl}carbonyl)pyrimidin-4-yl]amino}-2-hydroxycyclopentyl]methyl sulfamate;

{(1R,2S,4R)-4-[(5-{[1-(3-bromobenzyl)-5-(2-hydroxypropan-2-yl)-1H-pyrazol-3-yl]carbonyl}pyrimidin-4-yl)amino]-2-hydroxycyclopentyl}methyl sulfamate;

{(1R,2S,4R)-4-[(5-{[1-(3-bromobenzyl)-5-(methoxymethyl)-1H-pyrazol-3-yl]carbonyl}pyrimidin-4-yl)amino]-2-hydroxycyclopentyl}methyl sulfamate;

[(1R,2S,4R)-4-{[5-({1-(3-bromobenzyl)-5-[(1S)-1-methoxyethyl]-1H-pyrazol-3-yl}carbonyl)pyrimidin-4-yl]amino}-2-hydroxycyclopentyl]methyl sulfamate;

[(1R,2S,4R)-4-{[5-({1-(3-bromobenzyl)-5-[(1R)-1-methoxyethyl]-1H-pyrazol-3-yl}carbonyl)pyrimidin-4-yl]amino}-2-hydroxycyclopentyl]methyl sulfamate;

{(1R,2R,3S,4R)-3-amino-4-[(5-{[1-(3-bromobenzyl)-1H-pyrazol-3-yl]carbonyl}pyrimidin-4-yl)amino]-2-hydroxycyclopentyl}methyl sulfamate;

or a pharmaceutically acceptable salt thereof.

28. A pharmaceutical composition comprising the compound of or a pharmaceutically acceptable salt thereof and a pharmaceutically acceptable carrier.

29. A method of treating lung cancer, ovarian cancer, colon cancer, breast cancer, or lymphoma, comprising administering to the subject a therapeutically effective amount of a compound of formula (I):

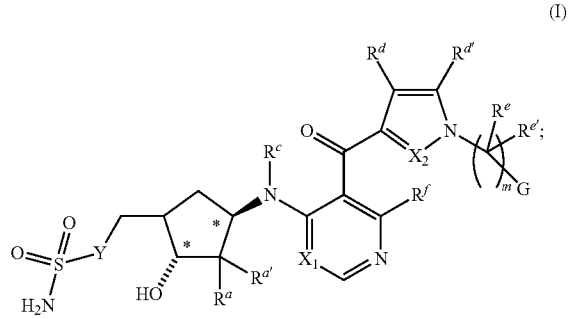

(I)

or a pharmaceutically acceptable salt thereof;
wherein:
stereochemical configurations depicted at asterisked positions indicate absolute stereochemistry;
Y is —O—, —CH$_2$—, —N(H)—;
R$^a$ is hydrogen, fluoro, —NH$_2$, or —OH;
R$^{a'}$ is hydrogen, or fluoro; provided that when R$^a$ is —NH$_2$ or —OH, R$^{a'}$ is hydrogen;
R$^c$ is hydrogen or C$_{1-4}$ alkyl;
X$_1$ is C(H), C(F) or N;
X$_2$ is C(R$^d$) or N;

each occurrence of $R^d$ is independently hydrogen, halogen, cyano, $C_{1-4}$ aliphatic, or $C_{1-4}$ fluoroaliphatic;

$R^{d'}$ is hydrogen, halogen, cyano, $C_{1-4}$ aliphatic, $C_{1-4}$ fluoroaliphatic, or $-T_2-R^3$;

$T_2$ is a $C_1-C_2$ alkylene chain optionally substituted with 0-3 independent occurrences of $R^{3c}$;

$R^3$ is —CN, —NO$_2$, —N(R$^{3a}$)$_2$, —OR$^{3a}$, —C(O)R$^{3b}$, —C(O)OR$^{3a}$, —C(O)N(R$^{3a}$)$_2$, or —S(O)$_2$N(R$^{3a}$)$_2$;

each occurrence of $R^{3a}$ is independently hydrogen or $C_{1-4}$alkyl;

$R^{3b}$ is $C_{1-4}$ alkyl;

each occurrence of $R^{3c}$ is independently $C_{1-4}$ alkyl;

$R^e$ is hydrogen or $C_{1-4}$ alkyl;

$R^{e'}$ is hydrogen or $C_{1-4}$ alkyl; or $R^e$ is taken together with $R^{e'}$ to form a 3-6 membered cycloaliphatic ring;

m is 0-2;

$R^f$ is hydrogen, chloro or $C_{1-4}$ alkyl;

G is $R^1$ or $-L_1-R^1$;

$L_1$ is

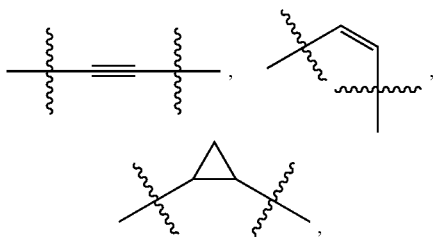

—C(O)—, or —SO$_2$—; provided that when $L_1$ is —SO$_2$—, m is zero;

$R^1$ is an optionally substituted group selected from $C_{1-6}$ aliphatic, 3- to 10-membered cycloaliphatic, 4- to 10-membered heterocycyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur, wherein $R^1$ is optionally substituted with n occurrences of $R^2$; wherein each occurrence of $R^2$ is independently —R$^{2a}$, $-T_1-R^{2d}$, $-T_1-R^{2a}$, or —V$_1-T_1-R^{2d}$;

n is 1-5;

each occurrence of $R^{2a}$ is independently halogen, —CN, —NO$_2$, —R$^{2c}$, —N(R$^{2b}$)$_2$, —OR$^{2b}$, —SR$^{2c}$, —S(O)R$^{2c}$, —S(O)$_2$R$^{2c}$, —C(O)R$^{2b}$, —C(O)OR$^{2b}$, —C(O)N(R$^{2b}$)$_2$, —S(CO)$_2$N(R$^{2b}$)$_2$, —OC(O)N(R$^{2b}$)$_2$, —N(R$^{2e}$)C(O)R$^{2b}$, —N(R$^{2e}$)SO$_2$R$^{2c}$, —N(R$^{2e}$)C(O)OR$^{2b}$, —N(R$^{2e}$)C(O)N(R$^{2b}$)$_2$, —N(R$^{2e}$)SO$_2$N(R$^{2b}$)$_2$, or Si(R$^{2c}$)$_3$, or an optionally substituted $C_1-C_6$ aliphatic or $C_1-C_6$ haloaliphatic;

each occurrence of $R^{2b}$ is independently hydrogen or an optionally substituted group selected from $C_1-C_6$ aliphatic, $C_1-C_6$ haloaliphatic, 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur, or two occurrences of $R^{2b}$, taken together with a nitrogen atom to which they are bound, form an optionally substituted 4- to -7-membered heterocyclyl ring having 0-1 additional heteroatoms selected from nitrogen, oxygen, and sulfur;

each occurrence of $R^{2c}$ is independently an optionally substituted group selected from $C_1-C_6$ aliphatic, $C_1-C_6$ haloaliphatic, 3- to 10-membered cycloaliphatic, 4- to 10-membered heterocyclyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur;

each occurrence of $R^{2d}$ is independently hydrogen or an optionally substituted group selected from 3- to 10-membered cycloaliphatic, 4- to 10-membered heterocycyl having 1-5 heteroatoms independently selected from nitrogen, oxygen, and sulfur, 6- to 10-membered aryl, or 5- to 10-membered heteroaryl having 1-5 heteroatoms independently selected from nitrogen, oxygen, and sulfur;

each occurrence of $R^{2e}$ is independently hydrogen or an optionally substituted $C_{1-6}$ aliphatic group;

each occurrence of $V_1$ is independently —N(R$^{2e}$)—, —O—, —S—, —S(O)—, —S(O)$_2$—, —C(O)—, —C(O)O—, —C(O)N(R$^{2e}$)—, —S(O)$_2$N(R$^{2e}$)—, —OC(O)N(R$^{2e}$)—, —N(R$^{2e}$)C(O)—, —N(R$^{2e}$)SO$_2$—, —N(R$^{2e}$)C(O)O—, —N(R$^{2e}$)C(O)N(R$^{2e}$)—, —N(R$^{2e}$)SO$_2$(R$^{2e}$)—, —OC(O)—, or —C(O)N(R$^{2e}$)—O—; and $T_1$ is an optionally substituted $C_1-C_6$ alkylene chain wherein the alkylene chain optionally is interrupted by —N(R$^4$)—, —O—, —S—, —S(O)—, —S(O)$_2$—, —C(O)—, —C(O)O—, —C(O)N(R$^4$)—, —S(O)$_2$N(R$^4$)—, —OC(O)N(R$^4$)—, —N(R$^4$)C(O)—, —N(R$^4$)SO$_2$—, —N(R$^4$)C(O)O—, —N(R$^4$)C(O)N(R$^4$)—, —N(R$^4$)S(O)$_2$N(R$^4$)— —OC(O)—, or —C(O)N(R$^4$)—O— or wherein $T_1$ or a portion thereof optionally forms part of an optionally substituted 3- to -7 membered cycloaliphatic or heterocyclyl ring, wherein $R^4$ is hydrogen or an optionally substituted $C_{1-4}$ aliphatic group.

30. A pharmaceutical composition for the treatment of lung cancer, ovarian cancer, colon cancer, breast cancer, or lymphoma in a patient in need thereof, comprising a compound of claim 1 or a pharmaceutically acceptable salt thereof in an amount effective for said treatment; and a pharmaceutically acceptable carrier.

31. The compound of claim 1, wherein the compound is:

{(1R,2S,4R)-4-[(5-{[1-(3-bromobenzyl)-1H-pyrazol-3-yl]carbonyl}pyrimidin-4-yl)amino]-2-hydroxycyclopentyl}methyl sulfamate of formula I-11:

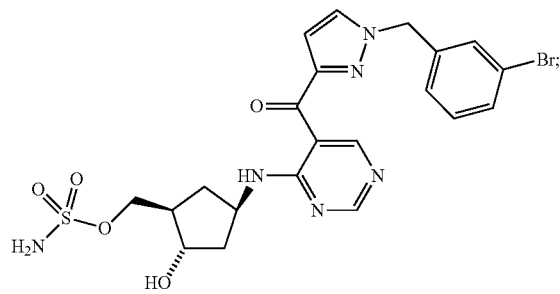

I-11

481

[(1R,2S,4R)-2-hydroxy-4-{[5-({1-[3-(trifluoromethoxy)
benzyl]-1H-pyrazol-3-yl}carbonyl)pyrimidin-4-yl]
amino}cyclopentyl]methyl sulfamate of formula I-20:

I-20

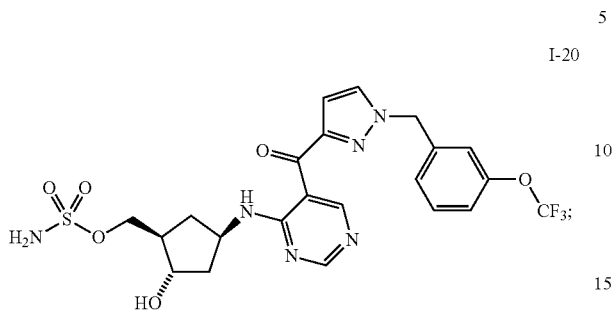

{(1R,2S,4R)-4-[(5-{[1-(4-chlorobenzyl)-1H-pyrazol-3-
yl]carbonyl}pyrimidin-4-yl)amino]-2-
hydroxycyclopentyl}methyl sulfamate of formula I-47:

I-47

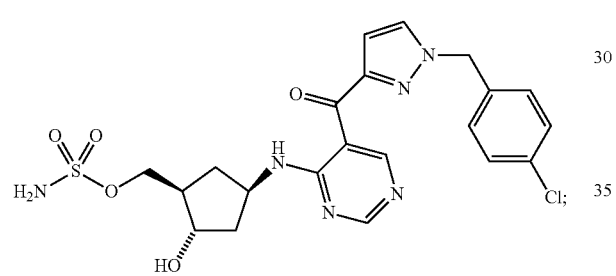

{(1R,2S,4R)-4-[(3-{[1-(3-chlorobenzyl)-1H-pyrazol-3-
yl]carbonyl}pyridin-4-yl)amino]-2-
hydroxycyclopentyl}methyl sulfamate of formula I-52:

I-52

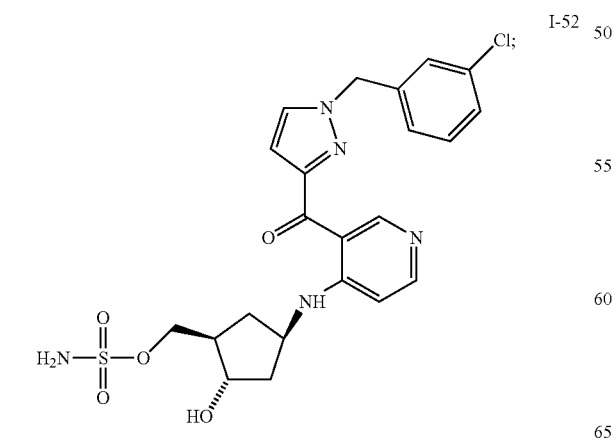

482

{(1R,2S,4R)-4-[(5-{[1-(3-ethynylbenzyl)-1H-pyrazol-3-
yl]carbonyl}pyrimidin-4-yl)amino]-2-
hydroxycyclopentyl}methyl sulfamate of formula I-85:

I-85

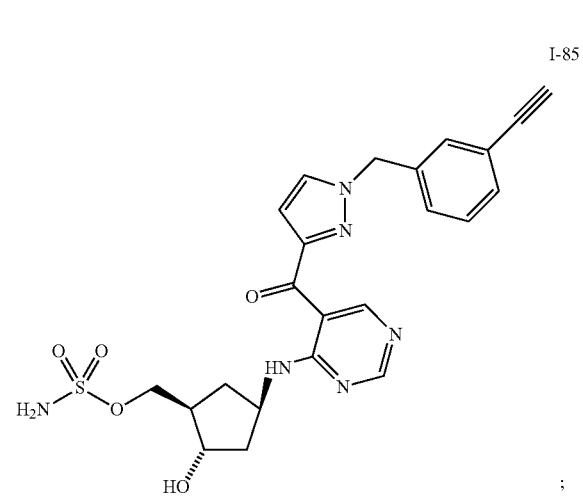 [SMILES: C#Cc1cccc(Cn2ccc(C(=O)c3cncnc3N[C@@H]3C[C@H](COS(N)(=O)=O)[C@@H](O)C3)n2)c1]

{(1R,2S,4R)-4-[(5-{[1-(cyclohexylmethyl)-1H-pyrazol-
3-yl]carbonyl}pyrimidin-4-yl)amino]-2-
hydroxycyclopentyl}methyl sulfamate of formula I-93:

I-93

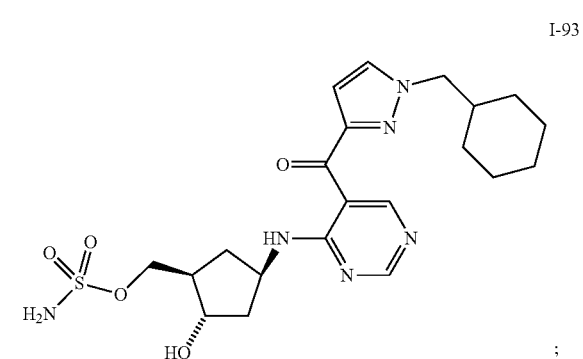 [SMILES: NS(=O)(=O)OC[C@H]1C[C@@H](Nc2ncncc2C(=O)c2ccn(CC3CCCCC3)n2)C[C@@H]1O]

[(1R,2S,4R)-4-{[5-({1-[(6-chloropyridin-2-yl)methyl]-
1H-pyrazol-3-yl}carbonyl)pyrimidin-4-yl]amino}-2-
hydroxycyclopentyl]methyl sulfamate of formula I-95:

I-95

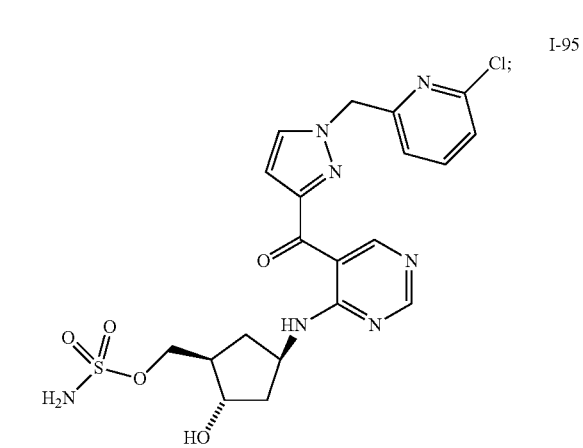 [SMILES: NS(=O)(=O)OC[C@H]1C[C@@H](Nc2ncncc2C(=O)c2ccn(Cc3cccc(Cl)n3)n2)C[C@@H]1O]

483

{(1R,2S,4R)-2-hydroxy-4-[(5-{[1-(3-methylbenzyl)-1H-pyrazol-3-yl]carbonyl}pyrimidin-4-yl)amino]cyclopentyl}methyl sulfamate of formula I-128:

I-128

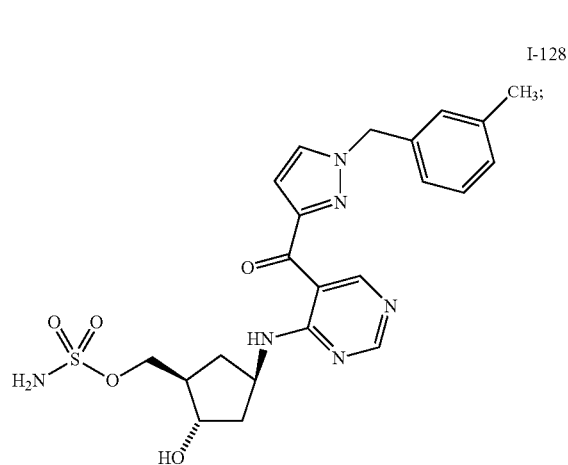 [SMILES: Cc1cccc(Cn2ccc(C(=O)c3cncnc3N[C@@H]3C[C@H](COS(N)(=O)=O)[C@@H](O)C3)n2)c1]

[(1R,2S,4R)-2-hydroxy-4-{[5-({1-[3-(trifluoromethyl)benzyl]-1H-pyrazol-3-yl}carbonyl)pyrimidin-4-yl]amino}cyclopentyl]methyl sulfamate of formula I-140:

I-140

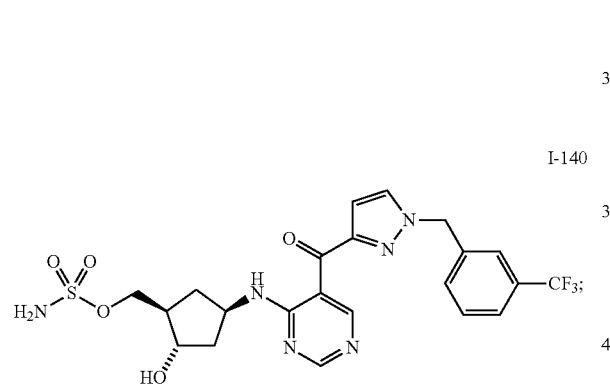

[(1R,2R,3S,4R)-4-({5-[(1-benzyl-1H-pyrazol-3-yl)carbonyl]pyrimidin-4-yl)}amino)-2,3-dihydroxycyclopentyl]methyl sulfamate of formula I-142:

I-142

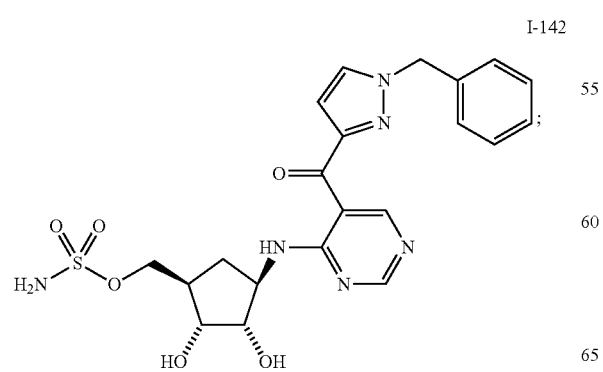

484

[(1R,2S,4R)-4-({5-[(1-benzyl-1H-pyrazol-3-yl)carbonyl]pyrimidin-4-yl}amino)-2-hydroxycyclopentyl]methyl sulfamate of formula I-158:

I-158

{(1R,2S,4R)-4-[(5-{[1-(3-fluorobenzyl)-1H-pyrazol-3-yl]carbonyl}pyrimidin-4-yl)amino]-2-hydroxycyclopentyl}methyl sulfamate of formula I-165:

I-165

[(1R,2S,4R)-4-{[5-({1-[(5-chloro-2-furyl)methyl]-1H-pyrazol-3-yl}carbonyl)pyrimidin-4-yl]amino}-2-hydroxycyclopentyl]methyl sulfamate of formula I-180:

I-180

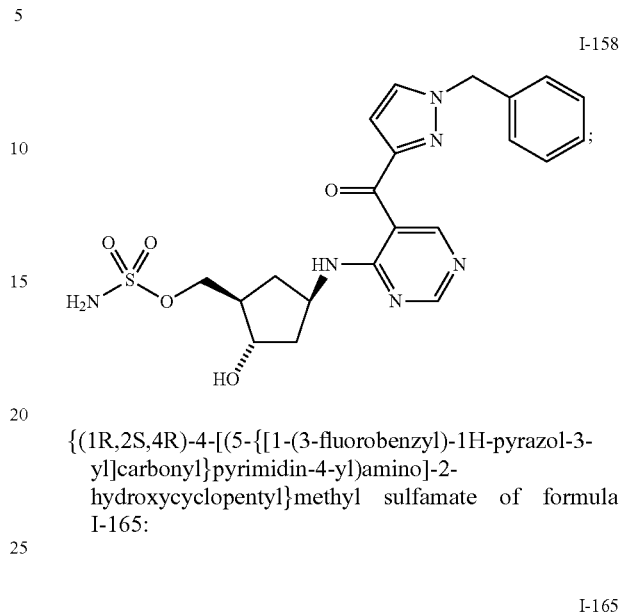

[(1R,2R,4R)-4-({5-[(1-benzyl-1H-pyrazol-3-yl)carbonyl]pyrimidin-4-yl}amino)-3,3-difluoro-2-hydroxycyclopentyl]methyl sulfamate of formula I-203:

{(1R,2S,4R)-4-[(5-{[1-(2-chlorobenzyl)-1H-pyrazol-3-yl]carbonyl}pyrimidin-4-yl)amino]-2-hydroxycyclopentyl}methyl sulfamate of formula I-206:

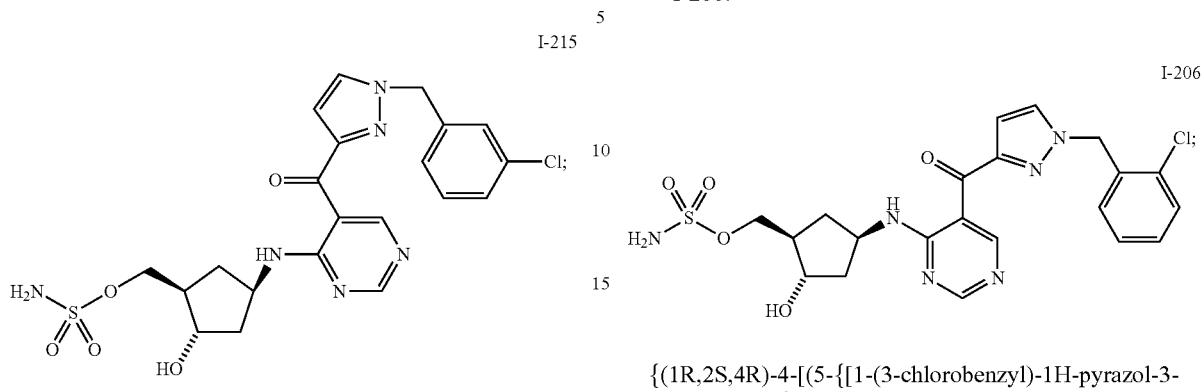

[(1R,2R,3S,4R)-4-({5-[(1-benzyl-1H-pyrrol-3-yl)carbonyl]pyrimidin-4-yl}amino)-2,3-dihydroxycyclopentyl]methyl sulfamate of formula I-217:

{(1R,2S,4R)-4-[(5-{[1-(3-chlorobenzyl)-1H-pyrazol-3-yl]carbonyl}pyrimidin-4-yl)amino]-2-hydroxycyclopentyl}methyl sulfamate of formula I-215:

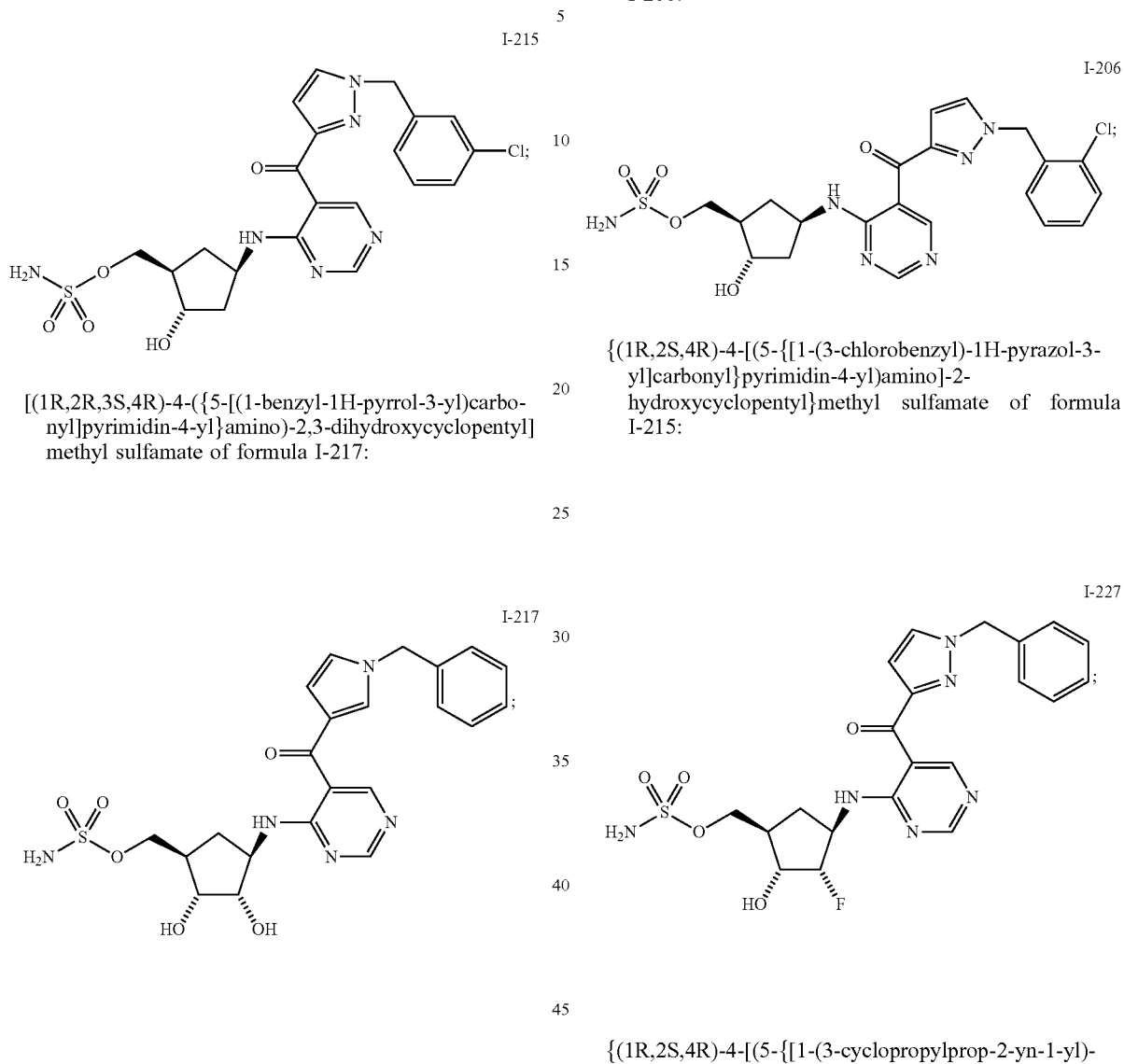

[(1R,2R,3S,4R)-4-({5-[(1-benzyl-1H-pyrazol-3-yl)carbonyl]pyrimidin-4-yl}amino)-3-fluoro-2-hydroxycyclopentyl]methyl sulfamate of formula I-227:

{(1R,2S,4R)-4-[(5-{[1-(3-cyclopropylprop-2-yn-1-yl)-1H-pyrazol-3-yl]carbonyl}pyrimidin-4-yl)amino]-2-hydroxycyclopentyl}methyl sulfamate of formula I-287:

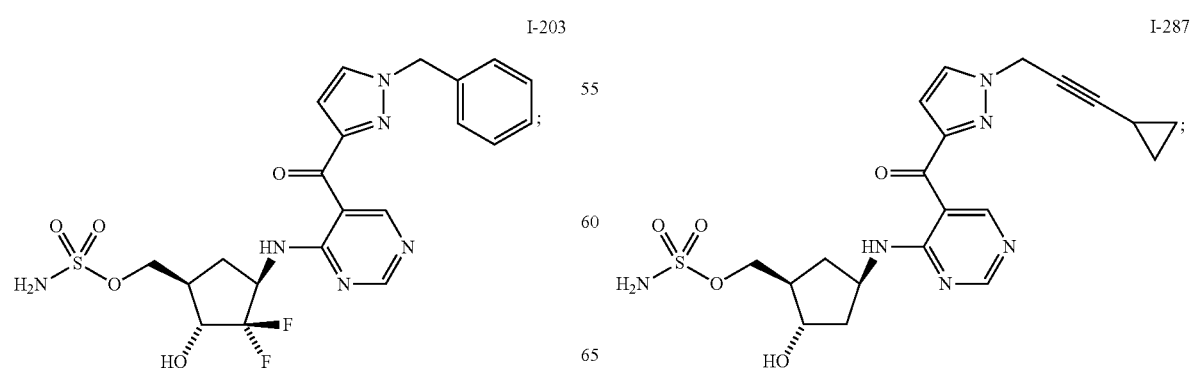

[(1R,2S,4R)-4-({5-[(1-benzyl-1H-pyrrol-3-yl)carbonyl]pyrimidin-4-yl}amino)-2-hydroxycyclopentyl]methyl sulfamate of formula I-300:

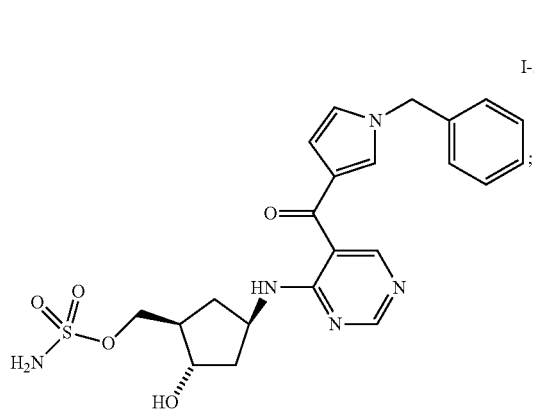

[(1R,2R,3R,4R)-4-({5-[(1-benzyl-1H-pyrazol-3-yl)carbonyl]pyrimidin-4-yl}amino)-3-fluoro-2-hydroxycyclopentyl]methyl sulfamate of formula I-317:

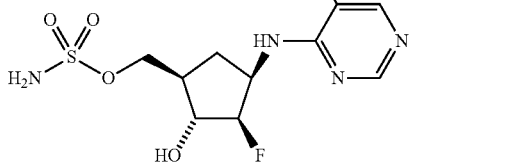

{(1R,2S,4R)-4-[(5-{[1-(3-bromobenzyl)-1H-pyrrol-3-yl]carbonyl}pyrimidin-4-yl)amino]-2-hydroxycyclopentyl}methyl sulfamate of formula I-333:

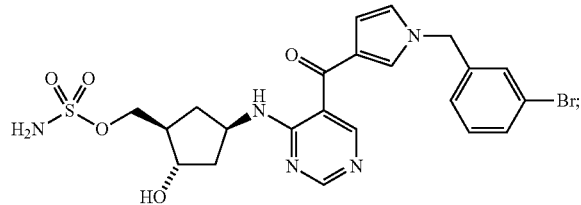

[(1R,2S,4R)-4-{[5-({1-[(6-bromopyridin-2-yl)methyl]-1H-pyrazol-3-yl}carbonyl)pyrimidin-4-yl]amino}-2-hydroxycyclopentyl]methyl sulfamate of formula I-352:

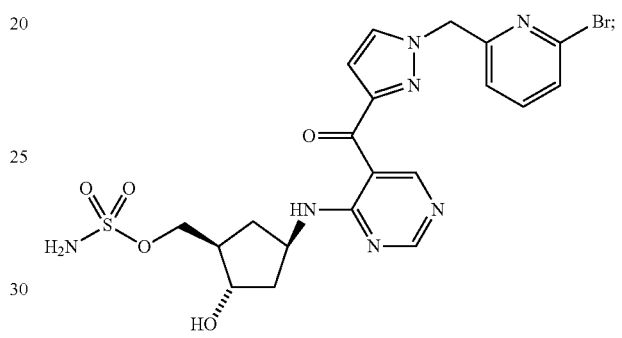

or a pharmaceutically acceptable salt thereof.

32. A pharmaceutical composition comprising the compound of claim 31 or a pharmaceutically acceptable salt thereof and a pharmaceutically acceptable carrier.

33. A method of treating lung cancer, ovarian cancer, colon cancer, breast cancer, or lymphoma, comprising administering to the subject a therapeutically effective amount of a compound of claim 31.

34. A method of treating melanoma or acute myeloid leukemia, comprising administering to the subject a therapeutically effective amount of a compound of claim 1.

* * * * *